United States Patent [19]

Kishimoto et al.

[11] Patent Number: 4,822,788
[45] Date of Patent: Apr. 18, 1989

[54] 1-SULFO-2-OXOZETIDINE DERIVATIVES AND THEIR PRODUCTION

[75] Inventors: Shoji Kishimoto, Takarazuka; Taisuke Matsuo, Ibaraki; Michihiko Ochiai, Suita, all of Japan

[73] Assignee: Takeda Chemical Industries, Ltd., Osaka, Japan

[21] Appl. No.: 326,938

[22] Filed: Dec. 3, 1981

[30] Foreign Application Priority Data

Dec. 5, 1980 [WO] PCT Int'l Appl. ... PCT/JP80/00297
Apr. 30, 1981 [WO] PCT Int'l Appl. ... PCT/JP81/00103
Aug. 21, 1981 [WO] PCT Int'l Appl. ... PCT/JP81/00183
Sep. 24, 1981 [WO] PCT Int'l Appl. ... PCT/JP81/00252

[51] Int. Cl.$^4$ ............... A61K 31/395; A61K 31/425; C07D 205/08; C07D 417/12
[52] U.S. Cl. .................................. 514/210; 540/355
[58] Field of Search ............ 260/239 A, 245 V; 424/244

[56] References Cited

U.S. PATENT DOCUMENTS

| 4,200,572 | 4/1980 | Gleason et al. | 260/239 A |
| 4,225,586 | 9/1980 | Imada et al. | 424/117 |
| 4,229,436 | 10/1980 | Imada et al. | 424/117 |
| 4,501,697 | 2/1985 | Kronenthal | 540/355 |
| 4,502,994 | 3/1985 | Wei et al. | 544/355 |

FOREIGN PATENT DOCUMENTS

0048953 4/1982 European Pat. Off.

OTHER PUBLICATIONS

Sykes et al., Chem. Abs. 95, 217370s (1981).
Matsuo et al., Chem. Abs. 95, 97566m (1981).
Imada et al., *Nature*, vol. 289, pp. 590–591 (1981).
Sykes et al., *Nature*, vol. 291, pp. 489–491 (1981).
*12th International Congress of Chemotherapy*, Florence, Italy, Jul. 19–24, 1981, pp. 55–56.
Sykes et al., *Journal of Antimicrobial Chemotherapy*, (1981) 8, Suppl. E 1–16.

*Primary Examiner*—Mark L. Berch
*Attorney, Agent, or Firm*—Wenderoth, Lind & Ponack

[57] ABSTRACT

Disclosed are compounds of the general formula:

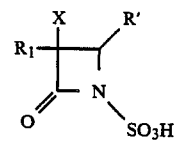

wherein $R_1$ is amino, an acylated amino or a protected amino group, X is hydrogen or methoxy, and $R'$ is hydrogen, R or $R^4$ wherein R is an organic residue attached to the azetidine ring through a carbon atom therein and $R_4$ is azido, a halogen, an amino group which may optionally be acylated or a group of the formula

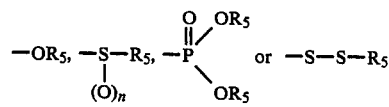

wherein $R_5$ is an organic residue and n is 0, 1 or 2, and pharmaceutically acceptable salts and esters thereof.

The compounds have antimicrobial and/or β-lactamase-inhibitory activity and are of value as drugs for human beings and domesticated animals.

23 Claims, No Drawings

1-SULFO-2-OXOZETIDINE DERIVATIVES AND THEIR PRODUCTION

This invention relates to novel azetidine derivatives and to the methods for producing them. In particular there are provided novel 1-sulfo-2-oxoazetidine compounds which have antimicrobial activity and/or β-lactamase-inhibitory activity.

Disclosed herein are compounds of the general formula:

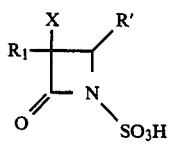

wherein $R_1$ is amino, an acylated amino or a protected amino group, X is hydrogen or methoxy and R' is hydrogen, R or $R_4$, werein R is an organic residue attached to the azetidine ring through a carbon atom therein and $R_4$ is azido, a halogen, an amino group which may optionally be acylated, or a group of the formula

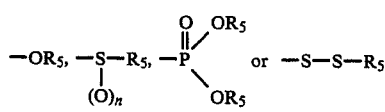

wherein $R_5$ is an organic residue and n is 0, 1 or 2, or a pharmaceutically acceptable salt thereof, or an ester thereof.

In a particular aspect the present invention relates to compounds of the formula

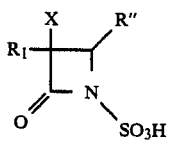

wherein $R_1$ represents amino, an acylated amino group or a protected amino group, X represents hydrogen or methoxy, and R" represents an organic residue attached to the azetidine ring through a carbon atom therein with the proviso that R" is not straight or branched chain unsubstituted alkyl, an amino-carbonyl group in which the amino may be protected or substituted, or a group —$COQ^5$ wherein $Q^5$ is hydroxy or protected hydroxy, or a pharmaceutically acceptable salt or ester thereof.

A. 1-Sulfo-2-Oxoazetidine derivatives which are unsubstituted in the 4-position In one aspect this disclosure is directed to: a 1-sulfo-2-oxoazetidine derivative of the general formula:

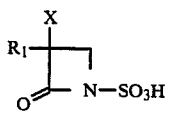

wherein $R_1$ is amino, acylated amino or protected amino and X is hydrogen or methoxy:

The objective compounds of the formula (I) may be produced by sulfonating a compound of the formula:

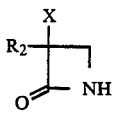

wherein $R_2$ is acylated amino or protected amino and X is as defined above, and optionally removing the amino-protecting group, or acylating the thus obtained compound of the formula

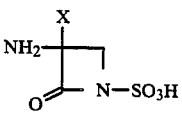

wherein X is as defined above.

Referring to the above general formulas, the acyl groups on the acylated amino groups $R_1$, and $R_2$ may for example be the acyl groups which are found as substitutents on the 6-amino group of the known penicillin derivatives and the 7-amino group of the known cephalosporin derivatives.

Among specific examples of such acyl groups are the following:

groups of the formula $R_6$—CO— wherein $R_6$ is a lower alkyl group or a substituted or unsubstituted heterocyclic group;

groups of the formula:

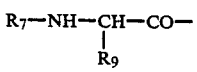

wherein $R_7$ is hydrogen, optionally substituted amino acid residue, amino-protecting group, a group of the formula $R_8$—$(CH_2)_n$—CO— [$R_8$ is optionally substituted heterocyclic group, optionally substituted phenyl, optionally substituted lower alkyl, optionally substituted phenylthio or lower alkylthio; n is an integer of 0 to 4, the group —$(CH_2)_n$— may optionally be substituted], a group of the formula

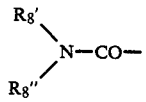

[$R_8'$ and $R_8''$ may be same or different, and is hydrogen, lower alkyl, lower alkyl carbamoyl, optionally substituted phenylcarbonyl or sulfo] or a group of the formula $R_8'''$—$SO_2$—[$R_8'''$ is optionally substituted lower alkyl]; $R_9$ is hydrogen, optionally substituted lower alkyl, optionally substituted phenyl, optionally substituted heterocyclic group, cycloalkenylene or optionally substituted heterocycliccarbonylamino in which an alkylene chain may stand between the heterocyclic and carbonylamino moieties;

groups of the formula:

[wherein $R_{10}$ is a group of the formula

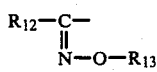

{R$_{12}$ is optionally substituted heterocyclic group or optionally substituted phenyl, R$_{13}$ is hydrogen, optionally substituted lower acyl, lower alkyl or a group of the formula —R$_{14}$—R$_{15}$(R$_{14}$ is lower alkylene or lower alkenylene group, R$_{15}$ is carboxyl, ester thereof or heterocyclic group)}, R$_{11}$ is a chemical bond or a group of the formula

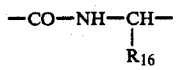

(R$_{16}$ is lower alkyl, optionally substituted phenyl or optionally substituted heterocyclic group)];
groups of the formula:

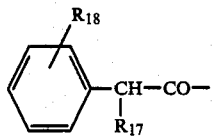

[wherein R$_{17}$ is hydroxyl, sulfoxy, carboxyl, optionally substituted sulfamoyl, sulfo, optionally substituted phenoxycarbonyl, benzyloxycarbonyl or formyloxy; R$_{18}$ is hydrogen, a lower alkyl group, a lower alkoxy group, halogen, nitro or hydroxy]; and
groups of the formula:

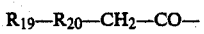

[wherein R$_{19}$ is a cyano, optionally substituted phenyl, optionally substituted phenoxy, optionally substituted lower alkyl, optionally substituted alkenyl or optionally substituted heterocyclic group; R$_{20}$ is a chemical bond or —S—].

The lower alkyl group R$_6$ is preferably a group of 1 to 6 carbon atoms. The heterocyclic moiety of the optionally substituted heterocyclic group R$_6$ is a 5- to 6-membered heterocyclic group including 1 to 2 nitrogen atoms and may optionally include a single oxygen atom. Examples of said heterocyclic group include isoxazolyl, piperazinyl, imidazolinyl etc. The substituents on such heterocyclic groups may, for example, be lower alkyl of 1 to 3 carbon atoms, lower alkoxy of 1 to 3 carbon atoms, halogen, nitro, amino, oxo, thioxo and optionally substituted phenyl. The substituent on the aforementioned optionally substituted phenyl group may include, for example, lower alkyl of 1 to 3 carbon atoms, lower alkoxy of 1 to 3 carbon atoms, halogen, nitro and amino.

As examples of the amino acid residue of the optionally substituted amino acid residue R$_7$, there may be mentioned glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophyl, prolyl, etc. However, in the case of X=methoxy, an example (R$_7$=glutamyl, R$_9$=methyl) is eliminated. The substituent on the aforementioned optionally substituted amino acid residue may include, for example, amino, lower alkyl amino, amino-protecting group, carbamoyl, methylcarbamoyl, sulfamoyl, benzyl, 4-ethyl-2,3-dioxo-1-piperazinocarbonyl and 4-ethyl-2,3-dioxo-1-piperazinocarbonylamino.

The lower alkyl moiety of the lower alkylamino is preferably alkyl of 1 to 3 carbon atoms.

The amino-protecting group may, for example, be one of the protective groups mentioned hereinafter for amino group. The amino-protecting group R$_7$ may, for example, be one of the protective groups mentioned hereinafter for amino group.

The optionally substituted heterocyclic group R$_8$ in the group represented by the formula R$_8$—(CH$_2$)$_n$—CO— includes, for example, 5- to 6-membered heterocyclic groups including one sulfur, nitrogen or oxygen atom, 5- to 6-membered heterocyclic groups including 2 to 4 nitrogen atoms, and 5- to 6-membered heterocyclic groups including one or two nitrogen atoms and one sulfur or oxygen atom. These heterocyclic groups may each be fused to a 6-membered ring including 1 or 2 nitrogen atoms, a benzene ring or a 5-membered ring including one sulfur atom. As examples of said heterocyclic group R$_8$, there may be mentioned 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthyridinyl, 1,5-naphthyridinyl, 1,6-naphthyridinyl, 1,7-naphthyridinyl, 2,7-naphthyridinyl, 2,6-naphthyridinyl, quinolyl, thieno[2,3-b]pyridyl, tetrazolyl, thiadiazolyl, oxadiazolyl, triazinyl, thienyl, pyrrolyl, furyl, etc. The substituents on such optionally substituted heterocyclic groups R$_8$ include, for example, optionally substituted alkyl of 1 to 12 carbon atoms, lower alkoxy of 1 to 3 carbon atoms, hydroxyl, oxo, thioxo, formyl, trifluoromethyl, amino, halogen, lower alkylsulfonyl of 1 to 3 carbon atoms, coumarin-3-carbonyl, 4-formyl-1-piperazinyl, pyrrolealdimino, furanaldimino, thiophenealdimino, mesyl, amino-protecting group, acylamino of 2 to 4 carbon atoms which may be substituted by halogen, etc. The amino-protecting group may for example be one of the protective groups mentioned hereinafter for amino group. The substituents on the optionally substituted alkyl of 1 to 12 carbon atoms include, for example, phenyl, halogen, hydroxy, dialkylamino, etc. The alkyl moiety of the dialkylamino is preferably alkyl of 1 to 3 carbon atoms.

The substituents on the optionally substituted phenyl group R$_8$ include, for example, lower alkyl of 1 to 3 carbon atoms, lower alkoxy of 1 to 3 carbon atoms, halogen, hydroxyl and amino. The lower alkyl moiety of the lower alkylthio group R$_8$ is preferably alkyl of 1 to 3 carbon atoms.

The substituents on the optionally substituted phenylthio group R$_8$ include, for example, lower alkyl of 1 to 3 carbon atoms, lower alkoxy of 1 to 3 carbon atoms, halogen, hydroxy, amino, etc.

The substituents which may optionally be substituted on the group representedd by the formula —(CH$_2$)$_n$— include, for example, amino and group of the formula —NH—COR$_8$''''[R$_8$'''' is amino or optionally substituted piperazinyl]. As examples of the substituent on said optionally substituted piperazinyl group R$_8$'''', there may be mentioned lower alkyl of 1 to 3 carbon atoms, lower alkoxy of 1 to 3 carbon atoms, hydroxy, oxo, thioxo and halogen.

Referring to the above formula, the lower alkyl represented by R$_8$' and/or R$_8$'' is preferably a group of 1 to 3 carbon atoms. The lower alkyl moiety of the lower alkylcarbamoyl is preferably a group of 1 to 3 carbon atoms. As examples of the substituents on said optionally substituted phenylcarbonyl group, there may be mentioned lower alkyl of 1 to 3 carbon atoms, lower alkoxy of 1 to 3 carbon atoms, halogen, hydroxy, sulfoxy, benzyloxy, etc. The lower alkyl moiety of the optionally substituted lower alkyl group $R_8'''$ in the formula $R'''_8—SO_2—$ is preferably a moiety of 1 to 6 carbon atoms, which may be substituted by one or two substituents such as amino, carboxyl benzyloxycarbonyl or protected amino. The protective group in the protected amino may for example be one of the protective groups mentioned hereinafter for amino group.

The lower alkyl moiety of the optionally substituted lower alkyl group $R_9$ is preferably a moiety of 1 to 3 carbon atoms. As examples of the substituent on the optionally substituted lower alkyl, there may be mentioned phenyl, carbamoyl, methylcarbamoyl, methylthio, thienylacetamide, ethoxycarbonylmethylcarbamoyl, N-methyltetrazolylthio, halogen and sulfamoyl. The substituents on optionally substituted phenyl groups $R_9$ include, for example, lower alkyl of 1 to 3 carbon atoms, lower alkoxy of 1 to 3 carbon atoms, halogen, hydroxy, sulfoxy, benzyloxy, benzoyloxy, trimethylsilyl, acyloxy of 2 to 10 carbon atoms, etc.

The heterocyclic ring on said optionally substituted heterocyclic group $R_9$ may, for example, be five-membered heterocyclic groups with one sulfur, nitrogen or oxygen atom, five-membered heterocyclic groups with one to two nitrogen atoms and one sulfur or oxygen atom and five- to six-membered heterocyclic groups with 2 to 4 nitrogen atoms. Examples of such heterocyclic groups are thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl, oxadiazolyl, etc. The substituents in these cases are lower alkyl of 1 to 3 carbon atoms, lower alkoxy of 1 to 3 carbon atoms, halogen, hydroxy, nitro, sulfoxy, amino and acylamino of 2 to 4 carbon atoms which may optionally be substituted by halogen, to name but a few.

The cycloalkenylene $R_9$ is preferably five- to six-membered cycloalkenylene, such as cyclohexenyl, cyclohexadienyl. The heterocyclic moiety of said optionally substituted heterocycliccarbonylamino which may optionally have alkylene chain between the heterocyclic and carbonylamino group represented by $R_9$ includes, for example, six-membered heterocyclic group with two nitrogen atoms. Among such heterocyclic groups is piperazinyl. the substituents may for example be alkyl of 1 to 12 carbon atoms, lower alkoxy of 1 to 3 carbon atoms, oxo, thioxo, amino and so forth. The alkylene chain is preferably an alkylene chain of 1 to 3 carbon atoms and as examples of the chain there may be mentioned methylene, ethylene and n-propylene.

Referring, further, to the above formulas, the heterocyclic ring of said optionally substituted heterocyclic group $R_{12}$ in the group $R_{10}$ represented by the formula:

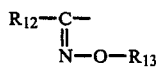

includes, for example, five-membered heterocyclic groups including one nitrogen, sulfur or oxygen atom, which five-membered heterocyclic groups may optionally include one nitrogen atom or no nitrogen atom. Among examples of said heterocyclic group are 2-thiazolyl, 4-thiazolyl, 5-thiazolyl, 2-thienyl, 3-thienyl, 2-furyl, 3-furyl, 2-pyrrolyl, 3-pyrrolyl, etc. The substituents on such heterocyclic groups include, for example, lower alkyl of 1 to 3 carbon atoms, lower alkoxy of 1 to 3 carbon atoms, hydroxy, halogen, amino, and acylamino group of 2 to 4 carbon atoms which may optionally be substituted by halogen.

The substituents on the optionally substituted phenyl group $R_{12}$ include, for example, lower alkyl of 1 to 3 carbon atoms, lower alkoxy of 1 to 3 carbon atoms, halogen, nitro, amino, hydroxy and substituted hydroxy. The substituents of said substituted hydroxy may for example be benzyl, benzoyl, acyl of 2 to 10 carbon atoms, γ-D-glutamyl, 3-amino-3-carboxypropyl.

The lower alkyl group $R_{13}$ is preferably a group of 1 to 3 carbon atoms. The optionally substituted lower acyl group $R_{13}$ is preferably a group of 2 to 4 carbon atoms and the substituents of said acyl group may for example be halogen. The lower alkylene $R_{14}$ in the group $—R_{14}—R_{15}$ of the group $R_{13}$ is preferably a group of 1 to 3 carbon atoms, such as methylene, ethylene, propylene, isopropylene, etc. The lower alkenylene $R_{14}$ is preferably a group of 1 to 3 carbon atoms, such as vinylene, propenylene, etc. The carboxyl ester $R_{15}$ may for example be the methyl ester, ethyl ester, propyl ester, etc. The heterocyclic group $R_{15}$ may, for example, be six-membered heterocyclic groups with one nitrogen and oxygen atom, such as morpholino, etc.

The lower alkyl group $R_{16}$ in the group $R_{11}$ as represented by the formula:

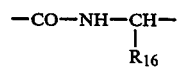

is preferably a group of 1 to 3 carbon atoms. As examples of substituents on optionally substituted phenyl groups $R_{16}$, there may be mentioned lower alkyl of 1 to 3 carbon atoms, lower alkoxy of 1 to 3 carbon atoms, halogen, nitro, amino, acyloxy of 2 to 10 carbon atoms, etc. The optionally substituted heterocyclic group $R_{16}$ may, for example, be five-membered heterocyclic groups with one sulfur, nitrogen or oxygen atom, five-membered heterocyclic groups with one to two nitrogen atoms and one sulfur or oxygen atom and five-membered heterocyclic groups with two to four nitrogen atoms, such as thiazolyl, isothiazolyl, oxazolyl, isoxazolyl, thienyl, furyl, pyrrolyl, thiadiazolyl, oxadiazolyl, tetrazolyl, imidazolyl, pyrazinyl, and also hetercyclics pyrimidinyl, pyridazinyl, piperazinyl, etc. substituents on said optionally substituted heterocyclic group include, for example, lower alkyl of 1 to 3 carbon atoms, lower alkoxy of 1 to 3 carbon atoms, halogen, hydroxy, amino and acylamino group of 2 to 4 carbon atoms which may optionally be substituted by halogen.

Substituents on optionally substituted sulfamoyl groups $R_{17}$ include, for example, lower alkyl of 1 to 3 carbon atoms, amidino, etc. Substituents on optionally substituted phenoxycarbonyl group $R_{17}$ include, for example, lower alkyl of 1 to 3 carbon atoms and lower alkoxy of 1 to 3 carbon atoms.

The lower alkyl or lower alkoxy $R_{18}$ is preferably a group of 1 to 3 carbon atoms, respectively.

Substituents on optionally substituted phenyl groups $R_{19}$ include, for example, lower alkyl of 1 to 3 carbon atoms, lower alkoxy of 1 to 3 carbon atoms, halogen, nitro, amino, hydroxy, optionally substituted aminomethyl, etc. Substituents on said optionally substituted aminomethyl may for example be carbamoyl, (2-oxo-3-benzylideneamino-imidazolidin-1-yl)carbonyl, (2-oxoimidazolidin-1-yl)carbonyl, etc. Substituents on optionally substituted phenoxy group $R_{19}$, for example, include lower alkyl of 1 to 3 carbon atoms, lower alkoxy of 1 to 3 carbon atoms, halogen, nitro, amino, hydroxy, aminomethyl. The optionally substituted lower alkyl group $R_{19}$ is preferably a group of 1 to 6 carbon atoms, the substituents being exemplified by halogen, hydroxy, cyano, trifluoromethyl, etc.

The alkenyl of optionally substituted alkenyl group $R_{19}$ may for example be vinyl, propenyl etc., and the substituents may for example be carboxyl, cyano, etc. Examples of the heterocyclic ring of optionally substituted heterocyclic group $R_{19}$ include five- to six-membered heterocyclic groups including one sulfur atom or one to 4 nitrogen atoms and five- to six-membered heterocyclic groups including one sulfur atom and one nitrogen or oxygen atom. Thus, 2-thienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl, 1,4-oxathiinyl, etc. may be mentioned by way of example. Substituents on such optionally substituted heterocyclic group $R_{19}$ include, for example, lower alkyl of 1 to 3 carbon atoms, lower alkoxy of 1 to 3 carbon atoms, halogen, nitro, hydroxy, amino, carboxy, oxo, acylamino of 2 to 4 carbon atoms which may optionally be substituted by halogen, acyl of 2 to 4 carbon atoms and so forth.

The alkyl group of 1 to 12 carbon atoms, mentioned hereinbefore, may for example be methyl, trifluoromethyl, ethyl, n-propyl, isopropyl, n-butyl, isobutyl, sec-butyl, tert-butyl, pentyl, isopentyl, hexyl, isohexyl, heptyl, octyl, nonyl, decyl, undecyl, dodecyl or the like.

The lower alkyl group of 1 to 6 carbon atoms, mentioned hereinbefore, may for example be methyl, trifluoromethyl, ethyl, n-propyl, isopropyl, n-butyl, isobutyl, sec-butyl, tert-butyl, pentyl, isopentyl, hexyl, isohexyl, etc.

The lower alkyl group of 1 to 3 carbon atoms, also mentioned hereinbefore, may for example be methyl, trifluoromethyl, ethyl, n-propyl, isopropyl or the like.

The lower alkoxy group of 1 to 3 carbon atoms, mentioned hereinbefore, may for example be methoxy, ethoxy, n-propoxy, isopropoxy or the like.

The halogen includes chlorine, bromine, iodine and fluorine.

The lower alkylsulfonyl group containing 1 to 3 carbon atoms include, for example, methylsulfonyl, ethylsulfonyl, n-propylsulfonyl, isopropylsulfonyl, etc.

The acylamino group of 2 to 4 carbon atoms include, for example, acetylamino, propionylamino, n-butyrylamino, isobutyrylamino, etc.

The acyloxy group of 2 to 10 carbon atoms include, for example, acetoxy, n-propionyloxy, n-butyryloxy, isobutyryloxy, n-pentanoyloxy, n-hexanoyloxy, n-heptanoyloxy, n-octanoyloxy, n-nonanoyloxy, n-decanoyloxy, etc.

Referring to the aforementioned acyl group, the acyl group represented by the formula $R_6$—CO—(wherein $R_6$ has the same meaning as defined hereinbefore) includes, for example, 3-(2,6-dichlorophenyl)-5-methylisoxazol-4-yl-carbonyl, 4-ethyl-2,3-dioxo-1-piperazinocarbonyl, (2-oxoimidazolidin-1-yl)carbonyl, etc.

The acyl group represented by the formula:

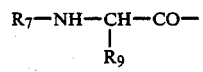

(wherein $R_7$ and $R_9$ have the same meanings as defined hereinbefore) includes, for example, D-alanyl, D-phenylalanyl, α-benzyl N-carbobenzoxy-γ-D-glutamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltryptophyl-D-phenylglycyl, methylamidoasparaginyl-D-phenylglycyl, N-carbobenzoxymethylamidoasparaginyl-D-phenylglycyl, N-carbobenzoxy-D-phenylglycyl-D-phenylglycyl, 2-(2,3-diaminopropionamido)-2-phenylacetyl, D-alanyl-D-alanyl, 2-[2-amino-3-(N-methylcarbamoyl)propionamido]acetyl, 2-(2-amino-3-sulfamoylpropionamido)-2-phenylacetyl, 2-[2-amino-3-(4-ethyl-2,3-dioxo-1-piperazinocarboxamido)propionamido]-2-phenylacetyl, D-2-(4-ethyl-2,3-dioxo-1-piperazinocarboxamido)-2-(4-methoxyphenyl)acetyl, 4-ethyl-2,3-dioxo-1-piperazinocarbonyl, D2-[2-(4-ethyl-2,3-dioxo-1-piperazinocarboxamido)-3-(N-methylcarbamoyl)propionamido]-2-phenylacetyl, D-2-[2-(4-ethyl-2,3-dioxo-1-piperazinocarboxamido)acetamido]-2-phenylacetyl, D-2-(3-sulfamoyl-2-benzyloxycarboxamidopropionamido)-2-phenylacetyl, D-2-[2-benzyloxycarboxamido-3-(4-methoxyphenyloxycarboxamido)-propionamido]-2-phenylacetyl, 2-[2-benzyloxycarboxamido-3-(N-methylcarbamoyl)propionamido]acetyl, 2-(N-carbobenzoxy-D-phenylglycylamino)-3-(N-methylcarbamoyl)propionyl, N-carbobenzoxy-D-alanyl, 2-(benzyloxycarboxamido)-2-phenylacetyl, 2-benzyloxycarboxamido-3-N-methylcarbamoylpropionyl, N-(4-ethyl-2,3-dithioxo-1-piperazinocarbonyl)-D-phenylglycyl, 2-(2-amino-4-thiazoyl)-2-(4-ethyl-2,3-dioxo-1-piperazinocarboxamido)acetyl, 2-(2-phenylacetamido)propionyl, 2-(4-ethyl-2,3-dioxo-1-piperazinocarboxamido)-2-thienylacetyl, 2-(3-furfurylideneamino-2-oxoimidazolidine-1-carboxamido)-2-(4-hydroxyphenyl)acetyl, 2-(8-hydroxy-1,5-naphthyridine-7-carboxamido)-2-phenylacetyl, 2-(4-ethyl-2,3-dioxo-1-piperazinocarboxamido)-2-phenylacetyl, 2-(4-n-octyl-2,3-dioxo-1-piperazinocarboxamido)-2-phenylacetyl, 2-(4-ethyl-2,3-dioxo-1-piperazinocarboxamido)-2-(4-sulfoxyphenyl)acetyl, 2-(4-ethyl-2,3-dioxo-1-piperazinocarboxamido)-2-(4-chlorophenyl)acetyl, 2-(4-n-octyl-2,3-dioxo-1-piperazinocarboxamido)-2-(4-hydroxysulfonyloxyphenyl)acetyl, 2-(4-ethyl-2,3-dioxo-1-piperazinocarboxamido)-2-(4-methoxyphenyl)acetyl, 2-(4-ethyl-2,3-dioxo-1-piperazinocarboxamido)-2-(4-trimethylsilylphenyl)acetyl, 2-(4-ethyl-2,3-dioxo-1-piperazinocarboxamido)-2-(3-chloro-4-methoxyphenyl)acetyl, 2-(4-ethyl-2,3-dioxo-1-piperazinocarboxamido)-2-(3-chloro-4-hydroxysulfonyloxyphenyl)acetyl, 2-(4-ethyl-2,3-dioxo-1-piperazinocarboxamido)-2-(3-chloro-4-hydroxyphenyl)acetyl, 2-(4-ethyl-2,3-dioxo-1-piperazinocarboxamido)-2-(4-benzyloxyphenyl)acetyl, 2-(4-n-octyl-2,3-dioxo-1-piperazinocarboxamido)-2-(4-hydroxyphenyl)acetyl, N-(4-ethyl-2,3-dioxo-1-piperazinocarbonyl)glutaminyl, N-(4-ethyl-2,3-dioxo-1-piperazinocarbonyl)phenylalanyl, N-(4-ethyl-2,3-dioxo-1-piperazinocarbonyl)-D-alanyl, 2-(4-ethyl-2,3-dioxo-1-piperazinocarboxamido)-2-(4-hydroxyphenyl)acetyl, 2,2-bis(4-ethyl-2,3-dioxo-1-piperazinocarboxamido)acetyl, 2-(4-ethyl-2,3-dioxo-1-piperazinocarboxamido)-2-(1-cyclohexen-1-yl)acetyl, 2-(4-n-octyl-2,3-dioxo-1- piperazinocarboxamido)-2-thienylacetyl, 2-(4-ethyl-2,3-dioxo-1-piperazinocarboxamido)-2-(2-amino-4-thiazolyl)acetyl, 2-(4-ethyl-2,3-dioxo-1-piperazinocarboxamido)-2-(2-chloroacetamido-4-thiazolyl)acetyl, 2-(4-ethyl-2,3-dioxo-1-piperazinocarboxamido)-2-(2-methyl-4-thiazolyl)acetyl, 2-(4-ethyl-2,3-dioxo-1-piperazinocarboxamido)-2-(2-acetamido-4-thiazolyl)acetyl, 2-(4-n-octyl-2,3-dioxo-1-piperazinocarboxamido)-2-(2-amino-4-thiazolyl)acetyl, 2-(4-ethyl-2,3-dioxo-1-piperazinocarboxamido)-2-furylacetyl, 2-(4-ethyl-2,3-dioxo-1-piperazinocarboxamido)-2-(2-pyrrolyl)acetyl, 2-(4-ethyl-2,3-dioxo-1-piperazinocarboxamido)-2-(4-hydroxyphenyl)acetyl, 2-(4-n-octyl-2,3-dioxo-1-piperazinocarboxamido)-2-(2-chloroacetamido-4-thiazolyl)acetyl, N-(4-ethyl-2,3-dioxo-1-piperazinocarbonyl)-D-methionyl, D-2-[4-(2-phenylethyl)-2,3-dioxo-1-piperazinocarboxamido]phenylacetyl, D-2-(4-ethyl-2,3-dioxo-1-piperazinocarboxamido)-2-(4-benzoyloxyphenyl)acetyl, 2,5-bis(4-ethyl-2,3-dioxo-1-piperazinocarboxamido)pentanoyl, 2-(4-ethyl-2,3-dioxo-1-piperazinocarboxamido)-3-(N-methylcarbamoyl)-propionyl, 2,3-bis(4-ethyl-2,3-dioxo-1-piperazinocarboxamido)propionyl, 2-(4-ethyl-2,3-dioxo-1-piperazinocarboxamido)-3-chloropropionyl, 2-(4-ethyl-2,3-dioxo-1-piperazinocarboxamido)-2-(4-n-octanoyloxyphenyl)acetyl, 2-(4-ethyl-2,3-dioxo-1-piperazinocarboxamido)-3-sulfamoylpropionyl, 2-(4-ethyl-2,3-dioxo-1-piperazinocarboxamido)-3-[(1-methyl-1H-tetrazol-5-yl)thio]propionyl, 2-(4-ethyl-2,3-dioxo-1-piperazinocarboxamido)acetyl, D-2-[4-(2-hydroxyethyl)-2,3-dioxo-1-piperazinocarboxamido]-2-phenylacetyl, D-2-[4-(2-chloroethyl)-2,3-dioxo-1-piperazinocarboxamido]-2-phenylacetyl, 2-(4-ethyl-2,3-dioxo-1-piperazinocarboxamido)-3-(ethoxycarbonylmethylcarbamoyl)propionyl, 2-(4-ethyl-2,3-dioxo-1-piperazinocarboxamido)-3-(thienylacetamido)propionyl, 2-(4-ethyl-2,3-dioxo-1-piperazinocarboxamido)-3-[2(1H-tetrazol-1-yl)acetamido]propionyl, 2-(4-ethyl-2,3-dioxo-1-piperazinocarboxamido)-2-(1H-tetrazol-1-yl)acetyl, 2-[(2-oxo-3-furfurylideneaminoimidazolidin-1-yl)carboxamido]-2-phenylacetyl, 2-[(2-oxo-3-furfurylideneaminoimidazolidin-1-yl)carboxamido]-2-(4-hydroxyphenyl)acetyl, 2-[(2-oxo-3-furfurylideneaminoimidazolidin-1-yl)carboxamido]-2-(4-hydroxysulfonyloxyphenyl)acetyl, 2-[[2-oxo-3-(thiophene-2-aldimino)imidazolidin-1-yl]carboxamido]-2-phenylacetyl, 2-[(2-oxo-3-furfurylideneaminoimidazolidin-1-yl)carboxamido]-2-thienylacetyl, 2-(3-methylsulfonyl-2-oxoimidazolidine-1-carboxamido)-2-phenylacetyl, 2-[(2-oxo-3-furfurylideneaminoimidazolidin-1-yl)carboxamido]-2-(2-amino-4-thiazoyl)acetyl, 2-[(2-oxo-3-furfurylideneaminoimidazolidin-1-yl)carboxamido]-2-(2-chloroacetamido-4-thiazolyl)acetyl, 2-[(3-mesyl-2-oxoimidazolidin-1-yl)-carboxamido]-2-phenylacetyl, 2-[[2-oxo-3-(thiophene-2-aldimino)imidazolidin-1-yl]carboxamido]-2-thienylacetyl, 2-[(3-mesyl-2-oxoimidazolidin-1-yl)carboxamido]-2-thienylacetyl, D-2-[(2-oxo-3-furfurylideneaminoimidazolidin-1-yl)carboxamido]propionyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, 2-(3-furfurylideneamino-2-oxoimidazolidine-1-carboxamido)-2-phenylacetyl, 2-(coumarine-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4-thiazolyl)acetyl]-D-phenylglycyl, 2-(6-bromo-1-ethyl-1,4-dihydro-4-oxothieno[2,3-b]pyridine-3-carboxamido)-2-phenylacetyl, 2-[2-(2-amino-4-thiazolyl)acetamido]-2-phenylacetyl, 2-[2-(2-chloroacetamido-4-thiazolyl)acetamido]-2-phenylacetyl, 2-(2,5-dioxo-1,2,4-triazino-6-carboxamido)-2-thienylacetyl, 2-(2,4-dioxopyrimidino-5-carboxamido)-2-thienylacetyl, 2-(6-hydroxy-1,5-naphthyridinylcarboxamido)-2-phenylacetyl, 2-[2-(4-ethyl-2,3-dioxo-1-piperazinocarboxamido)-2-thienylacetamido]-2-phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxypropylamino)-2-furylacetyl, α-(thienylmethylcarbonyl)alanyl, 2-(4-chlorobenzoylureido)-2-thienylacetyl, 2-(2-thienylacetamido)acetyl, N-benzylcarboxamido-D-alanyl, N-(4-hydroxybenzoyl)-D-alanyl, 2-(4-chlorobenzamido)propionyl, 2-(4-aminobenzamido)acetyl, N-(4-ethyl-2,3-dioxo-1-piperazinocarbonyl)methionyl-D-phenylglycyl, D-2-[2-(2,6-dichlorophenylthio)acetamido]-2-phenylacetyl, 2-(carbamoyl)amino-2-thienylacetyl, N-carbamoyl-D-phenylglycyl, 2-(3-methylcarbamoyl-3-methyl-1-ureido)-2-phenylacetyl, 2-(3-methylcarbamoyl-3-methyl-1-ureido)-2-(4-hydroxyphenyl)acetyl, 2-(3-methylcarbamoyl-3-methyl-1-ureido)-2-thienylacetyl, 2-[3-(2-hydroxybenzoyl)-1-ureido]-2-phenylacetyl, 2-[3-(2-benzyloxybenzoyl)-1-ureido]-2-(4-hydroxysulfonyloxyphenyl)acetyl, 2-[3-(2-hydroxybenzoyl)-1-ureido]-2-(4-hydroxyphenyl)acetyl, 2-[3-(2-benzyloxybenzoyl)-1-ureido]-2-phenylacetyl, 2-3-(2-benzyloxybenzoyl)-1-ureido]-2-(4-hydroxyphenyl)acetyl, D-2-[2-(benzyloxycarboxamido)-2-(benzyloxycarbonyl)ethanesulfonamido]-2-phenylacetyl, N-mesyl-D-phenylglycyl, etc.

The acyl group represented by the formula $R_{10}$—$R_{11}$—CO— (wherein $R_{10}$ and $R_{11}$ have the same meanings as defined hereinbefore) includes, for example, N-[2-(2-amino-4-thiazolyl)-2-methoxyiminoacetyl]-D-alanyl, N-[2-(2-amino-4-thiazolyl)-2-methoxyiminoacetyl]-D-phenylglycyl, 2-(2-amino-4-thiazolyl)-2-[2-(2-amino-4-thiazolyl)-2-methoxyiminoacetamido]acetyl, 2-(2-chloroacetamido-4-thiazolyl)-2-[2-(2-chloroacetamido-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-dichloroacetyloxyiminoacetyl, 2-[4-(γ-D-glutamyloxy)phenyl]-2-oxyiminoacetyl, 2-[4-(3-amino-3-carboxypropoxy)-phenyl]-2-oxyiminoacetyl, 2-thienyl-2-(3-morpholinopropoxyimino)acetyl, 2-[2-(2-amino-4-thiazolyl)-2-methoxyiminoacetamido]-2-phenylacetyl, 2-[2-(2-chloroacetamido-4-thiazolyl)-2-methoxyiminoacetamido]-2-phenylacetyl, 2-[2-(2-amino-4-thiazolyl)-2-methoxyiminoacetamido]acetyl, etc.

The acyl group represented by the formula:

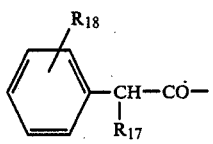

(wherein $R_{17}$ and $R_{18}$ have the same meanings as defined hereinbefore) includes, for example, α-sulfophenylacetyl, α-sulfoxyphenylacetyl, α-hydroxyphenylacetyl, α-sulfamoylphenylacetyl, α-phenoxycarbonylphenylacetyl, α-(p-tolyloxycarbonyl)phenylacetyl, α-formyloxyphenylacetyl, α-carbonylphenylacetyl, α-benzyloxycarbonylphenylacetyl, 2-(N,N-dimethylsulfamoyl)-2-phenylacetyl, etc.

The acyl group of the formula:

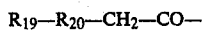

(wherein $R_{19}$ and $R_{20}$ have the same meanings as defined hereinbefore) includes, for example, cyanoacetyl, phenylacetyl, phenoxyacetyl, trifluoromethylthioacetyl, cyanomethylthioacetyl, 1H-tetrazoyl-1-acetyl, 2-thienylacetyl, 2-(2-amino-4-thiazolyl)acetyl, 2-(2-chloroacetamido-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-[2-(2-oxoimidazolidin-1-yl)carbonylaminomethylphenyl)acetyl, 2-[2-(2-oxo-3-benzylideneaminoimidazolidin-1-yl)carbonylaminomethylphenyl]acetyl, 2-(5,6-dihydro-1,4-oxathiin-2-yl)acetyl, 2-(2,5-dioxopyrrolidin-3-yl)acetyl, 2-succinimidoacetyl, 2-(1-acetyl-2,4-dioxoimidazolidin-3-yl)acetyl, etc.

The amino and/or carboxyl group in the acyl group described above may optionally carry a protective group.

Such amino-protecting groups include those groups which will be mentioned hereinafter as "amino-protecting groups." The carboxyl-protecting groups include any and all, such as ester and silyl residues, groups which are usually employed for the protection of carboxyl in the field of β-lactam chemistry and in organic chemistry in general, such as ester and silyl residues. Thus, for example, the ester and silyl residues may be methyl, ethyl, propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxide-2-methyl, methylsulfinylmethyl, bis(p-methoxyphenyl)methyl, 2-cyano-1,1-dimethylethyl, etc. This invention provides new monocyclic compounds and the selection of such protective groups is only marginal to the gist of this invention. Especially, benzyl, β,β,β-trichloroethyl, p-nitrobenzyl or p-methoxybenzyl is preferable.

The "amino-protecting group" which is used to protect the amino group in the practice of this invention may expediently be one of those groups used in the field of β-lactan chemistry or in the field of peptide synthesis. Thus, use may be made, for example, of aromatic acyl groups such as phthaloyl, p-nitrobenzoyl, p-tert-butylbenzoyl, p-tert-butylbenzenesulfonyl, benzenesulfonyl, toluenesulfonyl, etc.; aliphatic acyl groups such as formyl, acetyl, propionyl, monochloroacetyl, dichloroacetyl, trichloroacetyl, methanesulfonyl, ethanesulfonyl, trifluoroacetyl, maloyl, succinyl, etc.; esterified carboxyl groups such as methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl; methylene groups such as (hexahydro-1H-azepin-1-yl)methylene; sulfonyl groups such as 2-amino-2-carboxyethylsulfonyl, etc.; and amino-protecting groups other than acyl groups, such as trityl, 2-nitrophenylthio, benzylidene, 4-nitrobenzylidene, di- or trialkylsilyl, benzyl, p-nitrobenzyl, etc. The present invention is not particularly concerned with limitations on the selection of amino-protecting groups as it is not regarding the carboxyl-protecting groups. Especially, monochloroacetyl, benzyloxycarbonyl, p-methoxybenzyloxycarbonyl or p-nitrobenzyloxycarbonyl is preferable.

The starting compound (II) can be produced, for example by the following procedures.

(Procedure 1)

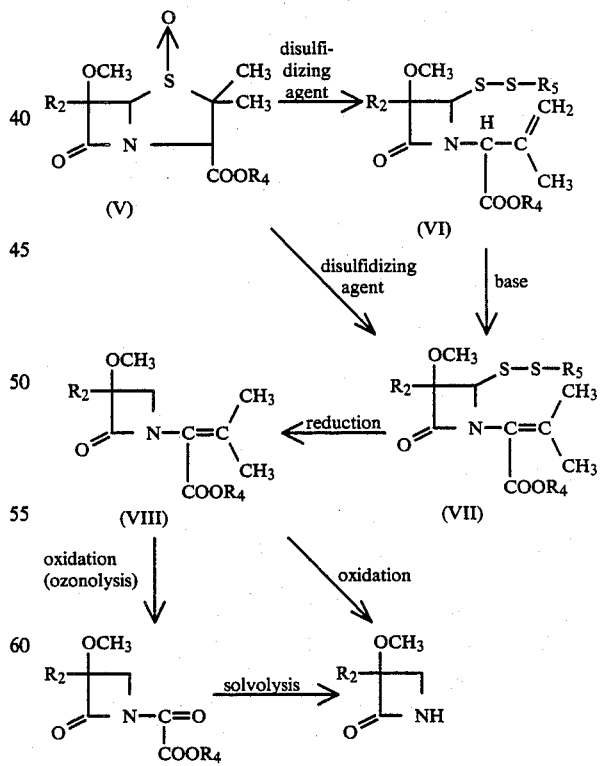

(Procedure 2)

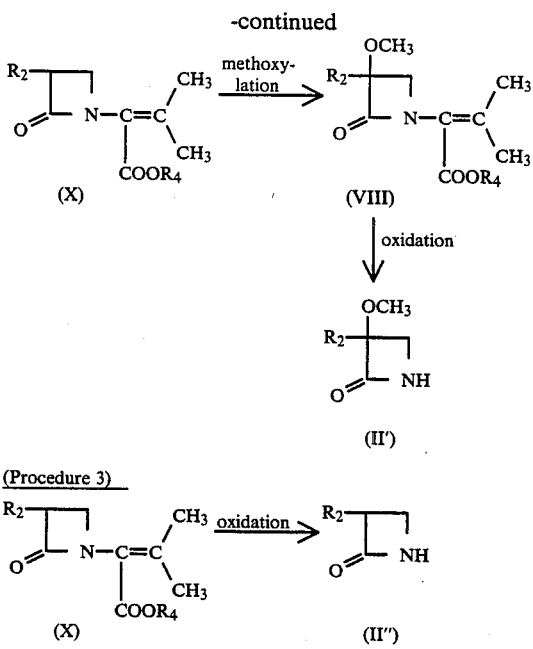

(Procedure 3)

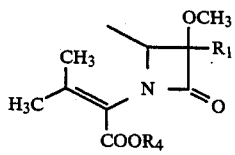

Regarding the symbols used in the above reaction formula, R₂ has the same meaning as defined hereinbefore; R₄ is an ester residue and R₅ is a thiol residue.

Exemplary species of the members defined in the above definitions are as follows.

The ester residue R₄ includes, for example, methyl, ethyl, propyl, isopropyl, n-butyl, t-butyl, pentyl, cyclopentyl, cyclohexyl, benzyl, p-nitrobenzyl, benzhydryl, alkoxyalkyl, alkanoyloxymethyl, alkenyl, trichloroethyl, methylsulfonylethyl, benzoylmethyl, methoxybenzyl, trityl, methylthiomethyl, pivaloyloxymethyl, α-acetoxybutyl, etc.

The thiol residue R₅ include, for example, alkyl groups (e.g. methyl, ethyl, propyl, isopropyl, n-butyl, t-butyl, isobutyl, n-amyl, vinyl, 1-isopropenyl, etc.), substituted alkyl groups (e.g. methoxymethyl, ethoxymethyl, benzyl, phenethyl, xylylmethyl, p-chlorobenzyl, p-nitrobenzyl, p-methoxybenzyl, etc.), unsubstituted and substituted aryl groups (e.g. phenyl, xylyl, tolyl, naphthyl, chlorophenyl, nitrophenyl, methoxyphenyl, etc.), heterocyclic groups (e.g. benzothiazolyl, benzoxazolyl, thiazolyl, thiadiazolyl, oxazolyl, thienyl, pyridyl, oxadiazolyl, oxatriazolyl, imidazolyl, benzimidazolyl, triazolyl, tetrazolyl, etc.), acyl groups (e.g. acetyl, propionyl, benzoyl, thioacetyl, thiopropionyl, thibenzoyl, etc.), carbamoyl groups (e.g. methylcarbamoyl, dimethylcarbamoyl, phenylcarbamoyl, etc.), the corresponding and other thiocarbamoyl groups, and groups of the formula:

[Structure showing CH₃/H₃C-C=C with N, OCH₃, R₁, COOR₄ substituents and =O]

The above-mentioned procedures for producing the azetidine derivatives (I) will be described in detail.

Procedure (1)

This method is related to a fundamental synthetic method for optically active azetidine derivatives (II').

The compound (V) used as a starting material can be easily prepared, for example by the method described in Journal of the American Chemical Society 95, 2401 (1973) or a method analogous thereto. In the first stage, compound (V) is reacted with a disulfidizing agent. The term "disulfidizing agent" is used herein to include all the reactants that are capable of disulfidizing the sulfur in 1-position of compound (V) and, in particular, thiol compounds of the formula R₅—SH and disulfides of the formula R₅—S—S—R₅ (R₅ has the same meaning as defined hereinbefore).

This reaction is carried out the absence of a solvent or in an appropriate solvent. The solvent includes, for example, dioxane, N,N-dimethylacetamide, N,N-dimethylformamide, benzene, toluene, tert-butanol, isopropanol, methyl ethyl ketone, etc., mixtures of such solvents, and other solvents which will not interfere with the reaction. While the reaction temperature is not particularly critical, it is normally advantageous to carry out the reaction at a temperature between 70° C. and 150° C.

When a disulfide compound of R₅—S—S—R₅ is employed as said disulfidizing agent, the reaction is catalytically accelerated by the presence of an acid or a base. This acid includes, for example, sulfuric acid, phosphoric acid, hydrochloric acid and other mineral acids, p-toluenesulfonic acid, methanesulfonic acid, phenylphosphonic acid, acetic acid, formic acid and other organic acids, and Lewis acids such as ferric chloride, zinc chloride, boron trifluoride, etc. When such an acid is employed, there is predominantly obtained a 1-(α-isopropenyl)-azetidine (VI) which contains a double bond in exo-position. The base mentioned above includes, for example, pyridine, quinoline, N,N-dimethyl-aniline, triethylamine, etc. In this case, depending on the reaction solvent, time, temperature, etc., there is obtained a 1-(α-isopropylidene)-azetidine (VII) having a double bond in endo-position in addition to the 1-(α-isopropenyl)-azetidine (VI). This 1-(α-isopropylidene)-azetidine (VII) can also be easily obtained by treating 1-(α-isopropenyl)-azetidine (VI) with a base. The reaction according to this procedure is preferably carried out in streams of an inert gas such as nitrogen, helium or the like. The useful molar ratio of disulfidizing agent to starting compound (V) depends on the S-nucleophilicity of the disulfidizing agent used but, generally speaking, about 1 to about 10 equivalents of said agent are employed. After completion of the reaction, the product compound (VI) can be isolated in optional purity by the purification procedures known per se, e.g. extraction with solvents, recrystallization, chromatography, etc.

The compound (VI), on treatment with a base, yields the compound (VII). The base used for this purpose may be the above-mentioned base which can be used as a catalyst in the reaction between compound (VI) and disulfidizing agent. In carrying out this reaction, the base need not be employed in a large amount. Thus, relative to compound (VI), about 0.01 to about 0.2 mol equivalent is sufficient. The reaction is generally carried out in a solvent such as dichloromethane, chloroform, benzene, toluene, tert-butanol, methanol, ethanol, tetrahydrofuran, dioxane, methyl ethyl ketone, N,N-dimethylacetamide, N,N-dimethylformamide, etc. or a mixture of such solvents. Any other solvent that will not interfere with the reaction may also be employed. While the reaction temperature is not particularly critical, the reaction proceeds at room temperature in many instances. The product derivative (VII) in which R₅ is a group of the formula:

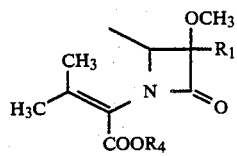

is a compound which is obtained simultaneously or partially in this reaction step and can be converted to compound (VIII) by treatment with a reducing agent.

Then, compound (VII) is subjected to a reductive desulfurization reaction. The reductive desulfurizing agent used for this purpose may, for example, be Raney nickel, Raney cobalt or the like. This reaction is usually carried out in a solvent. The solvent includes, for example, methanol, ethanol, propanol, tetrahydrofuran, dioxane, ethyl acetate, water, etc., although other common organic solvents which do not interfere with the reaction may also be employed. This reaction proceeds readily under mild conditions, e.g. at room temperature to about 80° C.

The compound (VIII) is then oxidized in order to remove the N-side chain. This oxidation reaction includes an oxidization reaction with an oxidizing agent and a subsequent solvolysis with a solvent or a basic or acidic catalyst.

The oxidizing agent used in the above oxidation reaction includes, for example, ozone, alkali metal permanganate (e.g. potassium permanganate, sodium permanganate, etc.), alkaline earth metal permanganate (e.g. barium permanganate, etc.), osmium tetraoxide, lead tetraacetate, etc. This oxidation reaction is usually carried out in a solvent. This solvent includes, for example, tetrahydrofuran, dioxane, N,N-dimethylformamide, N,N-dimethylacetamide, benzene, acetone, pyridine, methanol, ethanol, propanol, butanol, water, chloroform, dichloromethane, carbon tetrahcloride, etc. It may be a mixture of such solvents. The proportion of the oxidizing agent relative to compound (VIII) may be about 1.0 to 4.0 molar equivalents, preferably about 1.0 to 1.2 molar equivalents, although excess ozone if it is used may be employed. While the reaction temperature is not particularly critical, the reaction usually proceeds under cooling or at room temperature. The reaction normally goes to completion within a short time. When a permanganate, for instance, is employed as the oxidizing agent, it is preferable to employ in a buffer solution such as phosphate buffer and carry out the reaction in the neutral pH region so as to minimize the decomposition of starting compound (VI) or/and product compound (I). When ozone is used as said oxidizing agent, the conversion of compound (VIII) to compound (IX) can be effected by ozonolysis e.g. by carrying out the reaction in a solvent such as chloroform, dichloromethane or carbon tetrachloride, followed by removing the excess ozone and decomposing the ozonide of compound (VIII) with dimethyl sulfide.

The conversion of compound (IX) to compound (II') is effected by subjecting compound (IX) to solvolysis. This reaction is carried out in a suitable solvent and may be optionally conducted with the aid of a basic or acidic catalyst. The base used in such a procedure includes, for instance, inorganic bases such as the hydroxides, carbonates, etc, of alkali metals such as lithium, potassium, sodium, etc. or alkaline earth metals such as calcium, magnesium, etc.; organic bases such as metal alkoxides, organic amines, quaternary ammonium salts, etc.; basic ion exchange resins and so forth. The acid used in a similar manner includes inorganic acids and their salts such as hydrochloric acid, sulfuric acid, phosphoric acid, zinc chloride, zinc sulfate, ferric chloride, ferric sulfate, etc., organic acids such as formic acid, acetic acid, p-toluenesulfonic acid, trifluoroacetic acid, etc., silica gel, acidic ion exchange resins and so forth. The solvent used for this reaction includes, for example, water, methanol, ethanol, propanol, tetrahydrofuran, dioxane, ethyl acetate, etc. as well as mixtures thereof. Any other solvent that will not interfere with the reaction may also be employed likewise. This reaction usually proceeds easily under mild conditions, e.g. under cooling to a slightly elevated temperature.

The reaction product in each step can be separated in optional purity by purification procedure known per se, e.g. extraction with solvents, recrystallization, chromatography, etc.

Procedure (2)

This procedure relates to a fundamental route of snythesis for the production of optically inactive azetidine derivative (II').

The starting compound (X) can be easily prepared by the method described in Molecular Modification in Drug Design 45, 15 (1964) or a method analogous thereto.

The methoxylation reaction of compound (X) to compound (VIII) is carried out by reacting an alkali metal salt of methanol, which is of the formula MOCH₃ (wherein M is an alkali metal), and a halogenating agent with the compound (X) in the presence of methanol. As examples of the alkali metal salt of methanol may be mentioned lithium methoxide, sodium methoxide, potassium methoxide, etc. The halogenating agent is a halogen compound capable of acting as a positive-halogen donor, e.g. halogen (chlorine, bromine, etc.), N-haloimides (N-chlorosuccinimide, N-bromosuccinimide, etc.), haloamides (N-chloroacetamide, N-bromoacetamide, etc.), N-halosulfonamides (N-chlorobenzenesulfonamide, N-chloro-p-toluenesulfonamide, etc.), 1-halobenzotriazoles, organic hypochlorite, etc.). This reaction is carried out in a solvent. Examples of the solvent include tetrahydrofuran, dioxane, dichloromethane, chloroform, acetonitrile, methanol, N,N-dimethylformamide, N,N-dimethylacetamide, etc. as well as various mixtures thereof. Any other solvent that will not interfere with the contemplated reaction may likewise be employed. To carry out the reaction, the starting compound (X) is dissolved or suspended in the above-mentioned solvent and, then, the alkali metal salt of methanol, methanol and halogenating agent are added. The desirable proportions of these agents, relative to each mol of starting compound (X), are not less than 1 mol of methanol, about 1 to 3.5 mols of the alkali metal salt of methanol and about 1 to 2 mols of halogenating agent. The reaction proceeds readily under cooling or at room temperature to about 30° C. The reaction can be quenched by making the reaction system acidic. The suitable acid to quench the reaction may for example be formic acid, acetic acid or trichloroacetic acid. After the reaction has thus been quenched, any excess halogenating agent can be removed by treatment with a reducing agent such as sodium thiosulfate or a trialkyl phosphite, for instance.

After completion of the above reaction, the product compound (VIII) can be isolated in an optional purity by conventional separation-purification procedures, for example by extraction with a solvent, recrystallization, chromatography, etc.

The compound (VIII) is then subjected to procedure similar to the oxidation procedures described hereinbefore in connection with the conversion of compound (VIII) to compound (II'), whereby an optically inactive form of compound (II') is obtained.

Procedure (3)

In this procedure, the compound (X) obtained for example by the method described in Molecular Modification in Drug Design 45, 15 (1964) or a method analogous thereto is oxidized to compound (II').

This oxidation reaction can be effected by procedures similar to those used in the conversion of compound (VIII) to compound (II') according to the above procedure (1).

The sulfonation reaction according to this aspect is a reaction by which a sulfo group is introduced into the substrate compound. Thus, for example, it can be carried out by reacting the compound (II) with sulfur trioxide or a reactive derivative of sulfur trioxide.

The above-mentioned reactive derivative of sulfur trioxide includes, for example, sulfur trioxide-pyridine, sulfur trioxide-dioxane, sulfur trioxide-trimethylamine, sulfur trioxide-chlorosulfonic acid and other addition compounds of sulfur trioxide.

To conduct this reaction, about 1 to 5 mols, preferably about 1 to 2 mols, of sulfur trioxide or said reactive sulfur trioxide derivative is added to one mol of compound (II). The reaction temperature is about 0° to 80° C. and preferably about 10° to 40° C. The above reaction may be carried out in a solvent. The solvent includes, for example, water, ethers (e.g. dioxane, tetrahydrofuran, diethyl ether, etc.) esters (e.g. ethyl acetate, ethyl formate, etc.), halogenated hydrocarbons (e.g. chloroform, dichloromethane, etc.), hydrocarbons (e.g. benzene, toluene, n-hexane, etc.), amides (e.g. dimethylformamide, dimethylacetamide, etc.) and other common organic solvents. These solvents may be used alone or in combination. After completion of the reaction, the compound (I) can be isolated in an optional purity by the conventional separation-purification procedures, for example by extraction with a solvent, recrystallization, chromatography, etc.

The compound (I) wherein $R_1$ is amino, i.e. compound (IV), is useful as an intermediate for the production of a useful medicine. The compound (I) wherein $R_1$ is acylated amino, i.e. compound (III), can be produced by acylating the compound (IV).

The compound (III) is representable by the formula:

(III)

wherein $R_3$ an acylated amino group and X is hydrogen or methoxy.

The acylation is accomplished by reacting the compound (IV) with an acylating agent containing the acyl group corresponding to the one contained in the acylated amino group which is represented by $R_1$, $R_2$ or $R_3$.

The acylating agent used in this reaction may, for example, be an organic carboxylic acid containing such an acyl group or a reactive derivative of such acid. The reactive derivative of organic acid includes, for example, the acid anhydride, activated amide, activated ester or the like. More specifically, the following reactive derivatives of organic acids may be mentioned.

(1) Acid anhydrides

The acid anhydrides include, for example, mixed acid anhydrides with hydrogen halides (e.g. hydrochloric acid, hydrobomic acid, etc.) monoalkyl carbonic acid mixed acid anhydrides, aliphatic carboxylic acid mixed acid anhydrides (mixed acid anhydrides with e.g. acetic acid, pivalic acid, valeric acid, isopentanoic acid, trichloroacetic acid, etc.), aromatic carboxylic acid mixed acid anhydrides (mixed acid anhydrides with e.g. benzoic acid, etc.), symmetric acid anhydrides, etc.

(2) Activated amides

The activated amides include, for example, the amides with pyrazole, imidazole, 4-substituted-imidazole, dimethylpyrazole, benzotriazole, etc.

(3) Activated esters

The activated esters include, for example, methyl ester, ethyl ester, methoxymethyl ester, propargyl ester, 4-nitrophenyl ester, 2,4-dinitrophenyl ester, trichlorophenyl ester, pentachlorophenyl ester, mesylphenyl ester, esters of said carboxylic or other acids with 1-hydroxy-1H-2-pyridone, N-hydroxysuccinimide, N-hydroxyphthalimide, etc.

The said reactive derivative of organic acid is selected according to the type of acid chosen and when a free acid is used as the acylating agent, the reaction is desirably carried out in the presence of a condensing agent. The condensing agent includes, for example, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.

This acylation reaction is generally carried out in a solvent. The solvent includes, for example, water, acetone, dioxane, acetonitrile, dichloromethane, chloroform, dichloroethane, tetrahydrofuran, ethyl acetate, dimethylformamide, pyridine, etc. as well as the common organic solvents which do not interfere with the reaction. These solvents, if they are hydrophilic, may be used in a mixture with water.

Further, the acylatin reaction can be conducted in the presence of a base, for example alkali metal carbonates, trialkylamines (e.g. trimethylamine, triethylamine, tributylamine, N-methylmorpholine, N-methylpiperidine, etc.), N.N-dialkylaniline, N,N-dialkylbenzylamine, pyridine, picoline, lutidine, 1,5-diazabicyclo[4,3,0]non-5-ene, 1,4-diazabicyclo[2,2,2]octane, 1,8-diazabicyclo[5,4,4]undecene-7, etc. The base, as well as said condensing agent, may be used as the solvent as well, only if it is liquid. The reaction temperature is not particularly critical and, in many cases, the reaction is carried out under cooling to room temperature.

Referring to the acylation reaction, when the reactive derivative of starting compound (IV) with respect to its amino group or a salt thereof and the acylating agent respectively contain an asymmetric carbon atom, the corresponding stereoisomers can be employed respectively or as a mixture. Moreover, when the reaction yields such isomers in admixture, they may be fractionally isolated by procedures known per se, for example by column chromatography, recrystallization, etc.

The compounds (I) which has a protective group is useful as an intermediate for the production of a useful medicine. For example, the compound (I) which has not a protective group can be obtained by the removal of the protective group.

The removal of the protective group from the azetidine derivative (I) can be effected by a choice of the hitherto known procedures, the choice depending on the type of protective group. Thus, for example, the method may comprise the use of an acid, a base or hydrazine, or may be a reductive method or a method comprising permitting an iminohalogenating agent to act on the substrate compound and, then, an imminoetherifying agent to act thereon and, finally and if necessary, hydrolyzing the same. In the method employing an acid, while the choice depends on the type of protective group and other conditions, the acid may for example be an inorganic acid (e.g. hydrochloric acid, sulfuric acid, phosphoric acid, etc.), an organic acid (e.g. formic acid, acetic acid, trifluoroacetic acid, propionic acid, benzenesulfonic acid, p-toluenesulfonic acid, etc.) or an acidic ion exchange resin. In the method involving the use of a base, while the choice depends on the type of protective group and other conditions, the base may for example be an inorganic base such as the hydroxide or carbonate of an alkali metal (e.g. sodium, potassium, etc.) or alkaline earth metal (e.g. calcium, magnesium, etc.), an alkali metal alkoxide, an organic base (e.g. organic amines, quaternary ammonium salts, etc.) or a basic ion exchange resin.

When, in the above methods involving the use of a base or an acid, a solvent is employed, it is generally desirable, in many cases, to use a hydrophilic organic solvent, water or a mixture thereof.

The reductive method, while the choice depends on the type of protective group and other conditions, may be a method employing a metal (e.g. tin, zinc, etc.) or a metal compound (e.g. chromous dichloride, chromous acetate, etc.) and an organic, inorganic or other acid (e.g. acetic acid, propionic acid, hydrochloric acid, etc.), or a method involving the presence of a metal catalyst for catalytic reduction. As examples of the catalyst used for such catalytic reduction, there may be mentioned platinum catalysts such as platinum wire, platinum sponge, platinum black, platinum oxide, colloidal platinum, etc., palladium catalysts such as palladium sponge, palladium black, palladium oxide, palladium-barium sulfate, palladium-barium carbonate, palladium-carbon, palladium-silica gel, colloidal palladium, etc., and nickel catalysts such as reduced nickel, nickel oxide, Raney nickel, Urushibara nickel, etc.

In the reductive method employing a metal and an acid, the combination of a metal compound, e.g. a compound of iron, chromium or the like, with an inorganic acid, e.g. hydrochloric acid, or an organic acid, e.g. formic acid, acetic acid, propionic acid or the like, is employed. The reductive procedure is normally carried out in a solvent. In the case of catalytic reduction, alcohols such as methanol, ethanol, propanol, isopropyl alcohol, etc. and ethyl acetate, etc. are commonly employed. In the procedure involving the use of a metal and an acid, the solvent is usually water, acetone or the like, but when the acid is liquid, it may be utilized as the solvent as well.

The reaction is usually carried out under cooling to under warming, preferably at a temperature range of about 0° C. to about 30° C.

Referring to the procedure comprising the use of an iminohalogenating agent and, then, an iminoetherifying agent, followed by hydrolysis to remove the protective group, the iminohalogenating agent may for example be phosphorus trichloride, phosphorus pentachloride, phosphorus tribromide, phosphorus pentabromide, phosphorus oxychloride, thionyl chloride or phosgene. The reaction temperature is not critical and, in many cases, the reaction is carried out under room temperature to under cooling. The iminoetherifying agent which is then permitted to act on the resultant reaction product may for example be an alcohol or a metal alkoxide. Thus, the alcohol includes, for example, alkanols such as methanol, ethanol, propanol, isopropyl alcohol, n-butanol, tert-butanol, etc.; and compounds such that the alkyl moieties of such alkanols as mentioned above have been substituted by alkoxy groups such as methoxy, ethoxy, propoxy, isopropoxy, butoxy, etc. The metal alkoxide includes, for example, alkali metal alkoxides (sodium alkoxides, potassium alkoxides, etc.) and alkaline earth metal alkoxides (calcium alkoxides, barium alkoxides, etc.), as may be derived from the above-mentioned and other alcohols.

When, for example, the protective group is an organic carboxylic acid residue and the carbon atom adjacent to its carbonyl group carries a certain substituent such as a free amino, hydroxyl, mercapto, carboxyl or sulfo group, it is advantageous first to carry out a treatment for enhancing the adjacent group effect of such group so as to increase the reactivity of the carbonyl group before carrying out the removal of the protective group. In this connection, the case in which the substituent group on the carbon atom adjacent to said carbonyl group is a free amino group will be described by way of illustration. Thus, the free amino group may be converted to a thioureido group and, then, the necessary deacylation reaction is carried out. This and other procedures known in the art of cleavage of peptide bonds can be utilized to remove the protective group.

The temperature for this reaction is not especially critical but may be suitably selected according to the type of protective group and the method then applied for removing the protective group. It is preferable, after all, that the reaction be carried out under cooling to a slightly elevated temperature.

There are cases in which the derivative in the carboxyl function of the compound wherein $R_1$ is a group containing such a carboxyl group is transformed into a carboxyl group in the course of this reaction and such cases are also subsumed in the concept and ambit of this invention.

The compound (I) thus obtained by removal of the protective group can be converted, if desired, to a desired salt thereof in a conventional manner.

The compound (I), which contains a sulfo group, is generally capable of forming a salt with a base. Therefore, the compound (I) may then be isolated as a salt which, in turn, may be converted to the free form or to a different salt. The free compound (I) may of course be converted to a salt. The base mentioned above may be an inorganic base, e.g. lithium, potassium, sodium, calcium, ammonium, etc. or an organic base, e.g. pyridine, collidine, triethylamine, triethanolamine, etc.

The salt form of compound (I) is also included in the scope of this disclosure.

To convert the salt form of compound (I) to the free compound (I), a method using an acid, for example, can be employed. The type of acid varies with different protective groups and other conditions. However, such inorganic acids as hydrochloric acid, sulfuric acid, phosphoric acid, etc. and such organic acids as formic acid, acetic acid, p-toluenesulfonic acid, etc. are generally employed. Aside from the types of acids mentioned above, acidic ion exchange resins are also useful. The solvent may for example be acetone, tetrahydrofuran, methanol, ethanol, dioxane or the like, water, or a mixture of water and such a solvent.

The compound (IV), as the starting compound for said acylation reaction, may be used in the form of a salt. The salt may be any of the salts mentioned in connection with salts of compound (I).

The acylation reaction, where the starting material is a salt as mentioned above, may give rise to a salt of compound (III). In such cases, the salt of compound (III) can be converted to a different salt and isolated as such, just as mentioned for compound (I).

Such salts may be converted to free compound (III) and isolated as such. This conversion of a salt to the free compound (III) can be effected in the same manner as described hereinbefore in connection with compound (I).

The compound (I) may exist as diastereoisomers or optical-isomers. In such cases, the respective isomers and their mixtures are also included in the scope of the disclosure. These isomers, respectively or as mixtures, can be used as medicines.

When such mixtures of isomers are recovered as products, each mixture may be resolved into the component isomers by the conventional optical resolution method or the other purification methods, e.g. extraction with solvent, recrystallization, chromatography, etc.

The compounds (I) thus obtained are useful as drugs, being active against certain gram-positive and gram-negative bacteria. By way of example, the compounds are active against the following microorganisms.

The following is media and compounds employed in the antibacterial test.

Media

TSA=Trypticase soy agar [Baltimore Biologicals (U.S.A.)]
B-TSA=Blood trypticase soy agar

Compounds

Compound A=Sodium 3-[2-(2-amino-4-thiazolyl)-2-methoxyiminoacetamido]-2-oxoazetidine-1-sulfonate
Compound B=Sodium 3- [D(−)-N-(4-ethyl-2,3-dioxo-1-piperazinocarbonyl)-phenylglycinamido]-2-oxoazetidine-1-sulfonate
Compound C=Sodium 3-[D(−)-N-(4-ethyl-2,3-dioxo-1-piperazinocarbonyl)phenylglycinamido]-3-methoxy-2-oxoazetidine-1-sulfonate
Compound D=Sodium 3-[2-(4-ethyl-2,3-dioxo-1-piperazinocarboxamido)-2-(2-amino-4-thiazolyl)-acetamido]-2-oxoazetidine-1-sulfonate
Compound E=Sodium 3-[DL-2-(4-ethyl-2,3-dioxo-1-piperazinocarboxamido)-2-thienylacetamido]-2-oxoazetidine-1-sulfonate
Compound F=Sodium 3-[D-2-(4-ethyl-2,3-dioxo-1-piperazinocarboxamido)-2-thienylacetamido]-2-oxoazetidine-1-sulfonate
Compound G=Sodium 3-[D-2-(4-n-octyl-2,3-dioxo-1-piperazinocarboxamido)-2-phenylacetamido]-2-oxoazetidine-1-sulfonate
Compound H=Sodium 3-[2-(4-n-octyl-2,3-dioxo-1-piperazinocarboxamido)-2-(2-amino-4-thiazolyl)-acetamido]2-oxoazetidine-1-sulfonate
Compound I=Sodium 3-[D-2-[(2-oxo-3-furylideneaminoimidazolidin-1-yl)-carboxamido]-2-phenylacetamido]-2-oxoazetidine-1-sulfonate
Compound J=Sodium 3-[2-(4-n-octyl-2,3-dioxo-1-piperazinocarboxamido)-2-thienylacetamido]-2-oxoazetidine-1-sulfonate
Compound K=Sodium 3-[D-2-[[2-oxo-3-(thiophen-2-aldoimino)-imidazolidin-1-yl]-carboxamido]-2-phenylacetamido]-2-oxoazetidine-1-sulfonate
Compound L=Sodium 3-[2-[(2-oxo-3-furylideneaminoimidazolidin-1-yl)-carboxamido]-2-thienylacetamido]-2-oxoazetidine-1-sulfonate

TABLE 1

| Test organism | Medium | Minimum inhibitory concentration (μg/ml) | |
| --- | --- | --- | --- |
| | | Compound A | Compound B |
| Staphylococcus aureus FDA209P | TSA | 50 | 6.25 |
| Staphylococcus aureus 308A-1 | TSA | 25 | 3.13 |
| Staphylococcus aureus 1840 | TSA | 100 | 25 |
| Staphylococcus aureus FDA209P | B-TSA | 50 | 6.25 |
| Escherichia coli NIHJ JC-2 | TSA | 0.78 | 1.56 |
| Escherichia coli 0-111 | TSA | 0.39 | 0.2 |
| Escherichia coli T-7 | TSA | >100 | >100 |
| Citrobacter freundii IFO 12681 | TSA | 1.56 | 6.25 |
| Klebsiella pneumoniae DT | TSA | 0.78 | 0.2 |
| Enterobacter cloacae IFO 12937 | TSA | >100 | 50 |
| Serratia marcescens IFO 12648 | TSA | 12.5 | 3.13 |
| Proteus vulgaris IFO 3988 | TSA | 1.56 | 0.1 |
| Proteus mirabilis IFO 3849 | TSA | 6.25 | 0.78 |
| Proteus morganii IFO 3168 | TSA | 25 | 25 |
| Pseudomonas aeruginosa IFO 3455 | TSA | 6.25 | 1.56 |
| Pseudomonas aeruginosa U 31 | TSA | >100 | >100 |
| Acinetobacter calcoaceticus IFO 13006 | TSA | 6.25 | 25 |
| Candida albicans TA | TSA | >100 | >100 |
| Streptococcus pyogenes E-14 | B-TSA | 3.13 | 3.13 |
| Streptococcus pyogenes S-8 | B-TSA | 3.13 | 6.25 |
| Streptococcus mitis America | B-TSA | 25 | 25 |
| Streptococcus faecium IFO 3128 | B-TSA | >100 | >100 |
| Streptococcus pneumoniae Type I | B-TSA | 12.5 | 6.25 |
| Corynebacterium diphtheriae Toront | B-TSA | 1.56 | 3.13 |
| Bordetella bronchiseptica Sagami | B-TSA | 100 | >100 |

TABLE 2

| Test organism | Medium | Minimum inhibitory concentration (μg/ml) of Compound C |
| --- | --- | --- |
| Staphylococcus FDA209P | TSA | 100 |
| Escherichia coli NIHJ JC-2 | TSA | 50 |
| Escherichia coli 0-111 | TSA | 12.5 |
| Klebsiella pneumoniae DT | TSA | 12.5 |
| Enterobacter cloacae IFO 12937 | TSA | >100 |
| Serratia marcescens IFO 12648 | TSA | 50 |
| Proteus vulgaris IFO 3988 | TSA | 12.5 |
| Proteus mirabilis IFO 3849 | TSA | 50 |
| Pseudomonas morganii IFO 3168 | TSA | >100 |
| Pseudomonas aeruginosa U 31 | TSA | >100 |
| Candida albicans TA | TSA | >100 |
| Streptococcus pyogenes E-14 | B-TSA | 50 |
| Streptococcus pyogenes S-8 | B-TSA | 50 |
| Corynebacterium diphtheriae Toronto | B-TSA | 50 |

TABLE 3

Minimum inhibitory concentration (MIC) (μg/ml)

| Test organism | Medium | Compound D | Compound E | Compound F | Compound G | Compound H |
|---|---|---|---|---|---|---|
| Staphylococcus aureus FDA 209P | TSA | 12.5 | 6.25 | 6.25 | 1.56 | 6.25 |
| Staphylococcus aureus 308A-1 | TSA | 6.25 | 6.25 | 6.25 | 0.78 | 3.13 |
| Staphylococcus aureus 1840 | TSA | 25 | 25 | 25 | 25 | 12.5 |
| Escherichia coli NIHJ JC-2 | TSA | 0.39 | 1.56 | 0.78 | 3.13 | 12.5 |
| Escherichia coli 0-111 | TSA | 0.1 | 0.2 | 0.2 | 0.78 | 3.13 |
| Escherichia coli T-7 | TSA | >100 | >100 | >100 | >100 | >100 |
| Citrobacter freundii IFO 12681 | TSA | 1.56 | 3.13 | 1.56 | 3.13 | 12.5 |
| Klebsiella pneumoniae DT | TSA | 0.2 | 0.78 | 0.2 | 0.78 | 12.5 |
| Enterobacter cloacae IFO 12937 | TSA | 25 | 3.13 | 50 | 6.25 | 50 |
| Serratia marcescens IFO 12648 | TSA | 0.78 | 3.13 | 1.56 | 1.56 | 12.5 |
| Proteus vulgaris IFO 3988 | TSA | 0.1 | <0.1 | <0.1 | 0.78 | 6.25 |
| Proteus mirabilis IFO 3849 | TSA | 25 | 0.78 | 0.78 | 3.13 | 25 |
| Proteus morganii IFO 3168 | TSA | 12.5 | 12.5 | 12.5 | 1.56 | 6.25 |
| Pseudomonas aeruginosa IFO 3455 | TSA | 3.13 | 3.13 | 6.25 | 1.56 | 12.5 |
| Pseudomonas aeruginosa U 31 | TSA | >100 | >100 | >100 | 25 | 50 |
| Acinetobacter calcoaceticus IFO 13006 | TSA | 50 | 50 | 25 | 3.13 | 50 |
| Candida albicans TA | TSA | >100 | >100 | >100 | >100 | >100 |
| Staphylococcus aureus FDA 209P | B-TSA | 12.5 | 6.25 | 6.25 | 3.13 | 12.5 |
| Streptococcus pyogenes E-14 | B-TSA | 3.13 | 1.56 | 3.13 | 1.56 | 3.13 |
| Streptococcus pyogenes S-8 | B-TSA | 3.13 | 3.13 | 3.13 | 1.56 | 1.56 |
| Streptococcus mitis America | B-TSA | 25 | 25 | 25 | 25 | 25 |
| Streptococcus faecium IFO3128 | B-TSA | >100 | >100 | >100 | >100 | >100 |
| Streptococcus pneumoniae Type I | B-TSA | 6.25 | 3.13 | 6.25 | 3.13 | 3.13 |
| Corynebacterium diphtheriae Tronto | B-TSA | 3.13 | 0.39 | 0.78 | 25 | 0.78 |
| Bordetella bronchiseptica Sagami | B-TSA | >100 | >100 | >100 | >100 | >100 |

TABLE 4

Minimum inhibitory concentration (MIC) (μg/ml)

| Test organism | Medium | Compound I | Compound J | Compound K | Compound L |
|---|---|---|---|---|---|
| Staphylococcus aureus FDA 209P | TSA | 6.25 | 1.56 | 6.25 | 6.25 |
| Staphylococcus aureous 308 A-1 | TSA | 3.13 | 1.56 | 3.13 | 3.13 |
| Staphylococcus aureus 1840 | TSA | 50 | 6.25 | 50 | 25 |
| Escherichia coli NIHJ JC-2 | TSA | 1.56 | 3.13 | 1.56 | 1.56 |
| Escherichia coli 0-111 | TSA | 3.13 | 1.56 | 0.39 | <0.1 |

TABLE 4-continued

| | | Minimum inhibitory concentration (MIC) (μg/ml) | | | |
|---|---|---|---|---|---|
| | | Compound | | | |
| Test organism | Medium | Compound I | Compound J | Compound K | Compound L |
| *Escherichia coli* T-7 | TSA | >100 | >100 | >100 | >100 |
| *Citrobacter freundii* IFO 12681 | TSA | 6.25 | 3.13 | 1.56 | 1.56 |
| *Klebsiella pneumoniae* DT | TSA | 0.2 | 1.56 | 0.39 | <0.1 |
| *Enterobacter cloacae* IFO 12937 | TSA | 25 | 6.25 | 12.5 | 25 |
| *Serratia marcescens* IFO 12648 | TSA | 1.56 | 1.56 | 1.56 | 1.56 |
| *Proteus vulgaris* IFO 3988 | TSA | 0.2 | 1.56 | 0.39 | 0.2 |
| *Proteus mirabilis* IFO 3849 | TSA | 1.56 | 3.13 | 1.56 | 0.78 |
| *Proteus morganii* IFO 3168 | TSA | 12.5 | 1.56 | 12.5 | 12.5 |
| *Pseudomonas aeruginosa* IFO 3455 | TSA | 3.13 | 6.25 | 3.13 | 3.13 |
| *Pseudomonas aeruginosa* U 31 | TSA | >100 | 25 | >100 | >100 |
| *Acinetobacter calcoaceticus* IFO 13006 | TSA | 25 | 6.25 | 50 | 50 |
| *Candida albicans* TA | TSA | >100 | >100 | >100 | >100 |
| *Staphylococcus aureus* FDA 209P | B-TSA | 6.25 | 3.13 | 6.25 | 6.25 |
| *Streptococcus pyogenes* E-14 | B-TSA | 0.39 | 1.56 | 0.78 | 0.78 |
| *Streptococcus pyogenes* S-8 | B-TSA | 0.78 | 1.56 | 1.56 | 0.78 |
| *Streptococcus mitis* America | B-TSA | 3.13 | 25 | 1.56 | 6.25 |
| *Streptococcus faecium* IFO 3128 | B-TSA | >100 | >100 | >100 | >100 |
| *Streptococcus pneumoniae* Type I | B-TSA | 1.56 | 1.56 | 1.56 | 1.56 |
| *Corynebacterium diphtheriae* Tronto | B-TSA | 0.78 | 0.78 | 3.13 | 1.56 |
| *Bordetella bronchiseptica* Sagami | B-TSA | >100 | >100 | >100 | >100 |

The acute toxicity ($LD_{50}$) of compounds (I) in mice, by intravenous administration, is generally not less than 500 mg/kg.

The compounds (I) are of value in the treatment of mammalian animals (e.g. mouse, rat, human being, etc.) infected by the above-mentioned and other microorganisms.

As a bacterial infection remedy, the compounds (I) can be applied, for example, to the treatment of respiratory organ infections, urinary tract infections, suppurative diseases, bile duct infections, intestinal infections, gynecologic and obstetric infections, surgical infections, etc. in the abovementioned mammals. The daily dose is about 20 to about 200 mg/kg body weight as compounds (I) and is preferably administered in 2 to 4 portions daily, i.e. about 5 to about 100 mg/kg body weight per dose. The compounds (I), or a physiologically acceptable salt thereof, can be orally administered in such dosage forms as tablets, capsules, drops, etc. which can be prepared by the established pharmaceutical procedures. The compound and salt each can also be worked up into injectable preparations by the routine pharmaceutical procedure, for instance, and after mixing with a sterile vehicle which is obtainable by the conventional procedure, be administered parenterally.

This aspect of the disclosure is further described by way of the following reference and working examples.

REFERENCE EXAMPLE 1

A mixture of 4.1 g of methyl 6β-benzyloxycarboxamido-6α-methoxypenicillanate-1-oxide and 10 ml of n-amylmercaptan is stirred at 110° 1 C. for 24 hours. The excess n-amylmercaptan is distilled off and the residue is chromatographed on a column of silica gel [eluted with n-hexane-ethyl acetate (2:1)] to give 2.5 g of methyl 4β-n-amyldithio-3β-benzyloxycarboxamido-3α-methoxy-2-oxoazetidine-1-(α-isopropenyl)acetate.

$IR\nu_{max}^{KBr}cm^{-1}$; 3300, 1767, 1736.

NMR(CDCl$_3$, ppm); 0.93(t, —CH$_3$), 1.2–1.7(m, —CH$_2$—), 1.92(s, —CH$_3$), 2.76(t, —S—CH$_2$—), 3.60(s, —CH$_3$), 3.83(s, —CH$_3$), $$4.92(s, -\overset{|}{C}H-), \ 5.07(s, -\overset{|}{C}H-),$$

5.20(m, —CH$_2$), 5.23(s, —CH$_2$—), 5.66(s, —NH—), 7.42(s, aromatic H).

REFERENCE EXAMPLE 2

To a solution of 2.3 g of methyl 4β-n-amyldithio-3β-benzyloxycarboxamido-3α-methoxy-2-oxoazetidine-1-(α-isopropenyl)-acetate in 60 ml of methylene chloride is added 0.15 g of triethylamine and the mixture is stirred at room temperature for 1.5 hours. The solvent is distilled off and the residue is chromatographed on a column of silica gel [eluted with n-hexane-ethyl acetate (4:1)] to give 2.2 g of methyl 4β-n-amyldithio-3β-benzyloxycarboxamido-3α-methoxy-2-oxoazetidine-1-(α-isopropylidene)acetate.

$IR\nu_{max}^{KBr}cm^{-1}$; 3300, 1768, 1735.

NMR(CDCl$_3$, ppm); 0.92(t, —CH$_3$), 1.15–1.98(m, —CH$_2$—), 2.08(s, —CH$_3$), 2.32(s, —CH$_3$), 2.65(t, —S—CH$_2$—), 3.64(s, —CH$_3$), 3.83(s, —CH$_3$—), 5.23(s, —CH$_2$—), 5.32(s, —CH—), 5.70(s, NH), 7.42(s, aromatic H).

REFERENCE EXAMPLE 3

To a solution of 2.1 g of methyl 4β-n-amyldithio-3β-benzyloxycarboxamido-3α-methoxy-2-oxoazetidine-1-(α-isopropylidine)acetate in 40 ml of ethanol is added 18 ml of Raney nickel, and the mixture is stirred at room temperature for one hour. After removal of Raney nickel by filtration, the solvent is removed under reduced pressure and the residue is chromatographed on a column of silica gel [eluted with n-hexane-ethyl acetate (3:1)] to give 0.62 g of methyl 3-benzyloxycarboxamido-3-methoxy-2-oxoazetidine-1-(α-isopropylidine)acetate.

IR$\nu_{max}^{KBr}$cm$^{-1}$; 1760, 1718, 1510.

NMR(CDCl$_3$, ppm); 1.93(s, —CH$_3$), 2.20(s, —CH$_3$), 3.50(s, —CH$_3$), 3.70(s, —CH$_3$), 3.91(dd, J=4, 6 Hz, C$_4$—H), 5.13(s, —CH$_2$—), 6.03(s, NH), 7.26(aromatic H).

REFERENCE EXAMPLE 4

In 150 ml of methylene chloride is dissolved 6.0 g of methyl 3-benzyloxycarboxamido-3-methoxy-2-oxoazetidine-1-(α-isopropylidene)acetate, and ozone gas is introduced to the solution at −50° C. to −30° C. The reaction mixture is blue after one hour. Then, the excess ozone is removed by the introduction of nitrogen gas, followed by addition of dimethyl sulfide. After stirring at room temperature for an hour, the reaction mixture is washed with water and the solvent is evaporated to give 6.1 g of methyl 3-benzyloxycarboxamido-3-methoxy-2-oxoazetidine-1-α-ketoacetate. This product is dissolved in 75 ml of methanol, and to the solution is added 19 ml of 0.002% sodium methoxide in methanol. After stirring at room temperature for 15 minutes, 0.3 g of acetic acid is added, and the solvent is distilled off. The residue is dissolved in ethyl acetate and the solution is washed with water. After removal of the solvent, the residue is chromatographed on a column of silica gel [eluted with ethyl acetate-n-hexane (1:1)] to give 2.7 g of 3-benzyloxycarboxamido-3-methoxy-2-oxoazetidine as crystals.

Optical rotation: [α]$_D^{25}$ +68.2° (c=1, MeOH).

IR$\nu_{max}^{CHCl_3}$cm$^{-1}$, 3420, 1774, 1723.

NMR(CDCl$_3$, ppm); 3.45(s, CH$_3$), 3.60(d, J=6 Hz, C$_4$—H), 3.80(d, J=6 Hz, C$_4$—H), 5.14(s, —CH$_2$—), 6.74(broad s, NH), 7.34(s, aromatic H).

REFERENCE EXAMPLE 5

To a solution of 14 g of methyl 3-benzyloxycarboxyamido-2-oxoazetidine-1-(α-isopropylidine)acetate in 400 ml of dry tetrahydrofuran (=THF) are added 5.7 ml of t-butyl hypochlorite and, then, a solution of 0.348 g lithium in 32 ml methanol with stirring at −30° to −20° C. The mixture is maintained at −15° C. for 30 minutes, and 1 ml of acetic acid is added, and the solvent is distilled off. The residue is dissolved in ethyl acetate, and after washing with water, the solvent is distilled off. The residue is chromatographed on a column of silica gel [eluted with n-hexane-ethyl acetate (1:1)] to give 11.1 g of methyl 3-benzyloxycarboxamido-3-methoxy-2-oxoazetidine-1-(α-isopropylidine)acetate as crystals.

m.p. 77° C.

IR$_{max}^{KBr}$cm$^{-1}$; 1761, 1723.

NMR(CDCl$_3$, ppm); 1.91(s, CH$_3$), 2.22(s, CH$_3$), 3.53(s, CH$_3$), 3.73(s, CH$_3$), 4.1(ABq, J=6 Hz, C$_4$—H), 5.20(s, —CH$_2$—), 6.58(s, NH), 7.36(s, aromatic H).

REFERENCE EXAMPLE 6

In 150 ml of methylene chloride is dissolved 7.2 g of the methyl 3-benzyloxycarboxamido-3-methoxy-2-oxoazetidine-1-(α-isopropylidene)acetate obtained in Reference Example 5 and ozone gas is introduced to the solution of −50° C. to −30° C. The reaction mixture is blue after 55 minutes. Then, nitrogen gas is introduced until the solution becomes colorless. Then, 6 ml of dimethyl sulfide is added, followed by stirring at room temperature for 30 minutes. The reaction mixture is washed with water and the solvent is evaporated to give 8.1 g of methyl 3-benzyloxycarboxamido-3-methoxy-2-oxoazetidine-1-α-ketoacetate. This is dissolved in 100 ml of methanol, followed by the addition of 25 ml of 0.002% sodium methoxide in methanol. After stirring at room temperature for 15 minutes, the solvent is distilled off, and the residue is dissolved in ethyl acetate. The solution is washed with water, and the solvent is evaporated to give 3.3 g of 3-benzyloxycarboxamido-3-methoxy-2-oxoazetidine as crystals. In IR and NMR, this product is in agreement with the optically active compound obtained in Reference Example 4.

Optical rotation: [α]$_D^{25}$ 0° (c=1, MeOH).

REFERENCE EXAMPLE 7

A solution of 47.5 g of methyl 3-phenylacetamido-2-oxoazetidine-1-(α-isopropylidene)acetate in 750 ml of methylene chloride is cooled to a temperature below −70° C., followed by the addition of 93.7 g of finely divided phosphorus pentachloride and 71.2 g of pyridine. The mixture is stirred in ice-water for 70 minutes. The reaction mixture is cooled to −70° C. and after addition of 150 ml of n-butanol, the temperature is returned gradually to 0° C. After an hour, 300 ml of coldwater is added and the water layer is adjusted to pH 6.2 with sodium hydrogen carbonate. It is extracted with chloroform and the solvent is distilled off. By the above procedure is obtained 26 g of methyl 3-amino-2-oxoazetidine-1-(α-isopropylidene)acetate.

IR$\nu_{max}^{CHCl_3}$ cm$^{-1}$, 3400, 3330, 1750, 1720.

NMR(CDCl$_3$, ppm), 1.90(s, —CH$_3$), 2.04(br. s, —NH$_2$), 2.16(s, —CH$_3$), 3.2–3.9(m, —CH$_2$—), 3.73(s, —CH$_3$), 4.28(m, —CH—).

REFERENCE EXAMPLE 8

While a solution of 58 g of methyl 3-amino-2-oxoazetidine-1-(α-isopropylidine)acetate in 240 ml of methylene chloride is stirred under ice-cooling, 120 ml of propylene oxide and, then, 56.3 g of carbobenzoxy chloride are added. The reaction mixture is returned to room temperature and, then, stirred for 30 minutes. The solvent is distilled off and diethyl ether is added to the residue, whereupon crystals separate out. By the above procedure is obtained 82.6 g of methyl 3-benzyloxycarboxamido-2-oxoazetidine-1-(α-isopropylidine)acetate.
IR$\nu_{max}^{KBr}$ cm$^{-1}$; 3280, 1738, 1710.
NMR(CDCl$_3$, ppm); 1.95(s, —CH$_3$), 2.19(s, —CH$_3$), 3.4–3.9 (m, —CH$_2$—), 3.74(s, —OCH$_3$), 4.89(m, —CH—),
|

5.11(s, —CH$_2$—), 5.66(d, —NH$_{13}$), 7.34(s, aromatic H).

REFERENCE EXAMPLE 9

In 400 ml of methylene chloride is dissolved 13.3 g of methyl 3-benzyloxycarboxamido-2-oxoazetidine-1-(α-isopropylidene) acetate, and ozone gas is introduced under cooling at −30° C. to −20° C. The reaction mixture is blue after 2 hours. Nitrogen gas is introduced to remove the excess ozone and, after addition of 20 ml of dimethyl sulfide, the mixture is stirred at room temperature for an hour. The reaction mixture is washed with water and the solvent is distilled off to give 19.9 g of methyl 3-benzyloxycarboxamido-2-oxoazetidine-1-α-ketoacetate. This product is dissolved in 200 ml of methanol, then 30 ml of 0.002% sodium methoxide in methanol is added, and the mixture is stirred at room temperature for 15 minutes. To this reaction mixture is added 0.5 g of acetic acid, the solvent is distilled off and cold water-methanol (3:1) are added, whereby 7.62 g of 3-benzyloxycarboxamido-2-oxoazetidine is obtained.
IR$\nu_{max}^{KBr}$ cm$^{-1}$; 3350, 1740, 1725, 1700.
NMR(DMSO-d$_6$, ppm); 3.08–3.40(m, —CH$_2$—), 4.63(m, —CH),
|

5.00(s, —CH$_2$—), 7.28(s, aromatic H), 7.80(s, —NH),
|

7.85(d, —NH).

REFERENCE EXAMPLE 10

In 12 ml of alcohol are suspended 220 mg of 3-benzyloxycarboxamido-2-oxoazetidine and 400 mg of 10% palladium-carbon and the suspension is stirred intensely in hydrogen gas streams. After 30 minutes, the catalyst is filtered off and the filtrate is concentrated to give 76 mg of 3-amino-2-oxoazetidine as crystals.
IR$\nu_{max}^{CHCl_3}$ cm$^{-1}$; 3425, 3300, 1760.
NMR(DMSO-d$_6$, ppm); 2.63(br. s, —NH$_2$), 2.80–3.33(m, —CH$_2$—), 4.00(m, —CH—), 7.63(s, —NH).
|           |

REFERENCE EXAMPLE 11

A mixture of 0.20 g of 3-benzyloxycarboxamido-3-methoxy-2-oxoazetidine, 0.50 g of palladium black and 5 ml of THF is stirred in hydrogen gas streams for 90 minutes. The catalyst is filtered off and the filtrate is concentrated to give 0.09 g of 3-amino-3-methoxy-2-oxoazetidine.
IR$\nu_{max}^{Nujol}$ cm$^{-1}$; 3250, 1740.
NMR(CDCl$_3$, ppm); 2.35(broad s, NH$_2$), 3.40(dd, J=6 Hz, C$_4$—H), 3.45(s, CH$_3$), 6.7(broad s, NH).

REFERENCE EXAMPLE 12

In 20 ml of methylene chloride is dissolved 0.20 g of 3-amino-3-methoxy-2-oxoazetidine and under cooling at −15° C., 10 ml of propylene oxide is added, followed by addition of a solution of the acid chloride prepared from 0.76 g of D-N-(4-ethyl-2,3-dioxo-1-piperazinocarbonyl)phenylglycine in 10 ml of methylene chloride. The mixture is stirred at the same temperature for 30 minutes, after which 0.475 g of pyridine is added, followed by stirring for an additional hour. The reaction mixture is concentrated under reduced pressure and after cold-water is added to the residue, it is extracted with THF-ethyl acetate. The extract is washed with water and concentrated under reduced pressure, and the residue is purified by silica gel column chromatography. The above procedure provides 0.43 g of 3-[N-(4-ethyl-2,3-dioxo-1-piperazinocarbonyl)-D-phenylglycinamido]-3-methoxy-2-oxoazetidine.
IR$\nu_{max}^{KBr}$ cm$^{-1}$; 3270, 1760, 1710, 1670, 1505, 1190.
NMR(DMSO-d$_6$, ppm); 1.10(t, J=7 Hz, CH$_3$). 3.02(dd, J=3, 6 Hz, C$_4$—βH), 3.39(t, J=6 Hz, C$_4$—αH), 3.41(q, J=7 Hz, —CH$_2$—), 3.45–3.65(m, —CH$_2$—), 3.30–4.00(m, —CH$_2$—), 4.86(ddd, J=3, 6, 8 Hz, C$_3$—H, 5.46(d, J=8HZ, —CH—),
|

7.2–7.5(m, aromatic H), 8.00(s, NH), 9.12(d, J=8 Hz, NH), 9.81(d, J=8 Hz, NH).

REFERENCE EXAMPLE 13

To a solution of 0.331 g of 3-benzyloxycarboxamido-2-oxoazetidine in 25 ml of ethanol is added 0.5 g of 10% palladium-carbon and the mixture is stirred in hydrogen gas streams for an hour. The catalyst is filtered off and the filtrate is concentrated. The resulting 3-amino-2-oxoazetidine is dissolved in 5 ml of DMF, followed by addition of 0.535 g of D-N-(3-furfurylideneamino-2-oxo-1-imidazolidinecarbonyl)phenylglycine and 0.341 g of dicyclohexylcarbodiimide. The mixture is stirred for 2 hours and the crystals separated are filtered off. The filtrate is concentrated to provide 0.514 g of 3-[D-2[(3-furfurylideneamino-2-oxoimidazolidin-1-yl)-carboxamido]-2-phenylacetamido]-2-oxazetidine.
IR$\nu_{max}^{KBr}$ cm$^{-1}$; 3300, 1750, 1720, 1660.

REFERENCE EXAMPLE 14

To a solution of 0.344 g of 3-amino-2-oxoazetidine in a mixture of DMF (6 ml) and methylene chloride (6 ml) is added a solution of 0.693 g of 1-hexamethyleneiminecarboxaldehyde dimethyl acetal in 6 ml of methylene chloride. The mixture is stirred at room temperature for an hour, after which methylene chloride is added. It is then washed with water and concentrated to obtain 0.20 g of 3-[(hexahydro-1H-azepin-1-yl)methyleneamino]-2-oxoazetidine.
IR$\nu_{max}^{KBr}$ cm$^{-1}$; 3180, 2430, 1740, 1700, 1620.
NMR(DMSO-d$_6$, ppm); 1.64–3.40(m, —CH$_2$—), 3.36(t, J=6 Hz, C$_4$—βH), 3.90(dd, J=2, 6 Hz, C$_4$—αH), 4.40(dd, J=2, 6 Hz, C$_3$—H), 7.46(s, —CH=N—).

REFERENCE EXAMPLE 15

In 25 ml of THF is dissolved 2.5 g of the 3-benzyloxycarboxamido-3-methoxy-2-oxoazetidine obtained in Reference Example 4 and after 0.5 g of palladium black is added, the mixture is stirred in hydrogen gas streams for an hour, at the end of which time the catalyst is filtered off. On the other hand, a solution of 4.46 g of N-carbobenzoxy-D-alanine in 35 ml of THF is cooled to $-40°$ C. and 1.89 g of diphosgene and 4.2 g of triethylamine are added. To this solution is added the above filtrate at $-40°$ C. and the mixture is stirred at room temperature for 2 hours. After filtration, the filtrate is concentrated under reduced pressure and the residue is purified by silica gel column chromatography. The above procedure provides 0.905 g of 3-(N-carbobenzoxy-D-alaninamido)-3-methoxy-2-oxoazetidine.

$[\alpha]_D^{22°} +79.5°$ (c=1, MeOH).

IR$\nu_{max}^{KBr}$cm$^{-1}$; 1755, 1680, 1515.

NMR(DMSO-d$_6$, ppm); 1.22(d, J=7 Hz, CH$_3$), 3.32(s, —OCH$_3$), 3.40, 3.48(each d, J=7 Hz, C$_4$—H), 4.12(m, —CH—),
       |

5:04(s, CH$_2$), 7.36(s, aromatic H), 8.26(s, NH), 8.98(d, J=7 Hz, NH).

REFERENCE EXAMPLE 16

A mixture of 0.482 g of 3-(N-carbobenzoxy-D-alanylamino)-3-methoxy-2-oxoazetidine, 0.5 g of palladium black, 10 ml of THF and 5 ml of methanol is stirred in hydrogen streams for 30 minutes, the catalyst is filtered off and the filtrate is concentrated to dryness under reduced pressure. The residue is dissolved in 2 ml of dimethylacetamide, followed by addition of 0.2 g of triethylamine. While the mixture is stirred under ice-cooling, a solution of 0.337 g of 4-ethyl-2,3-dioxo-1-piperazinocarbonyl chloride is added. The mixture is stirred at room temperature for an hour, after which it is filtered and the filtrate is concentrated under reduced pressure. The residue is purified by silica gel chromatography.

By the above procedure is obtained 0.432 g of 3-[D-N-(4-ethyl-2,3-dioxo-1-piperazinocarbonyl)alanylamino]-3-methoxy-2-oxoazetidine.

IR$\nu_{max}^{KBr}$cm$^{-1}$; 1760, 1710, 1670, 1510.

NMR(DMSO-d$_6$, ppm); 1.10(t, J=7 Hz, CH$_3$), 1.34, 1.44(each d.J=7 Hz, —CH$_3$), 3.36(s, CH$_3$), 3.90(m, —CH$_2$—), 4.48(m, —CH—),
       |

8.31(broad s, NH), 9.74(d, J=7 Hz, NH), 9.82(s, NH).

REFERENCE EXAMPLE 17

In the same manner as Reference Example 12=A, Reference Example 13=B, Reference Example 14=C, Reference Example 15=D and Reference Example 16=E, 3-amino-2-oxoazetidine or 3-amino-3-methoxy-2-oxoazetidine is reacted with acylating agents to obtain the compounds described below. In the following description, (a) is the product, (b) the starting material, (c) the method used and (d) the physico-chemical constants of the product.

(1)
(a) 3-Phenylacetamido-2-oxoazetidine
(b) 3-Amino-2-oxoazetidine
(c) A
(d) IR$\nu_{max}^{KBr}$cm$^{-1}$; 3330, 3270, 1780, 1655. NMR(DMSO-d$_6$, ppm); 3.05(dd, J=3, 5 Hz, C$_4$—$\beta$H), 3.40(t, J=5 Hz, C$_4$—$\alpha$H), 3.46(s, —CH$_2$—), 4.38(ddd, J=3, 5, 8 Hz, C$_3$—H), 7.28(s, aromatic H), 7.93(broad s, NH), 8.67(d, J=8 Hz, NH).

(2)
(a) 3-Thienylacetamido-2-oxoazetidine
(b) 3-Amino-2-oxoazetidine
(c) A
(d) IR$\nu_{max}^{KBr}$cm$^{-1}$; 1775, 1715, 1650, 1530. NMR(DMSO-d$_6$, ppm); 3.07(dd, J=3, 5 Hz, C$_4$—$\beta$H), 3.42(t, J=5 Hz, C$_4$—$\alpha$H), 3.69(s, —CH$_2$—), 4.85(ddd, J=3, 5, 8 Hz, C$_3$—H), 6.8-7.4(m, thienyl H), 7.96(br.s, NH), 8.77(d, J=8 Hz, NH).

(3)
(a) 3-[2-(2-Chloroacetamido-4-thiazolyl)-2-methoxyiminoacetamido]-2-oxoazetidine(syn-isomer)
(b) 3-Amino-2-oxoazetidine
(c) A
(d) IR$\nu_{max}^{KBr}$cm$^{-1}$; 1740, 1690, 1660. NMR(DMSO-d$_6$, ppm); 3.14(dd, J=3, 5 Hz, C$_4$—$\beta$H), 3.49(t, J=5 Hz, C$_4$—$\alpha$H), 3.90(s, CH$_3$), 4.37(s, ClCH$_2$—), 4.99(ddd, J=3, 5, 8 Hz, C$_3$—H),

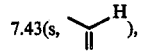
7.43(s,  ), 8.02(s, NH), 9.22(d, J=8 Hz, NH), 12.86(br.s, NH).

(4)
(a) 3-[2-(2-Chloroacetamido-4-thiazolyl)acetamido]-2-oxoacetidine
(b) 3-Amino-2-oxoazetidine
(c) A
(d) IR$\nu_{max}^{KBr}$cm$^{-1}$; 1740, 1825, 1703, 1655. NMR(DMSO-d$_6$, ppm); 3.09(dd, J=3, 5 Hz, C$_4$—$\beta$H), 3.42(t, J=5 Hz, C$_4$—$\alpha$H), 3.54(s, —CH$_2$—), 4.36(s, ClCH$_2$—), 4.86 (ddd, J=3, 5, 8 Hz, C$_3$—H),

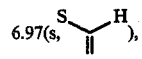
6.97(s,  ), 7.96(s, NH), 8.65(d, J=8 Hz, NH).

(5)
(a) 3-($\alpha$-Sulfophenylacetamido)-2-oxoazetidine sodium salt
(b) 3-Amino-2-oxoazetidine
(c) A
(d) IR$\nu_{max}^{KBr}$cm$^{-1}$; 1750, 1655, 1510, 1210, 1190, 1040. NMR(DMSO-d$_6$, ppm); 3.03(dd, J=2.5, 5 Hz, C$_4$—$\beta$H), 3.39(t, J=5 Hz, C$_4$—$\alpha$H), 4.54(s, —CH—),
       |

4.82(ddd, J=2.5, 5, 8 Hz, C$_3$—H), 7.1-7.6(m, aromatic H), 7.92(broad s, NH). 8.77(d, J=8 Hz, NH).

(6)
(a) 3-[D-2-(Benzyloxycarboxamido)-2-phenylacetamido]-2-oxoazetidine (b) 3-Amino-2-oxoazetidine
(c) B
(d) IR$\nu_{max}^{KBR}$cm$^{-1}$; 3330, 1760, 1740, 1690, 1670. NMR(DMSO-d$_6$, ppm); 2.92(dd, J=3, 6 Hz, C$_4$—$\beta$H), 3.33(t, J=6 Hz, C$_4$—$\alpha$H), 4.82(ddd, J=3, 6, 8 Hz, C$_3$—H), 5.03(s, —CH$_2$—), 5.23(d, J=8Hz, —CH—),
|

7.31(s, aromatic H), 7.81(d, J=8 Hz, NH), 7.93(s, NH), 8.88(d, J=8 Hz, NH).

(7)
(a) 3-[2-(2-Chloroacetamido-4-thiazolyl)-2-methoxyiminoacetamido]-3-methoxy-2-oxoazetidine (syn-isomer)
(b) 3-Amino-3-methoxy-2-oxoazetidine
(c) A
(d) IR$\nu_{max}^{KBr}$cm$^{-1}$; 3280, 1760, 1675, 1540. NMR(d$_6$-DMSO, ppm); 3.44(s, —CH$_3$), 3.60(ABq, J=6, 20 Hz, C$_4$—H$_2$), 3.92(s, —CH$_3$), 4.38(s, —CH$_2$—), 7.42(s, aromatic H), 8.33(s, —NH—), 9.78(s, NH), 12.75(s, NH).

(8)
(3-Cyanoacetamido-2-oxoazetidine
(b) 3-Amino-2-oxoazetidine
(c) A
(d) IR$\nu_{max}^{KBr}$cm$^{-1}$; 2270, 1770, 1715, 1662, 1511. NMR(DMSO-d$_6$, ppm); 3.10(dd, J=2, 6 Hz, C$_4$—$\beta$H), 3.35(s, —CH$_2$—), 3.40(t, J=6 Hz, C$_4$—$\alpha$H), 3.72(s, —CH$_2$—), 4.80(ddd, J=2, 6, 8 Hz, C$_3$—H), 7.93(s, NH), 8.84(d, J=8 Hz, NH).

(9)
(a) 3-(1H-Tetrazol-1-yl-1-acetamido)-2-oxoazetidine
(b) 3-Amino-2-oxoazetidine
(c) A
(d) IR$\nu_{max}^{KBr}$cm$^{-1}$; 3280, 1735, 1670. NMR(DMSO-d$_6$, ppm); 3.14(dd, J=2, 5 Hz, C$_4$—$\beta$H), 3.46(t, J=5 Hz, C$_4$—$\alpha$H), 4.90(q, J=2, 5 Hz, C$_3$—H), 5.35(s, —CH$_2$—), 8.03(broad s, NH), 9.15(broad s, NH), 9.35(s, ⫶⩘H ).

(10)
(a) 3-[3-(2,6-Dichlorophenyl)-5-methylisoxazol-4-yl]carboxamido-2-oxoazetidine
(b) 3-Amino-2-oxoazetidine
(c) A
(d) IR$\nu_{max}^{KBr}$cm$^{-1}$; 1760, 1660. NMR(DMSO-d$_6$, ppm); 2.68(s, CH$_3$), 3.07(dd, J=2, 5 Hz, C$_4$—$\beta$H), 3.39(t, J=5 Hz, C$_4$—$\alpha$H), 4.87(ddd, J=2, 5, 8 Hz, C$_3$—H), 7.53(s, aromatic H), 8.60(d, J=8 Hz, NH).

(11)
(a) 3-(N-Carbobenzoxy-D-alaninamido)-2-oxoazetidine
(b) 3-Amino-2-oxoazetidine
(c) B
(d) IR$\nu_{max}^{KBr}$cm$^{-1}$; 1770, 1720, 1675, 1645. NMR(DMSO-d$_6$, ppm); 1.22(d, J=7 Hz, —CH$_3$), 3.06(dd, J=2, 6 Hz, C$_4$—$\beta$H), 3.40(t, J=6 Hz, C$_4$—$\alpha$H), 4.06(dd, J=7, 8Hz, —CH—),
|

4.85(ddd, J=2, 6, 8 Hz, C$_3$—H), 5.05(s, —CH$_2$—), 7.38(s, aromatic H), 7.94(broad s, NH), 8.52(d, J=8 Hz, NH).

(12)
(a) 3-($\alpha$-Benzyl N-carbobenzoxy-$\gamma$-D-glutamyl-D-alaninamido)-2-oxoazetidine
(b) 3-Amino-2-oxoazetidine
(c) B
(d) IR$\nu_{max}^{KBr}$cm$^{-1}$; 3260, 1740, 1700, 1655, 1640, 1550, 1520. NMR(DMSO-d$_6$, ppm); 1.17(d, J=7 Hz, CH$_3$—), 1.93(m, —CH$_2$—), 2.22(dd, J=7 Hz, —CH$_2$CO—), 3.03(dd, J=2, 6 Hz, C$_4$—$\beta$H), 3.38(t, J=6 Hz, C$_4$—$\alpha$H), 4.84(ddd, J=2, 6, 8 Hz, C$_3$—$\alpha$H), 5.05(s, —CH$_2$—), 5.12(s, —CH$_2$—), 7.37(s, aromatic H), 7.73(d, J=8 Hz, NH), 7.92(s, NH), 7.95(d, J=8 Hz, NH), 8.48(d, J=8 Hz, NH).

(13)
(a) 3-($\alpha$-Ureidophenylacetamido)-2-oxoazetidine
(b) 3-Amino-2-oxoazetidine
(c) B
(d) IR$\nu_{max}^{KBr}$cm$^{-1}$; 3440, 3340, 3280, 3250, 1760, 1740, 1650, 1540. NMR(DMSO-d$_6$, ppm); 2.97(dd, J=3, 6 Hz, C$_4$—$\beta$H), 3.38(t, J=6 Hz, C$_4$—$\alpha$H), 4.86(ddd, J=3, 6, 8 Hz, C$_3$—H), 5.32(d, J=8Hz, —CH—),
|

5.70(s, NH$_2$), 6.82(d, J=8 Hz, NH), 7.35(broad s, aromatic H), 7.99(s, NH), 9.02(d, J=8 Hz, NH).

(14)
(a) 3-[D-2-(4-Ethyl-2,3-dioxo-1-piperazinocarboxamido)-2-phenylacetamido]-3-methoxy-2-oxoazetidine
(b) 3-Amino-3-methoxy-2-oxoacetidine
(c) A
(d) IR$\nu_{max}^{KBr}$cm$^{-1}$; 3270, 1760, 1710, 1670, 1505, 1190. NMR(DMSO-d$_6$, ppm); 1.09(t, J=7 Hz, CH$_3$), 3.36(s, —CH$_3$), 5.60(d, J=7Hz, —CH—),
|

8.25(s, NH), 9.60(s, NH), 9.78(d, J=7 Hz, NH).

(15)
(a) 3-[D-2-(4-Ethyl-2,3-dioxo-1-piperazinocarboxamido)-2-(4-hydroxyphenyl)acetamido]-2-oxoazetidine
(b) 3-Amino-2-oxoazetidine
(c) A
(d) IR$\nu_{max}^{KBr}$cm$^{-1}$; 1750, 1710, 1670, 1505. NMR(DMSO-d$_6$, ppm); 1.09(t, J=8 Hz, —CH$_3$), 4.86(m, C$_3$—H), 5.32(d, J=7Hz, —CH—),
|

6.98(ABq, J=9, 46 Hz, phenyl H), 7.96(s, NH), 8.99(d, J=8 Hz, NH), 9.70(d, J=7 Hz, NH).

(16)

(a) 3-(4-Ethyl-2,3-dioxo-1-piperazinocarboxamido)-2-oxoazetidine
(b) 3-Amino-2-oxoazetidine
(c) A
(d) IR$\nu_{max}^{KBr}$cm$^{-1}$; 3280, 1745, 1710, 1675, 1520. NMR(DMSO-d$_6$, ppm); 1.11(t, J=7 Hz, CH$_3$), 3.27(dd, J=3, 6 Hz, C$_4$—$\beta$H), 3.42(t, J=6 Hz, C$_4$—$\alpha$H), 3.42(q, J=7 Hz, —CH$_2$—), 3.5–4.1(m, —CH$_2$—), 4.87(ddd, J=3, 6, 8 Hz, C$_3$—H), 7.98(s, NH), 9.18(d, J=8 Hz, NH).

(17)
(a) 3-[N-(4-Ethyl-2,3-dioxo-1-piperazinocarbonyl)-D-alaninamido]-2-oxoazetidine
(b) 3-Amino-2-oxoazetidine
(c) A
(d) IR$\nu_{max}^{KBr}$cm$^{-1}$; 3290, 1730, 1700, 1665. NMR(DMSO-d$_6$, ppm); 1.10(t, J=7 Hz, —CH$_3$), 1.30(d, J=7 Hz, —CH$_3$), 3.06(dd, J=3, 6 Hz, C$_4$—$\beta$H), 3.4–4.1(m, —CH$_2$—), 3.43(q, J=7 Hz, —CH$_2$—), 3.46(t, J=6 Hz, C$_4$—$\alpha$H), 4.34(quintet, J=7Hz, —$\overset{|}{\text{CH}}$—), 4.88(ddd, J=3, 6, 8 Hz, C$_3$—H), 7.99(s, NH), 8.78(d, J=8 Hz, NH), 9.25(d, J=7 Hz, NH).

(18)
(a) 3-(2-Methoxyimino-2-phenylacetamido)-2-oxoazetidine (syn-isomer)
(b) 3-Amino-2-oxoazetidine
(c) B
(d) NMR(CDCl$_3$, ppm); 3.26(dd, J=2, 5 Hz, C$_4$—$\beta$H), 3.52(t, J=5 Hz, C$_4$—$\alpha$H), 3.92(s, CH$_3$), 4.96(ddd, J=2, 5, 8 Hz, C$_3$—H), 6.47(br.s, NH), 7.2–7.7(m, aromatic H).

(19)
(a) 3-[D-2-(4-Ethyl-2,3-dioxo-1-piperazinocarboxamido)-2-(4-methoxyphenyl)acetamido]-2-oxoazetidine
(b) 3-Amino-2-oxoazetidine
(c) A
(d) IR$\nu_{max}^{KBr}$cm$^{-1}$; 3280, 1750, 1710, 1670, 1505. NMR(DMSO-d$_6$, ppm); 1.09(t, J=7 Hz, —CH$_3$), 2.94(dd, J=3, 6 Hz, C$_4$—$\beta$H), 3.38(t, J=6 Hz, C$_4$—$\alpha$H), 3.41(q, J=7 Hz, —CH$_2$—), 3.4–4.1(m, —CH$_2$—), 3.76(s, —CH$_3$), 4.86(ddd, J=3, 6, 8 Hz, C$_3$—H), 5.38(d, J=7Hz, —$\overset{|}{\text{CH}}$—), 6.93, 7.33(ABq, J=9 Hz, aromatic H), 7.98(s, NH), 9.04(d, J=8 Hz, NH), 9.74(d, J=7 Hz, NH).

(20)
(a) 3-[D-2-[2-(2-Chloroacetamido-4-thiazolyl)-2-methoxyiminoacetamido]-2-phenylacetamido]-2-oxoazetidine (a mixture of syn- and anti-isomers)
(b) 3-amino-2-oxoazetidine
(c) E
(d) IR$\nu_{max}^{KBr}$cm$^{-1}$; 3270, 1740, 1660, 1540. NMR(DMSO-d$_6$, ppm); 2.97(dd, J=3, 6 Hz, C$_4$—$\beta$H), 3.42(t, J=6 Hz, C$_4$—$\alpha$H), 3.88(s, —CH$_3$), 4.39(s, ClCH$_2$—), 4.93(ddd, J=3, 6, 8 Hz, C$_3$—H), 5.62(d, J=8Hz, —$\overset{|}{\text{CH}}$—), 7.2–7.6(m, aromatic H), 7.47(s, 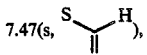), 8.03(s, NH), 8.93(d, J=8 Hz, NH), 9.34(d, J=8 Hz, NH), 12.7(broad s, NH).

(21)
(a) 3-[D-2-(6-Bromo-1,4-dihydro-1-ethyl-4-oxothieno[2,3-b]pyridine-3-carboxamido)-2-phenylacetamido]-2-oxoazetidine
(b) 3-Amino-2-oxoazetidino
(c) E
(d) IR$\nu_{max}^{KBr}$cm$^{-1}$; 3290, 1770, 1660, 1600, 1530, 1500. NMR(DMSO-d$_6$, ppm); 1.43(t, J=7 Hz, CH$_3$—), 2.97(dd, J=3, 6 Hz, C$_4$—$\beta$H), 3.40(t, J=6 Hz, C$_4$—$\alpha$H), 4.27(q, J=7 Hz, —CH$_2$—), 4.90(ddd, J=3, 6, 8 Hz, C$_3$—H), 5.70(d, J=7Hz, —$\overset{|}{\text{CH}}$—), 7.2 7.6(m, phenyl H), 7.63(s, aromatic H), 7.98(s, NH), 8.70(s, aromatic H), 9.11(d, J=8 Hz, NH), 10.95(d, J=7 Hz, NH).

(22)
(a) 3-[2-(4-Ethyl-2,3-dioxo-1-piperazinocarboxamido)-2-(2-chloroacetamido-4-thiazolyl)acetamido]-2-oxoazetidine
(b) 3-Amino-2-oxoazetidine
(c) B
(d) IR$\nu_{max}^{KBr}$cm$^{-1}$; 3270, 1740, 1702, 1670. NMR(DMSO-d$_6$, ppm); 1.10(t, J=7 Hz, CH$_3$), 3.40(q, J=7 Hz, —CH$_2$—), 3.4–4.1(m, —CH$_2$—), 4.87(broad s, C$_3$—H), 4.37(s, ClCH$_2$—), 5.55(d, J=7Hz, —$\overset{|}{\text{CH}}$—), 7.22(s, aromatic H), 7.98(s, NH), 8.91(d, J=8 Hz, NH), 9.76(d, J=7 Hz, NH), 12.6(broad s, NH).

(23)
(a) 3-[2-(4-Ethyl-2,3-dioxo-1-piperazinocarboxamido)-2-(2-acetamido-4-thiazolyl)acetamido]-2-oxoazetidine
(b) 3-Amino-2-oxoazetidine
(c) B
(d) IR$\nu_{max}^{KBr}$cm$^{-1}$; 3270, 1740, 1710, 1670. NMR(DMSO-d$_6$, ppm); 1.10(t, J=7 Hz, —CH$_3$), 2.14(s, CH$_3$), 3.0–3.7(m, C$_4$—H), 4.83(m, C$_3$—H), 5.56(d, J=7Hz, —$\overset{|}{\text{CH}}$—), 7.18(s, $\overset{H}{\underset{\|}{\curlyvee}}$), 7.97(s, NH), 9.13(d, J=8 Hz, NH), 9.73(d, J=7 Hz, NH), 12.2(broad s, NH).

(24)

(a) 3-[2-[2-(2-Chloroacetamido-4-thiazolyl)-2-methoxyiminoacetamido]-2-(2-chloroacetamido-4-thiazolyl)acetamido]-2-oxoazetidine(syn-isomer)
(b) 3-Amino-2-oxoazetidine
(c) B
(d) IR$\nu_{max}^{KBr}$cm$^{-1}$; 3250, 1745, 1655, 1550. NMR(DMSO-d$_6$, ppm); 3.0–3.2(m, C$_4$—βH), 3.44(t, J=6 Hz, C$_4$—αH), 3.88(s, —CH$_3$), 4.32(s, ClCH$_2$—), 4.86(m, C$_3$—H),

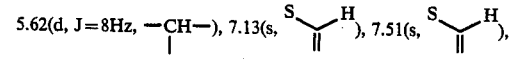

5.62(d, J=8Hz, —CH—),  7.13(s, ...), 7.51(s, ...), 8.00(s, NH), 8.76(d, J=8 Hz, NH), 9.21(d, J=8 Hz, NH), 12.2(broad s, NH).

(25)
(a) 3-[D-2-(2,3-Dioxo-4-n-octyl-1-piperazinocarboxamido)-2-phenylacetamido]-2-oxoazetidine
(b) 3-Amino-2-oxoazetidine
(c) B
(d) IR$\nu_{max}^{KBr}$cm$^{-1}$; 1755, 1710, 1670, 1500, 1085. NMR(DMSO-d$_6$, ppm); 0.7–1.7(m, —CH$_2$—, CH$_3$), 2.93(dd, J=3, 6 Hz, C$_4$—βH), 3.36(t, J=6 Hz, C$_4$—αH), 3.2–4.1(m —CH$_2$—), 4.85(ddd, J=3, 6, 8 Hz, C$_3$—H),

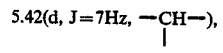

5.42(d, J=7Hz, —CH—), 7.2–7.5(m, aromatic H), 7.98(s, NH), 9.12(d, J=8 Hz, NH), 9.83(d, J=7 Hz, NH).

(26)
(a) 3-[D-2-(Coumarin-3-carboxamido)-2-phenylacetamido]-2-oxoazetidine
(b) 3-Amino-2-oxoazetidine
(c) E
(d) IR$\nu_{max}^{KBr}$cm$^{-1}$; 3280, 1795, 1740, 1710, 1660, 1610, 1560, 1180. NMR(DMSO-d$_6$, ppm); 3.01(dd, J=3, 6 Hz, C$_4$—H), 3.43(t, J=6 Hz, C$_4$—H), 4.95(ddd, J=3, 6, 8 Hz, C$_3$—H), 5.72(d, J=7Hz, —CH—), 7.3–9.0(m, aromatic H), 9.23(d, J=8 Hz, NH), 9.68(d, J=7 Hz, NH).

(27)
(a) 3-[2-(2,3-Dioxo-4-n-octyl-1-piperazinocarboxamido)-2-(2-chloroacetamido-4-thiazolyl)acetamido]-2-oxoazetidine
(b) 3-Amino-2-oxoazetidine
(c) B
(d) IR$\nu_{max}^{KBr}$cm$^{-1}$; 3270, 2925, 1750, 1710, 1670. NMR(DMSO-d$_6$, ppm); 4.31(s, ClCH$_2$—), 4.81(m, C$_3$—H),

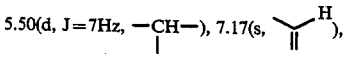

5.50(d, J=7Hz, —CH—), 7.17(s, ...), 7.96(s, NH), 8.88(d, J=9 Hz, NH), 9.75(d, J=7 Hz, NH), 12.63(s, NH).

(28)
(a) 3-[D-2-(4-Hydroxy-7-trifluoromethylquinoline-3-carboxamido)-2-phenylacetamido]-2-oxoazetidine
(b) 3-Amino-2-oxoazetidine
(c) B
(d) IR$\nu_{max}^{KBr}$cm$^{-1}$; 3240, 1740, 1645, 1520. NMR(DMSO-d$_6$, ppm); 3.12(dd, J=3, 5 Hz, C$_4$—βH), 3.45(t, J=5 Hz, C$_4$—αH), 4.87(m, C$_3$—H),

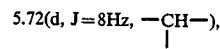

5.72(d, J=8Hz, —CH—), 7.99(s, NH), 9.07(d, J=8 Hz, NH), 10.86(d, J=8 Hz, NH).

(29)
(a) 3-[2-(2,3-Dioxo-4-n-octyl-1-piperazinocarboxamido)-2-thienylacetamido]-2-oxoazetidine
(b) 3-Amino-2-oxoazetidine
(c) B
(d) IR$\nu_{max}^{KBr}$cm$^{-1}$; 3270, 2920, 1755, 1710, 1670. NMR(DMSO-d$_6$, ppm); 0.86(t, J=7 Hz, CH$_3$), 3.01, 3.09(dd, J=3, 6 Hz, C$_4$—βH), 3.37(t, J=7 Hz, —CH$_2$—), 3.4–4.1(m, —CH$_2$—), 4.86(m, C$_3$—H),

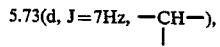

5.73(d, J=7Hz, —CH—), 6.9–7.6(m, aromatic H), 8.01(s, NH), 9.14, 9.17(d, J=8 Hz, NH), 9.76(d, J=7 Hz, NH).

(30)
(a) 3-[D-2-(2,3-Dioxo-4-n-octyl-1-piperazinocarboxamido)-2-(4-hydroxypheny)acetamido]-2-oxoazetidine
(b) 3-Amino-2-oxoazetidine
(c) B
(d) IR$\nu_{max}^{KBr}$cm$^{-1}$; 3260, 2910, 1740, 1705, 1670. NMR(DMSO-d$_6$, ppm); 0.86(t, J=7 Hz, CH$_3$), 2.95(dd, J=3, 6 Hz, C$_4$—βH), 4.86(ddd, J=3, 6, 8 Hz, C$_3$—H),

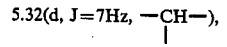

5.32(d, J=7Hz, —CH—), 6.97(ABq, J=8, 46 Hz, aromatic H), 7.98(s, NH), 8.99(d, J=8 Hz, NH), 9.42(s, OH), 9.70(d, J=7 Hz, NH).

(31)
(a) 3-[D-2-[(3-Furfurylideneamino-2-oxoimidazolidin-1-yl)-carboxamido]-2-(4-hydroxyphenyl)acetamido]-2-oxoazetidine
(b) 3-Amino-2-oxoazetidine
(c) B
(d) IR$\nu_{max}^{KBr}$cm$^{-1}$; 1750, 1720, 1660, 1420. NMR(DMSO-d$_6$, ppm); 2.97(dd, J=3, 6 Hz, C$_4$—βH), 3.35(t, J=6 Hz, C$_4$—αH), 3.80(broad s, —CH$_2$—), 4.88(ddd, J=3, 6, 8 Hz, C$_3$—H),

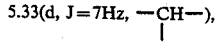

5.33(d, J=7Hz, —CH—), 6.6–7.9(m, furyl H), 6.74, 7.22(ABq, J=46, 9 Hz, phenyl H), 7.74(s, —CH=), 7.98(s, NH), 8.92(d, J=7 Hz, NH), 9.00(d, J=7 Hz, NH), 9.44(s, OH).

(32)

(a) 3-[D-2-[(3-Furfurylideneamino-2-oxoimidazolidin-1-yl)-carboxamido]-2-thienylacetamido]-2-oxoazetidine
(b) 3-Amino-2-oxoazetidine
(c) B
(d) IR$\nu_{max}^{KBr}$cm$^{-1}$; 3300, 1750, 1720, 1660, 1415.

(33)
(a) 3-[D-2-[[3-(Thiophen-2-aldoimino)-2-oxoimidazolidin-1-yl]-carboxamido]-2-phenylacetamido]-2-oxoazetidine
(b) 3-Amino-2-oxoazetidine
(c) B
(d) IR$\nu_{max}^{KBr}$cm$^{-1}$; 1755, 1720, 1660.

(34)
(a) 3-[2-(4-Ethyl-2,3-dioxo-1-piperazinocarboxamido)-2-(2-pyrrolyl)acetamido]-2-oxoazetidine
(b) 3-Amino-2-oxoazetidine
(c) B
(d) IR$\nu_{max}^{KBr}$cm$^{-1}$; 3280, 1745, 1705, 1670, 1500, 1190. NMR(DMSO-d$_6$, ppm); 1.10(t, J=7 Hz, —CH$_3$), 3.03 3.10(dd, J=3, 6 Hz, C$_4$—$\beta$H), 3.40(q, J=7 Hz, —CH$_2$—), 3.4–4.1(m, —CH$_2$—), 4.86(m, C$_3$—H), 5.46(d, J=7Hz, —CH—), 5.9–6.8(m, pyrrolyl H), 7.98(s, NH), 8.89, 8.91(d, J=8 Hz, NH), 9.48(d, J=7 Hz, NH), 10.72(broad s, NH).

(35)
(a) 3-[2-(2,3-Dioxo-4-n-octyl-1-piperazinocarboxamido)-2-thienylacetamido]-3(S)-methoxy-2-oxoazetidine
(b) 3-Amino-3-methoxy-2-oxoazetidine
(c) A
(d) IR$\nu_{max}^{KBr}$cm$^{-1}$; 3270, 2920, 1760, 1705, 1675. NMR(d$_6$-DMOS, ppm); 0.86(t, CH$_3$), 3.20(s, OCH$_3$), 3.4–4.1(m, ring CH$_2$), 3.44, 3.57(ABq, J=6, 13 Hz, C$_4$—H), 5.90(d, J=7Hz, —CH—), 6.9–7.6(m, thienyl H), 8.36(s, NH), 9.74(d, J=7 Hz, NH).

(36)
(a) 3-[2-(2,3-Dioxo-4-n-octyl-1-piperazinocarboxamido)-2-thienylacetamido]-3(R)-methoxy-2-oxoazetidine
(b) 3-Amino-3-methoxy-2-oxoazetidine
(c) A
(d) IR$\nu_{max}^{KBr}$cm$^{-1}$; 3270, 2920, 1760, 1705, 1675. NMR(d$_6$-DMSO, ppm); 0.86(t, CH$_3$), 3.36(s, OCH$_3$), 3.39, 3.48(ABq, J=9, 6 Hz, C$_4$—H), 3.4–4.1(m, ring CH$_2$), 5.89(d, J=7Hz, —CH—), 6.9–7.6(m, thienyl H), 8.31(s, NH), 9.67(s, NH), 9.70(d, J=7 Hz, NH).

(37)
(a) 3-(D-$\alpha$-Sulfophenylacetamido)-3-methoxy-2-oxoazetidine sodium salt
(b) 3-Amino-3-methoxy-2-oxoazetidine
(c) A
(d) IR$\nu_{max}^{KBr}$cm$^{-1}$; 3270, 1745, 1670, 1200, 1040. NMR(DMSO-d$_6$, ppm); 3.31, 3.41(s, CH$_3$), 3.47(ABq, J=6, 12 Hz, C$_4$—H), 5.65, 5.70(s, —CH—), 7.2–7.5(m, aromatic H), 8.29(s, NH), 9.2, 9.29(s, NH).

(38)
(a) 3-(N-Carbobenzoxy-D-alanyl-D-phenylglycinamido)-2-oxoazetidine
(b) 3-Amino-2-oxoazetidine
(c) B
(d) IR$\nu_{max}^{KBr}$cm$^{-1}$; 3290, 1750, 1690, 1640, 1520. NMR(DMSO-d$_6$, ppm); 1.20(d, J=6 Hz, CH$_3$—), 2.91(dd, J=2, 6 Hz, C$_4$—$\beta$H), 3.35(t, J=6 Hz, C$_4$—$\alpha$H), 4.17(m, —CH—), 4.83(ddd, J=2, 6, 8 Hz, C$_3$—H), 4.99(s, —CH$_2$—), 5.42(d, J=9Hz, —CH—), 7.30(s, aromatic H, 7.94(br. s, NH), 8.97(d, J=9 Hz, NH).

(39)
(a) 3-[D-2-(2-Ureido-2-thienylacetamido)-2-phenylacetamido]-2-oxoazetidine
(b) 3-Amino-2-oxoazetidine
(c) B
(d) IR$\nu_{max}^{KBr}$cm$^{-1}$; 1758, 1640, 1520.

(40)
(a) 3-Cyanomethylacetamido-2-oxoazetidine
(b) 3-Amino-2-oxoazetidine
(c) B
(d) IR$\nu_{max}^{KBr}$cm$^{-1}$; 2270, 1770, 1715, 1662, 1511. NMR(DMSO-d$_6$, ppm); 3.10(dd, J=2, 6 Hz, C$_4$—$\beta$H), 3.35(s, —CH$_2$—), 3.72(s, —CH$_2$—), 3.40(t, J=6 Hz, C$_4$—$\alpha$H), 4.80(ddd, J=2, 6, 8 Hz, C$_3$—H), 7.93(s, NH), 8.84(d, J=8 Hz, NH).

(41)
(a) 3-[D-2-[2-(2-chlroacetamido-4-thiazolyl)acetamido]-2-phenylacetamido]-2-oxoazetidine
(b) 3-Amino-2-oxoazetidine
(c) E
(d) IR$\nu_{max}^{KBr}$cm$^{-1}$; 1741, 1680, 1650, 1634, 1530.

(42)
(a) 3-[2-(4-Ethyl-2,3-dioxo-1-piperazinocarboxamido)-2-thienylacetamido]-2-oxoazetidine
(b) 3-Amino-2-oxoazetidine
(c) A
(d) IR$\nu_{max}^{KBr}$cm$^{-1}$; 1752, 1707, 1670, 1497, 1160, 1182. NMR(DMSO-d$_6$, ppm); 1.08(t, J=7 Hz, CH$_3$), 3.02(dd, J=3, 6 Hz, C$_4$—$\beta$H), 3.3, 4.1(m, —CH$_2$—, C$_4$—$\alpha$H), 4.86(ddd, J=3, 6, 8 Hz, C$_3$—H), 5.71(d, J=7Hz, —CH—),
|

6.9–7.5(m, thienyl H), 8.01(s, NH), 9.20, 9.18(each d, J=8 Hz, NH), 9.77(d, J=7 Hz, NH).

(43)
(a) 3-(2-Methoxyimino-2-thienylacetamido)-2-oxoazetidine
(b) 3-Amino-2-oxoazetidine
(c) B
(d) IR$\nu_{max}^{KBr}$cm$^{-1}$; 1760, 1652, 1528.

(44)
(a) 3-[2-Thienyl-2-(3-morpholinopropoxyimino)acetamido]-2-oxoazetidine
(b) 3-Amino-2-oxoazetidine
(c) B
(d) IR$\nu_{max}^{KBr}$cm$^{-1}$; 3240, 1750, 1658, 1540–1520. NMR(DMSO-d$_6$, ppm); 3.18(dd, J=3, 6 Hz, C$_4$—H), 4.21(t, J=6 Hz, C$_4$—H), 4.93(ddd, J=2, 6, 8 Hz, C$_3$—H), 8.01(s, NH), 9.25(d, J=8 Hz, NH).

(45)
(a) 3-[D-2-[2-(4-Ethyl-2,3-dioxo-1-piperazinocarboxamido)-2-thienylacetamido]-2-phenylacetamido]-2-oxoazetidine
(b) 3-Amino-2-oxoazetidine
(c) B
(d) IR$\nu_{max}^{KBr}$cm$^{-1}$; 3290, 1760, 1708, 1672, 1648, 1510, 1190.

(46)
(a) 3-[2-(2,5-Dioxo-1,2,4-triazino-6-carboxamido]-2-oxoazetidine
(b) 3-Amino-2-oxoazetidine
(c) B
(d) IR$\nu_{max}^{KBr}$cm$^{-1}$; 3250, 1760, 1720, 1680, 1504, 1420, 1210. NMR(DMSO-d$_6$, ppm); 3.10(dd, J=2, 6 Hz, C$_4$—H), 3.40(t, J=6 Hz, C$_4$—H), 4.85(ddd, J=2, 6, 8 Hz, C$_3$—H), 5.85(d, J=7Hz, —CH—),
|

8.00(s, NH), 9.16, 9.19(each d, J=8 Hz, NH), 9.60(d, J=7 Hz, NH).

(47)
(a) 3-[2-(4-Ethyl-2,3-dioxo-1-piperazinocarboxamido)-2-(2-methyl-4-thiazolyl)acetamido]-2-oxoazetidine
(b) 3-Amino-2-oxoazetidine
(c) B
(d) IR$\nu_{max}^{KBr}$cm$^{-1}$; 3280, 1708, 1670, 1500, 1187. NMR(DMSO-d$_6$, ppm); 1.08(t, J=7 Hz, CH$_3$), 2.63(s, CH$_3$), 3.34(dd, J=3, 6 Hz, C$_4$—H), 4.83(ddd, J=2, 6, 8 Hz, C$_3$—H), 5.52(d, J=7Hz, —CH—), 7.40(s, $\overset{S}{\underset{\|}{\diagup}}\overset{H}{\diagdown}$ ),
|

7.96(s, NH), 8.95(d, J=8 Hz, NH), 9.78(d, J=7 Hz, NH).

(48)
(a) 3-[2-[3-(4-Chlorobenzoyl)ureido]-2-thienylacetamido]-2-oxoazetidine
(b) 3-Amino-2-oxoazetidine
(c) B (d) IR$\nu_{max}^{KBr}$cm$^{-1}$; 3270, 1760, 1685, 1664, 1525, 1463, 1282. NMR(DMSO-d$_6$, ppm); 3.25(dd, J=3, 6 Hz, C$_4$—H), 3.57(t, J=6 Hz, C$_4$—H), 4.94(ddd, J=2, 6.8 Hz, C$_3$—H), 5.82(s, —CH—).

(49)
(a) 3-Cyanomethylthioacetamido-3-methoxy-2-oxoazetidine
(b) 3-Amino-3-methoxy-2-oxoazetidine
(c) A
(d) IR$\nu_{max}^{KBr}$cm$^{-1}$; 1758, 1670, 1520. NMR(DMSO-d$_6$, ppm); 3.33(s, CH$_3$), 3.33, 3.70(each s, —CH$_2$—), 3.2–3.8(m, C$_4$—H), 8.27(s, NH), 9.28(s, NH).

(50)
(a) 3-(2-Benzyloxycarbonyl-2-phenylacetamido)-3-methoxy-2-oxoazetidine
(b) 3-Amino-3-methoxy-2-oxoazetidine
(c) A
(d) IR$\nu_{max}^{KBr}$cm$^{-1}$; 1775, 1722, 1685, 1160.

(51)
(a) 3-[2-(5,6-Dihydro-1,4-oxathiin-2-yl)acetamido]-2-oxoazetidine
(b) 3-Amino-2-oxoazetidine
(c) B
(d) IR$\nu_{max}^{KBr}$cm$^{-1}$; 1745, 1720, 1650, 1640. NMR(DMSO-d$_6$, ppm); 3.05(dd, J=3, 6 Hz, C$_4$—H), 3.40(t, J=6 Hz, C$_4$—H), 4.20(t, J=5 Hz, —CH$_2$—), 4.83(ddd, J=2, 6, 8 Hz, C$_3$—H), 5.10(s, $\overset{S}{\underset{\|}{\diagup}}\overset{H}{\diagdown}$ ), 7.91(br.s, NH), 8.42(d, J=8 Hz, NH).

(52)
(a) 3-N-Carbamoyl-D-tryptophyl-D phenylglycinamido)-2-oxoazetidine
(b) 3-Amino-2-oxoazetidine
(c) B
(d) IR$\nu_{max}^{KBr}$cm$^{-1}$; 1755, 1640, 1540–1520. NMR(DMSO-d$_6$, ppm); 2.97(dd, J=2, 6 Hz, C$_4$—H), 3.48(t, J=6 Hz, C$_4$—H), 4.52(m, —CH—),
|

4.86(ddd, J=2, 6, 8 Hz, C$_3$—H), 5.51(s, —CH$_2$—), 5.52(d, J=8Hz, —CH—),
|

5.55(br.s, NH), 7.21(s, $\overset{\|}{\diagup}\overset{}{\underset{H}{\diagdown}}$ ), 7.45(s, aromatic H).

(53)
(a) 3-[D-N-(4-Ethyl-2,3-dioxo-1-piperazinocarbonyl)phenylalaninamido]-2-oxoazetidine
(b) 3-Amino-2-oxoazetidine
(c) B
(d) IR$\nu_{max}^{KBr}$cm$^{-1}$; 1750, 1710, 1670, 1518. NMR(DMSO-d$_6$, ppm); 1.08(t, J=7 Hz, CH$_3$), 2.90(dd, J=2, 6 Hz, C$_4$—βH), 3.38(m, —CH$_2$—), 3.42(t, J=6 Hz, C$_4$—αH), 4.56(dd, J=6, 8Hz, —CH—),
            |

4.84(ddd, J=2, 6, 8 Hz, C$_3$—H), 7.21(s, aromatic H), 7.95(s, NH), 8.79(d, J=8 Hz, NH), 9.15(d, J=8 Hz, NH).

(54)
(a)     3-[2-(2,4-Dioxopyrimidino-5-carboxamido)-2-thienylacetamido]-2-oxoazetidine
(b) 3-Amino-2-oxoazetidine
(c) B
(d) IR$\nu_{max}^{KBr}$cm$^{-1}$; 1740, 1700, 1650-1680(broad), 1508. NMR(DMSO-d$_6$ppm); 3.04(dd, J=2,6 Hz, C$_4$—βH), 3.42(t, J=6 Hz, C$_4$—αH), 4.84(ddd, J=2, 6, 8 Hz, C$_3$—H), 5.85(d, J=8Hz, —CH—),
            |

7.99(s, NH), 9.16, 9.19(each d, J=8 Hz, NH), 9.60(d, J=8 Hz, NH).

(55)
(a)     3-[D-2-(2-Ureido-2-thienylacetamido)-2-(4-hydroxyphenyl)acetamido]-2-oxoazetidine
(b) 3-Amino-2-oxoazetidine
(c) B
(d) IR$\nu_{max}^{KBr}$cm$^{-1}$; 1760, 1650, 1530, 1510.

(56)
(a) 3-[D-N-(4-Ethyl-2,3-dioxo-1-piperazinocarbonyl)glutaminylamino]-2-oxoazetidine
(b) 3-Amino-2-oxoazetidine
(c) B
(d) IR$\nu_{max}^{KBr}$cm$^{-1}$; 1757, 1700, 1670.

(57)
(a)     3-[2-(4-Ethyl-2,3-dioxo-1-piperazinocarboxamido)-2-(1-cyclohexen-1-yl)acetamido]-2-oxoazetidine
(b) 3-Amino-2-oxoazetidine
(c) B
(d) IR$\nu_{max}^{KBr}$cm$^{-1}$; 3300, 2930, 1755, 1710, 1670. NMR(DMSO-d$_6$, ppm); 1.10(t, J=8 Hz, CH$_3$), 1.33-1.70(m, —CH$_2$—), 1.70-2.13(m, —CH$_2$—), 3.40(q, —CH$_2$—), 4.76(d, J=8Hz, —CH—), 5.73(broad s, ),
            |

7.93(s, NH), 8.73, 8.76(d, J=8 Hz, NH), 9.40(d, J=8 Hz, NH).

(58)
(a)     3-[2-(4-Ethyl-2,3-dioxo-1-piperazinocarboxamido)-2-(4-chlorophenyl)acetamido]-2-oxoazetidine
(b) 3-Amino-2-oxoazetidine
(c) IR$\nu_{max}^{KBr}$cm$^{-1}$; 1755, 1710, 1670, 1520. NMR(DMSO-d$_6$, ppm); 1.10(t, J=7 Hz, CH$_3$), 3.0(m, C$_4$—H), 3.42 (q, J=7 Hz, —CH$_2$—), 4.85(m, C$_3$—H), 5.44, 5.46(d, J=7Hz, —CH—),
            |

7.46(s, aromatic H), 8.02(broad s, NH), 9.16(d, J=8 Hz, NH), 9.84(d, J=7 Hz, NH).

(59)
(a)     3-[2-(4-Ethyl-2,3-dioxo-1-piperazinocarboxamido)-2-(4-trimethylsilylphenyl)acetamido]-2-oxoazetidine
(b) 3Amino-2-oxoazetidine
(c) IR$\nu_{max}^{KBr}$cm$^{-1}$; 1755, 1710, 1570, 1500. NMR(DMSO-d$_6$, ppm); 0.26(s, CH$_3$—), 3.0(m, C$_4$—H), 4.85(m, C$_3$—H), 5.42, 5.44(d, J=8Hz, —CH—),
            |

7.40(d, J=8 Hz, phenyl H), 7.54(d, J=8 Hz, phenyl H), 8.02(broad s, NH), 9.10(s, NH), 9.48(d, J=8 Hz, NH).

(60)
(a) 3-[D-N-(4-Ethyl-2,3-dioxo-1-piperazinocarbonyl)-methionyl-D-phenylglycinamido]-2-oxoazetidine
(b) 3-Amino-2-oxoazetidine
(c) B
(d) IR$\nu_{max}^{KBr}$cm$^{-1}$; 3300, 1760, 1710, 1675, 1640, 1520. NMR(DMSO-d$_6$, ppm); 1.08(t, J=7 Hz, CH$_3$), 2.06(s, CH$_3$), 2.96(dd, J=6 Hz, C$_4$—βH), 5.54(d, J=8Hz, —CH—),
            |

4.86(m, C$_3$—H), 7.96(broad s, NH), 9.26(d, J=8 Hz, NH).

(61)
(a)     3-[2-(4-Ethyl-2,3-dioxo-1-piperazinocarboxamido)-2-(1-cyclohexen-1-yl)acetamido]-3-methoxy-2-oxoazetidine
(b) 3-Amino-3-methoxy-2-oxoazetidine
(c) B
(d) IR$\nu_{max}^{KBr}$cm$^{-1}$; 3300, 1760, 1710, 1675. NMR(DMSO-d$_6$, ppm); 1.10(t, J=7 Hz, CH$_3$), 1.52(m, —CH$_2$—), 1.96(m, —CH$_2$—), 3.30(s, CH$_3$), 3.41(q, J=7 Hz, —CH$_2$—), 3.54(m, —CH$_2$—), 3.90(m, —CH$_2$—), 4.70, 4.97(each d, J=7Hz, —CH—), 5.84(broad s, ),
            |

8.31(broad s, NH), 9.44(broad s, NH), 9.38(d, J=7 Hz, NH).

(62)
(a) 3-[D-2-(3-Methylcarbamoyl-3-methyl-1-ureido)-2-phenylacetamido]-2-oxoazetidine
(b) 3-Amino-2-oxoazetidine
(c) B
(d) IR$\nu_{max}^{KBr}$cm$^{-1}$; 3270, 1756, 1687, 1662, 1626. NMR(DMSO-d$_6$, ppm); 2.72(d, J=4 Hz, —CH$_3$), 3.11(s, CH$_3$), 3.42(t, J=5 Hz, C$_4$—αH), 4.93(m, C$_3$—H), 5.42(d, J=7Hz, —CH—),
|

7.43(s, aromatic H, NH), 8.03(s, NH), 9.15(d, J=9 Hz, NH), 10.08(d, J=7 Hz, NH).

(63)
(a) 3-[2-(2-Methylcarbamoyl-3-methyl-1-ureido)-2-thienylacetamido]-2-oxoazetidine.
(b) 3-Amino-2-oxoazetidine
(c) B
(d) IR$\nu_{max}^{KBr}$cm$^{-1}$; 3275, 1755, 1680.

(64)
(a) 3-[D-2-(3-Methylcarbamoyl-3-methyl-1-ureido)-2-(4-benzyloxy)phenylacetamido]-2-oxoazetidine
(b) 3-Amino-2-oxoazetidine
(c) B
(d) IR$\nu_{max}^{KBr}$cm$^{-1}$; 3330, 3270, 1752, 1688, 1662, 1625.

(65)
(a) 3-[D-2-[3-(2-Benzyloxybenzoyl)-1-ureido]-2-phenylacetamido]-2-oxoazetidine
(b) 3-Amino-2-oxoazetidine
(c) B
(d) IR$\nu_{max}^{KBr}$cm$^{-1}$; 3330, 1763, 1692, 1668. NMR(DMSO-d$_6$, ppm); 3.03(dd, J=3, 6 Hz, C$_4$—H), 3.47(t, J=6 Hz, C$_4$—H), 4.93(m, C$_3$—H), 5.37(s, —CH$_2$—), 5.56(d, J=7Hz, —CH—),
|

7.47(s, aromatic H), 7.25-8.10(m, aromatic H), 8.17(s, NH), 9.27(d, J=7 Hz, NH), 9.63(d, J=7 Hz, NH), 10.43(s, NH).

(66)
(a) 3-[D-2-[3-(2-Benzyloxybenzoyl)-1-ureido]-2-(4-hydroxyphenyl)acetamido]-2-oxoazetidine
(b) 3-Amino-2-oxoazetidine
(c) B
(d) IR$\nu_{max}^{KBr}$cm$^{-1}$; 3300, 1743, 1688, 1662.

(67)
(a) 3-[D-2-(3-Chloro-4-hydroxyphenyl)-2-(4-ethyl-2,3-dioxo-1-piperazinocarboxamido)acetamido]-2-oxoazetidine
(b) 3-Amino-2-oxoazetidine
(c) B
(d) IR$\nu_{max}^{KBr}$cm$^{-1}$; 3300, 1750, 1713, 1685. NMR(DMSO-d$_6$, ppm); 1.13(t, J=7 Hz, —CH$_3$), 3.05(dd, J=2, 5 Hz, C$_4$—H), 3.30-3.53(m, —CH$_2$—, C$_4$—H), 3.53-4.2(m, —CH$_2$—), 4.97(m, C$_3$—H), 5.47(d, J=7Hz, —CH—),
|

7.00-7.73(m, aromatic H), 8.13(s, NH), 9.25(d, J=9 Hz, NH), 9.97(d, J=7 Hz, NH).

(68)
(a) 3-[D-2-(3-Chloro-4-methoxyphenyl)-2-(4-ethyl-2,3-dioxo-1-piperazinocarboxamido)acetamido]-2-oxoazetidine
(b) 3-Amino-2-oxoazetidine
(c) B
(d) IR$\nu_{max}^{KBr}$cm$^{-1}$; 3270, 1755, 1708, 1668.

(69)
(a) 3-[D-2-(2-Benzyloxycarboxamido-3-N-methylcarbamoylpropionamido)-2-phenylacetamido]-2-oxoazetidine (a mixture of diastereoisomers)
(b) 3-Amino-2-oxoazetidine
(c) B
(d) IR$\nu_{max}^{KBr}$cm$^{-1}$; 3290, 1766, 1690, 1640.

(70)
(a) 3-[D-2-(3-Benzyloxycarboxamido-3-N-methylcarbamoylpropionamido)-2-phenylacetamido]-2-oxoazetidine
(b) 3-Amino-2-oxoazetidine
(c) B
(d) IR$\nu_{max}^{KBr}$cm$^{-1}$; 3300, 1750, 1690, 1640, 1620.

(71)
(a) 3-[2-(2,5-Dioxopyrrolidin-3-yl)acetamido]-2-oxoazetidine
(b) 3-Amino-2-oxoazetidine
(c) B
(d) IR$\nu_{max}^{KBr}$cm$^{-1}$; 3240, 1750, 1710, 1680. NMR(DMSO-d$_6$, ppm); 2.3-3.6(m, —CH$_2$—, C$_4$—H), 4.6-5.0(m, C$_3$—H), 7.95(broad s, NH), 8.64(d, J=8 Hz, NH).

(72)
(a) 3-(2-Succinimidoacetamido)-2-oxoazetidine
(b) 3-Amino-2-oxoazetidine
(c) B
(d) IR$\nu_{max}^{KBr}$cm$^{-1}$; 3240, 1750, 1710, 1680. NMR(DMSO-d$_6$, ppm); 2.68(s, —CH$_2$—CH$_2$—), 3.02(dd, J=3, 5, 6 Hz, C$_4$—$\beta$H), 3.41(t, J=6 Hz, C$_4$—$\alpha$H), 3.98(s, —CH$_2$—), 4.6-5.0(m, C$_3$—H), 7.95(broad s, NH), 8.72(d, J=8 Hz, NH).

(73)
(a) 3-[2-(2-Carbobenzoxyaminomethylphenyl)acetamido]-2-oxoazetidine
(b) 3-Amino-2-oxoazetidine
(c) B
(d) IR$\nu_{max}^{KBr}$cm$^{-1}$; 3280, 1760, 1700, 1665. NMR(DMSO-d$_6$, ppm); 3.04(dd, J=3, 6 Hz, C$_4$—$\beta$H), 3.37(t, J=6 Hz, C$_4$—$\alpha$H), 3.54(s, —CH$_2$—), 4.25(d, J=6 Hz, —CH$_2$—), 4.65-5.0(m, C$_3$—H), 5.02(s, —CH$_2$—), 7.20(s, aromatic H), 7.33(s, aromatic H), 7.98(broad s, NH), 7.98(d, J=6 Hz, NH), 8.72(d, J=8 Hz, NH).

(74)
(a) 3-(2-Methoxyimino-2-furylacetamido)-2-oxoazetidine
(b) 3-Amino-2-oxoazetidine
(c) B
(d) IR$\nu_{max}^{KBr}$cm$^{-1}$; 3240, 1760, 1670. NMR(DMSO-d$_6$, ppm); 3.19(dd, J=3.5, 6 Hz, C$_4$—H), 3.28(s, —CH$_3$), 3.48(t, J=6 Hz, C$_4$—H), 4.7-5.1(m, C$_3$—H), 6.63(m, 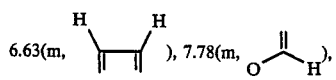), 7.78(m, ), 7.98(broad s, NH), 9.27(d, J=8 Hz, NH).

(75)
(a) 3-[2-[2-(3-Trichloroacetylureidomethyl)phenyl]acetamido]-2-oxoazetidine
(b) 3-Amino-2-oxoazetidine
(c) B
(d) IR$\nu_{max}^{KBr}$cm$^{-1}$; 3300, 1760, 1725, 1700, 1670. NMR(DMSO-d$_6$, ppm); 2.8-3.6(m, C$_4$—H), 3.58(s, —CH$_2$—), 4.42(d, J=6 Hz, —CH$_2$—), 4.6-5.1(m, C3—H), 7.27(s, aromatic H), 7.97(broad s, NH), 8.23(d, J=6 Hz, NH), 8.26(broad s, NH), 8.79(d, J=8.5 Hz, NH).

(76)
(a) 3-[2-(3,5-Dichloro-4-pyrridon-1-yl)acetamido]-2-oxoazetidine
(b) 3-Amino-2-oxoazetidine
(c) A
(d) IR$\nu_{max}^{KBr}$cm$^{-1}$; 3260, 3200, 1760, 1670, 1630, 1230. NMR(DMSO-d$_6$, ppm); 3.10(dd, J=3, 5.5 Hz, C$_4$—βH), 3.33(t, J=5.5 Hz, C$_4$—αH), 4.74(s, —CH$_2$—), 4.5-5.05(m, C$_3$—H), 7.99(broad s, NH), 8.17(s, 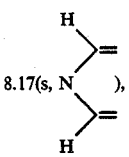 ), 8.93(d, J=8.5 Hz, NH).

(77)
(a) 3-(2-Benzyloxycarbonyl-2-phenylacetamido)-2-oxoazetidine
(b) 3-Amino-2-oxoazetidine
(c) B
(d) IR$\nu_{max}^{KBr}$cm$^{-1}$; 3380, 3320, 1780, 1735, 1665.

(78)
(a) 3-[2-(N-Carbobenzoxyprolinamido)-2-furylacetamido]-2-oxoazetidine
(b) 3-Amino-2-oxoazetidine
(c) B
(d) IR$\nu_{max}^{KBr}$cm$^{-1}$; 3270, 1765, 1700, 1665.

(79)
(a) 3-[2-(1-Acetyl-2,4-dioxoimidazolidin-3-yl)acetamido]-2-oxoazetidine
(b) 3-Amino-2-oxoazetidine
(c) B
(d) IR$\nu_{max}^{KBr}$cm$^{-1}$; 3290, 1810, 1763, 1735, 1690. NMR(DMSO-d$_6$, ppm); 2.45(s, CH$_3$), 3.01(dd, J=6, 3.5 Hz, C$_4$—βH), 3.44(t, J=6 Hz, C$_4$—αH), 4.07(s, —CH$_2$—), 4.28(s, —CH$_2$—), 4.87(ddd, J=3.5, 6 Hz, C$_3$—H), 7.99(broad s, NH), 8.83(d, J=8 Hz, NH).

(80)
(a) 3-[2-(2-Oxoimidazolidin-1-yl)acetamido]-2-oxoazetidine
(b) 3-Amino-2-oxoazetidine
(c) A
(d) IR$\nu_{max}^{KBr}$cm$^{-1}$; 3260, 1730, 1670. NMR(DMSO-d$_6$, ppm); 3.1-4.0(m, —CH$_2$—, C$_4$—H), 4.6-5.0(m, C$_3$—H), 7.54(broad s, NH), 7.88(broad s, NH), 8.56(d, J=8.5 Hz, NH).

(81)
(a) 3-[2-(4-Ethyl-2,3-dioxo-1-piperazinocarboxamido)-2-furylacetamido]-2-ozoazetidine
(b) 3-Amino-2-oxoazetidine
(c) B
(d) IR$\nu_{max}^{KBr}$cm$^{-1}$; 3290, 1770, 1725, 1700, 1680. NMR(DMSO-d$_6$, ppm); 1.10(t, J=7 Hz, CH$_3$—), 3.1-4.1(m, —CH$_2$—, C$_4$—H), 5.69(d, J=6.5Hz, —CH—), 7.20(m, 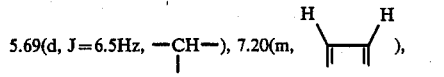

7.45(m, 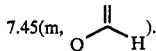 ).

(82)
(a) 3-[D-α-(Thienylmethylcarbonyl)alaninamido]-2-oxoazetidine
(b) 3-Amino-2-oxoazetidine
(c) E
(d) IR$\nu_{max}^{KBr}$cm$^{-1}$; 3260, 1740, 1645. NMR(DMSO-d$_6$, ppm); 1.19(d, J=6.5 Hz, —CH$_3$), 3.01(dd, J=3, 6 Hz, C$_4$—H), 3.28(s, —CH$_2$—), 3.37(t, J=6 Hz, C$_4$—H), 3.8-4.6(m, —CH—), 4.65(m, C$_3$—H), 6.87(m, 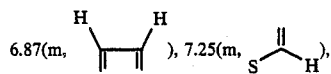 ), 7.25(m, 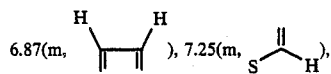 ), 7.81(broad s, NH), 8.17(d, J=8 Hz, NH), 8.53(d, J=6.5 Hz, NH).

(83)
(a) 3-(N-Carbobenzoxy-D-alaninamido)-3-methoxy-2-oxoazetidine
(b) 3-Amino-3-methoxy-2-oxoazetidine
(c) D
(d) IR$\nu_{max}^{KBr}$cm$^{-1}$; 1755, 1680, 1515. NMR(DMSO-d$_6$, ppm); 1.22(d, J=7 Hz, CH$_3$), 3.32(s, CH$_3$), 3.40, 3.48(each m, C$_4$—H), 4.12(m, —CH—), 5.04(s, CH$_2$), 7.36(s, aromatic H), 8.26(s, NH), 8.98(d, J=7 Hz, NH).

(84)
(a) 3-[N-(4-Ethyl-2,3-dioxo-1-piperazinocarbonyl)-D-alaninamido]-3-methoxy-2-oxoazetidine
(b) 3-Amino-3-methoxy-2-oxoazetidine
(c) E
(d) IR$\nu_{max}^{KBr}$cm$^{-1}$; 1760, 1710, 1670, 1510. NMR(DMSO-d$_6$, ppm); 1.10(t, J=7 Hz, CH$_3$), 1.34, 1.44(d, J=7 Hz, CH$_3$), 3.36(s, CH$_3$), 3.90(m, —CH$_2$—), 4.48(m, —CH—), 8.31(broad s, NH), 9.74(d, J=7 Hz, NH), 9.82(s, NH).

(85)
(a) 3-(N-Carbobenzoxy-D-phenylglycyl-D-phenylglycinamido)-3-methoxy-2-oxoazetidine
(b) 3-Amino-3-methoxy-2-oxoazetidine
(c) E
(d) IR$\nu_{max}^{KBr}$cm$^{-1}$; 1765, 1680, 1640, 1510. NMR(DMSO-d$_6$, ppm); 3.06, 3.26(s, CH$_3$), 3.40(m, C$_4$—H), 5.05(s, —CH$_2$—), 5.46(d, J=8Hz, —CH—), 5.60(d, J=8Hz, —CH—),
|

7.84(broad s, NH), 8.73(d, J=8 Hz, NH), 9.40(s, NH).

(86)
(a) 3-[N-(4-Ethyl-2,3-dioxo-1-piperazinocarbonyl)-D-methioninamido]-2-oxoazetidine
(b) 3-Amino-2-oxoazetidine
(c) B
(d) IR$\nu_{max}^{KBr}$cm$^{-1}$; 1750, 1705, 1670, 1520, 1190. NMR(DMSO-d$_6$, ppm); 1.10(t, J=7 Hz, CH$_3$), 1.96(m, —CH$_2$—), 2.05(s, CH$_3$), 2.44(t, J=7 Hz, —CH$_2$—), 3.08(q, J=2, 6 Hz, C$_4$—$\beta$H), 3.41(q, J=7 Hz, —CH$_2$—), 3.58(m, —CH$_2$—), 3.90(m, —CH$_2$—), 4.43(q, J=7Hz, —CH—),
|

4.84(m, C$_3$—H), 7.97(broad, s, NH), 8.82(d, J=7 Hz, NH), 9.43(d, J=7 Hz, NH).

(87)
(a) 3-[D-2-[2,3-Dioxo-4-(2-phenethyl)-1-piperazinocarboxamido]-2-phenylacetamido]-2-oxoazetidine
(b) 3-Amino-2-oxoazetidine
(c) B
(d) IR$\nu_{max}^{KBr}$cm$^{-1}$; 3280, 1755, 1710, 1670, 1500, 1190. NMR(DMSO-d$_6$, ppm); 2.84(t, J=7 Hz, —CH$_2$—), 2.95(dd, J=3, 6 Hz, C$_4$—$\beta$H), 4.88(ddd, J=3, 6, 8 Hz, C$_3$—H), 5.46(d, J=7Hz, —CH—),
|

7.25–7.5(m, aromatic H), 8.00(s, NH), 9.12(d, J=8 Hz, NH), 9.80(d, J=7 Hz, NH).

(88)
(a) 3-[D-2-(4-Ethyl-2,3-dioxo-1-piperazinocarboxamido)-2-(4-benzoyloxyphenyl)acetamido]-2-oxoazetidine
(b) 3-Amino-2-oxoazetidine
(c) B
(d) IR$\nu_{max}^{KBr}$cm$^{-1}$; 3280, 1755, 1730, 1710, 1670, 1500, 1265, 1205. NMR(d$_6$-DMSO, ppm); 1.10(t, —CH$_3$), 2.99(dd, J=3, 6 Hz, C$_4$—H), 3.41(q, —CH$_2$—), 3.42(t, J=6 Hz, C$_4$—H), 3.4–4.1(m, ring CH$_2$), 4.91(ddd, J=3, 6, 8 Hz, C$_3$—H), 5.53(d, J=7Hz, —CH—),
|

7.2–8.2(m, phenyl H), 8.02(s, NH), 9.19(d, J=8 Hz, NH), 9.88(d, J=7 Hz, NH).

(89)
(a) 3-(2-Benzyloxycarboxamido-3-N-methylcarbamoylpropionamido)-3-methoxy-2-oxoazetidine
(b) 3-Amino-3-methoxy-2-oxoazetidine
(c) B
(d) IR$\nu_{max}^{KBr}$cm$^{-1}$; 3350, 1760, 1700, 1650. NMR(CDCl$_3$, ppm); 2.73(m, CH$_3$, —CH$_2$—), 3.43(s, CH$_3$), 3.66(m, C$_4$—H), 4.63(m, —CH—),
|

5.12(s, —CH$_2$—), 6.70 (d, J=7 Hz, NH), 6.77(m, NH), 7.12(m, NH), 8.53(s, NH).

(90)
(a) 3-[2-(2-Chloroacetamido-4-thiazolyl)-2-[(3-furfurylideneamino-2-oxoimidazolidin-1-yl)-carboxamido]acetamido]-2-oxoazetidine
(b) 3-Amino-2-oxoazetidine
(c) B
(d) IR$\nu_{max}^{KBr}$cm$^{-1}$; 3310, 1750, 1725, 1660.

(91)
(a) 3-[D-2-(2-Phenylacetamido)propionamido]-3-methoxy-2-oxoazetidine
(b) 3-Amino-3-methoxy-2-oxoazetidine
(c) E
(d) IR$\nu_{max}^{KBr}$cm$^{-1}$; 1758, 1645, 1520. NMR(DMSO-d$_6$, ppm); 1.23, 1.24(each d, J=7 Hz, CH$_3$), 2.79, 2.95(each s, —CH$_2$—), 3.31, 3.47(each s, CH$_3$), 4.46(m, —CH—),
|

7.27(s, aromatic H), 8.1–8.35(m, NH), 8.98(d, J=7 Hz, NH).

(92)
(a) 3-[2-[[2-Oxo-3-(thiophene-2-aldimino)imidazolidin-1-yl]-carboxamido]-2-thienylacetamido]-2-oxoazetidine
(b) 3-Amino-2-oxoazetidine
(c) B
(d) IR$\nu_{max}^{KBr}$cm$^{-1}$; 3300, 1750, 1715, 1660.

(93)
(a) 3-[D-2-[(3-Mesyl-2-oxoimidazolidin-1-yl)-carboxamido]-2-phenylacetamido]-2-oxoazetidine
(b) 3-Amino-2-oxoazetidine
(c) B
(d) IR$\nu_{max}^{KBr}$cm$^{-1}$; 3320, 1750, 1730, 1665, 1165.

(94)
(a) 3-[2-[(3-Mesyl-2-oxoimidazolidin-1-yl)-carboxamido]-2-thienylacetamido]-2-oxoazetidine
(b) 3-Amino-2-oxoazetidine
(c) B
(d) IR$\nu_{max}^{KBr}$cm$^{-1}$; 3310, 1750, 1730, 1665, 1520.

(95)
(a) 3-[D-2-(2,6-Dichlorophenylthioglycolamido)-2-phenylacetamido]-2-oxoazetidine
(b) 3-Amino-2-oxoazetidine
(c) B
(d) IR$\nu_{max}^{KBr}$cm$^{-1}$; 1753, 1657, 1639. NMR(DMSO-d$_6$, ppm); 2.97(dd, J=3, 6 Hz, C$_4$—H), 3.36(t, J=6 Hz, C$_4$—H), 3.93(s, —CH$_2$—), 4.86(ddd, J=2, 6, 8 Hz, C$_3$—H), 5.47(d, J=7Hz, —CH—),
|

7.25, 8.0(m, aromatic H), 8.98(d, J=7 Hz, NH), 9.09(d, J=8 Hz, NH).

(96)
(a) 3-[D-2-(4-Ethyl-2,3-dioxo-1-piperazinocarboxamido)-3-phenylpropionamido]-3-methoxy-2-oxoazetidine (b) 3-Amino-3-methoxy-2-oxoazetidine
(c) A
(d) IR$\nu_{max}^{KBr}$cm$^{-1}$; 1760, 1700, 1660, 1518. NMR(DMSO-d$_6$, ppm); 1.09(t, J=7 Hz, CH$_3$—), 4.72(m, —CH—),
       |

5.32(s, NH), 9.15(d, J=7 Hz, NH), 9.43(s, NH).
(97)
(a) 3-(2-Dichloroacetoxyimino-2-thienylacetamido)-2-oxoazetidine
(b) 3-Amino-2-oxoazetidine
(c) A
(d) IR$\nu_{max}^{KBr}$cm$^{-1}$; 1745, 1720, 1670, 1650. NMR(DMSO-d$_6$, ppm); 3.18(dd, J=2, 6 Hz, C$_4$—$\beta$H), 3.45(t, J=6 Hz, C$_4$—$\alpha$H), 4.92(ddd, J=2, 6, 8 Hz, C$_3$—H), 6.44(s, —CH<), 7.06, 7.71(m, thienyl H), 7.91(s, NH), 9.14(d, J=8 Hz, NH).
(98)
(a) 3-(2-Phenyl-2-sulfamoylacetamido)-2-oxoazetidine
(b) 3-Amino-2-oxoazetidine
(c) B
(d) IR$\nu_{max}^{KBr}$cm$^{-1}$; 3320, 1730, 1662, 1540. NMR(DMSO-d$_6$, ppm); 3.20(dd, J=3, 6 Hz, C$_4$—H), 3.50(t, J=6 Hz, C$_4$—H), 4.87, 4.98(each dd, J=3, 6 Hz, C$_3$—H), 5.17(s, —CH—),
       |

7.3–7.8(m, aromatic H).
(99)
(a) 3-[2-(N,N-Dimethylsulfamoyl)-2-phenylacetamido]-2-oxoazetidine
(b) 3-Amino-2-oxoazetidine
(c) B
(d) IR$\nu_{max}^{KBr}$cm$^{-1}$; 3320, 1723, 1672, 1639, 1140. NMR(DMSO-d$_6$, ppm); 2.63, 2.67(s, CH$_3$), 3.02(m, C$_4$—H), 3.40, 3.46(t, J=6 Hz, C$_4$—H), 4.82(m, C$_3$—H), 5.28(s, —CH—),
       |

8.01(s, NH), 9.06(d, J=8 Hz, NH).
(100)
(a) 3-[2,5-Bis(4-ethyl-2,3-dioxo-1-piperazinocarboxamido)-pentanamido]-2-oxoazetidine
(b) 3-Amino-2-oxoazetidine
(c) B
(d) IR$\nu_{max}^{KBr}$cm$^{-1}$; 3300, 2930, 1760, 1720, 1670, 1520, 1188. NMR(DMSO-d$_6$, ppm); 1.09(t, J=7 Hz, —CH$_3$), 4.37(m, —CH—),
       |

4.80(m, C$_3$—H), 7.93(s, NH), 8.78(d, J=7 Hz, NH), 8.82(t, J=6 Hz, NH), 9.22(d, J=8 Hz, NH).
(101)
(a) 3-[2,5-Bis(4-ethyl-2,3-dioxo-1-piperazinocarboxamido)-pentanamido]-3-methoxy-2-oxoazetidine
(b) 3-Amino-3-methoxy-2-oxoazetidine
(c) B
(d) IR$\nu_{max}^{KBr}$cm$^{-1}$; 3300, 1768, 1712, 1679, 1520, 1190. NMR(DMSO-d$_6$, ppm); 1.09(t, J=7 Hz, CH$_3$), 3.33(s, CH$_3$), 4.51(m, —CH—),
       |

8.29(s, NH), 8.83(t, j=6 Hz, NH), 9.20(d, J=7 Hz, NH), 9.37(s, NH).
(102)
(a) 3-[D-2-[4-(2-Chloroethyl)-2,3-dioxo-1-piperazinocarboxamido]-2-phenylacetamido]-2-oxoazetidine
(b) 3-Amino-2-oxoazetidine
(c) B
(d) IR$\nu_{max}^{KBr}$cm$^{-1}$; 3250, 1760, 1705, 1670.
(103)
(a) 3-[D-3-Chloro-2-(4-ethyl-2,3-dioxo-1-piperazinocarboxamido)propionamido]-2-oxoazetidine
(b) 3-Amino-2-oxoazetidine
(c) B
(d) IR$\nu_{max}^{KBr}$cm$^{-1}$; 1750, 1710, 1670, 1510, 1185. NMR(DMSO-d$_6$, ppm); 1.10(t, J=7 Hz, CH$_3$), 3.05(dd, J=2, 6 Hz, C$_4$—$\beta$H), 3.42(q, J=7 Hz, —CH$_2$—), 3.56(m, —CH$_2$—), 3.92(m, —CH$_2$—), 4.72(m, —CH—),
       |

4.90(m, C$_3$—H), 8.00(broad s, NH), 8.92(d, J=7 Hz, NH), 9.48(d, J=7 Hz, NH).
(104)
(a) 3-[2-Benzyloxycarboxamido-2-benzyloxycarbonylethanesulfonamido]-2-oxoazetidine
(b) 3-Amino-2-oxoazetidine
(c) A
(d) IR$\nu_{max}^{KBr}$cm$^{-1}$; 1745, 1720, 1700, 1520, 1340, 1270, 1200, 1145. NMR(DMSO-d$_6$, ppm); 3.03(dd, J=2, 6 Hz, C$_4$—$\beta$H), 3.40(d, J=6 Hz, C$_4$—$\alpha$H), 3.58(dd, J=6, 14 Hz, —CH$_2$—), 4.60(m, —CH—, C$_3$—H),
       |

5.07(s, —CH$_2$—), 5.16(s, —CH$_2$—), 7.36, 7.38(each s, aromatic H), 7.88(d, J=7 Hz, NH), 8.02(broad s, NH), 8.34(d, J=7 Hz, NH).
(105)
(a) 3-[2-(4-Ethyl-2,3-dioxo-1-piperazinocarboxamido)-3-[(1-methyl-5H-tetrazol-5-yl)thio]propionamido]-2-oxoazetidine
(b) 3-Amino-2-oxoazetidine
(c) B
(d) IR$\nu_{max}^{KBr}$cm$^{-1}$; 1750, 1710, 1675, 1510, 1190. NMR(DMSO-d$_6$, ppm); 1.10(t, J=7 Hz, CH$_3$), 3.04(dd, J=2, 6 Hz, C$_4$—$\beta$H), 3.41(q, J=7 Hz, —CH$_2$—), 3.92(s, CH$_3$), 4.74(m, —CH—),
    |

4.82(m, C₃—H), 8.01(broad s, NH), 8.79(d, J=7 Hz, NH), 9.38(d, J=7 Hz, NH).

(106)
(a) 3-[D-2-(2-Benzyloxycarboxamido-2-benzyloxycarbonylethanesulfonamido)-2-phenylacetamido]-2-oxoazetidine
(b) 3-Amino-2-oxoazetidine
(c) E
(d) IR$\nu_{max}^{KBr}$cm$^{-1}$; 1750, 1710, 1680, 1520. NMR(DMSO-d₆, ppm); 2.96(dd, J=2, 6 Hz, C₄—βH), 4.40(m, —CH—),
    |

4.78(m, C₃—H), 5.04(s, —CH₂—), 5.11(s, —CH₂—), 7.2–7.6(m, aromatic H), 7.80(d, J=7 Hz, NH), 7.96(broad s, NH), 8.20(d, J=7 Hz, NH), 8.97(d, J=7 Hz, NH).

(107)
(a) 3-[D-2-(2-Benzyloxycarboxamido-3-sulfamoylpropionamido)-2-phenylacetamido]-2-oxoazetidine
(b) 3-Amino-2-oxoazetidine
(c) B
(d) IR$\nu_{max}^{KBr}$cm$^{-1}$; 1760, 1715, 1670, 1530.

(108)
(a) 3-[D-2-[2-Benzyloxycarboxamido-3-(4-methoxyphenyloxycarboxamido)propionamido]-2-phenylacetamido]-2-oxoazetidine
(b) 3-Amino-2-oxoazetidine
(c) B
(d) IR$\nu_{max}^{KBr}$cm$^{-1}$; 3300, 1762, 1675, 1640.

(109)
(a) 3-[D-2-[3-Benzyloxycarboxamido-2-(4-ethyl-2,3-dioxo-1-piperazinocarboxamido)propionamido]-2-phenylacetamido]-2-oxoazetidine
(b) 3-Amino-2-oxoazetidine
(c) B
(d) IR$\nu_{max}^{KBr}$cm$^{-1}$; 3295, 1758, 1705, 1670, 1640.

(110)
(a) 3-[2-[2-Benzyloxycarboxycarboxamido-3-(N-methylcarbamoyl)propionamido]acetamido-3-methoxy-2-oxoazetidine
(b) 3-Amino-3-methoxy-2-oxoazetidine
(c) E
(d) IR$\nu_{max}^{KBr}$cm$^{-1}$; 3390–3270, 1762, 1695–1650.NMR(DMSO-d₆, ppm); 2.55(d, J=5 Hz, CH₃), 2.40–2.60(m, —CH₂—), 3.30(s, CH₃), 3.40(ABq, J=6, 10 Hz, C₄—H), 3.75(d, J=6 Hz, CH₂), 4.33(m, —CH—),
    |

5.01(s, CH₂), 7.33(s, aromatic H), 7.70(m, NH), 8.04(d, J=5 Hz, NH), 8.25(s, NH), 8.88(s, NH), 9.10(m, NH).

(111)
(a) 3-[2-(4-Ethyl-2,3-dioxo-1-piperazinocarboxamido)acetamido]-3-methoxy-2-oxoazetidine
(b) 3-Amino-3-methoxy-2-oxoazetidine
(c) E
(d) IR$\nu_{max}^{KBr}$cm$^{-1}$; 3275, 1760, 1708, 1670. NMR(DMSO-d₆, ppm); 1.18(t, J=7 Hz, CH₃), 3.40(s, CH₃), 3.47(q, J=7 Hz, —CH₂—), 3.57–3.80(m, —CH₂—), 3.65(ABq, J=5, 11 Hz, C₄—H), 3.93–4.20(m, —CH₂—), 4.07(d, J=6 Hz, —CH₂—), 7.58(s, NH), 8.70(s, NH), 9.23(t, J=6 Hz, NH).

(112)
(a) 3-[D-2-[2-(4-Ethyl-2,3-dioxo-1-piperazinocarboxamido)-3-(N-methylcarbamoyl)propionamido]-2-phenylacetamido]-2-oxoazetidine
(b) 3-Amino-2-oxoazetidine
(c) B
(d) IR$\nu_{max}^{KBr}$cm$^{-1}$; 3300, 1748, 1708, 1662.

(113)
(a) 3-[2-(4-Ethyl-2,3-dioxo-1-piperazinocarboxamido-3-(N-methylcarbamoyl)propionamido]-2-oxoazetidine
(b) 3-Amino-2-oxoazetidine
(c) B
(d) IR$\nu_{max}^{KBr}$cm$^{-1}$; 3300, 1750, 1712, 1672.

(114)
(a) 3-[2-(D-2-Benzyloxycarboxamido-2-phenylacetamido)-3-(N-methylcarbamoyl)propionamido]-2-oxoazetidine
(b) 3-Amino-2-oxoazetidine
(c) B
(d) IR$\nu_{max}^{KBr}$cm$^{-1}$; 3300, 1752, 1690, 1645.

(115)
(a) 3-[D-2-(3-Furfurylideneamino-2-oxoimidazolidin-1-yl)carboxamido]-2-phenylacetamido]-3(S)-methoxy-2-oxoazetidine
(b) 3-Amino-3-methoxy-2-oxoazetidine
(c) A
(d) IR$\nu_{max}^{KBr}$cm$^{-1}$; 3280, 1760, 1670, 1475, 1410, 1230. NMR(DMSO-d₆, ppm); 3.08(s, CH₃), 3.42, 3.56(d, J=6 Hz, C₄—H), 3.79(s, —CH₂—), 5.62(d, J=7Hz, —CH—),
    |

6.5–7.9(m, aromatic H), 7.73(s, —CH=N—), 8.35(s, NH), 9.04(d, J=7 Hz, NH), 9.59(s, NH).

(116)
(a) 3-[D-2-[(3-Furfurylideneamino-2-oxoimidazolidin-1-yl)carboxamido]-2-phenylacetamido]-3(R)-methoxy-2-oxoazetidine
(b) 3-Amino-3-methoxy-2-oxoazetidine
(c) A
(d) IR$\nu_{max}^{KBr}$cm$^{-1}$; 3280, 1760, 1720, 1670, 1475, 1410, 1230. NMR(DMSO-d₆, ppm); 3.26, 3.42(d, J=6 Hz, C₄—H), 3.34(s, CH₃), 3.78(s, —CH₂—)

5.61(d, J=7Hz, —CH—),
    |

6.5–7.9(m, aromatic H), 7.73(s, —CH=N—), 8.23(s, NH), 8.98(d, J=7 Hz, NH), 9.54(s, NH).

(117)
(a) 3-[D-2-(4-Ethyl-2,3-dioxo-1-piperazinocarboxamido)-2-(4-octanoyloxyphenyl)acetamido]-2-oxoazetidine
(b) 3-Amino-2-oxoazetidine
(c) B (d) IR$\nu_{max}^{KBr}$cm$^{-1}$; 3280, 2925, 2850, 1750, 1710, 1670, 1500, 1190.

(118)
(a) 3-[D-3-(N-Ethoxycarbonylmethyl)carbamoyl-2-(4-ethyl-2,3-dioxo-1-piperazinocarboxamido)propionamido]-2-oxoazetidine
(b) 3-Amino-2-oxoazetidine
(c) B
(d) IR$\nu_{max}^{KBr}$cm$^{-1}$; 3300, 1740, 1705, 1668.

(119)
(a) 3-[D-2-(4-Ethyl-2,3-dioxo-1-piperazinocarboxamido)-3-(2-thienylacetamido)propionamido]-2-oxoazetidine
(b) 3-Amino-2-oxoazetidine
(c) B
(d) IR$\nu_{max}^{KBr}$cm$^{-1}$; 3300, 1750, 1710, 1670.

(120)
(a) 3-(N-mesyl-D-phenylglycinamido)-2-oxoazetidine
(b) 3-Amino-2-oxoazetidine
(c) B
(d) IR$\nu_{max}^{KBr}$cm$^{-1}$; 1750, 1705, 1670, 1520.

(121)
(a) 3-[D-2-[2-(4-Ethyl-2,3-dioxo-1-piperazinocarboxamido)acetamido]-2-phenylacetamido]-2-oxoazetidine
(b) 3-Amino-2-oxoazetidine
(c) B
(d) IR$\nu_{max}^{KBr}$cm$^{-1}$; 3275, 1760, 1712, 1673, 1665, 1650. NMR(DMSO-d$_6$, ppm); 1.10(t, J=7 Hz, CH$_3$), 3.00(dd, J=3, 5 Hz, C$_4$—H), 3.33–3.77(m, —CH$_2$—), 3.77–4.27(m, —CH$_2$—), 4.05(d, J=6 Hz, —CH$_2$—), 4.90(m, C$_3$—H), 5.53(d, J=9Hz, —CH—),
         |

7.37(s, aromatic H), 7.97(s, NH), 8.88(d, J=9 Hz, NH), 9.13(d, J=9 Hz, NH), 9.32(t, J=6 Hz, NH).

REFERENCE EXAMPLE 18

To a solution of 0.104 g of 3-amino-2-oxoazetidine in 4 ml of DMF are added 0.354 g of D-N-(3-furfurylideneamino-2-oxo-1-imidazolidinecarbonyl)alanine and 0.269 g of dicyclohexylcarbodiimide, and the mixture is stirred at room temperature for 8 hours. The crystalline precipitate is filtered off, and the filtrate is concentrated. Ethyl acetate is added to the residue, and the insoluble matters are collected by filtration and washed well with ethyl acetate (or the residue is purified by silica gel column chromatography) to give 0.373 g of 3-[D-2-[(3-furfurylideneamino-2-oxoimidazolidin-1-yl)carboxamido]propionamido]-2-oxoazetidine.
IR$\nu_{max}^{KBr}$cm$^{-1}$: 3275, 1760, 1725, 1660, 1415.

REFERENCE EXAMPLE 19

6.0 g of methyl 3-benzyloxycarboxamido-3-methoxy-2-oxoazetidine-1-(α-isopropylidene)acetate are dissolved in 150 ml of methylene chloride, and ozone gas is introduced into the solution at −50° to −30° C. The reaction mixture is blue after one hour. Then, the excess ozone gas is removed by the introduction of nitrogen gas, followed by addition of dimethyl sulphide. After stirring at room temperature for an hour, the reaction mixture is washed with water and the solvent is distilled off to give 6.1 g of methyl 3-benzyloxycarboxamido-3-methoxy-2-oxoazetidine-1-α-ketoacetate. 19 ml of 0.002% sodium methoxide in methanol are added to a solution of this product in 75 ml of methanol, and the mixture is stirred at room temperature for 15 minutes. After the addition of 0.3 g of acetic acid, the solvent is distilled off, and the residue is dissolved in ethyl acetate. The solution is washed with water, and the solvent is distilled off. The residue is chromatographed on a column of silica gel [eluted with ethyl acetate-n-hexane (1:1)] to obtain 2.7 g of 3-benzyloxycarboxamido-3-methoxy-2-oxoazetidine as crystals.
Optical rotation: [α]$_D^{25}$+68.2°(c=1, CH$_3$OH).
IR$\nu_{max}^{CHCl_3}$cm$^{-1}$: 3420, 1774, 1723.
NMR(CDCl$_3$, ppm): 3.45(s, CH$_3$), 3.60(d, J=6 Hz, C$_4$—H), 3.80(d, J=6 Hz, C$_4$—H), 5.14(s, —CH$_2$—), 6.74(broad s, NH), 7.34(s, arom.H)

REFERENCE EXAMPLE 20

A mixture of 0.2 g of 3-benzyloxycarboxamido-3-methoxy-2-oxoazetidine and 0.50 g of palladium black in 5 ml of THF is stirred in a hydrogen gas stream for 1.5 hours. The catalyst is filtered off and the filtrate is concentrated to obtain 0.09 g of 3-amino-3-methoxy-2-oxoazetidine.
IR$\nu_{max}^{Nujol}$cm$^{-1}$: 3250, 1740.
NMR(CDCl$_3$, ppm): 2.35(broad s, NH$_2$), 3.40(dd, J=6 Hz, C$_4$—H), 3.45(s, CH$_3$), 6.7(broad s, NH).

REFERENCE EXAMPLE 21

In 20 ml of methylene chloride is dissolved 0.116 g of 3-amino-3-methoxy-2-oxoazetidine, and the solution is cooled to −15° C. At this temperature, 15 ml of propylene oxide is added, and then 20 ml of a methylene chloride solution containing the acid chloride prepared from 1.06 g of D-N-(3-furfurylideneamino-2-oxo-1-imidazolidinecarbonyl)alanine is added. After stirring at the same temperature for 5 minutes, 0.712 g of pyridine is added and stirring is continued for an hour. The reaction mixture is concentrated under reduced pressure, and to the residue is added ice-water, followed by extraction with chloroform. The extract is washed with water and concentrated under reduced pressure, and the residue is purified by silica gel column chromatography to give 3-[D-2-[(3-furfurylideneamino-2-oxoimidazolin-1-yl)carboxamido]propionamido]-3(S)-methoxy-2-oxoazetidine [I] and 3-[D-2-[(3-furfurylideneamino-2-oxoimidazolin-1-yl)carboxamido]propionamido]-3(R)-methoxy-2-oxoazetidine [II].
For [I]:
IR$\nu_{max}^{KBr}$cm$^{-1}$: 3230, 1755, 1725, 1655, 1520, 1415, 1230.
NMR(DMSO-d$_6$, ppm): 1.30(d, J=7 Hz, CH$_3$), 3.35(s, OCH$_3$), 3.47(q, J=6, 8 Hz, C$_4$—H), 3.80(s, —CH$_2$—), 4.46(quintet, J=7Hz, —CH—),
         |

6.5–7.9(m, arom.H), 7.73(s, —CH=N—), 8.29(s, NH), 8.44(d, J=7 Hz, NH), 9.23(s, NH)
For [II]:
IR$\nu_{max}^{KBr}$cm$^{-1}$: 3230, 1755, 1725, 1655, 1520, 1415, 1230.
NMR(DMSO-d$_6$, ppm): 1.32(d, J=7 Hz, CH$_3$), 3.36(s, —OCH$_3$), 3.50(q, J=6, 12 Hz, C$_4$—H), 3.80(s, —CH$_2$—), 4.46(quintet, J=7Hz, —CH—),
|

6.5–7.9(m, arom.H), 7.73(s, —CH=N—), 8.32(s, NH), 8.45(d, J=7 Hz, NH), 9.29(s, NH)

REFERENCE EXAMPLE 22

The compounds shown below are prepared by reacting 3-amino-2-oxoazetidine with an acylating agent and treating the reaction mixture following the procedure as described in Reference Example 18 (=A) or Reference Example 21 (=B). In the following, (a) stands for the product, (b) for the procedure used, and (c) for the physico-chemical constants for the product.

(1)
 (a) 3-[D-2-(4-n-octyl-2,3-dioxo-1-piperazinecarboxamido)-2-thienylacetamido]-2-oxoazetidine
 (b) A
 (c) IR$\nu_{max}^{KBr}$cm$^{-1}$: 3280, 2925, 2855, 1755, 1710, 1675, 1505, 1190

(2)
 (a) 3-[D-2-(4-n-dodecyl-2,3-dioxo-1-piperazinecarboxamido)-2-phenylacetamido]-2-oxoazetidine
 (b) A
 (c) IR$\nu_{max}^{KBr}$cm$^{-1}$: 3280, 2920, 2850, 1755, 1710, 1675, 1505, 1085. NMR(DMSO-d$_6$, ppm): 0.86(t, CH$_3$), 2.95(dd, J=3, 6 Hz, C$_4$—$\beta$H), 3,38(t, J=6 Hz, C$_4$—$\alpha$H), 3.4–4.1(m, —CH$_2$—), 4.87(ddd, J=3, 6, 8 Hz, C$_3$—H), 5.46(d, J=7Hz, —CH—),
|

7.2–7.5(m, arom.H), 7.99(s, NH), 9.12(d, J=8 Hz, NH), 9.81(d, J=7 Hz, NH).

(3)
 (a) 3-[D-2-(4-n-amyl-2,3-dioxo-1-piperazinecarboxamido)-2-phenylacetamido]-2-oxoazetidine
 (b) A
 (c) IR$\nu_{max}^{KBr}$cm$^{-1}$: 3280, 1755, 1710, 1675, 1510. NMR(DMSO-d$_6$, ppm): 0.87(t, CH$_3$), 2.95(dd, J=3, 6 Hz, C$_4$—$\beta$H), 3.39(t, J=6 Hz, C$_4$—$\alpha$H), 3.4–4.1(m, —CH$_2$—), 4.88(ddd, J=3, 6, 8 Hz, C$_3$—H), 5.46(d, J=7Hz, —CH—),
|

7.2–7.5(m, arom.H), 8.00(s, NH), 9.12(d, J=8 Hz, NH), 9.82(d, J=7 Hz, NH).

(4)
 (a) 3-[D-2-(4-n-amyl-2,3-dioxo-1-piperazinecarboxamido)-2-thienylacetamido]-2-oxoazetidine
 (b) A
 (c) IR$\nu_{max}^{KBr}$cm$^{-1}$: 3280, 1755, 1710, 1675, 1505. NMR(DMSO-d$_6$, ppm): 0.87(t, CH$_3$), 3.01(dd, J=3, 6 Hz, C$_4$—$\beta$H), 3.42(t, J=6 Hz, C$_4$—$\alpha$H), 3.4–4.1(m, —CH$_2$—), 4,88(ddd, J=3, 6, 8 Hz, C$_3$—H), 5.73(d, J=7Hz, —CH—),
|

6.9–7.3(m, arom.H), 8.01(s, NH), 9.16(d, J=8 Hz, NH), 9.74(d, J=7 Hz, NH).

(5)
 (a) 3-[2-(5-chloro-2-chloroacetamidothiazol-4-yl)-2-methoxyiminoacetamido]-2-oxoazetidine
 (b) B
 (c) IR$\nu_{max}^{KBr}$cm$^{-1}$: 3260, 1740, 1665, 1555, 1040. NMR(DMSO-d$_6$, ppm): 3.08(dd, J=3, 6 Hz, C$_4$—$\beta$H), 3.49(t, J=6Hz, C$_4$—$\alpha$H), 3.94(s, OCH$_3$), 4.39(s, —CH$_2$—), 5.00 (ddd, J=3, 6, 8 Hz, C$_3$—H), 8.02(s, NH), 9.23(d, J=8 Hz, NH), 13.0(broad s, NH).

(6)
 (a) 3-[D-2-(4,6(R)-diethyl-2,3-dioxo-1-piperazinecarboxamido)-2-phenylacetamido]-2-oxoazetidine
 (b) A
 (c) IR$\nu_{max}^{KBr}$cm$^{-1}$: 3270, 1750, 1705, 1670, 1500, 1090. NMR(DMSO-d$_6$, ppm): 0.89(t, J=7 Hz, CH$_3$), 1.09(t, J=7 Hz, CH$_3$), 1.58(quintet, J=7 Hz, —CH$_2$—), 2.94(dd, J=3, 6 Hz, C$_4$—$\beta$H), 3.38(t, J=6 Hz, C$_4$—$\alpha$H), 4.87(ddd, J=3, 6, 8 Hz, C$_3$—H), 5.41(d, J=7Hz, —CH—),
|

7.2–7.5(m, arom.H), 7.97(s, NH), 9.08(d, J=8 Hz, NH), 9.85(d, J=7 Hz, NH).

(7)
 (a) 3-[D-2-(4,6(S)-diethyl-2,3-dioxo-1-piperazinecarboxamido)-2-phenylacetamido]-2-oxoazetidine
 (b) A
 (c) IR$\nu_{max}^{KBr}$cm$^{-1}$: 3270, 1750, 1705, 1670, 1500, 1090. NMR(DMSO-d$_6$, ppm): 0.81(t, J=7 Hz, CH$_3$), 1.10(t, J=7 Hz, CH$_3$), 1.3–1.7(m, —CH$_2$—), 2.95(dd, J=3, 6 Hz, C$_4$—$\beta$H), 3.39(t, J=6 Hz, C$_4$—$\alpha$H), 4.87(ddd, J=3, 6, 8 Hz, C$_3$—H), 5.41(d, J=7Hz, —CH—),
|

7.2–7.3(m, arom.H), 7.99(s, NH), 9.14(d, J=8 Hz, NH), 9.84(d, J=7 Hz, NH).

(8)
 (a) 3-(2-phenyl-2-p-tolylthioiminoacetamido-2-oxoazetidine
 (b) A
 (c) IR$\nu_{max}^{KBr}$cm$^{-1}$: 3250, 1755, 1725, 1645. NMR(DMSO-d$_6$, ppm): 2.33(s, CH$_3$), 3.28(dd, J=3, 6 Hz, C$_4$—$\beta$H), 3.55(t, J=6 Hz, C$_4$—$\alpha$H), 4.8–5.2(m, C$_3$—H), 7.2–7.8(m, arom.H), 7.96, 8.06(each s, NH), 8.88(d, J=8 Hz, NH), 9.46(d, J=8 Hz, NH).

(9)
 (a) 3-[D-2-(4-cyclohexyl-2,3-dioxo-1-piperazinecarboxamido)-2-phenylacetamido]-2-oxoazetidine
 (b) A
 (c) IR$\nu_{max}^{Kbr}$cm$^{-1}$: 3280, 2930, 1755, 1710, 1670, 1505, 1180. NMR(DMSO-d$_6$, ppm): 2.94(dd, J=3, 6 Hz, C$_4$—$\beta$H), 3.38(t, J=6 Hz, C$_4$—$\alpha$H), 3.4–3.9(m, —CH$_2$—), 4.86(ddd, J=3, 6, 8 Hz, C$_3$—H), 5.44(d, J=7Hz, —CH—),
       |

7.2–7.5(m, arom.H), 7.97(s, NH), 9.09(d, J=8 Hz, NH), 9.78(d, J=7 Hz, NH).

(10)
(a) 3-(2,6-dimethoxybenzamido)-2-oxoazetidine
(b) A
(c) IR$\nu_{max}^{KBr}$cm$^{-1}$: 3370, 1760, 1725, 1648, 1593, 1470, 1250, 1110. NMR(DMSO-d$_6$, ppm): 3.08(dd, J=3, 6 Hz, C$_4$—H), 3.48(t, J=6 Hz, C$_4$—H), 3.76(s, CH$_3$), 5.01(ddd, J=3, 6, 9 Hz, C$_3$—H), 6.67(d, J=9 Hz, arom.H), 7.30(t, J=9 Hz, arom.H), 7.91(s, NH), 8.62(d, J=9 Hz, NH).

(11)
(a) 3-[D-2-(4-n-amyl-6(R)-methyl-2,3-dioxo-1-piperazinecarboxamido)-2-thienylacetamido]-2-oxoazetidine
(b) A
(c) IR$\nu_{max}^{KBr}$cm$^{-1}$: 3280, 1762, 1710, 1680, 1500, 1192. NMR(DMSO-d$_6$, ppm): 0.88(t, J=7 Hz, CH$_3$), 1.25(d, J=6 Hz, CH$_3$), 3.01(dd, J=2, 6 Hz, C$_4$—H), 3.41(t, J=6 Hz, C$_4$—H), 4.66(m, —CH—),
        |

4.88(ddd, J=2, 6, 8 Hz, C$_3$—H), 5.69(d, J=7Hz, —CH—),
        |
        N 6.9–7.2(m, arom.H), 7.42(m, arom.H), 9.15(d, J=8 Hz, NH), 9.80(d, J=7 Hz, NH).

(12)
(a) 3-[D-2-(4-n-amyl-6(S)-methyl-2,3-dioxo-1-piperazinecarboxamido)-2-thienylacetamido]-2-oxoazetidine
(b) A
(c) IR$\nu_{max}^{KBr}$cm$^{-1}$: 3275, 1760, 1710, 1670, 1500, 1190. NMR(DMSO-d$_6$, ppm): 0.88(t, J=7 Hz, CH$_3$), 1.22(d, J=6 Hz, CH$_3$), 3.03(dd, J=2, 6 Hz, C$_4$—H), 3.41(t, J=6 Hz, C$_4$—H), 4.68(m, —CH—),
        |

4.88(ddd, J=2, 6, 8 Hz, C$_3$—H), 5.72(d, J=7Hz, —CH—),
        |
        N 6.9–7.2(m, arom.H), 7.43(m, arom.H), 9.21 (d, J=8 Hz, NH), 9.80(d, J=7 Hz, NH)

(13)
(a) 3-[D-2-(4-n-amyl-6-methyl-2,3-dioxo-1-piperazinecarboxamido)-3-chloropropionamido]-2-oxoazetidine
(b) A
(c) IR$\nu_{max}^{KBr}$cm$^{-1}$: 3300, 1750, 1713, 1675, 1510, 1200. NMR (DMSO-d$_6$, ppm): 0.88(t, J=6 Hz, CH$_3$), 1.24(d, J=6 Hz, CH$_3$), 2.80(dd, J=2, 6 Hz, C$_4$—H), 4.28(m, —CH—), 4.65(m, —CH—),
        |                |

4.86(m, C$_3$—H), 7.96(broad s, NH), 8.72(d, J=8 Hz, NH), 9.35(d, J=7 Hz, NH).

(14)
(a) 3-[D-2-[[3-(2,6-dichlorophenyl)-5-methylisoxazol-4-yl]carboxamido]-2-thienylacetamido]-2-oxoazetidine
(b) A
(c) IR$\nu_{max}^{KBr}$cm$^{-1}$: 3270, 1755, 1653. NMR(DMSO-d$_6$, ppm): 2.71(s, CH$_3$), 2.96(dd, J=3, 6 Hz, C$_4$—H), 3.37(t, J=6 Hz, C$_4$—H), 4.80(m, C$_3$—H), 5.70(d, J=8Hz, —CH—),
        |

6.97(m, arom.H), 7.39(m, arom.H), 7.55 (s, arom.H), 7.94(d, J=7 Hz, NH), 7.91(broad s, NH), 9.01(d, J=8 Hz, NH).

(15)
(a) 3-[D-2-(4-ethyl-5(R)-methyl-2,3-dioxo-1piperazinecarboxamido)-2-thienylacetamido]-2-oxoazetidine
(b) A
(c) IR$\nu_{max}^{KBr}$cm$^{-1}$: 3270, 1755, 1702, 1665, 1500, 1180. NMR(DMSO-d$_6$, ppm): 1.14(t, J=7 Hz, CH$_3$), 1.20(d, J=7 Hz, CH$_3$), 3.02(dd, J=3, 6 Hz, C$_4$—H), 3.43(t, J=6 Hz, C$_4$—H), 4.88(m, C$_3$—H), 5.73(d, J=7Hz, —CH—),
        |

8.01(s, NH), 9.18(d, J=8 Hz, NH), 9.72(d, J=7 Hz, NH).

(16)
(a) 3-[D-2-(4-ethyl-5(S)-methyl-2,3-dioxo-1-piperazinecarboxamido)-2-thienylacetamido]-2-oxoazetidine
(b) A
(c) IR$\nu_{max}^{KBr}$cm$^{-1}$: 3270, 1755, 1705, 1665, 1500, 1180. NMR(DMSO-d$_6$, ppm): 1.12(t, J=7 Hz, CH$_3$), 1.22(d, J=6 Hz, CH$_3$), 3.00(dd, J=3, 6 Hz, C$_4$—H), 3.42(t, J=6 Hz, C$_4$—H), 4.90(m, C$_3$—H), 5.70(d, J=7Hz, —CH—),
        |

6.9–7.2(m, arom.H), 7.4–7.5(m, arom.H), 8.00(s, NH), 9.16(d, J=8 Hz, NH), 9.70(d, J=7 Hz, NH).

(17)
(a) 3-[D-2-[(2-oxoimidazolidin-1-yl)carboxamido]-2-thienylacetamido]-2-oxoazetidine
(b) A
(c) IR$\nu_{max}^{KBr}$cm$^{-1}$: 3270, 1750, 1725, 1658. NMR(DMSO-d$_6$, ppm): 2.90–4.00(m, —CH$_2$—, C$_4$—H), 4.83(m, C$_3$—H), 5.68(d, J=8Hz, —CH—), 7.10–7.37(m, arom.H), 7.45(s, NH), 7.87(s, NH), 9.00(d, J=8 Hz, NH).

(18)
(a) 3-[D-2-[(5-methoxycarbonyl-3-methyl-2-oxoimidazolidin-1-yl)carboxamido]-2-phenylacetamido]-2-oxoazetidine
(b) A
(c) IR$\nu_{max}^{KBr}$cm$^{-1}$: 3280, 1750, 1720, 1660. NMR(DMSO-d$_6$, ppm): 2.76(s, CH$_3$), 2.95(dd, J=3, 6 Hz, (C$_4$—H), 3.34(dd, J=4, 10 Hz, —CH$_2$—), 3.38(t, J=6 Hz, C$_4$—H), 3.69(s, OCH$_3$), 4.66(dd, J=4, 10Hz, —CH—), 4.85(m, C$_3$—H), 5.40(d, J=8Hz, —CH—), 7.33(s, arom.H), 7.98(s, NH), 9.07(d, J=8 Hz, NH), 9.11(d, J=8 Hz, NH).

(19)
(a) 3-[D-2-[(5-benzyloxycarbonyl-3-methyl-2-oxoimidazolidin-1-yl)carboxamido]-2-phenylacetamido]-2-oxoazetidine
(b) A
(c) IR$\nu_{max}^{KBr}$cm$^{-1}$: 3310, 1750, 1740, 1712, 1688, 1660. NMR(DMSO-d$_6$, ppm): 2.74(s, CH$_3$), 2.92(dd, J=3, 5 Hz, C$_4$—H), 3.20–3.47(m, C$_4$—H, —CH$_2$—), 3.68(t, J=10 Hz, —CH$_2$—), 4.65(dd, J=4, 10Hz, —CH—), 4.83(m, C$_3$—H), 5.15(s, —CH$_2$—), 5.39(d, J=8Hz, —CH—), 7.34(s, arom.H), 7.96(s, NH), 9.08(d, J=8 Hz, NH), 9.12(d, J=8 Hz, NH).

(20)
(a) 3-[2-(4-ethyl-2,3-dioxo-1-piperazinecarboxamido)-2-(2-chloro-1-cyclohexene-1-yl)acetamido]-2-oxoazetidine
(b) A
(c) IR$\nu_{max}^{KBr}$cm$^{-1}$: 1760, 1715, 1670, 1510

(21)
(a) 3-[2-(2-tritylaminothiazol-4-yl)-2-[(1-t-buthoxycarbonyl-1-methyl)ethoxyimino]acetamido]-2-oxoazetidine
(b) A
(c) IR$\nu_{max}^{KBr}$cm$^{-1}$: 1760, 1725, 1675, 1520, 1140 NMR(DMSO-d$_6$, ppm): 1.33(s, CH$_3$), 3.03(dd, J=2, 6 Hz, C$_4$—βH), 3.20(s, —CH$_2$—), 3.36(t, J=6 Hz, C$_4$—αH), 4.86 (m, C$_3$—H), 6.66(s, ⟩=CH—H), 7.15–7.40(m, arom.H), 7.90(broad s, NH), 8.66(s, NH), 8.70(d, J=8 Hz, NH).

(22)
(a) 3-[2-(2-chloroacetamidothiazol-4-yl)-2-(1-methylethoxyimino)acetamido]-2-oxoazetidine
(b) A
(c) IR$\nu_{max}^{KBr}$cm$^{-1}$: 3250, 1750, 1655, 1540 NMR(DMSO-d$_6$, ppm):

1.22(d, J=6Hz, —C(CH$_3$)(CH$_3$) ), 3.13(dd, J=2, 6 Hz, C$_4$—βH), 3.46(t, J=6 Hz, C$_4$—αH), 4.33(s, —CH$_2$—), 4.33(quintet, J=6Hz, —CH(CH$_3$)(CH$_3$) ), 5.0(m, C$_3$—H), 7.36(s, ⟩=CH—H), 8.0(broad s, NH), 9.10(d, J=8 Hz, NH)

(23)
(a) 3-(2-oxo-2-phenylacetamido)-2-oxoazetidine
(b) B
(c) IR$\nu_{max}^{KBr}$cm$^{-1}$: 3280, 1745, 1720, 1660. NMR(DMSO-d$_6$, ppm): 3.31(dd, J=3, 5 Hz, C$_4$—H), 3.49(t, J=5 Hz, C$_4$—H), 5.00(ddd, J=3, 5, 8 Hz, C$_3$—H), 7.45–8.20 (m, arom.H), 8.01(s, NH), 9.55(d, J=8 Hz, NH).

(24)
(a) 3-[2-(2-mesylaminothiazol-4-yl)-2-(1-methylethoxyimino)acetamido]-2-oxoazetidine
(b) B
(c) IR$\nu_{max}^{KBr}$cm$^{-1}$: 3275, 1750, 1660, 1535, 1120 NMR(DMSO-d$_6$, ppm):

1.27(d, J=6Hz, —⟨(CH$_3$)(CH$_3$) ), 2.96(s, CH$_3$), 3.14(dd, J=3, 5 Hz, C$_4$—H), 3.48(t, J=5 Hz, C$_4$—H), 4.36(heptet, J=6Hz, —CH—), 4.95(m, C$_3$—H), 6.88(s, ⟩=CH—H), 8.01(s, NH), 9.20(d, J=8 Hz, NH).

(25)

(a) 3-(2-bromo-2-phenylacetamido)-2-oxoazetidine
(b) A
(c) IR$\nu_{max}^{KBr}$cm$^{-1}$: 3280, 1755, 1730, 1660. NMR(DMSO-d$_6$, ppm): 3.03–3.73(m, C$_4$—H), 3.47, 3,52 (each t, J=5 Hz, C$_4$—H), 4.94(m, C$_3$—H), 5.63(s, —CH—),
         |

7.30–7.90(m, arom.H), 8.07(s, NH), 9.28(d, J=9 Hz, NH).

(26)
(a) 3-(2-azido-2-phenylacetamido)-2-oxoazetidine
(b) A
(c) IR$\nu_{max}^{KBr}$cm$^{-1}$: 3300, 2103, 1752, 1670. NMR(DMSO-d$_6$, ppm): 3.47(t, J=6 Hz, C$_4$—H), 3.50(t, J=6 Hz, C$_4$—H), 5.00(m, C$_3$—H), 5.09(s, —CH—),
         |

7.52(s, arom. H), 8.07(broad s, NH), 9.12(d, J=8 Hz, NH).

(27)
(a) 3-tosylamino-2-oxoazetidine
(b) B
(c) IR$\nu_{max}^{KBr}$cm$^{-1}$: 3265, 3080, 1745, 1330, 1155. NMR(DMSO-d$_6$, ppm): 2.49(s, CH$_3$), 2.98(dd, J=3, 5 Hz, C$_4$—H), 3.30(t, J=5 Hz, C$_4$—H), 4.60(m, C$_3$—H),

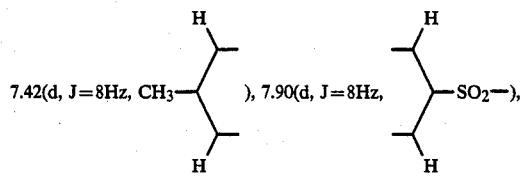

8.26(d, J=8 Hz, NH)

(28)
(a) 3-(2-phthalimido-2-thienylacetamido)-2-oxoazetidine
(b) A
(c) IR$\nu_{max}^{KBr}$cm$^{-1}$: 3280, 1760, 1710, 1660, 1520, 1380, 1100, 720. NMR(DMSO-d$_6$, ppm): 2.99, 3.20(each dd, J=4, 2 Hz, C$_4$—βH), 3.40, 3.43(each t, J=4 Hz, C$_4$—αH), 4.70–5.15 (m, C$_3$—H), 6.20

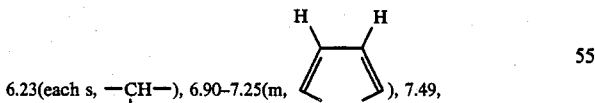

7.97, 8.00 (s, arom.H), 8.83, 8.93(each d, J=6 Hz, NH).

(29)
(a) 3-[2-azido-2-(3-chlorophenyl)acetamido]-2-oxoazetidine
(b) A
(c) IR$\nu_{max}^{KBr}$cm$^{-1}$: 3250, 2100, 1750, 1660. NMR(DMSO-d$_6$, ppm): 3.20–3.70(m, C$_4$—H), 5.08(s, —CH—),
         |

4.90–5.20(m, C$_3$—H), 6.93(s, NH), 7.40(s, arom.H), 8.03(m, NH)

(30)
(a) 3-(2-azido-2-phenylacetamido)-3-methoxy-2-oxoazetidine
(b) B
(c) IR$\nu_{max}^{KBr}$cm$^{-1}$: 3260, 2100, 1755, 1682 NMR(CDCl$_3$, ppm): 3.36, 3.43(each s, CH$_3$), 3.75(dd, J=6 Hz, C$_4$—H), 5.15(s, —CH—),
         |

6.95(s, NH), 7.50(s, arom.H), 8.08(s, NH).

(31)
(a) 3-[D-2-(4-cyclohexyl-2,3-dioxo-1-piperazinecarboxamido)-2-thienylacetamido]-2-oxoazetidine
(b) A
(c) IR$\nu_{max}^{KBr}$cm$^{-1}$: 3280, 2930, 1755, 1710, 1670, 1505, 1190 NMR(DMSO-d$_6$, ppm): 3.01(dd, J=3, 6 Hz, C$_4$—βH), 3.42(t, J=6 Hz, C$_4$—αH), 4.87(ddd, J=3, 6, 8 Hz, C$_3$—H), 5.72(d, J=7Hz, —CH—),
              |

6.9–7.5(m, arom.H), 7.99(s, NH), 9.15(d, J=8 Hz, NH), 9.73(d, J=7 Hz, NH).

(32)
(a) 3-[2-(2-aminothiazol-4-yl)-2-(1-methylethoxyimino)acetamido]-3-methoxy-2-oxoazetidine
(b) B
(c) IR$\nu_{max}^{KBr}$cm$^{-1}$: 1735, 1690, 1665, 1540, 1255. NMR(DMSO-d$_6$, ppm): 0.28, 0.30(each s, Si(CH$_3$)$_2$), 1.00(s, Si-t-Bu), 1.15,

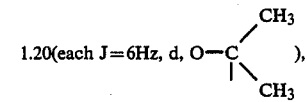

3.57(s, OCH$_3$), 3.70(d, J=7 Hz, C$_4$—H), 3.95(d, J=7 Hz, C$_4$—H), 4.25(s, —CH$_2$—), 4.28(quintet J=6 Hz, —CH<), 7.40(s, [thiazole H]), 8.00(broad s, NH), 10.66(broad s, NH).

(33)
(a) 3-[2-(2-mesylaminothiazol-4-yl)-2-(1-methylethoxyimino)acetamido]-3-methoxy-2-oxoazetidine
(b) B
(c) IR$\nu_{max}^{KBr}$cm$^{-1}$: 3250, 1760, 1672, 1535, 1120. NMR(DMSO-d$_6$, ppm): 1.25(d, J=6 Hz, CH$_3$), 2.94(s, CH$_3$), 3.41(s, CH$_3$), 4.36(m, —CH—), 6.90(s, 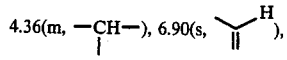,
|

8.34(s, NH).

(34)
(a) 3-[D-2-(4-cyclohexyl-2,3-dioxo-1-piperazinecarboxamido)-2-thienylacetamido]-3-methoxy-2-oxoazetidine
(b) B
(c) $IR\nu_{max}^{KBr}cm^{-1}$: 2920, 1760, 1705, 1670, 1500, 1170. NMR(DMSO-$d_6$, ppm): 3.18(s, $CH_3$), 3.48(ABq, J=6, 12 Hz, $C_4$—H), 5.87(d, J=7Hz, —CH—),
|

6.9–7.6(m, arom.H). 8.34 (s, NH), 9.66(s, NH), 9.71(d, J=7 Hz, NH).

(35)
(a) 3-methoxy-3-[D-2-(4-piperidinecarbonyl-2,3-dioxo-1-piperazinecarboxamido)-2-thienylacetamido]-2-oxoazetidine
(b) B
(c) $IR\nu_{max}^{KBr}cm^{-1}$: 3280, 2930, 1760, 1705, 1680, 1640. NMR(DMSO-$d_6$, ppm): 3.20(s, $CH_3$), 4.32(s, —$CH_2$—), 5.89(d, J=7Hz, —CH—),
|

6.9–7.6(m, arom.H), 8.36(s, NH), 9.69(s, NH), 9.72(d, J=7 Hz, NH).

(36)
(a) 3-methoxy-3-[D-2-(4-phenyl-2,3-dioxo-1piperazinecarboxamido)-2-thienylacetamido]-2-oxoazetidine
(b) B
(c) $IR\nu_{max}^{KBr}cm^{-1}$: 3275, 1760, 1705, 1680, 1490, 1200. NMR(DMSO-$d_6$, ppm): 3.21(s, $CH_3$), 3.44, 3.57(each d, J=6 Hz, $C_4$—H), 5.92(d, J=7Hz, —CH—),
|

6.9–7.6(m, arom.H), 8.36(s, NH), 9.70(s, NH), 9.78(d, J=7 Hz, NH).

(37)
(a) 3-[D-2-(4-t-butyl-2,3-dioxo-1-piperazinecarboxamido)-2-thienylacetamido]-3-methoxy-2-oxoazetidine
(b) B
(c) $IR\nu_{max}^{KBr}cm^{-1}$: 3280, 2970, 1760, 1710, 1675, 1505, 1200. NMR(DMSO-$d_6$, ppm): 1.4(s, $CH_3$), 3.43, 3.55(each d, J=6 Hz, $C_4$—H), 3.19(s, $CH_3$), 5.88(d, J=7Hz, —CH—),
|

6.9–7.6(m, arom.H), 8.36(s, NH), 9.67(d, J=7 Hz, NH), 9.67(s, NH).

(38)
(a) 3-[D-2-[4-(3-methyl-2-butenyl)-2,3-dioxo-1-piperazinecarboxamido]-2-thienylacetamido]-3-methoxy-2-oxoazetidine
(b) B
(c) $IR\nu_{max}^{KBr}cm^{-1}$: 3250, 1770, 1705, 1675, 1660, 1510, 1185. NMR(DMSO-$d_6$, ppm): 1.70(d, J=3 Hz, $CH_3$), 3.19(s, $CH_3$), 3.43, 3.55(each d, J=6 Hz, $C_4$—H), 5.88(d, J=7Hz, —CH—),
|

6.9–7.6(m, arom.H), 8.35(s, NH), 9.67(s, NH), 9.73(d, J=7 Hz, NH).

(39)
(a) 3-[D-2-phenyl-2-[[3-(3-thienylidene)amino-2-oxoimidazolydin-1-yl]carboxamido]acetamido]-2-oxoazetidine
(b) A
(c) $IR\nu_{max}^{KBr}cm^{-1}$: 3280, 1750, 1710.

(40)
(a) 3-[2-[4-(tetrahydropyran-2-yloxy)phenyl]-2-(4-methoxyphenyloxycarbonyl)acetamido]-3-methoxy-2-oxoazetidine
(b) B
(c) $IR\nu_{max}^{KBr}cm^{-1}$: 1750, 1680, 1505, 1240. NMR(DMSO-$d_6$, ppm): 1.4–1.9(m, —$CH_2$—), 3.14, 3.30 (each s, $CH_3$), 3.76(s, $CH_3$), 4.87(s, —CH—), 5.06(s, —$CH_2$—), 5.43(broad s, —CH<), 8.33, 8.24(each s, NH), 9.41, 9.45(each s, NH).

(41)
(a) 3-[2-[(1-carboxy-1-methylethoxy)imino]-2-(2-tritylaminothiazol-4-yl)acetamido]-2-oxoazetidine
(b) A
(c) $IR\nu_{max}^{KBr}cm^{-1}$: 1750, 1615, 1526. NMR(DMSO-$d_6$, ppm): 1.34(s, $CH_3$), 1.40(s, $CH_3$), 3.05 (dd, J=3,6 Hz, $C_4$—H), 3.18(t, J=6 Hz, $C_4$—H), 4.73(m, $C_3$—H), 6.72(s, 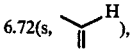), 7.17–7.50(m, arom.H), 7.83(s, NH), 8.58(s, NH), 9.58(d, J=9 Hz, NH).

EXAMPLE 1

In 15 ml of N,N-dimethylformamide (DMF) is dissolved 1.23 g of 3-phenylacetamido-2-oxoazetidine, followed by addition of 1.15 g of pyridine-sulfur trioxide complex. The mixture is stirred for 6 hours. After 50 ml of diethyl ether is added, the powdery precipitate is collected by filtration and washed with ether and, then, with ethanol. By the above procedure is obtained 1.47 g of pyridinium 3-phenoxyacetamido-2-oxoazetidine-1-sulfonate.

$IR\nu_{max}^{KBr}cm^{-1}$; 3300, 1775, 1665, 1300–1190, 1045. NMR($d_6$-DMSO, ppm); 3.25(dd, J=3, 6 Hz, $C_4$—H), 3.46(s, —$CH_2$—), 3.62(t, J=6 Hz, $C_4$—H), 4.84(ddd, J=3, 6, 8 Hz, $C_3$—H), 7.29 (s, aromatic H), 7.9–9.0(m, aromatic H), 8.83(d, J=8 Hz, NH).

EXAMPLE 2

In 2 ml of DMF is dissolved 0.21 g of 3-thienylacetamido-2-oxoazetidine, followed by addition of 0.318 g of pyridine-sulfur trioxide complex. The mixture is stirred for one day. To the reaction mixture is added 20 ml of diethyl ether and the oily precipitate is purified by Amberlite XAD-II [Rohm and Haas Co., (U.S.A)] chromatography. 0.175 g of 3-(thienylacetamido)-2-oxoazetidine-1-sulfonic acid is obtained.

IR$\nu_{max}^{KBr}$cm$^{-1}$; 1760, 1660, 1250, 1050.

NMR(d$_6$-DMSO, ppm); 3.32(dd, J=3, 6 Hz, C$_4$—H), 3.61(t, J=6 Hz, C$_4$—H), 3.69(s, —CH$_2$—), 4.84(ddd, J=3, 6, 8 Hz, C$_3$—H), 6,8–7.4(m, aromatic H), 8.88(d, J=8 Hz, NH).

EXAMPLE 3

In 10 ml of DMF is dissolved 0.631 g of 3-[2-(2-chloroacetamido-4-thiazolyl)-2-methoxyiminoacetamido]-2-oxoazetidine (syn-isomer), followed by addition of 0.637 g of pyridine-sulfur trioxide complex. The mixture is stirred for 3 days. To this reaction mixture is added 30 ml of diethyl ether, and the oily precipitate is passed through Dowex 50W resin (Na-form) (Dow Chemical (U.S.A.)]. The eluate is freeze-dried to obtain 0.89 g of crude sodium 3-[2-(2-chloroacetamido-4-thiazolyl)-2-methoxyiminoacetamido]-2-oxoazetidine-1-sulfonate (syn-isomer).

IR$\nu_{max}^{KBr}$cm$^{-1}$; 3430, 1760, 1690, 1650, 1140.

NMR(D$_2$O, ppm); 3.95(dd, J=3, 6 Hz, C$_4$—H), 4.12(s, —CH$_3$), 4.15(t, J=6 Hz, C$_4$—H), 4.93(s, —CH$_2$Cl), 5.22(dd, J=3, 6 Hz, C$_3$—H),

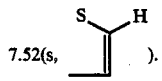

7.52(s, ).

The crude sodium 3-[2-(2-chloroacetamido-4-thiazolyl)-2-methoxyiminoacetamido]-2-oxoazetidine-1-sulfonate (syn-isomer) obtained above (0.556 g) is dissolved in 8 ml of water, and to the solution is added 0.172 g of sodium N-methyldithiocarbamate under ice-cooling and stirring. The mixture is stirred for 3 hours, after which any insoluble matter is filtered off. The filtrate is purified by XAD-II chromatography to yield 0.174 g of sodium 3-[2-(2-amino-4-thiazolyl)-2-methoxyiminoacetamido]-2-oxoazetidine-1-sulfonic (syn-isomer).

IR$\nu_{max}^{KBr}$cm$^{-1}$; 3450, 1770, 1670, 1610, 1260, 1050.

NMR(D$_2$O, ppm); 3.89(dd, J=4, 6 Hz, C$_4$—H), 4.03(s, —CH$_3$), 4.09(t, J=6 Hz, C$_4$—H), 5.16(dd, J=4, 6 Hz, C$_3$—H),

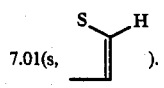

7.01(s, ).

EXAMPLE 4

In 20 ml of DMF is suspended 0.515 g of 3-[2-(2-chloroacetamido-4-thiazolyl)acetamido]-2-oxoazetidine, followed by addition of 0.325 g of pyridine-sulfur trioxide complex. The mixture is worked up as described in Example 3 to obtain 0.569 g of sodium 3-[2-(2-chloroacetamido-4-thiazolyl)acetamido]-2-oxoazetidine-1-sulfonate.

IR$\nu_{max}^{KBr}$cm$^{-1}$; 3430, 1760, 1660, 1550, 1260, 1150, 1050.

NMR(d$_6$-DMSO, ppm); 3.30(dd, J=3, 6 Hz, C$_4$—H), 3.52(s, —CH$_2$—), 3.60(t, J=6 Hz, C$_4$—H), 4.34(s, —CH$_2$Cl), 4.85(ddd, J=3, 6, 8 Hz, C$_3$—H),

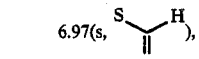

6.97(s, ), 8.74(d, J=8 Hz, NH).

In 6 ml of water is dissolved 0.486 g of sodium 3-[2-(2-chloroacetamido-4-thiazolyl)acetamido]-2-oxoacetidine-1-sulfonate, and to the solution is added 0.154 g of sodium N-methyldithiocarbamate under ice-cooling and stirring. The mixture is treated as described in Example 3 to obtain 0.144 g of sodium 3-[2-(2-amino-4-thiazolyl)acetamido]-2-oxoazetidine-1-sulfonate.

IR$\nu_{max}^{KBr}$cm$^{-1}$; 3400, 3270, 1760, 1650, 1610, 1270, 1235, 1200, 1050.

NMR(d$_6$-DMSO, ppm); 3.25(dd, J=3, 6 Hz, C$_4$—H), 3.30(s, —CH$_2$—), 3.62(t, J=6 Hz, C$_4$—H), 4.85(ddd, J=3, 6, 8 Hz, C$_3$—H),

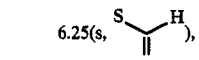

6.82(s, NH$_2$), 8.66(d, J=8 Hz, NH).

EXAMPLE 5

In 5 ml of DMF is dissolved 0.46 g of 3-(α-sulfophenylacetamido)-2-oxoazetidine sodium salt, followed by addition of 0.478 g of pyridine-sulfur trioxide complex. The mixture is stirred for 3 days. To the reaction mixture is added 30 ml of diethyl ether and the oily precipitate is passed through Dowex 50 W resin(Na-form). The eluate is purified by Amberlite XAD-II chromatography. By the above procedure is obtained 0.61 g of disodium 3-(α-sulfophenylacetamido)-2-oxoazetidine-1-sulfonate.

IR$\nu_{max}^{KBr}$cm$^{-1}$; 3450, 1760, 1660, 1630, 1200–1100, 1045.

NMR(d$_6$-DMSO, ppm); 3.17(dd, J=3, 6 Hz, C$_4$-H), 3.58(t, J=6 Hz, C$_4$—H),

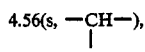

4.56(s, —CH—), 4.76(m, C$_3$—H), 7.2–7.6(m, aromatic H), 8.55(d, J=8 Hz, NH).

EXAMPLE 6

In 3 ml of DMF is dissolved 0.285 g of 3-[2-(4-ethyl-2,3-dioxo-1-piperazinocarboxamido)-2-phenylacetamido]-2-oxoazetidine, followed by addition of 0.234 g of pyridine-sulfur trioxide complex. The mixture is stirred for 4 days, after which it is worked up as described in Example 5. The above procedure yields 0.219 g of sodium 3-[2-(4-ethyl-2,3-dioxo-1-piperazinocarboxamido)-2-phenylacetamido]-2-oxoacetidine-1-sulfonate.

IR$\nu_{max}^{KBr}$cm$^{-1}$; 3470, 3280, 1760, 1705, 1670, 1510, 1250, 1190, 1050.

NMR(d$_6$-DMSO, ppm); 1.10(t, J=7 Hz, —CH$_3$), 3.13(dd, J=3, 6 Hz, C$_4$—H), 3.41(q, J=7 Hz, —CH$_2$—), 3.45-3.65(m, —CH$_2$—), 3.59(t, J=6 Hz, C$_4$—H), 3.80-4.00(m, —CH$_2$—), 4.85(ddd, J=3, 6, 8 Hz, C$_3$—H), 5.45(d, J=8Hz, —CH—),
|

7.2-7.5(m, aromatic H), 9.20(d, J=8 Hz, NH), 9.81(d, J=8 Hz, NH).

EXAMPLE 7

In 1 ml of DMF is dissolved 0.177 g of 3-(2-benzyloxycarboxamido-2-phenylacetamido)-2-oxoazetidine, followed by addition of 0.16 g of pyridine-sulfur trioxide complex. The mixture is stirred for 4 days. To this reaction mixture is added 10 ml of diethyl ether and the oily precipitate is treated with ethanol to obtain 0.092 g of pyridinium 3-(2-benzyloxycarboxamido-2-phenylacetamido)-2-oxoazetidine-1-sulfonate.

IR$\nu_{max}^{KBr}$cm$^{-1}$; 3280, 1765, 1685, 1660, 1300-2100, 1040.

NMR(d$_6$-DMSO, ppm); 3.16(dd, J=4, 6 Hz, C$_4$—H), 3.57(t, J=6 Hz, C$_4$—H), 4.83(ddd, J=4, 6, 8 Hz, C$_3$—H), 5.07(s, —CH$_2$—), 5.26(d, J=8Hz, —CH—),
|

7.36(s, aromatic H), 7.85(broad d, NH), 7.9-90(m, aromatic H).

EXAMPLE 8

In 2 ml of DMF is dissolved 0.25 g of 3-benzyloxycarboxamido-3-methoxy-2-oxoazetidine, followed by addition of 0.318 g of pyridine-sulfur trioxide complex. The mixture is stirred for 5 days. By working up as described in Example 3, 0.35 g of sodium 3-benzyloxycarboxamido-3-methoxy-2-oxoazetidine-1-sulfonate is obtained.

IR$\nu_{max}^{KBr}$cm$^{-1}$; 3450, 1760, 1715, 1250, 1140, 1050.

EXAMPLE 9

In 7 ml of DMF is dissolved 0.825 g of 3-[2-(2-chloroacetamido-4-thiazolyl)-2-methoxyiminoacetamido]-3-methoxy-2-oxoazetidine (syn-isomer), followed by addition of 0.796 g of pyridine-sulfur trioxide complex. The mixture is reacted for 3 days. By working up as described in Example 5, 0.568 g of sodium 3-[2-(2-chloroacetamido-4-thiazolyl)-2-methoxyiminoacetamido]-3-methoxy-2-oxoazetidine-1-sulfonate (syn-isomer) is obtained.

IR$\nu_{max}^{KBr}$cm$^{-1}$; 3470, 3250, 1770, 1670, 1540, 1280, 1230, 1170, 1050.

NMR(d$_6$-DMSO, ppm); 3.43(s, —CH$_3$), 3.61, 3.84(ABq, J=6 Hz, C$_4$—H), 3.92(s, —CH$_3$), 4.39(s, —CH$_2$—), 7.44(s, 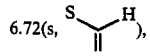 ), 9.89(s, NH), 12.7(broad, NH).

In 7 ml of water is dissolved 0.478 g of the above sodium 3-[2-(2-chloroacetamido-4-thiazolyl)-2-methoxyiminoacetamido]-3-methoxy-2-oxoazetidine-1-sulfonate (syn-isomer), followed by addition of 0.13 g of sodium N-methyl dithiocarbamate. The mixture is stirred for one hour. The insoluble matter is filtered off and the filtrate is purified by Amberlite XAD-II chromatography, whereupon 0.267 g of sodium 3-[2-(2-amino-4-thiazolyl)-2-methoxyiminoacetamido)-3-methoxy-2-oxoazetidine-1-sulfonate (syn-isomer) is obtained.

IR$\nu_{max}^{KBr}$cm$^{-1}$; 3425, 3325, 1765, 1670, 1615, 1520, 1290-20, 1170, 1045.

NMR(d$_6$-DMSO, ppm); 3.41(s, —CH$_3$), 3.59, 3.79(ABq, J=6 Hz, C$_4$—H), 3.87(s, —CH$_3$), 6.72(s, 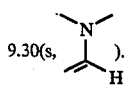 ), 7.12(broad s, NH), 9.79(s, NH).

EXAMPLE 10

In 0.5 ml of DMF is dissolved 0.15 g of 3-cyanoacetamido-2-oxoazetidine, followed by addition of 0.30 g of pyridine-sulfur trioxide complex. The mixture is stirred for 3 days, and the reaction mixture is treated as described in Example 5, whereupon 0.183 g of sodium 3-cyanoacetamido-2-oxoazetidine-1-sulfonate is obtained.

IR$\nu_{max}^{KBr}$cm$^{-1}$; 2270, 1760, 1660, 1250.

NMR(D$_2$O, ppm); 3.91(dd, J=2, 6 Hz, C$_4$—H), 3.96(s, —CH$_2$—), 4.05(t, J=6 Hz, C$_4$—H), 5.08(dd, J=2, 6 Hz, C$_3$—H).

EXAMPLE 11

In 1 ml of DMF is dissolved 0.16 g of 3-[2-(1H-tetrazol-1-yl)acetamido]-2-oxoazetidine, followed by addition of 0.26 g of pyridine-sulfur trioxide complex. The mixture is stirred at room temperature for 3 days. By working up as described in Example 5, 0.154 g of sodium 3-[2-(1H-tetrazol-1-yl)acetamido]-2-oxoazetidine-1-sulfonate is obtained.

IR$\nu_{max}^{KBr}$cm$^{-1}$; 1762, 1665, 1250.

NMR(d$_6$-DMSO, ppm); 3.21(dd, J=2, 6 Hz, C$_4$—H), 3.61(t, J=6 Hz, C$_4$—H), 4.85(ddd, J=2, 6, 8 Hz, C$_3$—H), 5.26(s, —CH$_2$—), 9.22(d, J=8 Hz, NH), 9.30(s, N—
         \\
          ).
         /
         H

EXAMPLE 12

In 1 ml of DMF is dissolved 0.214 g of 3-[3-(2,6-dichlorophenyl)-5-methylisoxazol-4-yl]carboxamido-2-oxoazetidine, followed by addition of 0.20 g of pyridine-sulfur trioxide complex. The mixture is stirred for 3 days. By working up as described in Example 5, 0.212 g of sodium 3-[3-(2,6-dichlorophenyl)-5-methylisoxazol-4-yl]carboxamido-2-oxoazetidine-1-sulfonate is obtained.

IR$\nu_{max}^{KBr}$cm$^{-1}$; 1762, 1665, 1250.

NMR(d$_6$-DMSO, ppm); 2.77(s, —CH$_3$), 3.25(dd, J=2, 6 Hz, C$_4$—H), 3.57(t, J=6 Hz, C$_4$—H), 4.86(ddd, J=2, 6, 8 Hz, C$_3$—H), 7.53(s, aromatic H), 8.74(d, J=8 Hz, NH).

EXAMPLE 13

A solution of 0.44 g of 3-benzyloxycarboxamido-2-oxoazetidine and 0.32 g of pyridine-sulfur trioxide complex in 2 ml of DMF is allowed to stand at room temperature for 2 days. By working up as described in Example 1, 0.613 g of pyridinium 3-benzyloxycarboxamido-2-oxoazetidine-1-sulfonate is obtained as light-yellow needles.

m.p. 134°–138° C. (decomp.).

Elemental analysis, $C_{16}H_{17}N_3O_6S$: Calcd.: C, 50.65; H, 4.52; N, 11.08. Found: C, 50.57; H, 4.51; N, 11.04.

$IR_{max}^{KBr}cm^{-1}$; 3320, 1760, 1695, 1530, 1270, 1240, 1055.

NMR($d_6$-DMSO, ppm); 3.30(dd, J=2, 6 Hz, $C_4$—H), 3.62(dd, J=6 Hz, $C_4$—H), 4.64(ddd, J=8, 6, 2 Hz, $C_3$—H), 5.06(s, —$CH_2$—), 6.60–7.40(broad s, NH), 8.0(d, J=8 Hz, NH),

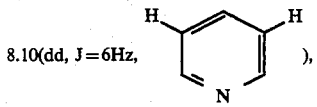
8.10(dd, J=6Hz, ),

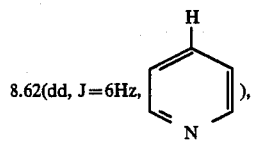
8.62(dd, J=6Hz, ),

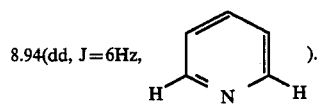
8.94(dd, J=6Hz, ).

EXAMPLE 14

A mixture of 2.185 g of 3-(N-carbobenzoxy-D-alaninamido)-2-oxoazetidine, 2.39 g of pyridine-sulfur trioxide complex and 10 ml of dry DMF is stirred at room temperature for 4 days. To this reaction mixture is added diethyl ether, whereby 2.7 g of pyridinium 3-(N-carbobenzoxy-D-alaninamido)-2-oxoazetidine-1-sulfonate is obtained as colorless needles.

m.p. 120°–125° C. (decomp.)

$IR\nu_{max}^{KBr}cm^{-1}$; 1762, 1678, 1660, 1525, 1250, 1040.

NMR($d_6$-DMSO, ppm); 1.22(d, J=7 Hz, $CH_3$), 3.27(dd, J=6, 2 Hz, $C_4$—H), 3.63(t, J=6 Hz, $C_4$—H), 4.03(q, J=7Hz, —CH—), 4.90(ddd, J=8, 6, 2 Hz, $C_3$—H), 5.03(s, —$CH_2$—), 7.33(s, aromatic H), 8.0–9.1(m, aromatic H).

The above pyridinium 3-(N-carbobenzoxy-D-alaninamido)-2-oxoazetidine-1-sulfonate (0.15 g) is treated with Dowex 50 W (Na-form) to obtain the sodium salt. To the solution is added 20 mg of acetic acid and 50 mg of palladium black, and the mixture is stirred in hydrogen gas streams for 20 minutes. The catalyst is filtered off and the filtrate is freeze-dried to obtain 84 mg of sodium 3-D-alaninamido-2-oxoazetidine-1-sulfonate acetate.

$IR\nu_{max}^{KBr}cm^{-1}$; 1760, 1670, 1550, 1260, 1240, 1045.

NMR($D_2O$, ppm); 1.62(d, J=7 Hz, —$CH_3$), 1.98(s, —$CH_3$), 3.80 (dd, J=2, 6 Hz, $C_4$—H), 3.99(t, J=6 Hz, $C_4$—H), 4.20(q, J=7Hz, —CH—), 5.00(dd, J=2, 6 Hz, $C_3$—H).

EXAMPLE 15

A mixture of 0.30 g of 3-(α-benzyl N-carbobenzoxy-γ-D-glutamyl-D-alaninamido)-2-oxoazetidine, 0.187 g of pyridine-sulfur trioxide complex and 1 ml of DMF is stirred until a homogenous solution is obtained and the solution is allowed to stand at room temperature for 12 hours. By working up as described Example 7, 0.26 g of pyridinium 3-(α-benzyl N-carbobenzoxy-γ-D-glutamyl-D-alaninamido)-2-oxoazetidine-1-sulfonate is obtained as crystals.

$IR\nu_{max}^{KBr}cm^{-1}$; 3300, 1760, 1740, 1690, 1640, 1570, 1270, 1210, 1045.

The above pyridinium 3-(α-benzyl N-carbobenzoxy-γ-D-glutamyl-D-alaninamido)-2-oxoazetidine-1-sulfonate (0.26 g) is passed through Dowex 50 W (Na-form), and the eluate is freeze-dried and dissolved in 20 ml of water. To the solution is added 0.20 g of palladium black and the mixture is stirred in hydrogen gas streams for an hour. The catalyst is filtered off and the filtrate is freeze-dried to yield 0.1 g of sodium 3-(γ-D-glutamyl-D-alaninamido)-2-oxoazetidine-1-sulfonate.

$IR\nu_{max}^{KBr}cm^{-1}$; 1760, 1650, 1630, 1530, 1260, 1240, 1050.

NMR($D_2O$, ppm); 1.43(d, J=7 Hz, —$CH_3$), 2.16(q, J=7 Hz, —$CH_2$—), 2.54(t, J=7 Hz, —$CH_2$—), 3.74(dd, J=2, 6 Hz, $C_4$—H), 3.80(t, J=6Hz, —CH—), 3.97(t, J=6 Hz, $C_4$—H), 4.34(q, J=7Hz, —CH—), 4.96(dd, J=2, 6 Hz, $C_3$—H).

EXAMPLE 16

In 4.5 ml of 60% ethanol is dissolved 0.13 g of pyridinium 3-benzyloxycarboxamido-2-oxoazetidine-1-sulfonate, followed by addition of 0.13 g of 10% palladium-carbon (hydrous; Nippon Engelhard Industries Ltd.). The mixture is stirred in hydrogen gas streams at room temperature for 1.5 hours. The catalyst is filtered off and the filtrate is concentrated to give 60 mg of 3-amino-2-oxoazetidine-1-sulfonic acid.

$IR\nu_{max}^{KBr}cm^{-1}$; 3400, 1750, 1240, 1050.

NMR($D_2O$, ppm); 3.56(dd, J=3, 6 Hz, $C_4$—H), 4.05(t, J=6 Hz, $C_4$—H), 4.45(dd, J=3, 6 Hz, $C_3$—H).

In 1 ml of water is dissolved 50 mg of the above 3-amino 2-oxoazetidine-1-sulfonic acid, followed by addition of a solution of 69 mg phenylacetyl chloride in 1 ml tetrahydrofuran and 101 mg of sodium hydrogen carbonate in alternate portions with ice-cooling and stirring. After stirring at room temperature for 30 minutes, the mixture is adjusted to pH 5.8 with phosphoric acid. The tetrahydrofuran is then distilled off under reduced pressure. The water layer is washed with ethyl acetate and purified by XAD-II chromatography, whereby 42 mg of sodium 3-phenylacetamido-2-oxoazetidine-1-sulfonate is obtained.

$IR\nu_{max}^{KBr}cm^{-1}$; 3310, 1780, 1670, 1300–1200, 1080, 1065.

NMR(d$_6$-DMSO, ppm); 3.27(dd, J=3, 6 Hz, C$_4$—H), 3.46(s, —CH$_2$—), 3.60(t, J=6 Hz, C$_4$—H), 4.84(ddd, J=3, 6, 8 Hz, C$_3$—H), 7.29(s, aromatic H), 8.83(d, J=8 Hz, NH).

EXAMPLE 17

In 5 ml of DMF is dissolved 0.349 g of 3-(α-ureidophenylacetamido)-2-oxoazetidine, followed by addition of 0.955 g of pyridine-sulfur trioxide complex. The mixture is stirred for 4 days. By working up as described in Example 5, the following two products are obtained. Sodium 3-(α-ureidophenylacetamido)-2-oxoazetidine-1-sulfonate, 86 mg.

IR$\nu_{max}^{KBr}$cm$^{-1}$; 3430, 3340, 1755, 1650, 1510, 1240, 1190, 1040.

NMR(d$_6$-DMSO, ppm); 3.14(dd, J=3, 6 Hz, C$_4$—H), 3.54(t, J=6 Hz, C$_4$—H), 4.83(ddd, J=3, 6, 8 Hz, C$_3$—H), 5.28(d, J=8Hz, —CH—), 5.68(s, NH$_2$), 6.80(d, J=8 Hz, NH), 7.35(broad s, aromatic H), 9.12(d, J=8 Hz, NH).

Disodium 3-(α-sulfonatoureidophenylacetamido)-2-oxoazetidine-1-sulfonate, 0.455 g.

IR$\nu_{max}^{KBr}$cm$^{-1}$; 3440, 1755, 1660, 1520, 1230, 1140, 1040.

NMR(d$_6$-DMSO, ppm); 3.14(dd, J=3, 6 Hz, C$_4$—H), 3.57(t, J=6 Hz, C$_4$—H), 4.83(ddd, J=3, 6, 8 Hz, C$_3$—H), 5.33(d, J=8Hz, —CH—), 7.2–7.5(m, aromatic H), 7.6(d, J=8 Hz, NH), 8.36(broad s, NH), 9.18(d, J=8 Hz, NH).

EXAMPLE 18

In 3 ml of DMF is dissolved 0.313 g of 3-[2-(4-ethyl-2,3-dioxo-1-piperazinocarboxamido)-2-phenylacetamido]-3-methoxy-2-oxoazetidine, followed by addition of 0.359 g of pyridine-sulfur trioxide complex. The mixture is stirred for 5 days, and the reaction mixture is treated in the manner as described in Example 5, 0.202 g of sodium 3-[2-(4-ethyl-2,3-dioxo-1-piperazinocarboxamido)-2-phenylacetamido]-3-methoxy-2-oxoazetidine-1-sulfonate is obtained.

IR$\nu_{max}^{KBr}$cm$^{-1}$; 3460, 1770, 1710, 1675, 1510, 1250, 1190, 1050.

EXAMPLE 19

In 4 ml of DMF is dissolved 0.404 g of 3-[2-(4-ethyl-2,3-dioxo-1-piperazinocarboxamido)-4-hydroxyphenylacetamido]-2-oxoazetidine, followed by addition of 0.637 g of pyridine-sulfur trioxide complex. The mixture is stirred for 4 days, and the reaction mixture is treated in the manner as described in Example 5, 0.203 g of disodium 3-[2-(4-ethyl-2,3-dioxo-1-piperazinocarboxamido)-2-(4-sulfonatoxyphenyl)acetamido]-2-oxoazetidine-1-sulfonate is obtained.

IR$\nu_{max}^{KBr}$cm$^{-1}$; 3470, 1760, 1710, 1675, 1500, 1250, 1190, 1050.

NMR(d$_6$-DMSO, ppm); 1.09(t, J=7 Hz, CH$_3$), 3.19(dd, J=3, 5 Hz, C$_4$—H), 3.42(q, J=7 Hz, —CH$_2$—), 4.86(m, C$_3$—H), 5.40(d, J=7Hz, —CH—), 7.24(ABq, J=9, 17 Hz, aromatic H), 9.20(d, J=8 Hz, NH), 9.76(d, J=7 Hz, NH).

EXAMPLE 20

In 2 ml of DMF is dissolved 0.404 g of 3-[2-(4-ethyl-2,3-dioxo-1-piperazinocarboxamido)-2-(4-hydroxyphenyl)acetamido]-2-oxoazetidine, followed by addition of 0.191 g of pyridine-sulfur trioxide complex. The mixture is stirred for 4 days. By working up as described in Example 5, 0.096 g of disodium 3-[2-(4-ethyl-2,3-dioxo-1-piperazinocarboxamido)-2-(4-sulfonatoxyphenyl)acetamido]-2-oxoazetidine-1-sulfonate and 0.08 g of sodium 3-[2-(4-ethyl-2,3-dioxo-1-piperazinocarboxamido)-2-(4-hydroxyphenyl)acetamido]-2-oxoazetidine-1-sulfonate are obtained. Properties of the latter compound:

IR$\nu_{max}^{KBr}$cm$^{-1}$; 3470, 3300, 1755, 1710, 1675, 1500, 1265, 1240, 1190, 1050.

NMR(d$_6$-DMSO, ppm); 1.09(t, J=7 Hz, —CH$_3$), 2.97(dd, J=3, 5 Hz, C$_4$—H), 3.34(q, J=7 Hz, —CH$_2$—), 3.35(t, J=5 Hz, C$_4$—H), 4.84(m, C$_3$—H), 5.40(d, J=7Hz, —CH—), 7.24(ABq, J=8, 16 Hz, aromatic H), 7.99(s, OH), 9.10(d, J=8 Hz, NH), 9.77(d, J=7 Hz, NH).

EXAMPLE 21

In 3 ml of DMF is dissolved 0.128 g of 3-(4-ethyl-2,3-dioxo-1-piperazinocarboxamido)-2-oxoazetidine, followed by addition of 0.16 g of pyridine-sulfur trioxide complex. The mixture is stirred for 3 days. By working up as described in Example 5, 0.095 g of sodium 3-(4-ethyl-2,3-dioxo-1-piperazinocarboxamido)-2-oxoazetidine-1-sulfonate is obtained.

IR$\nu_{max}^{KBr}$cm$^{-1}$; 3300, 1760, 1710, 1675, 1520, 1260, 1180, 1050.

EXAMPLE 22

In 3 ml of DMF is dissolved 0.326 g of 3-[N-(4-ethyl-2,3-dioxo-1-piperazinocarbonyl)-D-alaninamido]-2-oxoazetidine, followed by addition of 0.319 g of pyridine-sulfur trioxide complex. The mixture is stirred for 3 days, and the reaction mixture is treated in the manner as described in Example 5, whereby 0.253 g of sodium 3-[N-(4-ethyl-2,3-dioxo-1-piperazinocarbonyl)-D-alaninamido]-2-oxoazetidine-1-sulfonate is obtained.

IR$^{KBr}_{max}$cm$^{-1}$; 3300, 1760, 1710, 1675, 1520, 1250, 1190, 1050.

EXAMPLE 23

In 2 ml of DMF is added 0.152 g of 3-amino-2-oxoazetidine, followed by addition of 0.315 g of 2,4-dioxo-5-phenyl-1,3-dioxolan in small portions. After 10 minutes, 0.563 g of pyridine-sulfur trioxide complex is added. The mixture is allowed to stand at room temperature for 3 days, and the reaction mixture is treated in the manner as described in Example 5. The above procedure yields 0.790 g of disodium 3-(α-sulfonatoxyphenylacetamido)-2-oxoazetidine-1-sulfonate.

IR$\nu_{max}^{KBr}$cm$^{-1}$; 1762, 1663, 1240.

NMR(d6-DMSO, ppm); 3.32(dd, J=2, 5.5 Hz, C4—H), 3.52(t, J=5.5 Hz, C4—H), 4.77(ddd, J=2, 8, 5.5 Hz, C3—H), 5.39(s, —C<u>H</u>—), 7.33(s, aromatic H), 8.63(d, J=8 Hz, NH).

EXAMPLE 24

In 1 ml of DMF is dissolved 0.157 g of 3-(2-syn-methoxyimino-2-phenylacetamido)-2-oxoazetidine, followed by addition of 0.202 g of pyridine-sulfur trioxide complex. The mixture is allowed to stand at room temperature for 3 days, and the reaction mixture is treated in the manner as described in Example 5. The above procedure yields 0.183 g of sodium 3-(2-syn-methoxyimino-2-phenylacetamido)-2-oxoazetidine-1-sulfonate.

IR$\nu_{max}^{KBr}$cm$^{-1}$; 1760, 1660, 1530, 1250.

NMR(DMSO-d6, ppm); 3.67(t, J=5.5 Hz, C4—H), 3.90(s, —OCH3), 4.95(ddd, J=2, 8, 5.5 Hz, C3—H), 7.3–7.7(m, aromatic H), 9.38(d, J=9 Hz, NH).

EXAMPLE 25

In 3 ml of 60% ethanol is dissolved 0.18 g of pyridinium 3-methoxy-3-benzyloxycarboxamido-2-oxoazetidine-1-sulfonate, followed by addition of 0.15 g of 10% palladium-carbon. The mixture is stirred in hydrogen gas streams at room temperature for an hour, and the catalyst is filtered off. The filtrate is concentrated to give 35 mg of 3-amino-3-methoxy-2-oxoazetidine-1-sulfonic acid.

IR$\nu_{max}^{KBr}$cm$^{-1}$; 3400, 1758, 1240, 1050.

NMR(D2O, ppm); 3.76, 4.25(ABq, J=6 Hz, C4—H), 3.52(s, OCH3).

In 1 ml of water is dissolved 30 mg of the above 3-amino-3-methoxy-2-oxoazetidine-1-sulfonic acid, and to the solution are added a solution of 89 mg of the acid chloride prepared from 2-(2-chloroacetamido-4-thiazolyl)-2-methoxyiminoacetic acid (syn-isomer) in 1 ml of tetrahydrofuran and 36 mg of sodium hydrogen carbonate in alternate portions with ice-cooling and stirring. The mixture is further stirred at room temperature for 20 minutes and adjusted to pH 5.8 with phosphoric acid. After removal of tetrahydrofuran under reduced pressure, the water layer is washed with ethyl acetate and purified by Amberlite XAD-II chromatography. The above procedure yields 28 mg of sodium 3-[2-(2-chloroacetamido-4-thiazolyl)-2-methoxyiminoacetamido]-3-methoxy-2-oxoazetidine-1-sulfonate (syn-isomer) which is the same compound as the one described in Example 9.

EXAMPLE 26

In 2 ml of DMF is dissolved 0.126 g of 3-(D-2-(4-ethyl-2,3-dioxo-1-piperazinocarboxamido)-2-(4-methoxyphenyl)acetamido]-2-oxoazetidine, followed by addition of 0.096 g of pyridine-sulfur trioxide complex. The mixture is stirred for 3 days, after which it is treated as described in Example 5. The above procedure provides 0.071 g of sodium 3-[D-2-(4-ethyl-2,3-dioxo-1-piperazinocarboxamido)-2-(4-methoxyphenyl)acetamido]-2-oxoazetidine-1-sulfonate.

IR$\nu_{max}^{KBr}$cm$^{-1}$; 1760, 1670, 1245.

NMR(d6-DMSO, ppm); 1.10(t, J=7 Hz, —CH3), 3.12(dd, J=3, 6 Hz, C4—H), 3.40(q, J=7 Hz, —CH2—), 3.57(t, J=6 Hz, C4—H), 3.4–4.0(m, —CH2—), 3.76(s, OCH3), 4.84(ddd, J=3, 6, 8 Hz, C3—H), 5.36(d, J=7Hz, —C<u>H</u>—), 6.92, 7.33(ABq, J=8 Hz, aromatic H), 9.16(d, J=8 Hz, NH), 9.73(d, J=7 Hz, NH).

EXAMPLE 27

In 4 ml of DMF is dissolved 0.446 g of 3-[D-2-[2-(2-chloroacetamido-4-thiazolyl)-2-methoxyiminoacetamido]-2-phenylacetamido]-2-oxoazetidine (a mixture of syn- and anti-isomers), followed by addition of 0.297 g of pyridine-sulfur trioxide complex. The mixture is stirred for 3 days and worked up in the manner as described in Example 5. The above procedure provides 0.327 g of sodium 3-[D-2-[2-(2-chloroacetamido-4-thiazolyl)-2-methoxyiminoacetamido]-2-phenylacetamido]-2-oxoazetidine-1-sulfonate (a mixture of syn- and anti-isomers).

IR$\nu_{max}^{KBr}$cm$^{-1}$; 1765, 1670, 1550, 1270, 1200.

NMR(d6-DMSO, ppm); 3.17(dd, J=3, 6 Hz, C4—H), 3.62(t, J=6 Hz, C4—H), 3.89, 4.04(s, CH3), 4.40(s, ClCH2—), 4.90(ddd, J=3, 6, 8 Hz, C3—H), 5.61, 5.63(d, J=8Hz, —C<u>H</u>—), 7.2–7.6(m, aromatic H), 7.46,

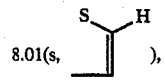
8.01(s, ), 9.01, 9.14(d, J=8 Hz, NH), 8.84, 9.32(d, J=8 Hz, NH), 12.6(broad s, NH).

In 3 ml of water is dissolved 0.233 g of the above sodium 3-[D-2-[2-(2-chloroacetamido-4-thiazolyl)-2-methoxyiminoacetamido]-2-phenylacetamido]-2-oxoazetidine-1-sulfonate (a mixture of syn- and anti-isomers), and under ice-cooling and stirring, 0.057 g of sodium N-methyldithiocarbamate is added, followed by stirring for 45 minutes. The insoluble matter is filtered off and the filtrate is purified by Amberlite XAD-II chromatography. The procedure provides 0.053 g of sodium 3-[D-2-[2-(2-amino-4-thiazolyl)-2-methoxyiminoacetamido]-2-phenylacetamido]-2-oxoazetidine-1-sulfonate (syn-isomer) and 0.087 g of the anti-isomer.

Syn-isomer:

IR$\nu_{max}^{KBr}$cm$^{-1}$; 3430, 3300, 1760, 1655, 1525, 1260, 1240, 1195, 1050.

NMR(d6-DMSO, ppm); 3.17(dd, J=3, 6 Hz, C4—H), 3.61(t, J=6 Hz, C4—H), 3.84(s, CH3), 4.87(ddd, J=3, 6, 8 Hz, C3—H),

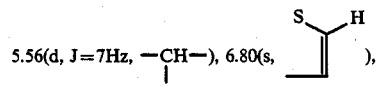
5.56(d, J=7Hz, —C<u>H</u>—), 6.80(s, ), 7.13(broad s, NH2), 7.2–7.6(m, aromatic H), 8.93(d, J=8 Hz, NH), 9.19(d, J=7 Hz, NH).

Anti-isomer:

IR$\nu_{max}^{KBr}$cm$^{-1}$; 3430, 3310, 1760, 1660, 1525, 1260, 1240, 1195, 1050, 1025.

NMR(d$_6$-DMSO, ppm); 3.17(dd, J=3, 6 Hz, C$_4$—H), 3.61(t, J=6 Hz, C$_4$—H), 3.98(s, CH$_3$), 4.88(ddd, J=3, 6, 8 Hz, C$_3$—H), 5.56(d, J=8Hz, —CH—), 7.02(broad s, NH), 7.44(s, 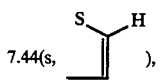 ), 7.2–7.6(m, aromatic H), 8.90(d, J=8 Hz, NH), 9.05(d, J=8 Hz, NH).

EXAMPLE 28

In 4 ml of DMF is dissolved 0.302 g of 3-[D-2-(6-bromo-1,4-dihydro-1-ethyl-4-oxothieno[2,3-b]pyridine-3-carboxamido)-2-phenylacetamido]-2-oxoazetidine, followed by addition of 0.191 g of pyridine-sulfur trioxide complex. The reaction mixture is stirred for one day and worked up in the manner as described in Example 5. The above procedure provides 0.17 g of sodium 3-[D-2-(6-bromo-1,4-dihydro-1-ethyl-4-oxothieno-[2,3-b]pyridine-3-carboxamido)-2-phenylacetamido]-2-oxoazetidine-1-sulfonate.

IR$\nu_{max}^{KBr}$cm$^{-1}$; 3440, 3270, 1755, 1650, 1590, 1525, 1495, 1260, 1235, 1050.

NMR(d$_6$-DMSO, ppm); 1.43(t, J=7 Hz, CH$_3$), 3.15(dd, J=3, 6 Hz, C$_4$—H), 3.59(t, J=6 Hz, C$_4$—H), 4.27(q, J=7 Hz, —CH$_2$—), 4.86(ddd, J=3, 6, 8 Hz, C$_3$—H), 5.78(d, J=8Hz, —CH—), 7.2–7.5(m, aromatic H), 7.62(s, aromatic H), 8.69(s, aromatic H), 9.22(d, J=8 Hz, NH), 10.95(d, J=8 Hz, NH).

EXAMPLE 29

In 6 ml of DMF is dissolved 0.729 g of 3-(2-(4-ethyl-2,3-dioxo-1-piperazinocarboxamido)-2-(2-chloroacetamido-4-thiazolyl)acetamido]-2-oxoazetidine, followed by addition of 0.478 g of pyridine-sulfur trioxide complex. The mixture is stirred for 2 days and, then, worked up as described in Example 5. The above procedure provides 0.434 g of sodium 3-[2-(4-ethyl-2,3-dioxo-1-piperazinocarboxamido)-2-(2-chloroacetamido-4-thiazolyl)acetamido]-2-oxoazetidine-1-sulfonate.

IR$\nu_{max}^{KBr}$cm$^{-1}$; 3450, 1760, 1675, 1270.

NMR(d$_6$-DMSO, ppm); 1.10(t, J=7 Hz, —CH$_3$), 3.19(dd, J=3, 6 Hz, C$_4$—H), 3.43(q, J=7 Hz, —CH$_2$—), 3.56(t, J=6 Hz, C$_4$—H), 4.36(s, —CH$_2$Cl), 4.80 and 4.86(m, C$_3$—H), 5.54(d, J=7Hz, —CH—), 7.21(s, 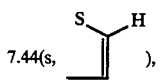 ), 9.01, 9.07(d, J=8 Hz, NH), 9.74(d, J=7 Hz, NH), 12.7(broad s, NH).

In 3 ml of water is dissolved 0.235 g of the above sodium 3-[2-(4-ethyl-2,3-dioxo-1-piperazinocarboxamido)-2-(2-chloroacetamido-4-thiazolyl)acetamido]-2-oxoazetidine-1-sulfonate and, under ice-cooling and stirring, 0.057 g of sodium N-methyldithiocarbamate is added. The mixture is stirred for 30 minutes, after which the insolubles are filtered off. The filtrate is purified by Amberlite XAD-II chromatography to provide 0.13 g of sodium 3-[2-(4-ethyl-2,3-dioxo-1-piperazinocarboxamido)-2-(2-amino-4-thiazolyl)acetamido]-2-oxoazetidine-1-sulfonate.

IR$\nu_{max}^{KBr}$cm$^{-1}$; 3430, 1760, 1675, 1515, 1260.

NMR(d$_6$-DMSO, ppm); 1.09(t, J=7 Hz, —CH$_3$), 3.19(dd, J=3, 6 Hz, C$_4$—H), 3.41(q, J=7 Hz, —CH$_2$—), 3.63(t, J=6 Hz, C$_4$—H), 4.80, 4.87(m, C$_3$—H), 5.27(d, J=7Hz, —CH—), 6.48(s, 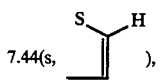 ), 7.01(s, NH$_2$), 8.90, 8.94(d, J=8 Hz, NH), 9.68(d, J=7 Hz, NH).

EXAMPLE 30

In 3 ml of DMF is dissolved 0.303 g of 3-[2-(4-ethyl-2,3-dioxo-1-piperazinocarboxamido)-2-(2-acetamido-4-thiazolyl)acetamido]-2-oxoazetidine, followed by addition of 0.213 g of pyridine-sulfur trioxide complex. The mixture is stirred for 3 days and, then, worked up in the manner as described in Example 5. The above procedure provides 0.101 g of sodium 3-[2-(4-ethyl-2,3-dioxo-1-piperazinocarboxamido)-2-(2-acetamido-4-thiazolyl)acetamido]-2-oxoazetidine-1-sulfonate.

IR$\nu_{max}^{KBr}$cm$^{-1}$; 3430, 1760, 1705, 1670, 1275.

NMR(d$_6$-DMSO, ppm); 1.10(t, J=7 Hz, —CH$_3$), 2.13(s, —COCH$_3$), 3.18(dd, J=3, 6 Hz, C$_4$—H), 3.42(q, J=7 Hz, —CH$_2$—), 3.57(t, J=6 Hz, C$_4$—H), 4.78, 4.85(m, C$_3$—H), 5.52(d, J=7Hz, —CH—), 7.11(s, 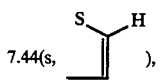 ), 8.99, 9.05(d, J=8 Hz, NH), 9.71(d, J=7 Hz, NH), 12.25(broad s, NH).

EXAMPLE 31

In 5 ml of DMF is dissolved 0.635 g of 3-[2-[2-(2-chloroacetamido-4-thiazolyl)-2-methoxyiminoacetamido]-2-(2-chloroacetamido-4-thiazolyl)acetamido]-2-oxoazetidine (syn-isomer), followed by addition of 0.35 g of pyridine-sulfur trioxide complex. The mixture is stirred for one day and, then, worked up in the manner as described in Example 5. The above procedure provides 0.271 g of sodium 3-[2-[2-(2-chloroacetamido-4-thiazolyl)-2-methoxyiminoacetamido]-2-(2-chloroacetamido-4-thiazolyl)acetamido]-2-oxoazetidine-1-sulfonate (syn-isomer).

IR$\nu_{max}^{KBr}$cm$^{-1}$; 3430, 1760, 1660, 1540, 1265, 1190, 1050.

NMR(d6-DMSO, ppm); 3.27(m, C4—H), 3.67(t, J=6 Hz, C4—H), 3.91(s, CH3), 4.38(s, ClCH2—), 4.90(m, C3—H),

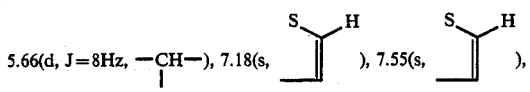

5.66(d, J=8Hz, —CH—), 7.18(s, ), 7.55(s, ), 8.84, 8.88(d, J=8 Hz, NH), 9.25, 9.30(d, J=8 Hz, NH), 12.6(broad s, NH), 12.75(broad s, NH).

In 3 ml of water is dissolved 0.204 g of the above sodium 3-[2-[2-(2-chloroacetamido-4-thiazolyl)-2-methoxyiminoacetamido]-2-(2-chloroacetamido-4-thiazolyl)acetamido]-2-oxoazetidine-1-sulfonate (syn-isomer) and while the solution is stirred under ice-cooling, 0.085 g of sodium N-methyldithiocarbamate is added. The mixture is stirred for an hour, after which the insoluble matter is filtered off. The filtrate is purified by Amberlite XAD-II chromatography to provide 0.1 g of sodium 3-[2-[2-(2-amino-4-thiazolyl)-2-methoxyiminoacetamido]-2-(2-amino-4-thiazolyl)acetamido]-2-oxoazetidine-1-sulfonate (syn-isomer).

IR$\nu_{max}^{KBr}$cm$^{-1}$; 3410, 3310, 1760, 1655, 1620, 1540, 1260, 1240, 1195, 1050.

NMR(d6-DMSO, ppm); 3.30(m, C4—H), 3.64(m, C4—H), 3.85(s, CH3), 4.88(m, C3—H),

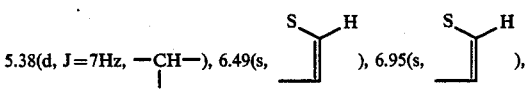

5.38(d, J=7Hz, —CH—), 6.49(s, ), 6.95(s, ), 7.10(broad s, NH2), 8.73(d, J=8 Hz, NH), 8.90(d, J=7 Hz, NH).

EXAMPLE 32

In 3 ml of DMF is dissolved 0.283 g of 3-[D-2-(4-n-octyl-2,3-dioxo-1-piperazinocarboxamido)-2-phenylacetamido]-2-oxoazetidine, followed by addition of 0.191 g of pyridine-sulfur trioxide complex. The mixture is stirred for one day and worked up in the manner as described in Example 5. The above procedure provides 0.234 g of sodium 3-[D-2-(4-n-octyl-2,3-dioxo-1-piperazinocarboxamido)-2-phenylacetamido]-2-oxoazetidine-1-sulfonate.

IR$\nu_{max}^{KBr}$cm$^{-1}$; 3470, 3290, 2925, 2850, 1760, 1710, 1670, 1510, 1260, 1190, 1050.

NMR(d6-DMSO, ppm); 0.86(t, CH3), 3.12(dd, J=3, 6 Hz, C4—H), 3.4-4.1(m, —CH2—), 4.86(ddd, J=3, 6, 8 Hz, C3—H), 5.45(d, J=7Hz, —CH—), 7.40(s, aromatic H), 9.25(d, J=8 Hz, NH), 9.81(d, J=7 Hz, NH).

EXAMPLE 33

In 3 ml of DMF is suspended 0.274 g of 3-[D-2-(coumarin-3-carboxamido)-2-phenylacetamido]-2-oxoazetidine, followed by addition of 0.223 g of pyridine-sulfur trioxide complex. The mixture is stirred for 2 days and worked up in the manner as described in Example 5. The above procedure provides 0.094 g of sodium 3-[D-2-(coumarin-3-carboxamido)-2-phenylacetamido]-2-oxoazetidine-1-sulfonate.

IR$\nu_{max}^{KBr}$cm$^{-1}$; 3440, 3300, 1755, 1700, 1640, 1600, 1560, 1515, 1240, 1190, 1045.

NMR(d6-DMSO, ppm); 3.18(dd, J=3, 6 Hz, C4—H), 3.54(t, J=6 Hz, C4—H), 4.90(ddd, J=3, 6, 8 Hz, C3—H), 5.67(d, J=7Hz, —CH—), 7.3-8.1(m, aromatic H), 8.89(s, aromatic H), 9.32(d, J=8 Hz, NH), 9.65(d, J=7 Hz, NH).

EXAMPLE 34

In 4 ml of DMF is dissolved 0.454 g of 3-[2-(4-n-octyl-2,3-dioxo-1-piperazinocarboxamido)-2-(2-chloroacetamido-4-thiazolyl)acetamido]-2-oxoazetidine, followed by addition of 0.255 g of pyridine-sulfur trioxide complex. The mixture is stirred for one day, and worked up in the manner of Example 5. The above procedure provides 0.182 g of sodium 3-[2-(4-n-octyl-2,3-dioxo-1-piperazinocarboxamido)-2-(2-chloroacetamido-4-thiazolyl)acetamido]-2-oxoazetidine-1-sulfonate.

IR$\nu_{max}^{KBr}$cm$^{-1}$; 3440, 2925, 1760, 1710, 1670, 1260, 1190, 1050.

NMR(d6-DMSO, ppm); 0.86(t, —CH3), 4.36(s, ClCH2—), 4.82(m, C3—H),

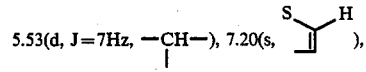

5.53(d, J=7Hz, —CH—), 7.20(s, ), 8.98, 9.04(d, J=8 Hz, NH), 9.72(d, J=7 Hz, NH), 12.63(broad s, NH).

In 2 ml of water is dissolved 0.115 g of the above sodium 3-[2-(4-n-octyl-2,3-dioxo-1-piperazinocarboxamido)-2-(2-chloroacetamido-4-thiazolyl)acetamido]-2-oxoazzetidine-1-sulfonate and, under ice-cooling and stirring, 0.025 g of sodium N-methyldithiocarbamate is added. The mixture is stirred for 90 minutes, after which the insoluble matter is filtered off. The filtrate is purified by Amberlite XAD-II chromatography to provide 0.046 g of sodium 3-[2-(4-n-octyl-2,3-dioxo-1-piperazinocarboxamido)-2-(2-amino-4-thiazolyl)acetamido]-2-oxoazetidine-1-sulfonate.

IR$\nu_{max}^{KBr}$cm$^{-1}$; 3400, 3300, 2920, 1755, 1710, 1670, 1510, 1250, 1195, 1050.

NMR(d6-DMSO, ppm); 0.86(t, CH3), 4.80(m, C3—H),

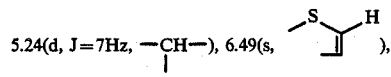

5.24(d, J=7Hz, —CH—), 6.49(s, ), 7.0(broad s, NH2), 8.88, 8.92(d, J=8 Hz, NH), 9.58(d, J=7 Hz, NH).

EXAMPLE 35

In 2 ml of DMF is dissolved 0.161 g of 3-[D-2-(4-hydroxy-7-trifluoromethylquinoline-3-carboxamido)-2-phenylacetamido]-2-oxoazetidine, followed by addition of 0.112 g of pyridine-sulfur trioxide complex. The mixture is stirred for one day and, then, worked up in the manner of Example 5. The above procedure provides 0.095 g of sodium 3-[D-2-(4-hydroxy-7-trifluoromethylquinoline-3-carboxamido)-2-phenylacetamido]-2-oxoazetidine-1-sulfonate.

IR$\nu_{max}^{KBr}$cm$^{-1}$; 3450, 3270, 1775, 1650, 1520, 1315, 1260, 1240, 1195, 1175, 1130, 1045.

NMR(d$_6$-DMSO, ppm); 3.30(dd, J=3, 6 Hz, C$_4$—H), 3.66(t, J=6 Hz, C$_4$—H), 4.88(ddd, J=3, 6, 8 Hz, C$_3$—H), 5.70(d, J=8Hz, —CH—),
|

7.3–8.9(m, aromatic H), 9.21(d, J=8 Hz, NH), 10.80(d, J=8 Hz, NH).

EXAMPLE 36

In 5 ml of DMF is dissolved 0.34 g of 3-[D-2-[(2-oxo-3-furfurylideneaminoimidazolidin-1-yl)carboxamido]-2-phenylacetamido]-2-oxoazetidine, followed by addition of 0.255 g of pyridine-sulfur trioxide complex. The mixture is stirred for one day and, then, worked up in the manner of Example 5. The above procedure provides 0.071 g of sodium 3-[D-2-[(2-oxo-3-furfurylideneamioimidazolidin-1-yl)carboxamido]-2-phenylacetamido]-2-oxoazetidine-1-sulfonate.

IR$\nu_{max}^{KBr}$cm$^{-1}$; 3450, 3300(sh), 1755, 1720, 1665, 1520, 1470, 1410, 1270, 1230, 1050.

NMR(d$_6$-DMSO, ppm); 3.12(dd, J=3, 6 Hz, C$_4$—H), 3.58(t, J=6 Hz, C$_4$—H), 3.80(s, —CH$_2$—), 4.86(ddd, J=3, 6, 8 Hz, C$_3$—H), 5.45(d, J=8Hz, —CH—),
|

6.5–7.9(m, aromatic H), 7.75(s, —CH=N—), 9.04(d, J=8 Hz, NH), 9.24(d, J=8 Hz, NH).

EXAMPLE 37

In 2 ml of DMF is dissolved 0.287 g of 3-[2-(4-n-octyl-2,3-dioxo-1-piperazinocarboxamido]-2-thienylacetamido]-2-oxoazetidine, followed by addition of 0.191 g of pyridine-sulfur trioxide complex. The mixture is stirred for one day and, then, worked up in the manner of Example 5. The above procedure provides 0.299 g of sodium 3-[2-(4-n-octyl-2,3-dioxo-1-piperazinocarboxamido)-2-thienylacetamido]-2-oxoazetidine-1-sulfonate.

IR$\nu_{max}^{KBr}$cm$^{-1}$; 3280, 2920, 1760, 1710, 1670, 1250, 1190, 1050.

NMR(d$_6$-DMSO, ppm); 0.86(t, CH$_3$), 3.4–4.1(m, —CH$_2$—), 4.86(m, C$_3$—H), 5.72(d, J=7Hz, —CH—),
|

6.9–7.6(m, thienyl-H), 9.26 and 9.30(d, J=8 Hz, NH), 9.73(d, J=7 Hz, NH).

EXAMPLE 38

In 2 ml of DMF is dissolved 0.439 g of 3-[D-2-(4-n-octyl-2,3-dioxo-1-piperazinocarboxamido)-2-(4-hydroxyphenyl)acetamido]-2-oxoazetidine, followed by addition of 0.172 g of pyridine-sulfur trioxide complex. The mixture is stirred for 2 days and, then, worked up in the manner of Example 5. The above procedure provides the following two products.

Sodium 3-[D-2-(4-n-octyl-2,3-dioxo-1-piperazinocarboxamido)-2-(4-hydroxylphenyl)acetamido]-2-oxoazetidine-1-sulfonate (0.213 g).

IR$\nu_{max}^{KBr}$cm$^{-1}$; 3290, 2920, 1745, 1710, 1670, 1260, 1050.

NMR(d$_6$-DMSO, ppm); 0.86(t, CH$_3$), 2.96(dd, J=3, 6 Hz, C$_4$—H), 4.86(m, C$_3$—H), 5.40(d, J=7Hz, —CH—),
|

7.13 (ABq, J=8, 18 Hz, aromatic H), 9.10(d, J=8 Hz, NH), 9.78(d, J=7 Hz, NH).

Disodium 3-[D-2-(4-n-octyl-2,3-dioxo-1-piperazinocarboxamido)-2-(4-sulfonatoxyphenyl)acetamido]-2-oxoazetidine-1-sulfonate (0.12 g).

IR$\nu_{max}^{KBr}$cm$^{-1}$; 2920, 1755, 1710, 1670, 1255, 1050.

NMR(d$_6$-DMSO, ppm); 0.86(t, CH$_3$), 3.16(dd, J=3, 6 Hz, C$_4$—H), 4.86(m, C$_3$—H), 5.38(d, J=7Hz, —CH—),
|

7.23(ABq, J=8, 15 Hz, aromatic H), 9.19(d, J=8 Hz, NH), 9.76(d, J=7 Hz, NH).

EXAMPLE 39

In 2 ml of DMF is dissolved 0.441 g of 3-[D-2-[(2-oxo-3-furfurylideneaminoimidazolidin-1-yl)carboxamido]-2-(4-hydroxyphenyl)acetamido]-2-oxoazetidine, followed by addition of 0.191 g of pyridine-sulfur trioxide complex. The mixture is stirred for 3 days and, then, worked up in the manner of Example 5. The above procedure provides the following two products.

Sodium 3-(D-2-[(2-oxo-3-furfurylideneaminoimidazolidin-1-yl)carboxamido]-2-(4-hydroxyphenyl)acetamido]-2-oxoazetidine-1-sulfonate (0.026 g).

IR$\nu_{max}^{KBr}$cm$^{-1}$; 1755, 1720, 1660, 1420, 1270, 1235, 1050.

Disodium 3-[D-2-[(2-oxo-3-furfurylideneaminoimidazolidin-1-yl)carboxamido]-2-(4-sulfonatoxyphenyl)acetamido]-2-oxoazetidine-1-sulfonate (0.025 g).

IR$\nu_{max}^{KBr}$cm$^{-1}$; 1760, 1725, 1670, 1420, 1270, 1240, 1050.

EXAMPLE 40

In 5 ml of DMF is suspended 0.25 g of 3-[2-[[2-oxo-3-furfurylideneaminoimidazolidin-1-yl)carboxamido]-2-thienylacetamido]-2-oxoazetidine, followed by addition of 0.185 g of pyridine-sulfur trioxide complex. The mixture is stirred for 3 days and, then, worked up in the manner of Example 5. The above procedure provides 0.121 g of sodium 3-[2-[(2-oxo-3-furfurylideneaminoimidazolidin-1-yl)carboxamido]-2-thienylacetamido]-2-oxoazetidine-1-sulfonate.

IR$\nu_{max}^{KBr}$cm$^{-1}$; 1760, 1720, 1660, 1410, 1270, 1230, 1050.

NMR(d$_6$-DMSO, ppm); 3.19, 3.25(dd, J=3, 6 Hz, C$_4$—H), 3.63, 3.65(t, J=6 Hz, C$_4$—H), 3.81(broad s, ring CH$_2$), 4.88(m, C$_3$—H), 5.72(d, J=7Hz, —CH—),
            |

6.5–7.9(m, aromatic H), 7.75(s, —CH=N—), 8.97, 8.98(d, J=7 Hz, NH), 9.26, 9.29(d, J=8 Hz, NH).

EXAMPLE 41

In 6 ml of DMF is suspended 0.441 g of 3-[D-2-[[2-oxo-3-(thiophene-2-aldoimino)imidazolidin-1-yl]carboxamido]-2-phenylacetamido]-2-oxoazetidine, followed by addition of 0.319 g of pyridine-sulfur trioxide complex. The mixture is stirred for 3 days, and then, worked up in the manner of Example 5. The above procedure provides 0.208 g of sodium 3-(D-2-[[2-oxo-3-(thiophene-2-aldoimino)imidazolidin-1-yl]carboxamido]-2-phenylacetamido]-2-oxoazetidine-1-sulfonate.

IR$\nu_{max}^{KBr}$cm$^{-1}$; 1760, 1725, 1665, 1410, 1270, 1235, 1050.

NMR(d$_6$-DMSO, ppm); 3.14(dd, J=3, 6 Hz, C$_4$—H), 3.59(t, J=6 Hz, C$_4$—H), 3.82(broad s, —CH$_2$—), 4.87(ddd, J=3, 6, 8 Hz, C$_3$—H), 5.45(d, J=8Hz, —CH—),
            |

7.0–7.7(m, aromatic H), 8.10(s, —CH=N—), 9.06(d, J=8 Hz, NH), 9.24(d, J=8 Hz, NH).

EXAMPLE 42

In 5 ml of DMF is dissolved 0.49 g of 3-[2-(4-ethyl-2,3-dioxo-1-piperazinocarboxamido)-2-(2-pyrrolyl)acetamido]-2-oxoazetidine, followed by addition of 0.312 g of pyridine-sulfur trioxide complex. The mixture is stirred for 4 days and, then, worked up in the manner of Example 5. The above procedure provides 0.228 g of sodium 3-[2-(4-ethyl-2,3-dioxo-1-piperazinocarboxamido)-2-(2-pyrrolyl)acetamido]-2-oxoazetidine-1-sulfonate.

IR$\nu_{max}^{KBr}$cm$^{-1}$; 1755, 1705, 1670, 1505, 1250, 1190, 1050.

NMR(d$_6$-DMSO, ppm); 1.09(t, J=7 Hz, —CH$_3$), 3.21(dd, J=3, 6 Hz, C$_4$—H), 3.41(q, J=7 Hz, —CH$_2$—), 3.4–4.1(m, —CH$_2$—), 4.86(m, C$_3$—H), 5.44(d, J=7Hz, —CH—),
            |

5.9–6.8(m, pyrrolyl-H), 9.01(d, J=8 Hz, NH), 9.55(d, J=8 Hz, NH), 10.7(broad s, NH).

EXAMPLE 43

(A) In 2 ml of DMF is dissolved 0.203 g of an equimolar mixture of 3-[D-2-(4-n-octyl-2,3-dioxo-1-piperazinocarboxamido)-2-thienylacetamido]-3(S)-methoxy-2-oxoazetidine and 3-[L-2-(4-n-octyl-2,3-dioxo-1-piperazinocarboxamido)-2-thienylacetamido]-3(R)-methoxy-2-oxoazetidine, followed by addition of 0.128 g of pyridine-sulfur trioxide complex. The mixture is stirred for 2 days and, then, worked up in the manner of Example 5. The above procedure provides 0.136 g of an equimolar mixture of sodium 3-[D-2-(4-n-octyl-2,3-dioxo-1-piperazinocarboxamido)-2-thienylacetamido]-3(S)-methoxy-2-oxoazetidine-1-sufonate and sodium 3-[L-2-(4-n-octyl-2,3-dioxo-1-piperazinocarboxamido)-2-thienylacetamido]-3(R)-methoxy-2-oxoazetidine-1-sulfonate.

IR$\nu_{max}^{KBr}$cm$^{-1}$; 3280, 2920, 1765, 1705, 1680, 1250, 1190, 1050.

NMR(d$_6$-DMSO, ppm); 0.86(t, CH$_3$), 3.16(s, OCH$_3$), 3.56 and 3.72(ABq, J=6, 16 Hz, C$_4$—H), 5.92(d, J=7Hz, —CH—),
            |

6.9–7.6(m, thienyl-H), 9.72(d, J=7 Hz, NH), 9.80(s, NH).

(B) In 1 ml of DMF is dissolved 0.095 g of an equimolar mixture of 3-[D-2-(4-n-octyl-2,3-dioxo-1-piperazinocarboxamido)-2-thienylacetamido)-3(R)-methoxy-2-oxoazetidine and 3-[L-2-(4-n-octyl-2,3-dioxo-1-piperazinocarboxamido)-2-thienylacetamido]-3(S)-methoxy-2-oxoazetidine, followed by addition of 0.09 g of pyridine-sulfur trioxide complex. The mixture is stirred for 2 days and, then, worked up in the manner of Example 5. The above procedure provides 0.06 g of an equimolar mixture of sodium 3-[D-2-(4-n-octyl-2,3-dioxo-1-piperazinocarboxamido]-2-thienylacetamido]-3(R)-methoxy-2-oxoazetidine-1-sulfonate and sodium 3-[L-2-(4-octyl-2,3-dioxo-1-piperazinocarboxamido)-2-thienylacetamido]-3(S)-methoxy-2-oxoazetidine-1-sulfonate.

IR$\nu_{max}^{KBr}$cm$^{-1}$; 3280, 2920, 1770, 1710, 1680, 1250, 1190, 1050.

NMR(d$_6$-DMSO, ppm); 0.86(t, —CH$_3$), 3.35(s, OCH$_3$), 5.88(d, J=7Hz, —CH—),
            |

6.9–7.6(m, thienyl-H), 9.68(d, J=7 Hz, NH), 9.78(s, NH).

EXAMPLE 44

In 3 ml of DMF is dissolved 0.202 g of a mixture of 3-(D-α-sulfophenylacetamido)-3(R)-methoxy-2-oxoazetidine sodium salt and 3-(D-α-sulfophenylacetamido)-3(S)-methoxy-2-oxoazetidine sodium salt, followed by addition of 0.191 g of pyridine-sulfur trioxide complex. The mixture is stirred for 3 days, after which it is treated as described in Example 5. The above procedure provides 0.039 g of a mixture of disodium 3-(D-α-sulfophenylacetamido)-3(R)-methoxy-2-oxoazetidine-1-sulfonate and disodium 3-(D-α-sulfophenylacetamido)-3(S)-methoxy-2-oxoazetidine-1-sulfonate.

IR$\nu_{max}^{KBr}$cm$^{-1}$; 1765, 1640, 1250–1200, 1040.

EXAMPLE 45

In 2 ml of DMF are dissolved 0.500 g of 3-(N-benzyloxycarbonyl-D-alanyl-D-phenylglycylamino)-2-oxoazetidine and 0.375 g of pyridine-sulfur trioxide complex. The mixture is stirred for 3 days, after which diethyl ether is added. The resultant oily precipitate is passed through Dowex 50W (Na-form) resin and the eluate is purified by Amberlite XAD-II chromatography to provide 0.453 g of sodium 3-(N-benzyloxycarbonyl-D-alanyl-D-phenylglycylamino)-2-oxoazetidine-1-sulfonate.

IR$\nu_{max}^{KBr}$cm$^{-1}$; 1758, 1680, 1639, 1520.

NMR(d$_6$-DMSO, ppm); 1.20(d, J=6 Hz, CH$_3$), 3.10(dd, J=3, 6 Hz, C$_4$—H), 3.54(t, J=6 Hz, C$_4$—H), 4.17(t, J=6Hz, —CH—),
|

4.82(ddd, J=3, 6, 8 Hz, C$_3$—H), 4.99(s, —CH$_2$—), 5.40(d, J=9Hz, —CH—),
|

8.30(d, J=9 Hz, NH), 9.08(d, J=9 Hz, NH).

In 10 ml of water is dissolved 0.115 g of the above sodium 3-(benzyloxycarbonyl-D-alanyl-D-phenylglycylamino)-2-oxoazetidine-1-sulfonate and after the addition of 0.065 g of palladium black, the mixture is stirred in hydrogen gas streams at room temperature for 45 minutes. The catalyst is filtered off and the filtrate is freeze-dried, whereby 0.085 g of sodium 3-(D-alanyl-D-phenylglycylamino)-2-oxoazetidine-1-sulfonate is produced.

IR$\nu_{max}^{KBr}$cm$^{-1}$; 1759, 1661, 1520, 1240, 1048.

NMR(d$_6$-DMSO, ppm); 1.16(d, J=6 Hz, CH$_3$), 3.13(dd, J=3, 6 Hz, C$_4$—H), 3.55(t, J=6 Hz, C$_4$—H), 4.17(t, J=6Hz, —CH—),
|

4.82(ddd, J=3, 6, 8 Hz, C$_3$—H), 5.41(d, J=9 Hz, NH), 7.31(s, aromatic H), 8.31(d, J=8 Hz, —NH), 9.16(d, J=8 Hz, NH).

EXAMPLE 46

In 4 ml of DMF are dissolved 0.401 g of 3-[D-2-(2-ureido-2-thienylacetamido)-2-phenylacetamido]-2-oxoazetidine and 0.239 g of pyridine-sulfur trioxide complex. The mixture is allowed to stand at room temperature for 3 days, after which it is treated as described in Example 1. The above procedure provides 0.180 g of pyridinium 3-[D-2-(2-ureido-2-thienylacetamido)-2-phenylacetamido]-2-oxoazetidine-1-sulfonate.

IR$\nu_{max}^{KBr}$cm$^{-1}$; 1750, 1645, 1510, 1225, 1040.

EXAMPLE 47

In 1 ml of DMF are dissolved 0.200 g of 3-cyanomethylthioacetamido-2-oxoazetidine and 0.318 g of pyridine-sulfur trioxide complex. The mixture is stirred for 3 days, after which diethyl ether is added. The resultant oily precipitate is passed through Dowex 50W (Na-form) resin to obtain 0.390 g of sodium 3-cyanomethylthioacetamido-2-oxoazetidine-1-sulfonate.

IR$\nu_{max}^{KBr}$cm$^{-1}$; 2240, 1758, 1660, 1530, 1240.

NMR(d$_6$-DMSO, ppm); 3.27(dd, J=3, 6 Hz, C$_4$-H), 3.35(s, —CH$_2$—), 3.66(t, J=6 Hz, C$_4$—H), 3.70(s, —CH$_2$—), 4.80(ddd, J=3, 6, 8 Hz, C$_3$—H), 8.93(d, J=8 Hz, NH).

EXAMPLE 48

In 3 ml of DMF are dissolved 0.330 g of 3-[D-2-[2-(2-chloroacetamido-4-thiazolyl)acetamido]-2-phenylacetamido]-2-oxoazetidine and 0.240 g of pyridine-sulfur trioxide complex. The mixture is stirred for 3 days, after which it is treated as described in Example 5. The above procedure provides 0.110 g of sodium 3-[D-2-[2-(2-chloroacetamido-4-thiazolyl)acetamido]-2-phenylacetamido]-2-oxoazetidine-1-sulfonate.

IR$\nu_{max}^{KBr}$cm$^{-1}$; 1758, 1660, 1530, 1260, 1230, 1043.

NMR(d$_6$-DMSO, ppm); 3.17(dd, J=3, 6 Hz, C$_4$—H), 3.60(t, J=6 Hz, C$_4$—H), 3.66(s, —CH$_2$—), 4.39(s, ClCH$_2$—), 4.86(ddd, J=3, 6, 8 Hz, C$_3$—H), 5.50(d, J=8Hz, —CH—),
|

6.99(s, thiazole-H), 7.2–7.6(s, aromatic H), 8.60, 9.13(each d, J=8 Hz, NH).

In 4 ml of water is dissolved 0.164 g of the above product and while the solution is stirred under ice-cooling, 0.043 g of CH$_3$NHCS$_2$Na is added. Then, the mixture is stirred at room temperature for 20 minutes, and the precipitate is removed by filtration. The filtrate is purified by Amberlite XAD-II chromatography to yield 0.075 g of sodium 3-[D-2-(2-amino-4-thiazolyl)acetamido]-2-phenylacetamido]-2-oxoazetidine-1-sulfonate.

IR$\nu_{max}^{KBr}$cm$^{-1}$; 1759, 1650, 1510, 1240, 1050.

NMR(d$_6$-DMSO, ppm); 3.16(dd, J=3, 6 Hz, C$_4$-H), 3.48(s, —CH$_2$—), 3.63(t, J=6 Hz, C$_4$—H), 3.7(br.s, NH$_2$), 4.85(ddd, J=3, 6, 8 Hz, C$_3$—H), 5.47(d, J=7Hz, —CH—),
|

6.36(s, thiazole-H), 7.37(br.s), 8.57(d, J=8 Hz, NH), 9.10(d, J=7 Hz, NH).

EXAMPLE 49

(A) In 2 ml of DMF are dissolved 0.650 g of 3-[DL-2-(4-ethyl-2,3-dioxo-1-piperazinocarboxamido)-2-thienylacetamido]-2-oxoazetidine and 0.579 g of pyridine-sulfur trioxide complex. The mixture is stirred for 30 hours, after which it is treated as described in Example 5. The above procedure provides 0.444 g of sodium 3-[DL-2-(4-ethyl-2,3-dioxo-1-piperazinocarboxamido)-2-thienylacetamido]-2-oxoazetidine-1-sulfonate.

$[\alpha]_D^{25°}$ +3.5° (c=0.627, H$_2$O).

IR$\nu_{max}^{KBr}$cm$^{-1}$; 1760, 1710, 1675, 1510, 1240, 1190, 1040.

NMR(d$_6$-DMSO, ppm); 1.12(t, J=7 Hz, —CH$_3$), 3.13(dd, J=3, 6 Hz, C$_4$—H), 3.38(q, J=7 Hz, —CH$_2$—), 3.78(t, J=6 Hz, C$_4$—H), 4.83(ddd, J=3, 6, 8 Hz, C$_3$—H), 5.68(d, J=7Hz, —CH—),
|

9.27, 9.30(1:1, d, J=8 Hz, NH), 9.72(d, J=7 Hz, NH).

(B) In 2 ml of DMF are dissolved 0.600 g of 3-[D-2-(4-ethyl-2,3-dioxo-1-piperazinocarboxamido)-2-thienylacetamido]-2-oxoazetidine and 0.40 g of pyridine-sulfur trioxide complex. The mixture is treated as described in (A) to obtain 0.402 g of sodium 3-[D-2-(4-ethyl-2,3-dioxo-1-piperazinocarboxamido)-2-thienylacetamido]-2-oxoazetidine-1-sulfonate.

$[\alpha]_D^{25°}$ −37.8° (c=0.761, H$_2$O).

NMR(d$_6$-DMSO, ppm); 9.30(d, J=8 Hz, C$_3$—CONH—), other signals agreeing with those of the product obtained in A).

(C) In 2 ml of DMF are dissolved 0.473 g of 3-[L-2-(4-ethyl-2,3-dioxo-1-piperazinocarboxamido)-2-thienylacetamido]-2-oxoazetidine and 0.315 g of pyridine-sulfur trioxide complex. The mixture is treated as described in (A) to obtain 0.206 g of sodium 3-[L-2-(4-ethyl-2,3-dioxo-1-piperazinocarboxamido)-2-thienylacetamido]-2-oxoazetidine-1-sulfonate.

$[\alpha]_D^{25°}$ +42.4° (c=0.321, H$_2$O). NMR(d$_6$-DMSO, ppm); 9.27(d, J=8 Hz, NH), other signals agreeing with those of the product obtained in (A).

EXAMPLE 50

In 2 ml of DMF are dissolved 0.290 g of 3-(2-thienyl-2-methoxyiminoacetamido)-2-oxoazetidine and 0.437 g of pyridine-sulfur trioxide complex. The mixture is stirred for 19 hours, and diethyl ether is added. The oily precipitate is washed with methanol to obtain 0.310 g of pyridinium 3-(2-thienyl-2-methoxyiminoacetamido)-2-oxoazetidine-1-sulfonate.

IR$\nu_{max}^{KBr}$cm$^{-1}$; 1758, 1643, 1523, 1280, 1223, 1045.
NMR(d$_6$-DMSO, ppm); 3.48(dd, J=3, 6 Hz, C$_4$—H), 3.65(t, J=6 Hz, C$_4$—H), 4.07(s, CH$_3$), 4.95(ddd, J=3, 6, 8 Hz, C$_3$—H).

EXAMPLE 51

In 1.5 ml of DMF are dissolved 0.300 g of 3-[2-thienyl-2-(3-morpholinopropoxyimino)acetamido]-2-oxoazetidine and 0.217 g of pyridine-sulfur trioxide complex. The mixture is stirred for 2 days, after which it is treated as described in Example 5. The above procedure provides 0.313 g of sodium 3-(2-thienyl-2-(3-morpholinopropoxyimino)acetamido]-2-oxoazetidine-1-sulfonate.

IR$\nu_{max}^{KBr}$cm$^{-1}$; 1760, 1665, 1540, 1260, 1040.
NMR(d$_6$-DMSO, ppm); 3.0–4.0(m), 4.96(ddd, J=3, 6, 8 Hz, C$_3$—H), 7.05–7.45, 7.6–7.9(m, aromatic H), 9.48(d, J=8 Hz, NH).

EXAMPLE 52

In 0.5 ml of DMF are dissolved 0.223 g of 3-[D-2-[DL-2-(4-ethyl-2,3-dioxo-1-piperazinocarboxamido)-2-thienylacetamido]-2-phenylacetamido]-2-oxoazetidine and 0.141 g of pyridine-sulfur trioxide complex. The mixture is stirred for 30 hours, after which it is treated as described in Example 5. The above procedure provides 0.290 g of sodium 3-[D-2-[DL-2-(4-ethyl-2,3-dioxo-1-piperazinocarboxamido)-2-thienylacetamido]-2-phenylacetamido]-2-oxoazetidine-1-sulfonate.

IR$\nu_{max}^{KBr}$cm$^{-1}$; 1760, 1708, 1670, 1508, 1230, 1180.

EXAMPLE 53

In 1 ml of DMF are dissolved 0.167 g of 3-[2-(2,5-dioxo-1,2,4-triazino-6-carboxamido)-2-thienylacetamido]-2-oxoazetidine and 0.117 g of pyridine-sulfur trioxide complex. The mixture is stirred for 3 days, after which it is treated as described in Example 5. The above procedure provides 0.052 g of sodium 3-[2-(2,5-dioxo-1,2,4-triazino-6-carboxamido)-2-thienylacetamido]-2-oxoazetidine-1-sulfonate.

IR$\nu_{max}^{KBr}$cm$^{-1}$; 1750, 1700, 1502, 1260, 1173, 1040.

EXAMPLE 54

In 2 ml of DMF are dissolved 0.530 g of 3-[2-(4-ethyl-2,3-dioxo-1-piperazinocarboxamido)-2-(2-methyl-4-thiazolyl)acetamido]-2-oxoazetidine and 0.413 g of pyridine-sulfur trioxide complex. The mixture is stirred for 3 days, after which it is treated as described in Example 5. The above procedure provides 0.270 g of 3-[2-(4-ethyl-2,3-dioxo-1-piperazinocarboxamido)-2-(2-methyl-4-thiazolyl)acetamido]-2-oxoazetidine-1-sulfonate.

IR$\nu_{max}^{KBr}$cm$^{-1}$; 1760, 1708, 1670, 1510, 1240–1280, 1185, 1048.

NMR(d$_6$-DMSO, ppm); 1.09(t, J=7 Hz, CH$_3$), 2.64(s, CH$_3$), 3.4–4.1(m, —CH$_2$—), 3.4–3.8(m, C$_4$—H), 3.83(q, J=7 Hz, —CH$_2$—), 4.81(ddd, J=3, 6, 8 Hz, C$_3$—H), 5.52(d, J=7Hz, —CH—), 7.40(s, thiazol-H), 9.05(br. d, J=8 Hz, NH), 9.75(d, J=7 Hz, NH).

EXAMPLE 55

In 1 ml of DMF are dissolved 0.170 g of 3-[2-(4-chlorobenzoylureido)-2-thienylacetamido]-2-oxoazetidine and 0.133 g pyridine-sulfur trioxide complex. The mixture is allowed to stand at room temperature for 18 hours and, then, worked up in the manner as described in Example 7 to obtain 0.085 g of pyridinium 3-[2-(4-chlorobenzoylureido)-2-thienylacetamido]-2-oxoazetidine-1-sulfonate.

IR$\nu_{max}^{KBr}$cm$^{-1}$; 1760, 1682, 1640, 1530, 1260, 1230, 1040.
NMR(d$_6$-DMSO, ppm); 3.26(dd, J=3, 6 Hz, C$_4$—H), 3.63(t, J=6 Hz, C$_4$—H), 4.85(ddd, J=3, 6, 8 Hz, C$_3$—H), 5.72(d, J=7Hz, —CH—).

EXAMPLE 56

In 3 ml of DMF is added 0.500 g of 3-cyanomethylthioacetamido-3-methoxy-2-oxoazetidine, followed by addition of 0.694 g of pyridine-sulfur trioxide complex. The mixture is stirred for 21 hours, and, then, worked up in the manner as described in Example 3. The above procedure provides 0.216 g of sodium 3-cyanomethylthioacetamido-3-methoxy-2-oxoazetidine-1-sulfonate.

IR$\nu_{max}^{KBr}$cm$^{-1}$; 2250, 1760, 1650, 1600, 1250, 1050.

EXAMPLE 57

In 1 ml of DMF are dissolved 0.450 of 3-(2-benzyloxycarbonyl-2-phenylacetamido)-3-methoxy-2-oxoazetidine and 0.292 g of pyridine-sulfur trioxide complex. The mixture is treated as described in Example 5 to obtain 0.286 g of sodium 3-(2-benzyloxy-carbonyl-2-phenylacetamido)-3-methoxy-2-oxoazetidine-1-sulfonate.

IR$\nu_{max}^{KBr\ L}$cm$^{-1}$; 1760, 1680, 1250, 1055.
NMR(d$_6$-DMSO, ppm); 3.54(s, CH$_3$), 3.55, 3.75(dd, J=6 Hz, C$_4$—H), 4.96(s, —CH—), 5.13(s, —CH$_2$—), 7.30(s, aromatic H), 9.61, 9.65 (each s, NH).

In 10 ml of water is dissolved 0.140 g of the above product and after the addition of 0.150 g of palladium black, the mixture is stirred in hydrogen gas streams for 25 minutes. The catalyst is filtered off and the filtrate is freeze-dried to obtain 0.105 g of sodium 3-(2-carboxy-2- phenylacetamido)-3-methoxy-2-oxoazetidine-1-sulfonate.

IR$\nu_{max}^{KBr}$cm$^{-1}$; 1760, 1720, 1680, 1523, 1240, 1050.
NMR(d$_6$-DMSO, ppm); 3.50(s, CH$_3$), 3.50, 3.71(dd, J=6 Hz, C$_4$—H), 4.97(s, —CH—),
|

7.31(s, aromatic H), 9.50(s, NH).

EXAMPLE 58

In 3 ml of DMF are dissolved 0.450 g of 3-[2-(5,6-dihydro-1,4-oxathiin-2-yl)acetamido]-2-oxoazetidine and 0.636 g of pyridine-sulfur trioxide complex. The mixture is allowed to stand at room temperature for 2 days, and treated as described in Example 5 to obtain 0.252 g of sodium 3-[2-(5,6-dihydro-1,4-oxathiin-2-yl)acetamido]-2-oxoazetidine-1-sulfonate.
IR$\nu_{max}^{KBr}$cm$^{-1}$; 1760, 1660, 1538, 1240, 1050.
NMR(d$_6$-DMSO, ppm); 3.28(dd, J=3, 6 Hz, C$_4$—H), 3.62(t, J=6 Hz, C$_4$—H), 4.84(ddd, J=3, 6, 8 Hz, C$_3$—H), 5.11(s, —CH$_2$—), 8.58(d, J=8 Hz, NH).

EXAMPLE 59

In 1 ml of DMF are dissolved 0.450 g of 3-(D-N-carbamoyltryptophyl-D-phenylglycylamino)-2-oxoazetidine and 0.240 g of pyridine-sulfur trioxide complex. The mixture is stirred for 20 hours, after which it is treated as described in Example 5. The above procedure provides 0.095 g of sodium 3-(D-N-carbamoyltryptophyl-D-phenylglycylamino)-2-oxoazetidine-1-sulfonate.
IR$\nu_{max}^{KBr}$cm$^{-1}$; 1755, 1660, 1520, 1230, 1042.

EXAMPLE 60

In 2 ml of DMF are dissolved 0.450 g of 3-[D-N-(4-ethyl-2,3-dioxo-1-piperazinocarbonyl)-phenylalanylamino]-2-oxoazetidine and 0.357 g of pyridine-sulfur trioxide complex. The mixture is allowed to stand at room temperature for 2 days, and treated as described in Example 5 to obtain 0.222 g of sodium 3-[D-N-(4-ethyl-2,3-dioxo-1-piperazinocarbonyl)-phenylalanylamino]-2-oxoazetidine-1-sulfonate.
IR$\nu_{max}^{KBr}$cm$^{-1}$; 1760, 1710, 1670, 1520, 1280, 1185, 1042.
NMR(d$_6$-DMSO, ppm); 1.08(t, J=7 Hz, CH$_3$), 2.93(dd, J=3, 6 Hz, C$_4$—H), 3.38(q, J=7 Hz, —CH$_2$—), 4.53(dd, J=6,8Hz, —CH—),
|

4.84(ddd, J=3, 6, 8 Hz, C$_3$—H), 7.22(s, aromatic H), 8.90(d, J=8 Hz, NH), 9.16(d, J=8 Hz, NH).

EXAMPLE 61

In 1 ml of DMF are dissolved 0.167 g of 3-[2-(2,4-dioxopyrimidino-5-carboxamido)-2-thienylacetamido]-2-oxoazetidine and 0.117 g of pyridine-sulfur trioxide complex. The mixture is stirred for 3 days, after which it is treated as described in Example 5. The above procedure provides 0.052 g of sodium 3-[2-(2,4-dioxopyrimidine-5-carboxamido)-2-thienylacetamido]-2-oxoazetidine-1-sulfonate.
IR$\nu_{max}^{KBr}$cm$^{-1}$; 1750, 1700, 1640, 1502, 1260, 1173, 1040.

EXAMPLE 62

In 2 ml of DMF are dissolved 0.510 g of 3-[D-2-(2-ureido-2-thienylacetamido)-2-(4-hydroxyphenyl)acetamido]-2-oxoazetidine and 0.285 g of pyridine-sulfur trioxide complex. The mixture is stirred for 20 hours, after which it is treated as described in Example 5. The above procedure provides 0.036 g of disodium 3-[D-2-(2-ureido-2-thienylacetamido)-2-(4-sulfonatoxyphenyl)acetamido]-2-oxoazetidine-1-sulfonate and 0.085 g of sodium 3-[D-2-(2-ureido-2-thienylacetamido)-2-(4-hydroxyphenyl)acetamido]-2-oxoazetidine-1-sulfonate.
Disodium derivative; IR$\nu_{max}^{KBr}$cm$^{-1}$; 1755, 1660, 1510, 1240, 1050.
Monosodium derivative; IR$\nu_{max}^{KBr}$cm$^{-1}$; 1745, 1660, 1500, 1220, 1040.

EXAMPLE 63

In 2 ml of DMF are dissolved 0.230 g of 3-[α-D-N-(4-ethyl-2,3-dioxo-1-piperazinocarbonyl)-glutaminylamino]-2-oxoazetidine and 0.199 g of pyridine-sulfur trioxide complex. The mixture is stirred for 4 days, after which it is treated as described in Example 5. The above procedure provides 0.015 g of sodium 3-[α-D-N-(4-ethyl-2,3-dioxo-1-piperazinocarbonyl)-glutaminylamino]-2-oxoazetidine-1-sulfonate.
IR$\nu_{max}^{KBr}$cm$^{-1}$; 1755, 1640, 1240, 1190, 1042.

EXAMPLE 64

In 2 ml of DMF are dissolved 0.391 g of 3-[2-(4-ethyl-2,3-dioxo-1-piperazinocarboxamido)-2-(1-cyclohexen-1-yl)acetamido]-2-oxoazetidine and 0.32 g of pyridine-sulfur trioxide complex. The mixture is stirred at room temperature for 4 days, after which it is treated as described in Example 5. The above procedure provides 0.345 g of sodium 3-[2-(4-ethyl-2,3-dioxo-1-piperazinocarboxamido)-2-(1-cyclohexen-1-yl)acetamido]-2-oxoazetidine-1-sulfonate.
IR$\nu_{max}^{KBr}$cm$^{-1}$; 2920, 1760, 1710, 1670, 1510.
NMR(d$_6$-DMSO, ppm); 1.10(t, J=8 Hz, CH$_3$), 1.30–1.70(m, —CH$_2$—), 1.70–2.20(m, —CH$_2$—), 3.40(q, CH$_2$, J=4 Hz),

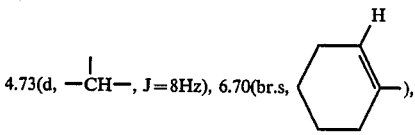

4.73(d, —CH—, J=8Hz), 6.70(br.s, 8.90(dd, J=8, 8 Hz, NH), 9.40(d, J=8 Hz, NH).

EXAMPLE 65

In 1 ml of DMF are dissolved 0.179 g of 3-[2-(4-ethyl-2,3-dioxo-1-piperazinocarboxamido)-2-(4-chlorophenyl)acetamido]-2-oxoazetidine and 0.14 g of pyridine-sulfur trioxide complex. The mixture is stirred at room temperature for 3 days, after which it is treated as described in Example 5. The above procedure provides 0.127 g of sodium 3-[2-(4-ethyl-2,3-dioxo-1-piperazinocarboxamido)-2-(4-chlorophenyl)acetamido]-2-oxoazetidine-1-sulfonate.
IR$\nu_{max}^{KBr}$cm$^{-1}$; 1760, 1710, 1670, 1510, 1250, 1192, 1043.
NMR(d$_6$-DMSO, ppm); 1.06(t, J=7 Hz, CH$_3$), 3.88(m, 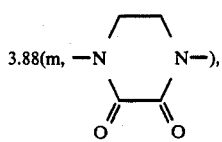

4.80(m, C₃—H), 5.38(d, J=8Hz, —CH—),
　　　　　　　　|

7.35(s, aromatic H), 9.20(dd, J=8, 8 Hz, NH), 9.78(d, J=8 Hz, NH).

EXAMPLE 66

In 1 ml of DMF are dissolved 0.3 g of 3-[DL-2-(4-ethyl-2,3-dioxo-1-piperazinocarboxamido)-2-(4-trimethylsilylphenyl)acetamido]-2-oxoazetidine and 0.21 g of pyridine-sulfur trioxide complex. The mixture is stirred at room temperature for 3 days, after which it is treated as described in Example 5. The above procedure provides 0.142 g of sodium 3-[DL-2-(4-ethyl-2,3-dioxo-1-piperazinocarboxamido)-2-(4-trimethylsilylphenyl)acetamido]-2-oxoazetidine-1-sulfonate.

IR$\nu_{max}^{KBr}$cm$^{-1}$; 1755, 1705, 1670, 1510, 1240, 1193, 1045.

NMR(d₆-DMSO, ppm); 0.23(s, SiMe₃), 1.06(t, J=8 Hz, CH₃), 3.85(m, —CH₂—), 4.80(m, C₃—H), 5.36(d, J=8Hz, —CH—),
　　　　　　　　|

7.22(d, J=7 Hz, aromatic H), 7.38(d, J=8 Hz, aromatic H), 9.15, 9.20(each d, J=8 Hz, NH), 9.76(d, J=8 Hz, NH).

EXAMPLE 67

In 3 ml of DMF are dissolved 0.36 g of 3-[D-N-(4-ethyl-2,3-dioxo-1-piperazinocarbonyl)methionyl-D-phenylglycylamino]-2-oxoazetidine and 0.22 g of pyridine-sulfur trioxide complex. The mixture is stirred at room temperature for 5 days, after which it is treated as described in Example 5. The above procedure provides 0.3 g of sodium 3-[D-N-(4-ethyl-2,3-dioxo-1-piperazinocarbonyl)methionyl-D-phenylglycylamino]-2-oxoazetidine-1-sulfonate.

IR$\nu_{max}^{KBr}$cm$^{-1}$; 1760, 1710, 1675, 1520, 1250, 1195, 1050.

NMR(d₆-DMSO, ppm); 1.06(t, J=7 Hz, CH₃), 2.04(s, SCH₃), 3.12(dd, J=3, 6 Hz, C₄—β—H), 3.54(m, —CH₂—), 3.90(m, —CH₂—), 4.55(m, —CH—),
　　　　　|

4.82(m, C₃—H), 5.43(d, J=8Hz, —CH—),
　　　　　　　　|

7.31(aromatic H), 8.78(d, J=8 Hz, NH), 9.02(d, J=8 Hz, NH), 9.22(d, J=8 Hz, NH).

EXAMPLE 68

In 3 ml of DMF are dissolved 0.34 g of 3-[2-(4-ethyl-2,3-dioxo-piperazinocarboxamido)-2-(1-cyclohexen-1-yl)acetamido]-3-methoxy-2-oxoazetidine and 0.26 g of pyridine-sulfur trioxide complex. The mixture is stirred for 3 days, after which it is treated as described in Example 5. The above procedure provides 0.17 g of sodium 3-[2-(4-ethyl-2,3-dioxo-1-piperazinocarboxamido)-2-(1-cyclohexene-1-yl)acetamido]-3-methoxy-2-oxoazetidine-1-sulfonate.

IR$\nu_{max}^{KBr}$cm$^{-1}$; 1765, 1810, 1675, 1510, 1250, 1190, 1055.

NMR(d₆-DMSO, ppm); 1.07(t, J=7 Hz, CH₃),

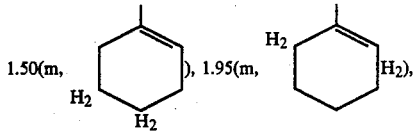

3.33(s, —CH₃), 3.90(m, —CH₂—),

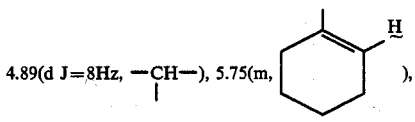

9.32(d, J=8 Hz, NH), 9.38(s, NH).

EXAMPLE 69

In 3 ml of DMF is dissolved 0.200 g of 3-[D-2-(3-methylcarbamoyl-3-methyl-1-ureido)-2-phenylacetamido]-2-oxoazetidine, followed by addition of 0.144 g of pyridine-sulfur trioxide complex. The mixture is stirred for 3 days, and treated as described in Example 5. The above procedure provides 0.080 g of sodium 3-[D-2-(3-methylcarbamoyl-3-methyl-1-ureido)-2-phenylacetamido]-2-oxoazetidine-1-sulfonate.

IR$\nu_{max}^{KBr}$cm$^{-1}$; 3370, 1750, 1685, 1650, 1633, 1273, 1230, 1202, 1050.

NMR(d₆-DMSO, ppm); 2.65(d, J=4 Hz, —CH₃), 3.06(s, CH₃), 3.10(dd, J=3, 5 Hz, C₄—H), 3.53(t, J=5 Hz, C₄—H), 4.79(m, C₃—H), 5.30(d, J=7Hz, —CH—),
　　　　　　　　|

7.33(s, aromatic H, NH), 9.13(d, J=7 Hz, NH), 9.90(d, J=7 Hz, NH).

EXAMPLE 70

In 3 ml of DMF is dissolved 0.3 g of a diastereoisomeric mixture of 3-[DL-2(3-methylcarbamoyl-3-methyl-1-ureido)-2-thienylacetamido]-2-oxoazetidine, followed by addition of 0.2 g of pyridine-sulfur trioxide complex. The mixture is stirred for 3 days and, then, worked up in the manner as described in Example 5. The above procedure provides 0.134 g of a diastereoisomeric mixture of sodium 3-[DL-2-(3-methylcarbamoyl-3-methyl-1-ureido)-2-thienylacetamido]-2-oxoazetidine-1-sulfonate.

IR$\nu_{max}^{KBr}$cm$^{-1}$; 3375, 1752, 1685, 1650, 1632, 1275, 1228, 1200, 1048.

NMR(d$_6$-DMSO, ppm); 2.64(d, J=5 Hz, CH$_3$), 3.07(s, CH$_3$), 3.18, 3.25(dd, J=3, 6 Hz, C$_4$—H), 3.57, 3.58(t, J=6 Hz, C$_4$—H), 4.80(m, C$_3$—H), 5.58(d, J=7Hz, —CH—),
         |

6.87–7.50(m, aromatic H, NH), 9.13, 9.18(d, J=8 Hz, NH), 9.83, 9.88(d, J=7 Hz, NH).

EXAMPLE 71

In 4 ml of DMF is dissolved 0.19 g of 3-[D-2-(3-methylcarbamoyl-3-methyl-1-ureido)-2-(4-benzyloxyphenyl)acetamido]-2-oxoazetidine, followed by addition of 0.11 g of pyridine-sulfur trioxide complex. The mixture is stirred for 3 days, then 30 ml of diethyl ether is added and the resultant crystals are collected and washed with ethanol (pyridinium salt). This salt is treated with Dowex 50W (Na-form) resin to obtain 0.138 g of sodium 3-[D-2-(3-methylcarbamoyl-3-methyl-1-ureido)-2-(4-benzyloxyphenyl)acetamido]-2-oxoazetidine-1-sulfonate.

IR$\nu_{max}^{KBr}$cm$^{-1}$; 3380, 1755, 1685, 1640, 1245, 1051.
NMR(d$_6$-DMSO, ppm); 2.63(d, J=5 Hz, CH$_3$), 3.03(s, CH$_3$), 3.10(dd, J=3, 6 Hz, C$_4$—H), 3.50(t, J=6 Hz, C$_4$—H), 4.78(m, C$_3$—H), 5.03(s, CH$_2$), 5.21(d, J=7Hz, —CH—),
         |

7.08(ABq, J=9.30 Hz, aromatic H), 7.37(s, aromatic H), 9.03(d, J=8 Hz, NH), 9.78(d, J=7 Hz, NH).

In 3 ml of water is added 43 mg of the above sodium 3-[D-2-(3-methylcarbamoyl-3-methyl-1-ureido)-2-(4-benzyloxyphenyl)acetamido]-2-oxoazetidine-1-sulfonate, followed by addition of 40 mg of palladium black. The mixture is stirred in hydrogen gas streams for 40 minutes, and the catalyst is filtered off. The filtrate is freeze-dried to provide 35 mg of sodium 3-[D-2-(3-methylcarbamoyl-3-methyl-1-ureido)-2-(4-hydroxyphenyl)acetamido]-2-oxoazetidine-1-sulfonate.

IR$\nu_{max}^{KBr}$cm$^{-1}$; 3350, 1760, 1680, 1638, 1270–1230, 1050.
NMR(d$_6$-DMSO, ppm); 2.63(d, J=5 Hz, CH$_3$), 3.05(s, CH$_3$), 3.12(dd, J=3, 5 Hz, C$_4$—H), 3.51(t, J=5 Hz, C$_4$—H), 4.77(m, C$_3$—H), 5.16(d, J=7Hz, —CH—),
         |

6.88(ABq, J=9, 40 Hz, aromatic H), 7.32(q, J=5 Hz, NH), 8.98(d, J=9 Hz, NH), 9.33(s, OH), 9.72(d, J=7 Hz, NH).

EXAMPLE 72

In 4 ml of DMF is dissolved 0.472 mg of 3-[D-2-[3-(2-benzyloxybenzoyl)-1-ureido]-2-phenylacetamido]-2-oxoazetidine, followed by addition of 0.318 g of pyridine-sulfur trioxide complex. The mixture is stirred for 3 days, after which it is treated as described in Example 5. The above procedure provides 0.13 g of sodium 3-[D-2-[3-(2-benzyloxybenzoyl)-1-ureido]-2-phenylacetamido]-2-oxoazetidine-1-sulfonate.

IR$\nu_{max}^{KBr}$cm$^{-1}$; 3310, 1760, 1705, 1668, 1290, 1240, 1050.

NMR(d$_6$-DMSO, ppm); 3.11(dd, J=3, 6 Hz, C$_4$—H), 3.62(t, J=6 Hz, C$_4$—H), 4.86(m, C$_3$—H), 5.30(s, —CH$_2$—), 5.40(d, J=8Hz, —CH—),
         |

7.04–7.88(m, aromatic H), 9.28(d, J=7 Hz, NH), 9.45(d, J=8 Hz, NH), 10.32(s, NH).

In 4 ml of water is added 60 mg of the above sodium 3-[D-2-[3-(2-benzyloxybenzoyl)-1-ureido]-2-phenylacetamido]-2-oxoazetidine-1-sulfonate, followed by addition of 60 mg of palladium black. The mixture is stirred in hydrogen gas streams for 30 minutes, and the catalyst is filtered off. The filtrate is freeze-dried to provide 48.5 mg of sodium 3-[D-2-[3-(2-hydroxybenzoyl)-1-ureido]-2-phenylacetamido]-2-oxoazetidine-1-sulfonate.

IR$\nu_{max}^{KBr}$cm$^{-1}$; 3450, 3270, 1760, 1660, 1240–1190, 1038.
NMR(d$_6$-DMSO, ppm); 3.13(dd, J=3, 6 Hz, C$_4$—H), 3.58(t, J=6 Hz, C$_4$—H), 4.87(m, C$_3$—H), 5.48(d, J=8Hz, —CH—),
         |

6.90–8.03(m, aromatic H), 9.28(d, J=9 Hz, NH), 9.52(d, J=8 Hz, NH), 10.52 (s, NH).

EXAMPLE 73

(A) In 4 ml of DMF is dissolved 0.3 g of 3-[D-2-[3-(2-benzyloxybenzoyl)-ureido]-2-(4-hydroxyphenylacetamido]-2-oxoazetidine, followed by addition of 0.116 g of pyridine-sulfur trioxide complex. The mixture is stirred for 3 days, after which it is treated as described in Example 5. The above procedure provides 0.021 g of disodium 3-[D-2-[3-(2-benzyloxybenzoly)-1-ureido]-2-(4-sulfonatoxyphenyl)acetamido]-2-oxoazetidine-1-sulfonate.

IR$\nu_{max}^{KBr}$cm$^{-1}$; 3450–3310, 1758, 1670, 1240, 1050.
NMR(d$_6$-DMSO, ppm); 3.24(dd, J=3, 6 Hz, C$_4$—H), 3.58(t, J=6 Hz, C$_4$—H), 4.88(m, C$_3$—H), 5.28(s, —CH$_2$—), 5.38(d, J=7Hz, —CH—),
         |

7.00–7.86(m, aromatic H), 9.21(d, J=9 Hz, NH), 9.37(d, J=7 Hz, NH), 10.28(s, NH).

In addition, 0.059 g of sodium 3-[D-2-[3-(2-benzyloxybenzoyl)-1-ureido]-2-(4-hydroxyphenyl)acetamido]-2-oxoazetidine-1-sulfonate is also obtained.

IR$\nu_{max}^{KBr}$cm$^{-1}$; 3425, 3325, 1758, 1670, 1240, 1050.
NMR(d$_6$-DMSO, ppm), 3.10(dd, J=3, 6 Hz, C$_4$—H), 3.49(t, J=6 Hz, C$_4$—H), 4.86(m, C$_3$—H), 5.28(s, —CH$_2$—), 5.57(d, J=7Hz, —CH—),
         |

6.70–7.88(m, aromatic H), 9.21(d, J=9 Hz, NH), OH), 9.33(s, 9.37(d, J=7 Hz, NH), 10.28(s, NH).

(B) In 3 ml of water is added 40 mg of the above sodium 3-[D-2-[3-(2-benzyloxybenzoyl)-1-ureido]-2-(4- hydroxyphenyl)acetamido]-2-oxoazetidine-1-sulfonate, followed by addition of 40 mg of palladium black. The mixture is stirred in hydrogen gas streams for 40 minutes, after which the catalyst is filtered off. The filtrate is freeze-dried to provide 31 mg of sodium 3-[D-2-[3-(2-hydroxybenzoyl)-1-ureido]-2-(4-hydroxyphenyl)acetamido]-2-oxoazetidine-1-sulfonate.

IR$\nu_{max}^{KBr}$cm$^{-1}$; 3500–3275, 1748, 1675–1640, 1260–1220, 1045.

NMR(d$_6$-DMSO, ppm); 3.15(dd, J=2, 6 Hz, C$_4$—H), 3.52(t, J=6 Hz, C$_4$—H), 4.88(m, C$_3$—H), 5.48(d, J=7Hz, —CH—), 6.70–8.00(aromatic H), 9.09(d, J=9 Hz, NH), 9.48(s, OH), 9.50(d, J=7 Hz, NH).

EXAMPLE 74

In 4 ml of DMF is dissolved 0.4 g of 3-[2-(3-chloro-4-hydroxyphenyl)-2-(4-ethyl-2,3-dioxo-1-piperazinocarboxamido)acetamido]-2-oxoazetidine, followed by addition of 0.175 g of pyridine-sulfur trioxide complex. The mixture is stirred for 4 days, after which it is treated as described in Example 5. The above procedure provides 0.02 g of disodium 3-[2-(3-chloro-4-sulfonatoxyphenyl)-2-(4-ethyl-2,3-dioxo-1-piperazinocarboxamido)acetamido]-2-oxoazetidine-1-sulfonate.

IR$\nu_{max}^{KBr}$cm$^{-1}$; 3290, 1750, 1708, 1670, 1230, 1040.

In addition, 0.065 g of sodium 3-[2-(3-chloro-4-hydroxyphenyl)-2-(4-ethyl-2,3-dioxo-1-piperazinocarboxamido)acetamido]-2-oxoazetidine-1-sulfonate is also obtained.

IR$\nu_{max}^{KBr}$cm$^{-1}$; 3420, 3280, 1755, 1703, 1688, 1280–1225, 1045.

NMR(d$_6$-DMSO, ppm); 1.09(t, J=7 Hz, —CH$_3$), 3.10(dd, J=2, 6 Hz, C$_4$—H), 3.40(q, J=7 Hz, —CH$_2$—), 3.44–3.68(m, —CH$_2$—, C$_4$—H), 3.82–4.04(m, —CH$_2$—), 4.84(m, C$_3$—H), 5.32(d, J=7Hz, —CH—), 6.91–7.40(m, aromatic H), 9.17(d, J=9 Hz, NH), 9.74(d, J=7 Hz, NH), 10.22(s, OH).

EXAMPLE 75

In 3 ml of DMF is dissolved 0.3 g of 3-[D-2-(3-chloro-4-methoxyphenyl)-2-(4-ethyl-2,3-dioxo-1-piperazinocarboxamido)acetamido]-2-oxoazetidine, followed by addition of 0.2 g of pyridine-sulfur trioxide complex. The mixture is stirred for 4 days, after which it is treated as described in Example 5. The above procedure provides 0.196 g of sodium 3-[D-2-(3-chloro-4-methoxyphenyl)-2-(4-ethyl-2,3-dioxo-1-piperazinocarboxamido)acetamido]-2-oxoazetidine-1-sulfonate.

IR$\nu_{max}^{KBr}$cm$^{-1}$; 3300, 1759, 1708, 1675, 1255, 1050.

NMR(d$_6$-DMSO, ppm); 1.09(t, J=7 Hz, —CH$_3$), 3.09(dd, J=3, 5 Hz, C$_4$—H), 3.40(d, J=7 Hz, —CH$_3$), 3.44–3.70(m, —CH$_2$—, C$_4$—H), 3.76–4.04(m, —CH$_2$—), 3.86(s, —CH$_3$), 4.83(m, C$_3$—H), 5.36(d, J=7Hz, —CH—), 7.10–7.50(m, aromatic H), 9.21(d, J=9 Hz, NH), 9.79(d, J=7 Hz, NH).

EXAMPLE 76

In 4 ml of DMF is dissolved 0.35 g of a diastereoisomeric mixture of 3-[D-2-(2-benzyloxycarboxamide-3-N-methylcarbamoylpropionamido)-2-phenylacetamido]-2-oxoazetidine, followed by addition of 0.231 g of pyridine-sulfur trioxide complex. The reaction mixture is stirred for 3 days, after which diethyl ether is added, whereupon the pyridinium salt is obtained as crystals. These crystals are treated in the manner as described in Example 71. The above procedure provides 0.37 g of a diastereoisomeric mixture of sodium 3-[D-2-(2-benzyloxycarbxamido-3-N-methylcarbamoylpropionamido)-2-phenylacetamido]-2-oxoazetidine-1-sulfonate.

IR$\nu_{max}^{KBr}$cm$^{-1}$; 3280, 1755, 1692, 1641, 1260–1230, 1048.

NMR(d$_6$-DMSO, ppm); 2.40–2.70(m, —CH$_2$—, —CH$_3$), 3.30(dd, J=2, 6 Hz, C$_4$—H), 3.60(t, J=6 Hz, C$_4$—H), 4.46(m, —CH—), 4.86(m, C$_3$—H), 5.03, 5.06(s, —CH$_2$—), 5.38, 5.40(d, J=8Hz, —CH—), 7.34(s, aromatic H), 7.35(s, aromatic H), 7.75(m, NH), 8.30(m, NH), 9.06(m, NH).

NMR(d$_6$-DMSO+D$_2$O, ppm); 2.40–2.70(m, —CH$_2$—, CH$_3$), 3.28(dd, J=2, 6 Hz, C$_4$—H), 3.62(t, J=6 Hz, C$_4$—H), 4.46(m, —CH—), 4.86(m, C$_3$—H), 5.04, 5.08(s, —CH$_2$—), 5.37, 5.39(s, —CH—), 7.35, 7.36(s, aromatic H).

In 5 ml of water is added 102 mg of a diastereoisomeric mixture of the above sodium 3-[D-2-(2-benzyloxycarboxamido-3-N-methylcarbamoylpropionamido)-2-phenylacetamido]-2-oxoazetidine-1-sulfonate, followed by addition of 60 mg of palladium black. The mixture is stirred in hydrogen gas streams for 35 minutes, after which the catalyst is filtered off. The filtrate is freeze-dried whereupon 69 mg of sodium 3-[D-2-(2-amino-3-N-methylcarbamoylpropionamido)-2-phenylacetamido]-2-oxoazetidine-1-sulfonate is obtained.

IR$\nu_{max}^{KBr}$cm$^{-1}$; 3500–3300, 3290, 1765, 1650, 1270, 1235, 1050.

NMR(d$_6$-DMSO+D$_2$O, ppm); 2.40–2.70(m, —CH$_2$—), 2.59(s, —CH$_3$), 3.26(dd, J=3, 6 Hz, C$_4$—H), 4.84 (m, C$_3$—H), 5.38(s, —CH—), 7.38(s, aromatic H).

EXAMPLE 77

In 3 ml of DMF is dissolved 0.24 g of a diastereoisomeric mixture of 3-[D-2-(3-benzyloxycarboxamido-3-N-methylcarbamoylpropionamido)-2-phenylacetamido]-2-oxoazetidine, followed by addition of 0.16 g of pyridine-sulfur trioxide complex. The mixture is stirred for 4 days, after which it is treated as described in Example 5.

The above procedure provides 0.08 g of a diastereoisomeric mixture of sodium 3-[D-2-benzyloxycarboxamido-3-N-methylcarbamoylpropionamido)-phenylacetamido]-2-oxoazetidine-1-sulfonate.

IR$\nu_{max}^{KBr}$cm$^{-1}$; 3275, 1753, 1682, 1650, 1633, 1235, 1043.

NMR(d$_6$-DMSO, ppm); 2.44–2.66(m, —CH$_2$—, —CH$_3$), 3.24(m, C$_4$—H), 3.54(m, C$_4$—H), 4.30(m, —CH—), 4.83(m, C$_3$—H), 5.00 and 5.02(s, —CH$_2$—), 5.43(d, J=7Hz, —CH—), 7.36(s, aromatic H), 7.76(m, NH), 8.46(m, NH), 9.06(m, NH).

NMR(d$_6$-DMSO+D$_2$O, ppm); 2.47–2.70(m, —CH$_2$—, —CH$_3$), 3.28(m, C$_4$—H), 3.58(m, C$_4$—H), 4.30(m, —CH—), 4.82(m, C$_3$—H), 5.01, 5.04(s, —CH$_2$—), 5.40(s, —CH—), 7.36(s, aromatic H).

In 3 ml of water is dissolved 60 mg of a diastereoisomeric mixture of the above sodium 3-[D-2-(3-benzyloxycarboxamido-3-N-methylcarbamoylpropionamido)-2-phenylacetamido]-2-oxoazetidine-1-sulfonate, followed by addition of 40 mg of palladium black. The mixture is stirred in hydrogen gas streams for 40 minutes, after which the catalyst is filtered off. The filtate is freeze-dried, whereupon 41 mg of a diastereoisomeric mixture of sodium 3-[D-2-(3-amino-3-N-methylcarbamoylpropionamido)-2-phenylacetamido]-2-oxoazetidine-1-sulfonate is obtained.

IR$\nu_{max}^{KBr}$cm$^{-1}$: 3500–3300, 1762, 1655, 1270, 1240, 1050.

NMR(d$_6$-DMSO+D$_2$O, ppm); 2.42–2.60(m, —CH$_2$—), 2.61 and 2.62(s, —CH$_3$), 3.25(dd, J=2, 5 Hz, C$_4$—H), 3.62(t, J=5 Hz, C$_4$—H), 4.83(m, C$_3$—H), 5.37, 5.41(s, —CH—).

7.38(s, aromatic H).

EXAMPLE 78

In 13 ml of DMF is dissolved 1.3 g of 3-[2-(2,5-dioxopyrrolidin-3-yl)acetamido]-2-oxoazetidine, followed by addition of 2.4 g of pyridine-sulfur trioxide complex. The mixture is stirred at room temperature for 3 days, after which it is treated as described in Example 5. The above procedure provides 0.81 g of sodium 3-[2-(2,5-dioxopyrrolidin-3-yl)acetamido]-2-oxoazetidine-1-sulfonate.

IR$\nu_{max}^{KBr}$cm$^{-1}$; 1760, 1710, 1670, 1540, 1250, 1065.

NMR(D$_2$O ppm); 2.5–3.55(m, —CH$_2$—), 3.81(dd, J=3, 6 Hz, C$_4$-H), 4.05(t, J=6 Hz, C$_4$-H), 5.04(dd, J=3, 6 Hz, C$_3$—H).

EXAMPLE 79

In 5 ml of DMF is dissolved 0.57 g of 3-(2-succinimidoacetamido)-2-oxoazetidine, followed by addition of 1.1 g of pyridine-sulfur trioxide complex. The mixture is stirred for 4 days, after which it is treated as described in Example 5. The above procedure provides 0.259 g of sodium 3-(2-succinimidoacetamido)-2-oxoazetidine-1-sulfonate.

IR$\nu_{max}^{KBr}$cm$^{-1}$; 1765, 1710, 1260, 1055.

NMR(D$_2$O, ppm); 3.01(s, —CH$_2$CH$_2$—), 3.83(dd, J=4, 6 Hz, C$_4$—H), 4.06(t, J=6 Hz, C$_4$—H), 4.43(s, —CH$_2$—), 5.08(dd, J=4, 6 Hz, C$_3$—H).

EXAMPLE 80

To a solution of 1.63 g of 3-[2-(2-carbobenzoxyaminomethylphenyl)acetamido]-2-oxoazetidine in 10 ml of DMF is added 2.5 g of pyridine-sulfur trioxide complex. The reaction mixture is stirred in 5 days, and treated as described in Example 5 to obtain 0.815 g of sodium 3-[2-(2-carbobenzoxyaminomethylphenyl)acetamido]-2-oxoazetidine-1-sulfonate.

IR$\nu_{max}^{KBr}$cm$^{-1}$: 1765, 1695, 1685, 1530, 1260, 1055.

NMR(D$_2$O, ppm); 3.70(dd, J=3, 5, 6 Hz, C$_4$—H), 3.78(s, —CH$_2$—), 3.88(t, J=6 Hz, C$_4$—H), 4.37(s, —CH$_2$—), 4.87(dd, J=3.5, 6 Hz, C$_4$—H), 5.19(s, —CH$_2$—), 7.42(s, aromatic H), 7.50(s, aromatic H).

In 35 ml of 30% methanol is dissolved 0.30 g of the above sodium 3-[2-(2-carbobenzoxyaminomethylphenyl)acetamido]-2-oxoazetidine-1-sulfonate, followed by addition of 0.68 ml of 6% acetic acid and 76 mg of palladium black. The mixture is stirred in hydrogen gas streams at room temperature for 90 minutes. The catalyst is filtered off and the filtrate is purified on an Amberlite XAD-II column. The above procedure provides 0.167 g of sodium 3-[2-(2-aminomethylphenyl)acetamido]-2-oxoazetidine-1-sulfonate.acetate.

IR$\nu_{max}^{KBr}$cm$^{-1}$; 1760, 1645, 1530, 1240, 1045.

NMR(D$_2$O, ppm); 2.01(s, CH$_3$), 3.69(dd, J=3.5, 6 Hz, C$_4$—H), 3.74(s, —CH$_2$—), 3.97(t, J=6 Hz, C$_4$—H), 4.41(s, —CH$_2$—), 4.98(dd, J=3.5, 6 Hz, C$_3$—H), 7.48(s, aromatic H).

EXAMPLE 81

To a solution of 0.50 g of 3-(2-methoxyimino-2-furylacetamido)-2-oxoazetidine in 2 ml of DMF is added 1.01 g of pyridine-sulfur trioxide complex. The reaction mixture is stirred for 2 days and treated as described in Example 5 to obtain 0.108 g of sodium 3-(2-methoxyimino-2-furylacetamido)-2-oxoazetidine-1-sulfonate.

IR$\nu_{max}^{KBr}$cm$^{-1}$: 1770, 1700, 1685, 1250, 1055.

NMR(D$_2$O, ppm); 3.91(dd, J=3.5, 6 Hz, C$_4$—H), 4.13(t, J=6 Hz, C$_4$—H), 4.10(s, CH$_3$—), 5.22(dd, J=3.5, 6 Hz, C$_3$—H), 6.72,

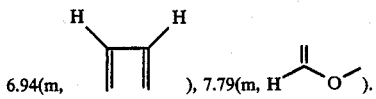

6.94(m, ), 7.79(m, ).

EXAMPLE 82

In 4 ml of DMF is dissolved 0.35 g of 3-[2-(2-N-trichloroacetylureidomethylphenyl)acetamido]-2-oxoazetidine, followed by addition of 0.70 g of pyridine-sulfur trioxide complex. The reaction mixture is stirred at room temperature for 4 days and, then, worked up in the manner as Example 5. The resultant sodium 3-[2-(2N-trichloroacetylureidomethylphenyl)acetamido]-2-oxoazetidine-1-sulfonate is dissolved in 20 ml of water, and the solution is adjusted to pH 7.5 with sodium hydrogen carbonate and stirred at room temperature for 2 hours. The solution is adjusted to pH 6 and, then, purified on an Amberlite XAD-II column. The above procedure provides 87 mg of sodium 3-[2-(2-ureidomethylphenyl)acetamido]-2-oxoazetidine-1-sulfonate.

IR$\nu_{max}^{KBr}$cm$^{-1}$; 1760, 1640, 1245, 1150.

EXAMPLE 83

In 4 ml of DMF is dissolved 0.50 g of 3-[2-(3,5-dichloro-4-pyridon-1-yl)acetamido]-2-oxoazetidine, followed by addition of 0.85 g of pyridine-sulfur trioxide complex. The mixture is stirred at room temperature for 3 days and, then, worked up in the manner as described in Example 5. The above procedure provides 0.265 g of sodium 3-[2-(3,5-dichloro-4-pyridon-1-yl)acetamido]-2-oxoazetidine-1-sulfonate.

IR$\nu_{max}^{KBr}$cm$^{-1}$; 1760, 1680, 1635, 1580, 1250, 1220, 1055.

NMR(D$_2$O, ppm); 3.85(dd, J=4, 6 Hz, C$_4$—H), 4.07(t, J=6 Hz, C$_4$—H), 5.05(dd, J=4, 6 Hz, C$_3$—H), 5.07(s, —CH$_2$—),

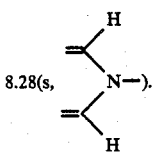

8.28(s, ).

EXAMPLE 84

In 3 ml of DMF is dissolved 0.676 g of 3-(2-phenyl-2-benzyloxycarbonylacetamido)-2-oxoazetidine, followed by addition of 0.955 g of pyridine-sulfur trioxide complex. The mixture is stirred at room temperature for 4 days and, then, worked up in the manner of Example 5. The above procedure provides 0.117 g of sodium 3-(2-phenyl-2-benzyloxycarbonylacetamido)-2-oxoazetidine-1-sulfonate.

IR$\nu_{max}^{KBr}$cm$^{-1}$; 1765, 1250, 1200, 1060.

NMR(D$_2$O, ppm); 3.52(dd, J=3.5, 5.5 Hz, C$_4$—H), 3.75(t, J=5.5 Hz, C$_4$—H), 4.75(dd, J=3.5, 5.5 Hz, C$_3$—H), 4.77(s, —CH—), 5.03(s, —CH$_2$—), 7.16(s, aromatic H), 7.26(s, aromatic H).

EXAMPLE 85

In 3 ml of DMF is dissolved 0.180 g of 3-[2-(N-carbobenzoxyprolylamino)-2-furylacetamido]-2-oxoazetidine, followed by addition of 0.19 g of pyridine-sulfur trioxide complex. The mixture is stirred for 2 days and, then, worked up in the manner as described in Example 5. The above procedure provides 46 mg of sodium 3-[2-(N-carbobenzoxyprolylamino)-2-furylacetamido]-2-oxoazetidine-1-sulfonate.

IR$\nu_{max}^{KBr}$cm$^{-1}$; 1775, 1700, 1685, 1250, 1055.

EXAMPLE 86

In 3 ml of DMF is dissolved 0.45 g of 3-[2-(1-acetyl-2,4-dioxoimidazolidin-3-yl)acetamido]-2-oxoazetidine, followed by addition of 1.0 g of pyridine-sulfur trioxide complex. The mixture is stirred for 2 days and, then, worked up in the manner of Example 5. The above procedure provides 0.38 g of sodium 3-[2-(1-acetyl-2,4-dioxoimidazolidin-3-yl)acetamido]-2-oxoazetidine-1-sulfonate.

IR$\nu_{max}^{KBr}$cm$^{-1}$; 1735, 1260, 1155.

NMR(D$_2$O, ppm); 2.66(s, CH$_3$—), 3.82(dd, J=3.5, 6 Hz, C$_4$—H), 4.04(t, J=6 Hz, C$_4$—H), 4.50(s, —CH$_2$—), 4.59(s, —CH$_2$—), 5.08(dd, J=3.5, 6 Hz, C$_3$—H).

EXAMPLE 87

In 2 ml of DMF is dissolved 0.30 g of 3-[2-(2-oxoimidazolidin-1-yl)acetamido]-2-oxoazetidine, followed by addition of 0.45 g of pyridine-sulfur trioxide complex. The mixture is reacted for 2 days and, then, worked up in the manner as described in Example 5. The above procedure provides 65 mg of sodium 3-[2-(2-oxoimidazolidin-1-yl)acetamido]-2-oxoazetidine-1-sulfonate.

IR$\nu_{max}^{KBr}$cm$^{-1}$; 1740, 1695, 1285, 1260, 1165.

NMR(D$_2$O, ppm); 3.45-4.3(m, —CH$_2$—, C$_4$—H), 5.02(dd, J=3.5, 6 Hz, C$_3$—H).

EXAMPLE 88

In 70 ml of 30% methanol is dissolved 0.30 g of the sodium 3-[2-(2-carbobenzoxyaminomethylphenyl)acetamido]-2-oxoazetidine-1-sulfonate obtained in Example 80 followed by addition of 0.68 ml of 6% acetic acid and 75 mg of palladium black. The mixture is stirred in hydrogen gas streams at room temperature for 90 minutes, after which the catalyst is filtered off. The filtrate is concentrated under reduced pressure, followed by addition of 30 ml of tetrahydrofuran. Then, under ice-cooling, 0.15 g of 1-chlorocarbonylimidazolid-2-one is added to the above tetrahydrofuran solution. The mixture is stirred for 90 minutes (its pH being maintained at 8.5 with a 1% aqueous solution of sodium hydrogen carbonate). The reaction mixture is adjusted to pH 6.5 with phosphoric acid, and the tetrahydrofuran is distilled off under reduced pressure. The residue is purified on an Amberlite XAD-II column to provide 0.24 g of sodium 3-[2-[2-(2-oxoimidazolidin-1-yl)carbonylaminomethylphenyl]acetamido]-2-oxoazetidine-1-sulfonate.

IR$\nu_{max}^{KBr}$cm$^{-1}$; 1770, 1740, 1675, 1280, 1060.

EXAMPLE 89

The sodium 3-[2-(2-carbobenzoxyaminomethylphenyl)acetamido]-2-oxoazetidine-1-sulfonate (0.30 g) obtained in Example 80 is treated in the manner as described in Example 88 except that 0.15 g of 1-chlorocarbonyl-3-benzylideneaminoimidazolid-2-one is used in lieu of 1-chlorocarbonylimidazolid-2-one. The procedure provides 0.21 g of sodium 3-[2-[2-(2-oxo-3-benzylideneaminoimidazolidin-1-yl)carboxyaminomethylphenylacetamido]-2-oxoazetidine-1-sulfonate.

IR$\nu_{max}^{KBr}$cm$^{-1}$; 1765, 1735, 1680, 1280, 1250, 1055.

EXAMPLE 90

In 4 ml DMF is dissolved 0.80 g of 3-[2-(4-ethyl-2,3-dioxo-1-piperazinocarboxamido)-2-furylacetamido]-2-oxoazetidine, followed by addition of 1.35 g of pyridine-sulfur trioxide complex. The mixture is stirred for 2 days and, then, worked up in the manner as described in Example 5. The above procedure provides 0.20 g of sodium 3-[2-(4-ethyl-2,3-dioxo-1-piperazinocarboxamido)-2-furylacetamido]-2-oxoazetidine-1-sulfonate.

NMR(D$_2$O, ppm); 1.30(t, J=7 Hz, —CH$_3$), 3.61(q, J=7 Hz, —CH$_2$—), 3.65-4.3(m, C$_4$—H, —CH$_2$—), 5.07(dd, J=3.5, 5.5 Hz, C$_3$—H),

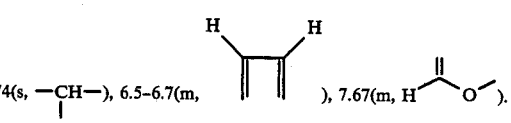

5.74(s, —CH—), 6.5-6.7(m, ), 7.67(m, H—O).

EXAMPLE 91

In 5 ml of DMF is dissolved 1.0 g of 3-[D-N-(thienylmethylcarbonyl)alanylamino]-2-oxoazetidine, followed by addition of 1.7 g of pyridine-sulfur trioxide complex. The mixture is stirred for 2 days and, then, worked up in the manner as described in Example 5. The above procedure provides 0.325 g of sodium 3-[D-N-(thienylmethylcarbonyl)alanylamino]-2-oxoazetidine-1-sulfonate.

IR$\nu_{max}^{KBr}$cm$^{-1}$; 1763, 1665, 1247, 1055.

NMR(D$_2$O, ppm); 1.48(d, J=7.5 Hz, —CH$_3$), 3.74(dd, 3.5, 6 Hz, C$_4$—H), 3.96(s, —CH$_2$—), 4.00(t, J=6 Hz, C$_4$—H), 4.47(q, J=7.5Hz, —CH—), 5.02(dd, J=3.5, 6 Hz, C$_3$—H),

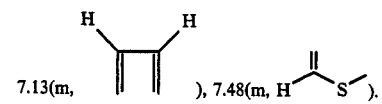

7.13(m, ), 7.48(m, H—S).

EXAMPLE 92

In 2 ml of DMF is dissolved 0.33 g of 3-(N-carbobenzoxy-D-alaninamido)-3-methoxy-2-oxoazetidine, followed by addition of 0.32 g of pyridine-sulfur trioxide complex. The mixture is stirred at room temperature for 2 days and, then, worked up in the manner of Example 5. The above procedure provides 52 mg of sodium 3-(N-carbobenzoxy-D-alaninamido)-3-methoxy-2-oxoazetidine-1-sulfonate.

IR$\nu_{max}^{KBr}$cm$^{-1}$; 1763, 1685, 1515, 1245, 1052.

NMR(DMSO-d$_6$, ppm); 1.22(d, J=7 Hz, CH$_3$), 3.30(s, CH$_3$), 3.54, 3.70(dd, J=7 Hz, —CH$_2$—), 4.26(m, J=7Hz, —CH—), 5.03(s, —CH$_2$—), 7.36(s, aromatic H), 9.12(d, J=7 Hz).

EXAMPLE 93

In 2 ml of DMF is dissolved 0.393 g of 3-[N-(4-ethyl-2,3-dioxo-1-piperazinocarbonyl)-D-alaninamido]-3-methoxy-2-oxoazetidine, followed by addition of 0.350 g of pyridine-sulfur trioxide complex. The mixture is stirred at room temperature for 4 days and, then, worked up in the manner as described in Example 5. The above procedure provides 45.5 mg of sodium 3-[N-(4-ethyl-2,3-dioxo-1-piperazinocarbonyl)-D-alaninamido]-3-methoxy-2-oxoazetidine-1-sulfonate.

IR$\nu_{max}^{KBr}$cm$^{-1}$; 1765, 1705, 1675, 1510, 1250, 1200, 1050.

NMR(DMSO-d$_6$, ppm); 1.10(t, J=7 Hz, CH$_3$), 1.32(d, J=7 Hz, CH$_3$), 3.35(s, CH$_3$), 3.43(q, J=7 Hz, —CH$_2$—), 3.60(m, —CH$_2$—), 3.90(m, —CH$_2$—), 4.47(m, —CH—), 9.23(d, J=7 Hz, NH), 9.40, 9.44(each s, NH).

EXAMPLE 94

In 2 ml of DMF is dissolved 516.5 mg of 3-[N-(N-carbobenzoxy-D-phenylglycyl)-D-phenylglycinamido]-3-methoxy-2-oxoazetidine, followed by addition of 320 mg of pyridine-sulfur trioxide complex. The mixture is stirred at room temperature for 4 days and, then, worked up in the manner as described in Example 5. The above procedure provides 145 mg of sodium 3-[(N-carbobenzoxy-D-phenylglycyl)-D-phenylglycinamido]-3-methoxy-2-oxoazetidine-1-sulfonate.

IR$\nu_{max}^{KBr}$cm$^{-1}$; 1760, 1705, 1680, 1505, 1240, 1045.

NMR(DMSO-d$_6$+D$_2$O, ppm); 3.08, 3.26(each s, CH$_3$), 3.40(m, —CH$_2$—), 5.06(s, —CH$_2$—), 5.45(s, —CH—), 5.59(s, —CH—), 7.2-7.55(m, aromatic H).

EXAMPLE 95

In 1.5 ml of DMF is dissolved 0.300 g of 3-[N-(4-ethyl-2,3-dioxo-1-piperazinocarbonyl)-D-methioinamido]-2-oxoazetidine followed by addition of 0.250 g of pyridine-sulfur trioxide complex. The mixture is stirred at room temperature for 4 days and, then, worked up in the manner as described in Example 5. The above procedure provides 0.168 g of sodium 3-[N-(4-ethyl-2,3-dioxo-1-piperazinocarbonyl)-D-methioninamido]-2-oxoazetidine-1-sulfonate.

IR$\nu_{max}^{KBr}$cm$^{-1}$; 1760, 1705, 1670, 1520, 1245, 1190, 1050.

NMR(DMSO-d$_6$, ppm); 1.10(t, J=7 Hz, CH$_3$), 1.96(m, —CH$_2$—), 2.06(s, CH$_3$), 2.44(t, J=7 Hz, —CH$_2$—), 3.42(q, J=7 Hz, —CH$_2$—), 3.58(m, —CH$_2$—), 3.92(m, 13 CH$_2$—), 4.42(m, —CH—),
|

4.84(m, C$_3$—H), 8.92(d, J=7 Hz, NH), 9.22(d, J=7 Hz, NH).

EXAMPLE 96

In 2 ml of DMF is dissolved 0.186 g of 3-[2-D-[4-(2-phenethyl)-2,3-dioxo-1-piperazinocarboxamido]-2-phenylacetamido]-2-oxoazetidine, followed by addition of 0.128 g of pyridine-sulfur trioxide complex. The mixture is stirred for 1 day and, then, worked up in the manner as described in Example 5. The above procedure provides 0.180 g of sodium 3-[2-D-[4-(2-phenethyl)-2,3-dioxo-1-piperazinocarboxamido]-2-phenylacetamido]-2-oxoazetidine-1-sulfonate.

IR$\nu_{max}^{KBr}$cm$^{-1}$; 3280, 1755, 1705, 1670, 1505, 1270–1230, 1190, 1050.

NMR(d$_6$-DMSO, ppm); 2.84(t, J=7 Hz, —CH$_2$—), 3.13(dd, J=3, 6 Hz, C$_4$—H), 4.85(ddd, J=3, 6, 8 Hz, C$_4$—H), 5.44(d, J=7Hz, —CH—),
|

7.2–7.5(m, aromatic H), 9.24(d, J=8 Hz, NH), 9.78(d, J=7 Hz, NH).

EXAMPLE 97

In 2 ml of DMF is dissolved 0.178 g of 3-[2-D-(4-ethyl-2,3-dioxo-1-piperazinocarboxamido)-2-(4-benzoyloxyphenyl)acetamido]-2-oxoazetidine, followed by addition of 0.112 g of pyridine-sulfur trioxide complex. The mixture is stirred for 1 day and, then, worked up in the manner as described in Example 5. The above procedure provides 0.125 g of sodium 3-[2-D-(4-ethyl-2,3-dioxo-1-piperazinocarboxamido)-2-(4-benzoyloxyphenyl)acetamido]-2-oxoazetidine-1-sulfonate.

IR$\nu_{max}^{KBr}$cm$^{-1}$; 3300, 1760, 1730, 1705, 1675, 1505, 1270, 1210–1170, 1055.

NMR(d$_6$-DMSO, ppm); 1.10(t, —CH$_3$), 3.18(dd, J=3, 6 Hz, C$_4$—H), 3.62(t, J=6 Hz, C$_4$—H), 3.4–4.1(m, —CH$_2$—), 4.90(ddd, J=3, 6, 8 Hz, C$_3$—H), 5.52(d, J=7Hz, —CH—),
|

7.2–8.2(m, aromatic H), 9.32(d, J=8 Hz, NH), 9.87(d, J=7 Hz, NH).

EXAMPLE 98

In 3 ml of DMF is dissolved 0.278 g of 3-[2-benzyloxycarboxamido-3-(N-methylcarbamoyl)propionamido]-3-methoxy-2-oxoazetidine, followed by addition of 0.175 g of pyridine-sulfur trioxide complex. The mixture is stirred for 2 days and, then, worked up in the manner as described in Example 5. The above procedure provides 32 mg of sodium 3-[2-benzyloxycarboxamido-3-(N-methylcarbamoyl)propionamido]-3-methoxy-2-oxoazetidine-1-sulfonate.

IR$\nu_{max}^{KBr}$cm$^{-1}$; 3395, 1768, 1670, 1655, 1250, 1052.

NMR(DMSO-d$_6$, ppm); 2.33–2.67(m, CH$_2$, CH$_3$), 3.40(s, CH$_3$), 3.50(m, C$_4$—H), 4.37(m, —CH—),
|

4.99(s, —CH$_2$—), 7.31(s, aromatic H), 7.70(m, NH), 9.07(s, NH).

EXAMPLE 99

In 10 ml of DMF is suspended 0.785 g of 3-[2-[(3-furfurylideneamino-2-oxoimidazolidin-1-yl)-carboxamido]-2-(2-chloroacetamido-4-thiazolyl)acetamido]-2-oxoazetidine, followed by addition of 0.478 g of pyridine-sulfur trioxide complex. The mixture is reacted for 1 day and, then, worked up in the manner as described in Example 5. The above procedure provides 0.465 g of sodium 3-[2-[(3-furfurylideneamino-2-oxoimidazolidin-1-yl)carboxamido]-2-(2-chloroacetamido-4-thiazolyl)acetamido]-2-oxoazetidine-1-sulfonate.

IR$\nu_{max}^{KBr}$cm$^{-1}$; 3300, 1755, 1720, 1665, 1525, 1410, 1270, 1230, 1050.

NMR(d$_6$-DMSO, ppm); 3.20, 3.28(dd, J=3, 6 Hz, C$_4$—H), 3.82(s, —CH$_2$—), 4.36(s, —CH$_2$Cl), 4.85(m, C$_3$—H), 5.54(d, J=8Hz, —CH—),
|

6.5–7.9(m, furyl—H),

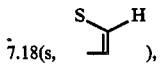

7.75(s, —CH=N—), 8.96(d, J=8 Hz, NH), 9.01, 9.05(d, J=8 Hz, NH), 12.66(broad s, NH).

In 5 ml of water is dissolved 0.25 g of the above sodium 3-[2-[(3-furfurylideneamino-2-oxoimidazolidin-1-yl)carboxamido]-2-(2-chloroacetamido-4-thiazolyl)acetamido]-2-oxoazetidine-1-sulfonate, followed by addition of 0.057 g of sodium N-methyldithiocarbamate under stirring and ice-cooling. The solution is stirred for 75 minutes. The insoluble matter is filtered off and the filtrate is purified by an Amberlite XAD-II column. The above procedure provides 0.089 g of sodium 3-[2-[(3-furfurylideneamino-2-oxoimidazolidin-1-yl)carboxamido]-2-(2-amino-4-thiazolyl)acetamido]-2-oxoazetidine-1-sulfonate.

IR$\nu_{max}^{KBr}$cm$^{-1}$; 3310, 3200, 1760, 1725, 1655, 1515, 1415, 1270, 1230, 1050.

NMR(d$_6$-DMSO, ppm); 3.61(t, J=6 Hz, C$_4$—H), 3.82(s, —CH$_2$—), 4.84(m, C$_3$—H),

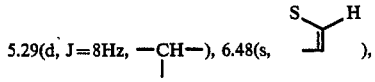

6.5–7.9(m, furyl-H), 7.74(s, —CH=N—), 8.80(d, J=8 Hz, NH), 8.89, 8.93(d, J=8 Hz, NH).

EXAMPLE 100

In 2 ml of DMF is dissolved 0.20 g of 3-[D-2-(2-phenylacetamido)propionamido]-3-methoxy-2-oxoazetidine, followed by addition of 0.208 g of pyridine-sulfur trioxide complex. The mixture is stirred at room temperature for 2 days and, then, worked up in the manner as described in Example 5. The above procedure provides 20 mg of sodium 3-[D-2-(2-phenylacetamido)propionamido]-3-methoxy-2-oxoazetidine-1-sulfonate.

IR$\nu_{max}^{KBr}$cm$^{-1}$; 1765, 1645, 1520, 1240.

NMR(DMSO-d$_6$, ppm); 1.23, 1.24(each d, J=7 Hz, CH$_3$), 2.80, 3.00(each s, —CH$_2$—), 3.47(s, CH$_3$), 4.45(m, —CH—), 7.29(s, aromatic H).

EXAMPLE 101

In 2 ml of DMF is dissolved 0.33 g of 3-(N-carbobenzoxy-D-alaninamido)-3-methoxy-2-oxoazetidine which is obtained in Reference Example 15, followed by addition of 0.32 g of pyridine-sulfur trioxide complex. The mixture is stirred at room temperature for 3 days and, then, worked up in the manner as described in Example 5. The above procedure provides 16.5 mg of sodium 3-(N-carbobenzoxy-D-alaninamido)-3-methoxy-2-oxoazetidine-1-sulfonate.

IR$\nu_{max}^{KBr}$cm$^{-1}$; 1765, 1695, 1520, 1245, 1050.

NMR(DMSO-d$_6$, ppm); 1.22(d, J=7 Hz, CH$_3$), 3.29(s, —CH$_3$), 3.54, 3.64(each d, J=7 Hz, —CH$_2$—), 4.10(m, —CH—), 5.03(s, —CH$_2$—), 7.36(s, aromatic H).

EXAMPLE 102

In 8 ml of DMF is dissolved 0.447 g of 3-[2-[[2-oxo-3-(thiophene-2-aldoimino)imidazolidin-1-yl]carboxamido]-2-thienylacetamido]-2-oxoazetidine, followed by addition of 0.319 g of pyridine-sulfur trioxide complex. The mixture is stirred for 1 day and, then, worked up in the manner as described in Example 5. The above procedure provides 0.234 g of sodium 3-[2-[[2-oxo-3-(thiophene-2-aldoimino)imidazolidin-1-yl)carboxamido]-2-thienylacetamido]-2-oxoazetidine-1-sulfonate.

IR$\nu_{max}^{KBr}$cm$^{-1}$; 3290, 1760, 1720, 1665, 1410, 1275, 1230, 1050.

NMR(d$_6$-DMSO, ppm); 3.20, 3.25(dd, J=3, 6 Hz, C$_4$—H), 3.63, 3.65(t, J=6 Hz, C$_4$—H), 3.83(s, ring CH$_2$), 4.89(m, C$_3$—H), 5.72(d, J=7Hz, —CH—), 6.9–7.7(m, thienyl—H), 8.10(s, —CH=), 8.99(d, J=7 Hz, NH), 9.26, 9.30(d, J=8 Hz, NH).

EXAMPLE 103

In 4 ml of DMF is dissolved 0.307 g of 3-[D-2-[(3-mesyl-2-oxoimidazolidin-1-yl)carboxamido]-2-phenylacetamido]-2-oxoazetidine, followed by addition of 0.239 g of pyridine-sulfur trioxide complex. The mixture is stirred for 1 day and, then, worked up in the manner as described in Example 5. The above procedure provides 0.244 g of sodium 3-[D-2-[[3-mesyl-2-oxoimidazolidin-1-yl)carboxamido]-2-phenylacetamido]-2-oxoazetidine-1-sulfonate.

IR$\nu_{max}^{KBr}$cm$^{-1}$; 3320, 1755, 1730, 1665, 1520, 1395, 1350, 1255, 1160, 1050.

NMR(d$_6$-DMSO, ppm); 3.14(dd, J=3, 6 Hz, C$_4$—H), 3.36(s, CH$_3$—), 3.58(t, J=6 Hz, C$_4$—H), 3.79(s, —CH$_2$—), 4.85(ddd, J=3, 6, 8 Hz, C$_3$—H), 5.43(d, J=7Hz, —CH—), 7.39(s, aromatic H), 8.77(d, J=7 Hz, NH), 9.25(d, J=8 Hz, NH).

EXAMPLE 104

In 4 ml of DMF is dissolved 0.313 g of 3-[2-[(3-mesyl-2-oxoimidazolidin-1-yl)carboxamido]-2-thienylacetamido]-2-oxoazetidine, followed by addition of 0.239 g of pyridine-sulfur trioxide complex. The mixture is stirred for 3 days and, then, worked up in the manner as described in Example 5. The above procedure provides 0.19 g of sodium 3-[2-[(3-mesyl-2-oxoimidazolidin-1-yl)carboxamido]-2-thienylacetamido]-2-oxoazetidine-1-sulfonate.

IR$\nu_{max}^{KBr}$cm$^{-1}$; 3320, 1760, 1725, 1670, 1520, 1395, 1355, 1250, 1165, 1050.

NMR(d$_6$-DMSO, ppm); 3.18(dd, J=3, 6 Hz, C$_4$—H), 3.35(s, CH$_3$), 3.61, 3.63(t, J=6 Hz, C$_4$—H), 4.85(m, C$_3$—H), 5.79(d, J=7Hz, —CH—), 6.7–7.6(m, thienyl—H), 8.65(d, J=7 Hz, NH), 9.26, 9.30(d, J=8 Hz, NH).

EXAMPLE 105

In 5 ml of DMF is dissolved 0.658 g of 3-[D-2-(2,6-dichlorophenylthioglycolamido)-2-phenylacetamido]-2-oxoazetidine, followed by addition of 0.480 g of pyridine-sulfur trioxide complex. The mixture is stirred for 2 days and, then, worked up in the manner as described in Example 7. The above procedure provides 0.774 g of pyridinium 3-[D-2-(2,6-dichlorophenylthioglycolamido)-2-phenylacetamido]-2-oxoazetidine-1-sulfonate.

IR$\nu_{max}^{KBr}$cm$^{-1}$; 1760, 1659(shoulder), 1631, 1228, 1040.

NMR(DMSO-d$_6$, ppm); 3.20(dd, J=3, 6 Hz, C$_4$—H), 3.60(t, J=6 Hz, C$_4$—H), 3.09, 3.90(ABq, J=15 Hz, —CH$_2$—), 4.86(dd, J=3, 6 Hz, C$_3$—H), 5.49(d, J=8Hz, —CH—), 8.95(d, J=7 Hz, NH), 9.18(d, J=8 Hz, NH).

EXAMPLE 106

In 1 ml of DMF is dissolved 0.172 g of 3-[(hexahydro-1H-azepin-1-yl)methylenamino]-2-oxoazetidine, followed by addition of 0.183 g of pyridine-sulfur trioxide complex. The mixture is stirred at room temperature for 2 days and, then, worked up in the manner as described in Example 5. The above procedure provides 0.056 g of sodium 3-[(hexahydro-1H-azepin-1-yl)methylenamino)]-2-oxoazetidine-1-sulfonate.

IR$\nu_{max}^{KBr}$cm$^{-1}$; 1762, 1684, 1270, 1242, 1042.

NMR(DMSO-d$_6$, ppm); 1.4–1.9(m, —CH$_2$—), 3.72(t, J=6 Hz, C$_4$—H), 4.90(dd, J=3, 6 Hz, C$_3$—H), 8.19(s, —CH=).

EXAMPLE 107

In 1.8 ml of DMF is dissolved 0.440 g of 3-[D-2-(4-ethyl-2,3-dioxo-1-piperazinocarboxamido)-3-phenyl-propionamido]-3-methoxy-2-oxoazetidine, followed by addition of 0.320 g of pyridine-sulfur trioxide complex. The mixture is stirred for 42 hours and, then, worked up in the manner as described in Example 5. The above procedures provides 0.152 g of sodium 3-[D-2-(4-ethyl-2,3-dioxo-1-piperazinocarboxamido)-3-phenyl-propinamido]-3-methoxy-2-oxoazetidine-1-sulfonate.

IR$\nu_{max}^{KBr}$cm$^{-1}$; 1760, 1705, 1670, 1510, 1250, 1190, 1042.

NMR(DMSO-d$_6$, ppm); 1.09(t, J=7 Hz, —CH$_3$), 3.22, 3.30(each s, CH$_3$), 4.70(m, —CH—), 8.90, 9.17(each d, J=7 Hz, NH).

EXAMPLE 108

In 2 ml of DMF is dissolved 0.35 g of 3-(2-dichloroacetoxyimino-2-thienylacetamido)-2-oxoazetidine, followed by addition of 0.289 g of pyridine-sulfur trioxide complex. The mixture is stirred for 24 hours and, then, worked up in the manner as described in Example 5. The procedure provides 0.28 g of sodium 3-(2-dichloroacetoxyimino-2-thienylacetamido)-2-oxoazetidine-1-sulfonate.

IR$\nu_{max}^{KBr}$cm$^{-1}$; 1760, 1660, 1613, 1530, 1240, 1190, 1150.

NMR(DMSO-d$_6$, ppm); 3.37(dd, J=3, 6 Hz, C$_4$—H), 3.68(t, J=6 Hz, C$_4$—H), 4.93(ddd, J=3, 6, 8 Hz, C$_3$—H), 7.10(s, —CHCl$_2$).

In 10 ml of water is dissolved 0.25 g of the above sodium 3-(2-dichloroacetoxyimino-2-thienylacetamido)-2-oxoazetidine-1-sulfonate and the solution is stirred at room temperature for 3 hours, the pH of the solution being maintained at 7 to 8 with sodium hydrogen carbonate. The reaction mixture is then purified on an Amberlite XAD-II column to obtain 0.1 g of sodium 3-(2-oxyimino-2-thienylacetamido)-2-oxoazetidine-1-sulfonate.

IR$\nu_{max}^{KBr}$cm$^{-1}$; 1760, 1670, 1615, 1515, 1250, 1200, 1050.

NMR(DMSO-d$_6$, ppm); 3.35(dd, J=3, 6 Hz, C$_4$—H), 3.65(t, J=6 Hz, C$_4$H), 4.85(ddd, J=2, 6, 8 Hz, C$_3$—H).

EXAMPLE 109

In 1 ml of DMF is dissolved 0.320 g of 3-(2-phenyl-2-sulfamoylacetamido)-2-oxoazetidine, followed by addition of 0.336 g of pyridine-sulfur trioxide complex. The mixture is stirred at room temperature for 2 days and, then, worked up in the manner as described in Example 5. The above procedure provides 0.085 g of sodium 3-(2-phenyl-2-sulfamoylacetamido)-2-oxoazetidine-1-sulfonate.

IR$\nu_{max}^{KBr}$cm$^{-1}$; 1760, 1670, 1230, 1153, 1042.

NMR(DMSO-d$_6$, ppm); 3.22(dd, J=3, 6 Hz, C$_4$—H), 3.65(t, J=6 Hz, C$_4$H), 4.85(m, C$_3$—H), 5.04(s, —CH—), 7.3–7.7(m, aromatic H).

EXAMPLE 110

In 1 ml of DMF is dissolved 0.197 g of 3-(2-N,N-dimethylsulfamoyl-2-phenylacetamido)-2-oxoazetidine, followed by addition of 0.202 g of pyridine-sulfur trioxide complex. The mixture is stirred at room temperature overnight and, then, worked up in the manner as described in Example 5. The above procedure provides 0.125 g of sodium 3-(2-N,N-dimethylsulfamoyl-2-phenylacetamido)-2-oxoacetidine-1-sulfonate.

IR$\nu_{max}^{KBr}$cm$^{-1}$; 3350, 1760, 1678, 1518, 1280, 1240, 1142, 1052.

NMR(DMSO-d$_6$, ppm); 2.66, 2.70(each s, CH$_3$), 3.22(dd, J=3, 6 Hz, C$_4$—H), 3.69(t, J=6 Hz, C$_4$—H), 4.87(ddd, J=3, 6, 8 Hz, C$_3$—H), 5.30(s, —CH—), 9.19, 9.22(each d, J=8 Hz, NH), 7.3—7.8(m, aromatic H).

EXAMPLE 111

In 1.5 ml of DMF is dissolved 0.465 g of 3-[2,5-bis(4-ethyl-2,3-dioxo-1-piperazinocarboxamido)pentanamido]-2-oxoazetidine, followed by addition of 0.284 g of pyridine-sulfur complex. The mixture is stirred at room temperature for 2 days and, then, worked up in the manner as described in Example 5. The above procedure provides 0.145 g of sodium 3-[2,5-bis(4-ethyl-2,3-dioxo-1-piperazinocarboxamido)pentanamido]-2-oxoazetidine-1-sulfonate.

IR$\nu_{max}^{KBr}$cm$^{-1}$; 1760, 1710, 1670, 1520, 1250, 1190, 1050.

NMR(DMSO-d$_6$, ppm); 1.12(t, J=7 Hz, CH$_3$), 3.27(dd, J=3, 6 Hz, C$_4$—H), 4.38(m, —CH—), 4.86(ddd, J=3, 6, 8 Hz, C$_3$—H), 8.7–9.1(m, NH), 9.21(d, J=8 Hz, NH).

EXAMPLE 112

In 1.5 ml of DMF is dissolved 0.405 g of 3-[2,5-bis(4-ethyl-2,3-dioxo-1-piperazinocarboxamido)pentanamido]-3-methoxy-2-oxoazetidine, followed by addition of 0.284 g of pyridine-sulfur trioxide complex. The mixture is stirred at room temperature for 3 days and, then, worked up in the manner as described in Example 5. The above procedure provides 0.105 of sodium 3-[2,5-bis(4-ethyl-2,3-dioxo-1-piperazinocarboxamido)-pentanamido]-3-methoxy-2-oxoazetidine-1-sulfonate.

IR$\nu_{max}^{KBr}$cm$^{-1}$; 3300, 1760, 1710, 1670, 1520, 1250, 1190, 1050.

NMR(DMSO-d$_6$, ppm); 1.09(t, J=7 Hz, CH$_3$), 3.27(dd, J=3, 6 Hz, C$_4$—H), 3.52(t, J=7 Hz, C$_4$—H), 8.79(m, NH) 9.20 (d, J=8 Hz, NH).

EXAMPLE 113

In 5 ml of DMF is dissolved 0.421 g of 3-[D-2-[4-(2-chloroethyl)-2,3-dioxo-piperazinocarboxamido]-2-phenylacetamido]-2-oxoazetidine, followed by addition of 0.30 g of pyridine-sulfur trioxide complex. The mixture is stirred at room temperature for 2 days and, then, worked up in the manner as described in Example 5. The above procedure provides 0.32 g of sodium 3-[D-2-[4-(2-chloroethyl)-2,3-dioxo-1-piperazinocarboxamido]-2-phenylacetamido]-2-oxoazetidine-1-sulfonate.

IR$\nu_{max}^{KBr}$cm$^{-1}$; 3450, 3280, 1760. 1705, 1665, 1510, 1255, 1190, 1050.

NMR(DMSO-d$_6$, ppm); 3.12(dd, J=3, 6 Hz, C$_4$—H), 3.40(t, J=7 Hz, —CH$_2$—), 3,80–4.00(m, —CH$_2$—), 4.72(m, —CH—), 4.92(m, C$_3$—H), 7.2–7.5(m, aromatic H), 9.20(d, J=8 Hz, NH), 9.80(d, J=8 Hz, NH).

EXAMPLE 114

In 2 ml of DMF is dissolved 0.36 g of 3-[D-3-chloro-2-(4-ethyl-2,3-dioxo-1-piperazinocarboxamido)propionamido]-2-oxoazetidine, followed by addition of 0.32 g of pyridine-sulfur trioxide complex. The mixture is stirred at room temperature for 4 days and, then, worked up in the manner as described in Example 5. The above procedure provides 0.28 g of sodium 3-[D-2-chloro-2-(4-ethyl-2,3-dioxo-1-piperazinocarboxamido)-propionamido]-2-oxoazetidine-1-sulfonate.

IR$\nu_{max}^{KBr}$cm$^{-1}$; 1760, 1710, 1675, 1720, 1260, 1195.

NMR(DMSO-d$_6$, ppm); 1.10(t, J=7 Hz, CH$_3$), 3.42(q, J=7 Hz, —CH$_2$—), 3.62(m, —CH$_2$—), 3.94(m, —CH$_2$—), 4.71(m, —CH—), 4.90(m, C$_3$—H), 9.05(d, J=7 Hz, NH), 9.42(d, J=7 Hz, NH).

EXAMPLE 115

In 2 ml of DMF dissolved 0.47 g of 3-(2-benzyloxycarboxamido-2-benzyloxycarbonylethanesulfonamido)-2-oxoazetidine, followed by addition of 0.32 g of pyridine-sulfur trioxide complex. The mixture is stirred at room temperature for 2 days and, then, worked up in the manner as described in Example 5. The above procedure provides 0.39 g of sodium 3-(2-benzyloxycarboxamido-2-benzyloxycarbonylethanesulfonamido)-2-oxoazetidine-1-sulfonate.

IR$\nu_{max}^{KBr}$cm$^{-1}$; 1750, 1720, 1520, 1260.
NMR(DMSO-d$_6$, ppm); 3.64(m, —CH$_2$—), 4.58(m, —CH—, C$_3$—H), 5.06 (s, —CH$_2$—), 5.15(s, —CH$_2$—), 7.34, 7.36(each s, aromatic H), 7.86(d, J=7 Hz, NH), 8.38(broad s, NH).

In 15 ml of water is dissolved 0.14 g of the above sodium 3-(2-benzyloxycarboxamido-2-benzyloxycarbonylethanesulfonamido)-2-oxoazetidine-1-sulfonate, followed by addition of 0.10 g of palladium black. The mixture is stirred in hydrogen gas streams for 1 hours, and the catalyst is filtered off. The filtrate is freeze-dried to provide 90 mg of sodium 3-(2-amino-2-carboxyethanesulfonamido)-2-oxoazetidine-1-sulfonate.

IR$\nu_{max}^{KBr}$cm$^{-1}$; 1760, 1640, 1240.

NMR(DMSO-d$_6$, ppm); 3.34(dd, J=2, 6 Hz, C$_4$—$\beta$H), 3.68(m, —CH$_2$—), 4.60(m, —CH—, C$_3$—H).

EXAMPLE 116

In 2 ml of DMF is dissolved 0.27 g of 3-[D-2-(4-ethyl-2,3-dioxo-1-piperazinocarboxamido)-3-[(1-methyl-5H-tetrazol-5-yl)thio]propionamido]-2-oxoazetidine, followed by addition of 0.195 g of pyridine-sulfur trioxide complex. The mixture is stirred at room temperature for 3 days and, then, worked up in the manner as described in Example 5. The above procedure provides 0.144 g of sodium 3-[D-2-(4-ethyl-2,3-dioxo-1-piperazinocarboxamido)-3-[(1-methyl-5H-tetrazol-5-yl)thio]propionamido]-2-oxoazetidine-1-sulfonate.

IR$\nu_{max}^{KBr}$cm$^{-1}$; 1760, 1710, 1670, 1520, 1260, 1190.

NMR(DMSO-d$_6$, ppm); 1.10(t, J=7 Hz, CH$_3$), 3.90(s, CH$_3$), 4.73(m, —CH—, C$_3$—H), 9.07(d, J=7 Hz, NH), 9.36(d, J=7 Hz, NH).

EXAMPLE 117

In 2 ml of DMF is dissolved 0.40 g of 3-[D-2-(2-benzyloxycarboxamido-2-benzyloxycarbonylethanesulfonamido)-2-phenylacetamido]-2-oxoazetidine, followed by addition of 0.214 g of pyridine-sulfur trioxide complex. The mixture is stirred at room temperature for 3 days and, then, worked up in the manner as described in Example 5. The above procedure provides 0.24 g of sodium 3-[D-2-(2-benzyloxycarboxamido-2-benzyloxycarbonylethanesulfonamido)-2-phenylacetamido]-2-oxoazetidine-1-sulfonate.

IR$\nu_{max}^{KBr}$cm$^{-1}$; 1750, 1720, 1680, 1520, 1260.

NMR(DMSO-d$_6$, ppm); 3.12(dd, J=2, 6 Hz, C$_4$—$\beta$H), 4.56(m, —CH—), 4.74(m, —CH—), 5.04, 5.12(each s, —CH$_2$—), 7.36(S, aromatic H), 7.80(d, J=7 Hz, NH), 8.21(broad s, NH), 9.12(d, J=7 Hz, NH).

In 15 ml of water is dissolved 0.18 g of the above sodium 3-[D-2-(2-benzyloxycarboxamido-2-benzyloxycarbonylethanesulfonamido)-2-phenylacetamido]-2-oxoacetidine-1-sulfonate, followed by addition of 0.10 g of palladium black. The mixture is stirred in hydrogen gas streams for 1 hour, and the catalyst is filtered off. The filtrate is freeze-dried to provide 0.13 g of sodium 3-[D-2-(2-amino-2-carboxyethanesulfonamido)-2-phenylacetamido]-2-oxoazetidine-1-sulfonate.

IR$\nu_{max}^{KBr}$cm$^{-1}$; 1760, 1645, 1520, 1265, 1235.

NMR(DMSO-d$_6$, ppm), 3.42(dd, J=2, 6 Hz, C$_4$—$\beta$H), 3.62(m, —CH$_2$—), 4.78(m, —CH—),
|

7.40(broad s, aromatic H) 9.22(d, J=7 Hz, NH).

EXAMPLE 118

In 7 ml of DMF is dissolved 0.523 g of 3-[D-2-(2-benzyloxycarboxamido-3-sulfamoylpropionamido)-2-phenylacetamido]-2-oxoazetidine, followed by addition of 0.30 g of pyridine-sulfur trioxide complex. The mixture is stirred at room temperature for 2 days and, then, worked up in the manner as described in Example 5. The above procedure provides 0.360 g of sodium 3-[D-2-(2-benzyloxycarboxamido-3-sulfamoylpropionamido)-2-phenylacetamido]-2-oxoazetidine-1-sulfonate.

IR$\nu_{max}^{KBr}$cm$^{-1}$; 1765, 1705, 1670, 1260–1230.

EXAMPLE 119

In 6 ml of DMF is dissolved 0.50 g of 3-[D-2-[2-benzyloxycarboxamido-3-(p-methoxybenzyloxycarboxamido)propionamido]-phenylacetamido]-2-oxoazetidine, followed by addition of 0.264 g of pyridine-sulfur trioxide complex. The mixture is stirred for 2 days and, then, worked up in the manner as described in Example 5. The above procedure provides 0.45 g of sodium 3-[D-2-(2-benzyloxycarboxamido)-3-(p-methoxybenzyloxycarboxamido)propionamido]-2-phenylacetamido]-2-oxoazetidine-1-sulfonate.

IR$\nu_{max}^{KBr}$cm$^{-1}$; 3285, 1758, 1688, 1645, 1243, 1048.

NMR(DMSO-d$_6$, ppm); 3.10–3.30)m, —CH$_2$—, C$_4$—H), 3.56(t, J=6 Hz, C$_4$—H), 3.74(s, CH$_3$), 4.22(m, —CH—),
|

4.84(m, C$_3$—H), 4.96(s, —CH$_2$—), 5.04(s, —CH$_2$—), 5.42(d, J=8Hz, —CH—),
|

6.90, 7.31(each d, J=8 Hz, aromatic H), 7.34(s, aromatic H), 8.40(d, J=7 Hz, NH), 9.06(d, J=8 Hz, NH).

In a solution of 10 ml of water and 2 ml of ethyl alcohol is dissolved 0.160 g of the above sodium 3-[D-2-[2-benzyloxycarboxamido-3-(p-methoxybenzyloxycarboxamido)propionamido]-2-phenylacetamido]-2-oxoazetidine-1-sulfonate, followed by addition of 0.115 g of palladium black. The mixture is stirred in hydrogen gas streams for 80 minutes, and the catalyst is filtered off. The filtrate is freeze-dried to provide 90 mg of sodium 3-[D-2-(2,3-diaminopropionamido)-2-phenylacetamido]-2-oxoazetidine-1-sulfonate.

IR$\nu_{max}^{KBr}$cm$^{-1}$; 3450–3270, 1757, 1652, 1235, 1046.

NMR(DMSO-d$_6$+D$_2$O, ppm); 3.26(dd, J=3, 6 Hz, C$_4$—H), 3.63(t, J=6 Hz, C$_4$—H), 4.82(dd, J=3, 6 Hz, C$_3$—H), 5.39(s, —CH—),
|

7.38(s, aromatic H).

EXAMPLE 120

In 4 ml of DMF is dissolved 0.30 g of 3-[D-2-[2-benzyloxycarboxamido-3-(4-ethyl-2,3-dioxo-1-piperazinocarboxamido)propionamido]-2-phenylacetamido]-2-oxoazetidine, followed by addition of 0.159 g of pyridine-sulfur trioxide complex. The mixture is stirred for 3 days and, then, worked up in the manner as described in Example 5. The above procedure provides 0.147 g of sodium 3-[D-2-[2-benzyloxycarboxamido-3-(4-ethyl-2,3-dioxo-1-piperazinocarboxamido)propionamido]-2-phenylacetamido]-2-oxoazetidine-1-sulfonate.

IR$\nu_{max}^{KBr}$cm$^{-1}$; 3300, 1768, 1705, 1670, 1260–1230, 1048.

NMR(DMSO-d$_6$, ppm), 1.07(t, J=7 Hz, —CH$_3$), 3.07(dd, J=3, 5 Hz, C$_4$—H), 3.30–3.70(m, —CH$_2$—), 3.38(q, J=7 Hz, —CH$_2$—), 3.87(m, —CH$_2$—), 4.30(m, —CH—),
|

4.80(m, C$_3$—H), 5.00(s, —CH$_2$—), 5.40(d, J=8Hz, —CH—),
|

7.31(s, aromatic H), 7.60(d, J=8 Hz, NH), 8.45(d, J=8 Hz, NH), 8.98(t, J=6 Hz, NH), 9.08(d, J=8 Hz, NH).

In 10 ml of water is dissolved 88.4 mg of the above sodium 3-[D-2-[2-benzyloxycarboxamido-3-(4-ethyl-2,3-dioxo-1-piperazinocarboxamido)propionamido]-2-phenylacetamido]-2-oxoazetidine-1-sulfonate, followed by addition of 90 mg of palladium black. The mixture is stirred in hydrogen gas streams for 1 hour, and the catalyst is filtered off. The filtrate is freeze-dried to provide 70 mg of sodium 3-[D-2-[2-amino-3-(4-ethyl-2,3-dioxo-1-piperazinocarboxamido)propionamido]-2-phenylacetamido]-2-oxoazetidine-1-sulfonate.

IR$\nu_{max}^{KBr}$cm$^{-1}$; 3500–3300, 1760, 1708, 1670, 1265–1230, 1048.

NMR(DMSO-d$_6$+D$_2$O, ppm); 1.11(t, J=7 Hz, —CH$_3$), 3.20(dd, J=3, 6 Hz, C$_4$—H), 3.82–4.0(m, —CH$_2$—), 4.81(dd, J=3, 6 Hz, C$_3$—H), 5.43(s, —CH—),
|

7.36(s, aromatic H).

EXAMPLE 121

In 5 ml of DMF is dissolved 0.34 g of 3-[2-(2-benzyloxycarboxamido-3-N-methylcarbamoylpropionamido)acetamido]-3-methoxy-2-oxoazetidine, followed by addition of 0.211 g of pyridine-sulfur trioxide complex. The mixture is stirred for 3 days and, then, worked up in the manner as described in Example 5. The above procedure provides 0.015 g of sodium 3-[2-(2-benzyloxycarboxamido-3-N-methylcarbamoylpropionamido)acetamido]-3-methoxy-2-oxoazetidine-1-sulfonate.

IR$\nu_{max}^{KBr}$cm$^{-1}$; 3350, 1770, 1690, 1660, 1248, 1053.

EXAMPLE 122

In 5 ml of DMF is dissolved 0.343 g of 3-[2-(4-ethyl-2,3-dioxo-1-piperazinocarboxamido)acetamido]-3-methoxy-2-oxoazetidine, followed by addition of 0.287 g of pyridine-sulfur trioxide complex. The mixture is stirred for 2 days and, then, worked up in the manner as described in Example 5. The above procedure provides 0.076 g of sodium 3-[2-(4-ethyl-2,3-dioxo-1-piperazinocarboxamido)acetamido]-3-methoxy-2-oxoazetidine-1-sulfonate.

IR$\nu_{max}^{KBr}$cm$^{-1}$; 3320, 1765, 1708, 1670, 1250, 1051.

NMR(DMSO-d$_6$, ppm); 1.10(t, J=7 Hz, CH$_3$), 3.30(s, CH$_3$), 3.42(q, J=7 Hz, —CH$_2$—), 3.60(m, —CH$_2$—), 3.61(ABq, J=4, 6 Hz, C$_4$—H), 3.90(m, —CH$_2$—), 3.97(d, J=5 Hz, —CH$_2$—), 9.09(t, J=5 Hz, NH), 9.27(s, NH).

EXAMPLE 123

In 4 ml of DMF is dissolved 0.30 g of 3-[D-2-[2-(4-ethyl-2,3-dioxo-1-piperazinocarboxamido)-3-(N-methylcarbamoyl)propionamido]-2-phenylacetamido]-2-oxoazetidine, followed by addition of 0.184 g of pyridine-sulfur trioxide complex. The mixture is stirred for 3 days and, then, worked up in the manner as described in Example 45. The above procedure provides 0.141 g of sodium 3-[D-2-[2-(4-ethyl-2,3-dioxo-1-piperazinocarboxamido)-3-(N-methylcarbamoyl)propionamido]-2-phenylacetamido]-2-oxoazetidine-1-sulfonate.

IR$\nu_{max}^{KBr}$cm$^{-1}$; 3350–3290, 1768, 1707, 1668, 1265–1230, 1048.

NMR(DMSO-d$_6$, ppm); 1.08(t, J=7 Hz, —CH$_3$), 2.40–2.75(m, —CH$_2$—, CH$_3$), 3.25(dd, J=2, 5 Hz, C$_4$—H), 3.38(q, J=7 Hz, —CH$_2$—), 3.53(m, —CH$_2$—), 3.90(m, —CH$_2$—), 4.60(m, —CH—),
|

4.83(m, C$_3$—H), 5.38(d, J=9Hz, —CH—),
|

7.33(s, aromatic H), 7.86(m, NH), 8.55(d, J=9 Hz, NH), 8.93, 8.95(each d, J=9 Hz, NH), 9.31, 9.42(each d, J=7 Hz, NH).

EXAMPLE 124

In 5 ml of DMF is dissolved 0.35 g of 3-[2-(4-ethyl-2,3-dioxo-1-piperazinocarboxamido)-3-(N-methylcarbamoyl)propionamido]-2-oxoazetidine, followed by addition of 0.234 g of pyridine-sulfur trioxide complex. The mixture is stirred for 3 days and, then, worked up in the manner as described in Example 5. The above procedure provides 0.178 g of sodium 3-[2-(4-ethyl-2,3-dioxo-1-piperazinocarboxamido)-3-(N-methylcarbamoyl)propionamido]-2-oxoazetidine-1-sulfonate.

IR$\nu_{max}^{KBr}$cm$^{-1}$; 3440–3270, 1755, 1705, 1655, 1260–1240, 1190, 1045.

NMR(DMSO-d$_6$, ppm); 1.10(t, J=7 Hz, CH$_3$), 2.58(d, J=5 Hz, CH$_3$), 2.40–2.67(m, —CH$_2$—), 3.42(q, J=7 Hz, —CH$_2$—), 3.57(m, —CH$_2$—), 3.93(m, —CH$_2$—), 4.55(m, —CH—),
|

4.80(m, C$_3$—H), 7.83(q, J=5 Hz, NH), 8.72(d, J=8 Hz, NH), 9.31, 9.35(d, J=8 Hz, NH).

EXAMPLE 125

In 8 ml of DMF is dissolved 0.40 g of 3-[2-(D-2-benzyloxycarboxamido-2-phenylacetamido)-3-(N-methylcarbamoyl)propionamido]-2-oxoazetidine, followed by addition of 0.264 g of pyridine-sulfur trioxide complex. The mixture is stirred for 4 days and, then, worked up in the manner as described in Example 45. The above procedure provides 0.212 g of sodium 3-[2-(D-2-benzyloxycarboxamido-2-phenylacetamido)-3-(N-methylcarbamoyl)propionamido]-2-oxoazetidine-1-sulfonate.

IR$\nu_{max}^{KBr}$cm$^{-1}$; 3290, 1760, 1690, 1645, 1245, 1050.

NMR(DMSO-d$_6$, ppm); 2.27–2.63(m, —CH$_2$—, CH$_3$), 3.27(m, C$_4$—H), 3.52, 3.57(t, J=6 Hz, C$_4$—H), 4.53(m, —CH—),
|

4.80(m, C$_3$—H), 5.03(s, —CH$_2$—), 5.22, 5.23(d, J=8Hz, —CH—),
|

7.33(s, aromatic H), 7.50–7.93(m, NH), 8.27–8.63(m, NH).

In 8 ml of water is dissolved 0.10 g of the above sodium 3-[2-(D-2-benzyloxycarboxamido-2-phenylacetamido)-3-(N-methylcarbamoyl)propionamido]-2-oxoazetidine-1-sulfonate, followed by addition of 50 mg of palladium black. The mixture is stirred in hydrogen gas streams for 1 hour, and the catalyst is filtered off. The filtrate is freeze-dried to provide 68 mg of sodium 3-[2-(D-2-amino-2-phenylacetamido)-3-(N-methylcarbamoyl)propionamido]-2-oxoazetidine-1-sulfonate.

IR$\nu_{max}^{KBr}$cm$^{-1}$; 1758, 1670–1640, 1270–1238, 1048.

NMR(DMSO-d$_6$+D$_2$O, ppm); 2.47–2.83(m, —CH$_2$—, CH$_3$), 3.48(m, C$_4$—H), 4.53(s, —CH—), 4.63(m, —CH—),
|                  |

4.87(m, C$_3$—H), 7.42(s, aromatic H).

EXAMPLE 126-(A)

In 2 ml of DMF is dissolved 0.228 g of 3-[2-D-[(2-oxo-3-furfurylideneaminoimidazolidin-1-yl)carboxamido]-2-phenylacetamido]-3(S)-methoxy-2-oxoazetidine, followed by addition of 0.199 g of pyridine-sulfur trioxide complex. The mixture is stirred for 1 day and, then, worked up in the manner as described in Example 5. The above procedure provides 0.11 g of sodium 3-[2-D-[(2-oxo-3-furfurylideneaminoimidazolidin-1-yl)carboxamido]-2-phenylacetamido]-3(S)-methoxy-2-oxoazetidine-1-sulfonate.

IR$\nu_{max}^{KBr}$cm$^{-1}$; 3300, 1770, 1720, 1670, 1475, 1420, 1270, 1235, 1050.

NMR(d$_6$-DMSO, ppm); 3.03(s, CH$_3$), 3.54, 3.72(d, J=6 Hz, C$_4$—H), 3.80(s, —CH$_2$—), 5.63(d, J=7Hz, —CH—),
         |

6.5–7.9(m, aromatic H), 7.74(s, —CH=N—), 9.02(d, J=7 Hz, NH), 9.71(s, NH).

EXAMPLE 126-(B)

In 1 ml of DMF is dissolved 0.114 g of 3-[2-D-[(2-oxo-3-furfurylideneaminoimidazolidin-1-yl)carboxamido]-2-phenylacetamido]-3(R)-methoxy-2-oxoazetidine, followed by addition of 0.1 g of pyridine-sulfur trioxide complex. The mixture is stirred for 1 day and, then, worked up in the manner as described in Example 5. The above procedure provides 0.044 g of sodium 3-[2-D-[(2-oxo-3-furfurylideneaminoimidazolidin-1-yl)carboxamido]-2-phenylacetamido]-3(R)-methoxy-2-oxoazetidine-1-sulfonate.

IR$\nu_{max}^{KBr}$cm$^{-1}$; 3300, 1770, 1720, 1670, 1475, 1420, 1270, 1235, 1050.

NMR(d$_6$-DMSO, ppm); 3.32(s, CH$_3$), 3.46, 3.55(d, J=6 Hz, C$_4$—H), 3.80(s, —CH$_2$—), 5.59(d, J=7Hz, —CH—),
         |

6.5–7.9(m, aromatic H), 7.74(s, —CH=N—), 8.96(d, J=7 Hz, NH), 9.65(s, NH).

EXAMPLE 127

In 1.5 ml of DMF is dissolved 0.096 g of 3-[2-(4-ethyl-2,3-dioxo-1-piperazinocarboxamido)-2-(4-n-octanoyloxyphenyl)acetamido]-2-oxoazetidine, followed by addition of 0.058 g of pyridine-sulfur trioxide complex. The mixture is stirred for 1 day and, then, worked up in the manner as described in Example 5. The above procedure provides 0.096 g of sodium 3-[2-(4-ethyl-2,3-dioxo-1-piperazinocarboxamido)-2-(4-n-octanoyloxyphenyl)acetamido]-2-oxoazetidine-1-sulfonate.

IR$\nu_{max}^{KBr}$cm$^{-1}$; 3280, 2920, 2850, 1750, 1710, 1670, 1500, 1270–1230, 1190, 1050.

NMR(d$_6$-DMSO, ppm); 0.87(t, CH$_3$), 1.09(t, CH$_3$), 1.2–2.6(m, —CH$_2$—), 3.13(dd, J=3, 6 Hz, C$_4$—H), 3.41(q, —CH$_2$—), 3.4–4.1 (m, —CH$_2$—), 4.86(ddd, J=3, 6, 8 Hz, C$_3$—H), 5.46(d, J=7Hz, —CH—),
         |

7.10, 7.44(d, J=8 Hz, aromatic H), 9.28(d, J=8 Hz, NH), 9.82(d, J=7 Hz, NH).

EXAMPLE 128

In 5 ml of DMF is dissolved 0.35 g of 3-[2-(4-ethyl-2,3-dioxo-1-piperazinocarboxamido)-3-(N-ethoxycarbonylmethylcarbamoyl)propionamido]-2-oxoazetidine, followed by addition of 0.23 g of pyridine-sulfur trioxide complex. The mixture is stirred for 2 days and, then, worked up in the manner as described in Example 5. The above procedure provides 0.165 g of sodium 3-[2-(4-ethyl-2,3-dioxo-1-piperazinocarboxamido)-3-(N-ethoxycarbonylmethylcarbamoyl)propionamido]-2-oxoazetidine-1-sulfonate.

IR$\nu_{max}^{KBr}$cm$^{-1}$; 3480–3300, 1758, 1708, 1670, 1260–1230, 1192, 1048.

NMR(DMSO-d$_6$, ppm); 1.10(t, J=7 Hz, CH$_3$), 1.19(t, J=7 Hz, CH$_3$), 2.66(m, —CH$_2$—), 3.35(dd, J=3, 6 Hz, C$_4$—H), 3.43(q, J=7 Hz, —CH$_2$—), 3.50–3.73(m, —CH$_2$—), 3.74–4.00(m, —CH$_2$—), 3.81(d, J=6 Hz, —CH$_2$—), 4.09(q, J=7 Hz, —CH$_2$—), 4.58(m, —CH—),
       |

4.82(m, C$_3$—H), 8.36(t, J=6 Hz, NH), 8.73(d, J=8 Hz, NH), 9.34(d, J=8 Hz, NH).

EXAMPLE 129

In 5 ml of DMF is dissolved 0.464 g of 3-[D-2-(4-ethyl-2,3-dioxo-1-piperazinocarboxamido)-3-(2-thienylacetamido)propionamido]-2-oxoazetidine, followed by addition of 0.30 g of pyridine-sulfur trioxide complex. The mixture is stirred at room temperature for 2 days and, then, worked up in the manner as described in Example 5. The above procedure provides 0.31 g of sodium 3-[D-2-(4-ethyl-2,3-dioxo-1-piperazinocarboxamido)-3-(2-thienylacetamido)propionamido]-2-oxoazetidine-1-sulfonate.

IR$\nu_{max}^{KBr}$cm$^{-1}$; 1760, 1710, 1670, 1250–1210.

NMR(DMSO-d$_6$, ppm); 1.10(t, J=7 Hz, CH$_3$), 3.20(dd, J=2.5, 6 Hz, C$_4$—H), 3.40(q, J=7 Hz, —CH$_2$—), 3.60–3.90(m, —CH$_2$—), 3.70(s, —CH$_2$—), 4.60(m, —CH—),
       |

4.82(m, C$_3$—H), 6.7–7.4 (m, thienyl-H), 8.68(d, J=8 Hz, NH), 9.30(d, J=8 Hz, NH).

EXAMPLE 130

In 4 ml of DMF is dissolved 0.28 g of 3-(N-mesyl-D-phenylglycinamido)-2-oxoazetidine, followed by addition of 0.30 g of pyridine-sulfur trioxide complex. The mixture is stirred for 2 days and, then, worked up in the manner as described in Example 5. The above procedure provides 0.12 g of sodium 3-(N-mesyl-D-phenylglycinamido)-2-oxoazetidine-1-sulfonate.

IR$\nu_{max}^{KBr}$cm$^{-1}$; 1750, 1715, 1670, 1520, 1250.

NMR(DMSO-d$_6$, ppm); 3.10(dd, J=3, 6 Hz, C$_4$—H), 3.32(s, CH$_3$), 4.52(m, —CH—), 4.75(m, —CH—),
       |                |

7.35(s, aromatic H), 8.30(broad s, NH), 9.20(d, J=7 Hz, NH).

EXAMPLE 131

In 4 ml of DMF is dissolved 0.30 g of 3-[D-2-[2-(4-ethyl-2,3-dioxo-1-piperazinocarboxamido)acetamido]-2-phenylacetamido]-2-oxoazetidine, followed by addition of 0.215 of pyridine-sulfur trioxide complex. The mixture is stirred for 4 days and, then, worked in the manner as described in Example 5. The above procedure provides 0.239 g of sodium 3-[D-2-[2-(4-ethyl-2,3-dioxo-1-piperazinocarboxamido)acetamido]-2-phenylacetamido]-2-oxoazetidine-1-sulfonate.

IR$\nu_{max}^{KBr}$cm$^{-1}$; 3300, 1756, 1708, 1670, 1240, 1048.

NMR(DMSO-d$_6$, ppm); 1.10(t, J=7 Hz, CH$_3$), 3.15(dd, J=3, 5 Hz, C$_4$—), 3.28(q, J=7 Hz, —CH$_2$—), 3.30–3.70(m, —CH$_2$—), 3.80–4.10(m, —CH$_2$—), 3.98(d, J=5 Hz, —CH$_2$—), 4.83(m, C$_3$—H), 5.47(d, J=8Hz, —CH—),
|

7.37(s, aromatic H), 8.68(d, J=8 Hz, NH), 9.05(d, J=8 Hz, NH), 9.16(d, J=5 Hz, NH).

EXAMPLE 132

In 2 ml of DMF is dissolved 0.287 g of 3-[2-D-(4-n-octyl-2,3-dioxo-1-piperazinocarboxamido)-2-thienylacetamido]-2-oxoazetidine, followed by addition of 0.191 g of pyridine-sulfur trioxide complex. The mixture is stirred for one day and, then, worked up in the manner as described in Example 5. The above procedure provides 0.314 g of sodium 3-[2-D-(4-n-octyl-2,3-dioxo-1-piperazinocarboxamido)-2-thienylacetamido]-2-oxoazetidine-1-sulfonate.

IR$\nu_{max}^{KBr}$cm$^{-1}$: 3280, 2920, 1760, 1710, 1670, 1250, 1190, 1050.

NMR(d$_6$-DMSO, ppm); 0.86(t, CH$_3$), 3.17(dd, J=3, 6 Hz, C$_4$—H), 3.4–4.1(m, —CH$_2$—), 3.62(t, J=6 Hz, C$_4$—H), 4.86(ddd, J=3, 6, 8 Hz, C$_3$—H), 5.72(d, J=7Hz, —CH—),
|

6.9–7.6(m, thienyl—H), 9.30(d, J=8 Hz, NH), 9.73(d, J=7 Hz, NH).

EXAMPLE 133

To a solution of 0.36 g of 3-[D-2-[(3-furfurylideneamino-2-oxoimidazolidin-1-yl)carboxamido]-propionamido]-2-oxoazetidine in 2 ml of DMF is added 0.15 g of pyridine-sulfuric anhydride complex, and the reaction is allowed to proceed at room temperature for 2 days. Diethyl ether is added to the reaction mixture, whereupon an oily substance separates. This is passed through a Dowex 50W Na-type resin (Dow Chemical) column and the eluate is purified with an Amberlite XAD-II(Rohm and Haas, USA) column to give 0.37 g of sodium 3-[D-2-[(3-furfurylideneamino-2-oxoimidazolidin-1-yl)carboxamido]propionamido]-2-oxoazetidine-1-sulfonate.

IR$\nu_{max}^{KBr}$cm$^{-1}$: 3300, 1755, 1725, 1415, 1270, 1235, 1050

NMR(DMSO-d$_6$, ppm): 1.29(d, J=7 Hz, CH$_3$), 3.26(dd, J=3, 6 Hz, C$_4$—$\beta$H), 3.68(t, J=6 Hz, C$_4$—$\alpha$H), 3.81(s, —CH$_2$—), 4.33(quintet, J=7Hz, —CH—),
|

4.86(ddd, J=3, 6, 8 Hz, C$_3$—H), 6.5–7.9(m, furyl H), 7.74(s, —CH=N—), 8.43(d, J=7 Hz, NH), 8.87 (d, J=8 Hz, NH)

In substantially the same manner as in Synthesis Example 1, the following compounds are produced by sulfonation of the corresponding 2-oxoazetidine derivatives:

EXAMPLE 134

Sodium 3-[D-2-[(3-furfurylideneamino-2-oxoimidazolidin-1-yl)carboxamido]propionamido]-3(S)-methoxy-2-oxoazetidine-1-sulfonate IV$\nu_{max}^{KBr}$cm$^{-1}$: 1768, 1722, 1670, 1520, 1480, 1420, 1270, 1240, 1050.

NMR(DMSO-d$_6$, ppm): 1.32(d, J=7 Hz, CH$_3$), 3.35(2, OCH$_3$), 3.68(q, J=7, 13 Hz, C$_4$—H), 3.80(s, —CH$_2$—), 4.46(quintet, J=7Hz, —CH—),
|

6.5–7.9(m, arom. H), 7.73(s, —CH=N—), 8.43 (d, J=7 Hz, NH), 9.38(s, NH).

EXAMPLE 135

Sodium 3-[D-2-[(3-furfurylideneamino-2-oxoimidazolidin-1-yl)carboxamido]propionamido]-3(R)-methoxy-2-oxoazetidine-1-sulfonate IR$\nu_{max}^{KBr}$cm$^{-1}$: 1768, 1722, 1670, 1520, 1480, 1420, 1270, 1240, 1050.

NMR(DMSO-d$_6$, ppm): 1.30(d, J=7 Hz, CH$_3$), 3.34(s, CH$_3$), 3.59(q, J=6, 12 Hz, C$_4$—H), 3.80(s, —CH$_2$—), 4.45(quintet, J=7Hz, —CH—),
|

6.5–7.9(m, arom. H), 7.73(s, —CH=N—), 8.42(d, J=7 Hz, NH), 9.35(s, NH)

EXAMPLE 136

Sodium 3-[D-2-(4-n-octyl-2,3-dioxo-1-piperazinecarboxamido)-2-thienylacetamido]-2-oxoazetidine-1-sulfonate IR$\nu_{max}^{KBr}$cm$^{-1}$: 3280, 2925, 2855, 1760, 1710, 1675, 1505, 1270–1240, 1190, 1050.

NMR(DMSO-d$_6$, ppm): 0.86(t, J=7 Hz, CH$_3$), 1.1–1.7(m, —CH$_2$—), 3.17(dd, J=3, 6 Hz, C$_4$—$\beta$H), 3.3–4.1(m, —CH$_2$—), 3.62(t, J=6 Hz, C$_4$—$\alpha$H), 4.87(ddd, J=3, 6, 8 Hz, C$_3$—H), 5.72(d, J=7Hz, —CH—),
|

6.9–7.6(m, arom. H), 9.30(d, J=8 Hz, NH), 9.37(d, J=7 Hz, NH).

EXAMPLE 137

Sodium 3-[D-2-(4-n-dodecyl-2,3-dioxo-1-piperazinecarboxamido)-2-phenylacetamido]-2-oxoazetidine-1-sulfonate IR$\nu_{max}^{KBr}$cm$^{-1}$: 3280, 2920, 2850, 1760, 1710, 1675, 1505, 1270–1240, 1190.

NMR(DMSO-d$_6$, ppm): 0.85(t, J=7 Hz, CH$_3$), 3.11(dd, J=3, 6 Hz, C$_4$—$\beta$H), 3.57(t, J=6 Hz, C$_4$—$\alpha$H), 3.4–4.1(m, —CH$_2$—), 4.85 (ddd, J=3, 6, 8 Hz, C$_3$—H), 5.44(d, J=7Hz, —CH—),
|

7.2–7.5 (m, arom. H), 9.24(d, J=8 Hz, NH), 9.79(d, J=7 Hz, NH)

EXAMPLE 138

Sodium 3-[D-2-(4-n-amyl-2,3-dioxo-1-piperazinecarboxamido)-2-phenylacetamido]-2-oxoazetidine-1-sulfonate IR$\nu_{max}^{KBr}$cm$^{-1}$: 3290, 1760, 1710, 1675, 1510, 1280–1240, 1195, 1050.

NMR(DMSO-d$_6$, ppm): 0.87(t, CH$_3$), 3.13(dd, J=3, 6 Hz, C$_4$—$\beta$H), 3.4–4.1(m, —CH$_2$—), 3.58(t, J=6 Hz, C$_4$—$\alpha$H), 4.85(ddd, J=3, 6, 8 Hz, C$_3$—H), 5.44(d, J=7Hz, —CH—),
|

7.2–7.5(m, arom. H), 9.25(d, J=8 Hz, NH), 9.80(d, J=7 Hz, NH).

EXAMPLE 139

Sodium 3-[D-2-(4-n-amyl-2,3-dioxo-1-piperazinecarboxamido)-2-thienylacetamido]-2-oxoazetidine-1-sulfonate IR$\nu_{max}^{KBr}$cm$^{-1}$: 3280, 1760, 1710, 1675, 1505, 1280–1230, 1195, 1050.

NMR(DMSO-d$_6$, ppm): 0.87(t, J=7 Hz, CH$_3$), 3.19(dd, J=3, 6 Hz, C$_4$—$\beta$H), 3.63(t, J=6 Hz, C$_4$—$\alpha$H), 3.4–4.1(m, —CH$_2$—), 4.88 (ddd, J=3, 6, 8 Hz, C$_3$—H), 5.74(d, J=7Hz, —CH—),
|

6.9–7.6(m, arom. H), 9.30(d, J=8 Hz, NH), 9.74(d, J=7 Hz, NH).

EXAMPLE 140

Sodium 3-[2-(5-chloro-2-chloroacetamidothiazol-4-yl)-2-methoxyiminoacetamido]-2-oxoazetidine-1-sulfonate IR$\nu_{max}^{KBr}$cm$^{-1}$: 1760, 1665, 1540, 1270, 1240, 1050.

NMR(DMSO-d$_6$, ppm): 3.32(dd, J=3, 6 Hz, C$_4$—$\beta$H), 3.68(t, J=6 Hz, C$_4$—$\alpha$H), 3.94(s, OCH$_3$), 4.40(s, ClCH$_2$—), 4.95(ddd, J=3, 6, 8 Hz, C$_3$—H), 9.36(d, J=8 Hz, NH).

The above compound is reacted, in an aqueous solution, with sodium monomethyldithiocarbamate and the product is purified with an XAD-II column to give sodium 3-[2-(2-amino-5-chlorothiazol-4-yl)-2-methoxyiminoacetamido]-2-oxoazetidine-1-sulfonate IR$\nu_{max}^{KBr}$cm$^{-1}$: 1755, 1650, 1625, 1530, 1270, 1240, 1050.

NMR(DMSO-d$_6$, ppm): 3.26(dd, J=3, 6 Hz, C$_4$—$\beta$H), 3.65(t, J=6 Hz, C$_4$—$\alpha$H), 3.89(s, OCH$_3$), 4.91(ddd, J=3, 6, 8 Hz, C$_3$—H), 9.23(d, J=8 Hz, NH).

EXAMPLE 141

Sodium 3-[D-2-(4,6(R)-diethyl-2,3-dioxo-1-piperazinecarboxamido)-2-phenylacetamido]-2-oxoazetidine-1-sulfonate IR$\nu_{max}^{KBr}$cm$^{-1}$: 3280, 1760, 1710, 1675, 1500, 1270, 1240, 1190, 1050.

NMR(DMSO-d$_6$, ppm): 0.89(t, J=7 Hz, CH$_3$), 1.09(t, J=7 Hz, CH$_3$), 1.58(quintet, J=7 Hz, —CH$_2$—), 3.10(dd, J=3, 6 Hz, C$_4$—$\beta$H), 3.57(t, J=6 Hz, C$_4$—$\alpha$H), 4.85(ddd, J=3, 6, 8 Hz, C$_3$—H), 5.40(d, J=7Hz, —CH—),
|

7.2–7.5(m, arom. H), 9.21(d, J=8 Hz, NH), 9.83(d, J=7 Hz, NH)

EXAMPLE 142

Sodium 3-[D-2-(4,6(S)-diethyl-2,3-dioxo-1-piperazinecarboxamido)-2-phenylacetamido]-2-oxoazetidine-1-sulfonate IR$\nu_{max}^{KBr}$cm$^{-1}$: 3280, 1760, 1710, 1675, 1500, 1270, 1240, 1190, 1050.

NMR(DMSO-d$_6$, ppm): 0.81(t, J=7 Hz, CH$_3$), 1.10(t, J=7 Hz, CH$_3$), 1.3–1.7(m, —CH$_2$—), 3.13(dd, J=3, 6 Hz, C$_4$—$\beta$H), 3.58(t, J=7 Hz, C$_4$—$\alpha$H), 4.85(ddd, J=3, 6, 8 Hz, C$_3$—H), 5.45(d, J=7Hz, —CH—),
|

7.2–7.5(m, arom. H), 9.25(d, J=8 Hz, NH), 9.83(d, J=7 Hz, NH).

EXAMPLE 143

Sodium 3-(2-phenyl-2-p-tolylthioiminoacetamido)-2-oxoazetidine-1-sulfonate

IR$\nu_{max}^{KBr}$cm$^{-1}$: 1760, 1655, 1505, 1265, 1240, 1050.

NMR(DMSO-d$_6$, ppm): 2.34(s, CH$_3$), 3.3–3.6(m, C$_4$—$\beta$H), 3.70, 3.75(t, J=6 Hz, C$_4$—$\alpha$H), 4.8–5.2(m, C$_3$—H), 7.2–7.8(m, arom. H), 9.02, 9.59(d, J=8 Hz, NH).

EXAMPLE 144

Sodium 3-[D-2-(4-cyclohexyl-2,3-dioxo-1-piperazinecarboxamido)-2-phenylacetamido]-2-oxoazetidine-1-sulfonate IR$\nu_{max}^{KBr}$cm$^{-1}$: 2925, 1760, 1705, 1665, 1505, 1250, 1180, 1045.

NMR(DMSO-d$_6$, ppm): 3.11(dd, J=3, 6 Hz, C$_4$—$\beta$H), 3.4–4.0(m, —CH$_2$—), 3.57(t, J=6 Hz, C$_4$—$\alpha$H), 4.83(ddd, J=3, 6, 8 Hz, C$_3$—H), 5.42(d, J=7Hz, —CH—),
|

7.2–7.5(m, arom. H), 9.22(d, J=8 Hz, NH), 9.77(d, J=7 Hz, NH).

EXAMPLE 145

Sodium 3-(2,6-dimethoxybenzamido)-2-oxoazetidine-1-sulfonate

IR$\nu_{max}^{KBr}$cm$^{-1}$: 3300, 1755, 1648, 1595, 1513, 1470, 1250, 1100, 1050.

NMR(DMSO-d$_6$, ppm): 3.27(dd, J=3, 6 Hz, C$_4$—H), 3.62(t, J=6 Hz, C$_4$—H), 3.71(s, OCH$_3$), 4.93(ddd, J=3, 6, 8 Hz, C$_3$—H), 6.60 (d, J=9 Hz, arom. H), 7.24(t, J=9 Hz, arom. H), 8.71(d, J=8 Hz, NH).

EXAMPLE 146

Sodium 3-[D-2-(4-n-amyl-6(R)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1760, 1710, 1678, 1503, 1272, 1240, 1198, 1050.

NMR(DMSO-d$_6$, ppm): 0.88(t, J=7 Hz, CH$_3$), 1.25(d, J=6 Hz, CH$_3$), 3.19(dd, J=2, 6 Hz, C$_4$—H), 3.63(t, J=6 Hz, C$_4$—H), 4.67(m, —CH—),
      |

4.89(ddd, J=2, 6, 7 Hz, C$_3$—H), 5.70(d, J=8Hz, —CH—),
              |
              N 6.94–7.16(m, arom. H), 7.42–7.54(m, arom. H), 9.78(d, J=7 Hz, NH).

EXAMPLE 147

Sodium 3-[D-2-(4-n-amyl-6(S)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1760, 1710, 1678, 1503, 1272, 1240, 1198, 1050.

NMR(DMSO-d$_6$, ppm): 0.87(t, J=7 Hz, CH$_3$), 1.21(d, J=6 Hz, CH$_3$), 3.19(dd, J=2, 6 Hz, C$_4$—H), 3.61(t, J=6 Hz, C$_4$—H), 4.66(m, —CH—),
      |

4.87(dd, J=2, 6, 7 Hz, C$_3$—H), 5.73(d, J=8Hz, —CH—),
              |
              N 6.92–7.16(m, arom. H), 7.42–7.53(m, arom. H), 9.76(d, J=7 Hz, NH)

EXAMPLE 148

Sodium 3-[D-2-(4-n-amyl-6-methyl-2,3-dioxo-1-piperazinecarboxamido)-3-chloropropionamido]-2-oxoazetidine-1-sulfonate IR$\nu_{max}^{KBr}$cm$^{-1}$: 1760, 1712, 1680, 1520, 1240, 1055, 1010.

NMR(DMSO-d$_6$, ppm): 0.88(t, J=6 Hz, CH$_3$), 1.24(d, J=6 Hz, CH$_3$), 3.60(t, J=6 Hz, C$_4$—H), 4.0(broad s, —CH$_2$—), 4.48(m, C$_3$—H), 8.90(d, J=8 Hz, NH), 9.28(d, J=7 Hz, NH)

EXAMPLE 149

Sodium 3-[D-2-[[3-(2,6-dichlorophenyl)-5-methylisoxazol-4-yl]-carboxamido]-2-thienylacetamido]-2-oxoazetidine-1-sulfonate IR$\nu_{max}^{KBr}$cm$^{-1}$: 1760, 1665, 1603, 1508, 1271, 1240, 1200, 1050.

NMR(DMSO-d$_6$, ppm): 2.71(s, CH$_3$), 3.16(dd, J=3, 6 Hz, C$_4$—H), 3.60(t, J=6 Hz, C$_4$—H), 4.81(m, C$_3$—H), 5.70(d, J=8Hz, —CH—),
              |

6.93(m, arom. H), 7.38(m, arom. H), 7.59(s, arom. H), 7.93 (d, J=7 Hz, NH), 9.14(d, J=8 Hz, NH)

EXAMPLE 150

Sodium 3-[D-2-(4-ethyl-5(R)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1759, 1703, 1667, 1505, 1275, 1240, 1190.

NMR(DMSO-d$_6$, ppm): 1.13(t, J=7 Hz, CH$_3$), 3.18(dd, J=3, 6 Hz, C$_4$—H), 4.87(m, C$_4$—H), 5.72(d, J=7Hz, —CH—),
              |

9.28(d, J=8 Hz, NH), 9.70(d, J=7 Hz, NH)

EXAMPLE 151

Sodium 3-[D-2-(4-ethyl-5(S)-methyl-2,3-dioxo-1-piperazinecarboxamido)-2-thienylacetamido]-2-oxoazetidine-1-sulfonate IR$\nu_{max}^{KBr}$cm$^{-1}$: 3275, 1759, 1703, 1667, 1505, 1275, 1240, 1190.

NMR(DMSO-d$_6$, ppm): 1.18(t, J=7 Hz, CH$_3$), 1.24(t, J=6 Hz, CH$_3$), 3.19(dd, J=3, 6 Hz, C$_4$—H), 3.62(t, J=6 Hz, C$_4$—H), 4.88(m, C$_3$—H), 5.69(d, J=7Hz, —CH—),
              |

9.29(d, J=8 Hz, NH), 9.69(d, J=7 Hz, NH).

EXAMPLE 152

Disodium 3-[D-2-[(2-oxo-3-sulfonatoimidazolidin-1-yl)carboxamido]-2-thienylacetamido]-2-oxoazetidine-1-sulfonate IR$\nu_{max}^{KBr}$cm$^{-1}$: 3470, 3300, 1755, 1710, 1668, 1260, 1052.

NMR(DMSO-d$_6$, ppm): 3.25(dd, J=3, 6 Hz, C$_4$—H), 3.52(t, J=6 Hz, C$_4$—H), 3.61(s, —CH$_2$—), 4.83(m, C$_3$—H), 5.64(d, J=8Hz, —CH—),
              |

6.9–7.5(m, arom. H), 8.92(d, J=8 Hz, NH), 9.25 (d, J=9 Hz, NH).

EXAMPLE 153

Sodium 3-[D-2-[(2-oxoimidazolidin-1-yl)carboxamido]-2-thienylacetamido]-2-oxoazetidine-1-sulfonate IR$\nu_{max}^{KBr}$cm$^{-1}$: 3420, 3270, 1750, 1730, 1650, 1270, 1240, 1045.

NMR(DMSO-d$_6$, ppm): 3.17(dd, J=2, 5 Hz, C$_4$—H), 3.10–3.47(m, —CH$_2$—), 3.58(t, J=5 Hz, C$_4$—H), 3.57–3.70(m, —CH$_2$—), 4.83(m, C$_3$—H), 5.63(d, J=8Hz, —CH—),
              |

6.87–7.47(m, arom. H), 7.54(s, NH), 9.02(d, J=8 Hz, NH), 9.25(d, J=8 Hz, NH).

EXAMPLE 154

Sodium 3-[D-2-[(5-methoxycarbonyl-3-methyl-2-oxoimidazolidin-1-yl)carboxamido]-2-phenylacetamido]-2-oxoazetidine-1-sulfonate IR$\nu_{max}^{KBr}$cm$^{-1}$: 3480, 3260, 1750, 1728, 1662, 1260, 1048.

NMR(DMSO-d$_6$, ppm): 2.76(s, CH$_3$), 3.10(dd, J=3, 5 Hz, C$_4$—H), 3.70(s, CH$_3$), 4.65(dd, J=4, 10Hz, —CH—), 4.84(m, C$_3$—H), 5.38(d, J=8Hz, —CH—), 7.34(s, arom. H), 9.12(d, J=8 Hz, NH), 9.21(d, J=8 Hz, NH).

EXAMPLE 155

Sodium 3-[D-2-[(5-benzyloxycarbonyl-3-methyl-2-oxoimidazolidin-1-yl)carboxamido]-2-phenylacetamido]-2-oxoazetidine-1-sulfonate IR$\nu_{max}^{KBr}$cm$^{-1}$: 3470, 3290, 1750, 1720, 1665, 1245, 1190, 1048.

NMR(DMSO-d$_6$, ppm): 2.76(s, CH$_3$), 3.08(dd, J=3, 5 Hz, C$_4$—H), 3.25(dd, J=4, 10 Hz, —CH$_2$—), 3.56(t, J=5 Hz, C$_4$—H), 3.70(t, 10 Hz, —CH$_2$—), 4.71(dd, J=4, 10Hz, —CH—), 4.80(m, C$_3$—H), 5.18(s, —CH$_2$—), 5.40(d, J=8Hz, —CH—), 7.36(s, arom. H), 7.38(s, arom. H), 9.12(d, J=8 Hz, NH), 9.21(d, J=8 Hz, NH).

An aqueous solution of the above compound is treated in a stream of hydrogen in the presence of palladium black to give sodium 3-[D-2-[(5-carboxy-3-methyl-2-oxoimidazolidin-1-yl)carboxamido]-2-phenylacetamido]-2-oxoazetidine-1-sulfonate.

IR$\nu_{max}^{KBr}$cm$^{-1}$: 3430, 3300, 1750, 1720, 1663, 1250, 1050.

NMR(DMSO-d$_6$, ppm): 2.75(s, CH$_3$), 3.10(dd, J=3, 5 Hz, C$_4$—H), 3.25-3.80(m, C$_4$—H, —CH$_2$—), 4.48(m, —CH—), 5.38(d, J=8Hz, —CH—), 7.33(s, arom. H), 9.12(d, J=8 Hz, NH), 9.20(d, J=8 Hz, NH).

EXAMPLE 156

Sodium 3-[2-(4-ethyl-2,3-dioxo-1-piperazinecarboxamido)-2-(2-chloro-1-cyclohexen-1-yl)acetamido]-2-oxoazetidine-1-sulfonate NMR(DMSO-d$_6$, ppm): 1.10(t, J=7 Hz, CH$_3$), 1.60(broad s, —CH$_2$—), 2.03(broad s, —CH$_2$—), 2.33(broad s, —CH$_2$—), 3.53(m, —CH$_2$—), 3.90(m, —CH$_2$—), 4.83(m, C$_4$—H), 5.43(d, J=7Hz, —CH—)

8.66(d, J=8 Hz, NH), 9.46(d, J=7 Hz, NH).

EXAMPLE 157

Disodium 3-[2-(2-sulfonatoaminothiazol-4-yl)-2-[(1-tertbutoxycarbonyl-1-methylethoxy)imino]acetamido]-2-oxoazetidine-1-sulfonate IR$\nu_{max}^{KBr}$cm$^{-1}$: 1760, 1730, 1665, 1630, 1525, 1250, 1145, 1050.

NMR(DMSO-d$_6$, ppm): 1.39(s, CH$_3$), 1.40(s, CH$_3$), 3.35(m, C$_4$—H), 4.95(m, C$_3$—H), 6.83(s, \>—H), 9.10(d, J=8 Hz, NH).

EXAMPLE 158

Sodium 3-[2-(2-tritylaminothiaozl-4-yl)-2-[(1-tertbutoxycarbonyl-1-methylethoxy)imino]acetamido]-2-oxoazetidine-1-sulfonate IR$\nu_{max}^{KBr}$cm$^{-1}$: 1760, 1730, 1675, 1590, 1570, 1280, 1260, 1200, 1140, 1040.

NMR(DMSO-d$_6$, ppm): 1.39(s, CH$_3$), 1.40(s, CH$_3$), 3.35(m, C$_4$—H), 4.90(m, C$_3$—H), 6.75(s, \>—H), 7.33(s, arom. H), 9.03(d, J=8 Hz, NH).

EXAMPLE 159

Sodium 3-[2-(2-chloroacetamidothiazol-4-yl)-2-(1-methylethoxyimino)acetamido]-2-oxoazetidine-1-sulfonate IR$\nu_{max}^{KBr}$cm$^{-1}$: 1755, 1700, 1540, 1250, 1050.

NMR(DMSO-d$_6$, ppm): 1.22(d, J=6 Hz, CH$_3$), 3.66(t, J=6 Hz, C$_4$—αH), 4.33(s, —CH$_2$—), 4.33(quintet, J=6 Hz, —CH<), 4.96 (m, C$_3$—H), 7.36(s, \>—H), 9.23(d, J=8 Hz, NH).

EXAMPLE 160

Sodium 3-benzyloxycarboxamido-3-methoxy-2-oxoazetidine-1-sulfonate

IR$\nu_{max}^{KBr}$cm$^{-1}$: 1760, 1720, 1625, 1505, 1260, 1050

NMR(DMSO-d$_6$, ppm): 3.36(s, OCH$_3$), 3.56, 3.76(each d, J=6 Hz, C$_4$—CH$_2$—), 5.13(s, —CH$_2$—), 7.40(s, arom. H), 8.90 (broad s, NH).

EXAMPLE 161

Sodium 3-[2-(2-aminothiazol-4-yl)-2-(1-methylethoxyimino)acetamido]-2-oxoazetidine-1-sulfonate IR$\nu_{max}^{KBr}$cm$^{-1}$: 1760, 1660, 1620, 1525, 1250, 1050.

NMR(DMSO-d$_6$, ppm):

1.22(d, J=6Hz, 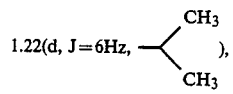), 3.66(t, J=6 Hz, C$_4$—αH), 4.33(s, —CH$_2$—), 4.33(quintet, J=6 Hz, —CH<), 4.96(m, C$_3$—H), 7.36(s, 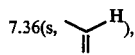), 9.23(d, J=8Hz, NH).

EXAMPLE 162

Sodium 3-(2-oxo-2-phenylacetamido)-2-oxoazetidine-1-sulfonate

IR$\nu_{max}^{KBr}$cm$^{-1}$: 3375, 1760, 1668, 1510, 1272, 1238, 1180, 1050.

NMR(DMSO-d$_6$, ppm): 3.45(dd, J=3, 6 Hz, C$_4$—H), 3.70(t, J=6 Hz, C$_4$—H), 5.01(ddd, J=3, 6, 9 Hz, C$_3$—H), 7.50–8.10(m, arom. H), 9.65(d, J=9 Hz, NH).

EXAMPLE 163

Sodium 3-[2-(2-mesylaminothiazol-4-yl)-2-(1-methylethoxyimino)acetamido]-2-oxoazetidine-1-sulfonate IR$\nu_{max}^{KBr}$cm$^{-1}$: 3450, 3275, 1760, 1660, 1532, 1470, 1240 1115, 1050.

NMR(DMSO-d$_6$, ppm):

1.23(d, J=6Hz, 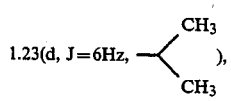)

2.73(s, CH$_3$), 3.33(dd, J=3, 6 Hz, C$_4$—H), 3.63(t, J=6 Hz, C$_4$—H), 4.33(heptet, J=6Hz, —CH—), 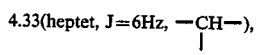

4.91(m, C$_3$—H), 6.67(s, 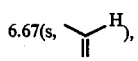), 9.12(d, J=9 Hz,

EXAMPLE 164

Sodium 3-[2-(2-imino-3-mesyl-4-thiazolin-4-yl)-2-(1-methylethoxyimino)acetamido]-2-oxoazetidine-1-sulfonate IV$\nu_{max}^{KBr}$cm$^{-1}$: 3430, 3300, 1768, 1650, 1538, 1270, 1245, 1120, 1058, 1040.

NMR(DMSO-d$_6$, ppm):

1.24(d, J=6Hz, 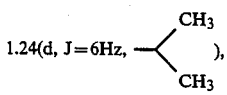)

2.91(s, CH$_3$), 3.30(dd, J=3, 6 Hz, C$_4$—H), 3.65(t, J=6 Hz, C$_4$—H), 4.36(heptet, J=6Hz, —CH—), 4.93(m, C$_3$—H), 6.86(s, 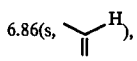), 9.32(d, J=9 Hz, NH).

EXAMPLE 165

Sodium 3-(2-bromo-2-phenylacetamido)-2-oxoazetidine-1-sulfonate

IR$\nu_{max}^{KBr}$cm$^{-1}$: 3325, 1760, 1670, 1533, 1240, 1055.

NMR(DMSO-d$_6$, ppm): 3.20(m, C$_4$—H), 3.58(t, J=5 Hz, C$_4$—H), 3.64(t, J=6 Hz, C$_4$—H), 4.83(m, C$_3$—H), 5.58(s, —CH—), 7.30–7.70(m, arom. H), 9.28(d, J=9 Hz, NH).

EXAMPLE 166

Sodium 3-(2-azido-2-phenylacetamido)-2-oxoazetidine-1-sulfonate

IR$\nu_{max}^{KBr}$cm$^{-1}$: 3460, 2110, 1755, 1670, 1240, 1053.

NMR(DMSO-d$_6$, ppm): 3.28, 3.35(each dd, J=3, 6 Hz, C$_4$—H), 3.60, 3.63(each t, J=6 Hz, C$_4$—H), 4.87(m, C$_3$—H), 5.00(s, —CH—), 7.45(s, arom. H), 9.17(d, J=9 Hz, NH).

EXAMPLE 167

Sodium 3-tosylamino-2-oxoazetidine-1-sulfonate

IR$\nu_{max}^{KBr}$cm$^{-1}$: 3265, 3175, 1745, 1332, 1280, 1245, 1115, 1050.

NMR(DMSO-d$_6$, ppm): 2.42(s, CH$_3$), 2.76(dd, J=3, 6 Hz, C$_4$—H), 3.30(t, J=6 Hz, C$_4$—H), 4.47(dd, J=3, 6 Hz, C$_3$—H), 7.58(ABq, J=9, 29 Hz, arom. H), 8.51(broad s, NH).

EXAMPLE 168

Sodium 3-(2-phthalimido-2-thienylacetamido)-2-oxoazetidine-1-sulfonate

IR$\nu_{max}^{KBr}$cm$^{-1}$: 3345, 3070, 1753, 1710, 1520, 1380, 1240, 1195, 1100, 1045, 720.

EXAMPLE 169

Sodium 3-[2-azido-2-(3-chlorophenyl)acetamido]-2-oxoazetidine-1-sulfonate

IR$\nu_{max}^{KBr}$cm$^{-1}$: 3400, 2110, 1755, 1670, 1240, 1050.

NMR(DMSO-d$_6$, ppm): 3.31, 3.33(each dd, J=3, 6 Hz, C$_4$—H), 3.60, 3.63(each, t, J=6 Hz, C$_4$—H), 4.86(m, C$_3$—H), 5.13(s, —CH—), 7.28–7.55(m, arom. H), 9.15(d, J=9 Hz, NH).

EXAMPLE 170

Sodium 3-(2-azido-2-phenylacetamido)-3-methoxy-2-oxoazetidine-1-sulfonate

IR$\nu_{max}^{KBr}$cm$^{-1}$: 3400, 2110, 1765, 1685, 1248, 1055.

NMR(DMSO-d$_6$, ppm): 3.13, 3.36(each s, CH$_3$), 3.40-3.80 (m, C$_4$—H), 5.08(s, —CH—), 7.44(s, arom. H), 9.63, 9.66 (each s, NH).

EXAMPLE 171

Sodium 3-[D-2-(4-cyclohexyl-2,3-dioxo-1-piperadinecarboxamido)-2-thienylacetamido]-2-oxoazetidine-1-sulfonate IR$\nu_{max}^{KBr}$cm$^{-1}$: 3280, 2930, 1760, 1710, 1670, 1505, 1280-1230.

NMR(DMSO-d$_6$, ppm): 3.17(dd, J=3, 6 Hz, C$_4$—βH), 3.61(t, J=6 Hz, C$_4$—αH), 4.85(ddd, J=3, 6, 8 Hz, C$_3$—H), 5.70(d, J=7Hz, —CH—), 6.9-7.5(m, arom. H), 9.29(d, J=7 Hz, NH), 9.72(d, J=7 Hz, NH).

EXAMPLE 172

Sodium 3-[2-(2-aminothiazol-4-yl)-2-(1-methylethoxyimino)acetamido]-3-methoxy-2-oxoazetidine-1-sulfonate IR$\nu_{max}^{KBr}$cm$^{-1}$: 1770, 1670, 1620, 1530, 1245, 1055.

NMR(DMSO-d$_6$, ppm): 1.20, 1.22(each d, J=6 Hz, CH$_3$), 3.41(s, CH$_3$), 4.30(quintet, J=6 Hz, —CH<), 6.67(s, \\_H), 7.11 (broad s, NH$_2$), 9.72(s, NH)

EXAMPLE 173

Sodium 3-[2-(2-mesylaminothiazol-4-yl)-2-(1-methylethoxyimino)acetamido]-3-methoxy-2-oxoazetidine-1-sulfonate IR$\nu_{max}^{KBr}$cm$^{-1}$: 3450, 3250, 1768, 1670, 1530, 1240, 1115, 1052.

NMR(DMSO-d$_6$, ppm): 1.22(d, J=6 Hz, CH$_3$), 2.74(s, CH$_3$), 3.41(s, CH$_3$)

4.37(m, —CH—), 6.63(s, \\_H), 9.80(s, NH)

EXAMPLE 174

Sodium 3-[D-2-(4-cyclohexyl-2,3-dioxo-1-piperadinecarboxamido)-2-thienylacetamido]-3-methoxy-2-oxoazetidine-1-sulfonate IR$\nu_{max}^{KBr}$cm$^{-1}$: 2930, 1765, 1710, 1675, 1505, 1250, 1175, 1050.

NMR(DMSO-d$_6$, ppm): 3.16(s, CH$_3$), 3.63(ABq, J=6, 16 Hz, C$_4$—H), 5.89(d, J=7Hz, —CH—), 6.9-7.6(m, arom. H), 9.71 (d, J=7 Hz, NH), 9.79(s, NH).

EXAMPLE 175

Sodium 3-methoxy-3-[D-2-(4-piperidinecarbonylmethyl-2,3-dioxo-1-piperadinecarboxamido)-2-thienylacetamido]-2-oxoazetidine-1-sulfonate IR$\nu_{max}^{KBr}$cm$^{-1}$: 2930, 1765, 1705, 1680, 1635, 1505, 1250, 1050.

NMR(DMSO-d$_6$, ppm): 3.17(s, CH$_3$), 3.57, 3.73(ABq, J=6 Hz), 4.33(s, —CH$_2$—), 5.90(d, J=7Hz, —CH—), 6.9-7.6(m, arom. H), 9.70(d, J=7 Hz, NH), 9.82(s, NH).

EXAMPLE 176

Sodium 3-methoxy-3-[D-2-(4-phenyl-2,3-dioxo-1-piperadinecarboxamido)-2-thienylacetamido]-2-oxoazetidine-1-sulfonate IR$\nu_{max}^{KBr}$cm$^{-1}$: 3275, 1770, 1705, 1680, 1490, 1250, 1050.

NMR(DMSO-d$_6$, ppm): 3.19(s, CH$_3$), 3.60, 3.74(each d, J=6 Hz, C$_4$—H), 5.95(d, J=7Hz, —CH—), 6.9-7.6(m, arom. H), 9.78(d, J=7 Hz, NH), 9.84(s, NH).

EXAMPLE 177

Sodium 3-[D-2-(4-t-butyl-2,3-dioxo-1-piperadinecarboxamido)-2-thienylacetamido]-3-methoxy-2-oxoazetidine-1-sulfonate IR$\nu_{max}^{KBr}$cm$^{-1}$: 3280, 2975, 1770, 1710, 1675, 1505, 1250, 1200, 1050.

NMR(DMSO-d$_6$, ppm): 1.40(s, CH$_3$), 3.15(s, CH$_3$), 3.55, 3.70(each d, J=6 Hz, C$_4$—H), 5.88(d, J=7Hz, —CH—), 6.9-7.0(m, arom. H), 9.65(d, J=7 Hz, NH), 9.79(s, NH).

EXAMPLE 178

Sodium 3-[D-2-[4-(3-methyl-2-butenyl)-2,3-dioxo-1-piperadinecarboxamido]-2-thienylacetamido]-3-methoxy-2-oxoazetidine-1-sulfonate IR$\nu_{max}^{KBr}$cm$^{-1}$: 3270, 1760, 1705, 1675, 1505, 1190.

NMR(DMSO-d$_6$, ppm): 1.70(d, J=3 Hz, CH$_3$), 3.19(s, CH$_3$), 3.43, 3.55(each d, J=6 Hz, C$_4$—H), 5.88(d, J=7Hz, —CH—), 6.9–7.6(m, arom. H), 8.35(s, NH), 9.69(s, NH), 9.73(d, J=7 Hz, NH).

EXAMPLE 179

Sodium 3-[D-2-phenyl-2-[[3-(3-thienylidene)amino-2-oxoimidazolydin-1-yl]carboxamido]acetamido]-2-oxoazetidine-1-sulfonate IR$\nu_{max}^{KBr}$cm$^{-1}$: 3290, 1755, 1720, 1660, 1525, 1270, 1225, 1050.

NMR(DMSO-d$_6$, ppm): 3.11(dd, J=3, 6 Hz, C$_4$—$\beta$H), 3,57(t, J=6 Hz, C$_4$—$\alpha$H), 3.80(s, —CH$_2$—), 4.84(ddd, J=3, 6, 8 Hz, C$_3$—H), 5.43(d, J=8Hz, —CH—), 7.2–7.9(m, arom. H), 7.89(s, —CH=N—), 9.05(d, J=8 Hz, NH), 9.21(d, J=8 Hz, NH)

EXAMPLE 180

Sodium 3-[2-(4-hydroxyphenyl)-2-(4-methoxybenzyloxycarbonyl)acetamido]-3-methoxy-2-oxoazetidine-1-sulfonate IR$\nu_{max}^{KBr}$cm$^{-1}$: 1770, 1740, 1510, 1250, 1175, 1050.

NMR(DMSO-d$_6$, ppm): 3.10, 3.26(each s, CH$_3$), 3.76(s, CH$_3$), 4.79(s, —CH—), 5.06(broad s, —CH$_2$—), 6.6–7.4(m, arom. H), 9.36(broad s, OH), 9.48, 9.51(each s, NH).

EXAMPLE 181

Disodium 3-[2-[(1-carboxy-1-methylethoxy)imino]-2-(2-tritylaminothiazol-4-yl)acetamido]-2-oxoazetidine-1-sulfonate IR$\nu_{max}^{KBr}$cm$^{-1}$: 3400, 1755, 1610, 1511, 1268, 1240, 1048.

NMR(DMSO-d$_6$, ppm): 1.36(s, CH$_3$), 1.40(s, CH$_3$), 3.36(dd, J=3, 6 Hz, C$_4$—H), 3.49(t, J=6 Hz, C$_4$—H), 4.70(m, C$_3$—H), 6.70(s, 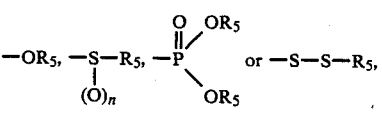), 7.34(s, arom. H), 8.59(s, NH), 9.71(d, J=8 Hz, NH).

B. 1-Sulfo-2-oxoazetidine derivatives which are substituted in the 4-position through a non-carbon atom This aspect of the disclosure relates to additional new 1-sulfo-3,4-substituted-2-oxoazetidine derivatives having antimicrobial or $\beta$-lactamase-inhibitory activity and a method of producing said derivatives.

Various 2-oxoazetidine derivatives have been synthesized in recent years, and in a known process, a vinyl ester and chlorosulfonyl isocyanate are reacted to give an 4-acetoxy-2-oxoazetidine compound which is then subjected to nucleophilic substitution reaction to introduce a benzoyloxy, alkylthio, benzylthio or other group into the 4-position thereof [Annalen der Chemie 1974, 539]. It appears that this process involves formation of a compound having a chlorosulfonyl group at 1-position but since the chlorosulfonyl group tends to be readily cleaved off, this intermediate compound cannot easily be isolated.

It has been found that azetidine derivatives having a sulfo group at 1-position are suitable for the above-stated purpose. This portion of the disclosure is directed to:

(1) A compound represented by the formula

 (I)B wherein R$_1$ is an amino group which may optionally be acylated or protected, X is hydrogen or methoxy and R$_4$ is azido, a halogen, amino group which may optionally be acylated, or a group of the formula

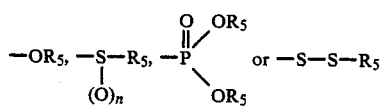

(R$_5$ means an organic residue and n is 0, 1 or 2) or a pharmaceutically acceptable salt thereof, or an ester thereof;

(2) A method of producing a compound of the formula (I)B which comprises (a) subjecting a compound of the formula

 (II)B wherein R$_2$ is an acylated or protected amino group, X and R$_4$ are of the same meanings as defined above, to sulfonation, as necessary followed by removal of the protective group when R$_2$ is a protected amino group, or (b) acylating a compound represented by the formula

 (III)B wherein X and R$_4$ are of the same meanings as defined above;

(3) An antimicrobial composition which contains a compound of the formula (I)B; and (4) A $\beta$-lactamase inhibitory composition which contains a compound of the formula (I)B.

Referring to the above formulas, R$_4$ is azido group, a halogen, amino group which may optionally be acylated or a group of —OR$_5$, —S—R$_5$, —P(=O)(OR$_5$)(OR$_5$) or —S—S—R$_5$,
(O)$_n$ wherein a halogen is fluorine, chlorine, bromine or iodine, and the organic residue R$_5$ is a hydrocarbon, acyl, heterocyclic or other group. The hydrocarbon group is an aliphatic group which may be straight-chain, branched or cyclic and may contain a double bond or a triple bond, or an aromatic group such as phenyl, naphthyl, etc. The acyl group is a carbonyl group substituted by such a hydrocarbon group. The heterocyclic group is a 5- or 6-membered heterocyclic group containing, for example, one sulfur atom or/and 1 to 4 nitrogen atoms, which heterocyclic group may optionally be fused to a benzene ring. Specific examples thereof include pyridyl, tetrazolyl, thiadiazolyl, thienyl, thiazolyl, isothiazolyl, benzothiazolyl, etc.

Such hydrocarbon groups, acyl groups and heterocyclic groups may each be substituted by a lower ($C_{1-3}$) alkoxy, a lower alkoxycarbonyl, carboxyl, a halogen (e.g. fluorine, chlorine, bromine), phenoxy, phenyl, heterocyclic groups (e.g. furyl, thienyl tetrazolyl, thiazolyl), a lower ($C_{1-3}$) alkylthio (e.g. methylthio, ethylthio), a heterocyclic-thio (e.g. tetrazolylthio, thiadiazolylthio), amino which may be acylated or substituted by iminomethyl or carbamoyl, cyano, etc. Preferred acyl moieties of said amino which may be acylated are formyl, acetyl, propionyl, etc.

As examples of said organic residues $R_5$, there may be mentioned formyl, acetyl, propionyl, n-butyryl, isobutyryl, t-butyryl, 2-methoxycarbonylacetyl, 2-ethoxycarbonylacetyl, 2-carboxyacetyl, methylthioacetyl, (1-methyl-5H-tetrazol-5-yl)thioacetyl, chloroacetyl, phenoxyacetyl, phenylacetyl, thienylacetyl, (2-aminothiazol-4-yl)acetyl, benzoyl, 2-chlorobenzoyl, 4-aminobenzoyl, methyl, ethyl, isopropyl, n-butyl, t-butyl, cyclohexyl, ethoxycarbonylmethyl, methoxycarbonylmethyl, benzyloxycarbonylmethyl, carboxymethyl, carbamoylmethyl, N-methylcarbamoylmethyl, methoxymethyl, methylthiomethyl, (1-methyl-5H-tetrazol-5-yl)thiomethyl, cyanomethyl, phenyl, 2-chlorophenyl, 4-aminophenyl, 2-aminoethyl, 2-formylaminoethyl, 2-(iminomethylamino)ethyl, 2-dimethylaminoethyl, 2-ureidoethyl, 2-morpholinoethyl, 2-acetamidoethyl, 2-acetamidovinyl, 2-carboxyvinyl, 2-carbamoylvinyl, 2-carbamoyloxyethyl, 2-formyloxyethyl, benzothiazolyl, 1-methyl-5H-tetrazol-5-yl, etc.

In the above formulas, the acyl moiety of the amino group which may optionally be acylated represented by $R_4$ may for example be carbonyl group which is substituted by a lower ($C_{1-4}$)alkyl (e.g. methyl, ethyl, propyl, isopropyl, n-butyl, tert-butyl), an aryl (e.g. phenyl, naphthyl), an aralkyl (e.g. benzyl, phenethyl), an aralkyloxy (e.g. benzyloxy) or a heterocyclic group (e.g. thienyl, benzothienyl, pyrolyl, isoxazolyl, piperazinyl, thiazolyl, tetrazolyl, oxathiiny). The substituents on said carbonyl group may have amino, halogen (e.g. chlorine, bromine, fluorine), hydroxyl, lower ($C_{1-4}$) alkyl, lower ($C_{1-4}$) alkoxy, optionally esterified carboxyl.

Referring, further, to the formulas given hereinbefore, the acyl moiety of the acylated amino group $R_1$, $R_2$ or $R_3$ may be one of the acyl groups on 6-amino of known penicillin derivatives or on 7-amino of known cephalosporin derivatives. As examples of such acyl groups, there may be mentioned.

(1) a group of the formula:

$R_6$—CO— wherein $R_6$ is a lower alkyl, phenyl which may optionally be substituted, a heterocyclic group which may optionally be substituted or benzoyl which may optionally be substituted, (2) a group of the formula:

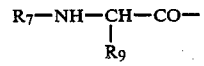

wherein $R_7$ is hydrogen, an amino acid residue which may optionally be substituted, an amino-protecting group, a group $R_8$—$(CH_2)_{n1}$—CO— [where $R_8$ is hydrogen, a heterocyclic group which may optionally be substituted, phenyl which may optionally be substituted, a lower alkyl which may optionally be substituted, phenylthio which may optionally be substituted, a lower alkylthio, carboxyl or carbamoyl, n1 is 0, or an integer of 1 to 4; and the —$(CH_2)_{n1}$— group may be substituted], a group

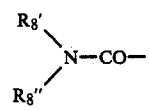

[where $R_{8'}$ and $R_{8''}$ may be the same or different and each is hydrogen, a lower alkyl, a lower alkylcarbamoyl, phenylcarbonyl which may optionally be substituted or sulfo] or a group $R_8'''$—$SO_2$— [where $R_8'''$ is a lower alkyl which may optionally be substituted]; $R_9$ is hydrogen, a lower alkyl which may optionally be substituted, phenyl which may optionally be substituted, a heterocyclic group which may optionally be substituted, a cycloalkenylene, a heterocyclic-carbonylamino which may optionally be substituted or be interrupted by an alkylene group, (3) a group of the formula:

wherein $R_{10}$ is a group

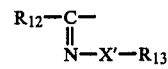

[where $X'$ is oxygen or sulfur, $R_{12}$ is a heterocyclic group which may optionally be substituted or phenyl which may optionally be substituted, $R_{13}$ is hydrogen, phenyl which may optionally be substituted, a lower acyl group which may optionally be substituted or a lower alkyl which may optionally be substituted, or a group —$R_{14}$—$R_{15}$ (where $R_{14}$ is a lower alkylene or lower alkenylene $R_{15}$ is carboxyl, an ester thereof or a heterocyclic group)]; $R_{11}$ is a chemical bond or a group

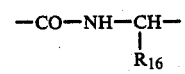

(where $R_{16}$ is a lower alkyl, phenyl which may optionally be substituted or a heterocyclic group which may be optionally be substituted), (4) a group of the formula:

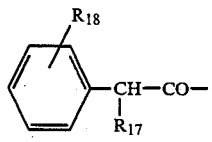

wherein $R_{17}$ is hydroxyl, hydroxysulfonyloxy, carboxyl, sulfamoyl which may optionally be substituted, sulfo, phenoxycarbonyl which may optionally be substituted, benzyloxycarbonyl, formyloxy, phthalimido, azido or a halogen; $R_{18}$ is hydrogen, a lower alkyl, a lower alkoxy, a halogen, azido, nitro or hydroxyl, or (5) a group of the formula:

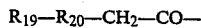

wherein $R_{19}$ is cyano, phenyl which may optionally be substituted, phenoxy which may optionally be substituted, a lower alkyl which may optionally be substituted, an alkenyl which may optionally be substituted, or a heterocyclic group which may optionally be substituted; $R_{20}$ is a chemical bond or —S—.

The lower alkyl group $R_6$ preferably contains 1 to 6 carbon atoms. The heterocyclic moiety of the optionally substituted heterocyclic group $R_6$ is a 5- or 6-membered heterocyclic group including 1 to 2 nitrogen atoms, which may optionally include a single oxygen atom. Examples of such heterocyclic group include isoxazolyl, piperazinyl, imidazolinyl, etc. The substituents on such heterocyclic groups may for example be lower alkyl groups of 1 to 3 carbon atoms, lower alkoxy groups of 1 to 3 carbon atoms, halogen, nitro, amino, oxo, thioxo, or phenyl group which may optionally be substituted. The substituents on the optionally substituted benzoyl group and those on said optionally substituted phenyl group may for example be lower alkyl groups of 1 to 3 carbon atoms, lower alkoxy groups of 1 to 3 carbon atoms, halogen, nitro, amino or the like.

The amino acid residue for the optionally substituted amino acid residue $R_7$ may for example be glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophyl, prolyl, etc. The substituents that may be present on such amino acid residues may for example be amino, lower alkylamino, amino-protecting groups, carbamoyl, methylcarbamoyl, sulfamoyl, benzyl, 4-ethyl-2,3-dioxo-1-piperazinecarbonyl, 4-ethyl-2,3-dioxo-1-piperazinecarbonylamino, etc. The lower alkyl moiety of said lower alkylamino preferably contains 1 to 3 carbon atoms. The protective group on this amino group may be one of those amino-protecting groups mentioned hereinafter.

The amino-protecting group $R_7$ may be one of those amino-protecting groups mentioned hereinafter.

The heterocyclic moiety of the optionally substituted heterocyclic group $R_8$ in the formula of $R_8$—($CH_2$)-$n_1$—CO— may for example be a 5- or 6-membered heterocyclic group including one sulfur, nitrogen or oxygen atom, a 5- to 6-membered heterocyclic group including 2 to 4 nitrogen atoms, or a 5- to 6-membered heterocyclic group including 1 to 2 nitrogen and one sulfur or oxygen atom, and these heterocyclic groups may each be fused to a 6-membered cyclic group including not more than 2 nitrogen atoms, a benzene ring or a 5-membered cyclic group including one sulfur atom.

Examples of the heterocyclic group $R_8$ include 2-pyridyl, 3-pyridyl, 4-pyridyl, pyrimidinyl, pyrazinyl, pyridazinyl, piperazinyl, pyrazolinyl, imidazolidinyl, thiazolyl, isothioazolyl, oxazolyl, isoxazolyl, pyrido[2,3-d]pyrimidinyl, benzopyranyl, 1,8-naphthyridinyl, 1,5-naphthyridinyl, 1,6-naphthyridinyl, 1,7-naphthyridinyl, 2,7-naphthyridinyl, 2,6-naphthyridinyl, quinolyl, thieno[2,3-b]pyridinyl, tetrazolyl, thiadiazolyl, oxadiazolyl, triazinyl, thienyl, pyrrolyl, furyl, etc.

The substituents on the optionally substituted heterocyclic group $R_8$ may for example be substituted or unsubstituted alkyl groups of 1 to 12 carbon atoms, lower alkoxy groups of 1 to 3 carbon atoms, hydroxyl, oxo, thioxo, aldehyde, trifluoromethyl, amino, halogen, lower ($C_{1-3}$) alkylsulfonyl, 2,6-dichlorophenyl, coumarin-3-carbonyl, 4-formyl-1-piperazinyl, pyrrolaldoimino, furanaldoimino, 2-thiophenaldoimino, 3-thiophenaldoimino, mesyl, amino-protecting groups, ($C_{2-4}$) acylamino which may be substituted by a halogen. The amino-protecting groups may be those mentioned hereinafter. The substituents optionally present on said ($C_{1-12}$) alkyl groups may for example be phenyl, a halogen, hydroxyl, dialkylamino, etc. The alkyl moiety of said dialkylamino is preferably a lower ($C_{1-3}$) alkyl.

The substituents on the optionally substituted phenyl $R_8$ may for example be lower alkyl groups of 1 to 3 carbon atoms, lower alkoxy groups of 1 to 3 carbon atoms, halogen, hydroxyl, amino, etc.

The lower alkyl moiety of lower alkylthio $R_8$ preferably contains 1 to 3 carbon atoms. The substituents on optionally substituted phenylthio $R_8$ may for example be lower ($C_{1-3}$) alkyl, lower ($C_{1-3}$) alkoxy, halogen, hydroxyl, amino, etc. As the lower alkyl which may be substituted $R_8$ there may be mentioned an alkyl whose carbon number ranges 1 to 3. The substituent in the optionally substituted lower alkyl includes carboxyl, amino, ureido, carbamoyl, etc. The substituents which may be present on the group —($CH_2$)$_{n1}$— may for example be amino, a group —NH—CO—$R_8''''$ [wherein $R_8''''$ is amino or a substituted or unsubstituted piperazinyl group]. The substituents on the optionally substituted piperazinyl group $R_8''''$ may for example be lower ($C_{1-3}$) alkyl, lower ($C_{1-3}$) alkoxy, hydroxyl, oxo, thioxo, halogen, etc.

The lower alkyls $R_8'$ and/or $R_8''$ preferably contain 1 to 3 carbon atoms. The lower alkyl moiety of said lower alkylcarbamoyl is preferably a group of 1 to 3 carbon atoms. The substituents on the optionally substituted phenylcarbonyl group may for example be lower ($C_{1-3}$) alkyl, lower ($C_{1-3}$) alkoxy, halogen, hydroxyl, hydroxysulfonyloxy, benzyloxy, etc.

The lower alkyl moiety of said optionally substituted lower alkyl group $R_8'''$ in $R_8'''$ —$SO_2$— preferably contains 1 to 6 carbon atoms and the substituents may be present in one or two positions and may for example be amino, carboxyl, benzyloxycarbonyl, protected amino, etc. The protective group on said protected amino may be one of those mentioned hereinafter as amino-protecting groups.

The lower alkyl moiety of the optionally substituted lower alkyl $R_9$ preferably contains 1 to 3 carbon atoms, the substituents being, for example, hydroxyl, formyloxy, phenyl, carbamoyl, methylcarbamoyl, methylthio, thienylacetamido, ethoxycarbonylmethylcarbamoyl, N-methyltetrazolylthio, halogen, sulfamoyl, etc.

The substituents on optionally substituted phenyl $R_9$ may for example be lower $(C_{1-3})$ alkyl, lower $(C_{1-3})$ alkoxy, halogen, hydroxyl, hydroxysulfonyloxy, benzyloxy, benzoyloxy, trimethylsilyl, acyloxy $(C_{2-10})$ e.g. alkanoyloxy etc.

The heterocyclic moiety of optionally substituted heterocyclic group $R_9$ includes among others five-membered heterocyclic groups containing one sulfur, nitrogen or oxygen atom, five-membered heterocyclic groups containing 1-2 nitrogen atoms and one sulfur or oxygen atom, and 5- or 6-membered heterocyclic groups containing 2-4 nitrogen atoms. Examples of such heterocyclic groups are thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl, oxadiazolyl, etc. The substituents on said heterocyclic groups include among others lower $(C_{1-3})$ alkyl, lower $(C_{1-3})$ alkoxy, halogen, hydroxyl, nitro, hydroxysulfonyloxy, amino, and $(C_{2-4})$ acylamino e.g. alkanoylamino which may be substituted by halogen.

The cycloalkenylene $R_9$ preferably has a 5- or 6-membered ring, and is, for example, cyclohexenyl or cyclohexadienyl.

The heterocyclic moiety of the heterocycle-carbonylamino group $R_9$ which may be substituted and/or interrupted by an alkylene chain may be a 6-membered heterocyclic group containing two nitrogen atoms and is, for example piperazinyl, which may have such a substituent as $(C_{1-12})$ alkyl, lower $(C_{1-3})$ alkoxy, oxo, thioxo or amino. The alkylene chain preferably contains 1-3 carbon atoms, and is, for example, methylene, ethylene or n-propylene.

The heterocyclic moiety of the optionally substituted heterocyclic group $R_{12}$ in the formula

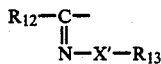

(or $R_{10}$) may be a 5-membered heterocyclic group containing one nitrogen, sulfur or oxygen atom with or without one nitrogen atom. Examples of such heterocyclic group are 2-thiazolyl, 4-thiazolyl, 5-thiazolyl, 2-thienyl, 3-thienyl, 2-furyl, 3-furyl, 2-pyrrolyl and 3-pyrrolyl. The substituents on these heterocyclic groups include among others lower $(C_{1-3})$ alkyl, lower $(C_{1-3})$ alkoxy, hydroxyl, mesyl, halogen, imino, amino, mesylamino, and $(C_{2-4})$ acylamino e.g. alkanoylamino, which may be substituted by halogen.

The substituent moiety of the optionally substituted phenyl $R_{12}$ includes lower $(C_{1-3})$ alkyl, lower $(C_{1-3})$ alkoxy, halogen, nitro, amino, hydroxyl, substituted hydroxyl. The substituent in said substituted hydroxyl is, for example, benzyl, benzoyl, $(C_{2-10})$ acyl, $\gamma$-D-glutamyl or 3-amino-3-carboxypropyl.

The lower alkyl moiety of the optionally substituted lower alkyl $R_{13}$ preferably contains 1-3 carbon atoms. The substituents on the optionally substituted lower alkyl $R_{13}$ includes carbamoyl, halogen, etc.

The substituents on the optionally substituted phenyl $R_{13}$ includes lower $(C_{1-3})$ alkyl, lower $(C_{1-3})$ alkoxy, halogen, etc.

With regard to the optionally substituted lower acyl $R_{13}$, the lower acyl preferably contains 2-4 carbon atoms, and the substituent is, for example, halogen.

The lower alkylene $R_{14}$ in the formula $-R_{14}-R_{15}$ (i.e. $R_{13}$) preferably contains 1-3 carbon atoms, and is for example methylene, ethylene, dimethylmethylene, methylethylene or ethylmethylene.

The lower alkenylene $R_{14}$ preferably contains 2-3 carbon atoms, and is for example vinylene or propenylene.

As examples of the carboxylate ester group $R_{15}$, there may be mentioned methyl, ethyl, propyl, t-butyl, p-nitrobenzyl, 2-trimethylsilylethyl and t-butyldiphenylsilyl, and diphenylmethyl esters.

The heterocyclic group $R_{15}$ may be a 6-membered one containing one nitrogen atom and one oxygen atom, or a 5-membered one containing 3-4 nitrogen atoms. Morpholino, tetrazolyl and triazolyl are examples.

The lower alkyl $R_{16}$ in the formula

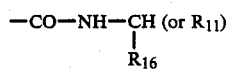

preferably contains 1-3 carbon atoms.

The substituent in the optionally substituted phenyl $R_{16}$ includes lower $(C_{1-3})$ alkyl, lower $(C_{1-3})$ alkoxy, halogen, nitro, amino, $(C_{2-10})$ acyloxy e.g. alkanoyloxy, etc.

The heterocyclic moiety of the optionally substituted heterocyclic group $R_{16}$ is, for example, a 5-membered heterocyclic group containing one sulfur, nitrogen or oxygen atom, a 5-membered heterocyclic group containing 1-2 nitrogen atoms and one sulfur or oxygen atom, or a 5-membered heterocyclic group containing 2-4 nitrogen atoms. Examples of such heterocyclic group are thiazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl. The substituents on these include lower $(C_{1-3})$ alkyl, lower $(C_{1-3})$ alkoxy, halogen, hydroxyl, amino, $(C_{2-4})$ acylamino e.g. alkanoylamino, which may be substituted by a halogen.

The substituents on the optionally substituted sulfamoyl $R_{17}$ may be, for example, lower $(C_{1-3})$ alkyl.

The substituents on the optionally substituted phenoxycarbonyl $R_{17}$ may be, for example, lower $(C_{1-3})$ alkyl or lower $(C_{1-3})$ alkoxy.

The lower alkyl or lower alkoxy $R_{18}$ preferably contains 1-3 carbon atoms.

The substituents on the optionally substituted phenyl $R_{19}$ may be for example, lower $(C_{1-3})$ alkyl, lower $(C_{1-3})$ alkoxy, halogen, nitro, amino, hydroxyl or substituted aminomethyl. The substituents on said substituted aminomethyl include among others carbamoyl, (2-oxo-3-benzylideneaminoimidazolidin-1-yl)carbonyl and (2-oxoimidazolidin-1-yl)carbonyl.

The substituents on the optionally substituted phenoxy $R_{19}$ may be, for example, lower $(C_{1-3})$ alkyl, lower $(C_{1-3})$ alkoxy, halogen, nitro, amino, hydroxyl or aminomethyl. The substituents are as mentioned above for the substituent on the optionally substituted phenyl $R_{19}$. The optionally substituted lower alkyl $R_{19}$ preferably contains 1-6 carbon atoms, and the substituents may be, for example, halogen, hydroxyl, cyano or trifluoromethyl.

The alkenyl in the optionally substituted alkenyl $R_{19}$ is, for example, vinyl or propenyl, and the substituents may be, for example, carboxyl or cyano.

The heterocyclic moiety in the optionally substituted heterocyclic group $R_{19}$ may be a 5- or 6-membered one containing one sulfur atom or 1-4 nitrogen atoms, or a 5- or 6-membered one containing one suflur atom and one nitrogen or oxygen atom. Examples of the heterocyclic group are 2-thienyl, benzothienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiin.

The substituents of the optionally substituted heterocyclic group $R_{19}$ may be, for example, lower ($C_{1-3}$) alkyl, lower ($C_{1-3}$) alkoxy, halogen, nitro, hydroxyl, optionally protected amino, carboxyl, oxo, ($C_{2-4}$) acylamino e.g. alkanoylamino, which may be substituted by halogen, or ($C_{2-4}$) acyl.

Among the terms as used hereinabove in relation to the acyl groups or moieties, the ($C_{1-12}$) alkyl includes, among others, methyl, trifluoromethyl, ethyl, n-propyl, isopropyl, n-butyl, isobutyl, sec-butyl, tert-butyl, pentyl, isopentyl, hexyl, isohexyl, heptyl, 3-heptyl, octyl, nonyl, decyl, undecyl, dodecyl and cyclohexyl. The lower ($C_{1-6}$) alkyl includes, among others, methyl, trifluoromethyl, ethyl, n-propyl, isopropyl, n-butyl, isobutyl, sec-butyl, tert-butyl, pentyl, isopentyl, hexyl and isohexyl. The lower ($C_{1-3}$) alkyl includes, among others, methyl, trifluoromethyl, ethyl, n-propyl and isopropyl. The lower ($C_{1-3}$) alkoxy includes methoxy, ethoxy, n-propoxy and isopropoxy.

Examples of the halogen mentioned in relation to the above formulas are fluorine, chlorine, bromine and iodine. Examples of the lower ($C_{1-3}$) alkylsulfonyl are methylsulfonyl, ethylsulfonyl, n-propylsulfonyl and isopropylsulfonyl. Examples of the ($C_{2-4}$) acylamino are acetylamino, propionylamino, n-butyrylamino and isobutyrylamino. Examples of the ($C_{2-10}$) acyloxy are acetoxy, n-propionyloxy, n-butyryloxy, isobutyryloxy, n-pentanoyloxy, n-hexanoyloxy, n-heptanoyloxy, n-octanoyloxy, n-nonanoyloxy and n-decanoyloxy.

Relative to the above-mentioned acyl groups, examples of the acyl of the formula $R_6$—CO— ($R_6$ being as above defined) are 3-(2,6-dichlorophenyl)-5-methylisoxazol-4-ylcarbonyl, 4-ethyl-2,3-dioxo-1-piperazinecarbonyl and 2-oxoimidazolidin-1-yl-carbonyl.

Examples of the acyl group of the formula

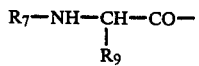

($R_7$ and $R_9$ being as above defined) are D-alanyl, D-phenylalanyl, α-benzyl-N-carbobenzoxy-γ-D-glutamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltryptophyl-D-phenylglycyl, N-[2-amino-3-(N-methylcarbamoyl)propionyl]-D-phenylglycyl, D-N-[2-carbobenzoxyamino-3-(N-methylcarbamoyl)propionyl]-D-phenylglycyl, N-carbobenzoxy-D-phenylglycyl-D-phenylglycyl, 2-(2,3-diaminopropionamido)-2-phenylacetyl, D-alanyl-D-alanyl, 2-[2-amino-3-(N-methylcarbamoyl)propionamido]acetyl, 2-(2-amino-3-sulfamoylpropionamido)-2-phenylacetyl, 2-[2-amino-3-(4-ethyl-2,3-dioxo-1-piperazinecarboxamido)propionamido]-2-phenylacetyl, D-2-(4-ethyl-2,3-dioxo-1-piperazinecarboxamido)-2-(4-methoxyphenyl)acetyl, D-2-[2-(4-ethyl-2,3-dioxo-1-piperazinecarboxamido)-3-(N-methylcarbamoyl)propionamido]-2-phenylacetyl, D-2-[2-(4-ethyl-2,3-dioxo-1-piperazinecarboxamido)acetamido]-2-phenylacetyl, D-2-(3-sulfamoyl-2-benzyloxycarboxamidopropionamido)-2-phenylacetyl, D-2-[2-benzyloxycarboxamido-3-(4-methoxyphenyloxycarboxamido)propionamido]-2-phenylacetyl, 2-[2-benzyloxycarboxamido-3-(N-methylcarbamoyl)propionamido]-acetyl, 2-(N-carbobenzoxy-D-phenylglycylamino)-3-(N-methylcarbamoyl)propionyl, N-carbobenzoxy-D-alanyl, 2-benzyloxy-carboxamido-3-(N-methylcarbamoyl)propionyl, D-2-(4-ethyl-2,3-dithioxo-1-piperazinecarboxamido)-2-phenylacetyl, 2-(2-aminothiazol-4-yl)-2-(4-ethyl-2,3-dioxo-1-piperazinecarboxamido)acetyl, 2-(2-phenylacetamido)propionyl, 2-(4-ethyl-2,3-dioxo-1-piperazinecarboxamido)-2-thienylacetyl, D-2-(4-n-dodecyl-2,3-dioxo-1-piperazinecarboxamido)-2-phenylacetyl, D-2-(4,6-dienyl-2,3-dioxo-1-piperazinecarboxamido)-2-phenylacetyl, D-2-(4-cyclohexyl-2,3-dioxo-1-piperazinecarboxamido)-2-phenylacetyl, D-2-(4-cyclohexyl-2,3-dioxo-1-piperazinecarboxamido)-2-thienylacetyl, D-2-(4-n-amyl-6(S)-methyl-2,3-dioxo-1-piperazinecarboxamido)-2-thienylacetyl, D-2-(4-ethyl-5(R)-methyl-2,3-dioxo-1-piperazinecarboxamido)-2-thienylacetyl, D-2-(4-ethyl-5(S)-methyl-2,3-dioxo-1-piperazinecarboxamido)-2-thienylacetyl, 2-(8-hydroxy-1,5-naphthyridine-7-carboxamido)-2-phenylacetyl, 2-(4-n-octyl-2,3-dioxo-1-piperazinecarboxamido)-2-phenylacetyl, 2-(4-ethyl-2,3-dioxo-1-piperazinecarboxamido)-2-(4-hydroxysulfonyloxyphenyl)acetyl, 2-(4-ethyl-2,3-dioxo-1-piperazinecarboxamido)-2-(4-chlorophenyl)acetyl, 2-(4-n-octyl-2,3-dioxo-1-piperazinecarboxamido)-2-(4-hydroxysulfonyloxyphenyl)acetyl, 2-(4-ethyl-2,3-dioxo-1-piperazinecarboxamido)-2-(4-trimethylsilylphenyl)acetyl, 2-(4-ethyl-2,3-dioxo-1-piperazinecarboxamido)-2-(3-chloro-4-methoxyphenyl)acetyl, 2-(4-ethyl-2,3-dioxo-1-piperazinecarboxamido)-2-(3-chloro-4-hydroxysulfonyloxyphenyl)acetyl, 2-(4-ethyl-2,3-dioxo-1-piperazinecarboxamido)-2-(3-chloro-4-hydroxyphenyl)acetyl, 2-(4-ethyl-2,3-dioxo-1-piperazinecarboxamido)-2-(4-benzyloxyphenyl)acetyl, 2-(4-n-octyl-2,3-dioxo-1-piperazinecarboxamido)-2-(4-hydroxyphenyl)acetyl, α-N-(4-ethyl-2,3-dioxo-1-piperazinecarbonyl)glutaminyl, N-(4-ethyl-2,3-dioxo-1-piperazinecarbonyl)phenylalanyl, N-(4-ethyl-2,3-dioxo-1-piperazinecarbonyl)-D-alanyl, 2-(4-ethyl-2,3-dioxo-1-piperazinecarboxamido)-2-(4-hydroxyphenyl)acetyl, 2,2-bis(4-ethyl-2,3-dioxo-1-piperazinecarboxamido)acetyl, 2-(4-ethyl-2,3-dioxo-1-piperazinecarboxamido)-2-(1-cyclohexen-1-yl)acetyl, 2-(4-n-octyl-2,3-dioxo-1-piperazinecarboxamido)-2-thienylacetyl, 2-(4-ethyl-2,3-dioxo-1-piperazinecarboxamido)-2-(2-chloroacetamidothiazol-4-yl)acetyl, 2-(4-ethyl-2,3-dioxo-1-piperazinecarboxamido)-2-(2-methylthiazol-4-yl)acetyl, 2-(4-ethyl-2,3-dioxo-1-piperazinecarboxamido)-2-(2-acetamidothiazol-4-yl)acetyl, 2-(4-n-octyl-2,3-dioxo-1-piperazinecarboxamido)-2-(2-aminothiazol-4-yl)acetyl, 2-(4-ethyl-2,3-dioxo-1-piperazinecarboxamido)-2-furylacetyl, 2-(4-ethyl-2,3-dioxo-1-piperazinecarboxamido)-2-(2-pyrrolyl)acetyl, 2-(4-ethyl-2,3-dithioxo-1-piperazinecarboxamido)-2-(4-hydroxyphenyl)acetyl, 2-(4-n-octyl-2,3-dioxo-1-piperazinecarboxamido)-2-(2-chloroacetamidothiazol-4-yl)acetyl, N-(4-ethyl-2,3-dioxo-1-piperazinecarbonyl)-D-methionyl, D-2-[4-(2-phenylethyl)-2,3-dioxo-1-piperazinecarboxamido]phenylacetyl, D-2-(4-ethyl-2,3-dioxo-1-piperazinecarboxamido)-2-(4-benzoyloxyphenyl)acetyl, 2,5-bis(4-ethyl-2,3-dioxo-1-piperazinecarboxamido)pentanoyl, 2-(4-ethyl-2,3-dioxo-1-piperazinecarboxamido)-3-(N-methylcarbamoyl)propionyl, 2,3-bis(4-ethyl-2,3-dioxo-1-piperazinecarboxamido)propionyl, 2-(4-ethyl-2,3-dioxo-1-piperazinecarboxamido)-3-chloropropionyl, 2-(4-ethyl- 2,3-dioxo-1-piperazinecarboxamido)-2-(4-n-octanoyloxyphenyl)acetyl, 2-(4-ethyl-2,3-dioxo-1-piperazinecarboxamido)-3-sulfamoylpropionyl, 2-(4-ethyl-2,3-dioxo-1-piperazinecarboxamido)-3-[(1-methyl-1H-tetrazol-5-yl)thio]propionyl, 2-(4-ethyl-2,3-dioxo-1-piperazinecarboxamido)acetyl, D-2-[4-(2-hydroxyethyl)-2,3-dioxo-1-piperazinecarboxamido]-2-phenylacetyl, D-2-[4-(2-chloroethyl)-2,3-dioxo-1-piperazinecarboxamido]-2-phenylacetyl, 2-(4-ethyl-2,3-dioxo-1-piperazinecarboxamido)-3-(ethoxycarbonylmethylcarbamoyl)propionyl, 2-(4-ethyl-2,3-dioxo-1-piperazinecarboxamido)-3-(thienylacetamido)propionyl, 2-(4-ethyl-2,3-dioxo-1-piperazinecarboxamido)-3-[2-(1H-tetrazol-1-yl)acetamido]propionyl, 2-(4-ethyl-2,3-dioxo-1-piperazinecarboxamido)-2-(1H-tetrazol-1-yl)acetyl, 2-[(3-furfurylideneamino-2-oxoimidazolidin-1-yl)carboxamido]-2-phenylacetyl, 2-[(3-furfurylideneamino-2-oxoimidazolidin-1-yl)carboxamido]-2-(4-hydroxyphenyl)acetyl, 2-[(3-furfurylideneamino-2-oxoimidazolidin-1-yl)carboxamido]-2-(4-hydroxysulfonyloxyphenyl)acetyl, 2-[[2-oxo-3-(thiophene-2-aldoimino)-imidazolidin-1-yl]carboxamido]-2-phenylacetyl, 2-[(3-furfurylideneamino-2-oxoimidazolidin-1-yl)carboxamido]-2-thienylacetyl, D-2-[(3-methylsulfonyl-2-oxoimidazolidin-1-yl)carboxamido]-2-phenylacetyl, 2-[(3-furfurylideneamino-2-oxoimidazolidin-1-yl)carboxamido]-2-(2-aminothiazol-4-yl)acetyl, 2-[(3-furfurylideneamino-2-oxoimidazolidine-1-yl)carboxamido]-2-(2-chloroacetamidothiazol-4-yl)acetyl, 2-[(2-oxo-3-(thiophene-2-aldimino)imidazolidin-1-yl]-carboxamido]-2-thienylacetyl, 2-[(3-mesyl-2-oxoimidazolidin-1-yl)carboxamido]-2-thienylacetyl, D-2-[(3-furfurylideneamino-2-oxoimidazolidin-1-yl)carboxamido]-propionyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, D-3-[(2-oxo-3-sulfoimidazolidin-1-yl)carboxamido]-2-thienylacetyl, D-2-[(5-methoxycarbonyl-3-methyl-2-oxoimidazolidin-1-yl)carboxamido]-2-phenylacetyl, D-2-[(5-benzyloxycarbonyl-3-methyl-2-oxoimidazolidin-1-yl)carboxamido]-2-phenylacetyl, D-2-[(5-carboxyl-3-methyl-2-oxoimidazolidin-1-yl)carboxamido]-2-phenylacetyl, 2-(coumarin-3-carboxamido)-2-phenylacetyl, 2-(4-ethyl-2,3-dioxo-1-piperazinecarboxamido)-2-(2-chloro-1-cyclohexen-1-yl)acetyl, D-2-(4-n-amyl-2,3-dioxo-1-piperazinecarboxamido)-2-phenylacetyl, D-2-(4-n-amyl-6(R)-methyl-2,3-dioxo-1-piperazinecarboxamido)-2-thienylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-aminothiazol-4-yl)acetyl]-D-phenylglycyl, 2-(6-bromo-1-ethyl-1,4-dihydro-4-oxothieno[2,3-b]pyridine-3-carboxamido)-2-phenylacetyl, 2-[2-(2-chloroacetamidothiazol-4-yl)acetamido]-2-phenylacetyl, 2-(2,5-dioxo-1,2,4-triazino-6-carboxamido)-2-thienylacetyl, 2-(2,4-dioxopyrimidino-5-carboxamido)-2-thienylacetyl, 2-[2-(4-ethyl-2,3-dioxo-1-piperazinecarboxamido)-2-thienylacetamido]-2-phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxypropylamino)-2-furylacetyl, α-(thienylmethylcarbonyl)alanyl, 2-(4-chlorobenzoylureido)-2-thienylacetyl, 2-(2-thienylacetamido)acetyl, N-benzyloxy carboxamido-D-alanyl, N-(4-hydroxybenzoyl)-D-alanyl, 2-(4-chlorobenzamido)propionyl, 2-(4-aminobenzamido)acetyl, N-(4-ethyl-2,3-dioxo-1-piperazinecarbonyl)methionyl-D-phenylglycyl, D-2-[[3-(2,6-dichlorophenyl)-5-methylisoxazol-4-yl]carboxamido]-2-thienylacetyl, 2-ureido-2-thienylacetyl, N-carbamoyl-D-phenylglycyl, 2-(3-methylcarbamoyl-3-methyl-1-ureido)-2-phenylacetyl, 2-(3-methylcarbamoyl-3-methyl-1-ureido)-2-(4-hydroxyphenyl)acetyl, 2-(3-methylcarbamoyl-3-methyl-1-ureido)-2-thienylacetyl, 2-[3-(2-hydroxybenzoyl)-1-ureido]-2-phenylacetyl, 2-[3-(2-benzyloxybenzoyl)-1-ureido]-2-(4-hydroxysulfonyloxyphenyl)acetyl, 2-[3-(2-hydroxybenzoyl)-1-ureido]-2-(4-hydroxyphenyl)acetyl, 2-[3-(2-benzyloxybenzoyl)-1-ureido]-2-phenylacetyl, 2-[3-(2-benzyloxybenzoyl)-1-ureido]-2-(4-hydroxyphenyl)acetyl, D-2-[2-(benzyloxycarboxamido)-2-(benzyloxycarbonyl)ethanesulfonamido]-2-phenylacetyl, N-mesyl-D-phenylglycyl, 2-(2-aminothiazol-4-yl)-2-ureidoacetyl, 2-(2-aminothiazol-4-yl)-2-formamidoacetyl, 2-(2-aminothiazol-4-yl)-2-acetamidoacetyl, 2-(2-aminothiazol-4-yl)-2-[(1-carboxy-1-methylethoxy)imino]acetyl, 2-(2-aminothiazol-4-yl)-2-pivalamidoacetyl, 2-(2-aminothiazol-4-yl)-2-(3-methyl-1-ureido)acetyl, 2-(2-aminothiazol-4-yl)-2-[(methoxycarbonyl-2-methylpropion)amido]acetyl, 2-(2-aminothiazol-4-yl)-2-[2-(methoxycarbonyl)acetamido]acetyl, 2-(2-aminothiazol-4-yl)-2-[[3-(3-thienylidene)amino-2-oxoimidazolidin-1-yl]carboxamido]acetyl, 2-thienyl-2-[[3-(3-thienylidene)amino-2-oxoimidazolidin-1-yl]carboxamido]acetyl, 2-(2-aminothiazol-4-yl)-2-(oxamoylamino)acetyl 2-(2-aminothiazol-4-yl)-2-(methoxalylamino)acetyl, 2-(2-aminothiazol-4-yl)-2-(oxaloamino)acetyl, D-2-(4-ethyl-2,3-dioxo-1-piperazinecarboxamido)-3-(S)-formyloxybutyryl, D-2-(4-ethyl-2,3-dioxo-1-piperazinecarboxamido)-3-(S)-hydroxybutyryl etc.

Examples of the acyl group of the formula $R_{10}$–$R_{11}$–CO— ($R_{10}$ and $R_{11}$ being as above defined) are N-[2-(2-aminothiazol-4-yl)-2-methoxyiminoacetyl]-D-alanyl, N-[2-(2-aminothiazol-4-yl)-2-methoxyiminoacetyl]-D-phenylglycyl, 2-(2-aminothiazol-4-yl)-2-(2-aminothiazol-4-yl)-2-methoxyiminoacetamido]acetyl, 2-(2-chloroacetamidothiazol-4-yl)-2-[2-(2-chloroacetamidothiazol-4-yl)-2-methoxyiminoacetamido]acetyl, 2-(2-chloroacetamidothiazol-4-yl)-2-methoxyiminoacetyl, 2-(2-aminothiazol-4-yl)-2-isopropoxyiminoacetyl, 2-(2-aminothiazol-4-yl(-2-methoxyiminoacetyl, 2-(2-aminothiazol-4-yl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-dichloroacetyloxyiminoacetyl, 2-[4-(γ-D-glutamyloxy)phenyl]-2-oxyiminoacetyl, 2-[4-amino-3-carboxypropoxy)phenyl]-2-oxyiminoacetyl, 2-thienyl-2-(3-morpholinopropyloxyimino)acetyl, 2-(5-chloro-2-(5-chloroacetamidothiazol-4-yl)-2-methoxyiminoacetyl, 2-(5-chloro-2-aminothiazol-4-yl)-2-methoxyiminoacetyl, 2-(2-aminothiazol-4-yl)-2-(1-carboxy-1-methylethoxyimino)acetyl, 2-[1-(t-butoxycarbonyl)-1-methylethoxyimino]-2-(2-sulfoaminothiazol-4-yl)acetyl, 2-[1-(t-butoxycarbonyl)-1-methylethoxyimino]-2-(2-triphenylmethylaminothiazol-4-yl)acetyl, 2-(2-chloroacetamidothiazol-4-yl)-2-(1-methylethoxyimino)acetyl, 2-methoxyimino-2-(2-hydroxysulfonylaminothiazol-4-yl)acetyl, 2-[2-(2-chloroacetamidothiazol-4-yl)-2-methoxyiminoacetamido]-2-phenylacetyl, 2-[2-(2-aminothiazol-4-yl)-2-methoxyiminoacetamido]acetyl, 2-(2- mesylaminothiazol-4-yl)-2-(1-methylethoxyimino)acetyl, 2-(2-aminothiazol-4-yl)-2-[(carboxy)methoxyimino]acetyl, 2-(2-aminothiazol-4-yl)-2-[(1-carboxy)ethoxyimino]acetyl, 2-(2-chloroacetamidothiazol-4-yl)-2-[1-(2-trimethylsilylethoxycarbonyl)-1-methylethoxyimino]acetyl, 2-[1-(2-trimethylsilylethoxycarbonyl)-1-methylethoxyimino]-2-(2-tritylaminothiazol-4-yl)acetyl, 2-(2-aminothiazol-4-yl)-2-[(1-carbamoyl-1-methyl)ethoxyimino]acetyl, 2-(2-aminothiazol-4-yl)-2-[(1-methoxycarbonyl-1-methyl)ethoxyimino]acetyl, 2-(2-aminothiazol-4-yl)-2-[(carbamoyl)methoxyimino]acetyl, 2-(2-aminothiazol-4-yl)-2-[(tetrazol-5-yl)methoxyimino]acetyl, 2-(2-aminothiazol-4-yl)-2-[(methoxycarbonyl)methoxyimino]acetyl, etc.

Examples of the acyl group of the formula

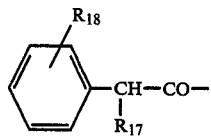

($R_{17}$ and $R_{18}$ being as above defined) are α-sulfophenylacetyl, α-hydroxysulfonyloxyphenylacetyl, α-hydroxyphenylacetyl, α-sulfamoylphenylacetyl, α-(phenoxycarbonyl)phenylacetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl, 2-bromo-2-phenylacetyl, 2-azido-2-phenylacetyl, 2-phthalimido-2-thienylacetyl, 2-azido-2-(3-chlorophenyl)acetyl, etc.

Examples of the acyl group of the formula $R_{19}$–$R_{20}$–$CH_2$—CO— ($R_{19}$ and $R_{20}$ being as above defined) are cyanoacetyl, phenylacetyl, phenoxyacetyl, trifluoromethylthioacetyl, cyanomethylthioacetyl, 1H-tetrazolyl-1-acetyl, 2-thienylacetyl, 2-(2-aminothiazol-4-yl)acetyl, 2-(2-chloroacetamidothiazol-4-yl)acetyl, 4-pyridylthioacetyl, 2-thienylthioacetyl, 3,5-dichloro-1,4-dihydro-4-oxypyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-[2-[(2-oxoimidazolidin-1-yl)carbonylaminomethyl]phenyl]acetyl, 2-[2-[(3-benzylideneamino-2-oxoimidazolidin-1-yl)carbonylaminomethyl]phenyl]acetyl, 2-(5,6-dihydro-1,4-oxathiin-2-yl)acetyl, 2-(2,5-dioxopyrrolidin-3-yl)acetyl, 2-succinimidoacetyl, 2-(1-acetyl-2,4-dioxoimidazolin-3-yl)acetyl, etc.

The amino and/or carboxyl group in the above acyl groups may be protected.

The protective groups for said amino group are those "amino-protective groups" that are to be mentioned hereinafter.

The protective groups for said carboxyl group include all groups generally usable as carboxyl-protecting groups in the field of β-lactam compounds and organic chemistry, their ester moieties being, for example, methyl, ethyl, propyl, isopropyl, t-butyl, t-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, t-butyldimethylsilyl, t-butyldiphenylsilyl, 2-trimethylsilylethyl, 2-cyanoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxido-2-methyl, methylsulfinylmethyl, bis(p-methoxyphenyl)methyl and 2-cyano-1,1-dimethylethyl. The disclosure provides the above-mentioned novel monocyclic compounds, and therefore no restrictions or limitations are posed in selecting the protective group. However, benzyl, β,β,β-trichloroethyl, 2-trimethylsilylethyl, benzhydryl, t-butyl, p-nitrobenzyl and p-methoxybenzyl are especially preferred.

The amino-protecting groups in the above formulas are conveniently those that are in use in the field of β-lactam and peptide synthesis. They are, for example, aromatic acyl groups, such as phthaloyl, p-nitrobenzoyl, p-tert-butylbenzoyl, p-tert-butylbenzenesulfonyl, benzenesulfonyl and toluenesulfonyl, aliphatic acyl groups, such as formyl, acetyl, propionyl, monochloroacetyl, dichloroacetyl, trichloroacetyl, methanesulfonyl, ethanesulfonyl, trifluoroacetyl, maloyl succinyl, benzyloxycarbonyl, p-nitrobenzyloxycarbonyl, p-methoxybenzyloxycarbonyl, 2-trimethylsilylethoxycarbonyl, and methoxycarbonyl, and further non-acyl amino-protecting groups, such as trityl, 2-nitrophenylthio, benzylidene, 4-nitrobenzylidene, di- or trialkylsilyl, t-butyldimethylsilyl, t-butyldiphenylsilyl, benzyl and p-nitrobenzyl. The selection of said protective group is not critical as it is not in the case of the carboxy-protecting group. Nevertheless, monochloroacetyl, benzyloxycarbonyl, p-methoxybenzyloxycarbonyl, 2-trimethylsilylethoxycarbonyl and p-nitrobenzyloxycarbonyl are especially preferred.

Among the optionally acylated or protected amino groups represented by $R_1$ in the above formulas, those adequate for better antibacterial and β-lactamase inhibitory activities may be represented by the formula

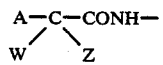

wherein A is hydrogen, a lower alkyl group such as methyl, ethyl or isobutyl, an alicyclic group such as cyclohexyl or cyclohexenyl, an aryl group such as phenyl, an aralkyl group such as phenoxybenzyl, or a heterocyclic group such as thienyl, benzothienyl, pyrrolyl, isoxazolyl, piperazinyl, thiazolyl, tetrazolyl or oxathiinyl and such A may have one or two substituents such as amino, a lower alkyl, a lower alkoxyphenoxy, oxo, hydroxyl, a halogen or chloroacetamido. W is, when Z is hydrogen, an optionally esterified carboxyl group, sulfo group, sulfamoyl group, hydroxysulfonyloxy group, an optionally protected amino group, amido group such as an arylcarboxamido (e.g. phenylcarboxamido) or a lower alkylcarboxamido group, or a heterocyclic-carboxamido group such as (2,3-dioxo-1-piperazine)carboxamido, imidazolidinecarboxamido, oxoimidazolidinecarboxamido, (isoxazol-4-yl)carboxamido, (2-aminothiazol-4-yl)methylcarboxamido or 3-(2,3-dioxo-1-piperazinecarboxamido)-2-carbobenzoxyaminopropionamido, or W and Z combined represent a group of the formula N—X'—G (in which X' is oxygen or sulfur atom or a sulfoxide group and G is a lower alkyl group, a carboxy(lower)alkyl group such as α,α-dimethyl-α-carboxymethyl, an aryl group such as phenyl, or an acyl group such as acetyl), or

may represent a direct bond or

In the above formula, the lower alkyl group A is preferably a straight or branched chain alkyl group containing 1-4 carbon atoms and may have, as a substituent other than such one as mentioned above, N-methylcarbamoyl, carbobenzyloxyamino, an aryl group such as phenyl, or a heterocyclic group such as tetrazolylacetamido, 4-ethyl-2,3-dioxo-1-piperazinecarboxamido, or 1,2-diazole which may have phenyl, methyl or ethyl at the 3-position thereof. The halogen as an optional substituent on A includes fluorine, chlorine and bromine, the lower alkyl includes methyl and ethyl, and the lower alkoxy includes methoxy and ethoxy. The optionally protected amino group W includes chloroacetylamino, aralkylamino and aralkyloxycarbonylamino. The heterocyclic moiety of the heterocyclic-carboxamido group W may be substituted by phenyl, a $(C_{1-12})$ alkyl group, a saturated alicyclic group, a $(C_{2-8})$ alkenyl group, an arylcarbonyl group which may optionally be substituted by a lower alkoxy such as methoxy or ethoxy, furfurylideneamino, sulfo, an alkoxycarbonyl, an aralkyloxycarbonyl or carboxyl. The lower alkyl moiety of the lower alkylcarboxamido group W is preferably a straight or branched alkyl group containing 1-4 carbon atoms and may be substituted by a halogen atom such fluorine, chlorine or bromine.

Among those mentioned above, preferred are those compounds of the formula (I)B in which A is phenyl, phenoxy, thiazolyl, thienyl or piperazinyl and such A is further substituted by amino, a lower alkyl or a lower alkoxy and which have or have not amino or methoxyimino at the α-position thereof.

Having a sulfo group, the compounds (I)B can in general form salts with bases. Therefore, the compounds (I)B may be recovered in the form of salts, and the salts recovered may be converted to the free form or to other salts. Furthermore, the compounds (I)B obtained in the free form may be converted to salts. The above-mentioned bases are, for example, inorganic bases, such as lithium, potassium, sodium, calcium and ammonia, and organic bases, such as pyridine, collidine, triethylamine, tetra-n-butylammonium hydroxide and triethanolamine.

The present disclosure also encompasses salts of the compounds (I)B. The method of converting the compounds in the salt form to the free form is, for example, the one which uses an acid. Usable acids depend on the kind of the protective group and other conditions, but such inorganic acids as hydrochloric, sulfuric and phosphoric acid and such organic acids as formic, acetic and p-toluenesulfonic acid are frequently used. Acidic ion exchange resins are also used. Among the solvents, hydrophilic organic solvents such as acetone, tetrahydrofuran, methanol, ethanol and dioxane, water and mixed solvents are frequently used.

According to the circumstances, the compounds (I)B may involve stereoisomers (e.g. D-isomer, L-isomer). In such a case, the individual isomers as well as mixtures therefore are also covered by the disclosure.

Not only these individual isomers but also mixtures thereof can be used as medicines. When a mixture of such isomers is obtained each isomer can be isolated as necessary by a conventional method of optional resolution.

The compounds (I)B obtained in this way are useful as medicines. For example, they have antibacterial activity against certain kinds of Gram-positive and Gram-negative bacteria.

As to the acute toxicity of the compounds (I)B, the intravenous $LD_{50}$ values in mice are 500 mg/kg or more.

The compounds (I)B, are useful, for example, in the treatment of mammals (e.g. mice, rats, humans) infected with the above-mentioned bacteria.

The compounds (I)B, can be used as therapeutic agents for bacterial infections, for example, in the treatment of infectious diseases of the respiratory organs, infectious diseases of the urinary tract, suppurative diseases, infectious diseases of the biliary tract, intestinal infectious diseases, and infectious diseases in obstretices and gynecology as well as in surgery. The daily dose is about 20 to about 200 mg/kg as compound (I)B adequately in 2-4 divided doses, the single dose being about 5 to about 100 mg/kg. The compounds (I)B or physiologically acceptable salts thereof can be administered orally, for example, in the form of tablets, capsules or lozenges prepared by per se conventional manner, or can be administered parenterally, for example, by making into injectable preparations followed by incorporating into a sterile carrier prepared by a conventional method.

The compounds (I)B have β-lactamase inhibitory activity, and are useful as β-lactamase inhibitors.

The compounds (I)B are used when β-lactam antibiotics are administered, for treatment and prevention of bacterial infections in humans or domestic animals.

When the compounds (I)B, alone are made into dosage forms, they are used before or after administration of β-lactam antibiotics or mixed therewith prior to administration. They may also be made into dosage forms as mixtures with β-lactam antibiotics. In this case, usable β-lactam antibiotics include, among others, benzylpenicillin, phenoxymethylpenicillin, sulbenicillin, carbenicillin, ampicillin, amoxicillin, mecillinam, cloxacillin, dicloxacillin, piperacillin, apalcillin, ticarcillin, cephaloridine, caphalothin, cefazolin, cephalexin, cefacetrile, cefamandolenaftate, cefuroxime, cefotiam, cefoxitin, cefmetazole, cefsulodine, cefaclor, cefatrizine, cefotaxime, cefmenoxime, ceftadizine, ceftezoxime, and other known penicillins and cephalosporins as well as hetacillin, methampicillin, talampicillin, carindacillin, carfecillin and pivmecillin, and they are prepared into injections, dry syrups, granules, tablets, capsules and so on in a conventional manner. Preferably, they are used as injections in the form of salts or hydrates. In such a method of use, the compounds (I)B can be used in amounts of 0.1 to 10 parts by weight per part by weight of β-lactam antibiotics, preferably in proportions of 1 to ⅓, for example 1/5 or 1/6. Generally, the compounds are administered at daily doses of 50–1,000 mg, or more usually at daily doses of 20–150 mg/kg, divided into 1-6 doses, for instance, usually into 2–4 divided doses.

The 1-sulfo-2-oxoazetidine derivatives (I)B can be produced, for example by subjecting a compound (II)B to sulfonation. This sulfonation reaction is a reaction for the introduction of a sulfo group, and can be carried out by bringing a compound (II)B into contact with sulfuric anhydride (sulfur trioxide) or a reactive derivative thereof, for instance.

The reactive derivative of sulfuric anhydride is, for example, sulfuric anhydride-N,N-dimethylformamide, sulfuric anhydride-pyridine, sulfuric anhydride-dioxane, sulfuric anhydride-trimethylamine or sulfuric anhydride-chlorosulfonic acid adduct.

In the above reaction, sulfuric anhydride or a reactive derivative thereof is added in an amount of about 1 to about 5 moles, preferably about 1 to about 2 moles, per mole of the compound (II)B.

The reaction temperature is about 0° C. to about 80° C., preferably about 10° C. to about 40° C. A solvent may be used in the above reaction. Usable solvents include ethers such as dioxane, tetrahydrofuran and diethyl ether, ethers such as ethyl acetate and ethyl formate, halogenated hydrocarbons such as chloroform and methylene chloride, hydrocarbons such as benzene, toluene and n-hexane, amides such as dimethylformamide and dimethylacetamide, and other usual organic solvents, alone or in combination. After the reaction, the compounds (I)B can be recovered in any desired purity by subjecting the reaction mixture to a purification/separation procedure known per se, such as solvent extraction, recrystallization and/or chromatography. The starting compounds (II)B may be subjected to the reaction in the form of various salts, esters, silyl derivatives and so on. The silyl derivatives may be prepared by silylating with a silylating agent including any of the known ones. For example the silyl compound represented by the general formula;

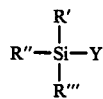

[A]

wherein R' and R" respectively stand for a lower alkyl group or a lower alkoxy group, R"' stands for halogen, phenyl, a lower alkoxy group or a lower alkyl group, and Y stands for a reactive group to be liberated from the silylating agent, can be used.

In a silylating agent represented by the above formula [A], the lower alkyl group may be exemplified by methyl, chloromethyl, ethyl, n-propyl, isopropyl, n-butyl or tert-butyl, the halogen may be exemplified by chlorine or bromine, the reactive group to be liberated from the silylating agent may be exemplified, other than the above-mentioned halogen, N-(trimethylsilyl)trifluoroacetimidoyloxy group, N-(trimethylsilyl)acetimidoyloxy group, halogeno, an acylamino group such as formylamino, acetylamino, propionylamino, butylylamino or trifluoroacetylamino, a (trialkylsilyl)amino group such as (trimethylsilyl)amino or (chloromethyldimethylsilyl)amino, amino, an alkylamino group such as methylamino, ethylamino or propylamino, an N,N-dialkylamino group such as N,N-dimethylamino, N-chloromethyl-N-methylamino, N,N-diethylamino, N,N-dipropylamino, N-methyl-N-ethylamino, N-methyl-N-propylamino or N-ethyl-N-propylamino, or a heterocyclic group such as imidazolyl.

As specific examples of the silyl compounds as described above, there may be mentioned N,O-bis(trimethylsilyl)trifluoroacetamide, N,O-bis(trimethylsilyl-)acetamide, bis(dimethylisopropylsilyl)acetamide, trimethylsilylacetamide, bis(dimethyl-tert-butylsilyl-)acetamide, N-methyl-N-trimethylsilylacetamide, N-methyl-N-trimethylsilyltrifluoroacetamide, N-trimethylsilyldimethylamine, hexamethyldisilazane, 1,3-bis(-chloromethyl)-1,1,3,3-tetramethyldisilazane, N-trimethylsilylimidazole, trimethylchlorosilane, triethylchlorosilane, dimethyldichlorosilane, diethoxydichlorosilane, tert-butyldimethylchlorosilane, isopropyldimethylchlorosilane, dimethylphenylchlorosilane or chloromethyldimethylchlorosilane.

When, among them, tert-butyldimethylchlorosilane or isopropyldimethylchlorosilane is used, the corresponding silyl derivatives can be stably isolated. In the above reaction, a silyl agent represented by [A] is used in amount of at least one equivalent, preferably 1 to 3 equivalent to a compound (II)B. The reaction temperature is in the range of 0°~50° C., preferably not higher than 38° C., usually at room temperature, and the reaction time is from several minutes to 24 hours. The reaction is conducted conveniently in, for example, ethyl acetate, dioxane, tetrahydrofuran, N,N-dimethylacetamide, N,N-dimethylformamide, dichloromethane, chloroform, benzene, toluene, acetone, methylethylketone, or acetonitrile, or an optional mixture of them, or any other solvent which is inert to this reaction. This reaction can be conducted also in the presence of an inorganic base such as sodium hydroxide, potassium hydroxide, sodium hydrogen carbonate, sodium carbonate or potassium carbonate or a trialkylamine such as triethylamine, tributylamine, tribenzylamine, N-methylmorpholine, or N-methylpiperidine, an organic tertiary amine such as N,N-dialkylaniline, N,N-dialkylbenzylamine, pyridine, picoline or rutidine, or an organic base such 1,5-diazabicyclo[2,2,2]octane or 1,8-diazabicyclo[5,4,4]undecene-7, and when the base is liquid, it can be used also as a solvent. Thus obtained 1-silyl derivative of a compound (II)B, where $R_2$ is a protected amino group, can be led to a 1-silyl derivative of a desired compound (II)B by eliminating the protective group, followed by subjecting to acylation.

Furthermore, the 1-sulfo-2-oxoazetidine derivatives

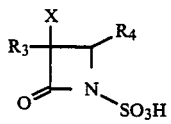

(IV)B can also be produced for example by subjecting a compound (III)B to acylation. The acylation is effected by reacting a compound (III)B with an acylating agent. The acylating agent to be used in this reaction may be an organic carboxylic acid or a reactive derivative thereof, which contains the acyl group $R_3$.

The reactive derivative of the organic acid includes, among others, acid anhydrides, active amides and active esters. Examples of such reactive derivatives of organic acids are as follows:

(1) acid anhydrides:

The acid anhydrides include, among others, mixed anhydrides with a hydrohalogenic acid (e.g. hydrochloric or hydrobromic acid), with a monoalkyl carbonate, with an aliphatic carboxylic acid (e.g. acetic acid, pivalic acid, valeric acid, isopentanoic acid or trichloroacetic acid) or with an aromatic carboxylic acid (e.g. benzoic acid), and symmetric acid anhydrides.

(2) Activated amides:

The activated amides include amides with pyrazole, imidazole, 4-substituted imidazole, dimethylpyrazole, benzotriazole, etc.

(3) Activated esters:

The activated esters include, among others, such esters as methyl, ethyl, methoxymethyl, propargyl, 4-nitrophenyl, 2,4-dinitrophenyl, trichlorophenyl, pentachlorophenyl and mesylphenyl esters as well as esters of such acids as the above-mentioned carboxylic acid with 1-hydroxy-1H-2-pyridone, N-hydroxysuccinimide, 1-hydroxybenzotriazole, N-hydroxy-5-norbornene-2,3-dicarboximide and N-hydroxyphthalamide.

Appropriate reactive derivatives of organic acids are selected from among those mentioned above depending on the type of the acid used. When a free acid is used as the acylating agent, the reaction is preferably carried out in the presence of a condensing agent. Examples of the condensing agent are N,N'-dicyclohexylcarbodiimide, N-cyclohexyl-N'-morpholinoethylcarbodiimide, N-cyclohexyl-N'-(4-diethylaminocyclohexyl)carbodiimide and N-ethyl-N'-(3-dimethylaminopropyl)carbodiimide.

The acylation is usually carried out in a solvent. The solvent includes water, acetone, dioxane, acetonitrile, methylene chloride, chloroform, dichloroethane, tetrahydrofuran, ethyl acetate, dimethylformamide, pyridine and other common organic solvents inert to the reaction. Among these, hydrophilic solvents may be used as mixtures with water.

The acylation may be carried out in the presence of an inorganic base, such as sodium hydroxide, sodium carbonate, potassium carbonate or sodium hydrogen carbonate, or in the presence of an organic base such as trialkylamine e.g. trimethylamine, triethylamine, tributylamine, N-methylmorpholine or N-methylpiperidine, or an organic tertiary amine e.g. N,N-dialkylaniline, N,N-dialkylbenzylamine, pyridine, picoline or lutidine, tetra-n-butylammonium hydroxide, or 1,5-diazabicyclo[4,3,0]non-5-ene, 1,4-diazabicyclo[2,2,2]octane or 1,8-diazabicyclo[5,4,4]undecene-7. When the base or the above-mentioned condensing agent is a liquid, it may also serve as a solvent. The reaction temperature is not critical, but the reaction is mostly carried out under cooling or at room temperature.

When the reactive derivative at the amino group of the starting material (III)B or a salt thereof or the acylating agent contains at least one asymmetric carbon atom, the respective stereoisomers alone as well as mixtures thereof can be subjected to the acylation. When the acylation product is a mixture of corresponding isomers, the individual isomers can be isolated as necesary by a conventional method, such as column chromatography or recrystallization.

The starting compound (III)B to be used in the acylation reaction may also be in the form of a salt or silyl derivative. Examples of said salt are as above mentioned in relation to the salt of compound (I)B and examples of said silyl derivative are as above mentioned.

When the starting compound used in said acylation reaction is in the form of a salt, the product (IV)B may also be in the form of a salt as the case may be. When the product is obtained in the form of a salt, the salt may also be converted to another salt form by the same method as is used in the salt exchange with the above-mentioned compound (I)B.

Furthermore, the compound (IV)B recovered in the form of a salt may be converted to the free form. For converting the salt to the free form, the same method as is used for converting a salt of the above-mentioned compound (I)B to the free form may be employed.

The compounds (I)B having protective groups are valuable as intermediates for the synthesis of useful medicines and, for example, can be converted to unprotected compounds (I)B by elimination of the protective groups.

The elimination of protective groups from azetidine derivatives (I)B can be effected by selective application of per se known methods such as the method involving the use of an acid, one using a base, a reductive method, the method involving the use of hydrazine, or the method involving the use of thiourea or sodium N-methyldithiocarbamate. The method involving the use of an acid employs, according to the type of protective group and other conditions of deprotection, such as inorganic acid as hydrochloric acid, sulfuric acid, phosphoric acid, etc., such an organic acid as formic acid, acetic acid, trifluoroacetic acid, propionic acid, benzenesulfonic acid, p-toluenesulfonic acid, etc., acidic ion exchange resins and so on. The method involving the use of a base employs, according to the type of protective group and other conditions, inorganic bases such as the hydroxides or carbonates of alkali metals (e.g. sodium, potassium, etc.) or of alkaline earth metals (e.g. calcium, magnesium, etc.), or organic bases such as metal alkoxides, organic amines, quaternary ammonium salts, or basic ion exchange resins, etc.

When the above method involving the use of an acid or a base is carried out in the presence of a solvent, the solvent is usually a hydrophilic organic solvent, water or a mixed solvent.

The reductive method employs, according to the type of protective group and other conditions, a metal (e.g. tin, zinc, etc.) or a metal compound (e.g. chromous chloride, chromous acetate, etc.) together with an acid such as an organic or inorganic acid (e.g. acetic acid, propionic acid, hydrochloric acid), or involves the use of a metal catalyst for catalytic reduction. The catalyst used for such catalytic reduction may for example be platinum catalysts (e.g. platinum wire, platinum sponge, platinum black, platinum oxide, colloidal platinum, etc.), palladium catalysts (e.g. palladium sponge, palladium black, palladium oxide, palladium-barium sulfate, palladium-barium carbonate, palladium-carbon, palladium-silica gel, colloidal palladium, etc.), reduced nickel, nickel oxide, Raney nickel, Urushihara nickel, etc.

The reductive method involving the use of a metal and an acid employs a metal compound (e.g. of iron or chromium) and an inorganic acid (e.g. hydrochloric acid) or organic acid (e.g. formic acid, acetic acid, propionic acid, etc.). The reductive method is usually conducted in a solvent. In the catalytic reduction method, for instance, the reaction is conducted usually in the presence of an alcohol (e.g. methanol, ethanol, propyl alcohol, isopropyl alcohol, etc.), ethyl acetate, etc. The method involving the use of a metal and an acid is usually carried out in the presence of water, acetone or the like, but when the acid is liquid, it may be utilized as the solvent as well.

The reaction is usually conducted in the range of from cooling to warming.

When the protective group is an organic carboxylic acid residue and there is such a substituent as free amino, hydroxyl, mercapto, carboxyl, sulfo, etc. on the carbon atom adjacent to its carbonyl group, it is advantageous to previously conduct a treatment for enhancing the adjacent group effect of such substituent group to render the carbonyl group more reactive and, then, remove the protective group. By way of illustration, when the substituent on the carbon atom adjacent to said carbonyl group is a free amino group, the free amino group is first transformed into a thioureido group before conducting the deacylation reaction. Thus, the protective group can be eliminated by the conventional procedure used for the cleavage of peptide bonds. The reaction temperature is not so critical and can be selected with reference to the type of protective group, the deprotection method used, etc., although the reaction is preferably conducted under cooling or mild warming.

When $R_1$ is a carboxyl-containing group, there are cases in which the derivative at the carboxyl function is transformed into a free carboxyl group in the course of reaction and these cases are also subsumed in the ambit of this disclosure.

The resulting unprotected compound (I)B can be converted to desired salts in the conventional manner.

The starting compounds (II)B and (III)B can be prepared, for example by the following methods.

The starting compound (II)B can be easily prepared, e.g. where $R_4$ is an acyloxy group, by the method described in Tetrahedron Letters 1978, 4059 or Japanese published unexamined patent application No. 76570/1979); where $R_4$ is a substituted dithio (—S—S—$R_5$) group, by the method described in Chemical Communication 1971, 845 or a method analogous thereto; or where $R_4$ is a group other than acyloxy or substituted dithio, by the method described in Annalen der Chemie 1974, 539 in the following alternative synthetic pathways (1) and (2)

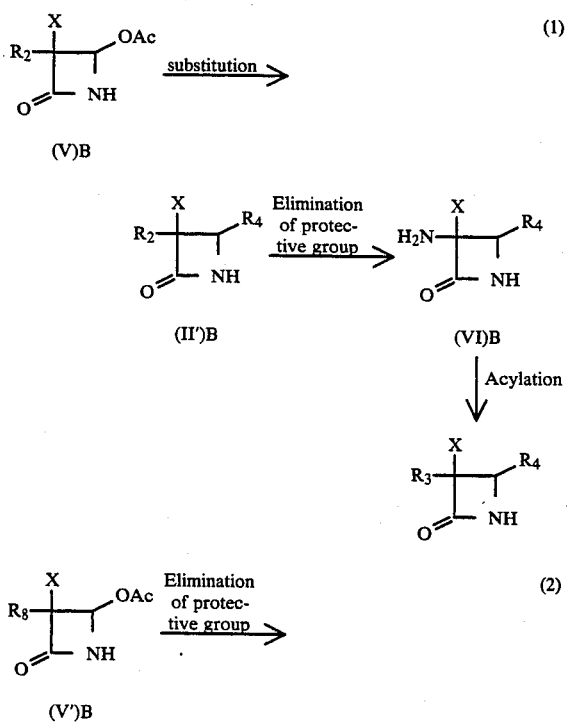

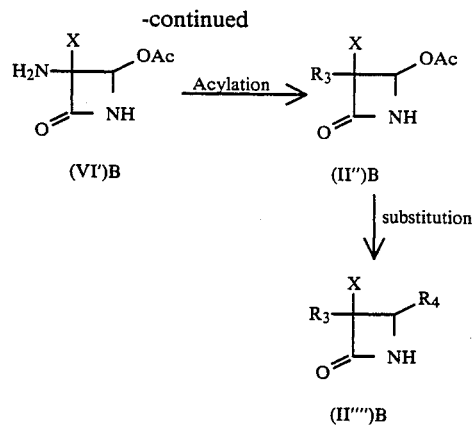

In each of the above reaction formulas, $R_2$, $R_3$, $R_4$ and X are as previously defined and $R_8$ is a protected amino group.

The following examples, reference examples and test example are given to illustrate in further detail. In these examples, NMR spectra were measured with Varian HA 100 (100 MHz), EM 390 (90 MHz) and T 60 (60 MHz) instruments, with tetramethylsilane as a reference standard, and the δ values are shown in ppm. In the chemical shift data, s means a singlet, br.s. a broad singlet, d a doublet, dd a double doublet, t a triplet, q a quartet, m a multiplet, ABq an AB pattern quartet, J a coupling constant, THF tetrahydrofuran, DMF dimethylformamide, DMSO dimethyl sulfoxide, br. or broad a broad, and arom aromatic.

In silica gel column-chromatography, Kiesel Gel 60 (Art 9385, 230–400 Mesh, Merck Co., Germany) was employed and the elution in the chromatography was carried out with observation of TLC. In the TLC were employed HPTLC Kiesel Gel 60 $F_{254}$ plate (Art 5642, Merck Co., Germany), a developing solvent which is the same as the eluent employed in the column-chromatography and UV detector.

Fractions containing the desired compound, which show the same Rf value as that of main spot appearing on TLC plate at TLC for the reaction solution to be subjected to the column-chromatography were collected.

In XAD-II column-chromatography were employed water-20% ethanol as an eluent. Fractions containing the desired compound, which show the absorbancy at 254 nm in UV spectrum by use of LKB UVICORD 2 were collected, followed by lyophilizing to give the objective compound.

Test Example

"Determination of the inhibitor concentration required to inhibit the enzyme activity by 50%"

The β-lactamase produced by *Enterobacter cloacae* PN 1282 is used as a typical example of cephalosporinase. The β-lactamase is incubated in 0.05M phosphate buffer (pH 7) with an appropriate dilution of an inhibitor preparation at 30° C. for 10 minutes. Cephalothin is then added in an amount sufficient to produce a final concentration of 0.1 mM, and the enzymatic reaction is allowed to proceed for 10 minutes. The enzyme activity is determined by the micro-iodometric method [Journal of general Microbiology, vol. 33, page 121 (1963)]. Hereinafter, the inhibitor concentration required to inhibit the enzyme activity by 50% is expressed as $I_{50}$.

The I$_{50}$ values for *Enterobacter cloacae* are shown in Table 1B.

TABLE 1B

| Compound | I$_{50}$ (μg/ml) |
|---|---|
| sodium (3R,4R)—4-methylthio-3-[2-(2-aminothiazol-4-yl)-2-(1-carboxy-1-methylethoxyimino)acetamido]-2-oxoazetidine-1-sulfonate | 0.19 |
| sodium (3R,4R)—3-[2-(2-aminothiazol-4-yl)-2-methoxyiminoacetamido]-4-methylthio-2-oxoazetidine-1-sulfonate | 0.3 |
| sodium (3R,4S)—3-[2-(2-aminothiazol-4-yl)-2-methoxyiminoacetamido]-4-phenylthio-2-oxoazetidine-1-sulfonate | 0.027 |
| sodium (3R,4R)—3-[3-(2,6-dichlorophenyl)-5-methyl-4-isoxazolylcarboxamido]-4-methylthio-2-oxoazetidine-1-sulfonate | 0.045 |

REFERENCE EXAMPLE 1B 21.9 g of methyl (3S,4S)-4-acetoxy-3-benzyloxycarboxamido-2-oxoazetidine-1-(6O-isopropylidene)acetate is treated with ozone in 400 ml of methylene chloride untill the reaction solution turns to blue colour, followed by addition of 10 ml of methyl sulfide and a small amount of sodium methoxide in 350 ml of methanol. The reaction yields 10.6 g of (3S,4S)-4-acetoxy-3-benzyl-oxycarboxamido-2-oxoazetidine.

IR $\nu_{max}^{KBr}$cm$^{-1}$; 3480, 3430, 1815(shoulder), 1800, 1770, 1725, 1695, 1522, 1260, 1240.

NMR(CDCl$_3$, ppm); 2.13(s, CH$_3$), 4.80(dd, J=2, 8 Hz, C$_3$—H), 5.20(s, —CH$_2$—), 5.90(d, J=2 Hz, C$_4$—H), 6.10(d, J=8 Hz, NH), 7.26(broad s, NH), 7.43(s, arom H).

REFERENCE EXAMPLE 2B 5 g of methyl(3S,4S)-4-acetoxy-3-phenoxyacetamido-2-oxoazetidine-1-(α-isopropylidene)acetate is treated in the same manner as Reference Example 1B to give 2.1 g of (3S,4S)-4-acetoxy-3-phenoxyacetamido-2-oxoazetidine.

IR $\nu_{max}^{KBr}$cm$^{-1}$; 3325, 1805, 1760, 1745, 1670, 1530, 1230, 1218.

NMR(CDCl$_3$, ppm); 2.17(s, CH$_3$), 4.62(s, —CH$_2$—), 5.03(dd, J=2, 7 Hz, C$_3$—H), 6.03(d, J=2 Hz, C$_4$—H), 6.95-7.80(m, NH, arom H).

REFERENCE EXAMPLE 3B 1 g of methyl(3R,4R)-4-methylthio-3-phenoxyacetamido-2-oxoazetidine-1-(α-isopropylidene)acetate is treated in aqueous acetone with 1.2 g of potassium permanganate and 2 ml of acetic acid to give 0.486 g of (3R,4R)-4-methylsulfonyl-3-phenoxyacetamido-2-oxoazetidine.

IR $\nu_{max}^{KBr}$cm$^{-1}$; 3290, 1770, 1675, 1525, 1290, 1275, 1215.

NMR(DMSO-d$_6$, ppm); 3.16(s, CH$_3$), 4.53(s, —CH$_2$—), 5.16(d, J=5 Hz, C$_4$—H), 5.71(dd, J=5, 10 Hz, C$_3$—H), 6.80-7.43(m, arom H), 8.35(d, J=10 Hz, NH), 9.51(s, NH)

REFERENCE EXAMPLE 4B 4.5 g of methyl(3R,4R)-3-benzyloxycarboxamido-4-methylthio-2-oxoazetidine-1-(α-isopropylidene)acetate is treated in the same manner as Reference Example 3B to give 2.3 g of (3R,4R)-3-benzyloxycarboxamido-4-methylsulfonyl-2-oxoazetidine.

IR $\nu_{max}^{KBr}$cm$^{-1}$; 3320, 3275, 1765, 1688, 1512, 1292, 1275, 1252, 1230.

NMR(DMSO-d$_6$, ppm); 2.96(s, CH$_3$), 5.07(d, J=5 Hz, C$_4$—H), 5.17(s, —CH$_2$—), 5.50(dd, J=5, 10 Hz, C$_3$—H), 7.42(s, arom H), 7.76(d, J=10 Hz, NH), 9.40(s, NH)

REFERENCE EXAMPLE 5B 6 g of methyl(3R,4R)-4-methylthio-3-phenoxyacetamido-2-oxoazetidine-1-(α-isopropylidene)acetate is treated in the same manner as Reference Example 1B to give 1.34 g of (3R,4R)-4-methylsulfinyl-3-phenoxyacetamido-2-oxoazetidine.

IR $\nu_{max}^{KBr}$cm$^{-1}$; 3275, 1765, 1665, 1530, 1212.

NMR(DMSO-d$_6$, ppm); 2.58(s, CH$_3$), 4.70(s, —CH$_2$—), 4.92(d, J=5 Hz, C$_4$—H), 5.75(dd, J=5, 10 Hz, C$_3$—H), 6.93-7.65(m, arom H), 8.61(d, J=10 Hz, NH), 9.28(s, NH).

REFERENCE EXAMPLE 6B 3.92 g of methyl(3R,4R)-4-ethylthio-3-phenoxyacetamido-2-oxoazetidine-1-(α-isopropylidene)acetate is treated in the same manner as Reference Example 1B to give 1.36 g of (3R,4R)-4-ethylsulfinyl-3-phenoxyacetamido-2-oxoazetidine.

IR $\nu_{max}^{KBr}$cm$^{-1}$; 3310, 3160, 1760, 1685, 1208.

NMR(DMSO-d$_6$, ppm); 1.23(t, J=8 Hz, CH$_3$), 2.70(q, J=8 Hz, —CH$_2$—), 4.65(s, —CH$_2$—), 4.75(d, J=5 Hz, C$_4$—H), 5.78(dd, J=5, 10 Hz, C$_3$—H), 6.85-7.63(m, arom H), 9.10(d, J=10 Hz, NH), 9.18(s, NH).

REFERENCE EXAMPLE 7B

To a solution of 1.39 g of (3S,4S)-4-acetoxy-3-phenoxyacetamido-2-oxoazetidine in 60 ml of 80% alcohol is added dropwise 5 ml of an ethanolic solution of 0.441 g of sodium ethylsulfide under ice-cooling. The mixture is stirred under ice-cooling for 30 minutes and, then, at room temperature for 15 minutes, the ethanol is distilled off under reduced pressure and the water layer is extracted twice with ethyl acetate. The organic layer is washed with water, dried over magnesium sulfate and concentrated under reduced pressure. Purifying the residue on a silica gel column (n-hexane:ethylacetate=2:1) gives: 0.680 g of (3R,4S)-4-ethylthio-3-phenoxyacetamido-2-oxoazetidine, IR $\nu_{max}^{nujol}$cm$^{-1}$; 3270, 3150, 1752, 1659.

NMR(CDCl$_3$, ppm); 1.27(t, J=7 Hz, CH$_3$), 2.62(q, J=7 Hz, —CH$_2$—), 4.46(s, —CH$_2$—), 4.80(d, J=2 Hz, C$_4$—H), 4.83(dd, J=2, 9 Hz, C$_3$—H), 6.70-7.40(m, arom H, NH), 7.68(d, J=9 Hz, NH); and 0.164 g of (3R,4R)-4-ethylthio-3-phenoxyacetamido-2-oxo-azetidine.

IR $\nu_{max}^{KBr}$cm$^{-1}$; 3260, 1770, 1725, 1665, 1525.

NMR(CDCl$_3$, ppm); 1.23(t, J=7 Hz, CH$_3$), 2.52(q, J=7 Hz, —CH$_2$—), 4.66(s, —CH$_2$—), 5.05(d, J=5 Hz, C$_4$—H), 5.75(dd, J=5, 10 Hz, C$_3$—H), 6.60(broad s, NH), 6.90-7.70(m, arom H, NH).

REFERENCE EXAMPLE 8B

To a solution of 0.224 g of (3R,4S)-4-ethylthio-4-phenoxyacetamido-2-oxoazetidine in 3 ml of methanol is added 0.16 ml of 30% aqueous hydrogen peroxide and the mixture is stirred at room temperature for 4 hours. Then, 0.1 ml of 30% aqueous hydrogen peroxide is added, and the mixture is further stirred for 4 hours, followed by addition of 10 ml of water. Extraction is carried out with ethyl acetate. The organic layer is washed with water, dried over magnesium sulfate and concentrated under reduced pressure to give 0.20 g of (3R,4S)-4-ethylsulfinyl-3-phenoxyacetamido-2-oxoazetidine.

IR $\nu_{max}^{KBr}$cm$^{-1}$; 3350, 3270, 1765, 1750, 1690.

NMR(DMSO-d$_6$, ppm); 1.22(3H, t, J=8 Hz, CH$_3$), 2.75(q, J=8 Hz, —CH$_2$—), 4.65(s, —CH$_2$—), 4.78(d, J=2 Hz, C$_4$—H), 5.15(dd, J=2, 10 Hz, C$_3$—H), 6.93-7.60(m, arom H), 8.95(s, NH), 9.08(d, J=10 Hz, NH).

REFERENCE EXAMPLE 9B

To a solution of 0.494 g of (3S,4S)-4-acetoxy-3-phenoxyacetamido-2-oxoazetidine in 14 ml of 50% methanol is added 0.51 g of sodium methylsulfinate and the mixture is stirred at room temperature for 18 hours. The methanol is distilled off under reduced pressure to give 222 mg of (3R,4S)-4-methylsulfonyl-3-phenoxyacetamido-2-oxoazetidine, IR $\nu_{max}^{KBr}$cm$^{-1}$; 3290, 1798, 1670, 1525, 1305, 1130.

NMR(DMSO-d$_6$, ppm); 3.08(s, CH$_3$), 4.60(s, —CH$_2$—), 5.02 (d, J=2 Hz, C$_4$—H), 5.23(dd, J=2, 9 Hz, C$_3$—H), 6.95-7.63(m, arom H), 9.05(d, J=9 Hz, NH), 9.28(s, NH).

REFERENCE EXAMPLE 10B 1.4 g of (3S,4S)-4-acetoxy-3-benzyloxycarboxamido-2-oxoazetidine is treated with 0.5 g of sodium methylsulfinate in the same manner as Reference Example 9B. The procedure yields 0.75 g of (3R,4S)-3-benzyloxycarboxamido-4-methylsulfonyl-2-oxoazetidine as colorless prisms. mp 178°-180° (dec.) IR $\nu_{max}^{KBr}$cm$^{-1}$; 3300, 1800, 1695, 1530, 1300, 1265, 1115

NMR(DMSO-d$_6$, ppm); 3.06(s, CH$_3$), 4.82(dd, J=8, 2 Hz, C$_3$—H), 5.00(d, J=2 Hz, C$_4$—H), 5.16(s, —CH$_2$—), 7.43(s, arom H), 8.33(d, J=8 Hz, NH), 9.33(broad s, NH).

REFERENCE EXAMPLE 11B

In 30 ml of methanol is dissolved 3 g of (3S,4S)-4-acetoxy-3-benzyloxycarboxamido-2-oxoazetidine, followed by addition of 2.36 g of zinc acetate and the mixture is refluxed for 45 minutes. The solvent is dissolved off, and the organic layer is separated after addition of ethyl acetate and water. The organic layer is washed with aqueous sodium chloride, dried over magnesium sulfate and concentrated under reduced pressure. Purifying the residue on a silica gel column (the eluent; ethyl acetate:n-hexane=1:1) yields 1.37 g of (3S,4S)-3-benzyloxycarboxamido-4-methoxy-2-oxoazetidine (A) and 0.82 g of (3S,4R)-3-benzyloxycarboxamido-4-methoxy-2-oxoazetidine (B).

(A) IR $\nu_{max}^{KBr}$cm$^{-1}$; 3370, 3320, 1775, 1758, 1690.

NMR(DMSO-d$_6$, ppm); 3.26(s, CH$_3$), 4.23(dd, J=1.5, 9 Hz, C$_3$—H), 4.79(d, J=1.5 Hz, C$_4$—H), 5.03(s, —CH$_2$—), 7.33(s, arom H), 7.94(d, J=9 Hz, NH), 8.86(s, NH).

(B) IR $\nu_{max}^{KBr}$cm$^{-1}$; 3320, 3240, 1768, 1740, 1720, 1700.

NMR(DMSO-d$_6$, ppm); 3.23(s, CH$_3$), 4.79(dd, J=4, 10 Hz, C$_3$—H), 4.91(d, J=4 Hz, C$_4$—H), 5.03(s, —CH$_2$—), 7.33(s, arom H), 7.87(d, J=10 Hz, NH), 8.86(s, NH).

REFERENCE EXAMPLE 12B

Following the procedure of Reference Example 11B but using 1.5 g of (3R,4R)-4-methylsulfonyl-3-phenoxyacetamido-2-oxoazetidine and 1.11 g of zinc acetate, there are obtained 0.574 g of (3S,4S)-4-methoxy-3-phenoxyacetamido-2-oxoazetidine (A) and 0.287 g of (3S,4R)-4-methoxy-3-phenoxyacetamido-2-oxoazetidine (B).

(A) IR $\nu_{max}^{KBr}$cm$^{-1}$; 3280, 3175, 1760, 1663.

NMR(acetone-d$_6$, ppm); 3.35(s, CH$_3$), 4.51(s, —CH$_2$—CH$_2$—), 4.68(dd, J=1.5, 9 Hz, C$_3$—H), 4.98(d, J=1.5 Hz, C$_4$—H), 6.83-7.43(m, arom H), 7.80-8.30(m, NH).

(B) IR $\nu_{max}^{KBr}$cm$^{-1}$; 3320, 3200, 1763, 1658.

REFERENCE EXAMPLE 13B

To a solution of 1 g of (3S,4S)-4-acetoxy-3-benzyloxycarboxamido-2-oxoazetidine in 30 ml of THF is added 500 mg of palladium black and the mixture is stirred in a hydrogen stream for one hour. The catalyst is filtered off and the filtrate is concentrated under reduced pressure to ca. 10 ml.

On the other hand, 2 g of 2-(2-chloroacetamidothiazol-4-yl)-2-methoxyiminoacetic acid (syn-isomer) is added to 20 ml of methylene chloride, and under ice-cooling 0.87 g of triethylamine and 1.5 g of phosphorous pentachloride are added. The mixture is stirred for 5 minutes under ice-cooling. It is further stirred at room temperature for 30 minutes, after which time it is concentrated under reduced pressure. The residue is washed with hexane, 10 ml of THF is added, and the insoluble matters are filtered off. Under ice-cooling, the filtrate is added dropwise to a mixture of the above-prepared solution and 3 ml of propylene oxide. The solvent is distilled off under reduced pressure and the residual ethyl acetate solution is washed with water, dried over magnesium sulfate and concentrated under reduced pressure. Purifying the residue on a silica gel column (ethyl acetate:n-hexane=2:1) yields 0.170 g(anti-isomer) and 0.20 g(syn-isomer) of 3S,4S)-4-acetoxy-3-[2-(2-chloroacetamidothiazol-4-yl)-2-methoxyiminoacetamido]-2-oxoazetidine and 0.30 g of a mixture of both isomers:

(Syn-isomer)

IR $\nu_{max}^{KBr}$cm$^{-1}$; 3270, 1770, 1740, 1720, 1665, 1545.

NMR(DMSO-d$_6$, ppm); 2.17(s, CH$_3$), 4.00(s, CH$_3$), 4.40 (s, —CH$_2$—), 4.90(dd, J=2, 8 Hz, C$_3$—H), 5.93(d, J=2 Hz, C$_4$—H),

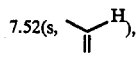
7.52(s, 9.30(s, NH), 9.43(d, J=8 Hz, NH), 12.87(s, NH).

(Anti-isomer)

IR$\nu_{max}^{KBr}$cm$^{-1}$; 3250, 1770, 1750(shoulder), 1665, 1540.

NMR(DMSO-d$_6$, ppm); 2.13(s, CH$_3$), 4.07(s, CH$_3$), 4.40(s, —CH$_2$—), 4.90(dd, J=2, 9 Hz, C$_3$—H), 5.88(d, J=2 Hz, C$_4$—H),

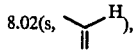
8.02(s, 9.30(d, J=9 Hz, NH), 9.35(s, NH), 12.77(s, NH).

REFERENCE EXAMPLE 14B

Following the procedure of Reference Example 13B but using 0.298 g of (3R,4R)-3-benzyloxycarboxamido-4-methylsulfonyl-2-oxoazetidine and 0.638 g of D-2-(4-ethyl-2,3-dioxo-1-piperazinecarboxamido)-2-phenylacetic acid, there is obtained 0.114 g of (3R,4R)-3-[D-2-(4-ethyl-2,3-dioxo-1-piperazinecarboxamido)-2-phenylacetamido]-4-methylsulfonyl-2-oxoazetidine.

IR $\nu_{max}^{KBr}$cm$^{-1}$; 3270, 1778, 1700, 1668, 1500.

NMR(DMSO-d₆, ppm); 1.09(t, J=7 Hz, CH₃), 2.27(s, CH₃), 3.40 (q, J=7 Hz, —CH₂—), 3.44–3.66(m, —CH₂—), 3.78–4.02(m, —CH₂—), 4.94(d, J=5 Hz, C₄—H), 5.61(dd, J=5, 9 Hz, C₃—H), 5.72(d, J=7Hz, —CH—),
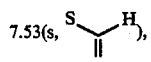

7.25–7.54(m, arom H), 9.08(d, J=9 Hz, NH), 9.33(s, NH), 9.85(d, J=7 Hz, NH).

REFERENCE EXAMPLE 15B

Following the procedure of Reference Example 13B but using 0.298 g of (3R,4R)-3-benzyloxycarboxamido-4-methylsulfonyl-2-oxoazetidine and 0.555 g of 2-(2-chloroacetamidothiazol-4-yl)-2-methoxyiminoacetic acid (syn-isomer), there is obtained 0.205 g of (3R,4R)-3-[2-(2-chloroacetamidothiazol-4-yl)-2-methoxyiminoacetamido]-4-methylsulfonyl-2-oxoazetidine.

(Syn-isomer)

IR $\nu_{max}^{KBr}$ cm⁻¹; 3370, 3270, 1790, 1680, 1540.

NMR(DMSO-d₆, ppm); 3.00(s, CH₃), 3.93(s, CH₃), 4.33(s, —CH₂—), 4.93(d, J=5 Hz, C₄—H), 5.57(dd, J=5, 9 Hz, C₃—H), 7.53(s, S\_/H),
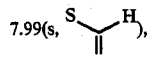

8.30(d, J=9 Hz, NH), 9.40(s, NH), 12.73 (s, NH).

(Anti-isomer)

IR $\nu_{max}^{KBr}$ cm⁻¹; 3380, 3250, 1790, 1680, 1540.

NMR(DMSO-d₆, ppm); 2.97(s, CH₃), 3.95(s, CH₃), 4.27(s, —CH₂—), 5.07(d, J=5 Hz, C₄—H), 5.75(dd, J=5, 9 Hz, C₃—H), 7.99(s, S\_/H), 8.67(d, J=9 Hz, NH), 9.40(s, NH), 12.77(s, NH).

REFERENCE EXAMPLE 16B

To a solution of 1.12 g of (3S,4S)-4-acetoxy-3-benzyloxycarboxamido-2-oxoazetidine in 30 ml of THF is added 400 mg of palladium black and the mixture is stirred in a hydrogen gas stream for hour hour. The catalyst is filtered off and the filtrate is concentrated to 5 ml under reduced pressure.

On the other hand, to a solution of 0.410 g of DMF in 10 ml of methylene chloride is added 0.475 g of diphosgene at −10° C. and the mixture is stirred at room temperature for 15 minutes. A solution of 1.23 g of 2-(2-chloroacetamidothiazol-4-yl)-2-isopropoxyiminoacetic acid (syn-isomer) and 0.530 g of triethylamine in 15 ml of methylene chloride is added dropwise at −60° to −50° C. and the mixture is stirred at −40° ~ −30° C. for 1.5 hours. Then, 0.490 g of triethylamine is added at −60° ~ −50° C. and the above prepared THF solution is further added. The mixture is allowed to stand at room temperature for 1 hour and the solvent is distilled off under reduced pressure. The residual ethyl acetate solution is washed with water and concentrated under reduced pressure. Purifying the residue on a silica gel column (ethyl acetate: n-hexane=2:1) yields 1.23 g of (3S,4S)-4-acetoxy-3-[2-(2-chloroacetamidothiazol-4-yl)-2-isopropoxyiminoacetamido]-2-oxoazetidine (syn-isomer).

IR $\nu_{max}^{KBr}$ cm⁻¹; 3280, 1762, 1670, 1226.

NMR(DMSO-d₆, ppm); 1.25(d, CH₃), 2.13(s, CH₃), 4.37(s, —CH₂—), 4.30–4.67(m, —CH—), 4.87(d, J=1.8 Hz, C₃—H), 5.89(d, J=1 Hz, C₄—H), 7.43(s, S\_/H),
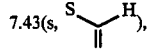

9.29(s, NH), 9.32 (d, J=8 Hz, NH), 13.05(s, NH).

REFERENCE EXAMPLE 17B

To a solution of 0.300 g of (3S,4S)-3-benzyloxycarboxamido-4-methoxy-2-oxoazetidine in 10 ml of THF is added 150 mg of palladium black and the mixture is stirred in a hydrogen gas stream for one hour. The catalyst is filtered off and the filtrate is concentrated to 3 ml under reduced pressure.

On the other hand, to a solution of 0.383 g of D-2-(4-ethyl-2,3-dioxo-1-piperazinecarboxamido)-2-phenylacetic acid in 5 ml of DMF is added 0.215 g of N-hydroxy-5-norbornene-2,3-dicarboximide and then, 0.248 g of DCC, and the mixture is stirred at room temperature for 3 hours. To the mixture is added the above-prepared concentrated solution, followed by stirring for 17 hours. The insoluble are filtered off and the filtrate is concentrated under reduced pressure. To the residue are added ethyl acetate and THF. The mixture is washed with 5% aqueous sodium bicarbonate solution and water in that order and dried over magnesium sulfate. Concentration under reduced pressure yields 0.250 g of (3S,4S)-3-[D-2-(4-ethyl-2,3-dioxo-1-piperazinecarboxamido)-2-phenylacetamido]-4-methoxy-2-oxoazetidine.

IR $_{max}^{KBr}$ cm⁻¹; 3275, 1770, 1710, 1670, 1508.

NMR(DMSO-d₆, ppm); 1.08(t, J=7 Hz, CH₃), 3.23(s, CH₃), 3.80(q, J=7 Hz, —CH₂—), 3.42–3.66(m, —CH₂—), 3.80–4.07 (m, —CH₂—), 4.41(dd, J=1, 8 Hz, C₃—H), 4.67(d, J=1 Hz, C₄—H), 5.42(d, J=7Hz, —CH—), 7.35(s, arom H), 8.98(s, NH), 9.09(d, J=8 Hz, NH), 9.78(d, J=7 Hz, NH).

REFERENCE EXAMPLE 18B

Following the procedure of Reference Example 17B but using 0.300 g of (3S,4R)-3-benzyloxycarboxamido-4-methoxy-2-oxoazetidine and 0.383 g of D-2-(4-ethyl-2,3-dioxo-1-piperazinocarboxamido)-2-phenylacetic acid, there is obtained 0.260 g of (3S,4R)-3-[D-2-(4-ethyl-2,3-dioxo-1-piperazinecarboxamido)-2-phenylacetamido]-4-methoxy-2-oxoazetidine.

IR $\nu_{max}^{KBr}$ cm⁻¹; 3275, 1770, 1700, 1665, 1500.

NMR(DMSO-d₆, ppm); 1.07(t, J=7 Hz, CH₃), 2.85(s, CH₃), 3.38(q, J=7 Hz, —CH₂—), 3.40–3.67(m, —CH₂—), 3.73–4.03 (m, —CH₂—), 4.80(d, J=4 Hz, C₄—H), 5.07(dd, J=4, 9 Hz, C₃—H), 5.58(d, J=7Hz, —CH—), 7.33(s, arom H), 8.95(s, NH), 9.07 (d, J=9 Hz, NH), 9.84(d, J=7 Hz, NH).

REFERENCE EXAMPLE 19B

Following the procedure of Reference Example 17B but using 2.8 g of (3S,4S)-4-acetoxy-3-benzyloxycarboxamido-2-oxoazetidine and 3.2 g of D-2-(4-ethyl-2,3-dioxo-1-piperazinecarboxamido)-2-phenylacetic acid, there is obtained 1.0 g of (3S,4S)-4-acetoxy-3-[D-2-(4-ethyl-b 2,3-dioxo-1-piperazinecarboxamido)-2-phenylacetamido]-2-oxoazetidine.

IR $\nu_{max}^{KBr}$cm$^{-1}$; 1785, 1715, 1675, 1510.

NMR(in DMSO-d$_6$, ppm); 1.10(t, J=6 Hz, CH$_3$), 2.05(s, CH$_3$), 3.52(m, —CH$_2$—), 3.90(m, —CH$_2$—), 4.60(dd, J=2, 8 Hz, C$_3$—H), 5.48(d, J=6Hz, —CH—), 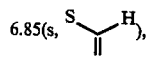

5.72(d, J=2 Hz, C$_4$—H), 7.40 (s, arom H), 9.06(d, J=8 Hz, NH), 9.16(broad s, NH), 9.78 (d, J=6 Hz, NH).

REFERENCE EXAMPLE 20B

To a solution of 500 mg of (3S,4S)-4-acetoxy-3-[2-(2-chloroacetamidothiazol-4-yl)-2-methoxyiminoacetamido]-2-oxoazetidine (syn-isomer) in 10 ml of DMF is added 0.245 g of sodium monomethyldithiocarbamate and the mixture is stirred at room temperature for one hour. The solvent is distilled off under reduced pressure, the residue is washed three times with ethyl acetate and the insolubles are filtered off after addition of ethanol. The filtrate is concentrated under reduced pressure. Then, purifying the residue on a silica gel column (ethyl acetate:CHCl$_3$:CH$_3$OH=2:2:1) yields 0.270 g of (3S,4S)-4-acetoxy-3-[2-(2-aminothiazol-4-yl)-2-methoxyiminoacetamido]-2-oxoazetidine (syn-isomer).

IR $\nu_{max}^{KBr}$cm$^{-1}$; 3280, 1770, 1740, 1720, 1660, 1520, 1215, 1035.

NMR(DMSO-d$_6$, ppm); 2.12(s, CH$_3$), 3.70(s, CH$_3$), 4.78(dd, J=1, 8 Hz, C$_3$—H), 5.88(d, J=1 Hz, C$_4$—H), 6.85(s, $\overset{S}{\underset{\|}{\diagdown}}\overset{H}{\diagup}$ ), 7.20(s, NH$_2$), 9.30(s, NH), 9.33(d, J=8 Hz, NH).

REFERENCE EXAMPLE 21B

To a solution of 0.380 g of (3S,4S)-4-acetoxy-3-[2-(2-chloroacetamidothiazol-4-yl)-2-methoxyiminoacetamido]-2-oxoazetidine in 1 ml of DMF is added a solution of 0.079 g of sodium azide in 1 ml of water and the mixture is stirred at room temperature for 15 hours. After addition of ethyl acetate and saturated aqueous sodium chloride solution, the organic layer is separated and washed with aqueous sodium chloride, dried over magnesium sulfate, and concentrated under reduced pressure. Purifying the residue on a silica gel column (ethyl acetate:CHCl$_3$:CH$_3$OH=4:4:1) yields 0.201 g of (3S)-4-azido-3-[2-(2-chloroacetamidothiazol-4-yl)-2-methoxyiminoacetamido]-2-oxoazetidine(syn-isomer; cis-trans mixture). IR $\nu_{max}^{KBr}$cm$^{-1}$; 3275, 2100, 1765, 1665, 1540.

REFERENCE EXAMPLE 22B

Following the procedure of Reference Example 21B but using 2.2 g of (3S,4S)-4-acetoxy-3-[D-2-(4-ethyl-2,3-dioxo-1-piperazinecarboxamido)-2-phenylacetamido]-2-oxoazetidine and 0.36 g of sodium azide, there is obtained 1.6 g (3S,4S)-4-azido-3-[D-2-(4-ethyl-2,3-dioxo-1-piperazinecarboxamido)-2-phenylacetamido]-2-oxoazetidine.

IR $\nu_{max}^{KBr}$cm$^{-}$; 2100, 1780, 1705, 1670, 1505.

REFERENCE EXAMPLE 23B

Similarly, as in Reference Example 7B, there is obtained 0.415 g of (3R,4S)-3-[D-2-(4-ethyl-2,3-dioxo-1-piperazinecarboxamido)-2-phenylacetamido]-4-methylthio-2-oxazetidine.

IR $\nu_{max}^{KBr}$cm$^{-1}$; 1765, 1705, 1670, 1510.

NMR(DMSO-d$_6$, ppm); 1.09(t, J=6 Hz, CH$_3$), 2.06(s, SCH$_3$), 3.32(q, J=6 Hz, —CH$_2$—), 3.64(m, —CH$_2$—), 3.90(m, —CH$_2$—), 4.68(dd, J=2, 8 Hz, C$_3$—H), 5.46(d, J=6Hz, —CH—), 5.72(d, J=2 Hz, C$_4$—H), 7.38(broad s, arom H), 8.72(broad s, NH), 9.18(d, J=8 Hz, NH), 9.78(d, J=6 Hz, NH).

REFERENCE EXAMPLE 24B 0.90 g of methyl(3R,4R)-3-[D-2-(4-ethyl-2,3-dioxo-1-piperazinecarboxamido)-2-phenylacetamido]-4-methylthio-1-(α-isopropylidene)acetate is treated with ozone in methylene chloride, with a reducing agent, and then, with a base in methanol. The reaction yields 0.42 g of (3R,4R)-3-[D-2-(4-ethyl-2,3-dioxo-1-piperazinecarboxamido)-2-phenylacetamido]-4-methylsulfinyl-2-oxoazetidine.

IR $\nu_{max}^{KBr}$cm$^{-1}$; 1775, 1710, 1675, 1510.

NMR(DMSO-d$_6$, ppm); 1.10(t, J=6 Hz, CH$_3$),

2.08(s, SCH$_3$), 3.41(q, J=6 Hz, —CH$_2$—), 3.56(m, —CH$_2$—), 3.90(m, —CH$_2$—), 4.64(d, J=4 Hz, C$_4$—H), 5.46(dd, J=4, 8 Hz, C$_3$—H), 5.64(d, J=6Hz, —CH—), 7.4(broad s, arom H), 9.06(d, J=8 Hz, NH), 9.18(broad s, NH), 9.93(d, J=6 Hz, NH).

REFERENCE EXAMPLE 25B

To a solution of 2.78 g of (3S,4S)-4-acetoxy-3-benzyloxycarboxamido-2-oxazetidine in 15 ml of DMF are added 1.11 g of triethylamine and 1.66 g of t-butyldimethylchlorosilane under ice-cooling, and the mixture is stirred at room temperature for 5 hours. The reaction mixture is poured into ice-water and ethyl acetate, and the organic layer is separated, washed with water and dried over magnesium sulfate. After concentration under reduced pressure, the residue is purified on a silica gel column (ethyl acetate:n-hexane=1:2) to give 2.98 g of (3S,4S)-4-acetoxy-3-benzyloxycarboxamido-1-t-butyldimethylsilyl-2-oxoazetidine.

IR $\nu_{max}^{neat}$cm$^{-1}$; 3330, 2950, 2930, 1750, 1720, 1620, 1250, 1152, 1045.

NMR(CDCl₃, ppm); 0.23(s, CH₃), 0.97(s, t-Bu), 2.05(s, CH₃), 4.40(dd, J=1, 8 Hz, C₃—H), 5.05(s, —CH₂—), 5.90(d, J=8 Hz, NH), 6.04(d, J=1 Hz, C₄—H), 7.23(s, arom H).

REFERENCE EXAMPLE 26B

To 15 ml of a THF solution containing 0.62 g of (3S,4S)-4-acetoxy-3-benzyloxycarboxamido-1-t-butyldimethylsilyl-2-oxoazetidine is added 0.3 g of palladium black and the mixture is stirred in a hydrogen gas stream for one hour. After addition 0.2 g of palladium black, the mixture is further stirred for 30 minutes and the catalyst is filtered off. Concentration under reduced pressure yields 0.387 g of (3S,4S)-4-acetoxy-3-amino-1-t-butyldimethylsilyl-2-oxoazetidine.

IR $\nu_{max}^{heat}$cm⁻¹; 3375, 3325, 2950, 2930, 1750, 1230.

NMR(CDCl₃, ppm); 0.24(s, CH₃), 0.26(s, CH₃), 0.97(s, t-Bu), 1.82(broad s, NH₂), 2.13(s, CH₃), 4.16(d, J=1 Hz, C₃—H), 5.69(d, J=1 Hz, C₄—H).

REFERENCE EXAMPLE 27B

To a solution of 0.387 g of (3S,4S)-4-acetoxy-3-amino-1-t-butyldimethylsilyl-2-oxoazetidine in 20 ml of THF is added 0.24 g of triethylamine under ice-cooling, and then, a solution of 0.32 g of phenylacetyl chloride in THF is added dropwise. The mixture is stirred under ice-cooling for one hour, the insolubles are filtered off, and the filtrate is concentrated under reduced pressure. Purifying the residue on a silica gel column (ethyl acetate:n-hexane=1:2) yields 0.511 g of (3S,4S)-4-acetoxy-1-t-butyldimethylsilyl-3-phenylacetamido-2-oxoazetidine.

IR $\nu_{max}^{neat}$cm⁻¹; 3290, 2950, 2930, 1750, 1658, 1525, 1252, 1235, 1042.

NMR(CDCl₃, ppm); 0.24(s, CH₃), 0.97(s, t-Bu), 2.04(s, CH₃), 3.55(s, —CH₂—), 4.36(dd, J=1, 8 Hz, C₃—H), 6.06(d, J=1 Hz, C₄—H), 6.57(broad s, NH), 7.19(s, arom H).

REFERENCE EXAMPLE 28B

Following the procedure of Reference Example 16B but using 0.385 g of (3S,4S)-4-acetoxy-3-amino-1-t-butyldimethylsilyl-2-oxoazetidine and 0.384 g of 2-bromo-2-phenylacetic acid there is obtained 0.40 g of (3S,4S)-4-acetoxy-3-(2-bromo-2-phenylacetamido)-1-t-butyldimethylsilyl-2-oxoazetidine.

IR $\nu_{max}^{neat}$cm⁻¹; 3305, 2950, 2930, 1750, 1675, 1515, 1222.

NMR(CDCl₃, ppm); 0.23, 0.30(each s, CH₃), 1.00(s, t-Bu), 2.13(s, CH₃), 4.70(m, C₃—H),

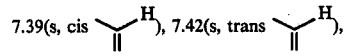
5.51(broad s, —CH—), 6.23 6.27(each d, J=2 Hz, C₄—H), 7.47(s, arom H).

REFERENCE EXAMPLE 29B

Following the procedure of Reference Example 17B but using 0.84 g of (3S,4S)-4-acetoxy-3-benzyloxycarboxamido-2-oxoazetidine and 1.18 g of 2-(2-oxoimidazolidin-1-ylcarboxamido)-2-(benzothiophen-3-yl)acetic acid, there is obtained 0.994 g of (3S,4S)-4-acetoxy-3-[2-(2-oxoimidazolidin-1-ylcarboxamido)-2-(benzothiophen-3-yl)acetamido]-2-oxoazetidine.

IR $\nu_{max}^{KBr}$cm⁻¹; 3290, 1785, 1720, 1675, 1520, 1270, 1228.

NMR(DMSO-d₆, ppm); 2.07(s, CH₃), 3.10-3.53(m, —CH₂—), 3.53-3.90(m, —CH₂—), 4.63, 4.65(each dd, J=1,8 Hz, C₃—H), 5.77, 5.81(each d, J=1 Hz, C₄—H),

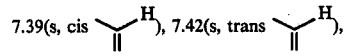
5.87(d, J=8Hz, —CH—), 7.30-8.15(m, arom H), 7.59(s, —NH—), 8.90-9.20(m, NH), 9.20(s, NH).

REFERENCE EXAMPLE 30B 3 g of methyl (3R,4R)-4-(benzothiazol-2-yl)dithio-3-phenoxyacetamido-2-oxoazetidine-1-(α-isopropylidene)acetate is treated in the same manner as Reference Example 1-B to give 1.74 g of (3R,4R)-4-(benzothiazol-2-yl)dithio-3-phenoxyacetamido-2-oxoazetidine.

IR $\nu_{max}^{KBr}$cm⁻¹; 3320, 1800, 1770, 1660.

NMR(DMSO-d₆, ppm); 4.68(s, —CH₂—), 5.38(m, C₃—H, C₄—H), 6.90-8.08(m, arom H), 9.10(d, J=5 Hz, NH), 9.17(s, NH).

REFERENCE EXAMPLE 31B

To a solution of 0.446 g of (3S,4S)-4-acetoxy-3-[2-(benzothiophen-3-yl)-2-(2-oxoimidazolidin-1-yl-carboxamido)acetoamido]-2-oxoazetidine in 4 ml of DMF is added under ice-cooling a solution of 0.085 g of sodium azide in 2 ml of water. The mixture is stirred for 15 hours at room temperature, to which is added water, then the resulting precipitates are collected by filtration to give 0.321 g of (3S)-4-azido-3-[2-(benzothiophen-3-yl)-2-(2-oxoimidazolidin-1-yl-carboxamido)acetamido]-2-oxoazetidine.

IR $\nu_{max}^{KBr}$cm⁻¹; 3270, 2110, 1775, 1720, 1670, 1522, 1268.

REFERENCE EXAMPLE 32B

To a solution of 0.308 g of (3S,4S)-4-acetoxy-3-[2-(2-chloroacetamidothiazol-4-yl)-2-methoxyiminoacetamido]-2-oxoazetidine in 3 ml of DMF is added under ice-cooling a solution of 0.061 g of sodium azide is 2 ml of water. The mixture is stirred for 18 hours at room temperature, to which is added water, then the resulting precipitates are collected by filtration to give 0.216 g of (3S)-4-azido-3-[2-(2-chloroacetamidothiazol-4-yl)-2-methoxyiminoacetamido]-2-oxoazetidine.

IR $\nu_{max}^{KBr}$cm⁻¹; 3270, 2110, 1768, 1662, 1540, 1275.

NMR(DMSO-d₆, ppm); 1.25(d, J=6 Hz, CH₃), 4.17(s, trans —CH₂—), 4.36(s, cis —CH₂—), 4.25-4.50(m, —CH—), 4.75(dd, J=2, 8 Hz, trans C₃—H), 5.11(d, J=2 Hz, trans C₄—H), 7.39(s, cis ⋎ᴴ), 7.42(s, trans ⋎ᴴ), 9.00(s, cis NH), 9.05(s, trans NH), 9.27(d, J=8 Hz, trans NH), 9.43(d, J=8 Hz, cis NH), 12.72(s, trans NH), 12.84(s, cis NH).

REFERENCE EXAMPLE 33B

To a solution of 0.532 g of (3S,4R)-3-benzyloxycarboxamido-4-phenylacetoxy-2-oxoazetidine in 15 ml of THF is added 0.35 g of palladium black, followed by stirring for one hour in a hydrogen gas stream. The catalyst is filtered off, and the filtrate is concentrated to the volume of 7 ml.

On the other hand, 0.11 ml of diphosgene is added to 0.154 g of DMF dissolved in 8 ml of methylene chloride at −10° C. The mixture is stirred for 20 minutes at room temperature to which is added dropwise at −60~−70° C. 7 ml of methylene chloride solution containing 0.46 g of 2-(2-chloroacetamidothiazol-4-yl)-2-methoxyiminoacetic acid and 0.213 mg of triethylamine. The mixture is then stirred for 1.5 hours at −25°~−20° C., followed by cooling to −70° C., to which are added 0.213 g of triethylamine, the THF solution prepared as above and 2 ml of propylene oxide. The temperature of the mixture is raised up to room temperature in the course of one hour with stirring, followed by concentration under reduced pressure. To the residue is added THF, and insolubles are filtered off. The filtrate is concentrated under reduced pressure, followed by addition of ethyl acetate. The resulting crystals are collected by filtration to give 0.236 g of (3S,4R)-3-[2-(2-chloroacetamidothiazol-4-yl)-2-methoxyiminoacetamido]-4-phenylacetoxy-2-oxoazetidine.

IR $\nu_{max}^{KBr}$ cm$^{-1}$; 3260, 1770, 1735, 1670, 1545, 1245, 1042.

NMR(DMSO-d$_6$, ppm); 3.68(s, —CH$_2$—), 3.90(s, OCH$_3$), 4.37 (s, —CH$_2$—), 5.45(dd, J=4,9 Hz, C$_3$—H), 6.04(d, J=4 Hz, C$_4$—H), 7.28(s,arom H), 7.36(s, 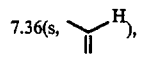), 9.17(s, NH), 9.41(d, J=9 Hz, NH).

REFERENCE EXAMPLE 34B

Into a solution of 0.815 g of pivaloyloxymethyl (3R,4R)-4-acetylthio-3-[D-2-(4-ethyl-2,3-dioxo-1-piperazinecarboxamido)-2-phenylacetamido]-2-oxoazetidine-1-(α-isopropylidene)acetate in 60 ml of methylene chloride is introded ozone for 14 minutes at −70° C., followed by introduction of nitrogen gas for 50 minutes. The solution is washed with a 5% aqueous solution of sodium hydrogensulfite and water in that order, then dried on magnesium sulfate, followed by concentration under reduced pressure. To the residue are added 100 ml of methanol and 2 ml of water. The mixture is stirred for 15 hours, and the solvent is distilled off. The residue is purified on a silica-gel column (ethyl acetate:n-hexane=1:1). The above procedure gives 0.468 g of (3R,4R)-4-acetylthio-3-[D -2-(4-ethyl-2,3-dioxo-1-piperazinecarboxamido)-2-phenylacetamido]-2-oxoazetidine.

IR $\nu_{max}^{KBr}$ cm$^{-1}$; 3275, 1775, 1708, 1670, 1502, 1180.

NMR(DMSO-d$_6$, ppm); 1.08(t, J=7 Hz, CH$_3$), 2.07(s, CH$_3$), 3.40(q, J=7 Hz, —CH$_2$—), 3.40-3.66(m, —CH$_2$—), 3.80-4.03 (m, —CH$_2$—). 5.30-5.50(m, C$_3$—H, C$_4$—H, 5.53(d, J=7Hz, —CH—), 7.25-7.56(m, arom H), 8.82(s, NH), 9.29(m, NH), 9.87(d, J=7 Hz, NH).

REFERENCE EXAMPLE 35B

To a solution of 10 g of (3S,4S)-4-acetoxy-3-benzyloxycarboxamido-2-oxoazetidine in 200 ml of THF is added 2.5 g of palladium black followed by stirring for one hour in a hydrogen gas stream. The catalyst is filtered off, and the filtrate is concentrated to the volume of 50 ml under reduced pressure. To the concentrate is added 50 ml of methylene chloride under ice-cooling. To the mixture is added dropwise a solution of 10.52 g of trityl chloride in 100 ml of methylene chloride, followed by stirring for 3 hours at room temperature. The reaction mixture is concentrated under reduced pressure. To the residue is added ether. The resulting crystals are collected by filtration to give 13.1 g of (3S,4S)-4-acetoxy-3-tritylamino-2-oxoazetidine.

IR $\nu_{max}^{KBr}$ cm$^{-1}$; 3320, 1775, 1735, 1230, 1030.

NMR(CDCl$_3$, ppm); 1.85(s, CH$_3$), 2.90(broad s, NH), 4.27(d, J=1 Hz, C$_3$—H), 4.87(d, J=1 Hz, C$_4$—H), 6.58(s, NH), 7.27-7.77(m, arom H).

REFERENCE EXAMPLE 36B

To a solution of 0.7 g of (3S,4S)-4-acetoxy-3-tritylamino-2-oxoazetidine in 10 ml of methanol is added a solution of 0.25 g of potassium thioacetate in 2 ml of water. The mixture is stirred for 30 minutes at 55°-60° C. Methanol is distilled off under reduced pressure. To the residue is added ethyl acetate, followed by washing with water, drying and concentration under reduced pressure. The residue is purified on a silica-gel column (ethyl acetate:n-hexane=1:1) to give 0.195 g of (3R,4R)-4-acetylthio-3-tritylamino-2-oxoazetidine IR $\nu_{max}^{KBr}$ cm$^{-1}$; 3290, 1775, 1765, 1690, 1665.

NMR(CDCl$_3$, ppm); 2.30(s, CH$_3$), 3.05(broad s, NH), 4.77(m, C$_3$—H), 5.13(d, J=5 Hz, C$_4$—H), 6.57(s, NH), 7.20-7.73(m, arom H).

Further, 0.417 g of the corresponding (3R,4S)-isomer is obtained.

IR $\nu_{max}^{KBr}$ cm$^{-1}$; 3320, 1760, 1685.

NMR(CDCl$_3$, ppm); 2.15(s, CH$_3$), 3.05(s, NH), 4.23(d, J=2 Hz, C$_3$—H), 4.66(d, J=2 Hz, C$_4$—H), 6.77(s, NH), 7.27-7.77(m, arom H).

REFERENCE EXAMPLE 37B

To a solution of 0.819 g of (3R,4S)-4-acetylthio-3-tritylamino-2-oxoazetidine in 6 ml of acetone is added 0.453 g of p-toluenesulfonic acid monohydrate under ice-cooling. The reaction is allowed to proceed for 15 hours. Acetone is distilled off under reduced pressure. The residue is washed with ether, then dissolved in 20 ml of methylene chloride. To the solution is added 0.174 g of pyridine at −10° C., then stirred for 5 minutes. On the other hand, to a solution of 0.703 g of D-2-(4-ethyl-2,3-dioxo-1-piperazinecarboxamido)-2-phenylacetic acid in 20 ml of methylene chloride are added 0.24 g of trimethylchlorosilane and 0.223 g of triethylamine. The mixture is stirred for 40 minutes at a room temperature, followed by cooling to −25~−20° C. To the solution are added 0.161 g of DMF and 0.13 ml of diphosgene, and the mixture is stirred for 2 hours, followed by cooling to −70° C. To the mixture are added 0.223 g of triethylamine, then a suspension prepared as above, and 2 ml of propylene oxide. The temperature of the mixture is raised to room temperature in the course of 1.5 hours. The reaction mixture is concentrated under reduced pressure. The residue is purified on a silica-gel column (ethyl acetate:n-hexane=1:1) to give 0.567 g of (3R,4S)-4-acetylthio-3-[D-2-(4-ethyl-2,3-dioxo-1- piperazinecarboxamido)-2-phenylacetamido]-2-oxoazetidine.

IR $\nu_{max}^{KBr}$ cm$^{-1}$; 3275, 1775, 1763, 1670, 1500, 1180.

NMR(DMSO-d$_6$, ppm); 1.09(t, J=7 Hz, CH$_3$), 2.34(s, CH$_3$), 3.41 (q, J=7 Hz), —CH$_2$—), 3.40-3.70(m, —CH$_2$—), 3.80-4.05(m, —CH$_2$—), 4.77(dd, J=2,9 Hz, C$_3$—H), 5.10(d, J=2 Hz, C$_4$—H), 7.40(s, arom H), 8.93(s, NH), 9.26(d, J=9 Hz, NH), 9.84 (d, J=8 Hz, NH).

REFERENCE EXAMPLE 38B

To a solution of 0.828 g of (3R,4R)-4-acetylthio-3-tritylamino-2-oxoazetidine in 5 ml of acetone is added under ice-cooling 0.45 g of p-toluenesulfonic acid monohydrate, which is stirred for one hour at room temperature. Acetone is distilled off under reduced pressure, and the residue is washed with ether, then dissolved in 20 ml of methylene chloride. To the solution is added 0.211 g of pyridine at −10° C., followed by stirring for 5 minutes. On the other hand, to a solution of 0.18 g of DMF in 5 ml of methylene chloride is added 0.148 ml of diphosgene at −10° C., and the mixture is stirred for 30 minutes at room temperature. To the reaction mixture cooled to a temperature of −70° C. is added dropwise 15 ml of methylene chloride solution containing 0.627 g of 2-(2-chloroacetamidothiazol-4-yl)-2-methoxyiminoacetic acid and 0.25 g of triethylamine. The whole mixture is stirred for 1.5 hours at a temperature range from −25° to −20° C., which is cooled to −70° C. To thus-cooled mixture are added 0.25 g of triethylamine, then a suspension prepared as above, and, further, 2 ml of propylene oxide, followed by raising the temperature up to room temperature in the course of one hour with stirring. The reaction mixture is concentrated under reduced pressure. The residue is purified on a silica-gel column (ethyl acetate:n-hexane=1:1) to give 0.296 g of (3R,4R)-4-acetylthio-3-[2-(2-chloroacetamidothiazol-4-yl)-2-methoxyiminoacetamido]-2-oxoazetidine.

IR $\nu_{max}^{KBr}$ cm$^{-1}$; 3240, 1770, 1755, 1655, 1530.

NMR(DMSO-d$_6$, ppm); 1.87(s, CH$_3$), 3.95(s, OCH$_3$), 4.38(s, —CH$_2$—), 5.36(dd, J=5,8 Hz, C$_3$—H), 5.68(d, J=5 Hz, C$_4$—H),

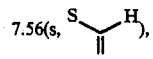
7.56(s, 8.72(d, J=8 Hz, NH), 8.99(s, NH), 12.87(s, NH).

REFERENCE EXAMPLE 39B

By employing 0.805 g of (3R,4S)-4-acetylthio-3-tritylamino-2-oxoazetidine, 0.437 g of p-toluenesulfonic acid monohydrate, 0.19 g of pyridine, and, 0.175 g of DMF, 0.144 ml of diphosgene, 0.61 g of 2-(2-chloroacetamidothiazol-4-yl)-2-methoxyiminoacetic acid, 0.243 g of triethylamine and 2 ml of propylene oxide, a procedure similar to Reference Example 38B is taken to give 0.548 g of (3R,4S)-4-acetylthio-3-[2-(2-chloroacetoamidothiazole-4-yl)-2-methoxyiminoacetoamido]-2-oxoazetidine.

IR $\nu_{max}^{KBr}$ cm$^{-1}$; 3260, 1752, 1690, 1662, 1525.

NMR(DMSO-d$_6$, ppm); 2.40(s, CH$_3$), 3.90(s, CH$_3$), 4.34(s, —CH$_2$—), 4.93(dd, J=2,8 Hz, C$_3$—H), 5.21(d, J=2 Hz, C$_4$—H),

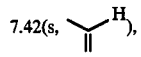
7.42(s, 8.97(s, NH), 9.40(d, J=8 Hz, NH), 12.93(s, NH).

REFERENCE EXAMPLE 40B

To a solution of 0.48 g of D-2-(4-ethyl-2,3-dioxo-1-piperazinecarboxamido)-2-phenylacetic acid in 10 ml of methylene chloride are added 0.18 g of trimethylchlorosilane and 0.17 g of triethylamine. The mixture is stirred for 30 minutes at room temperature, then cooled to a temperature ranging from −25° to −20° C., followed by addition of 0.12 g of DMF and 0.10 ml of diphosgene. The mixture is stirred for two hours, and cooled to −70° C., followed by addition of 0.17 g of triethylamine, a solution of 0.205 g of (3R,4R)-3-amino-4-methylsulfonyl-2-oxoazetidine in 3 ml of DMA and 2 ml of propylene oxide. The temperature of the reaction mixture is raised up to room temperature in the course of 1.5 hours, then the reaction mixture is concentrated under reduced pressure. The residue is purified on a silica-gel column (ethyl acetate:n-hexane=1:1) to give 0.418 g of (3R,4R)-3-[D-2-(4-ethyl-2,3-dioxo-1-piperazinecarboxamido)-2-phenylacetamido]-4-methylsulfonyl-2-oxoazetidine. This product is in agreement with the compound obtained by Reference Example 14B in IR and NMR.

REFERENCE EXAMPLE 41B

To a solution of 0.122 g of DMF in 5 ml of methylene chloride is added 0.10 ml of diphosgene at −10° C. The mixture is stirred for 30 minutes at room temperature, then cooled to a temperature of −70° C., followed by dropwise addition of 10 ml of methylene chloride solution containing 0.427 g of 2-(2-chloroacetamidothiazol-4-yl)-2-methoxyiminoacetic acid and 0.17 g of triethylamine. The mixture is stirred for 2 hours at a temperature ranging from −25° to −20° C., which is cooled to a temperature of −70° C., to which are added 0.17 g of triethylamine, a solution of 0.229 g of (3R,4R)-3-amino-4-methylsulfonyl-2-oxoazetidine in 3 ml of DMA, and 2 ml of propylene oxide, successively. The temperature of the mixture is raised up to room temperature in the course of 1.5 hours. The reaction mixture is concentrated under reduced pressure, and the residue is purified on a silica-gel column (ethyl acetate:n-hexane=1:1) to give 0.415 g of (3R,4R)-3-[2-(2-chloroacetamidothiazol-4-yl)-2-methoxyiminoacetamido]-4-methylsulfonyl-2-oxoazetidine. This is in agreement with the compound (syn-isomer) obtained in Reference Example 15B in IR and NMR.

REFERENCE EXAMPLE 42B

To a solution of 3 g of (3S,4S)-4-acetoxy-3-tritylamino-2-oxoazetidine in 30 ml of methanol is added 1.7 g of zinc acetate, and the mixture is refluxed for 30 minutes. The reaction mixture is concentrated under reduced pressure, followed by addition of ethyl acetate. The resulting insolubles are removed by filtration, and the filtrate is concentrated under reduced pressure. The residue is purified on a silica-gel column (ethyl acetate:n-hexane=1:1) to give 0.912 g of (3S,4R)-4-methoxy-3-tritylamino-2-oxoazetidine.

IR $\nu_{max}^{KBr}$ cm$^{-1}$; 3270, 3210, 1772, 1725, 1097.

NMR(CDCl$_3$, ppm); 298(s, OCH$_3$), 3.01(d, J=9 Hz, NH), 3.88(d, J=4 Hz, C$_4$—H), 4.08(dd, J=4,9 Hz, C₃—H), 6.60–8.05(m, arom H). Further, (3S,4S)-isomer is obtained.

IR $\nu_{max}^{KBr}$ cm⁻¹; 3280, 1760, 1100.

NMR(CDCl₃, ppm); 2.81(s, OCH₃), 3.27(s, NH), 3.95(s, C₃—H, C₄—H), 6.70–8.00(m, arom H).

REFERENCE EXAMPLE 43B

To a solution of 0.7 g of (3S,4S)-4-acetoxy-3-[2-(2-chloroacetamidothiazol-4-yl)-2-methoxyiminoacetamido]-2-oxoazetidine (syn-isomer) in 4 ml of DMF is added under ice-cooling 1.3 ml of a 15% aqueous solution of sodium methylsulfide, and the mixture is stirred for 2 hours at room temperature. To the mixture are added ethyl acetate and water, and the organic layer is separated, which is washed with water and concentrated. The residue is purified on a silica-gel column (CHCl₃:AcOEt:CH₃OH=7:7:1) to give 0.377 g of (3R,4S)-4-methylthio-3-[2-(2-methylthioacetamidothiazol-4-yl)-2-methoxyiminoacetamido]-2-oxoazetidine.

IR $\nu_{max}^{KBr}$ cm⁻¹; 3240, 3190, 1752, 1655, 1548, 1290, 1042.

NMR(DMSO-d₆, ppm); 2.17(s, SCH₃), 3.37(s, —CH₂—), 3.90(s, OCH₃), 4.67(d, J=2 Hz, C₄—H), 4.71(dd, J=2,8 Hz, C₃—H), 7.36(s, 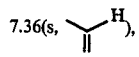), 8.77(s, NH), 9.33(d, J=8 Hz, NH), 12.56(s, NH).

REFERENCE EXAMPLE 44B

To a solution of 3.0 g of (3S,4S)-4-acetoxy-3-tritylamino-2-oxoazetidine in 50 ml of methanol is added a solution of 0.65 g of sodium azide in 5 ml of water under ice-cooling, followed by stirring for two hours at 40°–50° C. The solvent is distilled off under reduced pressure. To the residue is added ethyl acetate, and the organic layer is separated, which is washed with water and concentrated. The residue is purified on a silica-gel column (ethyl acetate:n-hexane=1:1) to give 1.01 g of (3S,4R)-4-azido-3-tritylamino-2-oxoazetidine.

IR $\nu_{max}^{KBr}$ cm⁻¹; 3315, 2102, 1775, 1765, 1255.

NMR(CDCl₃, ppm); 2.82(d, J=10 Hz, NH), 4.07–4.40(m, C₃—H, C₄—H), 6.48(s, NH), 6.95–7.50(m, arom H).

Further, 1.52 g of (3S,4S)-isomer is obtained.

IR $\nu_{max}^{KBr}$ cm⁻¹; 3315, 2098, 1765, 1245.

NMR(CDCl₃, ppm); 2.93(s, NH), 3.98(s, C₃—H, C₄—H), 6.92(s, NH), 7.00–7.57(m, arom H).

REFERENCE EXAMPLE 45B

To a solution of 0.45 g of (3S,4R)-4-azido-3-tritylamino-2-oxoazetidine in 4 ml of acetone is added under ice-cooling 0.255 g of p-toluenesulfonic acid monohydrate, and the mixture is stirred for one hour at room temperature. The solvent is distilled off, and the resulting crystals are washed with ether. The crystals are collected by filtration to give 0.33 g of tosyl salt of (3S,4R)-3-amino-4-azido-2-oxoazetidine.

IR $\nu_{max}^{KBr}$ cm⁻¹; 3125, 2870, 2130, 1788, 1763, 1200, 1138, 1125.

REFERENCE EXAMPLE 46B

To a solution 1.3 g of (3S,4S)-4-azido-3-tritylamino-2-oxoazetidine in 15 ml of acetone is added 0.736 g of p-toluenesulfonic acid monohydrate. The mixture is treated in a same manner to Reference Example 45B to give 0.886 g of tosyl salt of (3S,4S)-3-amino-4-azido-2-oxoazetidine.

IR $\nu_{max}^{KBr}$ cm⁻¹; 3070, 2110, 1778, 1762, 1195, 1122, 1030, 1010.

REFERENCE EXAMPLE 47B

To a suspension of 0.565 g of D-2-(4-ethyl-2,3-dioxo-1-piperazinecarboxamido)-2-thienylacetic acid in 20 ml of methylene chloride are added under ice-cooling 0.189 g of trimethylchlorosilane and 0.176 g of triethylamine, and the mixture is stirred for 30 minutes at room temperature, then cooled to a temperature ranging from −25° to −20° C. To the thus cooled mixture are added 0.127 g of DMF and 0.104 g of diphosgene, followed by stirring for 2 hours at the same temperature. On the other hand, to a suspension of 0.40 g of tosyl salt of (3S,4S)-3-amino-4-azido-2-oxoazetidine in 15 ml of methylene chloride are added 0.243 g of pyridine and 2 ml of propylene oxide at a temperature ranging from −25° to −20° C. To the above prepared mixture is added the thus prepared-solution, and the whole mixture is stirred for one hour at 0° C. Methylene chloride is distilled off, and the residue is purified on a silica-gel column (ethyl acetate:n-hexane=1:1) to give 0.546 g of (3S,4S)-4-azido-3-[D-2-(4-ethyl-2,3-dioxo-1-piperazinecarboxamido)-2-thienylacetamido]-2-oxoazetidine.

IR $\nu_{max}^{KBr}$ cm⁻¹; 3270, 2100, 1781, 1708, 1670, 1500.

NMR(DMSO-d₆, ppm); 1.09(t, J=7 Hz, CH₃), 3.39(q, J=7 Hz, —CH₂—), 3.46–3.68(m, —CH₂—), 3.84–4.40(m, —CH₂—), 4.59(dd, J=2,7 Hz, C₃—H), 5.08(d, J=2 Hz, C₄—H), 5.74

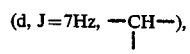

6.94–7.54(m, arom H), 9.02(s, NH), 9.24(d, J=7 Hz, NH), 9.70(d, J=7 Hz, NH).

REFERENCE EXAMPLE 48B

To a suspension of 0.475 g of D-2-(4-ethyl-2,3-dioxo-1-piperazinecarboxamido)-2-thienylacetic acid in 15 ml of methylene chloride are added under ice-cooling 0.173 g of trimethylchlorosilane and 0.161 g of triethylamine, and the mixture is stirred for 30 minutes at room temperature, followed by cooling to −25° C. To the mixture are added 0.116 g of DMF and 0.095 ml of diphosgene, and the mixture is stirred for two hours at the same temperature, then cooled to a temperature of −70° C. To the thus cooled mixture are added 0.222 g of pyridine, 0.33 g of tosyl salt of (3S,4R)-3-amino-4-azido-2-oxoazetidine, 2 ml of propylene oxide in that order. The temperature of the mixture is raised up to 0° C. in the course of one hour, while stirring the mixture, followed by stirring at 0° C. for further one hour. The methylene chloride is then distilled off, and the residue is purified on a silica-gel column (ethyl acetate:n-hexane=1:1) to give 0.337 g of (3S,4R)-4-azido-3-[2-(4-ethyl-2,3-dioxo-1-piperazinecarboxamido)-2-thienylacetamido]-2-oxoazetidine.

IR $\nu_{max}^{KBr}$ cm⁻¹; 3270, 2105, 1778, 1710, 1672, 1502.

NMR(DMSO-d₆, ppm); 1.09(t, J=7 Hz, CH₃), 3.30–3.68(m, —CH₂—), 3.40(q, J=7 Hz, —CH₂—), 3.77–4.05(m, —CH₂—), 5.02–5.40(m, C₃—H, C₄—H), 5.85(d, J=8Hz, —CH—), 6.93 7.52(m, arom H), 9.03(s, NH), 9.42(d, J=8 Hz, NH), 9.80(d, J=8 Hz, NH)

REFERENCE EXAMPLE 49B

To a solution of 0.127 g of DMF in 5 ml of methylene chloride is added 0.104 ml of diphosgene at −10° C. The mixture is stirred for 30 minutes at room temperature, followed by addition of a solution of 15 ml of methylene chloride containing 0.483 g of 2-(2-chloroacetamidothiazol-4-yl)-2-methoxyiminoacetic acid and 0.176 g of triethylamine at −70° C. The mixture is stirred for two hours at −25° C., then cooled to −70° C., followed by addition of 0.352 g of triethylamine, 0.40 g of tosyl salt of (3S,4S)-3-amino-4-azido-2-oxoazetidine and 2 ml of propylene oxide. The temperature of the mixture is raised up to room temperature in the course of one hour while stirring, followed by ice-cooling for one hour. The crystals separated out are collected by filtration to yield 0.383 g of (3S,4S)-4-azido-3-[2-(2-chloroacetamidothiazol-4-yl)-2-methoxyiminoacetamido]-2-oxoazetidine.

IR $\nu_{max}^{KBr}$ cm$^{-1}$; 3265, 2110, 1755, 1678, 1545.

NMR(DMSO-d$_6$, ppm); 3.90(s, CH$_3$), 4.35(s, —CH$_2$—), 4.70(dd, J=2,8 Hz, C$_3$—H), 5.13(d, J=2 Hz, C$_4$—H),

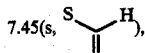

7.45(s, 9.13(s, NH), 9.44(d, J=8 Hz, NH).

REFERENCE EXAMPLE 50B

Similar procedure to Reference Example 49B by employing 0.40 g of tosyl salt of (3S,4S)-3-amino-4-azido-2-oxoazetidine yields 0.375 g of (3S,4R)-4-azido-3-[2-(2-chloroacetamidothiazol-4-yl)-2-methoxyiminoacetamido]-2-oxoazetidine.

IR $\nu_{max}^{KBr}$ cm$^{-1}$; 3260, 2110, 1768, 1670, 1540.

NMR(DMSO-d$_6$, ppm); 3.90(s, CH$_3$), 4.35(s, —CH$_2$—), 5.18, 5.40(m, C$_3$—H, C$_4$—H),

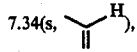

7.34(s, 9.07(s, NH), 9.59(d, J=8 Hz, NH).

REFERENCE EXAMPLE 51B

To a solution of 4.24 g of (3S,4S)-4-acetoxy-3-tritylamino-2-oxoazetidine in 30 ml of methanol is added under ice-cooling 8.64 ml of 15% aqueous solution of sodium methylsulfide. The mixture is stirred for one hour at room temperature. The solvent is distilled off, and the residue is dissolved in ethyl acetate, then washed with water. The ethyl acetate is distilled off, and the residue is purified on a silica-gel column (ethyl acetate:n-hexane=1:1) to yield 1.43 g of (3R,4S)-4-methylthio-3-tritylamino-2-oxoazetidine(A) and 1.62 g of (3R,4R)-methylthio-3-tritylamino-2-oxoazetidine(B).

(A) IR $\nu_{max}^{KBr}$ cm$^{-1}$; 3275, 1750. NMR(CDCl$_3$, ppm); 1.65(s, CH$_3$), 3.00(broad s, NH), 4.03-4.20(m, C$_3$—H, C$_4$—H), 7.01(s, NH), 6.80-7.90(m, arom H).

(B) IR$\nu_{max}^{KBr}$ cm$^{-1}$; 3260, 1752. NMR(CDCl$_3$, ppm); 1.73(s, CH$_3$), 2.98(d, J=8 Hz, NH), 4.15(d, J=5 Hz, C$_4$—H), 4.26(dd, J=5,8 Hz, C$_3$—H), 6.83(s, NH), 7.00-7.80(m, arom H).

REFERENCE EXAMPLE 52B

To a solution of 0.9 g of (3R,4S)-4-methylthio-3-tritylamino-2-oxoazetidine in 5 ml of acetone is added 0.503 g of p-toluenesulfonic acid monohydrate. The mixture is processed in similar manner to Reference Example 45B to yield 0.69 g of tosyl salt of (3R,4S)-3-amino-4-methylthio-2-oxoazetidine.

IR $\nu_{max}^{KBr}$ cm$^{-1}$; 3100-2900, 1798, 1770, 1755, 1190, 1165, 1120.

REFERENCE EXAMPLE 53B

To a solution of 0.228 g of DMF in 5 ml of methylene chloride is added at −10° C. 0.137 ml of diphosgene. The mixture is then stirred for 30 minutes at room temperature, to which is added at a temperature of −70° C. 15 ml of methylene chloride solution containing 0.80 g of 2-(2-chloroacetamidothiazol-4-yl)-2-methoxyiminoacetic acid and 0.316 g of triethylamine. The mixture is stirred for two hours at −25° C., then cooled to −70° C., followed by addition of 0.632 g of triethyl amine, 0.69 g of tosyl salt of (3R,4S)-3-amino-4-methylthio-2-oxoazetidine and 2 ml of propylene oxide. The temperature of the mixture is raised up to 0° C. in the course of one hour, while stirring. The mixture is stirred for further two hours at the same temperature, then concentrated, followed by addition of THF and removal of the resulting insolubles by filtration. The filtrate is concentrated and the residue is purified on a silica-gel column (AcOEt:CHCl$_3$:CH$_3$OH=3:3:1) to yield 0.461 g of (3R,4S)-3-[2-(2-chloroacetamidothiazol-4-yl)-2-methoxyiminoacetamido]-4-methylthio-2-oxoazetidine.

IR $\nu_{max}^{KBr}$ cm$^{-1}$; 3255, 1758, 1670, 1540, 1270, 1040.

NMR(DMSO-d$_6$, ppm); 2.14(s, CH$_3$), 3.90(s, OCH$_3$), 4.35(s, —CH$_2$—), 4.57-4.90(m, C$_3$—H, C$_4$—H),

7.40(s, 8.80(s, NH), 9.37(d, J=9 Hz, NH), 12.88(broad s, NH).

REFERENCE EXAMPLE 54B

To a suspension of 0.552 of D-2-(4-ethyl-2,3-dioxo-1-piperazinecarboxamido)-2-thienylacetic acid in 15 ml of methylene chloride are added under ice-cooling 0.20 g of trimethylsilyl chloride and 0.187 g of triethylamine. The mixture is stirred for 30 minutes at room temperature, then cooled to −25° C., to which are added 0.135 g of DMF and 0.11 ml of disphosgene, followed by stirring for two hours at the same temparature. The mixture is then cooled to −70° C., to which are added 0.258 g of pyridine, 0.426 g of tosyl salt of (3R,4S)-3-amino-4-methylthio-2-oxoazetidine and 2 ml of propylene oxide in that order. The temperature of the mixture is raised to 0° C. in the course of 30 minutes with stirring, followed by stirring for further one hour. The reaction mixture is concentrated under reduced pressure. The residue is purified on a silica-gel column to yield 0.308 g of (3R,4S)-3-[2-(4-ethyl-2,3-dioxo-1-piperazinecarboxamido)-2-thienylacetamido]-2-oxoazetidine.

IR $\nu_{max}^{KBr}$ cm$^{-1}$; 3270, 1768, 1710, 1670, 1502, 1182.

REFERENCE EXAMPLE 55B

To a solution of 5.0 g of (3S,4S)-4-acetoxy-3-tritylamino-2-oxoazetidine in 100 ml of methanol are added under ice-cooling 1.6 ml of thiophenol and 15.5 ml of 1N aqueous solution of sodium hydroxide. The mixture is stirred for 20 minutes at the same temperature and for further 50 minutes at room temperature. The crystals separated out are collected by filtration to give 2.35 g of (3R,4R)-4-phenylthio-3-tritylamino-2-oxoazetidine(A). The filtrate is concentrated, and the residue is dissolved in ethyl acetate, washed with water, and concentrated. The residue is purified on a silica-gel column (ethyl acetate:n-hexane=1:1) to yield 2.65 g of (3R,4S)-compound(B).

(A) IR $\nu_{max}^{KBr}$cm$^{-1}$; 3290, 1755, 1725. NMR(CDCl$_3$, ppm); 3.10(d, J=8 Hz, NH), 4.48-4.83(m, C$_3$—H, C$_4$—H), 6.08(s, NH), 7.17-7.65(m, arom H).

(B) IR $\nu_{max}^{KBr}$cm$^{-1}$; 3300-3220, 1755. NMR(CDCl$_3$, ppm); 2.87(d, J=8 Hz, NH), 4.00(dd, J=2, 9 Hz, C$_3$—H), 4.37(d, J=2 Hz, C$_4$—H), 6.52(s, NH), 7.10-7.70(m, arom H).

REFERENCE EXAMPLE 56B

To a solution of 1.5 g of (3R,4R)-4-phenylthio-3-tritylamino-2-oxoazetidine in 20 ml of acetone is added 0.72 g of p-toluenesulfonic acid monohydrate under ice-cooling. Following the procedure to Reference Example 45B, there is obtained 1.25 g of tosyl salt of (3R,4S)-3-amino-4-phenylthio-2-oxoazetidine.

IR $\nu_{max}^{KBr}$cm$^{-1}$; 3090, 2850, 2740, 1780, 1205, 1175, 1118.

REFERENCE EXAMPLE 57B

To a solution of 2.65 g of (3R,4)-4-phenylthio-3-tritylamino-2-oxoazetidine in 20 ml of acetone is added under ice-cooling 1.27 g of p-toluenesulfonic acid monohydrate, followed by similar procedure to Reference Example 45B to give 1.9 g of tosyl salt of (3R,4S)-3-amino-4-phenylthio-2-oxoazetidine.

IR $\nu_{max}^{KBr}$cm$^{-1}$; 3240, 3140, 3050, 2980, 2920, 1807, 1210, 1200, 1168, 1128.

REFERENCE EXAMPLE 58B

Following the procedure of Reference Example 49B but using 0.19 g of DMF, 0.156 ml of diphosgene, 0.732 g of tosyl salt of (3R,4S)-3-amino-4-phenylthio-2-oxoazetidine and 2 ml of propylene oxide, there is obtained 0.649 g of (3R,4S)-3-[2-(2-chloroacetamidothiazol-4-yl)-2-methoxyiminoacetamido]-4-phenylthio-2-oxoazetidine.

IR $\nu_{max}^{KBr}$cm$^{-1}$; 3240, 3170, 3055, 1752, 1652, 1535. NMR(DMSO-d$_6$, ppm); 3.90(s, CH$_3$), 4.37(s, —CH$_2$—), 4.69 (dd, J=2, 8 Hz, C$_3$—H), 4.98(d, J=2 Hz, C$_4$—H),

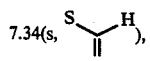

7.30-7.60(m, arom H), 9.04(s, NH), 9.38(d, J=8 Hz, NH), 12.84(s, NH).

REFERENCE EXAMPLE 59B

Following the procedure of Reference Example 54B but using 0.57 g of D-2-(4-ethyl-2,3-dioxo-1-piperazinecarboxamido)-2-phenylacetic acid, 0.212 g of trimethylchlorosilane 0.143 g of DMF, 0.193 g of diphosgene, 0.273 g of pyridine, 0.55 g of tosyl salt of (3R,4S)-3-amino-4-phenylthio-2-oxoazetidine and 2 ml of propylene oxide, there is obtained 0.696 g of (3R,4S)-3-[2-(4-ethyl-2,3-dioxo-1-piperazinecarboxamido)-2-phenylacetamido]-4-phenylthio-2-oxoazetidine.

IR $\nu_{max}^{KBr}$cm$^{-1}$; 3270, 1772, 1710, 1670, 1502.

REFERENCE EXAMPLE 60B

To a solution of 0.976 g of D-2-(4-ethyl-2,3-dioxo-1-piperazinecarboxamido)-2-thienylacetic acid and 0.304 g of triethylamine in 20 ml of methylene chloride is added under ice-cooling 0.625 g of pulverized phosphorus pentachloride, and the mixture is stirred at the same temperature for one hour. The reaction mixture is concentrated under reduced pressure, and the residue is washed with n-hexane, to which is added THF, followed by filtering off the insolubles. The filtrate is added under ice-cooling to a solution of 0.913 g of p-toluenesulfonate of (3R,4)-3-amino-4-methylthio-2-oxoazetidine and 0.910 g of triethylamine in 15 ml of THF. The mixture was stirred for one hour at room temperature, then the reaction mixture is subjected to filtration. The filtrate is concentrated, and the residue is purified on a silica-gel column chromatography (ethyl acetate:n-hexane=1:1) to give 0.960 g of (3R,4R)-3-[D-2-(4-ethyl-2,3-dioxo-1-piperazinecarboxamido)-2-thienylacetamide]-4-methylthio-2-oxoazetidine.

IR $\nu_{max}^{KBr}$cm$^{-1}$; 1760, 1710, 1673, 1500, 1130.

NMR(DMSO-d$_6$, ppm); 1.10(t, J=4 Hz, CH$_3$), 1.73(s, CH$_3$), 3.53(m, —CH$_2$—), 4.00(m, —CH$_2$—), 4.83(d, J=4 Hz, C$_4$—H), 5.30(dd, J=4, 6 Hz, C$_3$—H),

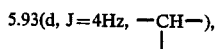

6.90-7.63(m, arom H), 8.90(s,NH), 9.36(d, J=6 Hz, NH), 9.83 (d, J=4 Hz, NH).

REFERENCE EXAMPLE 61B

To a solution of 0.833 g of 2-(2-chloroacetamidothiazol-4-yl)-2-methoxyiminoacetic acid and 0.304 g of triethylamine in 20 ml of methylene chloride is added 0.625 g of pulverized phosphorus pentachloride under ice-cooling, and the mixture is stirred for one hour. The reaction mixture is concentrated under reduced pressure, and the residue is washed with n-hexane, followed by addition of THF. The resulting insolubles are filtered off, and the filtrate is added under ice-cooling to a solution of 0.913 g of p-toluenesulfonate of (3R,4R)-3-amino-4-methylthio-2-oxoazetidine and 0.910 g of triethylamine in 15 ml of THF. The mixture is stirred for one hour at room temperature, followed by filtration. The filtrate is concentrated under reduced pressure. The residue is washed with an aqueous solution of sodium hydrogencarbonate and water in that order, which is then dried to give 0.780 g of (3R,4R)-3-[2-(2-chloroacetamidothiazol-4-yl)-2-methoxyiminoacetamido]-4-methylthio-2-oxoazetidine.

IR $\nu_{max}^{KBr}$cm$^{-1}$; 1760, 1660, 1545, 1050.

NMR(DMSO-d$_6$, ppm); 2.06(s, SCH$_3$), 3.90(s,OCH$_3$), 4.36 (s, —CH$_2$—), 4.93(d, J=4 Hz, C$_4$—H), 5.40(dd, J=4, 6 Hz, C$_3$—H),

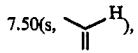

8.84(broad s, NH), 9.53(d, J=6 Hz, NH), 12.90(broad s, NH).

REFERENCE EXAMPLE 62B

To a solution of 0.608 g of p-toluenesulfonate of (3R,4R)-3-amino-4-methylthio-2-oxoazetidine and 0.380 g of pyridine in 10 ml of methylene chloride is added under ice-cooling with stirring a solution of 0.581 g of 3-(2,6-dichlorophenyl)-5-methyl-4-isoxazolylcarbonyl chloride in 5 ml of methylene chloride. The reaction mixture is stirred for one hour at room temperature, which is then concentrated under reduced pressure, and the residue is purified on a silica-gel column chromatography (ethyl acetate:n-hexane=1:1) to give 0.550 g of (3R,4R)-3-[3-(2,6-dichlorophenyl)-5-methyl-4-isoxazolylcarboxamido]-4-methylthio-2-oxoazetidine.

IR $\nu_{max}^{KBr}$cm$^{-1}$; 1760, 1660, 1595, 1500.

NMR(CDCl$_3$, ppm); 1.90(s, CH$_3$), 2.83(s, CH$_3$), 4.70(d, J=4 Hz, C$_4$—H), 5.50(dd, J=4, 8 Hz, C$_5$—H), 6.13(d, J=8 Hz, NH), 6.50(broad s, NH), 7.40(s, arom H).

REFERENCE EXAMPLE 63B

To a solution of 0.400 g of (3R,4R)-4-methylsulfonyl-3-tritylamino-3-oxoazetidine in 2 ml of DMF is added 0.590 g of tetra-n-butylammonium fluoride, and the mixture is stirred for 30 minutes at room temperature. To the reaction mixture are added ice-water and ethyl acetate. The ethyl acetate layer is separated and washed with water, followed by concentration. The residue is purified on a silica-gel column (ethyl acetate:n-hexane=1:1) to give 0.282 g of (3)-4-fluoro-3-tritylamino-2-oxoazetidine.

IR $\nu_{max}^{KBr}$cm$^{-1}$; 1765, 1480, 1440, 1300, 750, 695.

REFERENCE EXAMPLE 64B

To a solution of 3.3 g of (3S)-4-fluoro-3-tritylamino-2-oxoazetidine in 10 ml of acetone is added 1.82 g of p-toluenesulfonic acid monohydrate, and the mixture is treated in a same procedure to Reference Example 45B to give 2.67 g of p-toluenesulfonate of (3R)-3-amino-4-fluoro-2-oxoazetidine.

IR $\nu_{max}^{KBr}$cm$^{-1}$; 1790, 1170, 1035, 1010.

REFERENCE EXAMPLE 65B

Following the procedure of Reference Example 36B but using a mixture prepared by adding a solution of 0.965 g of sodium salt of 5-mercapto-1-methyltetrazole in 10 ml of methanol to a solution of 2.7 g of (3S,4S)-4-acetoxy-3-tritylamino-2-oxoazetidine in 30 ml of methanol, there are obtained 0.70 g of (3R,4R)-4-(1-methyl-1H-tetrazol-4-yl)thio-3-tritylamino-2oxoazetidine(A) and 1.32 g of (3R,4S)-isomer(B).

(A) IR $\nu_{max}^{KBr}$cm$^{-1}$; 3300, 1779, 1728(shoulder), 1442, 1340, 1331, 700. NMR(CDCl$_3$, ppm); 3.75(s, CH$_3$), 4.93(q, J=4, 12 Hz, C$_3$—H), 5.85(d, J=8 Hz, C$_4$—H), 6.59(broad s, NH), 7.0–7.6(m, arom H).

(B) IR $\nu_{max}^{KBr}$cm$^{-1}$; 3320, 1774, 1441, 1367, 1225, 1030, 698. NMR(CDCl$_3$, ppm); 3.72(s, CH$_3$), 5.04(broad s, C$_3$—H), 5.37(d, J=2 Hz, C$_4$—H), 6.72(broad s, NH), 7.0–7.6(m, arom H).

REFERENCE EXAMPLE 66B

To a solution of 0.535 g of (3R,4R)-4-(1-methyl-1H-tetrazol-4-yl)thio-3-tritylamino-2-oxoazetidine in 5 ml of acetone is added 0.230 g of p-toluenesulfonic acid monohydrate, and the mixture is stirred for 3 hours at room temperature. The reaction mixture is concentrated, and the residue is washed with ether, then dissolved in 15 ml of THF.

On the other hand, following the procedure of Reference Example 61 0.336 g of 2-(2-chloroacetamidothiazol-4-yl)-2-methoxyiminoacetic acid is treated to give a solution of the corresponding acid chloride in 10 ml of THF. The thus prepared solution is added under ice-cooling to a solution prepared by adding 0.270 g of triethylamine to the above prepared solution in 15 ml of THF. To the reaction mixture is added ethyl acetate, which is washed with water, followed by distilling off the solvent. The residue is purified on a silica-gel column (AcOEt:CHCl$_3$:CH$_3$OH=3:3:1) to give 0.380 g of (3R,4R)-3-[2-(2-chloroacetamidothiazol-4-yl)-2-methoxyiminoacetamido]-4-(1-methyl-1H-tetrazol-4-yl)thio-2-oxoazetidine.

IR $\nu_{max}^{KBr}$cm$^{-1}$; 3220, 1790, 1679, 1540, 1365, 1332, 1045.

NMR(DMSO-d$_6$, ppm); 3.72(s, CH$_3$), 3.37(s, CH$_3$), 4.35(s, —CH$_2$—), 5.73(dd, J=4, 8 Hz, C$_3$—H), 6.38(d, J=4 Hz, C$_4$—H), 7.23(s, 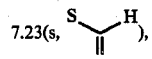), 9.20(broad s, NH), 9.50(d, J=8 Hz, NH), 12.84(broad s, NH).

REFERENCE EXAMPLE 67B

Following the procedure of Reference Example 66B, solution of 1.12 g of (3R,4S)-4-(1-methyl-1H-tetrazol-4-yl)thio-3-tritylamino-2-oxoazetidine in 5 ml of acetone, 0.491 g of p-toluenesulfonic acid monohydrate and 0.788 g of 2-(2-chloroacetamidothiazol-4-yl)-2-methoxyiminoacetic acid is treated to give 0.650 g of (3R,4S)-3-[2-(2-chloroacetamidothiazol-4-yl)-2-methoxyiminoacetamido]-4-(1-methyl-1H-tetrazol-4yl)thio-2oxoazetidine.

IR $\nu_{max}^{KBr}$cm$^{-1}$; 3250, 1787, 1670, 1540, 1365, 1038, 820.

NMR (DMSO-d$_6$, ppm); 3.88(s, CH$_3$), 3.92(s, CH$_3$), 4.36(s, —CH$_2$—), 5.38(dd, J=2, 8 Hz, C$_3$—H), 6.22(d, J=2 Hz, C$_4$—H), 7.43(s, 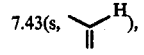), 9.40(s, NH), 9.51(d, J=8 Hz, NH), 12.84 (broad s, NH).

REFERENCE EXAMPLE 68B

To a suspension of 1.13 g of 2-(1-carboxyisopropoxyimino)-2-(2-tritylaminothiazol-4-yl)acetic acid in 15 ml of methylene chloride is added 0.454 g of dicyclohexylcarbodiimide (simply referred as DCC), and after the mixture is stirred at room temperature for 20 minutes, the insolubles are filtered off. On the other hand, in 10 ml of methylene chloride is suspended 0.598 g of p-toluenesulfonate of (3S,4S)-3-amino-4-azido-2-azetidinone, and under ice-cooling 0.159 g of pyridine and, then, 10 ml of DMF are added. To the resultant solution is added the above-prepared filtrate and the mixture is stirred at room temperature for 3 hours. The reaction mixture is concentrated and the residue is purified by silica gel colum chromatography (AcOEt:CHCl$_3$:CH$_3$OH=3:1:1) to give 0.63 g of (3S,4R)-4-azido-3-[2-[(2-tritylaminothiazol-4-yl)carboxymethyliminoxy]-2-methylpropionamido]-2-azetidinone.

IR $\nu_{max}^{KBr}$cm$^{-1}$: 3400~3200, 2105, 1768, 1600, 1520.
NMR (DMSO-d$_6$, ppm): 1.36(s, CH$_3$), 1.41(s, CH$_3$), 4.49(dd, J=2, 8 Hz, CH$_3$—H), 4.96(d, J=2 Hz, CH$_4$),

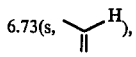
6.73(s, 7.14~7.55(m, arom H), 8.94(s, NH), 9.88(d, J=8 Hz, NH).

REFERENCE EXAMPLE 69B

A mixture of 0.615 g of 2-[1-(2-trimethyl silylethoxycarbonyl)isopropoxyimino]-2-(2-tritylaminothiazol-4-yl)acetic acid, 0.180 g of N-hydroxy-5-norborne-2,3-dicarboximide and 0.210 g of DCC in 6 ml of methylene chloride are stirred at room temperature. The precipitates are filtered off. To the filtrate are added 0.305 g of p-toluenesulfonate of (3R,4R)-3-amino-4-methylthio-2-azetidinone and, then, a solution of 0.105 g of triethylamine in 10 ml of methylene chloride and the mixture is stirred for 4 hours. The reaction mixture is concentrated and the residue is purified by silica gel column chromatography (AcOEt:CHCl$_3$:n-hexane=2:2:1) to give 0.40 g of (3R,4R)-3-[2-[1-(2-trimethylsilylethoxycarbonyl)isopropoxyimino]-2-(2-tritylaminothiazol-4-yl)acetamido]-4-methylthio-2-azetidinone.

IR $\nu_{max}^{KBr}$cm$^{-1}$: 1760, 1670, 1520.

NMR (DMSO-d$_6$, ppm): 0.03(s, CH$_3$), 0.9(t, J=8 Hz, —CH$_2$—), 1.5(s, CH$_3$), 2.10(s, CH$_3$), 4.90(d, J=4 Hz, C$_4$—H), 5.40(dd, J=4, 8 Hz, C$_3$—H), 7.0~7.6(m, arom H).

REFERENCE EXAMPLE 70B (1) To a solution of 1.93 g of (3S,4S)-4-acetoxy-3-tritylamino-2-oxoazetidine in 100 ml of methanol is added a solution of 0.64 g of methyl thioglycolate sodium salt with stirring under ice-cooling. After 1 hour, the solvent is distilled off and the residue is dissolved in ethyl acetate. The solution is washed with water, then the solvent is distilled off, and the residue is purified by silica gel column-chromatograpy (methylene chloride:ethyl acetate=11:1) to give 1.38 g of (3R,4R)-4-methoxycarbonylmethylthio-3-tritylamino-2-oxoazetidine (A) and 0.92 g of the corresponding (3R,4S)-isomer (B)

(A) IR $\nu_{max}^{KBr}$cm$^{-1}$: 3310, 1760, 1730, 1487, 1445, 1240, 1152, 700. NMR (DMSO-d$_6$, ppm): 2.86, 3.08(ABq, J=15 Hz, —CH$_2$—), 3.61(s, CH$_3$), 2.98(d, J=9 Hz, NH), 4.42(dd, J=6, 9 Hz, C$_3$—H), 4.43(d, J=6 Hz, C$_4$—H), 6.67(s, NH), 6.8~7.5(m, arom H).

(B) IR $\nu_{max}^{KBr}$cm$^{-1}$: 1760, 1730, 1275, 1150, 697. NMR (DMSO-d$_6$, ppm): 2.93(broad s, —CH$_2$—), 3.57(s, CH$_3$), 3.9~4.2(m, C$_3$—H, C$_4$—H), 6.55 (broad s, NH), 6.8~7.5(m, arom H).

(2) 0.59 g of (3R,4R)-trityl derivative obtained in (1) above is dissolved in 3 ml of acetone, to which is added 0.251 g of p-toluenesulfonic acid monohydrate, followed by stirring for 1 hour at room temperature. The solvent is distilled off to give (3R,4R)-3-amino-4-methoxycarbonylmethylthio-2-oxoazetidine.

To a solution of the product in a mixture of 20 ml of water and 15 ml of tetrahydrofuran is added with stirring under ice-cooling 0.388 g of sodium hydrogen carbonate. While the pH of the reaction mixture is kept at the range of 7-8 by adding sodium hydrogen carbonate, 0.571 g of 2-(2-chloroacetamidothiazol-4-yl)-2-methoxyiminoacetyl chloride hydrochloride is added to the reaction mixture.

The reaction mixture is stirred for 30 minutes at room temperature and extracted with ethyl acetate. The solvent is distilled off and the resultant is purified by silica gel column-chromatography (ethyl acetate-chloroform-methanol=4:4:1) to give 0.50 g of (3R,4R)-3-[2-(2-chloroacetamidothiazol-4-yl)-2-methoxyiminoacetamido]-4-methoxycarbonylmethylthio-2-oxoazetidine.

IR $\nu_{max}^{KBr}$cm$^{-1}$: 3252, 1762, 1745, 1663, 1540, 1160, 1052.

NMR (DMSO-d$_6$, ppm): 3.46(s, —CH$_2$—), 3.68(s, CH$_3$), 3.89(s, CH$_3$), 4.37(s, ClCH$_2$—), 5.09(d, J=4 Hz, C$_4$—H), 5.40(dd, J=4, 8 Hz, C$_3$—H),

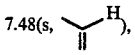
7.48(s, 8.80(broad s, NH), 9.50(d, J=8 Hz, NH), 12.86(broad s, NH).

REFERENCE EXAMPLE 71B

Following the procedure of Reference Example 70B, there is obtained (3R,4S)-3-[2-(2-chloroacetamidothiazol-4-yl)-2-methoxyiminoacetamido]-4-methoxycarbonylmethylthio-2-oxoazedidine.

IR $\nu_{max}^{KBr}$cm$^{-1}$: 3252, 1763, 1735, 1660, 1540, 1278, 1160.

NMR (DMSO-d$_6$, ppm): 3.56(s, —CH$_2$—), 3.68(s, CH$_3$), 3.91(s, CH$_3$), 4.36(s,ClCH$_2$—), 4.75(dd, J=2, 8 Hz, C$_3$—H), 4.82(d, J=2 Hz, C$_4$—H),

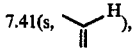
7.41(s, 8.81(s, NH), 9.36(d, J=8 Hz, NH), 12.38(broad s, NH).

REFERENCE EXAMPLE 72B (1) Following the procedure of Reference Example 70B, there is obtained (3R,4R)-3-[2-(2-chloroacetamidothiazol-4-yl)-2methoxyiminoacetamido]-4-n-butylthio-2-oxoazetidine.

IR $\nu_{max}^{KBr}$cm$^{-1}$: 3255, 1758, 1660, 1540.

NMR (DMSO-d$_6$, ppm): 0.88(m, CH$_3$), 1.46(m, —CH$_2$—), 2.56(t, J=7 Hz, —CH$_2$—), 3.89(s, CH$_3$), 4.34(s, —CH$_2$—), 4.98(d, J=5 Hz, C$_4$—H), 5.38(dd, J=5, 9 Hz, C$_3$—H),

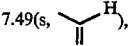
7.49(s, 8.81(s, NH), 9.47(d, J=9 Hz, NH).

(2) Following the procedure of Reference Example 70B the corresponding (3R,4S)-isomer is obtained.

IR $\nu_{max}^{KBr}$cm$^{-1}$: 3265, 1762, 1660, 1540.

NMR (DMSO-d$_6$, ppm): 0.89(t, J=7 Hz, CH$_3$), 1.48(m, —CH$_2$—), 2.65(t, J=7 Hz, —CH$_2$—), 3.91(s, CH$_3$), 4.37(s, —CH$_2$—), 4.68(dd, J=2, 9 Hz, C$_3$—H), 4.68(d, J=2 Hx, C$_4$—H),

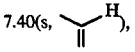
7.40(s, 8.81(s, NH), 9.34(d, J=9 Hz, NH).

REFERENCE EXAMPLE 73B (1) Following the procedure of Reference Example 70B, there is obtained (3R,4R)-3-[2-(2-chloroacetamidothiazol-4-yl)-2-methoxyiminoacetamido]-4-isopropylthio-2-oxoazetidine.

IR $\nu_{max}^{KBr}$cm$^{-1}$: 3250, 1760, 1660, 1540, 1050.

NMR (DMSO-d$_6$, ppm): 1.20, 1.25(each d, J=6 Hz, CH$_3$),

3.88(s, CH$_3$), 4.35(s, ClCH$_2$—), 5.06(d, J=5 Hz, C$_3$—H), 5.41(dd, J=5, 9 Hz, C$_4$—H), 7.46(s, ), 8.74(broad s, NH), 9.36(d, J=9 Hz, NH), 12.86(broad s, NH).

(2) Following the procedure of Reference Example 70B, the corresponding (3R,4S)-isomer is obtained.

IR $\nu_{max}^{KBr}$cm$^{-1}$: 3275, 1760, 1689, 1660, 1580, 1542, 1365, 1322, 1045.

NMR (DMSO-d$_6$, ppm): 1.28(d, J=7 Hz, CH$_3$),

3.90(s, CH$_3$), 4.37(s, ClCH$_2$—), 4.68(dd, J=2, 8 Hz, C$_3$—H), 4.74(d, J=2 Hz, C$_4$—H), 7.39(s, ), 8.83(s, NH), 9.35(d, J=8 Hz, NH), 12.88(broad s, NH).

REFERENCE EXAMPLE 74B

Following the procedure of Reference Example 70B, there is obtained (3R,4S)-3-[2-(2-chloroacetamidothiazol-4-yl)-2-methoxyiminoacetamido]-4-[[(n-propylthio)thiocarbonyl]thio]-2-oxoazetidine.

IR $\nu_{max}^{Kbr}$cm$^{-1}$: 3250, 1770, 1662, 1540, 1263, 1043.

NMR (DMSO-d$_6$, ppm): 1.97(t, J=7 Hz, CH$_3$), 1.70(m, —CH$_2$—), 3.39(t, J=7 Hz, —CH$_2$—), 3.90(s, CH$_3$), 4.36(s, ClCH$_2$—), 5.05(dd, J=2, 8 Hz, C$_3$—H), 5.73(d, J=2 Hz, C$_4$—H), 7.40(s, ), 12.8(broad s, NH).

REFERENCE EXAMPLE 75B (1) Following the procedure of Reference Example 70B, there is obtained (3R,4R)-3-[2-(2-chloroacetamidothiazol-4-yl)-2-methoxyiminoacetamido]-4-cyclohexylthio-2-oxoazetidine.

IR $\nu_{max}^{KBr}$cm$^{-1}$: 1765, 1665, 1545, 1050.

NMR (DMSO-d$_6$, ppm): 1.0~2.0(m, —CH$_2$—), 3.90(s, CH$_3$), 4.36(s, ClCH$_2$—), 5.10(d, J=4 Hz, C$_4$—H), 5.40(dd, J=4, 8 Hz, C$_3$—H), 7.48(s, ), 8.76(broad s, NH), 9.42(d, J=8 Hz, NH).

(2) Following the procedure of Reference Example 70B, the corresponding (3R,4S)-isomer is obtained.

IR $\nu_{max}^{KBr}$cm$^{-1}$: 1760, 1660, 1540, 1040.

NMR (DMSO-d$_6$, ppm): 1.0~2.1(m, —CH$_2$—), 3.90(s, C$_3$) 4.36(s, ClCH$_2$—), 4.66(dd, J=2, 8 Hz, C$_3$—H), 4.74(d, J=2 Hz, C$_4$—H), 7.38(s, ), 8.80(s, NH) 9.36(d, J=8 Hz, NH).

REFERENCE EXAMPLE 76B

Following the procedure of Reference Example 1B, there is obtained 3-benzyloxycarboxamido-4-ethoxy-3-methoxy-2-oxoazetidine.

IR $\nu_{max}^{KBr}$cm$^{-1}$: 3275, 1780, 1690, 1495, 1120.

NMR (DMSO-d$_6$, ppm): 1.15(t, J=7 Hz, CH$_3$), 3.48(s, CH$_3$), 3.62(q, J=7 Hz, —CH$_2$—), 4.91(s, C$_4$—H), 5.14(s, —CH$_2$—), 5.88(s, NH), 7.30(s, NH), 7.30(s, arom H).

REFERENCE EXAMPLE 77B

To a solution of 1.4 g of (3S,4S)-4-acetoxy-3-tritylamino-2-oxoazetidine in 30 ml of methanol is added with stirring under ice-cooling a solution of 0.51 g of N-acetylcysteamine sodium salt in 30 ml of methanol. After 30 minutes, the solvent is distilled off and the resultant is dissolved in ethyl acetate.

The solution is washed with water, then the solvent is distilled off to give 1.6 g of 4-(2-acetamidoethyl) thio-3-tritylamino-2-oxoazetidine, which is dissolved in 10 ml of acetone.

To the solution is added 0.682 g of p-toluenesulfonic acid monohydrate, followed by stirring for 45 minutes.

Acetone is distilled off, and the resultant is collected by filtration, and washed with ether to give 3-amino-4-(2-acetamidoethyl)thio-2-oxoazetidine p-toluenesulfonate. This product is dissolved in a mixture of 20 ml of water and 20 ml of tetrahydrofuran, to which is added 0.904 g of sodium hydrogen carbonate. While the pH of the reaction mixture is kept at the range of 7–8, sodium hydrogen carbonate and 1.432 g of 2-(2-acetamidothiazol-4-yl)-2-methoxyiminoacetyl chloride hydrochloride are added.

The reaction mixture is stirred for 30 minutes and extracted with ethyl acetate. After washing with water, the extract is subjected to distillation to remove the solvent. To the resultant is added ether, and the resulting solid product is collected by filtration to give 1.5 g of (3R)-4-[(2-acetamidoethyl)thio]-3-[2-(2-chloroacetamidothiazol-4-yl)-2-methoxyiminoacetamido]-2-oxoazetidine.

IR $\nu_{max}^{KBr}$cm$^{-1}$: 3370, 3270, 1735, 1650, 1530, 1360, 1270, 1040.

NMR (DMSO-d$_6$, ppm): 1.82, 1.84(s, CH$_3$), 2.68(m, —CH$_2$—), 3.89, 3.91(each s, CH$_3$), 4.40(s, ClCH$_2$—), 4.74(d, J=2 Hz, C$_4$—H), 5.02(d, J=5 Hz, C$_4$—H), 4.67(dd, J=2, 8 Hz, C$_3$—H), 5.37(dd, J=5, 8 Hz, C$_3$—H) 7.40, 7.48.

REFERENCE EXAMPLE 78B

To a suspension of 0.8 g of D-2-thienyl-2-ureidoacetic acid in 12 ml of acetonitrile is added under ice-cooling 0.952 g of thionyl chloride, and the mixture is stirred for 10 minutes, followed by evaporation to dryness to give crystals, which are collected by filtration.

On the other hand, to a suspension of 0.598 g of (3S,4R)-3-amino-4-azido-2-oxoazetidine p-toluenesulfate in 20 ml of methylene chloride are added 0.64 g of pyridine, 2 ml of propyleneoxide, the crystals obtained as above and 10 ml of dimethylformamide in that order at $-70°$ C. The reaction mixture is stirred for 3 hours at $0°$ C., followed by concentration. The resultant is purified by silica gel column-chromatography (ethyl acetate:n-hexane=2:1) to give 0.55 g of (3S,4R)-4-azido-3-(D-2-thienyl-2-ureidoacetoamido)-2-oxoazetidine.

IR $\nu_{max}^{KBr}$ cm$^{-1}$: 3260, 2110, 1770, 1650, 1535.

NMR (DMSO-d$_6$, ppm): 5.10–5.40(m, C$_3$—H, C$_4$—H), 5.69(d, J=8Hz, —CH—),
          |

5.73(s, NH$_2$), 6.76(d, J=8 Hz, NH), 6.90–7.60(m, arom H), 8.99(s, NH), 9.25(d, J=8 Hz, NH).

REFERENCE EXAMPLE 79B

Following the procedure of Reference Example 54B, there is obtained (3R,4S)-3-[D-2-(2-oxoimidazolidin-1-yl-carboxamido)-2-phenylacetamido]-4-phenylthio-2-oxoazetidine IR $\nu_{max}^{KBr}$ cm$^{-1}$: 3255, 1775, 1695, 1665, 1505, 1480, 1268.

NMR (DMSO-d$_6$, ppm): 3.19~3.43(m, —CH$_2$—), 3.62~3.84(m, —CH$_2$—), 4.56(dd, J=2,9 Hz, C$_3$—H), 4.83(d, J=2 Hz, C$_4$—H), 5.39(d, J=8Hz, —CH—),
          |

7.33(s, arom H), 7.36(s, arom H), 7.55(s, NH),8.95(s, NH), 9.03(d, J=8 Hz, NH), 9.19(d, J=9 Hz, NH).

REFERENCE EXAMPLE 80B

Following the procedure of Reference Example 54B, there is obtained (3S,4S)-4-azido-3-[D-2-(2-oxoimidazolidin--yl-carboxamido)-2-phenylacetamido]-2-oxoazetidine.

IR $\nu_{max}^{KBr}$ cm$^{-1}$: 3300~3240, 2090, 1772, 1705, 1660, 1505, 1255.

NMR (DMSO-d$_6$, ppm): 3.10~3.40(m, —CH$_2$—), 3.60~3.88(m, —CH$_2$—), 4.64(dd, J=2,8 Hz, C$_3$—H), 5.02(d, J=2 Hz, C$_4$—H), 5.42(d, J=8Hz, —CH—),
          |

7.36(s, arom H), 7.54(s, NH), 8.98(s, NH), 9.00~9.20(m, NH).

REFERENCE EXAMPLE 81B 0.405 g of methyl (3S-trans)-3-methoxy-4-methylthio-3-p-nitrobenzyloxycarboxamido-2-oxoazetidine-1-(α-isopropylidene)acetate is treated with 0.283 g of potassium permanganate in a solution of 7.5 ml of pyridine and 0.5 ml of water to give 0.096 g of (3S-trans)-3-methoxy-4-methylthio-3-p-nitrobenzyloxycarboxamido-2-oxoazetidine.

NMR (CDCl$_3$, ppm): 2.10(s, CH$_3$), 3.51(s, CH$_3$), 4.72(s, C$_4$—H), 5.29(s, —CH$_2$—), 6.22(s, NH), 6.98(s, NH), 7.55, 8.17(each d, J=9 Hz, arom H).

REFERENCE EXAMPLE 82B

Following the procedure of Reference Example 16B, there is obtained (3S-trans)-3-[D-2-(4-cyclohexyl-2,3-dioxo-1-piperazinecarboxamido)-2-phenylacetamido]-3-methoxy-4-methylthio-2-oxoazetidine.

IR $\nu_{max}^{KBr}$ cm$^{-1}$: 3270, 2925, 1770, 1705, 1670, 1500, 1170.

NMR (CDCl$_3$, ppm): 1.94(s, CH$_3$), 3.39(s, CH$_3$), 4.68(s, C$_4$—H), 5.57(d, J=7Hz, —CH—),
          |

3.3~4.1(m, —CH$_2$—), 6.95(s, NH), 7.2~7.6(m, arom H), 7.50(s, NH), 9.84(d, J=7 Hz, NH).

REFERENCE EXAMPLE 83B

Following the procedure of Reference Example 54B, there is obtained (3S,4S)-4-azido-3-[D-2-[3-methyl-3-(methylcarbamoyl)-1-ureido]-2-phenylacetamido]-2-oxoazetidine IR $\nu_{max}^{KBr}$ cm$^{-1}$: 3275, 2100, 1770, 1675, 1495.

NMR (DMSO-d$_6$, ppm): 2.67(d, J=4 Hz, CH$_3$), 3.08(s, CH$_3$), 4.55(m, C$_3$—H), 5.00, 5.02(each d, J=2 Hz, C$_4$—H), 5.37(d, J=7Hz, —CH—),
          |

7.36(s, arom H), 8.98(s, NH), 9.07(d, J=8 Hz, NH), 9.87, 9.92(each d, J=7 Hz, NH).

REFERENCE EXAMPLE 84B (1) Following the procedure of Reference Example 54B, there is obtained (3S,4R)-4-azido-3-[D-2-(4-ethyl-2,3-dioxo-1-piperazinecarboxamido)-3-(S)-formyloxybutanamido]-2-oxoazetidine IR $\nu_{max}^{KBr}$ cm$^{-1}$: 3270, 2102, 1772, 1703, 1665, 1510, 1175.

NMR (DMSO-d$_6$, ppm): 1.11(t, J=7 Hz, CH$_3$), 1.25(d, J=6 Hz, CH$_3$), 3.42(q, J=7 Hz, —CH$_2$—), 3.58(m, —CH$_2$—), 3.94(m, —CH$_2$—), 4.67(dd, J=4,8Hz, —CH—),
          |

5.14(m, C$_3$—H), 5.30(d, J=4 Hz, C$_4$—H), 5.36(m, —CH—),
          |

8.18(s, CHO), 9.04(s, NH), 9.14(d, J=8 Hz, NH), 9.39(d, J=8 Hz, NH).

(2) Following the procedure of Reference Example 54B, the corresponding (3S,4S)-isomer is obtained.

IR $\nu_{max}^{KBr}$ cm$^{-1}$: 3275, 2110, 1782, 1715, 1670, 1515, 1180.

NMR (DMSO-d6, ppm): 1.11(t, J=7 Hz, CH3), 1.23(d, J=6 Hz, CH3), 3.30~3.70(m, —CH2—), 3.42(q, J=7 Hz, —CH2—), 3.88~4.08(m, —CH2—), 4.50~4.67(m, C3—H, —CH—),
|

5.02(d, J=1 Hz, C4—H), 5.26~5.52(m, —CH—),
|

8.19(s, CHO), 8.99(s, NH), 9.02(d, J=8 Hz, NH), 9.39(d, J=8 Hz, NH).

REFERENCE EXAMPLE 85B

Following the procedure of Reference Example 54B, there is obtained 3-[2-(2-chloroacetamidothiazol-4-yl)-2-methoxyiminoacetamido]-4-fluoro-2-oxoazetidine.

IR $\nu_{max}^{KBr}$ cm$^{-1}$: 1780, 1670, 1540, 1300, 1040.

REFERENCE EXAMPLE 86B

Following the procedure of Reference Example 70B, there is obtained (3R,4R)-3-[D-2-(4-ethyl-2,3-dioxo-1-piperazinecarboxamido)-2-chloromethylacetamido]-4-methylthio-2-oxoazetidine.

IR $\nu_{max}^{KBr}$ cm$^{-1}$: 1750, 1710, 1670, 1510, 1180.

REFERENCE EXAMPLE 87B

Following the procedure of Reference Example 54B, there is obtained (3R,4R)-4-t-butylthio-3-[D-2-(4-ethyl-2,3-dioxo-1-piperazinecarboxamido)-3-(S)-formyloxybutanamido]-2-oxoazetidine IR $\nu_{max}^{KBr}$ cm$^{-1}$: 3270, 1765, 1710, 1672, 1512, 1188.

NMR (DMSO-d6, ppm): 0.87(m, CH3), 1.09(t, J=7 Hz, CH3), 1.25(d, J=7 Hz, CH3), 1.77(m, —CH2—), 2.48(t, J=8 Hz, —CH2—), 3.42(q, J=7 Hz, —CH2—), 3.60(m, —CH2—), 3.95(m, —CH2—), 4.74(dd, J=5,9Hz, —CH—),
|

4.92(d, J=5 Hz, C4—H), 5.26(m, C3—H, —CH—),
|

8.18(s, CHO), 8.84(s, NH), 9.10(d, J=9 Hz, NH), 9.45(d, J=9 Hz, NH).

REFERENCE EXAMPLE 88B

Following the procedure of Reference Example 54B, there is obtained (3S,4R)-4-azido-3-[D-2-(2-oxoimidazolidin-1-yl-carboxamido)-2-phenylacetamido]-3-(S)-formyloxybutanamido]-2-oxoazetidine.

IR $\nu_{max}^{KBr}$ cm$^{-1}$: 3260, 2105, 1775, 1722, 1705, 1665, 1518, 1265.

NMR (DMSO-d6, ppm): 3.10~3.50(m, —CH2—), 3.60~3.90(m, —CH2—), 5.19(m, C3—H, C4—H), 5.57(d, J=8Hz, —CH—),
|

7.37(m, arom H), 7.55(s, NH), 9.00(s, NH), 9.15(d, J=8 Hz, NH), 9.31(d, J=8 Hz, NH).

REFERENCE EXAMPLE 89B (1) 0.407 g of (3R,4R)-4-methylsulfonyl-3-tritylamino-2oxoazetidine is dissolved in 10 ml of acetonitrile, to which are added under ice-cooling 0.244 g of N-acetylcysteamine silver salt and 0.75 g of sodium iodide, followed by vigorous stirring for 5 hours. The insolubles are filtered off and the filtrate is concentrated. The residue is dissolved in ethyl acetate, washed with water and the solvent is distilled of. The residue is purified on a silica gel column-chromatography (AcOEt:CHCl3:CH3OH=8:8:1) to give 0.297 g of 4-(2-acetylamidoethyl)thio-3-tritylamino-2-oxoazetidine.

IR $\nu_{max}^{KBr}$ cm$^{-1}$: 3250, 1750, 1670, 1615, 1485, 1260.

(2) 0.076 g of the trityl-derivative obtained in (1) above is dissolved in 20 ml of acetone, to which is added under ice-cooling 0.46 g of p-toluenesulfonic acid monohydrate, followed by stirring for 40 minutes at room temperature. The mixture is concentrated. To the residue is added ether, whereby solid 3-amino-4-(2-acetamidoethyl) thio-2-oxoazetidine is obtained. This product is added with stirring at −70° C. to a suspension of 0.95 g of 2-(2-chloroacetamidothiazol-4-yl)-2-methoxyiminoacetylchloride hydrochloride and 1.0 g of triethylamine in 20 ml of methylene chloride, to which 2 ml of propylene oxide is added, followed by raising gradually the temperature of the reaction mixture up to room temperature in the course of 1 hour.

The reaction mixture is concentrated and insolubles are filtered off. The filtrate is purified on a silica gel column-chromatography (AcOEt:CHCl3:CH3OH=8:8:1) to give 0.814 g of 4-(E-2-acetamidovinyl)thio-3-[2-(2-chloroacetamido)-2-methoxyiminoacetamido]-2-oxoazetidine.

IR $\nu_{max}^{KBr}$ cm$^{-1}$: 3420, 3250, 1766, 1670, 1620, 1542, 1265, 1045.

REFERENCE EXAMPLE 90B (1) 3.0 g of (3S,4S)-3-carbobenzoxamido-4-acetoxy-2-oxoazetidine is dissolved in 25 ml of acetonitrile, to which are added 2.34 g of zinc acetate and 3.4 g of ethyl glycolate in that order, followed by stirring for 7 hours at 65°–70° C.

The solvent is distilled off and the residue is dissolved in ethyl acetate, followed by washing with water and concentration. The residue is purified on a silica gel column-chromatography (ethyl acetate:n-hexane=1:1) to give 0.372 g of (3S,4R)-3-carbobenzoxamido-4-ethoxycarbonylmethoxy-2-oxoazetidine (A) and 0.604 g of the corresponding (3S,4S)-isomer (B).

(A) IR $\nu_{max}^{KBr}$ cm$^{-1}$: 3310, 3200, 1785, 1755, 1730, 1700, 1522, 1260.

(B) IR $\nu_{max}^{KBr}$ cm$^{-1}$: 3310, 1790, 1772, 1736, 1690, 1525, 1240, 1112. NMR (DMSO-d6, ppm): 1.10(t, J=7 Hz, CH3), 4.15(q, J=7 Hz, —CH2—), 4.20(s, —CH2—), 4.31(dd, J=1,8 Hz, C3—H), 5.02(d, J=1 Hz, C4—H), 5.05(s, —CH2—), 7.36(s, arom H), 7.96(d, J=8 Hz, NH), 8.80(s, NH).

To a solution of 0.482 g of the (3S,4S)-isomer (B) obtained in (1) above in 20 ml of tetrahydrofuran is added 0.40 g of palladium black, and the mixture is stirred for 30 minutes in a stream of hydrogen. The catalyst is filtered off and the filtrate is concentrated to a volume of 3 ml. On the other hand, to a suspension of 0.574 g of 2-(2-chloroacetamidothiazol-4-yl)-2-methoxyiminoacetyl chloride hydrochloride and 0.456 g of triethylamine in 20 ml of methylene chloride, is added with stirring at −70° C. the above prepared tetrahydrofuran solution, to which is added 2 ml of propylene oxide, followed by raising gradually the temperature of the reaction mixture up to room temperature in the course of 1 hour.

The mixture is concentrated, and to the residue are added tetrahydrofuran and a saturated aqueous solution of sodium chloride.

The tetrahydrofuran layer is separated and dried over anhydrous magnesium sulfate.

The solvent is distilled off, and to the residue is added ether.

The above procedure yields 0.601 g of (3S,4S)-3-[2-(2-chloroacetamidothiazol-4-yl)-2-methoxyiminoacetamido]-4-(ethoxycarbonyl)methoxy-2-oxoazetidine.

IR $\nu_{max}^{KBr}$ cm$^{-1}$: 3260, 1762, 1660, 1542.

NMR (DMSO-d$_6$, ppm): 1.08(t, J=7 Hz, CH$_3$), 3.66(q, J=7 Hz, —CH$_2$—), 3.91(s, CH$_3$), 4.36(s, —CH$_2$—), 4.52(dd, J=1,8 Hz, C$_3$—H), 4.91(d, J=1 Hz, C$_4$—H),

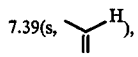

8.95(s, NH), 9.23(d, J=8 Hz, NH), 12.84(broad s, NH).

(2) The same procedure as above (1) yields the corresponding (3S,4R)-isomer.

IR $\nu_{max}^{KBr}$ cm$^{-1}$: 3260, 1760, 1665, 1555.

REFERENCE EXAMPLE 91B

To a solution of 0.612 g of (3S-trans)-3-methoxy-4-methylthio-3-p-nitrobenzyloxycarboxamido-2-oxoazetidine in 20 ml of methanol is added 0.9 g of 10% palladium-carbon (50% wet). The mixture is stirred for 50 minutes at room temperature in a stream of hydrogen.

The catalyst is filtered off, and to the filtrate is added 0.9 g of 10% palladium-carbon and stirred for 50 minutes in a stream of hydrogen.

The catalyst is filtered off and the filtrate is concentrated. The concentrate is dissolved in 30 ml of methylene chloride.

On the other hand, to a solution of 1.5 g of 2-(2-chloroacetamidothiazol-4-yl)-2-methoxyiminoacetic acid in 30 ml of methylene chloride containing 1.7 g of pyridine are added with stirring keeping the temperature at −30° C. the above prepared methylene chloride solution and 0.5 ml of phosphorus oxychloride in that order.

After 30 minutes, the solvent is distilled off and the residue is dissolved in ethyl acetate and washed with water. The solvent is distilled off and the residue is purified on a silica gel column-chromatography (CHCl$_3$:AcOEt=1:5) to give 0.384 g of (3S,4R)-3-[2-(2-chloroacetamidothiazol-4-yl)-2-methoxyiminoacetamido]-3-methoxy-4-methylthio-2-oxoazetidine.

IR $\nu_{max}^{KBr}$ cm$^{-1}$: 3230, 1765, 1670, 1535.

NMR (DMSO-d$_6$, ppm): 2.20(s, CH$_{3L}$), 3.63(s, CH$_3$), 4.05(s, CH$_3$), 4.37(s, ClCH$_2$—), 4.88(s, C$_4$—H),

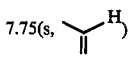

REFERENCE EXAMPLE 92B

Following the procedure of Reference Example 70B, there is obtained (3S,4R)-4-azido-3-[2-(4-ethyl-2,3-dioxopiperazinecarboxamido)-4-pentynamido]-2-oxoazetidine.

IR $\nu_{max}^{KBr}$ cm$^{-1}$: 3260, 2105, 1756, 1705, 1665, 1500.

NMR (DMSO-d$_6$, ppm): 1.10(t, J=7 Hz, CH$_3$), 2.71 (m, —CH$_2$—), 2.84(m, HC≡), 3.40(q, J=7 Hz, —CH$_2$—), 3.56(m, —CH$_2$—), 3.92(m, —CH$_2$—), 5.10, 5.16(each dd, J=4,8 Hz, C$_3$—H), 5.30, 5.32(each d, J=4 Hz, C$_4$—H), 9.06(m, NH), 9.41(d, J=8 Hz, NH).

REFERENCE EXAMPLE 93B

Following the procedure of Reference Example 77B, there is obtained 4-(2-acetamidoethyl)thio-3-[D-2-(4-ethyl-2,3-dioxopiperazinecarboxamido)-2-phenylacetamido]-2-oxoazetidine. (a mixture of cis- and trans-compounds).

IR $\nu_{max}^{KBr}$ cm$^{-1}$: 3280, 1755, 1710, 1670, 1500, 1220, 1180, 1012.

NMR (DMSO-d$_6$, ppm): 1.78, 1.80(each s, CH$_3$), 4.55(dd, J=2,8 Hz, C$_3$—H), 4.64(d, J=2 Hz, C$_4$—H), 4.86(d, J=5 Hz, C$_4$—H), 5.28(m, C$_3$—H), 5.47, 5.63(each d, J=8Hz, —CH—)
|

9.27, 9.31(each d, J=8 Hz, NH), 9.78, 9.82(each d, J=8 Hz, NH).

REFERENCE EXAMPLE 94B

Following the procedure of Reference Example 70B, there is obtained (3S,4R)-4-azido-3-[2-(2-formamidothiazol-4-yl)-2-methoxyiminoacetamido]-2-oxoazetidine IR $\nu_{max}^{KBr}$ cm$^{-1}$: 3230, 2102, 1770, 1660, 1540, 1280, 1048.

NMR (DMSO-d$_6$, ppm): 3.91(s, CH$_3$), 5.20–5.40(m, C$_3$—H, C$_4$—H),

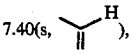

8.50(s, CHO), 9.02(s, NH), 9.54(d, J=8 Hz, NH).

REFERENCE EXAMPLE 95B

Following the procedure of Reference Example 77B, there is obtained 4-(2-acetamidoethyl)thio-3-[2-(2-chloroacetamidothiazol-4-yl)-2-[[2-oxo-3-(thiophene-3-aldimino)imidazolidin-1-yl]carboxamido]acetamido]-2-oxoazetidine.

IR $\nu_{max}^{KBr}$ cm$^{-1}$: 3290, 1760, 1720, 1670, 1520, 1390, 1264, 1220.

NMR (DMSO-d$_6$, ppm): 1.83(s, CH$_3$), 4.37(s, ClCH$_2$—), 5.49(d, J=8Hz, —CH—)
|

7.02(broad s, NH), 7.83, 7.85(each s, 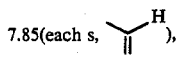), 7.71(broad s, NH), 9.0~9.3(broad m, NH).

REFERENCE EXAMPLE 96B

To a solution of 1.8 g of (3R,4R)-3-amino-4-(2-acetamidoethyl)thio-2-oxoazetidine.p-toluenesulfonate, 1.5 g of triethylamine and 10 ml of methylene chloride which is cooled with ice-water, is added a solution of the corresponding acid chloride in 10 ml of methylene chloride, the acid chloride being prepared from 2.2 g of 2-(2-chloroacetamidothiazol-4-yl)-2-[1-methyl-1(2-trimethylsilylethoxycarbonyl)ethoxyimino]acetic acid, 1.02 g of phosphorus pentachloride and 35 ml of methylene chloride according to per se known method.

The mixture is stirred for 30 minutes, concentrated under reduced pressure and the residue is purified on a silica gel column-chromatography (AcOEt:CH$_3$OH=9:1) to give 0.83 g of (3R,4R)-4-(2-acetamidoethyl)thio-3-[2-(2-chloroacetamidothiazol-4-yl)-2-[1-methyl-1-(2-trimethylsilylethoxycarbonyl)ethoxyimino]acetamido]-2-oxoazetidine IR $\nu_{max}^{KBr}$ cm$^{-1}$: 1760, 1660, 1545, 860, 840.

NMR (CDCl$_3$, ppm): 1.00(t, J=8 Hz, —CH$_2$—), 1.60(s, CH$_3$), 1.63(s, CH$_3$), 1.95(s, COCH$_3$), 2.76(m, —CH$_2$—), 3.60(m, —CH$_2$—), 4.20(t, J=8 Hz, —CH$_2$—), 4.26(s, —CH$_2$—), 5.03(d, J=4 Hz, C$_4$—H), 5.60(dd, J=4,8 Hz, C$_3$—H), 7.03(broad s, NH), 7.46(s, 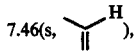), 7.80(broad, s, NH), 8.45(d, J=8 Hz, NH).

REFERENCE EXAMPLE 97B

To 0.915 g of (3R,4R)-3-amino-4-methylamino-2-oxoazetidine p-toluenesulfonate is added 3 ml of pyridine, which is stirred for 10 minutes at 25° C., and evaporated to dryness under reduced pressure.

On the other hand, a mixture of 1.85 g of 2-(2-tritylaminothiazol-4-yl)-2-[1-methyl-1-(2-trimethylsilylethoxycarbonyl)ethoxyimino]acetic acid, 0.54 g of N-hydroxy-5-norbornene-2,3-dicarboximide, 0.62 g of DCC and 15 ml of methylene chloride is stirred for 1 hour at 25° C.

To this mixture is added the above prepared solid amino-derivative, followed by stirring for 2 hours under reflux.

The reaction mixture is subjected to filtration, and the filtrate is purified on a silica gel column chromatography (AcOEt:n-hexane=1:1) to give 0.66 g of (3R,4R)-4-methylthio-3-[2-(2-tritylaminothiazol-4-yl)-2-[1-methyl-1-(2-trimethylsilylethoxycarbonyl)ethoxyimino]-2-oxoazetidine.

IR $\nu_{max}^{KBr}$ cm$^{-1}$: 1775, 1735, 1680, 1620, 1520.

NMR (CDCl$_3$, ppm): 0.03 (s, CH$_3$), 0.83(t, J=8 Hz, —CH$_2$—) 1.63(s, CH$_3$), 1.70(s, CH$_3$), 2.10(s, SCH$_3$), 4.20(t, J=8 Hz, —CH$_2$—), 4.96(d, J=4 Hz, C$_4$—H), 5.66(dd, J=4,8 Hz, C$_3$—H), 6.60(broad s, NH), 6.83(s, 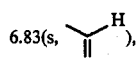), 6.90(broad s, NH), 7.30(s, arom H), 8.06(d, J=8 Hz, NH).

REFERENCE EXAMPLE 98B

Following the procedure of Reference Example 77B, there is obtained 3-[2-(2-chloroacetamidothiazol-4-yl)-2-methoxyiminoacetamido]-4-(2-formamidoethyl)thio-2-oxoazetidine (a mixture of cis- and trans-compound)

IR $\nu_{max}^{KBR}$ cm$^{-1}$: 3260, 1758, 1660, 1540, 1039.

NMR (DMSO-d$_6$, ppm): 3.75(t, J=7.5 Hz, —CH$_2$—), 3.89, 3.90(each s, CH$_3$), 4.37(s, ClCH$_2$—), 4.70(dd, J=2,8 Hz, C$_3$—H), 4.74(d, J=2 Hz, C$_4$—H), 5.04(d, J=5 Hz, C$_4$—H), 5.40(dd, J=5,8 Hz, C$_3$—H), 8.00, 8.10(each d, J=6 Hz, NH), 8.79, 8.81(each broad s, NH), 7.38, 9.46(each d, J=8 Hz, NH).

REFERENCE EXAMPLE 99B

Following the procedure of Reference Example 89B, there is obtained (3R,4R)-4-(Z-2-acetamidovinyl)thio-3-[2-(2-chloroacetamido)-2-methoxyiminoacetamido]-2-oxoazetidine IR $\nu_{max}^{KBr}$ cm$^{-1}$: 3260, 1770, 1666, 1542.

NMR (DMSO-d$_6$, ppm): 1.98(s, CH$_3$), 3.88(s, CH$_3$), 4.36(s, —CH$_2$—), 5.09(d, J=4 Hz, C$_4$—H), 5.28(d, J=8Hz, 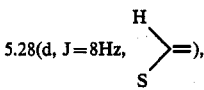), 5.4 1(dd, J=4,8 Hz, C$_3$—H), 6.89(dd, J=8, 10Hz, 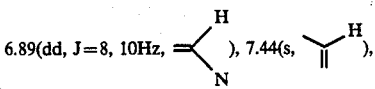), 7.44(s, ), 8.85(s, NH), 9.31(d, J=10 Hz, NH), 9.44(d, J=8 Hz, NH).

REFERENCE EXAMPLE 100B

Following the procedure of Reference Example 77B, there is obtained 3-[2-(2-chloroacetamidothiazol-4-yl)-2-methoxyiminoacetamido]-4-(2-p-nitrobenzyloxycarbonylethyl)thio-2-oxoazetidine (a mixture of cis- and trans-compound)

IR $\nu_{max}^{KBr}$ cm$^{-1}$: 3255, 2945, 1761, 1690, 1660, 1510, 1345, 1260, 1053, 820.

NMR (DMSO-d$_6$, ppm): 2.6~2.9(m, —CH$_2$—), 3.1~3.4(m, —CH$_2$—), 3.88, 3.90(each s, CH$_3$), 4.37(s, ClCH$_2$—), 4.71(dd, J=2,8 Hz, C$_3$—H), 4.73(d, J=2 Hz, C$_4$—H), 5.03(d, J=5 Hz, C$_4$—H), 5.18(s, —CH$_2$—), 5.40(dd, J=5,8 Hz, C$_3$—H), 7.40, 7.48(each s, 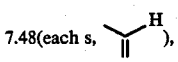), 7.59, 8.21(each d, J=8 Hz, arom H), 8.77, 8.79 each broad s, NH).

REFERENCE EXAMPLE 101B

Following the procedure of Reference Example 77B, there is obtained (3R,4R)-4-(2-acetamidoethyl)thio-3-[2-(2-formamidothiazol-4-yl)-2-(1-sodiotetrazol-5-yl)methoxyiminoacetamido]-2-oxoazetidine IR $\nu_{max}^{KBr}$ cm$^{-1}$: 1755, 1660, 1545, 1290, 1010.

NMR (DMSO-d$_6$, ppm): 1.85(s, CH$_3$), 2.86(m, —CH$_2$—), 3.24(m, —CH$_2$—), 4.98(d, J=5 Hz, C$_4$—H), 5.30(s, —CH$_2$—), 5.37(dd, J=5, 8 Hz, C$_3$—H),

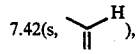
7.42(s,           ), 8.32(t, J=6 Hz, NH), 8.52(s, CHO), 8.75(s, NH), 10.00(d, J=8 Hz, NH).

REFERENCE EXAMPLE 102B

To an ice-cooled solution of 1.8 g of (3S,4R)-3-amino-4-azido-2-oxoazetidine.p-toluenesulfonate, 5 ml of methylene chloride, 20 ml of propylene oxide and 0.48 g of pyridine is added 1.2 g of 2-trimethylsilylethoxycarbonylchloride. The mixture is stirred for 30 minutes and concentrated under reduced pressure.

To the concentrate is added ethyl acetate and the insolubles are filtered off. The filtrate is concentrated, and is purified on a silica-gel column-chromatography (ethyl acetate-n-hexane=1:1) to give 1.085 g of (3S,4R)-4-azido-3-(2-trimethylsilylethoxycarboxamido)-2-oxoazetidine.

IR $\nu_{max}^{KBr}$cm$^{-1}$: 3300, 2100, 1780, 1750, 1700, 1530.

REFERENCE EXAMPLE 103B 0.845 g of (3S,4R)-4-azido-3-[2-(2-tritylaminothiazol-4-yl)-2-[1-methyl-1-(2-trimethylsilylethoxycarbonyl)ethoxyimino]acetamido]-2-oxoazetidine is obtained from 0.598 g of (3S,4R)-3-amino-3-azido-2-oxoazetidine.tosylate (obtained in Reference Example 45B) by a similar manner to that described in Reference Example 97B.

IR $\nu_{max}^{KBr}$cm$^{-1}$: 3350, 3820, 2112, 1780, 1730, 1675, 1520.

NMR (CDCl$_3$, ppm): 0.03(s, CH$_3$), 0.97(t, J=9 Hz, —CH$_2$—), 1.95(s, CH$_3$), 1.97(s, CH$_3$), 4.21(t, J=9 Hz, —CH$_2$—), 5.33(d, J=4, C$_4$—H), 5.56(dd, J=4, 8 Hz, C$_3$—H),

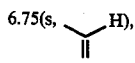
6.75(s,           ), 6.83(s, NH), 6.93(s, NH), 7.31(s, arom H), 8.15(d, J=8 Hz, NH).

EXAMPLE 1B

To a solution of 0.45 g of (3S,4S)-4-acetoxy-3-phenoxyacetamido-2-oxoazetidine in 4 ml of DMF is added 0.515 g of sulfuric anhydride-pyridine complex and the reaction is carried out for 5 days. Then, 20 ml of diethyl ether is added and the oil that separates out thereon is washed with 10 ml of diethyl ether, dissolved in water, treated with Dowex 50W-Na resin (Dow Chemical Co.) and purified on a column of XAD-II resin (Rohm and Haas Co.). The above procedure gives 0.462 g of sodium (3S,4S)-4-acetoxy-3-phenoxyacetamido-2-oxoazetidine-1-sulfonate.

IR $\nu_{max}^{KBr}$cm$^{-1}$; 3550, 3250, 1768, 1725, 1635, 1290, 1255, 1058.

NMR(DMSO-d$_6$, ppm); 2.05(s, CH$_3$), 4.54(s, —CH$_2$—), 4.76(dd, J=2, 9 Hz, C$_3$—H), 6.21(d, J=2 Hz, C$_4$—H), 6.90-7.44(m, arom H), 9.04(d, J=9 Hz, NH).

EXAMPLE 2B

To a solution of 0.586 g of (3S,4S)-4-acetoxy-3-[2-(2-chloroacetamidothiazol-4-yl)-2-methoxyiminoacetamido]-2-oxoazetidine (mixture of syn- and anti-isomers) in 5 ml of DMF is added 0.402 g of sulfuric anhydride-pyridine complex and the reaction is carried out for 7 days. The same procedure as in Example 1B yields 0.22 g of sodium (3S,4S)-4-acetoxy-3-[2-(2-chloroacetamidothiazol-4-yl)-2-methoxyiminoacetamido]-2-oxoazetidine-1-sulfonate (anti-isomer).

IR $\nu_{max}^{KBr}$cm$^{-1}$; 3450, 3280, 1780, 1750, 1663, 1280, 1245, 1038.

NMR(DMSO-d$_6$, ppm); 2.04(s, CH$_3$), 4.00(s, CH$_3$), 4.34(s, —CH$_2$—), 4.74(dd, J=2, 9 Hz, C$_3$—H), 6.23(d, J=2 Hz, C$_4$—H),

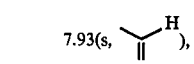
7.93(s,           ), 9.25(d, J=9 Hz, NH), 12.77(s, NH).

The procedure further yields 0.188 g of syn-isomer
IR $\nu_{max}^{KBr}$cm$^{-1}$; 3425, 3260, 1780, 1750, 1670, 1280, 1240, 1040.

NMR(d$_6$-DMSO, ppm); 2.06(s, CH$_3$), 3.87(s, CH$_3$), 4.33(s, —CH$_2$—), 4.77(dd, J=2, 9 Hz, C$_3$—H), 6.10(d, J=2 Hz, C$_4$—H),

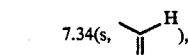
7.34(s,           ), 9.45(d, J=9 Hz, NH), 12.87(s, NH).

EXAMPLE 3B

To a solution of 0.101 g of the above sodium (3S,4S)-4-acetoxy-3-[2-(2-chloroacetamidothiazol-4-yl)-2-methoxyiminoacetamido]-2-oxoazetidine-1-sulfonate (syn-isomer) in 4 ml of water is added 28.4 mg of sodium monomethyldithiocarbamate under ice-cooling with stirring, and the mixture is stirred at room temperature for one hour. The insolubles are filtered off and the filtrate is purified on a column of XAD-II. The above procedure gives 55.4 mg of sodium (3S,4S)-4-acetoxy-3-[2-(2-aminothiazol-4-yl)-2-methoxyiminoacetamido]-2-oxoazetidine-1-sulfonate (syn-isomer).

IR $\nu_{max}^{KBr}$cm$^{-1}$; 3420, 1785, 1770, 1735, 1665, 1620, 1282, 1245, 1045.

NMR(DMSO-d$_6$, ppm); 2.05(s, CH$_3$), 3.15(s, CH$_3$), 4.71(dd, J=2, 8 Hz, C$_3$—H), 6.07(d, J=2 Hz, C$_4$—H),

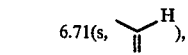
6.71(s,           ), 7.13 (s, —NH$_2$), 9.35(d, J=8 Hz, NH).

EXAMPLE 4B

To a solution of 0.101 g of sodium (3S,4S)-4-acetoxy-3-[2-(2-chloroacetamidothiazol-4-yl)-2-methoxyiminoacetamido]-2-oxoazetidine-1-sulfonate (anti-isomer) in 4 ml of water is added 29 mg of sodium monomethyldithiocarbamate under ice-cooling with stirring, and the mixture is stirred at room temperature for one hour. The insolubles are filtered off and the filtrate is purified on a column of XAD-II (Rohm and Haas Co.). The above procedure yields 48 mg of sodium (3S,4S)-4-acetoxy-3-[2-(2-aminothiazol-4-yl)-2-methoxyiminoacetamido]-2-oxoazetidine-1-sulfonate (anti-isomer).

IR $\nu_{max}^{KBr}$cm$^{-1}$; 3460, 3350, 1780, 1750, 1730, 1665, 1610, 1280, 1240, 1040.

NMR(DMSO-d$_6$, ppm); 2.04(s, CH$_3$), 3.94(s, CH$_3$), 4.73 (dd, J=2, 9 Hz, C$_3$—H), 6.23(d, J=2 Hz, C$_4$—H), 7.02(s, —NH$_2$), 7.32(s, 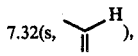), 9.18(d, J=9 Hz, NH).

EXAMPLE 5B

To a solution of 0.18 g of (3R,4R)-4-methylsulfonyl-3-phenoxyacetamido-2-oxoazetidine in 3 ml of DMF is added 0.19 g of sulfuric anhydride-pyridine complex and the reaction is carried out for 11 days. The same procedure as in Example 1B yields 0.13 g of sodium (3R,4R)-4-methylsulfonyl-3-phenoxyacetamido-2-oxoazetidine-1-sulfonate.

IR $\nu_{max}^{KBr}$cm$^{-1}$; 3370, 1785, 1685, 1290, 1250, 1058.

NMR(DMSO-d$_6$, ppm); 3.16(s, CH$_3$), 4.53(s, —CH$_2$—), 5.16 (d, J=5 Hz, C$_4$—H), 5.71(dd, J=5, 10 Hz, C$_3$—H), 6.80–7.43 (m, arom H), 8.35(d, J=10 Hz, NH).

EXAMPLE 6B

To a solution of 0.2 g of (3S,4R)-3-benzyloxycarboxamido-4-methoxy-2-oxoazetidine in 3 ml of DMF is added 0.255 g of sulfuric anhydride-pyridine complex and the reaction is carried out for 4 days. Then, 30 ml of diethyl ether is added and the oil that separates out thereon is washed with diethyl ether to give crystals, which is collected by filtration after washing with ethyl alcohol. The above procedure gives 0.226 g of pyridinium (3S,4R)-3-benzyloxycarboxamido-4-methoxy-2-oxoazetidine-1-sulfonate.

IR $\nu_{max}^{KBr}$cm$^{-1}$; 3180, 1770, 1690, 1250, 1060.

NMR(DMSO-d$_6$, ppm); 3.44(s, CH$_3$), 4.79(dd, J=5, 9 Hz, C$_3$—H), 5.02(s, —CH$_2$—), 5.05(d, J=5 Hz, C$_4$—H), 5.20(broad s, 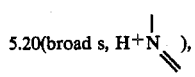), 7.33(s, arom H), 7.90(d, J=9 Hz, NH),

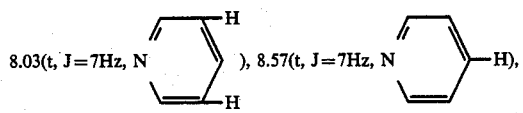

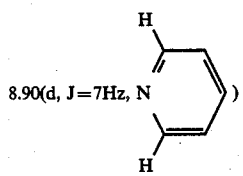

EXAMPLE 7B

To a solution of 0.201 g of (3S)-4-azido-3-[2-(2-chloroacetamidothiazol-4-yl)-2-methoxyiminoacetamido]-2-oxoazetidine (syn-isomer, cis-trans mixture) in 3 ml of DMF is added 0.16 g of sulfuric anhydride-pyridine complex and the reaction is carried out for 30 days. The same procedure as in Example 1B yields 0.023 g of sodium (3S)-4-azido-3-[2-(2-chloroacetamidothiazol-4-yl)-2-methoxyiminoacetamido]-2-oxoazetidine-1-sulfonate (syn-isomer, cis-trans mixture).

IR $\nu_{max}^{KBr}$cm$^{-1}$; 3420, 3275(shoulder), 2110, 1774, 1670, 1275, 1050.

NMR(DMSO-d$_6$, ppm); 3.88(s, CH$_3$), 4.13(s, —CH$_2$—), 4.53 (dd, J=2, 8 Hz, trans C$_3$—H), 5.19(d, J=2 Hz, trans C$_4$—H), 5.19(dd, J=4, 8 Hz, cis C$_3$—H), 5.42(d, J=4 Hz, cis C$_4$—H), 7.40(s, cis 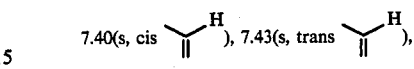

9.45(d, J=8 Hz, cis NH), 9.48(d, J=8 Hz, trans NH), 12.70(s, NH).

EXAMPLE 8B

To a solution of 0.233 g of (3R,4R)-3-[2-(2-chloroacetamidothiazol-4-yl)-2-methoxyiminoacetamido]-4-methylsulfonyl-2-oxoazetidine (mixture of syn- and anti-isomer) in 3 ml of DMF is added 0.18 g of sulfuric anhydride-pyridine complex and the reaction is carried out for 22 days. The same procedure as in Example 1B yields 0.023 g of sodium (3R,4R)-3-[2-(2-chloroacetamidothiazol-4-yl)-2-methoxyiminoacetamido]-4-methylsulfonyl-2-oxoazetidine-1-sulfonate (syn-isomer).

IR $\nu_{max}^{KBr}$cm$^{-1}$; 3450–3400, 1785, 1685, 1672, 1280, 1260, 1052.

NMR(DMSO-d$_6$, ppm); 3.84(s, CH$_3$), 4.33(s, —CH$_2$—), 5.15 (d, J=5 Hz, C$_4$—H), 5.71(dd, J=5, 9 Hz, C$_3$—H), 7.53(s, 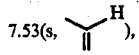), 9.45(d, J=9 Hz, NH), 12.88(s, NH).

Further purification by column chromatography yields 0.023 g of anti-isomer.

IR $\nu_{max}^{KBr}$cm$^{-1}$; 3450–3400, 1785, 1675, 1285, 1260, 1052.

NMR(DMSO-d$_6$, ppm); 3.98(s, CH$_3$), 4.33(s, —CH$_2$—), 5.20(d, J=6 Hz, C$_4$—H), 5.78(dd, J=6, 10 Hz, C$_3$—H), 7.83(s, 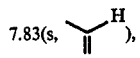), 8.35(d, J=10 Hz, NH), 12.77(s, NH).

EXAMPLE 9B

To a solution of 0.201 g of (3R,4S)-4-ethylthio-3-phenoxyacetamido-2-oxoazetidine in 3 ml of DMF is added 0.226 g of sulfuric anhydride-pyridine complex and the reaction is carried out for 5 days. The same procedure as Example 1B yields 0.084 g of sodium (3R,4S)-4-ethylthio-3-phenoxyacetamido-2-oxoazetidine-1-sulfonate.

IR $\nu_{max}^{KBr}$cm$^{-1}$; 3425, 1765, 1670, 1240, 1050.

NMR(DMSO-d$_6$, ppm); 1.18(t, J=7 Hz, CH$_3$), 2.62–2.90(m, —CH$_2$—), 4.55(s, —CH$_2$—), 4.70(dd, J=3, 9 Hz, C$_3$—H), 4.94 (d, J=3 Hz, C$_4$—H), 6.88–7.44(m, arom H), 9.04(d, J=9 Hz, NH).

EXAMPLE 10B

A solution of 0.128 g of (3R,4R)-4-ethylthio-3-phenoxyacetamido-2-oxoazetidine in 3 ml of DMF is added 0.145 g of sulfuric anhydride-pyridine complex and the reaction is carried out for 4 days. Then, 30 ml of diethyl ether is added and the oil that separates out thereon is washed with diethyl ether to give crystals. To a solution of this pyridinium salt in 20 ml of water is added Dowex 50W-Na resin and the mixture is stirred for 30 minutes. The resin is filtered off and the filtrate is lyophilized. The above procedure yields 0.115 g of sodium (3R,4R)-4-ethylthio-3-phenoxyacetamido-2-oxoazetidine-1-sulfonate.

IR $\nu_{max}^{KBr}$cm$^{-1}$; 3400, 3325, 1760, 1665, 1240, 1058.
NMR(d$_6$-DMSO, ppm); 1.16(t, J=7 Hz, CH$_3$), 2.73(q, J=7 Hz, —CH$_2$—), 4.57(s, —CH$_2$—), 5.12–5.38(m, C$_3$—H, C$_4$—H), 6.88–7.46(m, arom H), 8.83(d, J=9 Hz, NH).

EXAMPLE 11B

To a solution of 0.30 g of (3R,4R)-4-methylsulfinyl-3-phenoxyacetamido-2-oxoazetidine in 4 ml of DMF is added 0.338 g of sulfuric anhydride pyridine-complex and the reaction is carried out for 3 days. The same procedure as Example 1B yields 6 mg of sodium (3S,4R)-4-methylsulfinyl-3-phenoxyacetamido-2-oxoazetidine-1-sulfonate.

IR $\nu_{max}^{KBr}$cm$^{-1}$; 3500–3400, 1780, 1765, 1520, 1300–1200, 1055, 1020.

EXAMPLE 12B

To a solution of 0.220 g of (3S,4S)-4-acetoxy-3-[2-(2-aminothiazol-4-yl)-2-methoxyiminoacetamino]-2-oxoazetidine (syn-isomer) in 4 ml of DMF is added 0.430 g of sulfuric anhydride-pyridine and the reaction is carried out for 10 days. The same procedure as Example 1B yields 0.089 g (syn-isomer) and 36.2 mg (anti-isomer) of disodium (3S,4S)-4-acetoxy-3-[2-(2-sulfonatoaminothiazol-4-yl)-2-methoxyiminoacetamido]-2-oxoazetidine-1-sulfonate.

Syn-isomer

IR $\nu_{max}^{KBr}$cm$^{-1}$; 3450, 3230, 1782, 1665, 1512, 1232, 1045.

NMR(DMSO-d$_6$, ppm); 2.08(s, CH$_3$), 3.87(s, CH$_3$), 4.75(dd, J=2, 8 Hz, C$_3$—H), 6.09(d, J=2 Hz, C$_4$—H), 6.97(s, 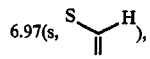), 9.46(d, J=8 Hz, NH), 10.00(broad s, NH).

Anti-isomer

IR $\nu_{max}^{KBr}$cm$^{-1}$; 3450, 3260, 1778, 1660, 1512, 1228, 1040.

NMR(DMSO-d$_6$, ppm); 2.05(s, CH$_3$), 3.99(s, CH$_3$), 4.73(dd, J=2, 8 Hz, C$_3$—H), 6.23(d, J=2 Hz, C$_4$—H), 7.58(s, 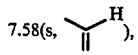), 9.40 (d, J=8 Hz, NH), 9.70(broad s, NH).

Further purification by column chromatography yields 34.1 mg of sodium (3S,4S)-4-acetoxy-3-[2-(2-sulfonatoaminothiazol-4-yl)-2-methoxyiminoacetamido]-2-oxoazetidine (syn-isomer).

IR $\nu_{max}^{KBr}$cm$^{-1}$; 3400, 3250, 1775, 1660, 1522, 1230, 1040.

NMR(DMSO-d$_6$, ppm); 2.09(s, CH$_3$), 3.88(s, CH$_3$), 4.70(dd, J=2, 8 Hz, C$_3$—H), 5.80(d, J=2 Hz, C$_4$—H), 6.97(s, 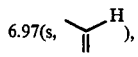), 9.17(s, NH), 9.28(d, J=8 Hz, NH), 9.96(broad s, NH).

EXAMPLE 13B

To a solution of 0.432 g of (3S,4S)-4-acetoxy-3-[2-(2-chloroacetamidothiazol-4-yl)-2-isopropoxyiminoacetamido]-2-oxoazetidine in 4 ml of DMF is added 0.318 g of sulfuric anhydride-pyridine complex and the reaction is carried out for 10 days. The same procedure as Example 1B yields 0.306 g of sodium (3S,4S)-4-acetoxy-3-[2-(2-chloroacetamidothiazol-4-yl)-2-isopropoxyiminoacetamido]-2-oxoazetidine-1-sulfonate.

IR $\nu_{max}^{KBr}$cm$^{-1}$; 3420, 3270, 1780, 1760, 1668, 1540, 1280–1230, 1042.

NMR(DMSO-d$_6$, ppm); 1.22(d, J=6 Hz, CH$_3$), 2.06(s, CH$_3$), 4.10–4.50(m, —CH—), 4.36(s, —CH$_2$—), 4.77(dd, J=2, 8 Hz, C$_3$—H), 6.13(d, J=2 Hz, C$_4$—H), 7.34(1H, s, 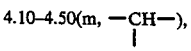), 9.33 (d, J=8 Hz, NH), 12.80(broad s, NH).

EXAMPLE 14B

To a solution of 0.250 g of sodium (3S,4S)-4-acetoxy-3-[2-(2-chloroacetamidothiazol-4-yl)-2-isopropoxyiminoacetamido]-2-oxoazetidine-1-sulfonate in 4 ml of water is added 73 mg of sodium monomethyldithiocarbamate under ice-cooling and the mixture is stirred at room temperature for one hour. The insolubles are filtered off and the filtrate is purified on a column of XAD-II. The above procedure gives 0.153 g of sodium (3S,4S)-4-acetoxy-3-[2-(2-aminothiazol-4-yl)-2-isopropoxyiminoacetamido]-2-oxoazetidine-1-sulfonate.

IR $\nu_{max}^{KBr}$cm$^{-1}$; 3420–3325, 1785, 1665, 1615, 1515, 1280, 1240, 1068, 1040.

NMR(DMSO-d$_6$, ppm); 1.20(d, J=6 Hz, CH$_3$), 2.06(s, CH$_3$), 4.28(heptet, J=6Hz, —CH—), 4.73(dd, J=2, 8 Hz, C$_3$—H), 6.12(d, J=2 Hz, C$_4$—H), 6.67(s, 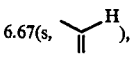), 7.14(s, NH$_2$), 9.21 (d, J=8 Hz, NH).

EXAMPLE 15B

To a solution of 0.50 g of (3S,4S)-4-acetoxy-3-[D-2-(4-ethyl-2,3-dioxo-1-piperazinecarboxamino)-2-phenylacetamido]-2-oxoazetidine in 1 ml of DMF is added 0.32 g of sulfuric anhydride-pyridine complex and the reaction is carried out for 6 days. The same procedure as Example 1B yields 0.19 g of sodium (3,4S)-4-acetoxy-3-[D-2-(4-ethyl-2,3-dioxo-1-piperazinecarboxamido)-2-phenylacetamido]-2-oxoazetidine-1-sulfonate.

IR $\nu_{max}^{KBr}$ cm$^{-1}$; 1780, 1705, 1670, 1510, 1280, 1240, 1180, 1060, 1040.

NMR[D$_2$O (external standard), ppm]; 1.20(t, J=7 Hz, CH$_3$), 2.20(s, CH$_3$), 3.50(q, J=7 Hz, —CH$_2$—), 3.68(m, —CH$_2$—), 3.98(m, —CH$_2$—), 4.80(d, J=2 Hz, C$_3$—H), 5.50(s, —CH—),
|

6.30(d, J=2 Hz, C$_4$—H), 7.50(s, arom H).

EXAMPLE 16B

To a solution of 0.415 g of (3S,4S)-3-[D-2-(4-ethyl-2,3-dioxo-1-piperazinecarboxamino)-2-phenylacetamido]-4-methylthio-2-oxoazetidine in 1.5 ml of DMF is added 0.32 g of sulfuric anhydride-pyridine complex and the reaction is carried out for 6 days. The same procedure as Example 1B yields 0.065 g of sodium (3R,4S)-3-[D-2-(4-ethyl-2,3-dioxo-1-piperazinecarboxamido)-2-phenylacetamido]-4-methylthio-2-oxoazetidine-1-sulfonate.

IR $\nu_{max}^{KBr}$ cm$^{-1}$; 1760, 1700, 1665, 1505, 1240, 1045.

NMR(DMSO-d$_6$, ppm); 1.10(t, J=6 Hz, CH$_3$), 2.02(s, SCH$_3$), 3.62(m, —CH$_2$—), 3.90(m, —CH$_2$—), 4.80(dd, J=2, 8 Hz, C$_3$—H), 5.42(d, J=6Hz, —CH—).
|

5.80(d, J=2 Hz, C$_4$—H), 7.40(s, arom H), 9.18(d, J=8 Hz, NH), 9.70(d, J=6 Hz, NH).

EXAMPLE 17B

To a solution of 0.44 g of (3S,4S)-4-azido-3-[D-2-(4-ethyl-2,3-dioxo-1-piperazinecarboxamido)-2-phenylacetamido]-2-oxoazetidine in 1.5 ml of DMF is added 0.4 g of sulfuric anhydride-pyridine complex and the reaction is carried out for 5 days. The same procedure as Example 1B yields 0.060 g of sodium (3S,4R)-4-azido-3-[D-2-(4-ethyl-2,3-dioxo-1-piperazinecarboxamido)-2-phenylacetamido]-2-oxoazetidine-1-sulfonate.

IR $\nu_{max}^{KBr}$ cm$^{-1}$; 2110, 1780, 1710, 1680, 1515, 1260, 1050.

NMR(DMSO-d$_6$, ppm); 1.10(t, J=6 Hz, CH$_3$), 3.56(m, —CH$_2$—), 3.90(m, —CH$_2$—), 4.44(dd, J=2, 8 Hz, C$_3$—), 5.10(d, J=2 Hz, C$_4$—H), 5.44(d, J=6Hz, —CH—),
|

7.38(s, arom H), 9.28(d, J=8 Hz, NH), 9.76(d, J=6 Hz, NH).

EXAMPLE 18B

To a solution of 0.50 g of (3S,4S)-4-acetoxy-3-benzyloxycarboxamido-2-oxoazetidine in 3 ml of DMF is added 3.75 ml of DMF at −70° C. and the reaction is carried out under ice-cooling for 10 hours. After addition of 0.285 g of pyridine, the same procedure as Example 1B yields 0.481 g of sodium (3S,4S)-4-acetoxy-3-benzyloxycarboxamido-2-oxoazetidine-1-sulfonate.

IR $\nu_{max}^{KBr}$ cm$^{-1}$; 3380, 1782, 1760, 1710, 1512, 1255, 1070, 1045.

NMR(DMSO-d$_6$, ppm); 2.05(s, CH$_3$), 4.45(dd, J=1, 9 Hz, C$_3$—H), 5.07(s, —CH$_2$—), 6.13(d, J=1 Hz, C$_4$—H), 7.40(s, arom H), 8.21(d, J=9 Hz, NH).

EXAMPLE 19B

To a solution of 0.214 g of (3S,4S)-4-acetoxy-1-t-butyldimethylsilyl-3-phenylacetamido-2-oxoazetidine in 3 ml of DMF is added a solution of 0.175 g of sulfuric anhydride-DMF complex in 1.19 ml of DMF at −70° C. and the reaction is carried out at −5° to 5° C. for 2 days. After addition of 0.091 g of pyridine, the same procedure as Example 1B yields 0.163 g of sodium (3S,4S)-4-acetoxy-3-phenylacetamido-2-oxoazetidine-1-sulfonate.

IR $\nu_{max}^{KBr}$ cm$^{-1}$; 3450-3370, 1785, 1760, 1662, 1528, 1280, 1240, 1068, 1043.

NMR(DMSO-d$_6$, ppm); 2.03(s, CH$_3$), 3.46(s, —CH$_2$—), 4.63(dd, J=2, 9 Hz, C$_3$—H), 6.10(d, J=2 Hz, C$_4$—H), 7.30(s, arom H), 8.96(d, J=9 Hz, NH).

EXAMPLE 20B

To a solution of 0.156 g of (3S,4S)-4-acetoxy-1-t-butyldimethylsilyl-3-(2-bromo-2-phenylacetamido)-2-oxoazetidine in 2 ml of DMF is added a solution of 0.105 g of sulfuric anhydride-DMF complex in 0.71 ml of DMF at −70° C. and the reaction is carried out at −5° to 5° C. for 2 days. After addition of 0.055 g of pyridine, the same procedure as Example 1B yields 0.06 g of sodium (3S,4S)-4-acetoxy-3-(2-bromo-2-phenylacetamido)-2-oxoazetidine-1-sulfonate.

IR $\nu_{max}^{KBr}$ cm$^{-1}$; 3425, 3275, 1785, 1672, 1520, 1280, 1235, 1070, 1042.

NMR(DMSO-d$_6$, ppm); 2.03(s, C$_3$), 4.65, 4.68(each dd, J=1, 8 Hz, C$_3$—H), 5.60(s, —CH—),
|

6.08, 6.13(each d, J=1 Hz, C$_4$—H), 7.26–7.70(m, arom H), 9.37(d, J=8 Hz, NH).

EXAMPLE 21B

To a solution of 0.10 g of sodium (3S,4S)-4-acetoxy-3-benzyloxycarboxamido-2-oxoazetidine-1-sulfonate in 5 ml of water are added 0.016 g of acetic acid and 0.05 g of palladium black and the mixture is stirred in a hydrogen gas stream for 40 minutes. The catalyst is filtered off and the filtrate is lyophilized. The above procedure yields 0.060 g of sodium (3S,4S)-4-acetoxy-3-amino-2-oxoazetidine-1-sulfonate monoacetate.

IR $\nu_{max}^{KBr}$ cm$^{-1}$; 3450, 3270, 1778, 1740, 1670, 1638, 1238, 1042.

NMR(DMSO-d$_6$, ppm); 2.03(s, CH$_3$), 3.81(d, J=1 Hz, C$_3$—H), 5.82(d, J=1 Hz, C$_4$—H).

EXAMPLE 22B

To a solution of 0.70 g of (3R,4R)-3-(benzothiazol-2-yl)dithio-3-phenoxyacetamido-2-oxoazetidine in 3 ml of DMF is added 0.8 g of sulfuric anhydride-pyridine complex and the reaction is carried out for 4 days. The same procedure as Example 1B yields 0.61 g of sodium (3R,4R)-4-(benzothiazol-2yl)dithio-3-phenoxyacetamido-2-oxoazetidine-1-sulfonate.

IR $\nu_{max}^{KBr}$cm$^{-1}$; 1768, 1670, 1520, 1280, 1240, 1052.

EXAMPLE 23B

To a solution of 0.446 g of (3S,4S)-4-acetoxy-3-[2-(benzothiophen-3yl)-2-(2-oxoimidazolidin-1-yl-carboxamido]-2-oxoazetidine in 3 ml of DMF is added at −70° C. a solution of 0.306 g of sulfuric anhydride-DMF complex in 2.09 ml of DMF, and the reaction is carried out at 0° C. for 2 days. After addition of 0.159 g of pyridine, the same procedure as Example 1B yields 0.141 g of disodium(3S,4S)-4-acetoxy-3-[2-(benzothiophen-3-yl)-2-(2-oxo-3-sulfonatoimidazolidin-1-yl-carboxamido)]-2-oxoazetidine-1-sulfonate.

IR $\nu_{max}^{KBr}$cm$^{-1}$; 3275, 1775, 1710, 1660, 1525, 1270–1220, 1041.

NMR(DMSO-d$_6$, ppm); 2.04(s, CH$_3$), 3.62(m, —CH$_2$—), 4.66, 4.70(each dd, J=2, 8 Hz, C$_3$—H), 5.84, 5.86(each d, J=8Hz, —CH—), 6.03, 6.15(each d, J=2 Hz, C$_4$—H), 7.30–8.10(m, arom H), 8.82, 8.91(each d, J=8 Hz, NH), 9.27 9.30(each d, J=8 Hz, NH).

Further, 0.162 g of sodium(3S,4S)-4-acetoxy-3-[2-(benzothiophen-3-yl)-2-(2-oxoimidazolidin-1-yl-carboxamido)]-2-oxoazetidine-1-sulfonate is obtained.

IR $\nu_{max}^{KBr}$cm$^{-1}$; 3450, 3310, 1780, 1710, 1668, 1520, 1250, 1045.

EXAMPLE 24B

To a solution of 0.30 g of (3S)-4-azido-3-[2-(benzothiophen-3-yl)-2-(2-oxoimidazolidin-1-yl-carboxamido]-2-oxoazetidine in 3 ml of DMF is added at −70° C. a solution of 0.322 g of sulfuric anhydride-DMF complex in 2.19 ml of DMF, and the reaction is carried out at 0° C. for 3 days. After addition of 0.167 g of pyridine, the same procedure as Example 1B yields 0.0732 g of disodium(3S)-4-azido-3-[2-(benzothiophen-3yl)-2-(2-oxo-3-sulfonatoimidazolidin-1-ylcarboxamido)]-2-oxoazetidine-1-sulfonate.

IR $\nu_{max}^{KBr}$cm$^{-1}$; 3500–3400, 3300, 2103, 1772, 1705, 1658, 1520, 1260–1225, 1050.

Further, 0.056 g of sodium(3S)-4-azido-3-[2-(benzothiophen-3-yl)-2-(2-oxoimidazolidin-1-ylcarboxamido)]-2-oxoazetidine-1-sulfonate is obtained.

IR $\nu_{max}^{KBr}$cm$^{-1}$; 3275, 2102, 1770, 1710, 1660, 1520, 1255, 1048.

EXAMPLE 25B

To a solution of 0.349 g of (3S)-4-azido-3-[2-(2-chloroacetamidothiazol-4-yl)-2-isopropoxyiminoacetamido]-2-oxoazetidine in 3 ml of DMF is added at −70° C. a solution of 0.322 g of sulfuric anhydride-DMF complex in 2.2 ml of DMF, and the reaction is carried out at 0° C. for 2 days. After addition of 0.17 g of pyridine, the same procedure as Example 1B yields 0.254 g of sodium (3S)-4-azido-3-[2-(2-chloroacetamidothiazol-4-yl)-2-isopropoxyiminoacetamido]-2-oxoazetidine-1-sulfonate.

IR $\nu_{max}^{KBr}$cm$^{-1}$; 3490–3380, 3275, 2120, 1778, 1670, 1542, 1275, 1050.

NMR(DMSO-d$_6$, ppm); 1.25(d, J=6 Hz, CH$_3$), 4.16(trans), 4.36(cis), (each s, —CH$_2$—), 4.30–4.50(m, —CH—), 4.61 (dd, J=2, 8 Hz, trans C$_3$—H), 5.21(d, J=2 Hz, trans, C$_4$—H), 5.23(dd, J=4, 8 Hz, cis C$_3$—H), 5.48(d, J=4 Hz, cis C$_4$—H), 7.41(cis), 7.44(trans),

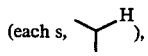
(each s, 9.34(trans), 9.38(cis), (each d, J=8 Hz, NH), 12.72(cis), 12.86 (trans), (each s, NH).

EXAMPLE 26B

To a solution of 0.22 g of (3S,4R)-3-[2-(2-chloroacetamidothiazol-4-yl)-2-methoxyiminoacetamido]-4-phenylacetoxy-2-oxoazetidine in 2 ml of DMF is added at −70° C. a solution of 0.24 g of sulfuric anhyride-DMF complex in 0.96 ml of DMF, and the reaction is carried out at 0° C. for 17 days. After addition of 0.109 g of pyridine, the same procedure as Example 1B yields 0.186 g of sodium (3S,4R)-3-[2-(2-chloroacetamidothiazol-4-yl)-2-methoxyiminoacetamido]-4-phenylacetoxy-2-oxoazetidine-1-sulfonate.

IR $\nu_{max}^{KBr}$cm$^{-1}$; 3400, 3275, 1780, 1750, 1670, 1540, 1278, 1250, 1042.

NMR(DMSO-d$_6$, ppm): 3.67(ABq, J=5, 9 Hz, —CH$_2$—), 3.87(s, CH$_3$), 4.36(s, —CH$_2$—), 5.42(dd, J=4, 9 Hz, C$_3$—H), 6.37 (d, J=4 Hz, C$_4$—H), 7.25(s, arom H),

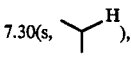
7.30(s, 9.42 (d, J=9 Hz, NH), 12.86(s, NH).

EXAMPLE 27B

To a solution of 0.10 g of sodium (3S,4R)-3-[2-(2-chloroacetamidothiazol-4-yl)-2-methoxyiminoacetamido]-4-phenylacetoxy-2-oxoazetidine-1-sulfonate in 7 ml of water is added under ice-cooling 0.027 g of sodium monomethyldithiocarbamate, and the mixture is stirred at room temperature for 1.5 hours. Insolubles are filtered off, and the filtrate is purified on an XAD-II column to yield 0.044 g of sodium (3S,4R)-3-[2-(2-aminothiazol-4-yl)-2-methoxyiminoacetamido]-4-phenylacetoxy-2-oxoazetidine-1-sulfonate.

IR $\nu_{max}^{KBr}$cm$^{-1}$; 3420, 3320, 1790, 1740, 1663, 1522, 1275, 1248, 1048.

NMR(DMSO-d$_6$, ppm); 3.87(ABq, J=11, 14 Hz, —CH$_2$—), 3.92 (s, CH$_3$), 5.38(dd, J=4, 9 Hz, C$_3$—H), 6.34(d, J=4 Hz, C$_4$—H),

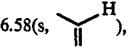
6.58(s, 7.15(s, NH), 7.25(s, arom H), 9.32(d, J=9 Hz, NH).

EXAMPLE 28B

To a solution of 0.294 g of (3R,4R)-4-acetylthio-3-phenoxyacetamido-2-oxoazetidine in 3 ml of DMF is added at −70° C. a solution of 0.459 g of sulfuric anhydride-DMF complex in 3.12 ml of DMF, and the reaction is carried out at 0° C. for 2 days. To the reaction mixture are added 0.24 g of pyridine and then 20 ml of ether, and the oily substance that separates out thereon is washed twice with ether, followed by addition of ethanol thereto. The resulting crystals (pyridinium salt) are collected by filtration. The crystals are suspended in water, and the suspension is treated with Dowex 50W-Na resin (Dow & Chemicals). The filtrate is lyophilized. The above procedure yields 0.326 g of sodium (3R,4R)-4-acetylthio-3-phenoxyacetamido2-oxoazetidine-1-sulfonate.

IR $\nu_{max}^{KBr}$cm$^{-1}$; 3390, 1770, 1690, 1522, 1240, 1052.

NMR(DMSO-d$_6$, ppm); 2.27(s, CH$_3$), 4.54(s, —CH$_2$—), 5.28 (dd, J=5, 9 Hz, C$_3$—H), 5.70(d, J=5 Hz, C$_4$—H), 6.85–7.47(m, arom H), 8.90(d, J=9 Hz, NH).

EXAMPLE 29B

To a solution of 0.267 g of (3R,4R)-4-acetylthio-3-[D-2-(4-ethyl-2,3-dioxo-1-piperiazinecarboxamido)-2-phenylacetamido]-2-oxoazetidine in 3 ml of DMF is added at −70° C. a solution of 0.26 g of sulfuric anhydride-DMF complex in 1.81 g of DMF, and the reaction is carried out at 0° C. for 2 days. After addition of 0.138 g of pyridine, the same procedure as Example 1 yields 0.302 g of sodium (3R,4R)-4-acetylthio-3-[D-2-(4-ethyl-2,3-dioxo-1-piperazinecarboxamido)-2-phenylacetamido]-2-oxoazetidine-2-sulfonate.

IR $\nu_{max}^{KBr}$cm$^{-1}$; 3390, 3280, 1768, 1708, 1670, 1505, 1275, 1250, 1182, 1045.

NMR(DMSO-d$_6$, ppm); 1.09(t, J=7 Hz, CH$_3$), 1.96(s, CH$_3$), 3.25–3.70(m, —CH$_2$—), 3.38(q, J=7 Hz, —CH$_2$—), 3.82–4.00(m, —CH$_2$—), 5.33(dd, J=5, 8 Hz, C$_3$—H), 5.43(d, J=7Hz, —CH—), 5.49(d, J=5 Hz, C$_4$—H), 7.38(s, arom H), 9.20(d, J=8 Hz, NH), 9.78 (d, J=7 Hz, NH).

EXAMPLE 30B

To a solution of 0.30 g of (3R,4S)-4-acetylthio-3-[D-2-(4-ethyl-2,3-dioxo-1-piperiazinecarboxamido)-2-phenylacetamido]-2-oxoazetidine in 3 ml of DMF is added at −70° C. a solution of 0.248 g of sulfuric anhydrid-DMF complex in 1.69 ml of DMF, and the reaction is carried out at 0° C. for 2 days. After addition of 0.129 g of pyridine, the same procedure as Example 1B yields 0.305 g of sodium (3R,4S)-4-acetylthio-3-[D-2-84-ethyl-2,3-dioxo-1-piperazinecarboxamido)-2-phenylacetamido]-2-oxoazetidine-1-sulfonate.

IR $\nu_{max}^{KBr}$cm$^{-1}$; 3460, 3280, 1772, 1708, 1675, 1508, 1278, 1255, 1180, 1048.

NMR(DMSO-d$_6$, ppm); 1.09(t, J=7 Hz, CH$_3$), 2.31(s, CH$_3$), 3.39(q, J=7 Hz, —CH$_2$—), 3.42–3.70(m, —CH$_2$—), 3.80–4.02 (m, —CH$_2$—), 4.78(dd, J=3, 8 Hz, C$_3$—H), 5.23(d, J=3 Hz, C$_4$—H), 5.43(d, J=7Hz, —CH—), 7.38(s, arom H), 9.38(d, J=8 Hz, NH), 9.75(d, J=7 Hz, NH).

EXAMPLE 31B

To a solution of 0.25 g of (3R,4R)-4-acetylthio-3-[2-(2-chloroacetamidothiazol-4-yl)-2-methoxyiminoacetamido]-2-oxoazetidine in 3 ml of DMF is added at −70° C. a solution of 0.227 g of sulfuric anhydride-DMF complex in 1.56 ml of DMF, and the reaction is carried out at 0° C. for 3 days. After addition of 0.12 g of pyridine, the same procedure as Example 1B yields 0.208 g of sodium (3R,4R)-4-acetylthio-3-[2-(2-chloroacetamidothiazol-4-yl)-2-methoxyiminoacetamido]-2-oxoazetidine-1-sulfonate.

IR $\nu_{max}^{KBr}$cm$^{-1}$; 3460, 3270, 1770, 1665, 1538, 1260, 1045.

NMR(DMSO-d$_6$, ppm); 1.86(s, CH$_3$), 3.93(s, CH$_3$), 4.38(s, —CH$_2$—), 5.34(dd, J=5, 8 Hz, C$_3$—H), 5.87(d, J=5 Hz, C$_4$—H), 7.70(s, 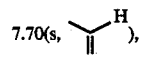), 8.65(d, J=8 Hz, NH), 12.94(broad s, NH).

EXAMPLE 32B

To a solution of 0.10 g of sodium (3R,4R)-4-acetylthio-3-[2-(2-chloroacetamidothiazol-4-yl)-2-methoxyiminoacetamido]-2-oxoazetidine-1-sulfonate in 5 ml of water is added under ice-cooling 0.030 g of sodium monomethyl dithiocarbamate, and the mixture is stirred for 3 hours at room temperature. The same procedure as Example 3B yields 0.016 of sodium (3R,4R)-4-acetylthio-3-[2-(2-aminothiazol-4-yl)-2-methoxyiminoacetamido]-2-oxoazetidine-1-sulfonate.

IR $\nu_{max}^{KBr}$cm$^{-1}$; 3400, 1770, 1668, 1522, 1270, 1245, 1050.

EXAMPLE 33B

To a solution of 0.30 g of (3R,4S)-4-acetylthio-3-[2-(2-chloroacetamidothiazol-4-yl)-2-methoxyiminoacetamido]-2-oxoazetidine in 3 ml of DMF is added at −70° C. a solution of 0.273 g of sulfuric anhydride-DMF complex in 1.86 ml of DMF, and the reaction is carried out at 0° C. for 2 days. After addition of 0.142 g of pyridine, the same procedure as Example 1B yields 0.22 g of sodium (3R, 4S)-4-acetylthio-3-[2-(2-chloroacetamidothiazol-4-yl)-2-methoxyiminoacetamido]-2-oxoazetidine-1-sulfonate.

IR $\nu_{max}^{KBr}$cm$^{-1}$; 3480, 3250, 1770, 1670, 1540, 1270, 1045.

NMR(DMSO-d$_6$, ppm); 2.37(s, CH$_3$), 3.89(s, CH$_3$), 4.36(s, —CH$_2$—), 4.95(dd, J=2, 8 Hz, C$_3$—H), 5.33(d, J=2 Hz, C$_4$—H), 7.44(s, 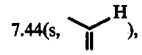), 9.54(d, J=8 Hz, NH), 12.86(broad s, NH).

EXAMPLE 34B

To a solution of 0.11 g of sodium (3R,4S)-4-acetylthio-3-[2-(2-chloroacetamidothiazol-4-yl)-2-methoxyiminoacetamido]-2-oxoazetidine-1-sulfonate in 5 ml of water is added under ice-cooling 0.036 g of sodium monomethyldithiocarbamate, and the mixture is stirred at room temperature for 2 hours. The same procedure as Example 3B yields 0.032 g of sodium (3R,4S)-4-acetylthio-3-[2-(2-aminothiazol-4-yl)-2-methoxyiminoacetamido]-2-oxoazetidine-1-sulfonate.

IR $\nu_{max}^{KBr}$cm$^{-1}$; 3410, 3315, 1768, 1665, 1515, 1270, 1245, 1045.

NMR(DMSO-d$_6$, ppm); 2.36(s, CH$_3$), 3.84(s, CH$_3$), 4.90(dd, J=2, 8 Hz, C$_3$—H), 5.33(d, J=2 Hz, C$_4$—H), 6.79(s, ), 7.16(s, NH), 9.42(d, J=8 Hz, NH).

EXAMPLE 35B

To a solution of 0.25 g of (3R,4R)-3-[D-2-(4-ethyl-2,3-dioxo-1-piperazinecarboxamido)-2-phenylacetamido]-4-methylsulfonyl-2-oxoazetidine in 3 ml of DMF is added at −70° C. a solution of 0.202 mg of sulfuric anhydride-DMF complex in 1.38 ml of DMF, and the reaction is carried out at 0° C. for 9 days. After addition of 0.158 g of pyridine, the same procedure as Example 1B yields 0.194 g of sodium (3R,4R)-3-[D-2-(4-ethyl-2,3-dioxo-1-piperazinecarboxamido)-2-phenylacetamido]-4-methylsulfonyl-2-oxoazetidine-1-sulfonate.

IR $\nu_{max}^{KBr}$cm$^{-1}$; 3420, 3290, 1780, 1705, 1670, 1505, 1280, 1252, 1050.

NMR(DMSO-d$_6$, ppm); 1.10(t, J=7 Hz, CH$_3$), 2.95(s, CH$_3$) 3.40(q, J=7 Hz, —CH$_2$—), 3.50–3.72(m, —CH$_2$—), 3.80–4.02 (m, —CH$_2$—), 5.08(d, J=5 Hz, C$_4$—H), 5.67(dd, J=5, 9 Hz, C$_3$—H), 5.75(d, J=7Hz, 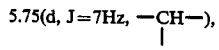), 7.22–7.50(m, arom H), 9.06(d, J=9 Hz, NH), 9.74(d, J=7 Hz, NH).

EXAMPLE 36B

To a solution of 0.15 g of sodium (3R,4R)-3-[2-(2-chloroacetamidothiazol-4-yl)-2-methoxyiminoacetamido)]-4-methylsulfonyl-2-oxoazetidine-1-sulfonate in 5 ml of water is added under ice-cooling 0.044 g of sodium monomethyldithiocarbamate, and the mixture is stirred at room temperature for 70 minutes. The same procedure as Example 3B yields 0.078 g of sodium (3R,4R)-3-[2-(2-aminothiazol-4-yl)-2-methoxyiminoacetamido)]-4-methylsulfonyl-2-oxoazetidine-1-sulfonate.

IR $\nu_{max}^{KBr}$cm$^{-1}$; 3400, 3325, 1782, 1670, 1612, 1520, 1278, 1250, 1050.

NMR(DMSO-d$_6$, ppm); 3.16(s, CH$_3$), 3.82(s, CH$_3$), 5.16(d, J=5 Hz, C$_4$—H), 5.70(dd, J=5, 8 Hz, C$_3$—H), 6.98(s, ), 7.13(broad s, NH$_2$), 9.34(d, J=8 Hz, NH).

EXAMPLE 37B

To a solution of 0.341 g of (3R,4S)-4-methylthio-3-[2-(2-methylthioacetamidothiazol-4-yl)-2-methoxyiminoacetamido]-2-oxoazetidine in 2 ml of DMF is added at −70° C. a solution of 0.400 g of sulfuric anhydride-DMF complex in 2.7 ml of DMF, and the reaction is carried out at 0° C. for 2 days. After addition of 0.206 g of pyridine, the same procedure as Example 1B yields 0.246 g of sodium (3R,4S)-4-methylthio-3-[2-(2-methylthioacetamidothiazol-4-yl)-2-methoxyiminoacetamido]-2-oxoazetidine-1-sulfonate.

IR $\nu_{max}^{KBr}$cm$^{-1}$; 3425, 3250, 1765, 1658, 1540, 1280–1245, 1045.

NMR(DMSO-d$_6$, ppm); 2.17(s, CH$_3$), 2.22(s, CH$_3$), 3.38(s, —CH$_2$—), 3.90(s, OCH$_3$), 4.62(d, J=3 Hz, C$_4$—H), 4.87(d, J=3 Hz, C$_3$—H), 7.38(s, 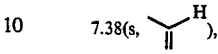),

EXAMPLE 38B

To a solution of 0.30 g of (3S,4S)-4-azido-3-[D-2-(4-ethyl-2,3-dioxo-1-piperazinecarboxamido)-2-thienylacetamido]-2-oxoazetidine in 2 ml of DMF is added at −70° C. a solution of 0.307 g of sulfuric anhydride-DMF complex in 1.18 ml of DMF, and the reaction is carried out at 0° C. for 2 days. After addition of 0.164 g of pyridine, the same procedure as Example 1B yields 0.272 g of sodium (3S,4R)-4-azido-3-[D-2-(4-ethyl-2,3-dioxo-1-piperazinecarboxamido)-2-thienylacetamido]-2-oxoazetidine-1-sulfonate.

IR $\nu_{max}^{KBr}$cm$^{-1}$; 3480, 3280, 2105, 1772, 1708, 1670, 1505, 1275, 1242, 1185, 1045.

NMR(DMSO-d$_6$, ppm); 1.09(t, J=7 Hz, CH$_3$), 3.40(q, J=7 Hz, —CH$_2$—), 3.52–3.68(m, —CH$_2$—), 3.86–4.04(m, —CH$_2$—), 4.47(dd, J=2, 8 Hz, C$_3$—H), 5.12(d, J=2 Hz, C$_4$—H), 5.72(d, J=8Hz, 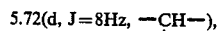), 6.96–7.54(m, arom H), 9.35(d, J=8 Hz, NH), 9.70(d, J=8 Hz, NH).

EXAMPLE 39B

To a solution of 0.25 g of (3S,4R)-4-azido-3-[D-2-(4-ethyl-2,3-dioxo-1-piperazinecarboxamido)-2-thienylacetamido]-2-oxoazeitidine in 2 ml of DMF is added a solution of 0.263 g of sulfuric anhydride-DMF complex in 0.99 ml in DMF, and the reaction is carried out at 0° C. for 3 days. After addition of 0.137 g of pyridine, the same procedure as Example 1B yields 0.244 g of sodium (3S,4S)-4-azido-3-[D-2-(4-ethyl-2,3-dioxo-1-piperazinecarboxamido)-2-thienylacetamido]-2-oxoazetidine-1-sulfonate.

IR $\nu_{max}^{KBr}$cm$^{-1}$; 3480, 3275, 2115, 1775, 1710, 1670, 1502, 1280–1245, 1185, 1048.

NMR(DMSO-d$_6$, ppm); 1.09(t, J=7 Hz, CH$_3$), 3.42(q, J=7 Hz, —CH$_2$—), 3.50–3.70(m, —CH$_2$—), 3.86–4.04(m, —CH$_2$—), 5.15(dd, J=5, 8 Hz, C$_3$—H), 5.44(d, J=5 Hz, C$_4$—H), 5.85(d, J=8Hz, 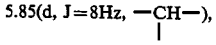), 6.94–7.50(m, arom H), 9.33(d, J=8 Hz, NH), 9.74(d, J=8 Hz, NH).

EXAMPLE 40B

To a solution of 0.40 g of (3R,4S)-3-[2-(2-chloroacetamidothiazol-4-yl)-2-methoxyiminoacetamido]-4-methylthio-2-oxoazetidine in 2 ml of DMF is added at −70° C. a solution of 0.468 g of sulfuric anhydride-DMF complex in 1.75 ml of DMF, and the reaction is carried out at 0° C. for 2 days. After addition of 0.243 g of pyridine, the same procedure as Example 1B yields 0.206 g of sodium (3R,4S)-3-[2-(2-chloroacetamidothiazol-4-yl)-2-methoxyiminoacetamido]-4-methylthio-2-oxoazetidine-1-sulfonate.

IR $\nu_{max}^{KBr}$cm$^{-1}$; 3450, 3250, 1765, 1668, 1540, 1260, 1042

NMR(DMSO-d$_6$, ppm); 2.22(s, CH$_3$), 3.90(s, OCH$_3$), 4.34(s, —CH$_2$—), 4.71(dd, J=2, 8 Hz, C$_3$—H), 4.79(d, J=2 Hz, C$_4$—H),

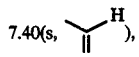

9.48(d, J=8 Hz, NH), 12.88(s, NH).

EXAMPLE 41B

To a solution of 0.15 g of the above-mentioned sodium (3R,4S)-3-[2-(2-chloroacetamidothiazol-4-yl)-2-methoxyiminoacetamido]-4-methylthio-2-oxoazetidine-1-sulfonate in 4 ml of water is added under ice-cooling 0.044 g of sodium monomethyldithiocarbamate, and the mixture is stirred for one hour at room temperature. The same procedure as Example 3B yields 0.057 g of sodium (3R,4S)-3-[2-(2-aminothiazol-4-yl)-2-methoxyiminoacetamido]-4-methylthio-2-oxoazetidine-1-sulfonate.

IR $\nu_{max}^{KBr}$cm$^{-1}$; 3410, 3320, 1765, 1665, 1528, 1250, 1050.

NMR(DMSO-d$_6$, ppm); 2.20(s, CH$_3$), 3.85(s, CH$_3$), 4.68(dd, J=2, 8 Hz, C$_3$—H), 4.74(d, J=2 Hz, C$_4$—H),

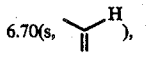

7.18 (broad s, NH$_2$), 9.36(d, J=8 Hz, NH).

EXAMPLE 42B

To a solution of 0.25 g of (3R,4S)-3-[D-2-(4-ethyl-2,3-dioxo-1-piperazinecarboxamido)-2-thienylacetamido]-4-methylthio-2-oxoazetidine in 2 ml of DMF is added at −70° C. a solution of 0.260 g of sulfuric anhydride-DMF complex in 0.98 ml of DMF, and the reaction is carried out at 0° C. for 3 days, After addition of 0.136 g of pyridine, the same procedure as Example 1B yields 0.157 g of sodium (3R,4S)-3-[D-2-(4-ethyl-2,3-dioxo-1-piperazinecarboxamido)-2-thienylacetamido]-4-methylthio-2-oxoazetidine-1-sulfonate.

IR $\nu_{max}^{KBr}$cm$^{-1}$; 3275, 1765, 1705, 1670, 1502, 1275, 1238, 1188, 1045.

NMR(DMSO-d$_6$, ppm); 1.10(t, J=7 Hz, CH$_3$), 2.15(s, CH$_3$), 3.40 (q, J=7 Hz, —CH$_2$—), 3.48–3.70(m, —CH$_2$—), 3.82–4.04(m, —CH$_2$—), 4.54–4.73(m, C$_3$—H, C$_4$—H),

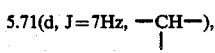

6.96–7.54(m, arom H), 9.40(d, J=9 Hz, NH), 9.72(d, J=7 Hz, NH).

EXAMPLE 43B

To a solution of 0.30 g of (3S,4S)-4-azido-3-[2-(2-chloroacetamidothiazol-4-yl)-2-methoxyiminoacetamido]-2-oxoazetidine in 2 ml of DMF is added at −70° C. a solution of 0.355 g of sulfuric anhydride-DMF complex in 1.33 ml of DMF, and the reaction is carried out at 0° C. for 2 days. After addition of 0.185 g of pyridine, the same procedure as Example 1B yields 0.269 g of sodium (3S,4R)-4-azido-3-[2-(2-chloroacetamidothiazol-4-yl)-2-methoxyiminodacetamido]-1-oxoazetidine-1-sulfonate.

IR $\nu_{max}^{KBr}$cm$^{-1}$; 3490, 3250, 2110, 1775, 1667, 1535, 1260, 1048.

NMR(DMSO-d$_6$, ppm); 3.91(s, CH$_3$), 4.36(s, —CH$_2$—), 4.57(dd, J=2, 8 Hz, C$_3$—H), 5.22(d, J=2 Hz, C$_4$—H),

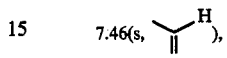

9.46(d, J=8 Hz, NH), 12.83(broad s, NH).

EXAMPLE 44B

To a solution of 0.30 g of (3S,4R)-4-azido-3-[2-(2-chloroacetamidothiazol-4-yl)-2-methoxyiminoacetamido]-2-oxoazetidine in 2 ml of DMF is added at −70° C. a solution of 0.356 g of sulfuric anhydride-DMF complex in 1.33 ml of DMF, and the reaction is carried out at 0° C. for 2 days. After addition of 0.185 g of pyridine, the same procedure as Example 1B yields 0.259 g of (3S,4S)-4-azido-3-[2-(2-chloroacetamidothiazol-4-yl)-2-methoxyiminoacetamido]-2-oxoazetidine-1-sulfonate.

IR $\nu_{max}^{KBr}$cm$^{-1}$; 3480, 3250, 2120, 1780, 1675, 1542, 1280, 1050.

NMR(DMSO-d$_6$, ppm); 3.90(s, CH$_3$), 4.36(s, —CH$_2$—), 5.22(dd, J=4, 8 Hz, C$_3$—H), 5.45(d, J=4 Hz, C$_4$—H),

9.49(d, J=8 Hz, NH).

EXAMPLE 45B

To a solution of 0.454 g of (3R,4S)-3-[2-(2-chloroacetamidothiazol-4-yl)-2-methoxyiminoacetamido]-4-phenylthio-2-oxoazetidine in 2 ml of DMF is added at −70° C. a solution of 0.459 g of sulfuric anhydride-DMF complex in 1.72 ml of DMF, and the reaction is carried out at 0° C. for 3 days. After addition of 0.238 g of pyridine, the same procedure as Example 1B yields 0.355 g of sodium (3R,4S)-3-[2-(2-chloroacetamidothiazol-4-yl)-2-methoxyiminoacetamido]-4-phenylthio-2-oxoazetidine-1-sulfonate.

IR $\nu_{max}^{KBr}$cm$^{-1}$; 3460, 3260, 1765, 1661, 1538, 1265, 1042.

EXAMPLE 46B

To a solution of 0.15 g of the above sodium (3R,4S)-3-[2-(2-chloroacetamidothiazol-4-yl)-2-methoxyiminoacetamido]-4-phenylthio-2-oxoazetidine-1-sulfonate in 4 ml of water is added under ice-cooling 0.039 g of sodium monomethyldithiocarbamate, and the mixture is stirred for 1.5 hours at room temperature. The procedure as Example 3B yields 0.064 g of sodium (3R,4S)-3-[2-(2-aminothiazol-4-yl)-2-methoxyiminoacetamido]-4-phenylthio-2-oxoazetidine-1-sulfonate.

IR $\nu_{max}^{KBr}$cm$^{-1}$; 3425, 3320, 1768, 1660, 1610, 1522, 1270, 1245, 1045.

EXAMPLE 47B

To a solution of 0.440 g of (3R,4R)-3-[D-2-(4-ethyl-2,3-dioxo-1-piperazinecarboxamido)-2-thienylacetamido]-4-methylthio-2-oxoazetidine in 2 ml of DMF is added at −70° C. a solution of 0.460 g of sulfuric anhydride-DMF complex in 3 ml of DMF, and the reaction is carried out at 0° C. for 48 hours. After addition of 0.5 ml of pyridine, the same procedure as Example 1B yields 0.154 g of sodium (3R,4R)-3-[D-2-(4-ethyl-2,3-dioxo-1-piperazinecarboxamido)-2-thienylacetamido]-4-methylthio-2-oxoazetidine-1-sulfonate.

IR $\nu_{max}^{KBr}$cm$^{-1}$; 1760, 1705, 1670, 1500, 1240, 1145.

NMR(DMSO-d$_6$, ppm); 1.10(t, J=4 Hz, CH$_3$), 1.93(s, SCH$_3$), 3.55(m, —CH$_2$—), 3.90(m, —CH$_2$—), 5.00(d, J=4 Hz, C$_4$—H), 5.26(dd, J=6, 4 Hz, C$_3$—H),

5.90(d, J=4Hz, —CH—), 6.90–7.53(m, arom H), 9.36(d, J=6 Hz, NH), 9.83(d, J=4 Hz, NH).

EXAMPLE 48B

To a solution of 0.470 g of (3R,4R)-3-[2-(2-chloroacetamidothiazol-4-yl)-2-methoxyiminoacetamido]-4-methylthio-2-oxoazetidine in 2 ml of DMF is added at −70° C. a solution of 0.550 g of sulfuric anhydride-DMF complex, and the reaction is carried out at 0° C. for 48 hours. After addition of 0.5 ml of pyridine, the same procedure as Example 1B yields 0.365 g of sodium (3R,4R)-3-[2-(2-chloroacetamidothiazol-4-yl)-2-methoxyiminoacetamido]-4-methylthio-2-oxoazetidine-1-sulfonate.

IR $\nu_{max}^{KBr}$cm$^{-1}$; 1765, 1670, 1540, 1260, 1045.

NMR(DMSO-d$_6$, ppm); 2.30(s, CH$_3$), 4.01(s, CH$_3$), 4.46(s, —CH$_2$—), 5.26(d, J=4 Hz, C$_4$—H), 5.50(d, J=4 Hz, C$_3$—H),

EXAMPLE 49B

To a solution of 0.250 g of sodium (3R,4R)-3-[2-(2-chloroacetamidothiazol-4-yl)-2-methoxyiminoacetamido]-4-methylthio-2-oxoazetidine-1-sulfonate in 8 ml of water is added under ice-cooling 0.078 g of sodium monomethyldithiocarbamate, and the mixture is stirred at room temperature for 1.5 hours. The same procedure as Example 3B yields 0.052 g of sodium (3R,4R)-3-[2-(2-aminothiazol-4-yl)-2-methoxyiminoacetamido]-4-methylthio-2-oxoazetidine-1-sulfonate.

IR $\nu_{max}^{KBr}$cm$^{-1}$; 1760, 1665, 1615, 1525, 1260, 1045.

NMR(DMSO-d$_6$ and D$_2$O, ppm); 2.30(s, CH$_3$), 3.96(s, —CH$_2$—), 5.23(d, J=4 Hz, C$_4$—H), 5.43(d, J=4 Hz, C$_3$—H),

EXAMPLE 50B

To a solution of 0.500 g of (3R,4R)-3-[3-(2,6-dichlorophenyl)-5-methyl-4-isoxazolylcarboxamido]-4-methylthio-2-oxoazetidine in 2 ml of DMF is added at −70° C. a solution of 0.643 g of sulfuric anhydride-DMF complex in 2.4 ml of DMF, and the reaction is carried out at 0° C. for 18 hours. After addition of 0.5 ml of pyridine, the same procedure as Example 1B yields 0.270 g of sodium (3R,4R)-3-[3-(2,6-dichlorophenyl)-5-methyl-4-isoxazolylcarboxamido]-4-methylthio-2-oxoazetidine-1-sulfonate.

IR $\nu_{max}^{KBr}$cm$^{-1}$; 1760, 1660, 1595, 1500, 1250.

NMR(DMSO-d$_6$, ppm); 2.16(s, CH$_3$), 2.75(s, CH$_3$), 5.02(d, J=4 Hz, C$_4$—H), 5.30(dd, J=4, 8 Hz, C$_3$—H), 7.56(s, arom H), 8.74(d, J=8 Hz, NH).

EXAMPLE 51B

To a solution of 0.558 g of (3R,4S)-3-[2-(2-chloroacetamidothiazol-4-yl)-2-methoxyiminoacetamido]-4-(1-methyl-1H-tetrazol-5-yl)thio-2-oxoazetidine in 5 ml of DMF is added at −70° C. a solution of 0.268 g of sulfuric anhydride-DMF complex in 2.0 ml of DMF, and the reaction is carried out at 0° C. for 3 days. After addition of 0.087 g of pyridine, the same procedure as Example 1B yields 0.443 g of sodium (3R,4S)-3-[2-(2-chloroacetamidothiazol-4-yl)-2-methoxyiminoacetamido]-4-(1-methyl-1H-tetrazol-5-yl)thio-2-oxoazetidine-1-sulfonate.

IR $\nu_{max}^{KBr}$cm$^{-1}$; 1795, 1676, 1540, 1285, 1043.

NMR(DMSO-d$_6$, ppm); 3.87(s, CH$_3$), 3.93(s, CH$_3$), 4.37(s, —CH$_2$—), 5.42(dd, J=2, 8 Hz, C$_3$—H), 6.30(d, J=2 Hz, C$_4$—H),

9.65(d, J=8 Hz, NH).

EXAMPLE 52B

To a solution of 0.300 g of the above sodium (3R,4S)-3-[2-(2-chloroacetamidothiazol-4-yl)-2-methoxyiminoacetamido]-4-(1-methyl-1H-tetrazol-5-yl)thio-2-oxoazetidine-1-sulfonate in 4 ml of water and 4 ml of a buffer (pH 6.56) is added under ice-cooling 0.0689 g of sodium monomethyl dithiocarbamate, and the mixture is stirred at room temperature for 2 hour. The same procedure as Example 3B yields 0.106 g of sodium (3R,4S)-3-[2-(2-aminothiazol-4-yl)-2-methoxyiminoacetamido]-4-(1-methyl-1H-tetrazol-5-yl)thio-2-oxoazetidine-1-sulfonate.

IR $\nu_{max}^{KBr}$cm$^{-1}$; 3320, 1786, 1661, 1608, 1520, 1270, 1045.

NMR(DMSO-d$_6$, ppm); 3.83(s, CH$_3$), 5.34(dd, J=2, 8 Hz, C$_3$—H), 6.31(d, J=2 Hz, C$_4$—H),

7.16(broad s, NH$_2$), 9.52(d, J=8 Hz, NH).

EXAMPLE 53B

To a solution of 3.40 g of (3R,4R)-3-[2-(2-chloroacetamidothiazol-4-yl)-2-methoxyiminoacetamido]-4-(1-methyl-1H-tetrazol-5-yl)thio-2-oxoazetidine in 3 ml of DMF is added at −70° C. a solution of 0.268 g of sulfuric anhydride-DMF complex in 1.27 ml of DMF, and the reaction is carried out at 0° C. for 7 days. After addition of 0.176 g of pyridine, the same procedure as Example 1B yields 0.318 g of sodium (3R,4R)-3-[2-(2-chloroacetamidothiazol-4-yl)-2-methoxyiminoacetamido]-4-(1-methyl-1H-tetrazol-5-yl)thio-2-oxoazetidine-1-sulfonate.

IR $\nu_{max}^{KBr}$cm$^{-1}$; 1778, 1660, 1540, 1300, 1048.

NMR(DMSO-d$_6$, ppm); 3.69(s, CH$_3$), 3.88(s, CH$_3$), 4.35(s, —CH$_2$—), 5.69(dd, J=4, 8 Hz, C$_3$—H), 6.48(d, J=4 Hz, C$_4$—H), 7.23(s, 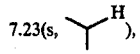), 9.58(d, J=8 Hz, NH).

EXAMPLE 54B

To a solution of 0.260 g of the above sodium (3R,4R)-3-[2-(2-chloroacetamidothiazol-4-yl)-2-methoxyiminoacetamido]-4-(1-methyl-1H-tetrazol-5-yl)thio-2-oxoazetidine-1-sulfonate in 20 ml of 50% methanol is added under ice-cooling 0.0597 g of sodium monomethyldithiocarbamate, and the mixture is stirred at room temperature for 5 hours. The same procedure as Example 3B yields 0.093 g of sodium (3R,4R)-3-[2-(2-aminothiazol-4-yl)-2-methoxyiminoacetamido]-4-(1-methyl-1H-tetrazol-5-yl)thio-2-oxoazetidine-1-sulfonate.

IR $\nu_{max}^{KBr}$cm$^{-1}$; 3420, 3320, 1786, 1671, 1520, 1285, 1053.

NMR(DMSO-d$_6$, ppm); 3.68(3H, CH$_3$), 3.87(3H, CH$_3$), 5.68 (dd, J=4, 8 Hz, C$_3$—H), 6.42(s, 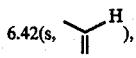), 6.46(d, J=4 Hz, C$_4$—H), 7.12(broad s, NH), 9.48(d, J=8 Hz, NH).

EXAMPLE 55B

To a solution of 0.367 g of (3S,4R)-4-acetoxy-2-[D-2-(4-ethyl-2,3-dioxo-1-piperazinecarboxamido)-2-thienylacetamido]-2-oxoazetidine in 2 ml of DMF is added at −70° C. a solution of 0.147 g of sulfuric anhydride-DMF complex in 2.5 ml of DMF, and the reaction is carried out at 0° C. for 7 days. After addition of 0.195 g of pyridine, the same procedure as Example 1B yields 0.162 g of sodium (3S,4R)-4-acetoxy-3-[D-2-(4-ethyl-2,3-dioxo-1-piperazinecarboxamido)-2-thienylacetamido]-2-oxoazetidine-1-sulfonate.

IR $\nu_{max}^{KBr}$cm$^{-1}$; 3280, 1780, 1750, 1710, 1668, 1502, 1280, 1230, 1182, 1042.

NRM(DMSO-d$_6$, ppm); 1.09(t, J=7 Hz, CH$_3$), 1.71(s, CH$_3$), 3.39 (q, J=7 Hz, —CH$_2$—), 5.28 (dd, J=4, 9 Hz, C$_3$—H), 5.80(d, J=8Hz, —CH—)
|

6.18(d, J=4 Hz, C$_4$—H), 9.28(d, J=9 Hz, NH), 9.72(d, J=4 Hz, C$_4$—H).

EXAMPLE 56B

To a solution of 0.206 g of (3S,4R)-4-acetoxy-3-thienylacetamido-2-oxoazetidine in 2 ml of DMF is added at −70° C. a solution of 0.147 g of sulfuric anhydride-DMF complex in 2.4 ml of DMF, and the reaction is carried out at 0° C. for 4 days. After addition of 0.182 g of pyridine, the same procedure as Example 1B yields 0.135 g of sodium (3S,4R)-4-acetoxy-3-thienylacetamido-2-oxoazetidine-1-sulfonate.

IR $\nu_{max}^{KBr}$cm$^{-1}$; 3450, 3350, 1770, 1740, 1668, 1530, 1290, 1240, 1050.

NMR(DMSO-d$_6$, ppm); 1.96(s, CH$_3$), 3.69(s, —CH$_2$—), 5.22(dd, J=4, 9 Hz, C$_3$—H), 6.21(d, J=4 Hz, C$_4$—H), 6.82-7.02(m, arom H), 7.23-7.44(m, arom H), 8.88(d, J=9 Hz, NH).

EXAMPLE 57B

To a solution of 0.404 g of (3S,4R)-4-acetoxy-3-[2-(2-chloroacetamidothiazol-4-yl)-2-methoxyiminoacetamido]-2-oxoazetidine in 3 ml of DMF is added at −70° C. a solution of 0.147 g of sulfuric anhydride-DMF complex in 3.1 ml of DMF, and the reaction is carried out at 0° C. for 7 days. After addition of 0.237 g of pyridine, the same procedure as Example 1B yields 0.373 g of sodium (3S,4R)-4-acetoxy-3-[2-(2-chloroacetamidothiazol-4-yl)-2-methoxyiminoacetamido]-2-oxoazetidine-1-sulfonate.

IR $\nu_{max}^{KBr}$cm$^{-1}$; 3270, 1785, 1760, 1675, 1521, 1285, 1240, 1050.

NMR(DMSO-d$_6$, ppm); 2.02(s, CH$_3$), 3.89(s, CH$_3$), 4.36(s, —CH$_2$—), 5.37(dd, J=4, 9 Hz, C$_3$—H), 6.29(d, J=4 Hz, C$_4$—H), 7.30(s, 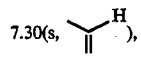), 9.37(d, J=9 Hz, NH), 12.8(broad s, NH).

EXAMPLE 58B

To a solution of 0.187 g of the above sodium (3S,4R)-acetoxy-3-[2-(2-chloroacetamidothiazol-4-yl)-2-methoxyiminoacetamido]-2-oxoazetidine-1-sulfonate in 6 ml of a buffer solution (pH 6.86) is added under ice-cooling 0.048 g of sodium monomethyldithiocarbamate, and the mixture is stirred for 2 hours at room temperature. The same procedure as Example 3B yields 0.078 g of sodium (3R,4R)-4-acetoxy-3-[2-(2-aminothiazol-4-yl)-2-methoxyiminoacetamido]-2-oxoazetidine-1-sulfonate.

IR $\nu_{max}^{KBr}$cm$^{-1}$; 3420, 3320, 1775, 1668, 1615, 1520, 1280, 1240, 1042.

NMR(DMSO-d$_6$, ppm); 2.01(s, CH$_3$), 3.84(s, CH$_3$), 5.34(dd, J=4, 9 Hz, C$_3$—H), 6.26(d, J=4 Hz, C$_4$—H), 6.58(s, 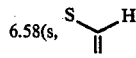), 7.15(broad s, NH), 9.29(d, J=9 Hz, NH).

EXAMPLE 59B

To a solution of 0.61 g of acetate of sodium (3S,4S)-4-acetoxy-3-amino-2-oxoazetidine-1-sulfonate obtained in Example 21B in 20 ml of a mixture of water and THF(1:1) is added under ice-cooling 0.61 g of phenylacetyl chloride while keeping the pH of the reaction mixture at pH 7.0-7.5 by use of sodium hydrogen carbonate. The stirring is continued for 1.5 hours at the same temperature. THF is removed by evaporation under reduced pressure. The residue is purified on an XAD-II (Rohm and Haas Co.) column chromatography to give 0.42 g of sodium (3S,4S)-4-acetoxy-3-phenylacetamido-2-oxoazetidine-1-sulfonate. The IR spectrum and NMR data of this compound are in agreement with those of the compound obtained in Example 19B.

EXAMPLE 60B (1) To a solution of 0.625 g of (3S,4R)-4-azido-3-[2-[(2-tritylaminothiazol-4-yl)carboxymethyliminoxy]-2-methylpropionamido]-2-azetidinone in 4 ml of DMF is added a solution of 0.459 g of sulfuric anhydride-DMF complex in 1.8 ml of DMF and the reaction is carried out at 0° C. for 2 days. To the reaction mixture is added 0.238 g of pyridine and the mixture is washed with ether. The residue is dissolved in 50% ethanol, and under ice-cooling 0.504 g of sodium hydrogen carbonate is added, after which the mixture is stirred for 30 minutes. The ethanol is distilled off and the residue is purified by XAD-II column chromatography to give 0.181 g of disodium (3S,4R)-4-azido-3-[2-[(2-tritylaminothiazol-4-yl)carboxylatomethyliminoxy]-2-methylpropionamido]-2-azetidinone-1-sulfonate.

IR $\nu_{max}^{KBr}$cm$^{-1}$; 3390, 2105, 1770, 1615, 1520, 1270, 1245, 1045.

NMR(DMSO-d$_6$, ppm); 1.58(s, CH$_3$), 1.65(s, CH$_3$), 4.46(d, J=2 Hz, C$_3$—H), 5.43(d, J=2 Hz, C$_4$—H), 6.63(s, 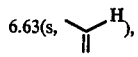), 7.00–7.50(m, arom H).

(2) To a solution of 0.156 g of disodium (3S,4R)-4-azido-3-[2-[(2-tritylaminothiazol-4-yl)carboxylatomethyliminoxy]-2-methylpropionamido]-2-azetidinone-1-sulfonate in 15 ml of 50% methanol is added 0.84 ml of N—HCl under ice-cooling and the mixture is stirred at room temperature for 2.5 hours. Under ice-cooling 0.070 g of sodium hydrogen carbonate is added and after the mixture is stirred for 20 minutes, the methanol is distilled off. The insolubles are filtered off and the filtrate is purified by XAD-II column chromatography to give 0.067 g of disodium (3S,4R)-3-[2-[(2-aminothiazol-4-yl)-carboxylatomethyliminoxy]-2-methylpropionamido]-4-azido-2-azetidinone-1-sulfonate.

IR $\nu_{max}^{KBr}$cm$^{-1}$: 3390, 2115, 1775, 1605, 1512, 1270, 1240, 1048.

NMR(DMSO-d$_6$, ppm); 1.67(s, CH$_3$), 4.70(d, J=2 Hz, C$_3$—H), 5.80(d, J=2 Hz, C$_4$—H), 7.09(s, 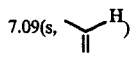)

EXAMPLE 61B (1) To a solution of 0.40 g of (3R,4R)-3-[2-[1-(2-trimethylsilylethoxycarbonyl)-1-methylethoxyimino]-2-(2-tritylaminothiazol-4-yl)acetamido]-4-methylthio-2-azetidinone in 2 ml of DMF is added 0.80 g of tetra-n-butylammonium fluoride and the mixture is stirred at room temperature for 30 minutes. The DMF is distilled off and the residue is dissolved in ethyl acetate and washed with water. The solvent is then distilled off to give 0.400 g of tetra-n-butylammonium salt of (3R,4R)-3-[2-(1-carboxy-1-methylethoxyimino)-2-(2-tritylaminothiazol-4-yl)acetamido]-4-methylthio-2-azetidinone. The product is dissolved in 2 ml of DMF and at −70° C. a solution of 0.511 g of sulfuric anhydride-DMF complex in 2 ml of DMF is added, after which the reaction is carried out for 2 days at 0° C. After addition of 0.5 ml of pyridine, the same procedure as that in Example 1B is followed to give 0.150 g of sodium (3R,4R)-3-[2-(1-carboxy-1-methylethoxyimino)-2-(2-tritylaminothiazol-4-yl)acetamido]-4-methylthio-2-azetidinone-1-sulfonate.

IR $\nu_{max}^{KBr}$cm$^{-1}$; 1760, 1660, 1610, 1525, 1250.

(2) To a solution of 0.188 g of sodium (3R,4R)-3-[2(1-carboxy-1-methylethoxyimino)-2-(2-tritylaminothiazol-4-yl)-acetamido]-4-methylthio-2-azetidinone-1-sulfonate in 15 ml of 50% methanol is added 1.0 ml of N—HCl under ice-cooling and the mixture is stirred at room temperature for 2 hours. By the same procedure as that in (2) of Example 60B, there is obtained 0.31 g of disodium (3R,4R)-3-[2-(2-aminothiazol-4-yl)-2-(1-carboxylato-1-methylethoxyimino)acetamido]-4-methylthio-2-azetidinone-1-sulfonate.

IR $\nu_{max}^{KBr}$cm$^{-1}$; 1760, 1675, 1600, 1250, 1050.

EXAMPLE 62B

To a solution of 0.40 g of (3S,4R)-4-azido-3-(D-2-ureido-2-thienylacetamido)-2-oxoazetidine in 3 ml of DMF is added at −20° C. a solution of 0.594 g of sulfuric anhydride-DMF complex in 2.2 ml of DMF. The reaction is allowed to proceed at 0° C. for two days. To the reaction mixture is added 0.307 g of pyridine, followed by purification in the same procedure as in Example 1B to give 0.131 g of sodium (3S,4R)-4-azido-3-(D-2-ureido-2-thienylacetamido)-2-oxoazetidine-1-sulfonate (A) and 0.198 g of disodium (3S,4S)-4-azido-3-[D-2-(3-sulfonatoureido)-2-thienylacetamido]-2-oxoazetidine-1-sulfonate (B).

(A) IR $\nu_{max}^{KBr}$cm$^{-1}$: 3315, 2120, 1770, 1660, 1520, 1240, 1050. NMR (DMSO-d$_6$, ppm): 5.25 (d, J=5 Hz, C$_3$—H), 5.54 (d, J=5 Hz, C$_4$—H), 5.76(s, 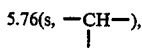), 7.03~7.67 (m, arom H).

(B) IR $\nu_{max}^{KBr}$cm$^{-1}$: 3320, 2120, 1775, 1665, 1520, 1242, 1050. NMR (DMSO-d$_6$, ppm): 5.26 (d, J=5 Hz, C$_3$—H), 5.56 (d, J=5 Hz), C$_4$—H), 5.76(s, 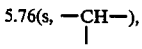), 7.05~7.63 (m, arom H).

EXAMPLE 63B (1) To a solution of 0.485 g of (3R,4S)-3-[2-(2-chloroacetamidothiazol-4-yl)-2-methoxyiminoacetamido]-4-methoxycarbonylmethylthio-2-oxoazetidine in 2 ml of DMF is added at −70° C. a solution of 0.495 g of sulfuric anhydride-DMF complex in 1.85 ml of DMF. The reaction is allowed to proceed at 0° C. for two days. To the reaction mixture is added 0.256 g of pyridine, followed by purification in the same procedure as in Example 1B to give 0.430 g of sodium (3R,4S)-3-[2-(2-chloroacetamidothiazol-4-yl)-2-methoxyiminoacetamido]-4-methoxycarbonylmethylthio-2-oxoazetidine-1-sulfonate.

IR $\nu_{max}^{KBr}$cm$^{-1}$: 2330, 1763, 1742, 1665, 1540, 1273, 1040.

NMR (DMSO-d$_6$, ppm): 3.67 (s, CH$_3$), 3.74 (ABq, J=16 Hz, S—CH$_2$—), 3.93 (s, CH$_3$), 4.37 (s, ClCH$_2$—), 4.74 (dd, J=2, 8 Hz, C₃—H), 5.01 (d, J=2 Hz, C₄—H),

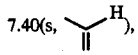

9.49 (d, J=8 Hz, NH).

(2) To a solution of 0.273 g of sodium (3R,4S)-3-[2-(2-chloroacetamidothiazol-4-yl)-2-methoxyiminoacetamido]-4-methoxycarbonylmethylthio-2-oxoazetidine-1-sulfonate in 6 ml of a buffer solution (pH 6.86) is added 67.8 mg of sodium monomethyldithiocarbamate under ice-cooling. After stirring for 2 hours at room temperature, the reaction mixture is purified in the same procedure as in Example 3B to give 0.120 g of sodium (3R,4S)-3-[2-(2-aminothiazol-4-yl)-2-methoxyiminoacetamido]-4-methoxycarbonylmethylthio-2-oxoazetidine-1-sulfonate.

IR ν_max^KBr cm⁻¹: 3420, 3320, 1763, 1722, 1661, 1610, 1520, 1275, 1043.

NMR (DMSO-d₆, ppm): 3.66 (s, CH₃), 3.72 (ABq, J=16 Hz, S—CH₂—), 3.86 (s, CH₃), 4.67 (dd, J=2, 8 Hz, C₃—H), 4.98 (d, J=2 Hz, C₄—H),

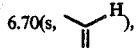

7.16 (broad s, NH₂), 9.36 (d, J=8 Hz, NH).

EXAMPLE 64B

To a solution of 0.74 g of 4-(E-2-acetamidovinyl)thio-3-[2-(2-chloroacetamido)-2-methoxyiminoacetamido]-2-oxoazetidine in 4 ml of DMF is added at −20° C. a solution of 0.734 g of sulfuric anhydride-DMF complex in 2.88 ml of DMF. The mixture is left standing at 0° C. for two days. To the reaction mixture is added 0.38 g of pyridine, followed by purification in the same procedure as in Example 1B to give 0.157 g of sodium (3R,4R)-4-(E-2-acetamidovinyl)thio-3-[2-(2-chloroacetamido)-2-methoxyiminoacetamido]-2-oxoazetidine-1-sulfonate.

IR ν_max^KBr cm⁻¹: 1766, 1670, 1620, 1542, 1265, 1045.

EXAMPLE 65B

To a solution of 0.138 g of (3S-cis)-3-benzyloxycarboxamido-4-ethoxy-3-methoxy-2-azetidinone in 1.5 ml of DMF is added at −70° C. a solution of 0.230 g of sulfuric anhydride-DMF complex in 0.86 ml of DMF. The reaction is allowed to proceed at 0° C. for four days. To the reaction mixture is added 0.12 ml of pyridine, followed by purification in the same procedure as in Example 1B to give 0.088 g of sodium (3S-cis)-3-benzyloxycarboxamido-4-ethoxy-3-methoxy-2-azetidinone-1-sulfonate.

IR ν_max^KBr cm⁻¹: 3390, 1775, 1715, 1490, 1250, 1050.

NMR (DMSO-d₆, ppm): 1.03 (t, J=7 Hz, CH₃), 3.34 (s, CH₃), 4.91 (s, C₄—H), 5.07 (ABq, —CH₂—), 7.37 (s, arom H), 8.12 (s, NH).

EXAMPLE 66B

To a solution of 0.161 g of (3S-trans)-3-methoxy-4-methylthio-3-p-nitrobenzyloxycarboxamido-2-azetidinone in 1.5 ml of DMF is added at −70° C. a solution of 0.230 g of sulfuric anhydride-DMF complex in 0.86 ml of DMF. The reaction is allowed to proceed at 0° C. for four days. To the reaction mixture is added 0.12 ml of pyridine, followed by purification in the same procedure as in Example 1B to give 0.138 g of sodium (3S-trans)-3-methoxy-4-methylthio-3-p-nitrobenzyloxycarboxamido-2-azetidinone-1-sulfonate.

IR ν_max^KBr cm⁻¹: 1770, 1720, 1515, 1350, 1280, 1250, 1050.

NMR (DMSO-d₆, ppm): 2.17 (s, CH₃), 3.41 (s, CH₃), 4.77 (s, C₄—H), 5.22 (s, —CH₂—), 7.66 and 8.23 (each d, J=8 Hz, arom H), 8.48 (s, NH).

EXAMPLE 67B (1) To a solution of 0.405 g of (3R,4R)-3-[2-(2-chloroacetamidothiazol-4-yl)-2-methoxyiminoacetamido]-4-methoxycarbonylmethylthio-2-azetidinone in 2 ml of DMF is added at −70° C. a solution of 0.416 g of sulfuric anhydride-DMF complex in 1.55 ml of DMF. The reaction is allowed to proceed at 0° C. for two days. To the reaction mixture is added 0.427 g of pyridine, followed by purification in the same procedure as in Example 1B to give 0.120 g of sodium (3R,4R)-3-[2-(2-chloroacetamidothiazol-4-yl)-2-methoxyiminoacetamido]-4-methoxycarbonylmethylthio-2-azetidinone-1-sulfonate.

IR ν_max^KBr cm⁻¹: 3460, 3260, 1778, 1729, 1660, 1540, 1270, 1040.

NMR (DMSO-d₆, ppm): 3.61, 3.84 (ABq, J=15 Hz, —CH₂—), 3.64 (s, CH₃), 3.88 (s, CH₃), 4.35 (s, ClCH₂—), 5.36 (d, J=5 Hz, C₄—H), 5.37 (dd, J=5, 8 Hz, C₃—H),

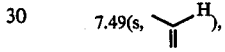

9.53 (d, J=8 Hz, NH).

(2) To a suspension of 0.315 g of sodium (3R,4R)-3-[2-(2-chloroacetamidothiazol-4-yl)-2-methoxyiminoacetamido]-4-methoxycarbonylmethylthio-2-azetidinone-1-sulfonate in 10 ml of 50% methanol is added 0.074 g of sodium monomethyldithiocarbamate under ice-cooling. After stirring for four hours at room temperature, the reaction mixture is purified in the same procedure as in Example 3B to give 87 mg of sodium (3R,4R)-3-[2-(2-aminothiazol-4-yl)-2-methoxyiminoacetamido]-4-methoxycarbonylmethylthio-2-azetidinone-1-sulfonate.

IR ν_max^KBr cm⁻¹: 3420, 3310, 1767, 1728, 1665, 1612, 1525, 1270, 1048.

NMR (DMSO-d₆, ppm): 3.60, 3.84 (ABq, J=15 Hz, —SCH₂—), 3.65 (s, CH₃), 3.84 (s, CH₃), 5.28 (d, J=5 Hz, C₄—H), 5.88 (dd, J=5, 8 Hz, C₃—H),

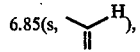

7.31 (br.s, NH₂), 9.42 (d, J=8 Hz, NH).

EXAMPLE 68B (1) To a solution of 0.40 g of (3R,4S)-3-[D-2-(2-oxoimidzolidin-1-yl-carboxamido-2-phenylacetamido]-4-phenylthio-2-azetidinone in 3 ml of DMF is added at −70° C. a solution of 0.28 g of sulfuric anhydride-DMF complex in 1.04 ml of DMF. The reaction is allowed to proceed at 0° C. for two days. To the reaction mixture is added 0.144 g of pyridine, followed by purification in the same procedure as in Example 1B to give 0.243 g of sodium (3R,4S)-3-[D-2-(2-oxoimidazolidin-1-yl-carboxamido)-2-phenylacetamido]-4-phenylthio-2-azetidinone-1-sulfonate.

IR $\nu_{max}^{KBr}$cm$^{-1}$: 3280, 1765, 1665, 1528, 1262, 1050.

NMR (DMSO-d$_6$, ppm): 3.24–3.46 (m, —CH$_2$—), 3.64–3.90 (m, —CH$_2$—), 4.54 (d, J=2 Hz, C$_3$—H), 4.86 (d, J=2 Hz, C$_4$—H), 5.36(s, —CH—),
　　　　|

7.36 (s, arom H), 7.37 (s, arom H).

(2) In addition, 0.119 g of disodium (3R,4S)-3-[D-2-(2-oxo-3-sulfonatoimidazolidin-1-yl-carboxamido)-2-phenylacetoamido]-4-phenylthio-2-azetidinone-1-sulfonate is obtained.

IR $\nu_{max}^{KBr}$cm$^{-1}$: 3450, 3305, 1765, 1715, 1668, 1525, 1255, 1050.

NMR (DMSO-d$_6$, ppm): 3.20–3.44 (m, —CH$_2$—), 3.54–3.84 (m, —CH$_2$), 4.45 (dd, J=2, 9 Hz, C$_3$—H), 4.83 (d, J=2 Hz, C$_4$—H), 5.36

(d, J=8Hz, —CH—),
　　　　　|

7.20–7.60 (m, arom H), 7.36 (s, arom H), 9.02 (d, J=8 Hz, NH), 9.31 (d, J=9 Hz, NH).

EXAMPLE 69B (1) To a solution of 0.40 g of (3S,4S)-4-azido-3-[D-2-(2-oxoimidazolidin-1-yl-carboxamido)-2-phenylacetamido]-2-azetidinone in 4 ml of DMF is added at −70° C. a solution of 0.337 g of sulfuric anhydride-DMF complex in 1.26 ml of DMF. The reaction is allowed to proceed at 0° C. for two days. To the reaction mixture is added 0.175 g of pyridine, followed by purification in the same procedure as in Example 1B to give 0.186 g of sodium (3S,4R)-4-aziod-3-[D-2-(2-oxoimidazolidin-1-yl-carboxamido)-2-phenylacetamido]-2-azetidinone-1-sulfonate.

IR $\nu_{max}^{KBr}$cm$^{-1}$: 3290, 2115, 1775, 1715, 1662, 1522, 1270, 1050.

NMR (DMSO-d$_6$, ppm): 3.16–3.48 (m, —CH$_2$—), 3.58–3.86 (m, —CH$_2$—), 4.41 (dd, J=2, 8 Hz, C$_3$—H), 5.09 (d, J=2 Hz, C$_4$—H), 5.39(d, J=7Hz, —CH—),
　　　　　　|

7.36 (s, arom H), 7.55 (s, NH), 9.02 (d, J=7 Hz, NH), 9.21 (d, J=7 Hz, NH).

(2) In addition, 0.111 g of disodium (3S,4R)-4-azido-3-[D-2-(2-oxo-3-sulfonatoimidazolidin-1-yl-carboxamido)-2-phenylacetamido]-2-azetidinone-1-sulfonate is obtained.

IR $\nu_{max}^{KBr}$cm$^{-1}$: 3460, 3300, 2120, 1765, 1708, 1663, 1522, 1255, 1052.

NMR (DMSO-d$_6$, ppm): 3.20–3.44 (m, —CH$_2$—), 3.57–3.80 (m, —CH$_2$—), 4.42 (dd, J=2, 8 Hz), 5.11 (d, J=2 Hz, C$_4$—H), 5.39(d, J=7Hz, —CH—),
　　　　　　|

7.36 (s, arom H), 9.02 (d, J=7 Hz, NH), 9.21 (d, J=8 Hz, NH).

EXAMPLE 70B

To a solution of 0.16 g of (3S-trans)-3-[D-2-(4-cyclohexyl-2,3-dioxo-1-pirerazinecarboxamido)-2-phenylacetamido]-3-methoxy-4-methylthio-2-azetidine in 1.5 ml of DMF is added at −70° C. a solution of 0.142 g of sulfuric anhydride-DMF complex in 0.53 ml of DMF. The reaction is allowed to proceed at 0° C. for two days. To the reaction mixture is added 0.075 ml of pyridine, followed by purification in the same procedure as in Example 1B to give 0.115 g of sodium (3S-trans)-3-[D-2-(4-cyclohexyl-2,3-dioxo-1-piperazinecarboxamido)-2-phenylacetamido]-3-methoxy-4-methylthio-2-azetidinone-1-sulfonate.

IR $\nu_{max}^{KBr}$cm$^{-1}$: 3275, 2925, 1770, 1705, 1665, 1500, 1250, 1050.

NMR (DMSO-d$_6$, ppm): 1.92 (s, CH$_3$), 3.26 (s, CH$_3$), 4.73 (s, C$_4$—H), 5.60(d, J=7Hz, —CH—),
　　　　　　|

7.2–7.6 (m, arom H), 9.22 (s, NH), 9.78 (d, J=7 Hz, NH).

EXAMPLE 71B

To a solution of 0.35 g of (3S,4S)-4-azido-3-[D-2-[3-methyl-3-methylcarbamoyl)-1-ureido]-2-phenylacetamido]-2-azetidinone in 3 ml of DMF is added at −70° C. a solution of 0.429 g of sulfuric anhydride-DMF complex in 1.6 ml of DMF. The reaction is allowed to proceed at 0° C. for two days. To the reaction mixture is added 0.222 g of pyridine, followed by purification in the same procedure as in Example 1B to give 0.22 g of sodium (3S,4R)-4-azido-3-[D-2-[3-methyl-3-(methylcarbamoyl)-1-ureido]-2-phenylacetamido]-2-azetidinone-1-sulfonate.

IR $\nu_{max}^{KBr}$cm$^{-1}$: 3380, 2120, 1778, 1678, 1676, 1502, 1250, 1050.

NMR (DMSO-d$_6$, ppm): 2.67 (d, J=4 Hz, CH$_3$) 3.09 (s, CH$_3$), 4.42, 4.46 (each dd, J=2, 8 Hz, C$_3$—H), 5.09, 5.13 (each d, J=2 Hz, C$_4$—H), 5.35(d, J=8Hz, —CH—),
　　　　　　|

7.36 (s, arom H), 9.17 (d, J=8 Hz, NH), 9.89 (d, J=8 Hz, NH).

EXAMPLE 72B (1) To a solution of 0.36 g of (3R,4R)-4-n-butylthio-3-[2-(2-chloroacetamidothiazol-4-yl)-2-methoxyiminoacetamido]-2-azetidinone in 4 ml of DMF is added at −70° C. a solution of 0.381 g of sulfuric anhydride-DMF complex in 1.43 ml of DMF. The reaction is allowed to proceed at 0° C. for two days. To the reaction mixture is added 0.198 g of pyridine, followed by purification in the same procedure as in Example 6B to give 0.445 g of pyridinium (3R,4R)-4-n-butylthio-3-[2-(2-chloroacetamidothiazol-4-yl)-2-methoxyiminoacetamido]-2-azetidinone-1-sulfonate.

IR $\nu_{max}^{KBr}$cm$^{-1}$: 3250, 1775, 1660, 1550–1530, 1270, 1245, 1208, 1036.

NMR (DMSO-d$_6$, ppm): 0.86 (m, CH$_3$), 1.43 (m, —CH$_2$—), 2.76 (t, J=7 Hz, —CH$_2$—), 3.86 (s, CH$_3$), 4.32 (s, —CH₂—), 5.13 (d, J=6 Hz, C₄—H), 5.34 (dd, J=6, 9 Hz, C₃—H),

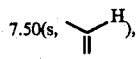

7.97–9.00 (m, arom H), 9.48 (d, J=9 Hz, NH)

(2) A mixture of 0.33 of pyridimum (3R,4R)-4-n-butylthio-3-[2-(2-chloroacetamidothiazol-4-yl)-2-methoxyiminoacetamido]-2-azetidinone-1-sulfonate, 10 ml of Dowex 50W resin (Na+ form) and 15 ml of 50% ethanol is stirred for 30 minutes. The resin is filtered off and the filtrate is lyophilized to give 0.215 g of sodium (3R,4R)-4-n-butylthio-3-[2-(2-chloroacetamidothiazol-4-yl)-2-methoxyiminoacetamido]-2-azetidinone-1-sulfonate.

IR $\nu_{max}^{KBr}$cm⁻¹: 3270, 1792, 1656, 1550–1525, 1248, 1050, 1036.

NMR (DMSO-d₆, ppm): 0.87 (m, CH₃), 1.45 (m, —CH₂—), 2.76 (t, J=7 Hz, —CH₂—), 3.88 (s, CH₃), 4.34 (s, —CH₂—), 5.16 (d, J=6 Hz, C₄—H), 5.35 (dd, J=6, 9 Hz, C₃—H),

9.51 (d, J=9 Hz, NH), 12.93 (broad S, NH).

(3) To a solution of 0.17 g of sodium (3R,4R)-4-n-butylthio-3-[2-(2-chloroacetamidothiazol-4-yl)-2-methoxyiminoacetamido]-2-azetidinone-1-sulfonate in 16 ml of 50% ethanol is added 0.053 g of sodium monomethyldithiocarbamate under ice-cooling. After stirring for 50 minutes at room temperature, ethanol is distilled off in vacuo. The residue is purified on a column of XAD-II to give 0.064 g of sodium (3R,4R)-3-[2-(2-aminothiazol-4-yl)-2-methoxyiminoacetamido]-4-n-butylthio-2-azetidinone-1-sulfonate.

IR$\nu_{max}^{KBr}$cm⁻¹: 3415, 3320, 1765, 1662, 1525, 1270, 1250, 1048.

NMR(DMSO-d₆, ppm): 0.88(t, J=7 Hz, CH₃), 1.46(m, —CH₂—), 2.76(t, J=7 Hz, —CH₂—): 3.84(s, CH₃), 5.14(d, J=6 Hz, C₄—H), 5.32(dd, J=6, 8 Hz, C₃—H),

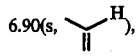

7.15(s, NH₂), 9.37(d, J=8 Hz, NH).

EXAMPLE 73B (1) To a solution of 0.40 g of (3R,4S)-4-n-butylthio-3-[2-(2-chloroacetamidothiazol-4-yl)-2-methoxyiminoacetamido]-2-azetidinone in 3 ml of DMF is added at −70° C. a solution of 0.424 g of sulfuric anhydride-DMF complex in 1.59 ml of DMF. The reaction is allowed to proceed at 0° C. for two days. To the reaction mixture is added 0.219 g of pyridine, followed by purification in the same procedure as in Example 1B to give 0.231 g of sodium (3R,4S)-4-n-butylthio-3-[2-(2-chloroacetamidothiazol-4-yl)-2-methoxyiminoacetoamido]-2-azetidinone-1-sulfonate.

IR$\nu_{max}^{KBr}$cm⁻¹: 3260, 1765, 1668, 1542, 1260, 1040.

NMR(DMSO-d₆, ppm): 0.88(m, CH₃), 1.48(m, —CH₂—), 2.77 (m, —CH₂—), 3.87(s, CH₃), 4.36(s, CH₃), 4.66(dd, J=3, 8 Hz, C₃—H), 4.80(d, J=3 Hz, C₄—H),

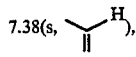

9.45(d, J=8 Hz, NH), 12.88(s, NH).

(2) To a solution of 0.18 g of sodium (3R,4S)-n-butylthio-3-[2-(2-chloroacetamidothiazol-4-yl)-2-methoxyiminoacetamido]-2-azetidinone-1-sulfonate in 15 ml of 30% ethanol is added 0.052 g of sodium monomethyldithiocarbamate under ice-cooling. The mixture is left standing at 0° C. for two days. After stirring for 1 hour at room temperature, the reaction mixture is purified in the same procedure as in Example 72B, 3) to give 0.056 g of sodium (3R,4S)-3-[2-(2-aminothiazol-4-yl)-2-methoxyiminoacetamido]-4-n-butylthio-2-azetidinone-1-sulfonate.

IR$\nu_{max}^{KBr}$cm⁻¹; 3400, 3320, 1765, 1662, 1530, 1270, 1250, 1048.

NMR(DMSO-d₆, ppm); 0.89(m, CH₃), 1.24–1.76(m, —CH₂—), 2.68(m, —CH₂—), 3.85(s, CH₃), 4.62(dd, J=3, 8 Hz, C₃—H), 4.81(d, J=3 Hz, C₄—H),

7.16(s, NH₂), 9.32(d, J=8 Hz, NH).

EXAMPLE 74B

To a solution of 0.420 g of (3R,4S)-3-[2-(2-chloroacetamidothiazol-4-yl)-2-methoxyiminoacetamido]-4-[(n-propylthio)thiocarbonyl]thio-2-azetidinone in 5 ml of DMF is added at −20° C. a solution of 0.39 g of sulfuric anhydride-DMF complex in 1.72 ml of DMF. The mixture is stirred at 5° C. for two days. To the reaction mixture is added 0.237 g of pyridine, followed by purification in the same procedure as in Example 1B to give 0.085 g of sodium (3R,4S)-3-[2-(2-chloroacetamidothiazol-4-yl)-2-methoxyiminoacetamido]-4-[(n-propylthio)thiocarbonyl]thio-2-azetidinone-1-sulfonate (A) and 0.119 g of the corresponding (3R,4R)-isomer (B).

(A) IR$\nu_{max}^{KBr}$cm⁻¹; 3240, 1778, 1663, 1539, 1278, 1039. NMR(DMSO-d₆, ppm); 0.97(t, J=7 Hz, CH₃), 1.68(m, —CH₂—) 3.36(t, J=7 Hz, —CH₂—), 3.93(s, CH₃), 4.37(s, ClCH₂—), 4.96(dd, J=2, 9 Hz, C₃—H), 5.88(d, J=2 Hz, C₄—H),

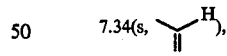

9.58(broad s, NH).

(B) IR$\nu_{max}^{KBr}$cm⁻¹; 3500, 3260, 1773, 1668, 1540, 1270, 1045.

NMR(DMSO-d₆, ppm): 0.96(t, J=7 Hz, CH₃), 1.68(m, —CH₂—), 3.36(t, J=7 Hz, —CH₂—), 3.86(s, CH₃), 4.35(s, ClCH₂—), 5.58(dd, J=5, 9 Hz, C₃—H), 6.16(d, J=5 Hz, C₄—h),

9.38(d, J=9 Hz, NH).

EXAMPLE 75B

A suspension of 0.128 g of sodium (3R)-3-[2-(2-chloroacetammidothiazol-4-yl)-2-methoxyiminoacetamido]-4-[(n-propylthio)thiocarbonyl]thio-2-azetidinone-1-sulfonate and 0.028 g of sodium monomethyldithiocarbamate in 3 ml of 30% methanol is stirred for two hours at room temperature. The reaction mixture is purified in the same procedure as in Example 3B to give 0.023 g of sodium (3R,4S)-3-[2-(2-aminothiazol-4-yl)-2-methoxyiminoacetamido]-4-[(n-propylthio)thiocarbonyl]thio-2-azetidinone-1-sulfonate(A) and 0.050 g of the corresponding (3R,4R)-isomer (B).

(A) IR$\nu_{max}^{KBr}$cm$^{-1}$; 3310, 1775, 1661, 1613, 1520, 1272, 1250, 1048. NMR(DMSO-d$_6$, ppm); 0.97(t, J=7 Hz, CH$_3$), 1.68(m, —CH$_2$—), 3.34(t, J=7 Hz, —CH$_2$—), 3.86(s, CH$_3$), 4.90(dd, J=2, 9 Hz, C$_3$—H), 5.87(d, J=2 Hz, C$_4$—H),

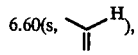
6.60(s, 7.18(broad s, NH), 9.48(d, J=9 Hz, NH).

(B) IR$\nu_{max}^{KBr}$cm$^{-1}$; 3310, 1774, 1661, 1612, 1520, 1272, 1250 NMR(DMSO-d$_6$, ppm); 0.97(t, J=7 Hz, CH$_3$), 1.68(m, —CH$_2$—), 3.34(t, J=7 Hz, —CH$_2$—), 3.80(s, CH$_3$), 5.52(dd, J=5, 9 Hz, C$_3$—H), 6.13(d, J=5 Hz, C$_4$—H),

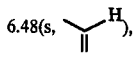
6.48(s, 7.18(broad s, NH$_2$), 9.28(d, J=9 Hz, NH).

EXAMPLE 76B (1) To a solution of 0.40 g of (3S,4S)-4-azido-3-[D-2-(4-ethyl-2,3-dioxo-1-piperazinecarboxamido)-3-(S)-formyloxybutanamido]-2-azetidinone in 3 ml of DMF is added at −20° C. a solution of 0.432 g of sulfuric anhydride-DMF complex in 1.61 ml of DMF. The reaction is allowed to proceed at 4° C. for two days. To the reaction mixture is added 0.224 g of pyridine, followed by purification in the same procedure as in Example 1B to give 0.282 g of sodium (3S,4R)-4-azido-3-[D-2-(4-ethyl-2,3-dioxo-1-piperazinecarboxamido)-3-(S)-formyloxybutanamido]-2-azetidinone-1-sulfonate.

IR$\nu_{max}^{KBr}$cm$^{-1}$; 3460, 3270, 2105, 1775, 1710, 1665, 1515, 1270, 1248, 1180, 1045.

NMR(DMSO-d$_6$, ppm); 1.11(t, J=7 Hz, CH$_3$), 1.23(d, J=6 Hz, CH$_3$) 3.43(q, J=7 Hz, —CH$_2$—), 3.40–3.80(m, —CH$_2$—), 3.86–4.04(m, —CH$_2$—), 4.46(dd, J=2, 8 Hz, C$_3$—H), 4.55(dd, J=4, 8Hz, —CH—), 5.11(d, J=2 Hz, C$_3$—H), 5.40(m, —CH—), 8.19(s, CHO), 9.10(d, J=8 Hz, NH), 9.36(d, J=8 Hz, NH).

(2) To a solution of 0.10 g of sodium (3S,4R)-4-azido-3-[D-2-(4-ethyl-2,3-dioxo-1-piperazinecarboxamido)-3-(S)-formyloxybutanamido]-2-azetidinone-1-sulfonate in 3 ml of water is added 0.57 ml of 1N-hydrochloric acid under ice cooling, followed by stirring for 30 minutes. To the reaction mixture is added 0.048 g of sodium bicarbonate followed by purification on a column of XAD-II to give 0.036 g of sodium (3S,4R)-4-azido-3-[D-2-(4-ethyl-2,3-dioxo-1-piperazinecarboxamido)-3-(S)-hydroxybutanamido]-2-azetidinone-1-sulfonate.

IR$\nu_{max}^{KBr}$cm$^{-1}$; 3430–3300, 2115, 1775, 1705, 1670, 1518, 1275, 1250, 1048.

NMR(DMSO-d$_6$, ppm); 1.08(d, J=6 Hz, CH$_3$), 1.10(t, J=7 Hz, CH$_3$), 3.42(q, J=7 Hz, —CH$_2$—), 3.56(m, —CH$_2$—), 3.94(m, —CH$_2$—), 4.00–4.24(m, —CH—), 4.42(dd, J=2, 8 Hz, C$_3$—H), 5.15(d, J=2 Hz, C$_4$—H), 5.18(s, OH), 8.75(d, J=8 Hz, NH), 9.28(d, J=8 Hz, NH).

EXAMPLE 77B (1) To a solution of 1.25 g of (3R)-4-(2-acetamidoethyl)thio-3-[2-(2-chloroacetamidothiazol-4-yl)-2-methoxyiminoacetamido]-2-azetidinone in 10 ml of DMF is added at −20° C. a solution of 1.25 g of sulfuric anhydride-DMF complex in 4.66 ml of DMF. The reaction is allowed to proceed at 4° C. for two days. To the reaction mixture is added 0.643 g of pyridine, followed by purification in the same procedure as in Example 1B to give 0.300 g of sodium (3R,4S)-4-(2-acetamidoethyl)thio-3-[2-(2-chloroacetamidothiazol-4-yl)-2-methoxyiminoacetamido]-2-azetidinone-1-sulfonate (A) and 0.367 g of the corresponding (3R,4R)-isomer (B).

(A) IR$\nu_{max}^{KBr}$cm$^{-1}$; 3250, 1767, 1660, 1540, 1260, 1038. NMR(DMSO-d$_6$, ppm); 1.85(s, CH$_3$), 2.86, 3.28(each m, —CH$_2$—), 3.90(s, CH$_3$), 4.37(s, ClCH$_2$—), 4.68(dd, J=2, 8 Hz, C$_3$—H), 4.86(d, J=2 Hz, C$_4$—H), 7.41(s, 9.46(d, J=8 Hz, NH).

(B) IR$\nu_{max}^{KBr}$cm$^{-1}$; 3275, 1763, 1658, 1540, 1270, 1050, 1038. NMR(DMSO-d$_6$, ppm); 1.81(s, CH$_3$), 2.86, 3.24(each m, —CH$_2$—), 3.88(s, CH$_3$), 4.36(s, ClCH$_2$—), 5.18(d, J=5 Hz, C$_4$—H), 5.36(dd, J=5, 8 Hz, C$_3$—H), 7.51(s, 9.50(d, J=8 Hz, NH).

(2) To a solution of 0.200 g of sodium (3R,4R)-4-(2-acetammidoethyl)thio-3-[2-(2-chloroacetamidothiazol-4-yl)-2-methoxyiminoacetamido]-2-azetidinone-1-sulfonate (B) in 5 ml of water is added 0.046 g of sodium monomethyldithiocarbamate under ice-cooling. After stirring for two hours at room temperature, the reaction mixture is purified in the same procedure as in Example 3B to give 0.081 g of sodium (3R,4R)-4-(2-acetamidoethyl)thio-3-[2-(2-aminothiazol-4-yl)-2-methoxyiminoacetamido]-2-azetidinone-1-sulfonate.

IR$\nu_{max}^{KBr}$cm$^{-1}$; 3320, 1762, 1658, 1522, 1270, 1048.

NMR(DMSO-d$_6$, ppm); 1.80(s, CH$_3$), 2.82, 3.21 (each m, —CH$_2$—), 3.84(s, CH$_3$), 5.17(d, J=5 Hz, C$_4$—H), 5.33 (dd, J=5, 8 Hz, C$_3$—H),

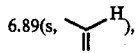
6.89(s, 7.18(broad s, NH₂), 7.88(m, NH), 9.40(d, J=8 Hz, NH).

EXAMPLE 78B

A mixture of 0.212 g of sodium (3R,4S)-4-(2-acetamidoethyl)thio-3-[2-(2-chloroacetamidothiazol-4-yl)-2-methoxyiminoacetamido]-2-azetidinone-1-sulfonate and 0.049 g of sodium monomethyldithiocarbamate is treated in the same manner as in Example 77B, 2) to give 0.037 g of sodium (3R,4S)-4-(2-acetamidoethyl)thio-3-[2-(2-aminothiazol-4-yl)-2-methoxyiminoacetamido]-2-azetidinone-1-sulfonate.

IR$\nu_{max}^{KBr}$cm$^{-1}$; 3310, 1763, 1656, 1528, 1270, 1248, 1043.

NMR(DMSO-d₆, ppm); 1.80(s, CH₃), 2.86, 3.23(each m, —CH₂—), 3.87(s, CH₃), 4.82(d, J=2 Hz, C₄—H), 4.64(dd, J=2, 8 Hz, C₃—H),

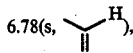
6.78(s, 9.40(d, J=8 Hz, NH).

EXAMPLE 79B (1) To a solution of 0.552 g of (3R,4R)-3-[2-(2-chloroacetamidothiazole-4-yl)-2-methoxyiminoacetamido]-4-cyclohexylthio-2-azetidinone in 2 ml of DMF is added at −70° C. a solution of 0.55 g of sulfuric anhydride-DMF complex in 2.1 ml of DMF. The reaction is allowed to proceed at 0° C. for 30 hours. To the reaction mixture is added 0.5 ml of pyridine, followed by purification in the same procedure as in Example 6B to give 0.657 g of pyridinium (3R,4R)-3-[2-(2-chloroacetamidothiazol-4-yl)-2-methoxyiminoacetamido]-4-cyclohexylthio-2-azetidinone-1-sulfonate.

IR$\nu_{max}^{KBr}$cm$^{-1}$; 1780, 1770, 1660, 1525, 1250, 1040.

NMR(DMSO-d₆, ppm); 3.88(s, OCH₃), 4.36(s, —CH₂—),

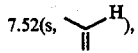
7.52(s, 9.44(dd, J=8 Hz, NH).

(2) A mixture of 0.45 g of the pyridinium derivative obtained in Example 79, 1) and 0.104 g of sodium monomethyldithiocarbamate suspended in 50% methanol is stirred for 30 minutes at room temperature, followed by treatment in the same procedure as in Example 3B to give 0.113 g of sodium (3R,4R)-3-[2-(2-aminothiazol-4-yl)-2-methoxyiminoacetamido]-4-cyclohexylthio-2-azetidinone-1-sulfonate.

IR$\nu_{max}^{KBr}$cm$^{-1}$; 1765, 1660, 1620, 1525, 1250, 1045.

NMR(DMSO-d₆, ppm); 3.84(s, OCH₃), 4.24(d, J=5 Hz, C₄—H), 5.30(dd, J=5, 8 Hz, C₃—H),

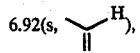
6.92(s, 9.32(d, J=8 Hz, NH).

EXAMPLE 80B (1) The treatment of (3R,4S)-3-[2-(2-chloroacetamidothiazol-4-yl)-2-methoxyiminoacetamido]-4-cyclohexylthio-2-azetidinone in the same procedure as in Example 79B, (1) gives pyridinium (3R,4S)-3-[2-(2-chloroacetamidothiazol-4-yl)-2-methoxyiminoacetamido]-4-cyclohexylthio-2-azetidinone-1-sulfonate.

IR$\nu_{max}^{KBr}$cm$^{-1}$; 1765, 1670, 1540, 1265, 1045.

NMR(DMSO-d₆, ppm): 3.90(s, OCH₃), 4.36(s, —CH₂—), 4.64(dd, J=2, 8 Hz, C₃—H), 4.90(d, J=2 Hz, C₄—H),

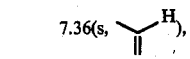
7.36(s, 9.45(d, J=8 Hz, NH).

(2) The treatment of pyridinium salt obtained in Example 80B, (1) in the same manner as in Example 79B, (2) gives sodium (3R,4S)-3-[2-(2-aminothiazol-4-yl)-2-methoxyiminoacetamido]-4-cyclohexylthio-2-azetidinone-1-sulfonate.

IR$\nu_{max}^{KBr}$cm$^{-1}$; 1765, 1660, 1520, 1250, 1040.

NMR(DMSO-d₆, ppm); 3.95(s, OCH₃), 4.89(d, J=2 Hz, C₄—H),

7.45(s, 9.50(d, J=8 Hz, NH).

EXAMPLE 81B

To a solution of 0.54 g of 3-[2-(2-chloroacetamidothiazol-4-yl)-2-methoxyiminoacetamido]-4-fluoro-2-azetidinone in 2 ml of DMF is added at −70° C. a solution of 0.70 g of sulfuric anhydride-DMF complex in 2.6 ml of DMF. The reaction is allowed to proceed at 0° C. for two days. To the reaction mixture is added 0.5 ml of pyridine, followed by purification in the same procedure as in Example 1B to give 0.233 g of sodium 3-[2-(2-chloroacetamidothiazol-4-yl)-2-methoxyiminoacetamido]-4-fluoro-2-azetidinone-1-sulfonate.

IR$\nu_{max}^{KBr}$cm$^{-1}$; 1780, 1675, 1540, 1270, 1040.

EXAMPLE 82B

To a solution of 0.1 g of (3R,4R)-3-[D-2-(4-ethyl-2,3-dioxo-1-piperazinecarboxamido)-2-chloromethylacetamido]-4-methylthio-2-oxoazetidine in 1 ml of DMF is added at −70° C. a solution of 0.11 g of sulfuric anhydride-DMF complex in 0.42 ml of DMF. The mixture is left standing at 0° C. for 3 days. To the reaction mixture is added 0.3 ml of pyridine, followed by purification in the same procedure as in Example 1B to give 0.038 g of sodium (3R,4R)-3-[D-2-(4-ethyl-2,3-dioxo-1-piperazinecarboxamido)-2-chloromethylacetamido]-4-methylthio-2-azetidinone-1-sulfonate.

IR$\nu_{max}^{KBr}$cm$^{-1}$; 1765, 1720, 1680, 1520, 1280, 1250, 1050.

EXAMPLE 83B

To a solution of 0.35 g of (3R,4R)-4-t-butylthio-3-[D-2-(4-ethyl-2,3-dioxo-1-piperazinecarboxamido)-3-(S)-formyloxybutanamido]-2-azetidinone in 3 ml of DMF is added at −20° C. a solution of 0.346 g of sulfuric anhydride-DMF complex in 1.27 ml of DMF. The mixture is left standing at 5° C. for two days. To the reaction mixture is added 0.18 g of pyridine, followed by purification in the same procedure as in Example 1B to give 0.27 g of sodium (3R,4R)-4-t-butylthio-3-[D-2-(4-ethyl- 2,3-dioxo-1-piperazinecarboxamido)-3-(S)-formyloxybutanamido]-2-azetidinone-1-sulfonate.

IR$\nu_{max}^{KBr}$cm$^{-1}$; 3475, 3280, 1760, 1712, 1675, 1520, 1275, 1250.

NMR(DMSO-d$_6$, ppm); 0.88(m, CH$_3$), 1.11(t, J=7 Hz, CH$_3$), 1.20-1.66(m, CH$_3$, —CH$_2$—), 2.74(t, J=7 Hz, —CH$_2$—), 3.42(q, J=7 Hz, —CH$_2$—), 3.60(m, —CH$_2$—), 3.94(m, —CH$_2$—), 4.67(dd, J=4, 8Hz, —CH—),
|

5.06-5.40(m, C$_3$—H, C$_4$—H, —CH—),
|

8.16(s, CHO), 9.11(d, J=8 Hz, NH), 9.37 (d, J=8 Hz, NH).

EXAMPLE 84B

To a solution of 0.45 g of (3S,4R)-4-azido-3-[D-2-(2-oxoimidazolidin-1-yl-carboxamido)-2-phenylacetamido]-2-azetidinone in 4 ml of DMF is added at −20° C. a solution of 0.55 g of sulfuric anhydride-DMF complex in 2.1 ml of DMF. The mixture is left standing at 5° C. for two days. To the reaction mixture is added 0.29 g of pyridine, followed by purification in the same procedure as in Example 1B to give 0.12 g of disodium (3S,4S)-4-azido-3-[D-2-(2-oxo-3-sulfonatoimidazolidin-1-yl-carboxamido)-2-phenylacetamido]-2-azetidinone-1-sulfonate.

IR$\nu_{max}^{KBr}$cm$^{-1}$; 3470, 3300, 1770, 1660, 1520, 1245, 1050.

NMR(DMSO-d$_6$, ppm): 3.30(m, —CH$_2$—), 3.70(m, —CH$_2$—), 5.12(dd, J=5, 8 Hz, C$_3$—H), 5.35(d, J=5 Hz, C$_4$—H), 5.54(d, J=8Hz, —CH—),
|

7.20–7.60 (m, arom H), 9.07(d, J=8 Hz, NH), 9.24 (d, J=8 Hz, NH).

EXAMPLE 85B (1) To a solution of 0.45 g of (3R,4R)-3-[2-(2-chloroacetamidothiazol-4-yl)-2-methoxyiminoacetamido]-4-i-propylthio-2-azetidinone in 5 ml of DMF is added at −20° C. a solution of 0.48 g of sulfuric anhydride-DMF complex in 1.82 ml of DMF. The mixture is left standing at 5° C. for two days. To the reaction mixture is added 0.25 g of pyridine, followed by purification in the same procedure as in Example 1B to give 0.45 g of sodium (3S,4R)-3-[2-(2-chloroacetamidothiazol-4-yl)-2-methoxyiminoacetamido]-4-i-propylthio-2-azetidinone-1-sulfonate.

IR$\nu_{max}^{KBr}$cm$^{-1}$; 3260, 2950, 1768, 1668, 1542, 1250, 1048.

NMR(DMSO-d$_6$, ppm); 1.19, 1.26(each d, J=6 Hz, CH$_3$), 3.3(m, —CH<), 3.88(s, CH$_3$), 4.35(s, ClCH$_2$—), 5.24(d, J=5 Hz, C$_4$—H), 5.39(dd, J=4, 9 Hz, C$_3$—H), 7.48(s, 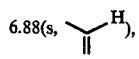), 9.43(d, J=9 Hz, NH).

(2) A solution of 0.275 g of sodium (3R,4R)-3-[2-(2-chloroacetamidothiazol-4-yl)-2-methoxyiminoacetamido]-4-i-propylthio-2-azetidinone-1-sulfonate and 0.068 g of sodium monomethyldithiocarbamate in 5 ml of 40% methanol is stirred for 2 hours at room temperature, followed by purification in the same procedure as in Example 3B to give 0.077 g of sodium (3R,4R)-3-[2-(2-aminothiazol-4-yl)-2-methoxyiminoacetamido]-4-i-propylthio-2-azetidinone-1-sulfonate.

IR$\nu_{max}^{KBr}$cm$^{-1}$; 3310, 1761, 1663, 1618, 1525, 1240, 1045.

NMR(DMSO-d$_6$, ppm); 1.20, 1.26(each d, J=6 Hz, CH$_3$), 3.3(m, —CH<), 3.84(s, CH$_3$), 5.22(d, J=5 Hz, C$_4$—H), 5.36(dd, J=5, 9 Hz, C$_3$—H), 6.88(s, 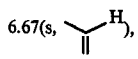), 7.15(broad s, NH$_2$), 9.33(d, J=9 Hz, NH).

EXAMPLE 86B

To a solution of 0.26 g of (3R,4S)-3-[2-(2-chloroacetamidothiazol-4-yl)-2-methoxyiminoacetamido]-4-i-propylthio-2-azetidinone in 2 ml of DMF is added at −20° C. a solution of 0.28 g of sulfuric anhydride-DMF complex in 1.1 ml of DMF. The mixture is left standing at 5° C. for two days. To the reaction mixture is added 0.145 g of pyridine, followed by purification in the same procedure as in Example 6B to give 82 mg of pyrridinium (3R,4S)-3-[2-(2-chloroacetamidothiazol-4-yl)-2-methoxyiminoacetamido]-4-i-propylthio-2-azetidinone-1-sulfonate. To a solution of this product in 10 ml of 50% methanol is added sodium hydrogen carbonate to adjust the pH of the solution to pH 7. To the mixture is added 0.08 g of sodium monomethyldithiocarbamate and the mixture is stirred for 1.5 hours at room temperature, followed by purification in the same procedure as in Example 3B to give sodium (3R,4S)-3-[2-(2-aminothiazol-4-yl)-2-methoxyiminoacetamido]-4-i-propylthio-2-azetidinone-1-sulfonate.

IR$\nu_{max}^{KBr}$cm$^{-1}$; 3320, 1763, 1670, 1618, 1523, 1242, 1045.

NMR(DMSO-d$_6$, ppm); 1.20, 1.28(each d, J=6 Hz, CH$_3$), 3.84(s, CH$_3$), 4.60(dd, J=2, 9 Hz, C$_3$—H), 4.89(d, J=2 Hz, C$_4$—H), 6.67(s, 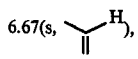), 7.16(broad s, NH$_2$), 9.34(d, J=9 Hz, NH).

EXAMPLE 87B (1) To a solution of 0.40 g of (3S,4R)-3-[2-(2-chloroacetamidothiazol-4-yl)-2-methoxyiminoacetamido]-4-(ethoxycarbonyl)methoxy-2-azetidinone in 3 ml of DMF is added at −20° C. a solution of 0.41 g of sulfuric anhydride-DMF complex in 1.53 ml of DMF. The mixture is left standing at 5° C. for two days. To the reaction mixture is added 0.212 g of pyridine, followed by purification in the same procedure as in Example 1B to give 0.35 g of sodium (3S,4R)-3-[2-(2-chloroacetamidothiazol-4-yl)-2-methoxyiminoacetamido]-4-(ethoxycarbonyl)methoxy-2-azetidinone-1-sulfonate.

IR$\nu_{max}^{KBr}$cm$^{-1}$; 3400, 3250, 1772, 1740, 1670, 1540, 1262, 1042.

NMR(DMSO-d$_6$, ppm); 1.20(t, J=7 Hz, CH$_3$), 3.87(s, CH$_3$), 4.15(q, J=7 Hz, —CH$_2$—), 4.33(s, —CH$_2$—), 4.45(ABq, J=24, 39 Hz, —CH$_2$—), 5.18(dd, J=5, 9 Hz, C$_3$—H), 5.38(d, J=5 Hz, C$_4$—H),

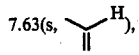
7.63(s,      ), 9.43(d, J=9 Hz, NH), 12.80(broad s, NH).

(2) To a solution of 0.20 g of the sulfonate derivative as obtained in (1) above in 7 ml of water is added under ice-cooling 0.052 g of sodium monomethyldithiocarbamate and the mixture is stirred for 50 minutes at room temperature. Purification on an XAD-II column-chromatography under ice-cooling given 0.053 g of sodium (3S,4R)-3-[2-(2-aminothiazol-4-yl)-2-methoxyiminoacetamido]-4-(ethoxycarbonyl)methoxy-2-azetidinone-1-sulfonate.

IR$\nu_{max}^{KBr}$cm$^{-1}$; 3400, 3320, 1772, 1735, 1665, 1522, 1270, 1238, 1128, 1045.

NMR(DMSO-d$_6$, ppm); 1.22(t, J=7 Hz, CH$_3$), 3.82(s, CH$_3$), 4.14(q, J=7 Hz, —CH$_2$—), 4.48(s, —CH$_2$—), 5.15(dd, J=5, 8 Hz, C$_3$—H), 5.36(d, J=5 Hz, C$_4$—H),

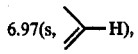
6.97(s,      ), 7.10(s, NH$_2$), 9.29(d, J=8 Hz, NH).

EXAMPLE 88B (1) To a solution of 0.40 g of (3S,4R)-4-azido-3-[D-2-(4-ethyl-2,3-dioxo-1-piperazinecarboxamido)-3-(S)-formyloxybutanamido]-2-azetidinone in 3 ml of DMF is added at −20° C. a solution of 0.433 g of sulfuric anhydride-DMF complex in 1.62 ml of DMF. The mixture is left standing at 0° C. for two days. To the reaction mixture is added 0.224 g of pyridine, followed by purification in the same procedure as in Example 1B to give 0.202 g of sodium (3S,4S)-4-azido-3-[D-2-(4-ethyl-2,3-dioxo-1-piperazinecarboxamido)-3-(S)-formyloxybutanamido]-2-azetidinone-1-sulfonate.

IR$\nu_{max}^{KBr}$cm$^{-1}$; 3450, 1770, 1708, 1670, 1515, 1275, 1185, 1048.

NMR(DMSO-d$_6$, ppm): 1.10(t, J=7 Hz, CH$_3$), 1.24(d, J=6 Hz, CH$_3$), 3.41(q, J=7 Hz, —CH$_2$—), 3.56(m, —CH$_2$—), 3.93(m, —CH$_2$—), 4.64(dd, J=3, 9Hz, —CH—), 5.08(dd, J=5, 8 Hz, C$_3$—H), 5.37(m, —CH—), 5.43(d, J=5 Hz, C$_4$—H), 8.17(s, CHO), 9.10 (d, J=8 Hz, NH), 9.36(d, J=9 Hz, NH).

(2) To a solution of 0.15 g of the sulfonate derivative as obtained in (1) above in 3 ml of water is added 0.86 ml of N-HCl under ice-cooling. The mixture is stirred for 1.5 hours at room temperature, to which is added 0.072 g of sodium hydrogen carbonate.

Purification on an XAD-II column chromatography yields 84 mg of sodium (3S,4S)-4-azido-3-[D-2-(4-ethyl-2,3-dioxo-1-piperazinecarboxamido)-3-(S)-hydroxybutanamido]-2-azetidinone-1-sulfonate.

IR $\nu_{max}^{KBr}$cm$^{-1}$; 3440, 3300, 1772, 1705, 1670, 1510, 1270, 1192.

NMR(DMSO-d$_6$, ppm); 1.10(t, J=7 Hz, CH$_3$), 1.14(d, J=6 Hz, CH$_3$), 3.42(q, J=7 Hz, —CH$_2$—), 3.56(m, —CH$_2$—), 3.92(m, —CH$_2$—), 4.07(m, —CH—), 5.13(dd, J=5, 8 Hz, C$_3$—H), 5.40(d, J=5 Hz, C$_4$—H), 8.78(d, J=8 Hz, NH), 9.24(d, J=8 Hz, NH).

EXAMPLE 89B

By employing 0.40 g of (3S,4S)-3-[2-(2-chloroacetamidothiazol-4-yl)-2-methoxyiminoacetamido]-4-(ethoxycarbonyl)methoxy-2-azetidinone, the same procedure as in Example 88B, 1) gives 0.07 g of sodium (3S,4S)-3-[2-(2-chloroacetamidothiazol-4-yl)-2-methoxyiminoacetamido]-4-(ethoxycarbonyl)methoxy-2-azetidinone-1-sulfonate.

IR $\nu_{max}^{KBr}$cm$^{-1}$; 3420, 1772, 1738, 1668, 1640, 1270, 1230, 1035.

NMR(DMSO-d$_6$, ppm); 1.21(t, J=7 Hz, CH$_3$), 3.90(s, CH$_3$), 4.13(q, J=7 Hz, —CH$_2$—), 4.36(s, —CH$_2$—), 4.49(s, —CH$_2$—), 4.66(dd, J=2, 8 Hz, C$_3$—H), 5.23(d, J=2 Hz, C$_4$—H),

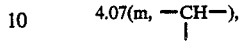
7.42(s,      ), 9.38(d, J=8 Hz, NH).

EXAMPLE 90B (1) To a solution of 0.262 g of (3S,4R)-3-[2-(2-chloroacetamidothiazol-4-yl)-2-methoxyiminoacetamido]-3-methoxy-4-methylthio-2-oxoazetidine in 3 ml of DMF is added at −70° C. a solution of 0.287 g of sulfuric anhydride-DMF complex in 1.07 ml of DMF. The mixture is left standing at 0° C. for two days. To the reaction mixture is added 0.15 g of pyridine, followed by purification in the same procedure as in Example 1B to give 0.254 g of sodium (3S,4R)-3-[2-(2-chloroacetamidothiazol-4-yl)-2-methoxyiminoacetamido]-3-methoxy-4-methylthio-2-oxoazetidine-1-sulfonate.

IR $\nu_{max}^{KBr}$cm$^{-1}$; 3230, 1770, 1675, 1540, 1260, 1045.

(2) To a solution of 0.158 g of the sulfonate derivative as obtained in (1) above in 2 ml of water is added under ice-cooling 43 mg of sodium monomethyldithiocarbamate, and the mixture is stirred for 1 hour at room temperature, followed by purification in the same procedure as in Example 3B to give 78 mg of sodium (3R,4R)-3-[2-(2-aminothiazol-4-yl)-2-methoxyiminoacetamido]-3-methoxy-4-methylthio-2-oxoazetidine-1-sulfonate.

IR $\nu_{max}^{KBr}$cm$^{-1}$; 1773, 1670, 1620, 1525, 1250, 1050.

EXAMPLE 91B

To a solution of 0.40 g of (3S,4R)-4-azido-3-[2-(4-ethyl-2,3-dioxo-1-piperazinecarboxamido)-4-pentynamido]-2-oxoazetidine in 3 ml of DMF is added at −70° C. a solution of 0.47 g of sulfuric anhydride-DMF complex in 1.76 ml of DMF. The mixture is left standing at 0° C. for two days.

To the reaction mixture is added 0.244 g of pyridine, followed by purification in the same procedure as in Example 1B to give 0.297 g of sodium (3S,4S)-4-azido-3-[2-(4-ethyl-2,3-dioxo-1-piperazinecarboxamido)-4-pentynamido]-2-oxoazetidine-1-sulfonate.

IR $\nu_{max}^{KBr}$cm$^{-1}$; 3470, 3270, 2110, 1775, 1708, 1670, 1510, 1280–1240, 1048.

NMR (DMSO-d$_6$, ppm): 1.10(t, J=7 Hz, CH$_3$), 2.70(m, —CH$_2$—), 2.84(m, HC≡), 3.41(q, J=7 Hz, —CH$_2$—), 3.57(m, —CH$_2$—), 3.92(m, —CH$_2$—), 4.53(m, —CH—),
    |

5.09, 5.13(each dd, J=5, 8 Hz, C$_3$—H), 5.44, 5.47(each dd, J=5 Hz, C$_4$—H), 8.99, 9.02 (each d, J=8 Hz, NH), 9.42(d, J=8 Hz, NH).

EXAMPLE 92B

To a solution of 1.0 g of (3R)-4-(2-acetamidoethyl)thio-3-[D-2-(4-ethyl-2,3-dioxo-1-piperazinecarboxamido)-2-phenylacetamido]-2-oxoazetidine in 5 ml of DMF is added at −70° C. a solution of 0.90 g of sulfuric anhydride-DMF complex in 3.4 ml of DMF. The mixture is left standing at 0° C. for two days.

To the reaction mixture is added 0.470 g of pyridine, followed by purification in the same procedure as in Example 1B to give 0.402 g of sodium (3R,4R)-4-(2-acetamidoethylthio)-3-[D-2-(4-ethyl-2,3-dioxo-1-piperazinecarboxamido)-2-phenylacetamido]-2-oxoazetidine-1-sulfonate (A) and 0.132 g of the corresponding (3R,4S)-isomer (B).

(A) IR $\nu_{max}^{KBr}$cm$^{-1}$: 3280, 1768, 1712, 1670, 1505, 1272, 1243, 1042. NMR (DMSO-d$_6$): 1.08(t, J=7 Hz, CH$_3$), 1.78(s, CH$_3$), 3.40(q, J=7 Hz, —CH$_2$—), 5.05(d, J=5 Hz, C$_4$—H), 5.26(dd, J=5, 8 Hz, C$_3$—H), 5.58(d, J=8Hz, —CH—),
    |

9.27(d, J=8 Hz, NH), 9.79(d, J=8 Hz, NH) (ppm).

(B) IR $\nu_{max}^{KBr}$cm$^{-1}$; 3290, 1765, 1710, 1670, 1503, 1250, 1185, 1043. NMR (DMSO-d$_6$, ppm): 1.09(t, J=7 Hz, CH$_3$), 1.78(s, CH$_3$), 3.40(q, J=7 Hz, —CH$_2$—), 4.57(dd, J=3, 8 Hz, C$_3$—H), 4.70(d, J=3 Hz, C$_4$—H), 5.43(d, J=8Hz, —CH—),
    |

9.32(d, J=8 Hz, NH), 9.77(d, J=8 Hz, NH).

EXAMPLE 93B (1) To a solution of 0.60 g of (3S,4R)-4-azido-3-[2-(2-formamidothiazol-4-yl)-2-methoxyiminoacetamido]-2-oxoazetidine in 4 ml of DMF is added at −20° C. a solution of 0.814 g of sulfuric anhydride-DMF complex in 3.04 ml of DMF. The mixture is left standing at 0° C. for two days.

To the reaction mixture is added 0.422 g of pyridine, followed by purification in the same procedure as in Example 1B to give 0.571 g of sodium (3S,4S)-4-azido-3-[2-(2-formamidothiazol-4-yl)-2-methoxyiminoacetamido]-2-oxoazetidine-1-sulfonate.

IR $\nu_{max}^{KBr}$cm$^{-1}$; 3480, 3280, 2112, 1775, 1660, 1540, 1280, 1242, 1053.

NMR (DMSO-d$_6$, ppm); 3.90(s, CH$_3$), 5.21(dd, J=2, 8 Hz, C$_3$—H), 5.45(d, J=5 Hz, C$_4$—H), 7.42(s, 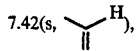), 8.50(s, CHO), 9.50(d, J=8 Hz, NH), 12.55(s, NH).

(2) To 0.25 g of the sulfonate derivative as obtained in (1) above are added 1.7 ml of N-HCl and 2 ml of methanol, and the mixture is stirred for 2.5 hours at room temperature.

To the mixture is 0.144 g of sodium hydrogen carbonate under ice-cooling, whereby crystals separate out, which are collected by filtration to give 0.074 g of (3S,4S)-4-azido-3-[2-(2-aminothiazol-4-yl)-2-methoxyiminoacetamido]-2-oxoazetidine-1-sulfonic acid.

IR $\nu_{max}^{KBr}$cm$^{-1}$; 3395, 2125, 1795, 1660, 1528, 1275, 1055

NMR(DMSO-d$_6$, ppm); 3.95(s, CH$_3$), 5.18(dd, J=5, 8 Hz, C$_3$—H), 5.51(d, J=5 Hz, C$_4$—H), 7.01(s, 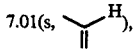), 9.62(d, J=8 Hz, NH).

EXAMPLE 94B (1) To a solution of 0.774 g of 4-(2-acetamidoethyl)thio-3-[2-(2-chloroacetamidothiazol-4-yl)-2-[[2-oxo-3-(thiophene-3-aldimino)imidazolidin-1-yl]carboxamido]acetamido]-2-oxoazetidine in 7 ml of DMF is added at −20° C. a solution of 0.54 g of sulfuric anhydride-DMF complex in 2.03 ml of DMF. The mixture is left standing at 5° C. for two days.

To the reaction mixture is added 0.280 g of pyridine, followed by purification in the same procedure as in Example 1B to give 0.107 g of sodium 4-(2-acetamidoethyl)thio-3-[2-(2-chloroacetamidothiazol-4-yl)-2-[[2-oxo-3-(thiophene-3-aldimino)imidazolidin-1-yl]carboxamido]acetamido]-2-oxoazetidine-1-sulfonate (a mixture of cis- and trans-isomers).

IR $\nu_{max}^{KBr}$cm$^{-1}$; 3300, 1761, 1722, 1670, 1523, 1268, 1228, 1045.

NMR(DMSO-d$_6$, ppm): 1.80(s, CH$_3$), 4.34(s, ClCH$_2$—), 5.10(dd, J=5, 8 Hz, C$_3$—H), 5.51, 5.64(each d, J=8Hz, —CH—),
    |

7.19, 7.25(each s, ), 7.4–7.65(m, arom H), 7.85, 7.89(each s, =CH—), 8.92, 9.02 (each d, J=8 Hz, NH).

(2) To a solution of 80 mg of the sulfonate derivative as obtained in (1) above in 4 ml of water is added 14 mg of sodium monomethyldithiocarbamate under ice-cooling and stirred for 3.5 hours at room temperature, followed by purification in the same procedure as Example 3B to give 24.3 mg of sodium 4-(2-acetamidoethyl)thio-3-[2-(2-aminothiazol-4-yl)-2-[[2-oxo-3-(thiophene-3- aldimino)imidazolidin-1-yl]carboxamido]acetamido]-2-oxoazetidine-1-sulfonate (a mixture of cis- and trans-isomers)

IR $\nu_{max}^{KBr}$cm$^{-1}$; 3300, 1760, 1720, 1660, 1510, 1268, 1225, 1043.

NMR(DMSO-d$_6$, ppm): 1.79, 1.81(each s, CH$_3$), 3.83(broad, s —CH$_2$—), 4.62(dd, J=2, 8 Hz, C$_3$—H), 4.83(d, J=2 Hz, C$_4$—H), 5.12(dd, J=5, 8 Hz, C$_3$—H), 5.30(d, J=5 Hz, C$_4$—H), 5.40, 5.43

(each d, J=8Hz, —CH—), 6.54, 6.62(each s, ⌇H), 7.4–7.65 (m, arom H), 7.86, 7.89(each s, =CH—), 8.84, 8.88 (each d, J=8 Hz, NH).

EXAMPLE 95B (1) To a solution of 0.43 g of (3R,4R)-4-(2-acetamidoethyl)thio-3-[2-(2-chloroacetamidothiazol-4-yl)-2-[1-methyl-1-(2-trimethylsilylethoxycarbonyl)ethoxyimino]acetamido]-2-oxoazetidine in 2 ml of DMF is added at −20° C. a solution of 0.55 g of sulfuric anhydride-DMF complex in 2 ml of DMF. The mixture is left standing at 0° C. for three days.

To the reaction mixture is added 0.5 g of pyridine. The mixture is concentrated under reduced pressure and the residue is dissolved in 4 ml of methanol, to which is added 0.6 g of tetra-n-butylammonium fluoride, followed by concentration. The residue is purified by a silica gel column-chromatography to give 0.63 g of tetran-butylammonium (3R,4R)-4-(2-acetamidoethyl)thio-3-[2-(2-chloroacetamidothiazol-4-yl-2-[1-methyl-1-(2-trimethylsilylethoxycarbonyl)ethoxyimino]acetamido]-2-oxoazetidine-1-sulfonate.

(2) To a solution of 0.62 g of the chloroacetyl derivative as obtained in (1) above in 2 ml of DMF is added a solution of 0.096 g of sodium monomethyldithiocarbamate in 0.3 ml of water and stirred for 15 minutes at 25° C.

To the mixture is added 0.6 g of tetra-n-butylammonium fluoride and the mixture is stirred for 30 minutes at 25° C.

The reaction mixture is concentrated under reduced pressure and the resultant is dissolved in 20 ml of ethyl acetate, followed by extraction with water (5 ml×5).

To the combined extract is added 8 ml of Dowex 50W H+ type ion exchange resin and the mixture is stirred for 15 minutes.

The reaction mixture is subjected to filtration and the filtrate is purified by an XAD-II column-chromatography to give 0.044 g of (3R,4R)-4-(2-acetamidoethyl)thio-3-[2-(2-aminothiazol-4-yl)-2-(1-carboxy-1-methylethoxyimino)acetamido]-2-oxoazetidine-1-sulfonic acid.

IR $\nu_{max}^{KBr}$cm$^{-1}$; 1765, 1630, 1540, 1260, 1040.

NMR(DMSO-d$_6$, ppm); 1.50(s, CH$_3$), 1.80(s, COCH$_3$), 2.84 (t, J=6 Hz, —SCH$_2$—), 3.22(m, —CH$_2$—), 5.21(d, J=4 Hz, C$_4$—H), 5.34(dd, J=4, 8 Hz, C$_3$—H), 7.10(s, ⌇H), 7.80–8.00(m, NH), 9.38(d, J=8 Hz, NH)

EXAMPLE 96B (1) To a solution of 0.58 g of (3R,4R)-4-methylthio-3-[2-(2-trimethylaminothiazol-4-yl)-2-[1-methyl-1-(2-trimethylsilylethoxycarbonyl)ethoxyimino]acetamido]-2-oxoazetidine in 2 ml of DMF is added 0.6 g of tetra-n-butylammonium fluoride and, the mixture is stirred for 30 minutes, followed by concentration to dryness under reduced pressure. The residue is dissolved in 2 ml of DMF, to which a solution of 0.55 g of sulfuric anhydride-DMF complex in 2 ml of DMF is added at −70° C., followed by leaving standing at 0° C. for two days.

To the reaction mixture is added 0.5 g of pyridine and the mixture is concentrated under reduced pressure. The residue is dissolved in 50% methanol, to which 10 ml of Dowex 50W H+ type ion exchange resin is added, followed by stirring for 30 minutes.

The mixture is filtered and to the filtrate is added sodium hydrogen carbonate to adjust the pH of the solution to pH 6.5.

Purification on an XAD-II column-chromatography gives 0.24 g of disodium (3R,4R)-4-methylthio-3-[2-(2-tritylaminothiazol-4-yl)-2-(1-carboxylato-1-methylethoxyimino)acetamido]-2-oxoazetidine-1-sulfonate.

IR $\nu_{max}^{KBr}$cm$^{-1}$; 1760, 1670, 1590, 1525, 1270, 1050.

NMR(DMSO-d$_6$, ppm); 1.38(s, CH$_3$), 1.45(s, CH$_3$), 2.14(s, SCH$_3$), 5.03(d, J=4 Hz, C$_4$—H), 5.30(dd, J=4, 8 Hz, C$_3$—H), 6.70(s, ⌇H), 7.20–7.45(m, arom H), 8.70(broad s, NH), 11.04(d, J=8 Hz, NH)

(2) To a solution of 0.19 g of the sulfonate derivative as obtained in (1) above 3 ml of 50% methanol is added 0.5 ml of 1N-HCl and the mixture is stirred for 3 hours at 25° C.

Evaporation under reduced pressure of methanol separates triphenylcarbinol, which is filtered off. The filtrate is purified on an XAD-II column-chromatography to give 0.09 g of (3R,4R)-4-methylthio-3-[2-(2-aminothiazol-4-yl)-2-(1-carboxy-1-methylethoxyimino)acetamido]-2-oxoazetidine-1-sulfonic acid.

IR $\nu_{max}^{KBr}$cm$^{-1}$; 1760, 1630, 1540, 1260, 1040.

NMR(D$_2$O, external standard, ppm); 1.64(s, CH$_3$), 2.35(s, SCH$_3$), 5.50(d, J=5 Hz, C$_4$—H), 5.60(d, J=5 Hz, C$_3$—H), 7.30(s, ⌇H).

EXAMPLE 97B (1) To a solution of 0.710 g of 3-[2-(2-chloroacetamidothiazol-4-yl)-2-methoxyiminoacetamido]-4-(2-formamidoethyl)thio-2-oxoazetidine in 3 ml of DMF is added at −20° C. a solution of 0.77 g of sulfuric anhydride-DMF complex in 3 ml of DMF. The mixture is left standing at 4° C. for two days.

To the reaction mixture is added 0.40 g of pyridine, followed by purification in the same procedure as in Example 1B to give 0.332 g of sodium 3-[2-(2-chloroacetamidothiazol-4-yl)-2-methoxyiminoacetamido]-4-(2-formamidoethyl)thio-2-oxoazetidine-1-sulfonate (a mixture of cis- and trans-isomers).

IR $\nu_{max}^{KBr}$cm$^{-1}$; 3450, 3250, 1761, 1660, 1535, 1250, 1042.

NMR(DMSO-d$_6$, ppm); 2.8–3.1(m, —CH$_2$—), 3.5–3.8(m, —CH$_2$—), 3.90(s, CH$_3$), 4.38(s, ClCH$_2$—), 4.75(dd, J=2, 8 Hz, C$_3$—H trans), 5.02(d, J=2 Hz, C$_4$—H trans), 5.34(dd, J=5, 8 Hz, C$_3$—H cis), 7.42, 7.52(each s, \\/H \|\| ), 9.46(d, J=8 Hz, NH), 8.74(s, CHO).

(2) A solution of 0.273 g of the sulfonate derivative as obtained in (1) above and 0.064 g of sodium monomethyldithiocarbamate in 2 ml of water is stirred for 1 hour at room temperature, followed by purification in the same manner as in Example 3 to give 0.110 g of sodium 3-[2-(2-aminothiazol-4-yl)-2-methoxyiminoacetamido]-4-(2-formamidoethyl)thio-2-oxoazetidine-1-sulfonate (a mixture of cis- and trans-isomers).

IR $\nu_{max}^{KBr}$cm$^{-1}$; 3430, 3310, 1766, 1660, 1522, 1240, 1052.

NMR(DMSO-d$_6$, ppm); 2.7–3.0(m, —CH$_2$—), 3.86(s, CH$_3$) 5.00(d, J=2 Hz, C$_4$—H trans), 5.24(d, J=2 Hz, C$_3$—H trans), 5.25(d, J=5 Hz, C$_4$—H cis), 5.28(dd, J=5, 8 Hz, C$_3$—H cis), 6.78, 6.96(each s, \\/H \|\| ), 8.69, 8.70(each s, CHO), 9.38 (d, J=8 Hz, NH).

EXAMPLE 98B

To a solution of 0.30 g of (3R,4R)-4-(Z-2-acetamidovinyl)thio-3-[2-(2-chloroacetamido)-2-methoxyiminoacetamido]-2-oxoazetidine in 3 ml of DMF is added at −20° C. a solution of 0.299 g of sulfuric anhydride-DMF complex in 1.17 ml of DMF. The mixture is left standing at 0° C. for two days.

To the reaction mixture is added 0.154 g of pyridine, followed by purification in the same procedure as in Example 1B to give 0.071 g of sodium (3R,4R)-4-(Z-2-acetamidovinyl)thio-3-[2-(2-chloroacetamido)-2-methoxyiminoacetamido]-2-oxoazetidine-1-sulfonate.

IR $\nu_{max}^{KBr}$cm$^{-1}$: 3470, 3280, 1768, 1660, 1620, 1545, 1260, 1050.

NMR(DMSO-d$_6$, ppm): 1.98(s, CH$_3$), 3.88(s, CH$_3$), 4.36(s, —CH$_2$—), 5.11(d, J=5 Hz, C$_4$—H), 5.32(d, J=8Hz, H\\>=), S 5.36(dd, J=5, 8 Hz, C$_2$—H),

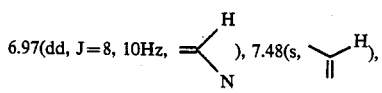

9.42(d, J=8 Hz, NH), 9.49(d, J=10 Hz, NH).

EXAMPLE 99B (1) To a solution of 1.4 g of 3-[2-(2-chloroacetamidothiazol-4-yl)-2-methoxyiminoacetamido]-4-[2-(p-nitrobenzyloxycarboxamidoethyl)thio]-2-oxoazetidine in 10 ml of DMF is added at −20° C. a solution of 1.37 g of sulfuric anhydride-DMF complex in 4.13 ml of DMF. The mixture is left standing at 4° C. for two days.

To the reaction mixture is added 0.76 g of pyridine, followed by purification in the same procedure as in Example 1B to give 1.1 g of sodium 3-[2-(2-chloroacetamidothiazol-4-yl)-2-methoxyiminoacetamido]-4-[2-(p-nitrobenzyloxycarboxamidoethyl]thio-2-oxoazetidine-1-sulfonate (a mixture of cis- and trans-isomers).

IR $\nu_{max}^{KBr}$cm$^{-1}$; 3250, 1792, 1762, 1700, 1685, 1656, 1510, 1344, 1250, 1038.

(2) 0.688 g of the sulfonate derivative as obtained in (1) above and 0.142 g of sodium monomethyldithiocarbamate are dissolved in a mixture of 4.5 ml of DMF and 0.3 ml of H$_2$O, and the mixture is stirred for 5 hours at room temperature.

The solvent is distilled off and the residue is purified following the same procedure as Example 3B to give 0.324 g of sodium (3R,4R)-3-[2-(2-aminothiazol-4-yl)-2-methoxyiminoacetamido]-4-[2-(p-nitrobenzyloxycarboxamido)ethyl]thio-2-oxoazetidine-1-sulfonate.

IR $\nu_{max}^{KBr}$cm$^{-1}$; 3320, 1765, 1708, 1670, 1608, 1517, 1347, 1250, 1048.

NMR(DMSO-d$_6$, ppm); 2.7–3.0(m, —CH$_2$—), 3.1–3.5(m, —CH$_2$—), 3.84(s, CH$_3$), 5.18(s, —CH$_2$—), 5.24(d, J=5 Hz, C$_4$—H), 5.30 (dd, J=5, 8 Hz, C$_3$—H), 6.89(s, \\/H \|\| ), 7.60, 8.20(each d, J=9 Hz, arom H), 9.39(d, J=8 Hz, NH).

(3) 0.257 g of the sulfonate derivative as obtained in (2) above is dissolved in a mixture of 6 ml of THF and 4 ml of a buffer solution (pH 7), to which is added 0.250 g of 10% palladium-carbon, followed by stirring for 30 minutes in a stream of hydrogen.

The resultant solid is filtered off, and the filtrate is evaporated to remove THF, followed by purification on an XAD-II column-chromatography to give 0.10 g of (3R,4R) 3-[2-(2-aminothiazol-4-yl)-2-methoxyiminoacetamido]-4-(2-aminoethyl)thio-2-oxoazetidine-1-sulfonate.

IR $\nu_{max}^{KBr}$cm$^{-1}$; 3310, 3200, 1769, 1660, 1610, 1525, 1240, 1040.

NMR(DMSO-d$_6$, ppm); 2.8–3.3(m, —CH$_2$—), 3.85(s, CH$_3$), 5.23(d, J=5 Hz, C$_4$—H), 5.32(dd, J=5, 8 Hz, C$_3$—H), 6.86(s, \\/H \|\| ), 7.13(broad s, NH₂), 7.76(broad s, NH₂), 9.40(d, J=8 Hz, NH).

EXAMPLE 100B

To a solution of 0.144 g of (3R,4R)-4-(2-acetamidoethyl)thio-3-[2-(2-formamidothiazol-4-yl)-2-(1-sodiotetrazol-5-yl)methoxyiminoacetamido]-2-oxoazetidine in 1.5 ml of DMF is added at −20° C. a solution of 0.285 g of sulfuric anhydride-DMF complex in 0.86 ml of DMF. The mixture is left standing at 0° C. for three days.

To the reaction mixture is added 0.12 ml of pyridine, followed by purification in the same procedure as in Example 1B to give 0.120 g of sodium (3R,4R)-4-(2-acetamidoethyl)thio-3-[2-(2-formamidothiazol-4-yl)-2-(tetrazol-5-yl)methoxyiminoacetamido]-2-oxoazetidine-1-sulfonate.

IR $\nu_{max}^{KBr}$cm⁻¹; 1765, 1655, 1545, 1270, 1050.

NMR(DMSO-d₆, ppm); 1.83(s, CH₃), 5.18(d, J=5 Hz, C₄—H), 5.30(s, —CH₂—), 5.36(dd, J=5, 8 Hz, C₃—H),

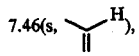 7.46(s, 8.1–8.35(m, NH), 8.52(s, CHO), 9.98(d, J=8 Hz, NH).

EXAMPLE 101B (1) To a solution of 1.085 g of (3S,4R)-4-azido-3-(2-trimethylsilylethoxycarboxamido)-2-oxoazetidine in 3 ml of DMF is added a solution of 1.225 g of SO₃-DMF complex in 4.8 ml of DMF with stirring at −70° C. and the mixture is allowed to stand for 60 hrs. at 0° C.

After the addition of 0.632 g of pyridine, the solvent is distilled off under reduced pressure and the residue is dissolved in a solution of 2.220 g of tetra-n-butylammonium chloride in 10 ml of dichloromethane.

The resulting mixture is chromatographed on a column of silica gel [eluting with ethyl acetate:chloroform:methanol (4:4:1)] to obtain 2.300 g of tetra-n-butylammonium (3S,4R)-4-azido-3-(2-trimethylsilylethoxycarboxamido)-2-oxoazetidine-1-sulfonate.

IR $\nu_{max}^{KBr}$cm⁻¹; 2110, 1780, 1720, 1670, 1250.

NMR(CDCl₃, ppm); 0.03(s, si(CH₃)₃), 0.90(t, J=6 Hz, CH₃), 2.10–2.80(m, —CH₂—), 3.00–3.30(m, —CH₂—), 4.20(t, J=8 Hz, —CH₂O—), 4.90(d, J=4 Hz, C₄—H), 5.20(dd, J=4, 8 Hz, C₃—H), 6.20(d, J=8 Hz, NH).

(2) A mixture of 1.185 g of tetra-n-butylammonium (3S,4R)-4-azido-3-(2-trimethylsilylethoxycarboxamido)-2-oxoazetidine-1-sulfonate, 0.500 g of 10% palladium-carbon, 0.500 g of acetic anhydride and 10 ml of ethylacetate is stirred for 2 hours in a stream of hydrogen at room temperature.

The reaction mixture is filtered and the filtrate is chromatographed on a column of silica gel [eluting with ethylacetate:chloroform:methanol (4:4:1)] to give 0.432 g of tetra-n-butylammonium (3S,4S)-4-acetamido-3-(2-trimethylsilylethoxycarboxamido)-2-oxoazetidine-1-sulfonate.

IR $\nu_{max}^{KBr}$cm⁻¹: 1780, 1720, 1670, 1530, 1250.

NMR(in CDCl₃, ppm); 0.03(s, Si(CH₃)₃), 0.90(t, J=6 Hz, CH₃), 2.00(s, COCH₃), 2.10–2.80(m, —CH₂—), 3.00–3.30(m, —CH₂—), 4.20(t, J=8 Hz, —CH₂O—), 4.70(m, C₄—H), 5.10(m, C₃—H), 6.00 (d, J=8 Hz, NH), 6.80(d, J=8 Hz).

EXAMPLE 102B

To a solution of 0.80 g of (3S,4R)-4-azido-3-[2-(2-tritylaminothiazol-4-yl)-2-[1-methyl-1-(2-trimethylsilylethoxycarbonyl)ethoxyimino]acetamido]-2-oxoazetidine in 4 ml of DMF is added 0.505 g of sulfuric anhydride-DMF complex in 1.98 ml of DMF at −20° C., and the reaction is allowed to proceed at 0° C. for 2 days. To the reaction mixture are added 0.26 g of pyridine and diethyl ether and, then, worked up in the manner of Example 1B. The above procedure provides 0.673 g of sodium (3S,4S)-4-azido-3-[2-(2-tritylaminothiazol-4-yl)-2-[1-methyl-1-(2-trimethylsilylethoxycarbonyl)ethoxyimino]acetamido]-2-oxoazetidine-1-sulfonate.

IR $\nu_{max}^{KBr}$cm⁻¹; 3380, 2115, 1778, 1728, 1676, 1512, 1282, 1245, 1050.

NMR(DMSO-d₆, ppm); 0.05(s, CH₃), 0.95(t, J=8 Hz, —CH₂—), 4.13(t, J=8 Hz, —CH₂—), 5.14(dd, J=5, 8 Hz, C₃—H), 5.44(d, J=5 Hz, C₄—H),

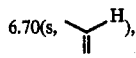 6.70(s, 7.15–7.53(m, arom H), 8.73(s, NH), 9.08(d, J=8 Hz, NH).

EXAMPLE 103B (3R,4R)-4-(2-acetamidoethyl)thio-3-[2-(2-aminothiazol-4-yl)-2-(1-carboxy-1-methylethoxyimino)acetamido]-2-oxoazetidine-1-sulfonic acid is placed in a sterile 12 ml vial in an amount of 250 mg (potency). The vial is then stoppered under vacuum (50 mmHg).

EXAMPLE 104B (3R,4R)-4-methylthio-3-[2-(2-aminothiazol-4-yl)-2-(1-carboxy-1-methylethoxyimino)acetamido]-2-oxoazetidine-1-sulfonic acid (500 mg) is placed in a 17 ml vial, which is then stoppered.

EXAMPLE 105B

Cefotiam (250 g) and (3R,4R)-4-methylthio-3-[2-(2-aminothiazol-4-yl)-2-(1-carboxy-1-methylethoxyimino)acetamido]-2-oxoazetidine-1-sulfonic acid (250 g) are mixed under aseptic conditions, and the mixture is placed in sterile 12 ml—vials in an amount of 250 mg potency) per vial. The vials are then stoppered under vacuum (50 mmHg).

EXAMPLE 106B

Sodium (3R,4R)-3-[2-(2-aminothiazol-4-yl)-2-methoxyiminoacetamido]-4-methylthio-2-oxoazetidine-1-sulfonate is placed in a sterile 12 ml vial in an amount of 250 mg (potency).

EXAMPLE 107B

Sodium (3R,4S)-3-[2-(2-aminothiazol-4-yl)-2-methoxyiminoacetamido]-4-phenylthio-2-oxoazetidine-1-sulfonate (500 mg) is placed in a 17 ml vial, which is then stoppered.

C. 1-Sulfo-2-Oxoazetidine derivatives which are substituted in the 4-position through a carbon atom Third aspect of the disclosure relates to additional novel 1-sulfo-2-oxoazetidine derivatives having excellent antimicrobial and β-lactamase-inhibitory activities, and a process for preparing the same, and using of the same.

Heretofore, various 2-oxoazetidine derivatives have been synthesized and reported in e.g. Tetrahedron, 34 (1978), 1731-1767; Chemical Reviews, 76 (1976), 113-346; Synthesis (1973), 327-346, etc. However, none of those 2-oxoazetidines which have a sulfo group at the 1-position and a substituent at the 4-position have been known yet.

This portion of the disclosure is directed to novel 1-sulfo-2-oxoazetidine derivatives of the formula:

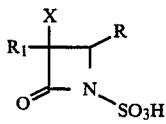
(I)C wherein R is an organic residue attached to the azetidine ring through a carbon atom therein; $R^1$ is an amino group which may optionally be acylated or protected; X is hydrogen or methoxyl, or a pharmaceutically acceptable salt or ester thereof and a process for the preparation thereof, and the use thereof.

It has been found that the 1-sulfo-2-oxoazetidine derivative (I)C can be obtained by sulfonating a compound of the formula:

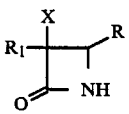
(II)C wherein R, $R^1$ and X are as defined above, or a salt or ester thereof, or by acylating a compound of the formula

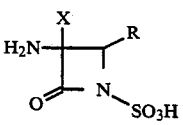
(III)C wherein R and X are as defined above, or a salt or ester thereof, and that the resulting compound (I)C possesses excellent antimicrobial and β-lactamase-inhibitory activities.

In the foregoing formulas (I)C, (II)C and (III)C, the symbol R is an organic residue attached to the 2-oxoazetidine nucleus at the 4-position through a carbon atom in said organic residue, i.e. a residue derived from an organic compound by removal of one hydrogen atom attached to a carbon atom thereof. Such organic residue includes, for example, alkyl, cycloalkyl, alkenyl, alkynyl, cycloalkenyl, aryl, a heterocyclic group, and the like, which may optionally be substituted by one or more substituents. Hereinafter, in this specification, any group which may optionally be substituted will be designated by a superscript asterisk "*". For example, an alkyl which may optionally be substituted will be represented by "alkyl*". In such cases, the number of the substituents is not restricted to one, and some substituted groups may have two to a few substituents which may be the same or different. The alkyl is preferably a straight or branched-chain lower alkyl having 1 to 6 carbon atoms, such as methyl, ethyl, n-propyl, isopropyl, n-butyl, isobutyl, sec-butyl, tert-butyl, n-pentyl, isopentyl, n-hexyl, isohexyl or the like. The cycloalkyl preferably has 3 to 8 carbon atoms and includes, for example, cyclopropyl, cyclobutyl, cyclopentyl, cyclohexyl, cycloheptyl, adamantyl, etc. The alkenyl is preferably a straight or branched-chain lower alkenyl having 2 to 6 carbon atoms such as vinyl, allyl, isopropenyl, 2-methallyl, 2-butenyl, 3-butenyl or the like. The alkynyl is preferably a straight or branched-chain lower alkynyl having 2 to 6 carbon atoms such as ethynyl, 1-propynyl, 2-propynyl or the like. The cycloalkenyl includes, for example, those having 3 to 8 carbon atoms such as 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, 1,4-cyclohexadienyl, etc. Among others, a cycloalkenyl having 4 to 6 carbon atoms is preferred. The aryl includes, for example, phenyl, α-naphthyl, β-naphthyl, biphenyl, anthryl and the like. Of these, phenyl and naphthyl are usually advantageous. The heterocyclic group includes, for example, 5 to 8-membered heterocyclic rings having one to a few hetero-atoms such as nitrogen (inclusive of N-oxide), oxygen and sulfur, as well as fused rings corresponding thereto, which have an available bonding site at a carbon atom thereof. Examples of such heterocyclic group which are usually advantageous include 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidyl, benzopyranyl, 1,8-, 1,5-, 1,6-, 1,7- 2,7- or 2,6-naphthyridyl, quinolyl, thieno[2,3-b]pyridyl and the like. Among others, a 5- or 6-membered heterocyclic ring having one to four hetero-atoms selected from nitrogen and sulfur, such as thienyl, thiazolyl, thiadiazolyl, triazolyl, tetrazolyl or the like is preferred.

Of these groups, the alkyl, alkenyl and alkynyl groups may be substituted with 1 to 3 substituents such as, for example, cycloalkyl*, cycloalkenyl*, aryl*, a heterocyclic group*, alkoxycarbonyl, acyl, oxo, halogen, cyano, hydroxy, alkoxy, aryl*-oxy, acyloxy, carbamoyloxy, hydroxysulfonyloxy, alkylsulfonyloxy, aryl*-sulfonyloxy, nitro, amino, carboxy, aminocarbonyl, alkylthiocarbonyl, mercapto, alkylthio, aminoalkylthio, acylaminoalkylthio, aralkyl*-thio, aryl*-thio, heterocyclic*-thio, quaternary ammonium* or the like. The substituted alkyl group includes, for example, a group of the formula [A]:

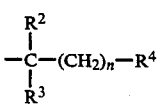
[A]

wherein n is an integer of 0 to 3; $R^2$ and $R^3$ which may be the same or different, stand for hydrogen, alkyl, cycloalkyl*, aralkyl*, aryl*, heterocyclic group*, alkoxycarbonyl or acyl, or $R^2$ and $R^3$ taken together stand for oxo; and $R^4$ is hydrogen, alkyl, cycloalkyl*, aryl*, a heterocyclic group*, halogen, cyano, hydroxy, alkoxy, aryl\*-oxy, aralkyl\*-oxy, acyloxy, carbamoyloxy, hydroxysulfonyloxy, alkylsulfonyloxy, aryl\*-sulfonyloxy, sulfoxy, nitro, amino, azido, carboxy, alkoxycarbonyl, alkoxycarbonylalkyloxy, aminocarbonyl, alkylthiocarbonyl, acyl, mercapto, alkylthio, aminoalkylthio, acylaminoalkylthio, aralkyl\*-thio, aryl\*-thio, heterocycle\*-thio or quaternary ammonium\*. In the substituent on the alkyl, alkenyl and alkynyl group, and the group represented by $R^2$, $R^3$ or $R^4$, the alkoxy is preferably a straight or branched-chain lower alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy or the like. Aralkyl includes, for example, benzyl, phenethyl, phenylpropyl, naphthylmethyl, etc. The halogen includes fluorine, chlorine, bromine and iodine. The quaternary ammonium group includes, for example, a group of the formula:

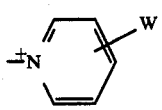

wherein W is hydrogen, an alkyl, carbamoyl, carboxyl, sulfo or alkoxyl, which may be derived from pyridine derivatives such as pyridine, carbamoyl-substituted pyridine (e.g. nicotinamide, isonicotinamide, etc.), carboxyl-substituted pyridine (e.g. nicotinic acid, isonicotinic acid, etc.), sulfo-substituted pyridine (e.g. pyridine sulfonic acid, etc.); quinolinium, etc. These quaternary ammonium may form an inner salt with sulfo group at 1-position of the 2-oxoazetidine nucleus. The acyl includes, for example, formyl, alkylcarbonyl, aryl\*-carbonyl, aralkyl\*-carbonyl, heterocyclic\*-acetyl, etc. as well as the acyl groups in $R^1$ mentioned below. Of these, for example, $C_{1-6}$ alkylcarbonyl (e.g. acetyl, propionyl, n-butyryl, isobutyryl, n-pentanoyl, n-hexanoyl, etc.), benzoyl which may be substituted (e.g. benzoyl, 4-hydroxybenzoyl, 4-methoxybenzoyl, etc.), $C_{7-9}$ (aralkylcarbonyl which may be substituted (e.g. phenylacetyl, 4-hydroxyphenylacetyl, 4-methoxyphenylacetyl, etc.), 5-membered heterocyclic-carbonyl or -acetyl group containing at least one of oxygen, nitrogen and sulfur, which may be substituted (e.g. 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl, etc.) are preferred. And, the alkyl moiety of alkylsulfonyloxy, alkylthiocarbonyl, alkylthio, aminoalkylthio, acylaminoalkylthio and alkoxycarbonylalkyloxy; the alkoxyl moiety of alkoxycarbonyl and alkoxycarbonylalkyloxy; and the acyl moiety of acyloxy and acylaminoalkylthio have the same meanings as mentioned above.

The substituents which can be present on the cycloalkyl, cycloalkenyl, aralkyl, aryl, heterocyclic and quaternary ammonium groups include, for example, alkyl, alkoxy, alkenyl, aryl, aralkyl, mercapto, alkylthio, arylthio, aralkylthio, alkylsulfonyl, arylsulfonyl, aralkylsulfonyl, hydroxy, oxo, thioxo, halogen, nitro, amino, cyano, carbamoyl, carboxy, acyl, acyloxy, acylamino, hydroxyalkyl, carboxyalkyl, haloalkyl, mono- or dialkylaminoalkyl and the like (wherein the alkyl, alkoxy, alkenyl, aryl, aralkyl, acyl and halogen are those as exemplified above).

When the organic residue R attached to the azetidine ring through a carbon atom therein contains an amino group, said amino group may be substituted or protected, and a carboxyl and a hydroxyl group, if any, may be likewise protected. The substituents which can be present on the amino group includes the acyl in $R^1$ mentioned below, as well as alkyl, alkoxy, hydroxyalkyl, aralkyl\*, aryl\*, heterocyclic group\*, sulfo, alkylsulfonyl, aralkyl\*-sulfonyl, aryl\*-sulfonyl, alkoxycarbonyl, aralkyl\*-oxycarbonyl, aryl\*-oxycarbonyl and the like (wherein the alkyl, alkoxy, aralkyl\*, aryl\* and heterocyclic group\* are those as exemplified above). Optionally the amino group, taken together with such substituent, may form a cyclic amino group such as pyrrolidino, piperidino, morpholino, piperazino or the like. The protective group for amino includes, for example, those exemplified below as the "protective group for amino" for $R^1$. The protective group for carboxyl includes any group which can be conventionally used as a carboxy-protecting group in the fields of $\beta$-lactam and other organic chemistry, such as ester residues (e.g., methyl, ethyl, n-propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, $\beta$-methylsulfonylethyl, $\beta$-trimethylsilylethyl, methylthiomethyl, trityl, $\beta,\beta,\beta$-trichloroethyl, $\beta$-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxido-2-methyl, methylsulfinylmethyl, bis(p-methoxyphenyl)-methyl, 2-cyano-1,1-dimethylethyl, etc.), silyl, and the like. The protective group for hydroxyl includes any group which can be conventionally used as a hydroxy-protecting group in the fields of $\beta$-lactam and other organic chemistry, such as ester residues, e.g., acetyl, chloroacetyl, etc.; esterified carboxyl groups, e.g., $\beta,\beta,\beta$-trichloroethoxycarbonyl, $\beta$-trimethylsilylethoxycarbonyl, etc.; ether residues, e.g., tert-butyl, benzyl, p-nitrobenzyl, trityl, methylthiomethyl, $\beta$-methoxyethoxymethyl, etc.; silylether residues, e.g., trimethylsilyl, tert-butyldimethylsilyl, etc.; acetal residues, e.g., 2-tetrahydropyranyl, 4-methoxy-4-tetrahydropyranyl, etc. and the like. The choice of the above-mentioned hydroxy-protecting group is not critical as is the case with the amino- and carboxy-protecting groups.

Preferred examples of the organic residue R are groups represented by the formula [A], which may be accompanied with the proviso that when both $R^2$ and $R^3$ are hydrogen, $R^4$ is other than hydrogen or an alkyl (especially, a straight-chain alkyl) group; or when one of $R^2$ and $R^3$ is hydrogen, and the other of them is an alkyl (especially, a straight-chain alkyl) group, and n is zero, $R^4$ is other than hydrogen. Among groups [A], a group of the formula [B]:

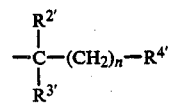

[B]

wherein n is as defined above, $R^{2'}$ and $R^{3'}$, which may be the same or different, respectively stand for hydrogen or alkyl, or $R^{2'}$ and $R^{3'}$ taken together stand for oxo, and $R^{4'}$ is hydrogen, alkyl, aryl\*, halogen, cyano, hydroxyl, alkoxyl, aralkyl\*-oxy, acyloxy, carbamoyloxy, alkylsulfonyloxy, sulfo-oxy, amino, azido, carboxyl, alkoxycarbonyl, alkoxycarbonylalkyloxy, alkylthio, heterocyclic*-thio or quaternary ammonium* group, among these groups, the amino being optionally substituted or protected and the carboxyl being optionally protected, with the proviso as mentioned above in $R^2$, $R^3$ and $R^4$, is availably used. And, more favorable ones among the groups [A] and [B] are (1) the case that $R^2$ and $R^3$, $R^{2'}$ and $R^{3'}$ taken together stand for oxo; and $R^4$, $R^{4'}$ is amino group which may be substituted or protected, e.g. a group of the formula [C]:

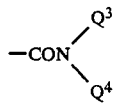   [C]

wherein $Q^3$ and $Q^4$, which may be the same or different, respectively stand for hydrogen; alkyl*; alkoxy; aralkyl*; aryl*; heteroxyclic* group; sulfo; alkylsulfonyl; amino; aralkyl*-sulfonyl; aryl*-sulfonyl; alkoxycarbonyl; aralkyl*-oxycarbonyl, aryl*-oxycarbonyl; the acyl or protective group as mentioned below in the symbol $R^1$, preferably, a group of the formula;

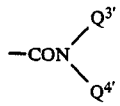

wherein $Q^{3'}$ and $Q^{4'}$ which may be the same or different, respectively stand for hydrogen; $C_{1-6}$ alkyl; $C_{1-6}$ alkoxyl; amino; carboxy-$C_{1-6}$ alkyl; $C_{1-6}$ alkylcarbonyl which may be substituted with a halogen; sulfo; phenyl; benzoyl; carbamoyl-$C_{1-6}$ alkyl; p-nitrobenzyloxycarbonyl; or β-$C_{1-6}$ alkylsulfonyl-$C_{1-6}$ alkoxycarbonyl, and especially, carbamoyl, mono- or di-$C_{1-6}$ alkylcarbamoyl, phenylcarbamoyl, sulfocarbamoyl, $C_{1-6}$ alkoxycarbamoyl, carboxy-$C_{1-6}$ alkylcarbamoyl, etc., (2) the case that $R^2$ and $R^3$, $R^{2'}$ and $R^{3'}$, taken together, respectively stand for oxo; and $R^4$, $R^{4'}$ is hydroxyl group, alkoxyl, aryl*-oxy, aralkyl*-oxy or alkoxycarbonylalkyloxy group, i.e. a group of the formula [D]:

—$COQ^5$   [D]

wherein $Q^5$ is hydroxyl group which may be protected; alkoxyl; aryloxy which may be substituted; aralkyloxy which may be substituted; or alkoxycarbonylalkyloxy group, preferably, a group of the formula;

—$COQ^{5'}$ wherein $Q^{5'}$ is $C_{1-6}$ alkoxyl, p-nitrobenzyloxy or $C_{1-6}$ alkoxycarbonyl-$C_{1-6}$ alkyloxy group, (3) the case that $R^2$ and $R^3$, $R^{2'}$ and $R^{3'}$ are both hydrogen, for example, a group of the formula [E]:

—$(CH_2)_m$—$X^1$—$Q^6$   [E]

wherein m is an integer of 1 to 4, $X^1$ is —NH—, —S—, —O— or a direct bond, and $Q^6$ is hydrogen; carbamoyl; an acyl which may be substituted; an alkyl; a heterocyclic group which may be substituted; or a carboxyl group which may be protected, among them [E], a group of the formula;

—$(CH_2)_m$—$X^1$—$Q^{6'}$ wherein m and $X^1$ are as defined above, and $Q^{6'}$ is an $C_{1-6}$ alkylcarbonyl which may be substituted with a halogen; $C_{1-6}$ alkyl; benzoyl; 5- or 6-membered nitrogen-containing heterocyclic group (e.g. pyrrolyl, thiazolyl, thiadiazolyl, diazolyl, oxazolyl, oxadiazolyl, triazolyl, tetrazolyl, etc.) which may be substituted with a $C_{1-6}$ alkyl group; or 5- or 6-membered nitrogen-containing heterocyclic-thioacetyl which heterocyclic ring may be substituted with a $C_{1-6}$ alkyl. Concrete examples of the group [C] include carbamoyl, N-methylcarbamoyl, N-ethylcarbamoyl, N-propylcarbamoyl, N-isopropylcarbamoyl, N-butylcarbamoyl, N,N-dimethylcarbamoyl, N,N-diethylcarbamoyl, N-sulfocarbamoyl, N-methoxycarbamoyl, N-ethoxycarbamoyl, N-propoxycarbamoyl, N-isopropoxycarbamoyl, N-hydroxycarbamoyl, N-aminocarbamoyl, [1-(L)-benzyloxycarbonylethyl]aminocarbonyl, [1-(L)-carboxyethyl]aminocarbonyl, N-phenylcabamoyl, N,N-diphenylcarbamoyl, N-(p-chlorophenyl)carbamoyl, N-benzylcarbamoyl, N,N-dibenzylcarbamoyl, N-hydroxymethylcarbamoyl, N-hydroxyethylcarbamoyl, N-chloromethylcarbamoyl, N-acetylcarbamoyl, N-propionylcarbamoyl, N-carboxycarbamoyl, N-methoxycarbonylcarbamoyl, N-ethoxycarbonylcarbamoyl, N-phenoxycarbonylcarbamoyl and the like. Concrete examples of the group [D] include carboxyl, methoxycarbonyl, ethoxycarbonyl, propoxycarbonyl, isopropoxycarbonyl, n-butyloxycarbonyl, isobutyloxycarbonyl, secbutyloxycarbonyl, pentoxycarbonyl, benzyloxycarbonyl, phenethyloxycarbonyl, methoxycarbonylmethyloxycarbonyl, ethoxycarbonylmethyloxycarbonyl, phenyloxycarbonyl, p-chlorophenyloxycarbonyl, hydroxymethyloxycarbonyl, sulfomethyloxycarbonyl and the like. Concrete examples of the group [E] include an acylaminoalkyl (e.g. acetylaminomethyl, propionylaminomethyl, n-butyrylaminomethyl, isobutyrylaminomethyl, acetylaminoethyl, propionylaminoethyl, acetylaminopropyl, acetylaminobutyl, benzoylaminomethyl, benzoylaminoethyl, benzoylaminopropyl, formylaminomethyl, phenylacetylaminomethyl, 4-hydroxyphenylacetylaminomethyl, 2-thienylcarbonylaminomethyl, 2-furylcarbonylaminomethyl, thienylacetylaminomethyl, 2-amino-4-thiazolylacetylaminomethyl, etc.), a carbamoylaminoalkyl (e.g. carbamoylaminomethyl, carbamoylaminoethyl carbamoylaminopropyl, etc.), an acyloxyalkyl (e.g. acetoxymethyl, propionyloxymethyl, isopropionyloxymethyl, acetoxyethyl, 2-(2-chloroacetamido-4-thiazolyl)-(Z)-2-methoxyiminoacetoxymethyl, 2-(2-amino-4-thiazolyl)-(Z)-2-methoxyiminoacetoxymethyl, 2-thienylacetoxymethyl, 2-furylacetoxymethyl, thiazolylacetoxymethyl, 2-amino-4-thiazolylacetoxymethyl, benzoyloxymethyl, benzoyloxyethyl, 4-hydroxybenzoyloxymethyl, 4-methoxybenzoyloxymethyl, monochloroacetoxymethyl, trichloroethoxycarbonyloxymethyl, acetoacetoxymethyl, (1-methyl-1H-tetrazol-5-yl)thioacetoxymethyl, (1-N,N-dimethylaminoethyl-1H-tetrazol-5-yl)thioacetoxymethyl, (1-carboxymethyl-1H-tetrazol-5-yl)thioacetoxymethyl, (2-methylthiadiazol-5-yl)thioacetoxymethyl, (2-methyloxadiazol-5-yl)thioacetoxymethyl, (1-methyl-1H-triazol-5-yl)thioacetoxymethyl, etc.), carbamoyloxyalkyl (e.g. carbamoyloxymethyl, carbamoyloxyethyl, carbamoyloxypropyl, carbamoyloxyisopropyl, etc.), a hetrocyclic-thioalkyl (e.g. thienylthiomethyl, thienylthioethyl, thienylthiopropyl, furyl-thiomethyl, furylthioethyl, thiazolylthiomethyl, thiazolylthioethyl, 2-aminothiazolylthiomethyl, 2-aminothiazolylthioethyl, 2-aminothiazolylthioisopropyl, (2-methyl-thiadiazol-5-yl)thiomethyl, (2-methyloxadiazol-5-yl)thiomethyl, oxazolylthiomethyl, (1-methyl-1H-triazol-5-yl)thiomethyl, (1-methyl-1H-tetrazol-5-yl)thiomethyl, (1-N,N-dimethylaminoethyl-1H-tetrazol-5-yl)thiomethyl, (1-carboxymethyl-1H-tetrazol-5-yl)thiomethyl, (1-methyl-1H-tetrazol-5-yl)thioethyl, (1-methyl-1H-tetrazol-5-yl)thiopropyl, etc.), a alkylthioalkyl (e.g. methylthiomethyl, methylthioethyl, methylthiopropyl, methylthioisopropyl, ethylthiomethyl, ethylthioethyl, propylthiomethyl, propylthioethyl, isopropylthiomethyl, n-butylthiomethyl, isobutylthiomethyl, sec-butylthiomethyl, etc.) a carboxy- or esterified carboxyalkyl group (e.g. carboxymethyl, carboxyethyl, carboxypropyl, carboxyisopropyl, carboxy-n-butyl, carboxyisobutyl, carboxy-sec-butyl, methoxycarbonylmethyl, ethoxycarbonylmethyl, methoxycarbonylethyl, propoxycarbonylmethyl, isopropoxycarbonylmethyl, phenoxycarbonylmethyl, phenoxycarbonylethyl, benzyloxycarbonylmethyl, benzyloxycarbonylethyl, p-hydroxybenzyloxycarbonylmethyl, p-methoxybenzyloxycarbonylmethyl, carboxymethyloxycarbonylmethyl, etc.) and the like.

In the foregong Formulas (I)C, (II)C and (III)C, $R^1$ is an amino group which may optionally be acylated or protected, and the acyl group in the acylated amino group includes any of the conventional acyl groups on the 6- and 7-amino groups of known penicillin derivatives and cephalosporin derivatives, respectively. Examples of the acyl group include (i) a group of the formula [F]:

$$R^5-CO- \qquad [F]$$

wherein $R^5$ is a lower alkyl or a heterocyclic* group, (ii) a group of the formula [G]:

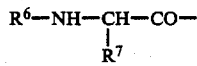

[G]

wherein $R^6$ is hydrogen, an amino acid residue, an aminoprotective group or a group $R^8-(CH_2)_{n1}-CO-$ where $R^8$ is a heterocyclic* group and $n_1$ is an integer of 0 to 2, and $R^7$ is a lower alkyl, phenyl*, heterocyclic*-carbonylamino or a heterocyclic group, (iii) a group of the formula [H]:

$$R^9-R^{10}-CO- \qquad [H]$$

wherein $R^9$ is a group

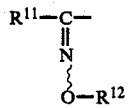

where $R^{11}$ is alkyl*, a heterocyclic* group or phenyl* and $R^{12}$ is hydrogen, a lower alkyl, lower alkenyl or a group $-R^{13}-R^{14}$ where $R^{13}$ is a lower alkylene or lower alkenylene and $R^{14}$ is phenyl*, carboxyl or an ester thereof, or mono- or di(lower alkyl)amino, and $R^{10}$ is a direct bond or a group

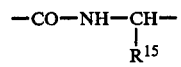

where $R^{15}$ is a lower alkyl, phenyl* or thiazolyl*, (iv) a group of the formula [I]:

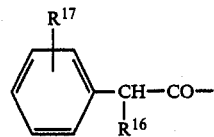

[I]

wherein $R^{16}$ is hydroxy, hydroxysulfonyloxy, carboxy, ureido*, sulfamoyl*, sulfo, phenoxycarbonyl or formyloxy and $R^{17}$ is hydrogen, a lower alkyl, a lower alkoxy, halogen, nitro or hydroxy, (v) a group of the formula [J]:

$$R^{18}-R^{19}-CH_2-CO- \qquad [J]$$

wherein $R^{18}$ is cyano, phenyl*, phenoxy*, a lower alkyl*, alkenyl* or a heterocyclic* group and $R^{19}$ is a direct bond or —S—, and the like.

In symbols $R^5$ through $R^{19}$, the alkyl, heterocyclic group, alkoxy and halogen include those exemplified above for R. The amino acid residue includes, for example, glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophanyl, prolyl and the like. The protective group for amino includes those exemplified below as the "protective group for amino" for $R^1$. The alkylene has preferably a straight or branched-chain lower alkylene having 1 to 3 carbon atoms and includes, for example, methylene, ethylene, propylene, isopropylene, etc. The alkenylene is preferably a straight or branched-chain lower alkenylene having 2 to 4 carbon atoms such as vinylene, propenylene, or the like. The carboxylic ester includes lower alkyl esters having 1 to 6 carbon atoms in said alkyl moiety such as methyl ester, ethyl ester, propyl ester, n-butyl ester, isobutyl ester, tert-butyl ester, etc. The substituents on the heterocyclic* group, phenyl*, thiazolyl*, phenoxycarbonyl and phenoxy* include those substituents on the heterocyclic* group and aryl* described above for R. In addition, the substituent on the thiazolyl* may include, for example, an acylamino having 2 to 4 carbon atoms substituted with alkyl, alkoxy, halogen, hydroxy, amino, or the like, and the substituent on the heterocyclic* group may include, for example, phenyl substituted with alkyl, alkoxy, halogen, nitro, amino, etc. The substituent on the ureido* include, for example, sulfo in the form of salt with a suitable cation such as sodium or potassium; carbamoyl; sulfamoyl; amidino; an alkyl having 1 to 3 carbon atoms; and the like. The substituent on the sulfamoyl* includes, for example, a lower alkyl having 1 to 3 carbon atoms, amidino and the like. The substituent on the lower alkyl* includes, for example, halogen, hydroxy, cyano, trifluoromethyl and the like. The substituent on the alkenylene* includes, for example, carboxy, cyano and the like.

The formula

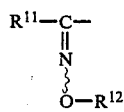

for R⁹ represents either the syn isomer

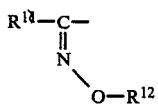

or the anti isomer

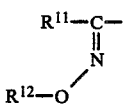

or a mixture thereof.

Among them, preferably one of the groups [G] is a group of the formula:

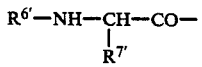

wherein R⁶' is an amino protective group or a group R⁸—(CH₂)ₙ₁—CO— where R⁸ is a heterocyclic* group and n₁ is an integer of 0 to 2, and R⁷' is phenyl* or heterocyclic* group; preferably one of the groups [H] is a group of the formula:

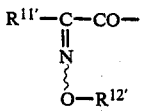

wherein R¹¹' is a heterocyclic* group or phenyl*, R¹²' is hydrogen, a lower alkyl or a group —R¹³—R¹⁴' wherein R¹³ is as defined above and R¹⁴' is carboxyl or an esterified carboxyl group; and preferably one of the groups [J] is a group of the formula:

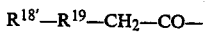

wherein R¹⁸' is a heterocyclic* group and R¹⁹ is as defined above, and the like.

Especially, in view of the antibiotic activities, a group of the formula:

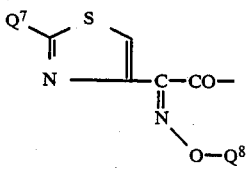

wherein Q⁷ is amino or a protected amino group, and Q⁸ is a lower alkyl, a lower alkenyl, a group —CH₂COOQ⁹ or a group

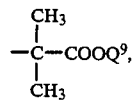

and COOQ⁹ is carboxyl or an esterified carboxyl group, is more useful as the acyl moiety of the acylated amino group for R¹.

In the above-mentioned acyl groups, examples of the acyl group R⁵—CO— include 3-(2,6-dichlorophenyl)-5-methylisoxazol-4-yl-carbonyl, 4-ethyl-2,3-dioxo-1-piperazinocarbonyl and the like.

Examples of the acyl group

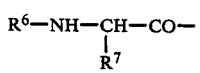

include D-alanyl, benzyl-Nᵅ-carbobenzoxy-γ-D-glutamyl-D-alanyl, D-phenylglycyl-D-alanyl, N-carbobenzoxy-D-alanyl, N-carbobenzyl-D-phenylglycyl, D-alanyl-D-phenylglycyl, γ-D-glutamyl-D-alanyl, 2-(4-ethyl-2,3-dioxo-1-piperazinocarboxamido)-2-phenylacetyl, 2-(4-ethyl-2,3-dioxo-1-piperazinocarboxamido)-2-(4-sulfoxyphenyl)acetyl, N-(4-ethyl-2,3-dioxo-1-piperazinocarbonyl)-D-alanyl, N-(4-ethyl-2,3-dithiooxo-1-piperazinocarbonyl)-D-phenylglycyl, 2,2-bis-(4-ethyl-2,3-dioxo-1-piperazinocarboxamido)acetyl, 2-(2-amino-4-thiazolyl)-2-(4-ethyl-2,3-dioxo-1-piperazinocarboxamido)acetyl, 2-(4-hydroxy-6-methylnicotinamido)-2-phenylacetyl, 2-(4-hydroxy-6-methylnicotinamido)-2-(4-hydroxyphenyl)acetyl, 2-{5,8-dihydro-2-(4-formyl-1-piperazinyl)-5-oxopyrido-[2,3-d]pyrimidine-6-carboxamido}-2-phenylacetyl, 2-(3,5-dioxo-1,2,4-triazine-6-carboxamido)-2-(4-hydroxyphenyl)acetyl, 2-(3-furfurideneamino-2-oxoimidazolidine-1-carboxamido)-2-phenylacetyl, 2-(coumarin-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4-thiazolyl)acetyl]-D-phenylglycyl, 2-(6-bromo-1-ethyl-1,4-dihydro-4-oxothieno[2,3-b]pyridine-3-carboxamido)-2-phenylacetyl, 2-(4-ethyl-2,3-dioxo-1-piperazinocarboxamido)-2-thienylacetyl, 2-(4-n-penthyl-2,3-dioxo-1-piperazinocarboxamido)-2-thienylacetyl, 2-(4-n-octyl-2,3-dioxo-1-piperazinocarboxamido)-2-thienylacetyl, 2-(4-cyclohexyl-2,3-dioxo-1-piperazinocarboxamido)-2-thienylacetyl, 2-[4-(2-phenylethyl)-2,3-dioxo-1-piperazinocarboamido]-2-thienylacetyl, 2-(3-methylsulfonyl-2-oxoiminodazoline-1-carboxamido)-2-phenylacetyl, 2-(3-furfurideneamino-2-oxoimidazolidine-1-carboxamido)-2-(4-hydroxyphenyl)acetyl, 2-(4-ethyl-2,3-dioxo-1-piperazinocarboxamido)-2-(4-benzyloxyphenyl)acetyl, 2-(4-ethyl-2,3-dioxo-1-piperazinocarboxamido)-2-(4-methoxyphenyl)acetyl, 2-(8-hydroxy-1,5-naphthyridine-7-carboxamido)-2-phenylacetyl, 2-(2-amino-4-thiazolyl)-2-formamidoacetyl, 2-(2-amino-4-thiazolyl)-2-acetamidoacetyl, and the like.

Examples of the acyl group R⁹—R¹⁰—CO— include N-[2-(2-amino-4-thiazolyl)-2-methoxyiminoacetyl]-D-alanyl, N-[2-(2-amino-4-thiazolyl)-2-methoxyiminoacetyl]-D-phenylgycyl, 2-(2-amino-4-thiazolyl)-2-[2-(2-amino-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-ethoxyiminoacetyl, 2-(2-amino-4-thiazolyl)-2-propoxyiminoacetyl, 2-(2-amino-4-thiazolyl)-2-butoxyiminoacetyl, 2-(2-amino-4-thiazolyl)-2-benzyloxyiminoacetyl, 2-(2-amino-4-thiazolyl)-2-allyloxyiminoacetyl, 2-(2-amino-4-thiazolyl)-2-[(1-methyl-1-carboxyethyl)oxyimino]acetyl, 2-(2-amino-4-thiazolyl)-2-[(1-methyl-1-methoxycarbonylethyl)oxyimino]acetyl, 2-(2-amino-4-thiazolyl)-2-carboxymethyloxyiminoacetyl, 2-(2-amino-4-thiazolyl)-2-carboxyvinyloxyiminoacetyl, 2-(2-amino-5-chloro-4-thiazolyl)-2-methoxyiminoacetyl, 2-(2-amino-5-bromo-4-thiazolyl)-2-methoxyiminoacetyl, 2-(2-amino-4-thiazolyl)-2-oxyiminoacetyl, 2-(2-amino-4-thiazolyl)-2-carboxyethyloxyiminoacetyl, 2-(2-amino-4-thiazolyl)-2-methoxycarbonylethyloxyiminoacetyl, 2-thienyl-2-methoxyiminoacetyl, 2-furyl-2-methoxyiminoacetyl, 2-(1,2,4-thiadiazol-3-yl)-2-methoxyiminoacetyl, 2-(1,2,4-thiadiazol-5-yl)-2-methoxyiminoacetyl, 2-(1,3,4-thiadiazolyl)-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-[4-(γ-D-glutamyloxy)phenyl]-3-oxyiminoacetyl, 2-(4-(3-amino-3-carboxypropoxy)phenyl]-2-oxyiminoacetyl, and the like.

Examples of the acyl group

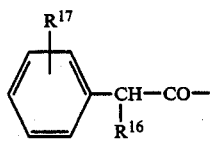

include α-sulfophenylacetyl, α-hydroxyphenylacetyl, α-ureidophenylacetyl, α-sulfoureidophenylacetyl, α-sulfamoylphenylacetyl, α-phenoxycarbonylphenylacetyl, α-(p-tolyloxycarbonyl)phenylacetyl, α-formyloxyphenylacetyl and the like.

Examples of the acyl group $R^{18}$—$R^{19}$—$CH_2$—CO— include cyanoacetyl, phenylacetyl, phenoxyacetyl, trifuloromethylthioacetyl, cyanomethylthioacetyl, 1H-tetrazolyl-1-acetyl, thienylacetyl, 2-(2-amino-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl and the like.

The amino, carboxyl and/or hydroxyl group in the above-exemplified acyl groups may be protected by a protective group.

The protective group for amino includes those described below as the "protective group for amino".

The protective groups for carboxyl or hydroxyl include those described above for R.

As the protective group for amino for $R^1$ which may optionally be protected, any of those used for this purpose in the field of β-lactam or peptide synthesis may conveniently be employed. Examples of such amino-protecting group include aromatic acyl groups such as phthaloyl, p-nitrobenzoyl, p-tert-butylbenzoyl, p-tert-butylbenzenesulfonyl, benzenesulfonyl, toluenesulfonyl, etc., aliphatic acyl groups such as formyl, acetyl, propionyl, monochloroacetyl, dichloroacetyl, trichloroacetyl, methanesulfonyl, ethanesulfonyl, trifluoroacetyl, maleyl, succinyl, etc., and esterified carboxyl groups such as methoxycarbonyl, ethoxycarbonyl, t-butoxycarbonyl, isopropoxycarbonyl, 2-cyanoethoxycarbonyl, β,β,β-trichloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl, etc., as well as non-acyl amino-protecting groups such as trityl, 2-nitrophenylthio, benzylidene, 4-nitrobenzylidene, trialkylsilyl, benzyl, p-nitrobenzyl, proton, etc. The choice of amino-protecting group is not critical in the present invention.

The objective compounds (I)C may have the 1-sulfo group and the carboxyl group or groups and R and/or $R^1$ in their free form. Alternatively, it may be in the form of a salt formed with a non-toxic cation, e.g., sodium, potassium, etc., a basic amino acid e.g., arginine, ornithine, lysine, histidine, etc., a polyhydroxyalkylamine, e.g., N-methylglucamine, diethanolamine, triethanolamine, trishydroxymethylaminomethane, etc. or the like. When R and/or $R^1$ contains a basic group, the compounds (I)C may be in the form of a salt formed with an organic acid, e.g., acetic acid, tartaric acid, methanesulfonic acid, etc., an inorganic acid, e.g., hydrochloric acid, hydrobromic acid, sulfuric acid, phosphoric acid, etc., an acidic amino acid, e.g., aspartic acid, glutamic acid, etc., or the like. In addition, when R and/or $R^1$ contains a carboxyl group, the compounds (I)C may be converted into their biologically active ester derivative conducive to increased blood concentration and prolonged in vivo activity. The ester groups effective in such cases include, for example, α-alkoxy-α-substituted-methyl groups (e.g., alkoxymethyl or α-alkoxyethyl such as methoxymethyl, ethoxymethyl, isopropoxymethyl, α-methoxyethyl, α-ethoxyethyl, etc.), alkylthiomethyl groups such as methylthiomethyl, ethylthiomethyl, isopropylthiomethyl, etc., acyloxymethyl or α-acyloxy-α-substituted-methyl groups such as pivaloyloxymethyl, α-acetoxybutyl, etc., α-alkoxycarbonyloxy-α-substituted-methyl groups such as ethoxycarbonyloxymethyl, α-ethoxycarbonyloxyethyl, etc., and the like.

The compounds (I)C can be present as various steric isomers (e.g., cis, trans, syn, anti and optically active isomers) as in the case with the starting compounds (II)C as mentioned below, and it is to be understood that the present disclosure encompasses these individual isomers as well as mixtures thereof. These isomers can be used as a medicament either singly or in admixture.

Accordingly, a type of the steric isomer of the compounds (I)C, for example, may be described by the formula:

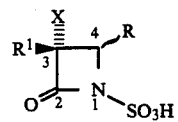

wherein R, $R^1$ (β-configuration) and X (α-configuration) are as defined above, and the wave line means trans or cis configuration of the group R to the group $R^1$ at 3-position.

The objective compounds (I)C include the compounds listed below;

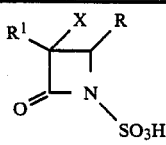
| Compound | R₁ | X | R |
|---|---|---|---|
| 1 | ClCH₂CONH-[2-thiazolyl]-CH=C(=NOCH₃)-CONH- | H | —COOCH₃ |
| 2 | H₂N-[2-thiazolyl]-CH=C(=NOCH₃)-CONH- | H | —COOCH₃ |
| 3 | ClCH₂CONH-[2-thiazolyl]-CH=C(=NOCH₃)-CONH- | H | —CH₂OCOCH₃ |
| 4 | H₂N-[2-thiazolyl]-CH=C(=NOCH₃)-CONH- | H | —CH₂OCOCH₃ |
| 5 | C₆H₅—CH₂OCONH— | H | —CH₂S-[1-methyl-1H-tetrazol-5-yl] |
| 6 | ClCH₂CONH-[2-thiazolyl]-CH=C(=NOCH₃)-CONH- | H | —COOCH₃ |
| 7 | H₂N-[2-thiazolyl]-CH=C(=NOCH₃)-CONH- | H | —COOCH₃ |
| 8 | C₆H₅—CH₂CONH— | H | —COOCH₃ |

-continued

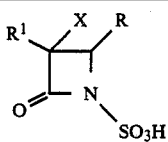

| Compound | R₁ | X | R |
|---|---|---|---|
| 9 | C₆H₅—CH₂CONH— | H | —CH₂NHCOCH₃ |
| 10 | C₂H₅—N(piperazine)NCONHCHCONH— with phenyl, dioxo | H | —COOCH₃ |
| 11 | n-C₈H₁₇—N(piperazine)NCONHCHCONH— with thienyl, dioxo | H | —COOCH₃ |
| 12 | n-C₄H₉—N(piperazine)NCONHCHCONH— with thienyl, dioxo | H | —COOCH₃ |
| 13 | cyclohexyl—N(piperazine)NCONHCHCONH— with thienyl, dioxo | H | —COOCH₃ |
| 14 | C₂H₅—N(piperazine)NCONHCHCONH— with phenyl, dioxo | —OCH₃ | —COOCH₃ |
| 15 | C₂H₅—N(piperazine)NCONHCHCONH— with phenyl, dioxo | H | —COOC₂H₅ |

-continued

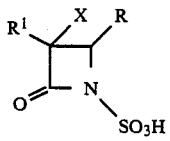

| Compound | R₁ | X | R |
|---|---|---|---|
| 16 | C₂H₅—N(piperazine-2,3-dione)NCONHCHCONH— with phenyl | H | —COOC₄H₉(n) |
| 17 | C₂H₅—N(piperazine-2,3-dione)NCONHCHCONH— with phenyl | H | —COOH |
| 18 | C₂H₅—N(piperazine-2,3-dione)NCONHCHCONH— with phenyl | H | —CH₂S-(1-methyltetrazol-5-yl) |
| 19 | 2-aminothiazol-4-yl C(=N-OC₂H₅)CONH— | H | —COOCH₃ |
| 20 | 2-aminothiazol-4-yl C(=N-OC₃H₇(i))CONH— | H | —COOCH₃ |
| 21 | 2-aminothiazol-4-yl C(=N-OC(CH₃)₂CO₂H)CONH— | H | —COOCH₃ |
| 22 | 2-aminothiazol-4-yl C(=N-OCH₃)CONH— | H | —COOC₂H₅ |

-continued

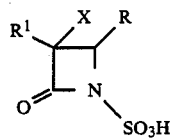

| Compound | R₁ | X | R |
|---|---|---|---|
| 23 | H₂N-C(S)=N- thiazole-CH=C(=N-OCH₃)-CONH- | H | —COOC₄H₉(n) |
| 24 | H₂N-C(S)=N- thiazole-CH=C(=N-OCH₃)-CONH- | H | —CH₂S-(1-methyl-tetrazol-5-yl) |
| 25 | H₂N-C(S)=N- thiazole-CH=CH-CH₂CONH- | H | —COOCH₃ |
| 26 | H₂N-C(S)=N- thiazole-CH=CH-CH(NHCONH₂)-CONH- | H | —COOCH₃ |
| 27 | H₂N-C(S)=N- thiazole-CH=CH-CH(NH₂)-CONH- | H | —COOCH₃ |
| 28 | H₂N-C(S)=N- thiazole-CH=C(=N-OCH₃)-CONH- | H | —CH₂⁺N(pyridinium) |
| 29 | H₂N-C(S)=N- thiazole-C(Cl)=C(=N-OCH₃)-CONH- | H | —COOCH₃ |
| 30 | H₂N-C(S)=N- thiazole-CH=C(=N-OCH₃)-CONH- | H | —CONH-(pyridyl) |

-continued
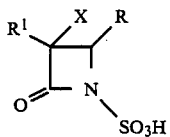
| Compound | R₁ | X | R |
|---|---|---|---|
| 31 | H₂N-thiazole-C(=NOCH₃)-CONH— | H | —CH₃ |
| 32 | H₂N-thiazole-C(=NOCH₃)-CONH— | H | phenyl |
| 33 | H₂N-thiazole-C(=NOCH₃)-CONH— | H | 2-furyl |
| 34 | H₂N-thiazole-C(=NOCH₃)-CONH— | H | —CH₂CH₂-phenyl |
| 35 | H₂N-thiazole-C(=NOCH₃)-CONH— | H | —COCH₃ |
| 36 | H₂N-thiazole-C(=NOCH₃)-CONH— | H | —CH₂COOCH₃ |
| 37 | NH₂— | H | —COOCH₃ |
| 38 | H₂N-thiazole-C(=NOCH₃)-CONH— | H | —COOH |

-continued
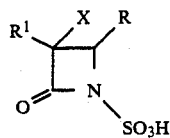
| Compound | R₁ | X | R |
|---|---|---|---|
| 39 | H₂N-thiazole-C(=N-OCH₃)-CONH- | H | —CH₂NH₂ |
| 40 | H₂N-thiazole-C(=N-OCH₃)-CONH- | H | —CH₂OH |
| 41 | H₂N-thiazole-C(=N-OCH₃)-CONH- | H | —CH₂OCH₃ |
| 42 | H₂N-thiazole-C(=N-OCH₃)-CONH- | H | —CONH₂ |
| 43 | H₂N-thiazole-C(=N-OCH₂COOH)-CONH- | H | —COOCH₃ |
| 44 | H₂N-thiazole-C(=N-OC(CH₃)₂COOH)-CONH- | H | —CONH₂ |
| 45 | H₂N-thiazole-C(=N-OC(CH₃)₂COOH)-CONH- | —OCH₃ | —CONH₂ |

-continued
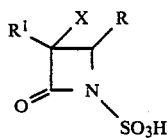
| Compound | R₁ | X | R |
|---|---|---|---|
| 46 | aminothiazolyl-C(=N-O-C(CH₃)₂-COOH)-CONH- | H | —CH₂N₃ |
| 47 | aminothiazolyl-C(=N-O-C(CH₃)₂-COOH)-CONH- | H | —CH₂OCH₃ |
| 48 | aminothiazolyl-C(=N-O-C(CH₃)₂-COOH)-CONH- | H | —CH₂(CH₂)₃OCONH₂ |
| 49 | aminothiazolyl-C(=N-O-C(CH₃)₂-COOH)-CONH- | H | —CH₂OH |
| 50 | aminothiazolyl-C(=N-OCH₂COOH)-CONH- | H | —CH(CH₃)₂ |
| 51 | aminothiazolyl-C(=N-O-C(CH₃)₂-COOH)-CONH- | H | —CH₂OCOCH₃ |

-continued
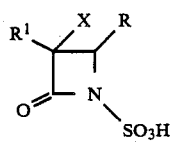
| Compound | R₁ | X | R |
|---|---|---|---|
| 52 | H₂N-thiazole-C(=N-O-C(CH₃)₂-COOH)-CONH- | H | —CH₂NHCOCH₃ |
| 53 | H₂N-thiazole-C(=N-O-C(CH₃)₂-COOH)-CONH- | H | —CH₂CONHCH₃ |
| 54 | H₂N-thiazole-C(=N-O-C(CH₃)₂-COOCH₃)-CONH- | H | —COOCH₃ |
| 55 | H₂N-thiazole-C(=N-O-C(CH₃)₂-COOC₂H₅)-CONH- | H | —COOCH₃ |
| 56 | H₂N-thiazole-CH(NHCOCH₃)-CONH- | H | —CONH₂ |
| 57 | H₂N-thiazole-C(=N-O-cyclopentyl)-CONH- | H | —CONH₂ |

-continued

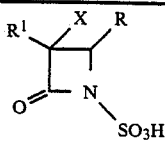

| Compound | $R_1$ | X | R |
|---|---|---|---|
| 58 | (H₂N-thiazole)-C(=N-O-C(CH₃)₂-COOH)-CONH— | H | —CH₂CONH₂ |

Among others, preferably one of the objective compounds (I)C may be a compound represented by the formula:

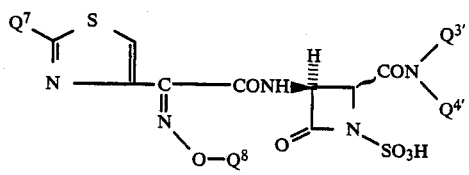

wherein $Q^{3'}$, $Q^{4'}$, $Q^7$, $Q^8$ and wave line are as defined above, or a salt or ester thereof. In the above formula, when $Q^7$ is amino group, the compound of the formula may form an inner salt between the amino group of $Q^7$ and sulfo group at 1-position.

The objective compounds (I)C and salts or esters thereof are valuable antibiotics active against a variety of gram-positive or gram-negative bacteria, are applied as medicaments to human beings or domestic animals and are used with safety as antimicrobial agents for the treatment of infections caused by gram-positive or gram-negative bacteria. In addition, the antimicrobial agents are added to animal rations as disinfectants for preservation of feeds. The antibiotics can also be used in the form of an aqueous formulation having a concentration in the range of 0.1 to 100 ppm (i.e., 0.1 to 100 parts of the antibiotic per million parts of the solution) as antimicrobial preparations in order to destroy and inhibit growth of harmful bacteria, for example, on medical and dental equipment or in order to inhibit growth of harmful bacterial life in an industrial aqueous medium, for example, water-based paints or paper mill white water.

The objective compounds (I)C and their salts or esters can be used singly or in combination with one or more other active components in any of various pharmaceutical preparations such as capsules, tablets and powders as well as solutions, suspensions and elixers. These preparations can be administered orally, intravenously or intramuscularly.

The oral tablets may contain a conventional excipient such as, for example, a binder, e.g., a syrup, gum arabic, gelatin, sorbitol, gum tragacanth or polyvinylpyrrolidone; a filler, e.g., lactose and other sugars, corn starch, calcium phosphate, sorbitol or glycine; a lubricant, e.g., magnesium stearate, talc, polyethylene glycol or silica; a disintegrator, e.g., potato starch; or an available wetting agent such as sodium lauryl sulfate. The tablets may be coated in a manner well known in the art. The oral liquid preparations may be in such dosage forms as aqueous or oil suspensions, solutions, emulsions, syrups, elixirs, etc., or in the form of lyophilisates for extemporaneous dissolution in water or a suitable solvent. These liquid preparations may contain a suspending agent, e.g., sorbitol syrup, methyl cellulose, glucose/sugar syrup, gelatin, hydroxyethyl-cellulose, carboxymethylcellulose or aluminum stearate gel; a hydrogenated edible oil, e.g., almond oil, coconut oil fractions, oily esters, propylene glycol or ethyl alcohol; or a preservative, e.g., methyl or propyl p-hydroxybenzoate or sorbic acid. Suppositories may contain a conventional suppository base, e.g., theobroma oil or other glycerides.

Injectable compositions can be made available in ampules or other unit-dose containers with the addition of a preservative. These compositions may be in such dosage forms as suspensions, solutions or emulsions in an oily or aqueous vehicle, and may contain a suitable adjuvant or adjuvants such as a suspending agent, stabilizer and/or dispersing agent. Alternatively, the active component may be in powder form reconstitutable with a suitable solvent such as sterilized pyrogen-free water prior to use.

The active component also can be formulated into suitable dosage forms absorbable through the mucous membranes of the nose and throat or the bronchial tissues, for example, powders, liquid sprays or inhalants, lozenges, throat paints, etc. For opthalmological or otological application, it can be administered as liquid or semisolid capsules or as drops for instillation. In addition it may be formulated with hydrophobic or hydrophilic pharmaceutical bases in such dosage forms as ointments, creams, lotions, paints, powders, etc. to provide pharmaceutical preparations for external application.

In addition to the carriers, these preparations may contain other components such as stabilizers, binding agents, antioxidants, preservatives, lubricants, suspending agents, rheology modifiers, or flavoring agents. Moreover, other active component or components can be incorporated in the composition to provide for a broader antimicrobial spectrum.

For administration to domestic animals, the active component can be formulated with time-release media to provide intramammary preparations.

The compounds (I)C can be applied to mammals as therapeutic agents for microbial infections in the treatment of, for example, respiratory tract infections, urinary tract infections, suppurative infections, bile duct infections, intestinal infections, gynecological infections, surgical infections, etc. The daily dosage varies with the condition of the patient to be treated, the weight of the host, the route and frequency of administration and the particular parentheral procedure suitable for general infections or oral procedure employed for intestinal infections. Generally the oral daily dosage comprises the active component in an amount of about 15–600 mg/kg of body weight of the patient in one or more doses. The daily dosage suitable for administration to an adult human is about 10 to about 200 mg/kg/body weight as the active ingredient, which can suitably be administered daily in 2 to 4 doses of about 2.5 to 100 mg/kg each by a route other than the oral.

A pharmaceutical composition containing the compound (I)C can be administered, for example, in various solid or liquid orally ingestable unit dosage forms. The liquid or solid composition may contain 0.5 to 99% of the active component. The preferred concentration range of the active component is about 10 to about 60%. The composition generally contains about 15 to 1500 mg of the active component in each unit dose, and it is generally preferred to use a unit dose in the range of about 250 to 1000 mg as the active component.

In addition to the uses mentioned above, the compounds (I)C and their salts and esters may be used in combination with a β-lactam antibiotic since they possess β-lactamase-inhibitory activities. Examples of such β-lactam antibiotic include penicillin antibiotics such as benzylpenicillin, phenoxymethylpenicillin, carbenicillin, ampicillin, amoxicillin, sulbenicillin, etc., cephalosporin antibiotics such as cephaloridine, cephalothin, cefazolin, cephalexin, cefoxitin, cephacetrile, cefamandole, cefmenoxime, cefsulodin, cefotiam, cefotaxime, cephapirin, ceftizoxime, cefradin, cephaloglycin, etc. and the like.

The 1-sulfo-2-oxoazetidine derivatives (I)C that are the objective compounds of this apsect of the disclosure can be prepared, for example, by sulfonating a compound (II)C.

The compounds (II)C may be used as the starting material in the process in the form of salts with various acids or bases, or esters or silyl derivatives. The compounds (II)C includes the cis- and trans-isomers because it has substituents at the 3- and 4-positions. In addition, since the 3- and 4-carbon atoms are asymmetric, theoretically there exist at least four stereoisomers in a total. These stereoisomers may be used either singly or in admixture. This is also the case when the group R or $R^1$ contains as asymmetric carbon, and the resulting stereoisomers may also be used either singly or in admixture.

As salts and esters of the compounds (II)C, use is made of, for example, those exemplified above for the compounds (I)C, and so on. The compounds (II)C may also be silylated by the silylating agent. The silylating agent may be a compound of the formula:

wherein each of $P^1$, $P^2$ and $P^3$ is a hydrocarbon residue such as a lower alkyl of 1 to 4 carbon atoms (e.g. methyl, ethyl, n-propyl, i-propyl, n-butyl, etc.), an aryl group (e.g. phenyl, tolyl, etc.) or the like, and Hal is halogen, preferably chlorine or bromine, and one or two of $P^1$, $P^2$ and $P^3$ may be halogen, preferably chlorine or bromine, and one of $P^1$, $P^2$ and $P^3$ may be hydrogen. Furthermore, hexa-alkyl($C_1$-$C_4$) cyclotrisilazane, octaalkyl ($C_1$-$C_4$)cyclotetrasilazane, trialkyl($C_1$-$C_4$)silylacetamide, bis-tri-alkyl($C_1$-$C_4$)silylacetamide may be used as the silylating agent. The preferred silylating agent is a group of the formula:

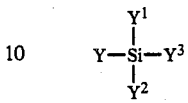

wherein Y stands for a reactive group to be liberated from the silyl compound, $Y^1$ and $Y^2$ respectively stand for a lower ($C_{1-4}$)alkyl, phenyl, benzyl or a lower ($C_{1-4}$) alkoxyl group, and $Y^3$ stands for t-butyl or isopropyl group.

As the lower alkyl represented by $Y^1$ and $Y^2$, there may be mentioned methyl, ethyl, n-propyl, isopropyl, n-butyl, t-butyl and the like, and as the lower alkoxy represented by $Y^1$ and $Y^2$, there may be mentioned methoxy, ethoxy, n-propoxy, isopropoxy, n-butoxy, t-butoxy and the like.

As the reactive group to be liberated from the silyl compound may be exemplified halogen (e.g. chloro, bromo); N-(trialkylsilyl)trifluoroacetimidoyloxy group; N-(trialkylsilyl)acetimidoyloxy group; an acylamino group such as formylamino, acetylamino, propionylamino, butylylamino or trifluoroacetylamino; a (trialkylsilyl)amino group such as (tri-t-butyldimethylsilyl)amino, isopropyldimethylsilylamino or (chloromethyldimethylsilyl)amino; amino; an alkylamino group such as methylamino, ethylamino or propylamino; and N,N-dialkylamino group such as N,N-dimethylamino, N-chloromethyl-N-methylamino, N,N-diethylamino, N,N-dipropylamino, N-methyl-N-ethylamino, N-methyl-N-propylamino or N-ethyl-N-propylamino; or a heterocyclic group such as imidazolyl. As the alkyl moiety in said reactive group, ones having 1 to 4 carbon atoms are preferable, and it is exemplified by methyl, ethyl, n-propyl, isopropyl, n-butyl and t-butyl. Specific examples of the silyl compounds as described above, there may be mentioned N,O-bis(t-butyldimethylsilyl)trifluoroacetamide, N,O-bis(isopropyldimethylsilyl)acetamide, bis(dimethylisopropylsilyl)acetamide, isopropyldimethylsilylacetamide, bis(dimethyl-tert-butylsilyl)acetamide, N-methyl-N-t-butyldimethylsilylacetamide, N-methyl-N-isopropyldimethylsilyltrifluoroacetamide, N-t-butyldimethylsilyldiethylamine, 1,3-bis(chloromethyl)-1,1,3,3-tetra-t-butyldimethyldisilazane, N-isopropyldimethylsilylimidazole, t-butyldiphenylchlorosilane, isopropyldiethylchlorosilane, isopropylmethyldichlorosilane, tert-butyldimethylchlorosilane, isopropyldimethylchlorosilane or t-butyldiethylchlorosilane. Among them, tert-butyldimethylchlorosilane or isopropyldimethylchlorosilane is preferable. The present silylating reaction is followed by a per se conventional one. The reaction temperature of the silylation is in the range of about 0° to 50° C., preferably not higher than 38° C., usually at room temperature (about 20° C.), and the reaction time is from several minutes (about 10 minutes) to about 24 hours. The reaction is conducted conveniently in, for example, ethyl acetate, dioxane, tetrahydrofuran, N,N-dimethylacetamide, N,N-dimethylformamide, dichloromethane, chloroform, benzene, toluene, acetone, methylethylketone, or acetonitrile, or an optional mixture of them, or any other solvent which is inert to this reaction. This reaction can be conducted also in the presence of an inorganic base such as sodium hydroxide, potassium hydroxide, sodium hydrogen carbonate, sodium carbonate or potassium carbonate or a trialkylamine such as triethylamine, tributylamine; a triaralkylamine such as tribenzylamine; an organic tertiary amine such as N-methylmorpholine, N-methylpiperidine, N,N-dialkylaniline, N,N-dialkylbenzylamine, pyridine, picoline or lutidine; or an organic base such as 1,5-diazabicyclo[2,2,2]octane or 1,8-diazabicyclo[5,4,4]undecene-7, and when the base is liquid, it can be used also as a solvent. Thus obtained silyl derivative of the compound (II)C may be employed as the starting material in the present sulfonating reaction, as it is i.e. in the form of a reaction mixture, or after isolated or purified by means of the conventional method as mentioned below.

The sulfonation reaction means that a sulfo group is introduced into the compound (II)C at the 1-position, and is accomplished by reacting the compound (II)C with, for example, sulfuric anhydride or its reactive derivative. The reactive derivative of sulfuric anhydride includes, for example, its adducts such as sulfuric anhydride-base (e.g. sulfuric anhydride-pyridine, sulfuric anhydride-trimethylamine, sulfuric anhydride-picoline, sulfuric anhydridelutidine, etc.), sulfuric anhydride-N,N-dimethylformamide, sulfuric anhydride-dioxane, sulfuric anhydride-chlorosulfonic acid and the like.

For this reaction, about 1 to 10 moles, preferably about 1 to 5 moles of sulfuric anhydride or its reactive derivative is used for each mole of the compound (II)C. The reaction temperature is about −78° to 80° C., preferably about −20° to 60° C. The reaction may be carried out in the presence of a solvent. In such cases, conventional organic solvents including water, ethers such as dioxane, tetrahydrofuran, diethyl ether, etc., esters such as ethyl acetate, ethyl formate, etc., halogenated hydrocarbons such as chloroform, dichloromethane, etc., hydrocarbons such as benzene, toluene, n-hexane, etc., amides such as N,N-dimethylformamide, N,N-dimethylacetamide, etc. and the like can be used singly or in admixture. The reaction goes to completion usually in scores of minutes to scores of hours depending on the particular starting compounds (II)C, sulfonating agent, reaction temperature and solvent employed, but in some cases it takes scores of days to complete the reaction. After completion of the reaction, the reaction mixture can be subjected to a suitable purification and separation procedure known per se such as solvent extraction, recrystallization, chromatography or the like to give the desired compounds (I)C of any purity.

Alternatively, the objective compounds (I)C can be prepared by acylating a compound of the formula:

(III)C wherein R and X are as defined above.

The acylation according to this process is accomplished by reacting the compounds (III)C (inclusive of its various salts, esters and silyl derivatives) with an acylating agent in an amount of at least 1 mole, preferably 1.2 to 4 moles per each mole of the compounds (III)C. The acylating agent used in this reaction may be either the organic carboxylic acid comprising the acyl group in $R^1$ [R°COOH wherein R°CO is an acyl group defined above as the acyl group of the acylated amino group for $R^1$] or its reactive derivative at the carboxyl group.

The reactive derivative of the organic carboxylic acid includes, for example, acid anhydrides, active amides, active esters, etc., which are exemplified below.

(1) Acid anhydrides:

The acid anhydrides include, for example, mixed acid anhydrides with a hydrohalic acid (e.g., hydrochloric acid, hydrobromic acid, etc.), a monoalkylcarbonic acid, an aliphatic carboxylic acid (e.g., acetic acid, pivalic acid, valeric acid, isovaleric acid, trichloroacetic acid, etc.), and an aromatic carboxylic acid (e.g., benzoic acid, etc.), as well as symmetrical acid anhydrides.

(2) Active amides:

The active amides include, for example, amides with pyrazole, imidazole, a 4-substituted imidazole, dimethylpyrazole, benzotriazole, etc.

(3) Active esters:

The active esters include, for example, such esters as methyl, ethyl, methoxymethyl, propargyl, 4-nitrophenyl, 2,4-dinitrophenyl, trichlorophenyl, pentachlorophenyl, and mesylphenyl esters, as well as the esters of the above-mentioned carboxylic acids with 1-hydroxy-1H-2-pyridone, N-hydroxysuccinimide, N-hydroxyphthalimide or the like.

The choice of reactive derivative of an organic carboxylic acid depends on the particular acid used. When the acylating agent used is a free carboxylic acid, the reaction is preferably carried out in the presence of a condensation agent. Examples of such condensation agent include N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, and the like.

The acylation is usually carried out in a solvent. The solvent includes water, acetone, dioxane, acetonitrile, methylene chloride, chloroform, dichloroethane, tetrahydrofuran, ethyl acetate, N,N-dimethylformamide, N,N-dimethylacetamide, pyridine and other conventional organic solvents which do not affect the reaction. Of these, hydrophilic solvents may be used in combination with water.

The acylation may also be carried out in the presence of a base such as an alkali metal carbonate, an trialkylamine (e.g., trimethylamine, triethylamine, tributylamine, N-methylmorpholine and N-methylpiperidine, etc.), an N,N-dialkylaniline, an N,N-dialkylbenzylamine, pyridine, picoline, lutidine, 1,5-diazabicyclo[4,3,0]nonan-5-ene, 1,4-diazabicyclo[2,2,2]octane, 1,8-diazabicyclo[5,4,4]-undecene-7 and the like. Among the bases and the above-mentioned condensation agents, liquid compound can also function as a solvent as well. The reaction temperature is not critical, and the reaction is usually carried out under cooling to room temperature, and goes to completion in a few minutes to several ten hours. The resulting compounds (I)C can be isolated and purified in a manner known per se such as concentration, conversion of liquid nature from acidic to basic or vice versa, change of solvent, solvent extraction, crystallization, recrystallization, fractional distillation, chromatography and the like.

When the starting compounds (III)C or its salt and/or the acylating agent used in the acylation contains an asymmetric carbon in the molecule, the stereoisomers may be used either singly or in admixture. If the acylation causes the formation of two or more of stereoisomeric products, the individual stereoisomers can be isolated in a conventional manner such as column chromatography, recrystallization or the like, if necessary.

The group R in the objective compounds (I)C may be transformed into another group while the compounds (I)C retains the 1-sulfo group, which leads to the formation of another objective compound of this invention. For instance, if R is acetoxymethyl, methanesulfonyloxymethyl, iodomethyl or the like, it can be transformed into another desired group by the reaction with a nucleophilic reagent. The nucleophilic agents that can be used include, for example, alkyl*-thiols, aryl*-thiols, heterrocyclic*-thiols, pyridines* and the like and they can provide the objective compounds (I)C wherein R is a substituted thiomethyl, a quaternary ammonium*-methyl or the like. The alkyl*, aryl*, heterocyclic* group and quaternary ammonium* in these nucleophilic agents are as defined above. The reaction is preferably carried out in an aqueous solution, or in a water-miscible solvent such as acetone, acetonitrile, N,N-dimethylformamide or the like, or a mixture of water and such water-miscible solvent. There are cases in which the addition of a base such as an alkali carbonate, an alkali phosphate or the like is beneficial. The reaction is usually conducted at a temperature in the range of 20° to 100° C. The resulting compounds (I)C can be isolated and purified by a procedure known per se as is the case with those obtained by sulfonation or acylation.

When the objective compounds (I)C thus obtained has a protective group, the protective group can be removed if necessary. Removal of such protective group can be accomplished by the conventional methods such as the method involving the use of an acid, a base or hydrazine, reduction, and the method comprising the use of an iminohalogenerating agent and, then, an iminoetherifying agent, if necessary, followed by hydrolysis. The choice of any such method depends on the particular protective group to be removed. When the protective group is removed with an acid, the acids that can be used include inorganic acids such as hydrochloric acid, sulfuric acid, phosphoric acid, etc. and organic acids such as formic acid, acetic acid, trifluoroacetic acid, propionic acid, benzenesulfonic acid, p-toluenesulfonic acid, etc. as well as acidic ion-exchange resins, and the choice of acid depends on the particular protective group and other conditions. In the case in which the protective group is removed with a base, the bases that can be used include inorganic bases such as alkali metal (e.g., sodium, potassium, etc.) or alkaline earth metal (e.g. calcium, magnesium, etc.) hydroxides, carbonates, etc. and organic bases such as metal alkoxides, organic amines, quaternary ammonium salts, etc. as well as basic ion-exchange resins, and the choice of base depends on the particular protective group and other conditions.

When the removal of a protective group with an acid or base is conducted in a solvent, an hydrophilic organic solvent, water or a mixed solvent is generally used.

When the protective group is removed by reduction, for example, the reduction with a combination of a metal such as tin or zinc or a metal compound such as chromium dichloride or chromium acetate and an organic or inorganic acid such as acetic acid, propionic acid or hydrochloric acid, catalytic reduction in the presence of a metal hydrogenation catalyst or the like may be employed depending on the particular protective group and other conditions. The catalysts that can be used in the catalytic reduction include, for example, platinum catalysts such as platinum wire, platinum sponge, platinum black, platinum oxide, colloidal platinum, etc., palladium catalysts such as palladium sponge, palladium black, palldium oxide, palladium on barium sulfate, palladium on barium carbonate, palladium on charcoal, palladium on silica gel, colloidal palladium, etc., nickel catalysts such as reduced nickel, nickel oxide, Raney nickel, Urushihara nickel, etc. and the like.

In the case of reduction with a metal and an acid, a metal compound of such metal as iron, chromium or the like and an inorganic acid such as hydrochloric acid or an organic acid such as formic acid, acetic acid or propionic acid are used. The removal of a protective group by reduction is usually conducted in a solvent, and the solvent which is conveniently used in the catalytic reduction includes, for example, alcohols such as methanol, ethanol, propyl alcohol, isopropylalcohol, etc., ethyl acetate and the like. The reduction with a metal and an acid is conveniently conducted in water, acetone or the like, but if the acid is liquid, it can also function as a solvent.

In any of the methods involving the use of an acid or a base or reduction, the reaction is usually carried out under cooling to under warming.

When the protective group is removed by reacting an iminohalogenating agent and then an iminoetherifying agent, if necessary, followed by hydrolysis, the iminohalogenating agents that can be used include, for example, phosphorus trichloride, phosphorus pentachloride, phosphorus tribromide, phosphorus oxychloride, thionyl chloride, phosgene, etc. The reaction temperature is not critical, but the reaction is usually conducted at room temperature to under cooling. The resulting reaction product is then reacted with an iminoetherifying agent including alcohols and metal alkoxides. The alcohols include alkanols such as methanol, ethanol, propanol, isopropanol, n-butanol, tert-butanol, etc. as well as those compounds in which the alkyl moieties of the above-mentioned alcohols are substituted with an alkoxy group such as methoxy, ethoxy, propoxy, isopropoxy, butoxy or the like. The metal alkoxides include alkali metal alkoxides such as sodium alkoxides, potassium alkoxides, etc. and alkaline earth alkoxides such as calcium alkoxides, barium alkoxides, etc. derived from such alcohols as above.

In the case, for example, where the protective group is a residue of an organic carboxylic acid and a substituent such as free amino, hydroxyl, mercapto, carboxyl or sulfo group is attached to the carbon atom adjacent to the carbonyl of the carboxylic residue, it is advantageous to carry out a preliminary treatment for enhancing the adjacent group effect of such substituent to increase the reactivity of the carbonyl group prior to the deprotecting reaction. This will be illustrated, for example, with the case where the substituent on the carbon adjacent to the carbonyl is a free amino group. In such a case, the protective group can be removed by transforming the amino group into a thioureido group followed by deacylation, or by application of any other known method for cleaving a peptide linkage. The temperature at which the reaction is carried out is not critical and is selected depending on the particular protective group and deprotecting method, although it is preferred to carry out the reaction under mild conditions such as under cooling to under warming.

In the above-mentioned reactions, if R and/or R¹ is a carboxyl-containing group, a derivative at the carboxyl group may be converted into the corresponding free carboxyl compound, and this invention is naturally intended to include such case.

The deprotected compounds (I)C thus obtained may be converted into a desired salt in a conventional manner as mentioned above.

Compounds (I)C containing a sulfo group, generally can react with a base to form salts. Thus, compounds (I)C may be obtained as a salt, and the salt thus obtained may further be converted into the free form or into another salt. Compounds (I)C obtained in the free form may be converted into its salt. Compounds (I)C in the form of a salt can be converted into the free form, for example, using an acid. As the acid, for example, an inorganic acid such as hydrochloric acid, sulfuric acid or phosphoric acid, or an organic acid such as formic acid, acetic acid or p-toluenesulfonic acid is advantageously employed depending on the particular salt and other conditions. Alternatively, an acidic ion-exchange resin or the like may be used. As a solvent, a hydrophilic organic solvent such as acetone, tetrahydrofuran, methanol, ethanol, dioxane or the like, water or a mixed solvent is generally employed. The reaction is usally carried out at room temperature, but it may be carried out under cooling or under warming. The reaction time depends on the particular acid and solvent employed and the reaction temperature selected, and it is generally preferred that the reaction be completed in a short period. The resulting compounds (I)C in the free form can be isolated in a known manner as described above.

The starting compounds (II)C used can be prepared, for example, by the following processes or analogous processes.

(Process 1)

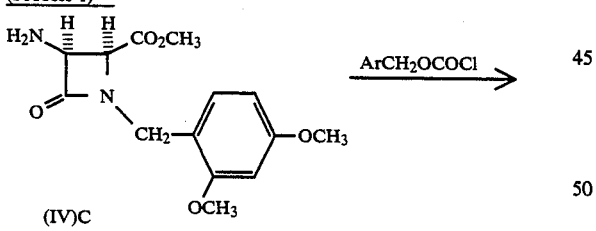

(IV)C

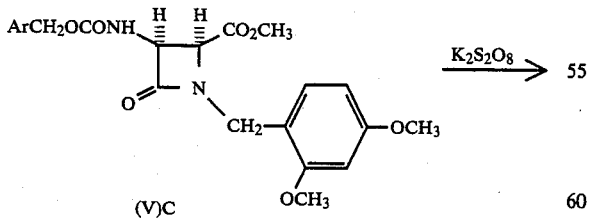

(V)C

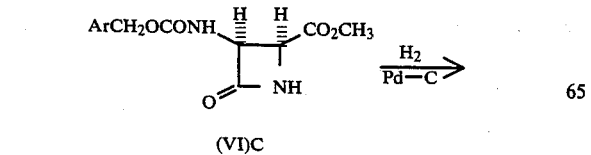

(VI)C

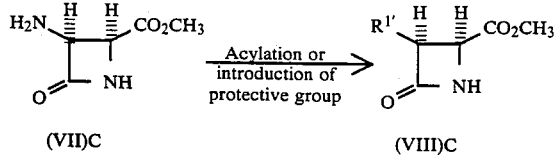

(VII)C (VIII)C (Process 2)

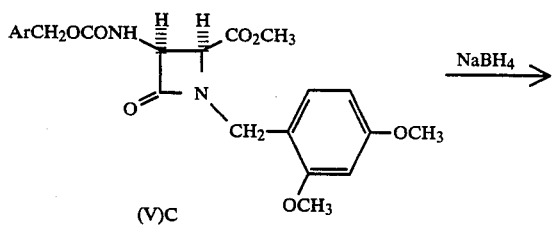

(V)C

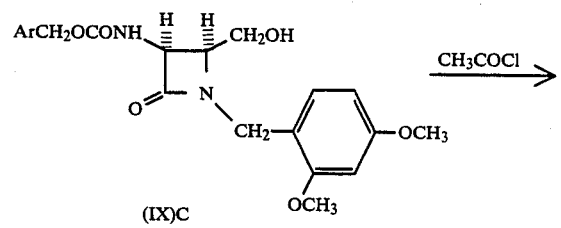

(IX)C

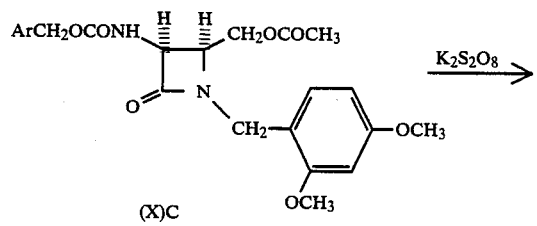

(X)C

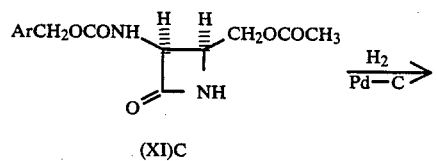

(XI)C

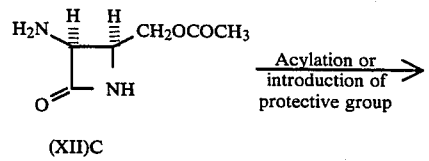

(XII)C

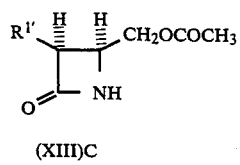

(XIII)C (Process 3)

-continued

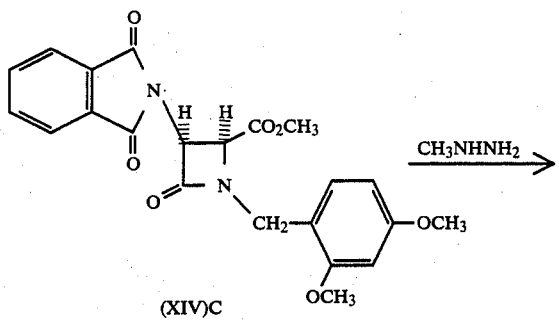

(XIV)C  →[CH₃NHNH₂]

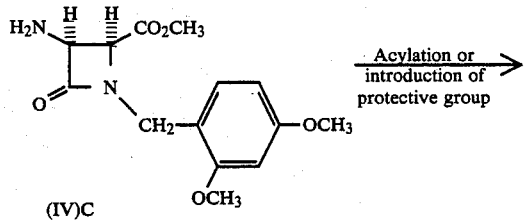

(IV)C  →[Acylation or introduction of protective group]

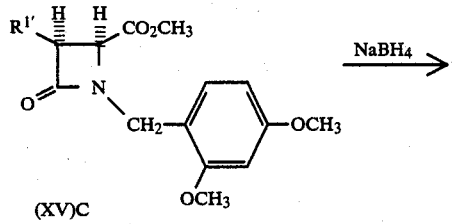

(XV)C  →[NaBH₄]

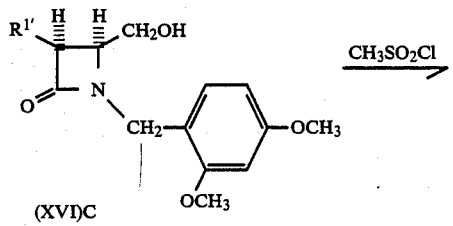

(XVI)C  →[CH₃SO₂Cl]

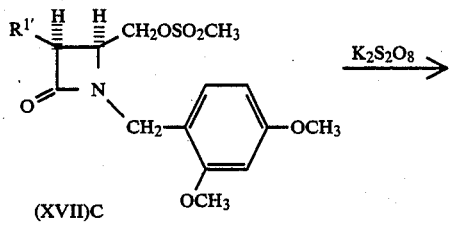

(XVII)C  →[K₂S₂O₈]

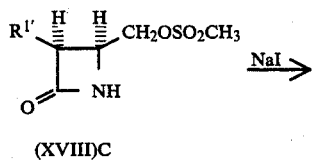

(XVIII)C  →[NaI]

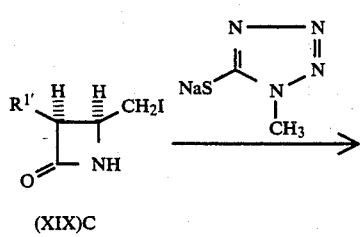

(XIX)C

-continued

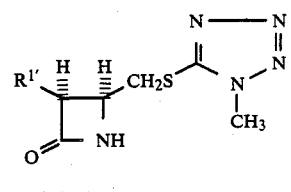

(XX)C (Process 4)

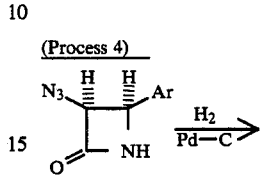

(XXI)C  →[H₂ / Pd—C]

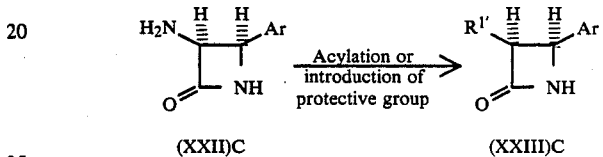

(XXII)C  →[Acylation or introduction of protective group]  (XXIII)C (Process 5)

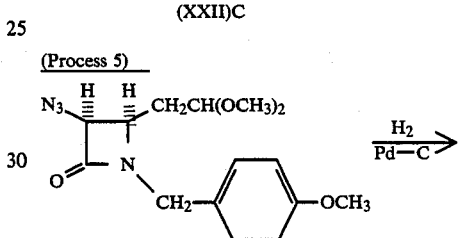

(XXIV)C  →[H₂ / Pd—C]

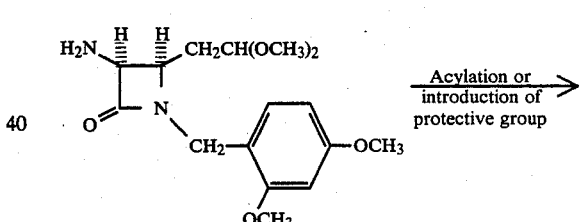

(XXV)C  →[Acylation or introduction of protective group]

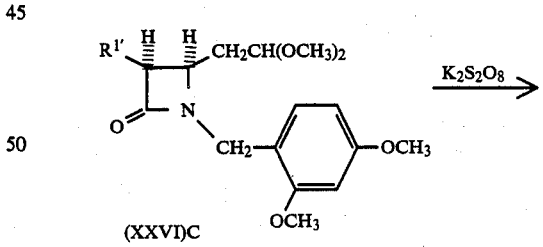

(XXVI)C  →[K₂S₂O₈]

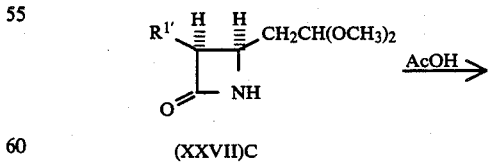

(XXVII)C  →[AcOH]

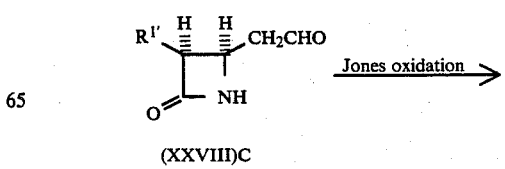

(XXVIII)C  →[Jones oxidation]

-continued
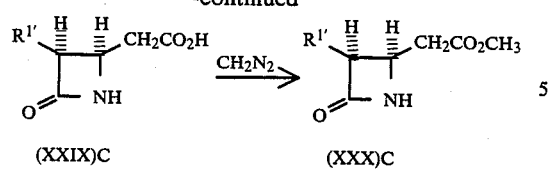
(Process 6)
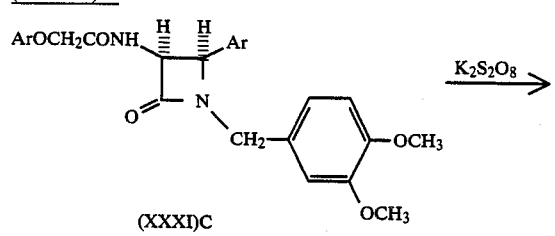
(Process 7)
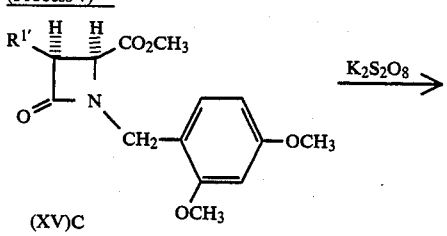
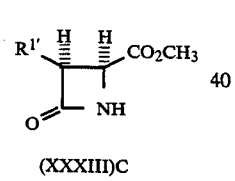
(Process 8)
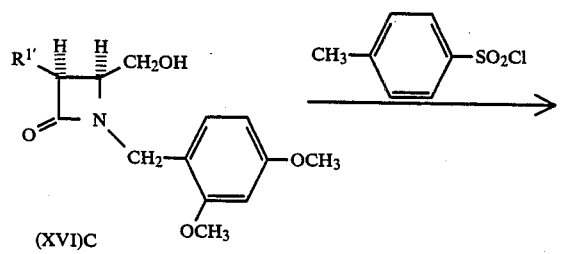
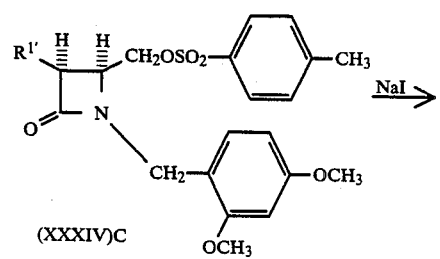
-continued
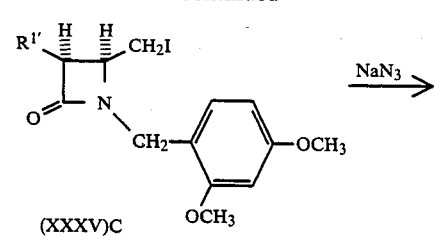
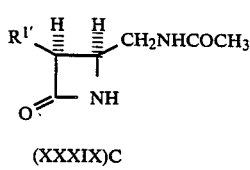
(Process 9)
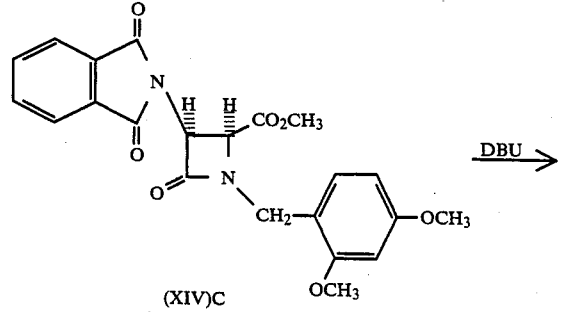

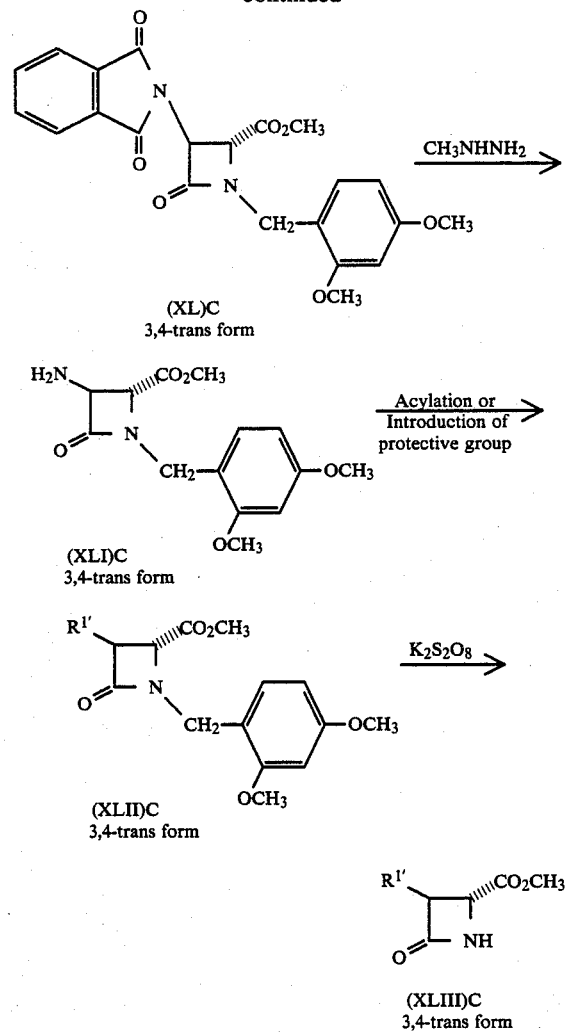
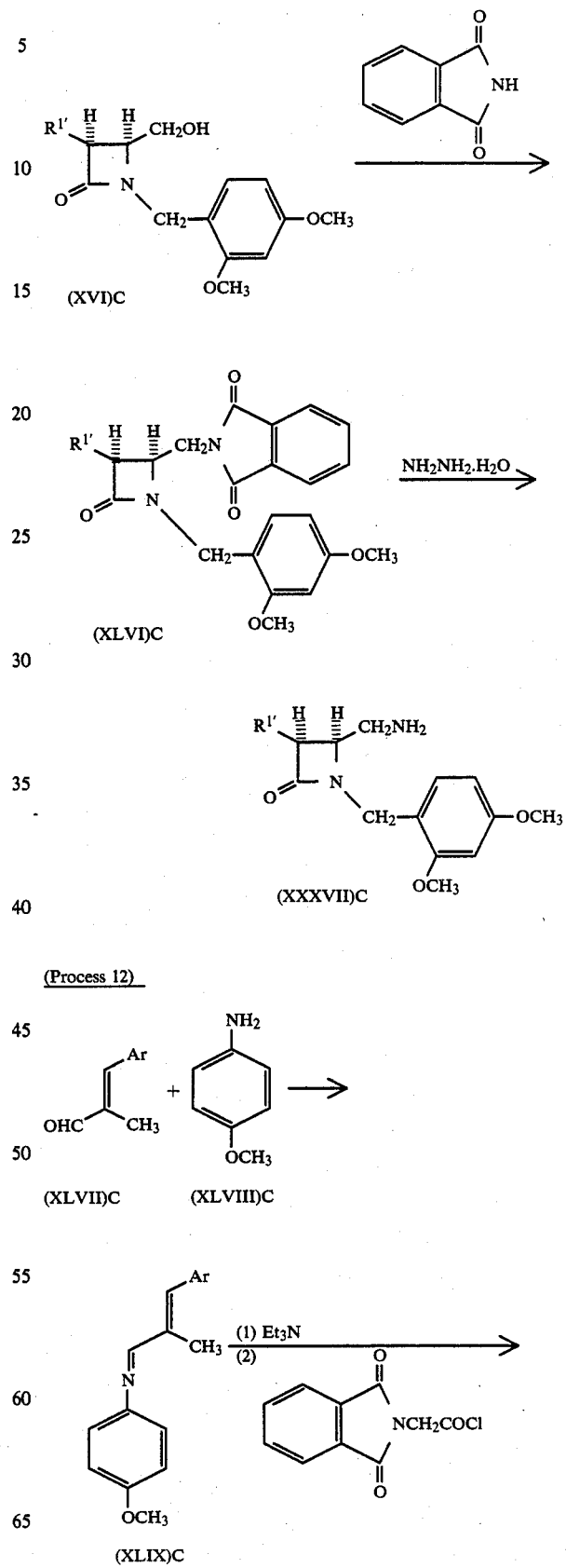
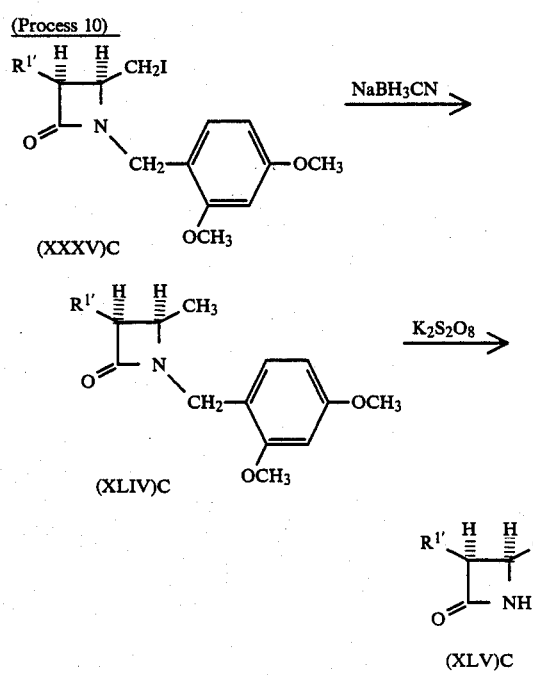
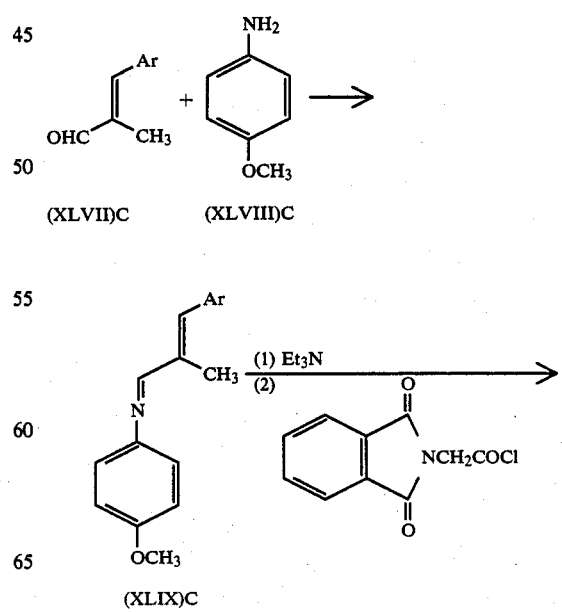

-continued
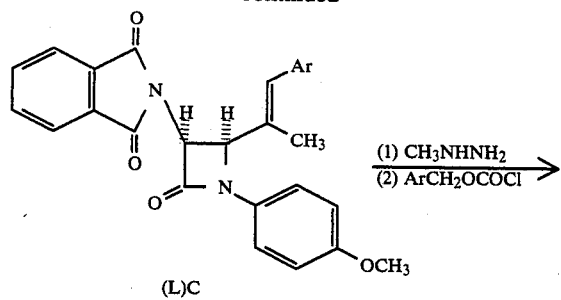
(L)C
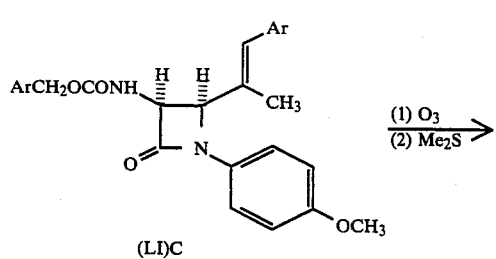
(LI)C
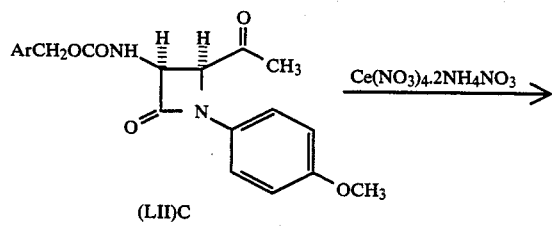
(LII)C
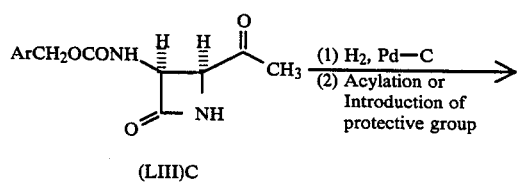
(LIII)C
(Process 13)
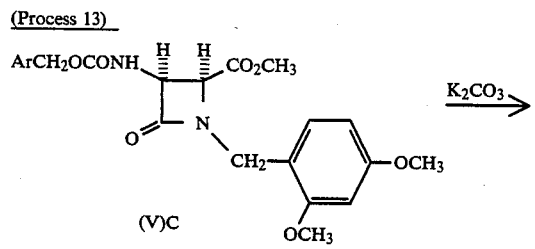
(V)C
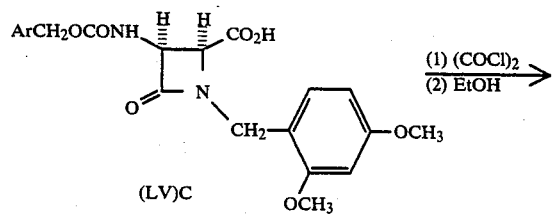
(LV)C
-continued
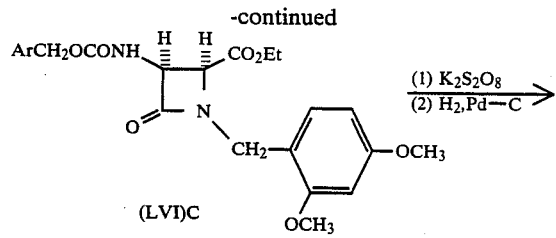
(LVI)C
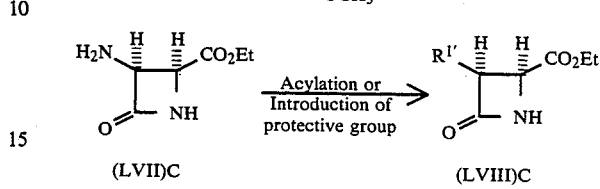
(LVII)C  (LVIII)C
(Process 14)
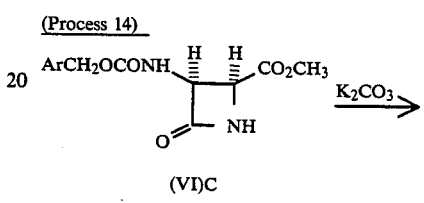
(VI)C
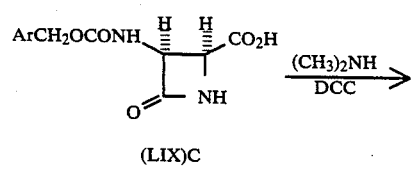
(LIX)C
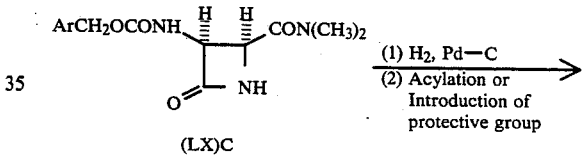
(LX)C
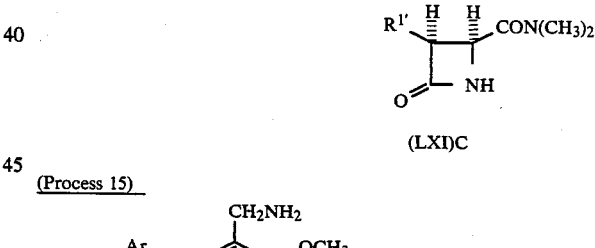
(LXI)C
(Process 15)
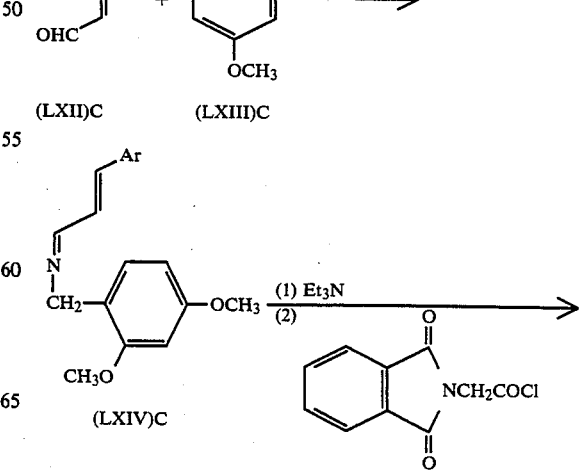
(LXII)C  (LXIII)C
(LXIV)C

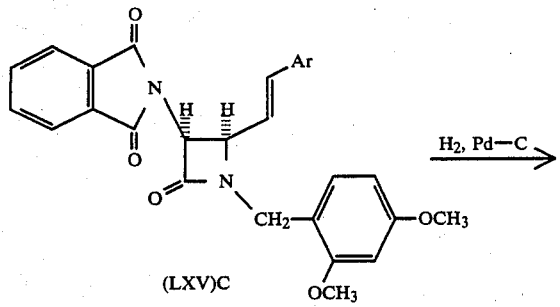

(LXV)C

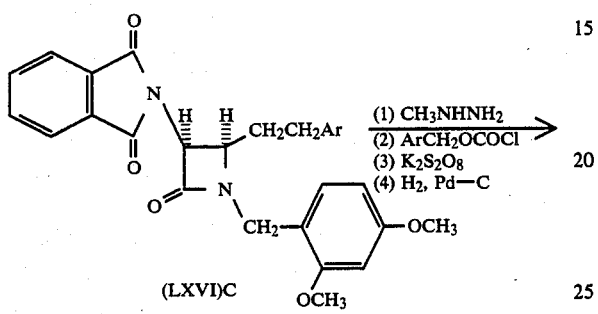

(LXVI)C

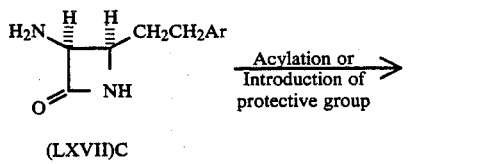

(LXVII)C

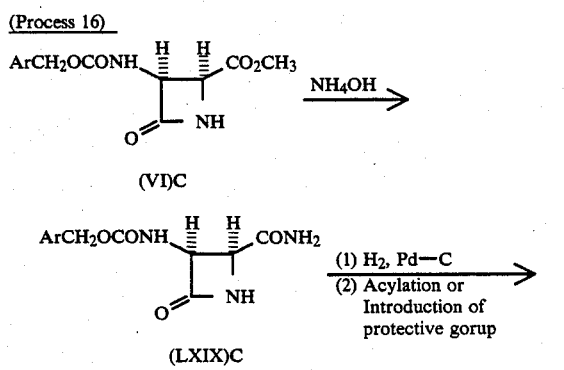

(LXVIII)C (Process 16)

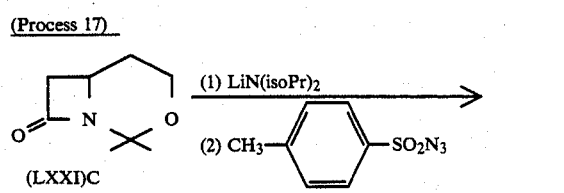

(VI)C

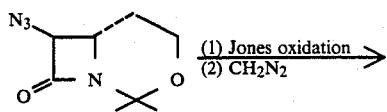

(LXIX)C

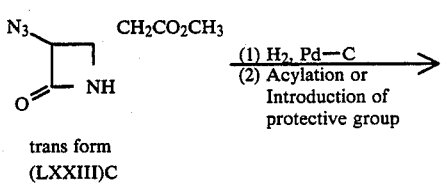

(LXX)C (Process 17)

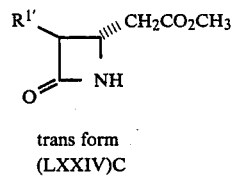

(LXXI)C trans form
(LXXII)C trans form
(LXXIII)C trans form
(LXXIV)C

In the above formulas, Ac is acetyl, Et is ethyl, Me is methyl, iso-Pr is isopropyl, Ar is aryl, $R^{1'}$ is an acylated or protected amino group, DBU is 1,3-diazabicyclo[5,4,0]-7-undecene, and DCC is dicyclohexylcarbodiimide.

The starting materials used in the above processes (1) to (17) include, for example, cis-3-amino-1-(2,4-dimethoxybenzyl)-2-oxoazetidine-4-carboxylic acid methyl ester (IV)C described in J. Am. Chem. Soc., 99, 2352 (1977), cis-1-(2,4-dimethoxybenzyl)-3-phthalimido-2-oxoazetidine-4-carboxylic acid methyl ester (XIV)C described in Japanese Patent Laid-Open Publication No. 136694/1976, cis-3-azido-4-phenyl-2-oxoazetidine (XXI)C described in J. Org. Chem., 34, 1477 (1969), cis-3-azido-1-(2,4-dimethoxybenzyl)-4-(2,2-dimethyoxyethyl)-2-oxoazetidine (XXIV)C described in J. Am. Chem. Soc., 101, 4730 (1979), cis-1-(3,4-dimethoxybenzyl)-3-phenoxyacetamido-4-phenyl-2-oxoazetidine (XXXI)C described in Synthesis (1979), 543 and 2,2-dimethyl-1-aza-3-oxabicyclo[4,2,0]octan-8-one (LXXI)C described in J. Am. Chem. Soc., 100, 313 (1978). These examples are not intended to restrict the starting materials thereto, and any compound meeting the purpose of this disclosure can be used. Examples of such starting materials will be given in the following reference examples.

The present aspect is illustrated in further detail below with Examples and Reference Examples, but it is to be understood that the examples are solely for the purpose of illustration and not to be construed as limitations, and that many variations may be resorted to without departing from the spirit and scope of the disclosure.

In the following Reference Examples and Examples, the elution in column chromatography was carried out with observation of TLC (Thin Layer Chromatography). In the TLC, were employed Merck pre-coated TLC plate 60F$_{254}$, a developing solvent which is the same as the eluent employed in the column chromatography, and UV detector. Fractions containing the desired compound, having spot which turns red-purple with ninhydrin when it is sprayed with 48% HBr and then heated to hydrolyze, were collected.

In case that two kinds of solvent are used as a developing solvent, first described solvent is used for eluting and removing by-product from a column, and second described solvent is used for eluting desired product, except specifically described. Process for drying a compound is conducted over anhydrous sodium sulfate, except specifically described. As eluent for purification by column chromatography using the resins "Amberlite" or "Sephadex", except specifically described in Examples and Reference Examples, use is made of water firstly, and then an aqueous ethanol with gradually increased concentration.

The resin named "Amberlite" is a product manufactured by Rohm & Haas Co. in U.S.A. "Dowex" is a product of The Dow Chemical Co. and "Sephadex" is a product of Pharmacia Fine Chemicals. All the temperatures are uncorrected and the percentages are all on weight basis, except the cases of solvents. In those cases, the percentages are all on volume basis. The NMR spectra given therein were measured using a Varian Model EM 390 (90 MHz) or T60 (60 MHz) spectrometer with tetramethylsilane as the internal or external reference and all δ values are in ppm. The symbol s stands for a singlet, d a doublet, q a quartet, ABq a AB type quartet, t a triplet, dd a double doublet, m a multiplet, sh a shoulder, br broad and J a coupling constant. And, symbols in Examples and Reference Examples have the following meanings, respectively;

mg: milligram
g: gram
ml: milliliter
l: liter
decomp: decomposition
ppm: part per million
mmol: millimole
M: molar (concentration)
Hz: Hertz
ph: phenyl
Me: methyl
Et: ethyl
Calcd. or Calc.: calculated
ca.: circa
°C.: centigrade degree
max: maximum
NMR: Nuclear Magnetic Resonance absorption
IR: Infra-Red absorption
DMSO: dimethylsulfoxide
D₂O: heavy water

Experiment C

The tables given below set forth the minimal inhibitory concentrations (MIC) of some typical compounds [I]C as obtained in the working examples.
Method:
The minimal inhibitory concentrations of the tested compounds are determined by the agar dilution method. Namely, 1.0 ml. of aqueous solution of the tested compounds diluted by serial dilutions is poured into test petri dish. Subsequently 9.0 ml. of Trypticase Soy agar is poured into the dish and mixed. On the mixed agar plate, one loopful of bacterial suspension (about $10^8$ CFU/ml.) of test microorganism is streaked. After the incubation at 37° C. overnight, the lowest concentration of the tested compounds which cause apparently complete inhibition of growth of the test microorganism is taken to be minimal inhibitory concentration.
Test Microorganism:
(1) *Enterobacter cloacae* IFO 12937

(2) *Klebsiella pneumoniae* TN 1711

| | Result: | |
|---|---|---|
| | Microorganism | (mcg/ml) |
| Compound | (1) | (2) |
| Example No. 65C | 6.25 | 0.2 |
| Example No. 68C | 3.13 | 0.78 |
| Example No. 72C | 1.56 | — |
| Example No. 133C | 1.56 | 0.39 |
| Example No. 136C | — | 1.56 |
| Example No. 138C | — | 6.25 |
| Example No. 144C | 6.25 | 3.13 |
| Example No. 147C | 3.13 | 0.39 |
| Example No. 158C | 3.13 | 6.25 |

EXAMPLE 1C

To a solution of 201.9 mg of cis-3-[2(2-chloroacetamido-4-thiazolyl)-2-methoxyiminoacetamido]-2-oxoazetidine-4-carboxylic acid methyl ester (syn-isomer) in 3.5 ml of N,N-dimethylformamide is added 159.2 mg of a pyridine-sulfuric anhydride complex and the mixture is stirred at room temperature for 5 days. Thereafter, an additional 80 mg of the pyridine-sulfuric anhydride complex is added and the stirring is continued for another 2 days. To the reaction mixture 50 ml of ether is added, resulting in solidification of the insoluble matters. The supernatant ether layer is decanted and another ether is added to wash the insoluble matters. The ether layer is decanted again and the residual insoluble solids are dissolved in 5 ml of water. The resulting solution is filtered and the filtrate is passed through a column of Dowex 50W resin (Na-form). The effluent is lyophilized and the lyophilisate is dissolved in a minimum quantity of water, then purified by columun chromatography on Amberlite XAD-II resin and lyophilized again to give sodium cis-3-[2-(2-chloroacetamido-4-thiazolyl)-2-methoxyiminoacetamido]-4-methoxycarbonyl-2-oxoazetidine-1-sulfonate (syn-isomer).

IR $\nu_{max}^{KBr}$cm$^{-1}$: 3400, 3225, 1780, 1735, 1670, 1055.
NMR(d₆-DMSO, ppm): 3.6(s, —COOCH₃), 3.84(s, =N—OCH₂), 4.29(s, Cl—CH₂—), 4.45(d, J=6 Hz, C₄—H), 5.38(d.d, J=6, 8 Hz, C₃—H),

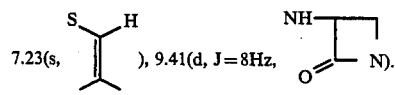

7.23(s, ), 9.41(d, J=8Hz,

EXAMPLE 2C

Under ice-cooling and stirring, 23.85 mg of sodium monomethyldithiocarbamate is added to 2 ml of an aqueous solution containing 85 mg of sodium cis-3-[2-(2-chloroacetamido-4-thiazolyl)-2-methoxyimionacetamido]-4-methoxycarbonyl-2-oxoazetidine-1-sulfoante (syn-isomer). The stirring is continued at room temperature for 40 minutes and another 7 mg of sodium monomethyldithiocarbamate is added. The stirring is continued for an additional 30 minutes. The reaction mixture is then filtered, and the filtrate is washed with ether. The aqueous layer is purified by column chromatography on Amberlite XAD-II and then lyophilized to give sodium cis-3-[2-(2-amino-4-thiazolyl)-2-methoxyiminoacetamido]-4-methoxycarbonyl-2-oxoazetidine-1-sulfonate (syn-isomer).

IR $v_{max}^{KBr}$cm$^{-1}$: 3350, 1775, 1055.

NMR(d$_6$-DMSO, ppm): 3.61(s, —COOCH$_3$), 3.81(s, =N—OCH$_3$), 4.45(d, J=6 Hz, C$_4$—H), 5.35(d.d, J=6, 8 Hz, C$_3$—H), 6.56(s, 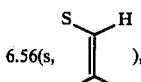 ), 7.1(br.s, —NH$_2$), 9.33(d, J=8Hz, 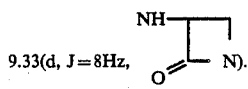 ).

EXAMPLE 3C

To a solution of 418 mg of cis-4-acetoxymethyl-3-[2-(2-chloroacetamido-4-thiazolyl)-2-methoxyiminoacetamido]-2-oxoazetidine (syn-isomer) in 3 ml of N,N-dimethylformamide is added 318 mg of a pyridine-sulfuric anhydride complex and the mixture is stirred at room temperature for 24 hours. Another 159 mg of the pyridine-sulfuric anhydride complex is added and the stirring is continued for an additional 48 hours, then second 159 mg of the complex is added and the stirring is further continued for 70 hours. Ether is then added to the reaction mixture, resulting in solidification of the insoluble matters. The ether is decanted and another ether is added to wash the insoluble matters, which are then collected by filtration. The collected crystals are dissolved in 5 ml of water and the solution is filtered. The filtrate is passed through a column of Dowex 50W resin (Na-form). The lyophilisate of the effluent from the column is dissolved in 5 ml of water, then purified by column chromatography on Amberlite XAD-II and lyophilized to give sodium cis-4-acetoxymethyl-3-[2-(2-chloroacetamido-4-thiazolyl)-2-methoxyiminoacetamido]-2-oxoazetidine-1-sulfonate (syn-isomer).

IR $v_{max}^{KBr}$cm$^{-1}$: 3400, 3250, 1760, 1665, 1045.

NMR(d$_6$-DMSO, ppm): 1.95(s, —OCOCH$_3$), 3.83(s, =N—OCH$_3$), 3.8–4.4(m, C$_4$—H & —CH$_2$OCO), 4.3(s, ClCH$_2$—), 5.15(d.d, J=4.5, 8 Hz, C$_3$—H), 7.3(s, 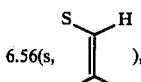 ), 9.3(d, J=8Hz, 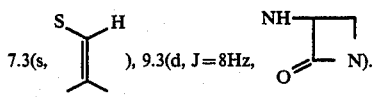

EXAMPLE 4C

Under ice-cooling and stirring, 41 mg of sodium monomethyldithiocarbamate is added to 4 ml of an aqueous solution containing 150 mg of sodium cis-4-acetoxymethyl-3-[2-(2-chloroacetamido-4-thiazolyl)-2-methoxyiminoacetamido]-2-oxoazetidine-1-sulfonate (syn-isomer). The mixture is stirred at room temperature for 30 minutes, and another 10 mg of sodium monomethyldithiocarbamate is added. The stirring is continued for an additional 30 minutes, and the reaction mixture is filtered. The filtrate is then washed with ether, and the aqueous layer is purified by column chromatography on Amberlite XAD-II and then lyophilized to give sodium cis-4-acetoxymethyl-3-[2-(2-amino-4-thiazolyl)-2-methoxyiminoacetamido]-2-oxoazetidine-1-sulfonate (syn-isomer).

IR $v_{max}^{KBr}$cm$^{-1}$: 3425, 3300, 1760, 1660, 1050.

NMR(d$_6$-DMSO, ppm): 1.94(s, —OCOCH$_3$), 3.78(s, =N—OCH$_3$), 3.9–4.4(m, C$_4$—H & —CH$_2$OCO), 5.15(d.d, J=4.5, 8 Hz, C$_3$—H), 6.66(s, 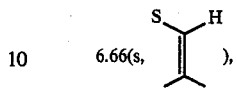 ), 7.1(br.s, —NH$_2$), 9.2(d, J=8Hz, 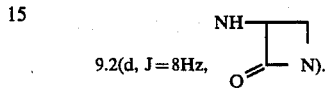 ).

EXAMPLE 5C

To a solution of 150 mg of cis-3-benzyloxycarboxamido-4-(1-methyl-5-tetrazolylthiomethyl)-2-oxoazetidine in 2 ml of N,N-dimethylformamide is added 137 mg of a pyridine-sulfuric anhydride complex and the mixture is stirred at room temperature for 24 hours. Another 70 mg of the pyridine-sulfuric anhydride complex is added and the stirring is continued for an additional 2 hours. Ether is then added to the reaction mixture, resulting in solidification of the insolubles. The ether is decanted and another ether is added to wash the insolubles, which are then collected by filtration. The collected crystals are then dissolved in 15 ml of water and filtered. The filtrate is passed through a column of Dowex 50W resin (Na-form). The effluent is lyophilized and the lyophilisate is dissolved in 5 ml of water, purified by column chromatography on Amberlite XAD-II and then lyophilized to give sodium cis-3-benzyloxycarboxamido-4-(1-methyl-5-tetrazolylthiomethyl)-2-oxoazetidine-1-sulfonate.

IR $v_{max}^{KBr}$cm$^{-1}$: 3300, 1775, 1690, 1055.

NMR(d$_6$-DMSO, ppm): 8.87(s, —NCH$_3$), 3.8–4.3(m, C$_4$—H & CH$_2$S—), 4.96(d.d, J=5, 10 Hz, C$_3$—H), 5.1(s, —CH$_2$O—), 7.35(s, —C$_6$H$_5$), 8.16(d, J=10 Hz, —NH).

EXAMPLE 6C

To a solution of 202 mg of cis-3-[2-(2-chloroacetamido-4-thiazolyl)-2-methoxyiminoacetamido]-2-oxoazetidine-4-carboxylic acid methyl ester (anti-isomer) in 3.5 ml of N,N-dimethylformamide is added 159 mg of a pyridine-sulfuric anhydride complex and the mixture is stirred at room temperature for 4 days. Another 80 mg of the pyridine-sulfuric anhydride complex is added and the stirring is continued for an additional 1 day. Thereafter 50 ml of ether is added, causing syrupy insolubles to be formed. The supernatant ether layer is decanted and another ether is added to wash the insolubles. The ether layer is decanted again and the remaining syrupy insolubles are dissolved in 6 ml of water. After filtration, the filtrate is passed through a column of Dowex 50W resin (Na-form). The lyophilisate of the effluent from the column is dissolved in a minimum quantity of water, then purified by column chromatography on Amberlite XAD-II and lyophilized to give sodium cis-3-[2-(2-chloroacetamido-4-thiazolyl)-2-methoxyiminoacetamido]-4-methoxycarbonyl-2-oxoazetidine-1-sulfonate (anti-isomer).

IR $\nu_{max}^{KBr}$cm$^{-1}$: 1760, 1670, 1040.

NMR(d$_6$-DMSO, ppm): 3.69(s, —COOCH$_3$), 3.98(s, NOCH$_3$), 4.35(s, Cl—CH$_2$—), 4.49(d, J=6 Hz, C$_4$—H), 5.41(d.d, J=6, 9 Hz, C$_3$—H),

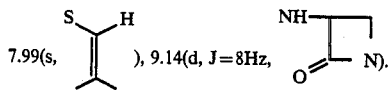

7.99(s, ), 9.14(d, J=8Hz, ).

EXAMPLE 7C

Under ice-cooling and stirring, 21 mg of sodium monomethyldithiocarbamate is added to 2 ml of an aqueous solution containing 85 mg of sodium cis-3-[2-(2-chloroacetamido-4-thiazolyl)-2-methoxyiminoacetamido]-4-methoxycarbonyl-2-oxoazetidine-1-sulfonate (anti-isomer). The mixture is stirred at room temperature for 1 hour and another 7 mg of sodium monomethyldithiocarbamate is added. The stirring is continued for an additional 1 hour, the reaction mixture is filtered and the filtrate is washed with ether. The aqueous layer is purified by column chromatography on Amberlite XAD-II and the lyophilized to give sodium cis-3-[2-(2-amino-4-thiazolyl)-2-methoxyiminoacetamido]-4-methoxycarbonyl-2-oxoazetidine-1-sulfonate (anti-isomer).

IR$\nu_{max}^{KBr}$cm$^{-1}$: 1760, 1050.

NMR(d$_6$-DMSO, ppm): 3.68(s, —COOCH$_3$), 3.92(s, =NOCH$_3$), 4.46(d, J=6 Hz, C$_4$—H), 5.36(d.d, J=6, 8 Hz, C$_3$—H), 7.03(br.s, —NH$_2$),

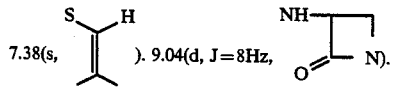

7.38(s, ). 9.04(d, J=8Hz, ).

EXAMPLE 8C

To a solution of 112 mg of cis-3-phenylacetamido-2-oxoazetidine-4-carboxylic acid methyl ester in 3.5 ml of N,N-dimethylformamide is added 159 mg of a pyridine-sulfuric anhydride complex, and the mixture is stirred at room temperature for 5 days. Another 80 mg of the pyridine-sulfuric anhydride complex is added and the stirring is continued for an additional 1 day. Thereafter 50 ml of ether is added to the reaction mixture, causing the formation of syrupy precipitates. The ether is decanted and another ether is added to wash the syrupy precipitates. The ether is decanted again and the syrupy precipitates are dissolved in 5 ml of water. After filtration of the solution, the filtrate is passed through a column of Dowex 50W resin (Na-form). The lyophilisate of the effluent from the column is dissolved in a minimum amount of water, then purified by column chromatography on Amberlite XAD-II and lyophilized to give sodium cis-4-methoxycarbonyl-3-phenylacetamido-2-oxoazetidine-1-sulfonate.

IR$\nu_{max}^{KBr}$cm$^{-1}$: 1770, 1740, 1650, 1255, 1055.

NMR(d$_6$-DMSO, ppm): 3.46(CH$_2$CO & OCH$_3$), 4.39(d, J=6 Hz), 5.25(d.d, J=6, 8 Hz), 7.24(s, C$_6$H$_5$), 8.82(d, CONH).

EXAMPLE 9C

To a solution of 30 mg of cis-4-acetamidomethyl-3-phenylacetamido-2-oxoazetidine in 0.7 ml of N,N-dimethylacetamide is added 52 mg of a pyridine-sulfuric anhydride complex and the mixture is stirred at room temperature for 69 hours. Thereafter 35 ml of ether is added to the reaction mixture, resulting in the formation of syrupy precipitates. The ether is decanted and another ether is added to wash the precipitates. The ether is decanted again and the remaining syrupy precipitates are dissolved in 1 ml of water. After filtration of the solution, the filtrate is passed through a column of Dowex 50W resin (Na-form). The lyophilisate of the effluent from the column is dissolved in a minimum amount of water, then purifed by column chromatography on Amberlite XAD-II and lyophilized to give sodium cis-4-acetamidomethyl-3-phenylacetamido-2-oxoazetidine-1-sulfonate.

IR$\nu_{max}^{KBr}$cm$^{-1}$: 3400(br), 1760, 1640, 1515, 1255, 1050.

NMR(D$_2$O, ppm): 1.91(s, COCH$_3$), 3.52(d, J=6 Hz, CH$_2$N), 3.68(s, CH$_2$CO), 4.37(d.d, J=5.5, 6 Hz, C$_4$—H), 5.19(d, J=5.5 Hz, C$_3$—H), 7.38(m, C$_6$H$_5$).

EXAMPLE 10C

To a solution of 250 mg of cis-3-[2-(chloroacetamido-4-thiazolyl)-2-ethoxyiminoacetamido]-2-oxoazetidine-4-carboxylic acid methyl ester (syn-isomer) in 2 ml of N,N-dimethylformamide is added 190.4 mg of sulfuric anhydride-pyridine complex, and the mixture is stirred at room temperature for 24 hours. To the mixture is further added 95 mg of sulfuric anhydride-pyridine complex, followed by stirring for further 24 hours. On addition of 20 ml of ether to the mixture, insolubles solidify. The supernatant ether layer is discarded. To the remainder is added 20 ml of fresh ether to wash the solid matter. Similar procedure is repeated, and the ether layer is discarded, and insoluble solid matter is suspended in 20 ml of water. To the suspension is added 12 ml of Dowex 50W (Na-type) resin, and the mixture is stirred at room temperature for 2 hours. The resin is removed by filtration, and the filtrate is lyophilised. The resulting powder is dissolved in 20 ml of water, followed by purification by means of column-chromatography on Amberlite XAD-II. Thus-purified product is lyophilised to give sodium cis-3-[2-(2-chloroacetamido-4-thiazolyl)-2-ethoxyiminoacetamido]-4-methoxycarbonyl-2-oxoazetidine-1-sulforate (syn-isomer).

IR$\nu_{max}^{KBr}$cm$^{-1}$: 3600–3200, 1790–1750, 1700–1670, 1055.

NMR(d$_6$-DMSO, ppm): 1.23(3H, t, J=6 Hz, CH$_2$CH$_3$), 3.62 3H, s, COOCH$_3$), 4.12(2H, q, J=6 Hz, CH$_2$CH$_3$), 4.34(2H, s, ClCH$_2$), 4.49(1H, d, J=6 Hz, C$_4$—H), 5.43(1H, d.d, J=6, 9 Hz, C$_3$—H),

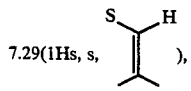

7.29(1Hs, s, ), 9.40(1H, d, J=9 Hz, C$_3$—NH), 12.92(1H, br.s, ClCH$_2$CONH).

| Elemental analysis: C$_{14}$H$_{15}$ClN$_5$NaO$_9$S$_2$.2H$_2$O | | | |
|---|---|---|---|
| | C (%) | H (%) | N (%) |
| Calcd. | 30.25 | 3.45 | 12.60 |
| Found | 30.01 | 3.46 | 12.46 |

EXAMPLE 11C

To a solution of 110 mg of sodium cis-3-[2-(2-chloroacetamido-4-thiazolyl)-2-ethoxyiminoacetamido]-4-methoxycarbonyl-2-oxoazetidine-1-sulfonate (syn-isomer) in 8 ml of water is added ice-cooling 30 mg of sodium monomethyl dithiocarbamate. The mixture is stirred at room temperature for one hour, then another 10 mg of sodium monomethyl dithiocarbamate is added thereto. After the mixture is stirred for further one hour, the resulting reaction mixture is subjected to filtration, and the filtrate is washed with ether. The aqueous layer is purified by column chromatography on Amberlite XAD-II and then lyophilized to give sodium cis-3-[2-(2-amino-4-thiazolyl)-2-ethoxyiminoacetamido]-4-methoxycarbonyl-2-oxoazetidine-1-sulfonate (syn-isomer).

IR$\nu_{max}^{KBr}$cm$^{-1}$: 3500–3300, 1790–1750, 1680, 1625, 1055.

NMR(d$_6$-DMSO, ppm): 1.21(3H, t, J=7 Hz, CH$_2$CH$_3$), 3.61(3H, s, COOCH$_3$), 4.07(2H, q, J=7 Hz, CH$_2$CH$_3$), 4.47 (1H, d, J=6 Hz, C$_4$—H), 5.39(1H, d.d, J=6, 9 Hz, C$_3$—H),

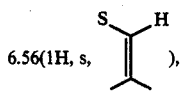
6.56(1H, s,         ), 7.15(2H, br.s, NH$_2$), 9.30(1H, d, J=9 Hz, C$_3$—NH).

| Elemental analysis: C$_{12}$H$_{14}$N$_5$NaO$_8$S$_2$.2H$_2$O | | | |
|---|---|---|---|
| | C (%) | H (%) | N (%) |
| Calcd. | 30.06 | 3.78 | 14.61 |
| Found | 30.33 | 3.53 | 14.76 |

EXAMPLE 12C

In the same manner as Example 10C, there was obtained sodium cis-3-[2-(2-chloroacetamido-4-thiazolyl)-2-(n-propoxyimino)acetamido]-4-methoxycarbonyl-2-oxoazetidine-1-sulfonate (syn-isomer).

IR$\nu_{max}^{KBr}$cm$^{-1}$: 3250, 2970, 1780, 1750, 1680, 1055.
NMR(d$_6$-DMSO, ppm): 0.89(3H, t, J=7 Hz, CH$_2$CH$_2$CH$_3$), 1.65 (2H, sextet, J=7 Hz, CH$_2$CH$_3$), 3.60(3H, s, COOCH$_3$), 4.01(2H, t, J=7 Hz, CH$_2$CH$_2$CH$_3$), 4.32(2H, s, ClCH$_2$), 4.48(1H, d, J=6 Hz, C$_4$—H), 5.43(1H, d.d, J=6, 9 Hz, C$_3$—H),

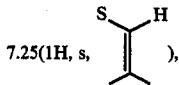
7.25(1H, s,         ), 9.4(1H, s, J=9 Hz, C$_3$—NH), 12.9(1H, br.s, ClCH$_3$CONH).

| Elemental analysis: C$_{15}$H$_{17}$ClN$_5$NaO$_9$S$_2$.½H$_2$O | | | |
|---|---|---|---|
| | C (%) | H (%) | N (%) |
| Calcd. | 33.18 | 3.34 | 12.90 |
| Found | 33.19 | 3.51 | 12.93 |

EXAMPLE 13C

In the same manner as Example 11C, there was obtained sodium cis-3-[2-(2-amino-4-thiazolyl)-2-(n-propoxyimino)acetamido]-4-methoxycarbonyl-2-oxoazetidine-1-sulfonate (syn-isomer).

IR$\nu_{max}^{KBr}$cm$^{-1}$: 3425, 1780, 1750, 1680, 1620, 1055.
NMR(d$_6$-DMSO, ppm): 0.88(3H, t, J=7 Hz, CH$_2$CH$_2$CH$_3$), 1.62(2H, sextet, J=7 Hz, CH$_2$CH$_2$CH$_3$), 3.61 (3H, s, COOCH$_3$), 3.98(2H, t, J=7 Hz, CH$_2$CH$_2$CH$_3$), 4.48(1H, d, J=6 Hz, C$_4$—H), 5.4(1H, d.d., J=6, 9 Hz, C$_3$—H),

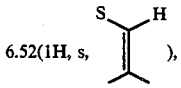
6.52(1H, s,         ), 7.14(2H, br.s, NH$_2$), 9.31(1H, d, J=9 Hz, C$_3$—NH).

| Elemental analysis: C$_{13}$H$_{16}$N$_5$NaO$_8$S$_2$.2H$_2$O | | | |
|---|---|---|---|
| | C (%) | H (%) | N (%) |
| Calcd. | 31.64 | 4.09 | 14.19 |
| Found | 31.70 | 3.81 | 14.43 |

EXAMPLE 14C

In the same manner as Example 10C, there was obtained sodium cis-3-[2-(2-chloroacetamido-4-thiazolyl)-2-isopropoxyiminoacetamido]-4-methoxycarbonyl-2-oxoazetidine-1-sulfonate (syn-isomer).

IR$\nu_{max}^{KBr}$cm$^{-1}$: 3600–3300, 1780–1750, 1700–1670, 1055.

NMR(d$_6$-DMSO, ppm): 1.23[6H, d, J=6 Hz, CH(CH$_3$)$_2$], 3.62 (3H, s, COOCH$_3$), 4.31[1H, m, CH(CH$_3$)$_2$], 4.33(2H, s, ClCH$_2$), 4.50(1H, d, J=6 Hz, C$_4$—H), 5.45(1H, d.d, J=6, 9 Hz, C$_3$—H),

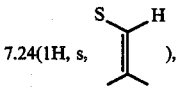
7.24(1H, s,         ), 9.32(1H, d, J=9 Hz, C$_3$—NH), 12.90(1H, br.s, ClCH$_2$CONH).

| Elemental analysis: C$_{15}$H$_{17}$ClN$_5$NaO$_9$S$_2$.2H$_2$O | | | |
|---|---|---|---|
| | C (%) | H (%) | N (%) |
| Calcd. | 31.61 | 3.71 | 12.29 |
| Found | 31.58 | 3.65 | 12.28 |

EXAMPLE 15C

In the same manner as Example 11C, there was obtained sodium cis-3-[2-(2-amino-4-thiazolyl)-2-isopropoxyiminoacetamido]-4-methoxycarbonyl-2-oxoazetidine-1-sulfonate (syn-isomer).

IR$\nu_{max}^{KBr}$cm$^{-1}$: 3600–3200, 1780–1750, 1680, 1620, 1055.

NMR(d$_6$-DMSO, ppm): 1.20[6H, d, J=6 Hz, CH(CH$_3$)$_2$], 3.62(3H, s, COOCH$_3$), 4.27[1H, septet, CH(CH$_3$)$_2$], 4.47(1H, d, J=6 Hz, C$_4$—H), 5.41(1H, d.d., J=6, 9 Hz, C$_3$—H),

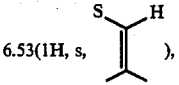
6.53(1H, s,         ), 7.12(2H, br.s, NH$_2$), 9.18(1H, d, J=9 Hz, C$_3$—NH).

| Elemental analysis: C$_{13}$H$_{16}$N$_5$NaO$_8$S$_2$.2H$_2$O | | | |
|---|---|---|---|
| | C (%) | H (%) | N (%) |
| Calcd. | 31.64 | 4.09 | 14.19 |

| Elemental analysis: $C_{13}H_{16}N_5NaO_8S_2.2H_2O$ | | | |
|---|---|---|---|
| | C (%) | H (%) | N (%) |
| Found | 31.92 | 3.85 | 14.37 |

EXAMPLE 16C

In the same manner as Example 10C, there was obtained sodium cis-3-[2-(2-chloroacetamido-4-thiazolyl)-2-(n-butoxyimino)acetamido]-4-methoxycarbonyl-2-oxoazetidine-1-sulfonate (syn-isomer).

IR$\nu_{max}^{KBr}$cm$^{-1}$: 2960, 1780, 1750, 1680, 1055.

NMR(d$_6$-DMSO, ppm): 0.89(3H, t, J=6 Hz, CH$_2$CH$_2$CH$_2$CH$_3$), 1.1–1.8(4H, m, CH$_2$CH$_2$CH$_2$CH$_3$), 3.60(3H, s, COOCH$_3$), 4.04(2H, t, J=6 Hz, CH$_2$CH$_2$CH$_2$CH$_3$), 4.30(2H, s, ClCH$_2$), 4.49(1H, d, J=6 Hz, C$_4$—H), 5.42(1H, d.d, J=6, 9 Hz, C$_3$—H),

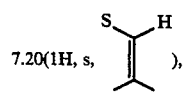

7.20(1H, s,   ), 9.37(1H, d, J=9 Hz, C$_3$—NH).

| Elemental analysis: $C_{16}H_{19}ClN_5NaO_9S_2.2H_2O$ | | | |
|---|---|---|---|
| | C (%) | H (%) | N (%) |
| Calcd. | 32.91 | 3.97 | 11.99 |
| Found | 32.58 | 3.80 | 11.83 |

EXAMPLE 17C

In the same manner as Example 11C, there was obtained sodium cis-3-[2-(2-amino-4-thiazolyl)-2-(n-butoxyimino)acetamido]-4-methoxycarbonyl-2-oxoazetidine-1-sulfonate (syn-isomer).

IR$\nu_{max}^{KBr}$cm$^{-1}$: 3450–3350, 1790–1750, 1680, 1620, 1050.

NMR(d$_6$-DMSO, ppm): 0.89(3H, t, J=6 Hz, CH$_2$CH$_2$CH$_2$CH$_3$), 1.1–1.8(4H, m, CH$_2$CH$_2$CH$_2$CH$_3$), 3.61(3H, s, COOCH$_3$), 4.01(2H, t, J=6 Hz, CH$_2$CH$_2$CH$_2$CH$_3$), 4.47(1H, d, J=6 Hz, C$_4$—H), 5.39(1H, d.d, J=6, 9 Hz), C$_3$—H),

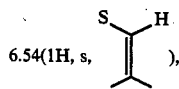

6.54(1H, s,   ), 7.13(2H, br.s, NH$_2$), 9.3(1H, d, J=9 Hz, C$_3$—NH).

| Elemental analysis: $C_{14}H_{18}N_5NaO_8S_2.2H_2O$ | | | |
|---|---|---|---|
| | C (%) | H (%) | N (%) |
| Calcd. | 33.13 | 4.37 | 13.80 |
| Found | 33.01 | 4.10 | 13.85 |

EXAMPLE 18C

In the same manner as described in Example 10C, there was obtained sodium cis-3-[2-(2-chloroacetamido-4-thiazolyl)-2-benzyloxyiminoacetamido]-4-methoxycarbonyl-2-oxoazetidine-1-sulfonate (syn-isomer).

IR$\nu_{max}^{KBr}$cm$^{-1}$: 3550–3250, 1780, 1750, 1680, 1055.

NMR(d$_6$-DMSO, ppm): 3.52(3H, s, COOCH$_3$), 4.33(2H, s, ClCH$_2$), 4.51(1H, d, J=6 Hz, C$_4$—H), 5.16(2H, s, PhCH$_2$), 5.49(1H, d.d, J=6, 9 Hz, C$_3$—H),

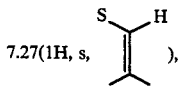

7.27(1H, s,   ), 7.38(5H, s, Ph—), 9.59 (1H, d, J=9 Hz, C$_3$—NH), 12.9(1H, br.s, ClCH$_2$CONH).

| Elemental analysis: $C_{19}H_{17}ClN_5NaO_9S_2.H_2O$ | | | |
|---|---|---|---|
| | C (%) | H (%) | N (%) |
| Calcd. | 38.03 | 3.19 | 11.67 |
| Found | 38.07 | 3.27 | 11.72 |

EXAMPLE 19C

In the same manner as Example 11C, there was obtained sodium cis-3-[2-(2-amino-4-thiazolyl)-2-benzyloxyiminoacetamido]-4-methoxycarbonyl-2-oxoazetidine-1-sulfonate (syn-isomer).

IR$\nu_{max}^{KBr}$cm$^{-1}$: 3450–3325, 1780, 1750, 1675, 1620, 1055.

NMR(d$_6$-DMSO, ppm): 3.54(3H, s, COOCH$_3$), 4.49(1H, d, J=6 Hz, C$_4$—H), 5.12(2H, s, PhCH$_2$), 5.42(1H, d.d, J=6, 9 Hz, C$_3$—H),

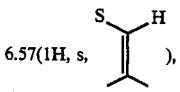

6.57(1H, s,   ), 7.16(2H, br.s, NH$_2$), 7.37(5H, s, Ph—), 9.48(1H, d, J=9 Hz, C$_3$—NH).

| Elemental analysis: $C_{17}H_{16}N_5NaO_8S_2.2H_2O$ | | | |
|---|---|---|---|
| | C (%) | H (%) | N (%) |
| Calcd. | 37.70 | 3.72 | 12.93 |
| Found | 37.26 | 3.37 | 12.93 |

EXAMPLE 20C

In the same manner as Example 10C, there was obtained sodium cis-3-[2-(5-chloro-2-chloroacetamido-4-thiazolyl)-2-methoxyiminoacetamido]-4-methoxycarbonyl-2-oxoazetidine-1-sulfonate (syn-isomer).

IR$\nu_{max}^{KBr}$cm$^{-1}$: 1790, 1740, 1680, 1550, 1060.

NMR(d$_6$-DMSO, ppm): 3.63(3H, s, COOCH$_3$), 3.89(3H, s, NOCH$_3$), 4.37(2H, s, ClCH$_3$), 4.46(1H, d, J=6 Hz, C$_4$—H), 5.40(1H, d.d, J=6, 9 Hz, C$_3$—H), 9.48(1H, d, J=9 Hz, C$_3$—NH), 13.1(1H, br.s, ClCH$_2$CONH).

| Elemental analysis: $C_{13}H_{12}Cl_2N_5O_9S_2Na.2H_2O$ | | | |
|---|---|---|---|
| | C (%) | H (%) | N (%) |
| Calcd. | 27.09 | 2.80 | 12.15 |
| Found | 27.42 | 2.80 | 12.39 |

EXAMPLE 21C

In the same manner as Example 11C, there was obtained sodium cis-3-[2-(2-amino-5-chloro-4-thiazolyl)-2- methoxyiminoacetamido]-4-methoxycarbonyl-2-oxoazetidine-1-sulfonate (syn-isomer).

IR$\nu_{max}^{KBr}$cm$^{-1}$: 3400, 1780, 1750, 1680, 1620, 1540, 1060.

NMR(d$_6$-DMSO, ppm): 3.64(3H, s, COOCH$_3$), 3.83(3H, s, NOCH$_3$), 4.44(1H, d, J=6 Hz, C$_4$—H), 5.36(1H, d.d, J=6, 9 Hz, C$_3$—H), 7.30(2H, s, NH$_2$), 9.32 (1H, d, J=9 Hz, C$_3$—NH).

| Elemental analysis: C$_{11}$H$_{11}$ClN$_5$NaO$_8$S$_2$.2H$_2$O | | | |
|---|---|---|---|
| | C (%) | H (%) | N (%) |
| Calcd. | 26.43 | 3.02 | 14.01 |
| Found | 26.11 | 3.15 | 14.13 |

EXAMPLE 22C

In the same manner as Example 10C, there was obtained sodium cis-3-[2-(2-chloroacetamido-4-thiazolyl)-2-methoxyiminoacetamido]-4-(n-butoxycarbonyl)-2-oxoazetidine-1-sulfonate (syn-isomer).

IR$\nu_{max}^{KBr}$cm$^{-1}$: 3250, 1780, 1740, 1680, 1060.

NMR(d$_6$-DMSO, ppm): 0.73-1.73(7H, m, CH$_2$CH$_2$CH$_2$CH$_3$), 3.86(3H, s, NOCH$_3$), 4.43(2H, s, ClCH$_2$). 4.46(1H, d, J=5 Hz, C$_4$—H), 5.40(1H, d.d, J=5, 9 Hz, C$_3$—H), 7.30(1H, s, 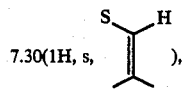 ), 9.41(1H, d, J=9 Hz, C$_3$—NH), 11.93(1H, br.s, ClCH$_2$CONH).

| Elemental analysis: C$_{16}$H$_{19}$ClN$_5$NaO$_9$S$_2$.H$_2$O | | | |
|---|---|---|---|
| | C (%) | H (%) | N (%) |
| Calcd. | 33.95 | 3.74 | 12.37 |
| Found | 33.79 | 3.79 | 12.39 |

EXAMPLE 23C

In the same manner as Example 11C, there was obtained sodium cis-3-[2-(2-amino-4-thiazolyl)-2-methoxyiminoacetamido]-4-(n-butoxycarbonyl)-2-oxoazetidine-1-sulfonate (syn-isomer).

IR$\nu_{max}^{KBr}$cm$^{-1}$: 3450, 3320, 1790, 1750, 1670, 1050.

NMR(d$_6$-DMSO, ppm): 0.7-1.76(7H, m, CH$_2$CH$_2$CH$_2$CH$_3$), 3.80(3H, s, NOCH$_3$), 4.00(2H, t, CH$_2$CH$_2$CH$_2$CH$_3$), 4.43(1H, d, J=5 Hz, C$_4$—H), 5.33(1H, d.d, J=5, 9 Hz, C$_3$—H), 6.56(1H, s, 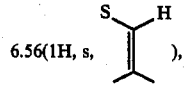 ), 7.13(2H, br.s, NH$_2$), 9.41(1H, d, J=9 Hz, C$_3$—NH).

| Elemental analysis: C$_{14}$H$_{18}$N$_5$NaO$_8$S$_2$.H$_2$O | | | |
|---|---|---|---|
| | C (%) | H (%) | N (%) |
| Calcd. | 34.35 | 4.11 | 14.30 |
| Found | 34.51 | 4.07 | 14.42 |

EXAMPLE 24C

To a solution of 180 mg of trans-3-[2-(2-chloroacetamido-4-thiazolyl)-2-methoxyiminoacetamido]-2-oxoazetidine-4-carboxylic acid methyl ester (syn-isomer) in 1.8 ml of N,N-dimethylformamide is added 142 mg of a pyridine-sulfuric anhydride complex, and the mixture is stirred at room temperature. Two days later, and four days layer, 142 mg each portion of a pyridine-sulfuric anhydride complex is supplemented, and the mixture is stirred for six days in total. To the reaction mixture is added 50 ml of ether. The ether layer is removed by decantation. This procedure is conducted three times. The resulting syrupy substance insoluble in ether is dissolved in a small amount of water, and the solution is allowed to pass through Dowex 50W resin (Na-form). The lyophilisate of the effluent is dissolved in a small volume of water, then purified by column chromatography on Amberlite XAD-II and lyophilized to give sodium trans-3-[2-(2-chloroacetamido-4-thiazolyl)-2-methoxyiminoacetamido]-4-methoxycarbonyl-2-oxoazetidine-1-sulfonate (syn-isomer).

IR$\nu_{max}^{KBr}$cm$^{-1}$: 1780, 1670, 1550.

NMR(d$_6$-DMSO, ppm): 3.7(3H, s, COOCH$_3$), 3.9(3H, s, NOCH$_3$), 4.1(1H, d, J=2 Hz, C$_4$—H), 4.35(2H, s, ClCH$_2$), 4.8(1H, d.d, J=2, 9 Hz, C$_3$—H), 7.4(1H, s, 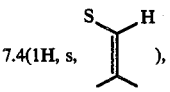 ), 9.6(1H, d, J=9 Hz, C$_3$—NH).

EXAMPLE 25C

To a solution of 320 mg of cis-3-[2-(2-chloroacetamido-4-thiazolyl)acetamido]-2-oxoazetidine-4-carboxylic acid methyl ester in 2 ml of N,N-dimethylformamide is added 282.3 mg of a pyridine-sulfuric anhydride complex, and the mixture is stirred at room temperature for 48 hours. Another 141 mg of pyridine-sulfuric anhydride complex is added and the stirring is continued for additional 24 hours. Thereafter, 30 ml of ether is added, and the ether layer is removed by decantation. This procedure is conducted twice. The resulting syrupy substance insoluble in ether is dissolved in 10 ml of water, and insolubles are removed by filtration, and the filtrate is allowed to pass through a column of Dowex 50W resin (Na-form). The effluent is concentrated under reduced pressure to a volume of 10 ml, and purified by column chromatography on Amberlite XAD-II and lyophilized to give sodium cis-3-[2-(2-chloroacetamido-4-thiazolyl)acetamido]-4-methoxycarbonyl-2-oxoazetidine-1-sulfonate.

IR$\nu_{max}^{KBr}$cm$^{-1}$: 3600-3200, 1790-1760, 1680, 1060.

NMR(d$_6$-DMSO, ppm):

8.26(2H, s, 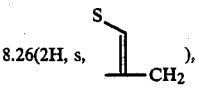 ), 3.56(3H, s, COOCH$_3$), 4.32(2H, s, ClCH$_2$), 4.43(1H, d, J=6 Hz, C$_4$—H), 5.29(1H, d.d, J=6, 9 Hz, C$_3$—H), 6.92(1H, s, 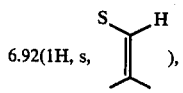 ), 8.70(1H, d, J=9 Hz, C$_3$—NH), 12.56(1H, br.s, ClCH$_2$CONH).

| Elemental analysis: C$_{12}$H$_{12}$ClN$_4$NaO$_8$S$_2$.H$_2$O | | | |
|---|---|---|---|
| | C (%) | H (%) | N (%) |
| Calcd. | 29.97 | 2.93 | 11.65 |
| Found | 30.13 | 3.29 | 12.02 |

EXAMPLE 26C

In the same manner as Example 11C, there was obtained sodium cis-3-[2-(2-amino-4-thiazolyl)acetamido]-4-methoxycarbonyl-2-oxoazetidine-1-sulfonate.

IR$\nu_{max}^{KBr}$cm$^{-1}$: 3330, 1790–1750, 1680, 1625, 1060.

NMR(d$_6$-DMSO, ppm): 3.32(2H, s, CH$_2$), 3.59(3H, s, COOCH$_3$), 4.42(1H, d, J=6 Hz, C$_4$—H), 5.29(1H, d.d, J=6, 9 Hz, C$_3$—H), 6.28(1H, s, 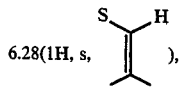 ), 7.20(2H, br.s, NH$_2$), 8.59(1H, d, J=9 Hz, C$_3$—NH).

| Elemental analysis: C$_{10}$H$_{11}$N$_4$NaO$_7$S$_2$.H$_2$O | | | |
|---|---|---|---|
| | C (%) | H (%) | N (%) |
| Calcd. | 29.70 | 3.24 | 13.85 |
| Found | 29.98 | 3.49 | 13.53 |

EXAMPLE 27C

To a solution of 169 mg of β-form of cis-3-{D-2-[4-(n-butyl)-2,3-dioxo-1-piperazinecarboxamido]-2-phenylacetamido}-2-oxoazetidine-4-carboxylic acid methyl ester (Reference Example 39C) in 1 ml of N,N-dimethylformamide is added 114 mg of a pyridine-sulfuric anhydride complex, and the mixture is stirred at room temperature. Ten days later, and further one day later, 57 mg portion each of a pyridine-sulfuric anhydride complex is supplemented, and the mixture is stirred for 12 days in total. To the mixture is then added 20 ml of ether. The ether layer is removed by decantation. This procedure is conducted twice. The remaining insolubles are suspended in 25 ml of water. To the suspension is added Dowex 50W (Na-form) resin, and the mixture is stirred at room temperature for 1.5 hours. The resin is removed by filtration, and the filtrate is lyophilized to give a powdery product, which is dissolved in a small volume of water. The aqueous solution is purified by column chromatography on Amberlite XAD-II, followed by lyophilization to afford sodium cis-3-{D-2-[4-(n-butyl)-2,3-dioxo-1-piperazinecarboxamido]-2-phenylacetamido}-4-methoxycarbonyl-2-oxoazetidine-1-sulfonate (β-form).

IR $\nu_{max}^{KBr}$cm$^{-1}$: 3410, 1775, 1720, 1685, 1290, 1055.

NMR (d$_6$-DMSO, ppm): 3.09(3H, s, COOCH$_3$), 4.37(1H, d, J=6 Hz, C$_4$—H, 5.20(1H, d.d, J=6,9 Hz, C$_3$—H), 5.54(1H, d, J=7.5 Hz, PhCH).

| Elemental analysis: C$_{22}$H$_{26}$N$_5$NaO$_{10}$S$_2$.2H$_2$O | | | |
|---|---|---|---|
| | C (%) | H (%) | N (%) |
| Calcd. | 43.21 | 4.94 | 11.45 |
| Found | 43.10 | 5.08 | 11.41 |

$[\alpha]_D^{22°} = -12.9°$ (c=0.155, H$_2$O).

Corresponding α-form compound was obtained in the same manner as above.

IR $\nu_{max}^{KBr}$cm$^{-1}$: 3450, 1780, 1720, 1680, 1270, 1055.

NMR(d$_6$-DMSO, ppm): 3.60(3H, s, COOCH$_3$), 4.47(1H, d, J=6 Hz, C$_4$—H), 5.13(1H, d.d, J=6,9 Hz, C$_3$—H), 5.48(1H, d, J=7.5 Hz, PhCH).

| Elemental analysis: C$_{22}$H$_{26}$N$_5$NaO$_{10}$S$_2$.2H$_2$O | | | |
|---|---|---|---|
| | C (%) | H (%) | N (%) |
| Calcd. | 43.21 | 4.94 | 11.45 |
| Found | 43.66 | 4.85 | 11.54 |

$[\alpha]_D^{22°} = -43.7°$ (c=0.135, H$_2$O).

EXAMPLE 28C

In the same manner as Example 27C, β- and α-form of sodium cis-3-{D-2-[4-(n-butyl)-2,3-dioxo-1-piperazinecarboxamido]-2-(2-thienyl)acetamido}-4-methoxycarbonyl-2-oxoazetidine-1-sulfonate.

Beta form

IR $\nu_{max}^{KBr}$cm$^{-1}$: 3300, 1775, 1710, 1675, 1520, 1370, 1184.

NMR(d$_6$-DMSO, ppm): 3.26(3H, s, COOCH$_3$), 4.40(1H, d, J=6 Hz, C$_4$—H), 5.31(1H, d.d, J=6,9 Hz, C$_3$—H), 5.82(1H, d, J=7.5Hz, 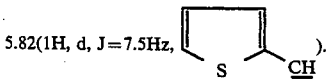 ).

| Elemental analysis: C$_{20}$H$_{24}$N$_5$NaO$_{10}$S$_2$.2H$_2$O | | | |
|---|---|---|---|
| | C (%) | H (%) | N (%) |
| Calcd. | 38.89 | 4.56 | 11.34 |
| Found | 38.50 | 4.56 | 11.30 |

Alpha form

IR $\nu_{max}^{KBr}$cm$^{-1}$: 3300, 1780, 1720, 1680, 1520, 1370, 1185.

NMR(d$_6$-DMSO, ppm): 3.61(3H, s, COOCH$_3$), 4.46(1H, d, J=6 Hz, C$_4$—H). 5.17(1H, d.d, J=6,9 Hz, C$_3$—H), 5.73(1H, d, J=7.5Hz, 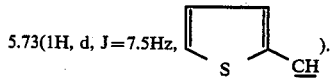 ),

| Elemental analysis: C$_{20}$H$_{24}$N$_5$NaO$_{10}$S$_2$.H$_2$O | | | |
|---|---|---|---|
| | C (%) | H (%) | N (%) |
| Calcd. | 40.06 | 4.37 | 11.68 |
| Found | 39.64 | 4.53 | 11.54 |

EXAMPLE 29C

To a solution of 261 mg of β-form of cis-3-{D-2-[4-(n-octyl)-2,3-dioxo-1-piperazinecarboxamido]-2-(2-thienyl)acetamido}-2-oxoazetidine-4-carboxylic acid methyl ester (Reference Example 39C) in 2 ml of N,N-dimethylformamide is added 155 mg of a pyridine-sulfuric anhydride complex, and the mixture is stirred at room temperature for 5 days. To the reaction mixture is added 20 ml of ether, and the ether layer is removed by decantation. This procedure is conducted three times. The ether-insoluble solids are suspended in 50 ml of water. To the suspension is added Dowex 50W (Na-form) resin, and the mixture is stirred at room temperature for 2 hours. The resin is removed by filtration, and the filtrate is lyophilized. The resulting powdery product is dissolved in a small volume of water, and the solution is purified by column chromatography on Amberlite XAD-II and lyophilized to give sodium cis-3-{D-2-[4-(n-octyl)-2,3-dioxo-1-piperazinecarboxamido]-2-(2-thienyl)acetamido}-4-methoxycarbonyl-2-oxoazetidine-1-sulfonate (β-form).

IR $\nu_{max}^{KBr}$ cm$^{-1}$: 3400, 1760, 1670.

NMR(d$_6$-DMSO, ppm): 3.62(3H, s, COOCH$_3$), 4.48(1H, d, J=6 Hz, C$_4$—H),

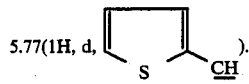
5.77(1H, d,

| Elemental analysis: C$_{24}$H$_{32}$N$_5$NaO$_{10}$S$_2$·2H$_2$O | | | |
|---|---|---|---|
| | C (%) | H (%) | N (%) |
| Calcd. | 42.79 | 5.39 | 10.40 |
| Found | 42.98 | 5.64 | 10.64 |

In the same manner as above, there was obtained the corresponding α-form.

IR $\nu_{max}^{KBr}$ cm$^{-1}$: 3400, 1765, 1675.

NMR(d$_6$-DMSO, ppm): 3.22(3H, s, COOCH$_3$), 4.42(1H, d, J=6 Hz, C$_4$—H), 5.35(1H, d.d, J=6,9 Hz, C$_3$—H), 5.88(1H, s,

| Elemental analysis: C$_{24}$H$_{32}$N$_5$NaO$_{10}$S$_2$·2H$_2$O | | | |
|---|---|---|---|
| | C (%) | H (%) | N (%) |
| Calcd. | 42.79 | 5.39 | 10.40 |
| Found | 42.64 | 5.51 | 10.62 |

EXAMPLE 30C

To a solution of 330 mg of β-form of trans-3-{D-2-[4-(n-octyl)-2,3-dioxo-1-piperazinecarboxamido]-2-(2-thienyl)acetamido}-2-oxoazetidine-4-carboxylic acid methyl ester (Reference Example 39C) in 2 ml of N,N-dimethylformamide is added 196 mg of a pyridine-sulfuric anhydride complex, and the mixture is stirred at room temperature. On the third and fourth day, 98 mg portion each of a pyridine-sulfuric anhydride complex is supplemented to the reaction mixture, which is stirred for 4 days in total. To the reaction mixture is added 20 ml of ether, and the ether layer is removed by decantation. This procedure is conducted twice. To the resulting gummy substance insoluble in ether are added 15 ml of water and 15 ml of Dowex 50W (Na-form) resin, and the mixture is stirred at room temperature for 1.5 hours. The resin is removed by filtration, and the filtrate is lyophilized to give a powdery product, which is dissolved in a small volume of water. The aqueous solution is purified by a column chromatography on Amberlite XAD-II, followed by lyophilization to yield sodium trans-3-{D-2-[4-(n-octyl)-2,3-dioxo-1-piperazinecarboxamido]-2-(2-thienyl)acetamido}-4-methoxycarbonyl-2-oxoazetidine-1-sulfonate (β-form).

IR $\nu_{max}^{KBr}$ cm$^{-1}$: 3420, 2930, 1780, 1720, 1680, 1515, 1255, 1050.

NMR(d$_6$-DMSO, ppm): 3.68(3H, s, COOCH$_3$), 3.98(1H, d, J=3 Hz, C$_4$—H), 4.70(1H, d.d, J=3,9 Hz, C$_3$—H),

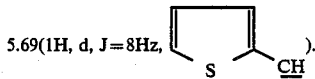
5.69(1H, d, J=8Hz,

In the same manner as above, there was obtained the corresponding α-form.

IR $\nu_{max}^{KBr}$ cm$^{-1}$: 3450, 2925, 1780, 1710, 1680, 1510, 1470, 1365, 1260, 1050.

NMR(d$_6$-DMSO, ppm): 3.66(3H, s, COOCH$_3$), 4.02(1H, d, J=3 Hz, C$_4$—H), 4.72(1H, d.d, J=3,9 Hz, C$_3$—H),

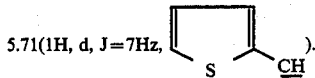
5.71(1H, d, J=7Hz,

EXAMPLE 31C

To a solution of 625 mg of cis-4-acetamidomethyl-3-[2-(2-chloroacetamido-4-thiazolyl)-2-methoxyiminoacetamido]-2-oxoazetidine (syn-isomer) in 6 ml of N,N-dimethylformamide is added 477 mg of a pyridine-sulfuric anhydride complex, and the mixture is stirred at 27°–28° C. for 28 hours. To the reaction mixture is added 90 ml of ether, and the ether layer is removed by decantation. This procedure is conducted twice. The remaining syrupy substance is dissolved in 90 ml of water. To the solution is added 70 ml of Dowex 50W (Na-form) resin, and the mixture is stirred at room temperature for 3 hours. The resin is removed by filtration, and the filtrate is concentrated under reduced pressure, and the concentrate is purified by column chromatography on Amberlite XAD-II, followed by lyophilization to give sodium cis-4-acetamidomethyl-3-[2-(2-chloroacetamido-4-thiazolyl)-2-methoxyiminoacetamido]-2-oxoazetidine-1-sulfonate (syn-isomer).

IR $\nu_{max}^{KBr}$ cm$^{-1}$: 3340, 1770, 1660, 1650, 1275, 1050.

NMR(d$_6$-DMSO, ppm): 1.84(3H, s, COCH$_3$), 3.1–3.4(2H, m, CH$_2$NH), 3.84(3H, s, NOCH$_3$), 3.9–4.2 (1H, m, C$_4$—H), 4.40(2H, s, ClCH$_2$), 5.19 (1H, d.d, J=5,9 Hz, C$_3$—H), 7.51(1H, s, 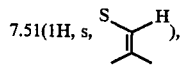), 9.40(1H, d, J=9 Hz, C₃—NH), 12.65(1H, br. s, ClCH₂CONH).

| Elemental analysis: C₁₄H₁₆ClN₆NaO₈S₂·2¼H₂O | | | |
|---|---|---|---|
| | C (%) | H (%) | N (%) |
| Calcd. | 29.82 | 3.75 | 14.90 |
| Found | 29.83 | 3.69 | 15.01 |

EXAMPLE 32C

In the same manner as Example 11C, there was obtained sodium cis-4-acetamidomethyl-3-[2-(2-amino-4-thiazolyl)-2-methoxyiminoacetamido]-2-oxoazetidine-1-sulfonate (syn-isomer).

IR $\nu_{max}^{KBr}$ cm⁻¹: 3400, 1765, 1660, 1540, 1280, 1250, 1050.

NMR(d₆-DMSO, ppm): 1.77(3H, s, COCH₃), 3.20–3.60(2H, m, CH₂NH), 3.86(3H, s, NOCH₃), 3.8–4.1(1H, m, C₄—H), 5.12(1H, d.d, J=5,9 Hz, C₃—H), 6.81

(1H, s, 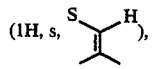), 7.15(2H, br.s, NH₂), 9.33(1H, d, J=9 Hz, C₃—NH).

| Elemental analysis: C₁₂H₁₅N₆NaO₇S₂·2H₂O | | | |
|---|---|---|---|
| | C (%) | H (%) | N (%) |
| Calcd. | 30.13 | 4.00 | 17.56 |
| Found | 30.43 | 4.12 | 17.34 |

EXAMPLE 33C

In the same manner as Example 31C, there was obtained sodium cis-4-benzamidomethyl-3-[2-(2-chloroacetamido-4-thiazolyl)-2-methoxyiminoacetamido]-2-oxoazetidine-1-sulfonate (syn-isomer).

IR $\nu_{max}^{KBr}$ cm⁻¹: 1770, 1645, 1550, 1280, 1050.

NMR(d₆-DMSO, ppm): 3.3–3.6(2H, m, CH₂NH), 3.92(3H, s, NOCH₃), 4.0–4.3(1H, m, C₄—H), 4.45(2H, s, ClCH₂), 5.28(1H, d.d, J=5,9 Hz, C₃—H), 7.54(1H, s, 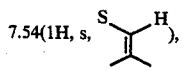), 7.4–7.9(5H, m, Ph-), 9.49 (1H, d, J=9 Hz, C₃—NH).

| Elemental analysis: C₁₉H₁₈ClN₆NaO₈S₂·2H₂O | | | |
|---|---|---|---|
| | C (%) | N (%) | H (%) |
| Calcd. | 36.99 | 3.59 | 13.62 |
| Found | 36.94 | 3.49 | 13.29 |

EXAMPLE 34C

In the same manner as Example 11C, there was obtained sodium cis-3-[2-(2-amino-4-thiazolyl)-2-methoxyiminoacetamido]-4-benzamidomethyl-2-oxoazetidine-1-sulfonate (syn-isomer).

IR $\nu_{max}^{KBr}$ cm⁻¹: 1765, 1645, 1280, 1050.

NMR(d₆-DMSO, ppm): 3.3–3.7(2H, m, CH₂NH), 3.86(3H, s, NOCH₃), 3.9–4.3(1H, m, C₄—H), 5.23(1H, d.d, J=5,9 Hz, C₃—H), 6.82(1H, s, 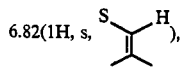), 7.17 (2H, br.s, NH₂), 7.4–7.9(5H, m, Ph-), 9.36 (1H, d, J=9 Hz, C₃—NH).

| Elemental analysis: C₁₇H₁₇N₆NaO₇S₂·2H₂O | | | |
|---|---|---|---|
| | C (%) | H (%) | N (%) |
| Calcd. | 37.78 | 3.92 | 15.55 |
| Found | 37.51 | 3.73 | 15.67 |

EXAMPLE 35C

In the same manner as Example 31C, there was obtained sodium cis-3-[2-(2-chloroazetamido-4-thiazolyl)-(Z)-2-methoxyiminoacetamido]-4-[2-(2-chloroacetamido-4-thiazolyl-(Z)-2-methoxyiminoacetoxymethyl]-2-oxoazetidine-1sulfonate.

IR $\nu_{max}^{KBr}$ cm⁻¹: 1770, 1765, 1670, 1560, 1275, 1050.

NMR(d₆-DMSO, ppm): 3.83, 3.89(2×3H, 2×s, 2×NOCH₃), 4.31(4H, s, 2×ClCH₂), $$4.1–4.4(2H, m, CH_2O\overset{O}{\overset{\|}{C}}),$$

4.80–5.10(1H, m, C₄—H), 5.31(1H, d.d, J=5,9 Hz, C₃—H), 7.19, 7.53(2 × 1H, 2 × s, 2 × 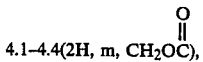), 9.34(1H, s, J=9 Hz, C₃—NH).

| Elemental analysis: C₂₀H₁₉Cl₂N₈NaO₁₁S₃·4H₂O | | | |
|---|---|---|---|
| | C (%) | H (%) | N (%) |
| Calcd. | 29.67 | 3.36 | 13.84 |
| Found | 29.53 | 3.11 | 13.83 |

EXAMPLE 36C

To a solution of 221 mg of sodium cis-3-[2-(2-chloroacetamido-4-thiazolyl)-(Z)-2-methoxyiminoacetamido]-4-[2-(2-chloroacetamido-4-thiazolyl)-(Z)-2-methoxyiminoacetoxymethyl]-2-oxoazetidine-1-sulfonate in 10 ml of water is added under ice-cooling 85 mg of sodium monomethyldithiocarbamate with stirring. The mixture is stirred at room temperature for one hour, followed by addition of 40 mg of sodium monomethyldithiocarbamate. The mixture is stirred at room temperature for further one hour. The reaction mixture is washed with ethyl acetate and ether in this order, followed by concentration under reduced pressure. The concentrate is purified by a column chromatography on Amberlite XAD-II, followed by lyophilization to give sodium cis-3-[2-(2-amino-4-thiazolyl)-(Z)-2-methoxyiminoacetamido]-4-[2-(2- amino-4-thiazolyl)-(Z)-2-methoxyiminoacetoxymethyl]-2-oxoazetidine-1-sulfonate.

IR $\nu_{max}^{KBr}$cm$^{-1}$: 1760, 1670, 1540, 1275, 1050.

NMR(d$_6$-DMSO, ppm): 3.80, 3.86(2×3H, 2×s, 2×NOCH$_3$),

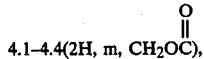
4.1–4.4(2H, m, CH$_2$OC), 4.8–5.05(1H, m, C$_4$—H), 5.25(1H, d.d, J=5,9 Hz, C$_3$—H), 6.63,

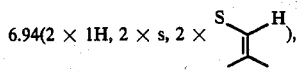
6.94(2 × 1H, 2 × s, 2 ×

7.10(2H, br. s, NH$_2$), 9.22(1H, d, J=9 Hz, C$_3$—NH).

| Elemental analysis: C$_{16}$H$_{17}$N$_8$NaO$_9$S$_3$.3H$_2$O | | | |
|---|---|---|---|
| | C (%) | H (%) | N (%) |
| Calcd. | 30.09 | 3.63 | 17.55 |
| Found | 30.18 | 3.51 | 17.68 |

EXAMPLE 37C

In the same manner as Example 30C, there was obtained sodium cis-3-[2-(2-chloroacetmaido-4-thiazolyl)-2-methoxyiminoacetamido]-4-(2-thienylacetoxymethyl)-2-oxoazetidine-1-sulfonate (syn-isomer).

IR $\nu_{max}^{KBr}$cm$^{-1}$: 3410, 1765, 1670, 1550, 1270, 1050.

NMR(d$_6$-DMSO, ppm):

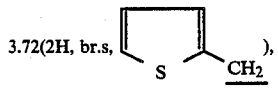
3.72(2H, br.s, 3.95–4.52 (1H, m, C$_4$—H), 4.30(2H, s, ClCH$_2$), 5.25(1H, d.d, J=6,9 Hz, C$_3$—H),

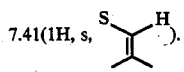
7.41(1H, s,

EXAMPLE 38C

In the same manner as Example 31C, there was obtained sodium cis-3-[2-(2-amino-2-4-thiazolyl)-2-methoxyiminoacetamido]-4-(2-thienylacetoxymethyl)-2-oxoazetidine-1sulfonate (syn-isomer).

IR $\nu_{max}^{KBr}$cm$^{-1}$: 3400, 1770, 1740, 1670, 1615, 1535, 1270, 1250, 1050.

NMR(d$_6$-DMSO, ppm): 3.75(3H, s, NOCH$_3$), 5.20(1H, d.d, J=6,9 Hz, C$_3$—H),

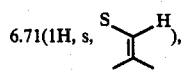
6.71(1H, s, 7.14 (2H, br.s, NH$_2$), 9.22(1H, d, C$_3$—NH).

| Elemental analysis: C$_{16}$H$_{16}$N$_5$NaO$_8$S$_3$.2H$_2$O | | | |
|---|---|---|---|
| | C (%) | H (%) | N (%) |
| Calcd. | 34.22 | 3.59 | 12.47 |
| Found | 34.42 | 3.23 | 12.30 |

EXAMPLE 39C

In the same manner as Example 30C, there was obtained sodium cis-3-[2-(2-chloroacetamido-4-thiazolyl)-2-methoxyiminoacetamido]-4 -(1-methyl-1H-tetrazol-5-yl-thiomethyl)-2-oxoazetidine-1-sulfonate (syn-isomer).

IR $\nu_{max}^{KBr}$cm$^{-1}$: 3420, 1765, 1660, 1560, 1050.

NMR(d$_6$-DMSO, ppm): 3.91(3H, s, NCH$_3$), 3.94(3H, s, OCH$_3$), 4,34(2H, s, ClCH$_2$), 5.29(1H, d.d, J=6,9 Hz, C$_3$—H),

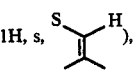
7.48(1H, s, 9.46(1H, d, J=9 Hz, C$_3$—NH).

EXAMPLE 40C

In the same manner as Example 11C, there was obtained sodium cis-3-[2-(2-amino-4-thiazolyl)-2-methoxyiminoacetamido]-4-(1-methyl-1H-tetrazol-5-ylthiomethyl)-2-oxoazetidine-1-sulfonate (syn-isomer).

IR $\nu_{max}^{KBr}$cm$^{-1}$: 3410, 1770, 1660, 1610, 1535, 1280, 1050.

NMR(d$_6$-DMSO, ppm): 3.88(3H, s, NCH$_3$), 3.92(3H, s, OCH$_3$), 5.22(1H, d.d, J=6,9 Hz, C$_3$—H),

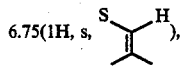
6.75(1H, s, 7.13(2H, br.s, NH$_2$), 9.31(1H, d, J=9 Hz, C$_3$—NH).

| Elemental analysis: C$_{12}$H$_{14}$N$_9$NaO$_6$S$_3$.2½H$_2$O | | | |
|---|---|---|---|
| | C (%) | H (%) | N (%) |
| Calcd. | 26.46 | 3.52 | 23.15 |
| Found | 26.46 | 3.59 | 22.70 |

EXAMPLE 41C

In the same manner as Example 10C, there was obtained sodium cis-3-[2-(2-chloroacetamido-4-thiazolyl)-2-methoxyiminoacetamido]-4-methylthiomethyl-2-oxoazetidine-1sulfonate (syn-isomer).

IR $\nu_{max}^{KBr}$cm$^{-1}$: 3420, 1760, 1660, 1550, 1270, 1240, 1050.

NMR(d$_6$-DMSO, ppm): 2.08(3H, s, SCH$_3$), 2.68–3.06(2H, m, CH$_2$S), 3.89(3H, s, NOCH$_3$), 4.32(2H, s, ClCH$_2$),

7.42(1H, s,

EXAMPLE 42C

In the same manner as Example 11C, there was obtained sodium cis-3-[2-(2-amino-4-thiazolyl)-2-methoxyiminoacetamido]-4-methylthiomethyl-2-oxoazetidine-1-sulfonate (syn-isomer).

IR $\nu_{max}^{KBr}$cm$^{-1}$: 3400, 1760, 1660, 1605, 1535, 1380, 1245, 1050.

NMR(d$_6$-DMSO, ppm): 2.08(3H, s, SCH$_3$), 2.70–3.12(2H, m, CH$_2$S), 3.71(3H, s, NOCH$_3$), 6.74(1H, s, 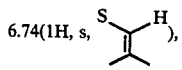), 7.14(2H, br.s, NH$_2$).

EXAMPLE 43C

In the same manner as Example 10C, there was obtained sodium cis-3-[2-(2-chloroacetamido-4-thiazolyl)-2-methoxyiminoacetamido]-4-methyl-2-oxoazetidine-1-sulfonate (syn-isomer).

IR $\nu_{max}^{KBr}$cm$^{-1}$: 3420, 1760, 1670, 1560, 1275, 1055.

NMR(d$_6$-DMSO, ppm): 1.25(3H, d, J=6 Hz, C$_4$—CH$_3$), 3.98(3H, s, NOCH$_3$), 4.32(2H, s, ClCH$_2$), 5.10(1H, d.d, J=6,9 Hz, C$_3$—H), 7.38(1H, s, 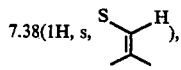), 9.33 (1H, d, J=9 Hz, C$_3$—NH).

EXAMPLE 44C

In the same manner as Example 11C, there was obtained sodium cis-3-[2-(2-amino-4-thiazolyl)-2-methoxyiminoacetamido]-4-methyl-2-oxoazetidine-1-sulfonate (syn-isomer).

IR $\nu_{max}^{KBr}$cm$^{-1}$: 3410, 1760, 1660, 1535, 1245, 1060.

NMR(d$_6$-DMSO, ppm): 1.22(3H, d, C$_4$—CH$_3$), 3.82(3H, s, NOCH$_3$), 5.08(1H, d.d, J=6,9 Hz, C$_3$—H), 6.72(1H, s, 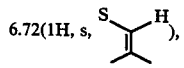), 7.16(2H, br.s, NH$_2$), 9.24 (1H, d, J=9 Hz, C$_3$—NH).

EXAMPLE 45C

To a solution of 500 mg of cis-3-[2-(2-chloroacetamido-4-thiazolyl)-2-methoxyiminoacetamido]-4-(4-chlorophenyl)-2-oxoazetidine (syn-isomer) in 12 ml of N,N-dimethylformamide is added 353 mg of a pyridine-sulfuric anhydride complex, and the mixture is left standing at room temperature for 18 days. To the reaction mixture is added 150 ml of ether, and the supernatant ether layer is discarded. To the remainder are added 30 ml of water, 30 ml of ethyl acetate and 10 ml of tetrahydrofuran, and the mixture is shaken. The organic layer is reextracted with 30 ml of water. Water layers are combined, to which is added 20 ml of Dowex 50W (Na-form) resin, followed by stirring at room temperature for 30 minutes. The resin is removed by filtration, and the filtrate is concentrated under reduced pressure on a bath whose temperature is not higher than 30° C. The concentrate is purified by column chromatography on Amberlite XAD-II, followed by lyophilization to give sodium cis-3-[2-(2-chloroacetamido-4-thiazolyl)-2-methoxyiminoacetamido]-4-(4-chlorophenyl)-2-oxoazetidine-1-sulfonate (syn-isomer).

IR $\nu_{max}^{KBr}$cm$^{-1}$: 3450, 1760, 1665, 1550, 1270, 1045.

NMR(d$_6$-DMSO, ppm): 3.73(3H, s, NOCH$_3$), 4.30(2H, s, ClCH$_2$), 5.11(1H, d, J=5 Hz, C$_4$—H), 5.32 (1H, d.d, J=5,8 Hz, C$_3$—H), 5.75(1H, s, 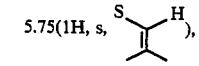), 9,23(1H, d, J=8 Hz, C$_3$—NH).

EXAMPLE 46C

In the same manner as Example 11C, there is obtained sodium cis-3-[2-(2-amino-4-thiazolyl)-2-methoxyiminoacetamido]-4-(4-chlorophenyl)-2-oxoazetidine-1-sulfonate (syn-isomer).

IR $\nu_{max}^{KBr}$cm$^{-1}$: 3420, 1758, 1660, 1525, 1270, 1050.

NMR(d$_6$-DMSO+D$_2$O, ppm): 3.88(3H, s, NOCH$_3$), 5.11(1H, s, 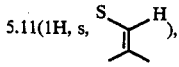), 5.33(1H, d, J=5 Hz, C$_4$—H), 5.45 (1H, d, J=5 Hz, C$_3$—H).

| Elemental analysis: C$_{15}$H$_{13}$ClN$_5$NaO$_6$S$_2$.3H$_2$O | | | |
|---|---|---|---|
| | C (%) | H (%) | N (%) |
| Calcd. | 33.61 | 3.57 | 13.07 |
| Found | 33.57 | 3.28 | 12.77 |

EXAMPLE 47C

In the same manner as Example 10C, there was obtained sodium cis-3-[2-(2-chloroacetamido-4-thiazolyl)-2-methoxyiminoacetamido]-4-(N,N-dimethylcarbamoyl)-2-oxoazetidine-1-sulfonate (syn-isomer).

IR $\nu_{max}^{KBr}$cm$^{-1}$: 1770, 1660, 1550.

NMR(d$_6$-DMSO, ppm): 2.8, 3.0[2×3H, 2×s, N(CH$_3$)$_2$], 3.86(3H, s, NOCH$_3$), 4.2(2H, s, ClCH$_2$), 5.0(1H, d, J=6 Hz, C$_4$—H), 5.53(1H, d.d, J=6,9 Hz, C$_3$—H).

EXAMPLE 48C

In the same manner as Example 11C, there was obtained sodium cis-3-[2-(2-amino-4-thiazolyl)-2-methoxyiminoacetamido]-4-(N,N-dimethylcarbamoyl)-2-oxoazetidine-1-sulfonate (syn-isomer).

IR $\nu_{max}^{KBr}$cm$^{-1}$: 3350, 1780, 1660.

NMR(d$_6$-DMSO, ppm): 2.8, 3.0[2×3H, 2×s, N(CH$_3$)$_2$], 3.83(3H, s, NOCH$_3$), 4.93(1H, d, J=6 Hz, C$_4$—H), 5.3(1H, d.d, J=6,9 Hz, C$_3$—H), 6.6(1H, s, 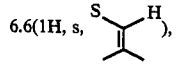), 8.96(1H, d, J=9 Hz, C$_3$—NH).

EXAMPLE 49C

To a solution of 278 mg of cis-3-benzyloxycarboxamido-2-oxoazetidine-4-carboxylic acid methyl ester in 2.8 ml of N,N-dimethylformamide is added 320 mg of a pyridine-sulfuric anhydride complex, and the mixture is stirred at room temperature for 2 days. To the reaction mixture is further added 120 mg of a pyridine-sulfuric anhydride complex, followed by stirring for one more day. To the reaction mixture is added 50 ml of ether, and the resulting powdery precipitates are collected by filtration and washed with ether. The powdery product is dissolved in 5 ml of water, and the solution is passed through a column of Dowex 50W (Na-form) resin. The lyophilisate of the effluent is dissolved in a small volume of water, followed by purification by column chromatography on Amberlite XAD-II. Lyophilization of thus-purified product gives sodium cis-3-benzyloxycarboxamido-4-methoxycarbonyl-2-oxoazetidine-1-sulfonate.

IR $\nu_{max}^{Nujol}$cm$^{-1}$: 3300, 1750,

NMR(d$_6$-DMSO, ppm): 3.56(3H, s, CH$_3$), 4.43(1H, d, J=5 Hz, C$_4$—H), 7.36(5H, s, Ph-), 8.13(1H, d, J=9 Hz, NH).

| Elemental analysis: C$_{13}$H$_{13}$N$_2$NaO$_8$S.H$_2$O | | | |
|---|---|---|---|
| | C (%) | H (%) | N (%) |
| Calcd. | 39.19 | 3.79 | 7.03 |
| Found | 39.04 | 3.99 | 7.26 |

EXAMPLE 50C

To a solution of 190 mg of sodium cis-3-benzyloxycarboxamido-4-methoxycarbonyl-2-oxoazetidine-1-sulfonate (monohydrate) in 10 ml of water is added 190 mg of 10% palladium-on-carbon, followed by catalytic reduction for one hour at ambient temperature under normal pressure. The reaction mixture is allowed to pass through a celite layer to filtrate the catalyst. The filtrate is lyophilized to give sodium cis-3-amino-4-methoxycarbonyl-2-oxoazetidine-1-sulfonate.

IR $\nu_{max}^{KBr}$cm$^{-1}$: 3450, 1770, 1740, 1060.

NMR(d$_6$-DMSO, ppm): 2.7–3.5(2H, br.s, NH$_2$), 3.67(3H, s, CH$_3$), 4.33(2H, s, C$_3$—H & C$_4$—H).

| Elemental analysis: C$_5$H$_7$N$_2$NaO$_6$S.1½H$_2$O | | | |
|---|---|---|---|
| | C (%) | H (%) | N (%) |
| Calcd. | 21.98 | 3.68 | 10.25 |
| Found | 22.10 | 3.69 | 10.48 |

EXAMPLE 51C

In the same manner as Example 30C, there was obtained sodium cis-3-(2-thienylacetamido)-4-methoxycarbonyl-2-oxoazetidine-1-sulfonate.

IR $\nu_{max}^{KBr}$cm$^{-1}$: 3350, 1770, 1680, 1540, 1440, 1260, 1060.

NMR(d$_6$-DMSO (ppm): 3.53(3H, s, CH$_3$), 3.68(2H, s, CH$_2$), 4.43(1H, d, J=6 Hz, C$_4$—H), 5.26(1H, d.d, J=6, 9 Hz, C$_3$—H), 8.85(1H, d, J=9 Hz, NH).

EXAMPLE 52C

To a solution of 380 mg of cis-3-(1H-tetrazol-1-ylacetamido)-2-oxoazetidine-4-carboxylic acid methyl ester in 3 ml of N,N-dimethylacetamido is added 807 mg of a pyridine-sulfuric anhydride complex. The mixture is stirred at 70° C. for 4 hours, followed by addition of 50 ml of ether. The ether layer is discarded. To the remainder is added 50 ml of ether again. The similar process is conducted twice. Insolubles are dissolved in 5 ml of water, and the aqueous solution is allowed to pass through a column packed with 40 ml of Amberlite IR-120 (SO$_3$Na-form) resin, followed by purification by column chromatography on Amberlite XAD-II. The desired fractions are lyophilized, followed by purification by column chromatography on Sephadex LH-20, which is again lyophilized to give sodium cis-3-(1H-tetrazol-1-yl-acetamido)-4-methoxycarbonyl-2-oxoazetidine-1-sulfonate.

IR $\nu_{max}^{KBr}$cm$^{-1}$: 3400, 1770, 1700, 1630, 1550, 1440, 1280, 1260, 1180, 1100, 1060.

NMR(d$_6$-DMSO, ppm): 3.68(3H, s, CH$_3$), 4.48(1H, d, J=6 Hz, C$_4$—H), 5.26(2H, s, CH$_2$), 5.29(1H, d.d, J=6, 9 Hz, C$_3$—H), 9.30(1H, s, 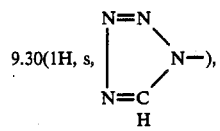), 9.31(1H, d, J=9 Hz, NH).

| Elemental analysis: C$_8$H$_9$N$_6$NaO$_7$S.1½H$_2$O | | | |
|---|---|---|---|
| | C (%) | H (%) | N (%) |
| Calcd. | 26.01 | 3.28 | 22.76 |
| Found | 25.89 | 3.25 | 22.72 |

EXAMPLE 53C

In the same manner as Example 52C, there was obtained sodium cis-3-(1-ethyl-1,4-dihydro-7-methyl-4-oxo-1,8-naphthylidin-3-ylcarbonylamino)-4-methoxycarbonyl-2-oxoazetidine-1-sulfonate, provided that the reaction time was shortened to one hour.

IR $\nu_{max}^{KBr}$cm$^{-1}$: 3450, 1770, 1660, 1615, 1540, 1500, 1450, 1370, 1260, 1060.

NMR(d$_6$-DMSO, ppm): 1.40(3H, t, J=7 Hz, CH$_2$CH$_3$), 2.63(3H, s, 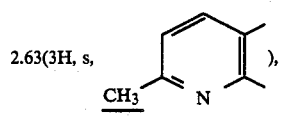), 3.66(3H, s, COOCH$_3$), 4.57(1H, d, J=6 Hz, C$_4$—H), 4.58(2H, q, J=7 Hz, CH$_2$CH$_3$), 5.68(1H, d.d, J=6, 9 Hz, C$_3$—H), 7.49, 8.58(2 × 1H, 2 × d, J=8Hz, 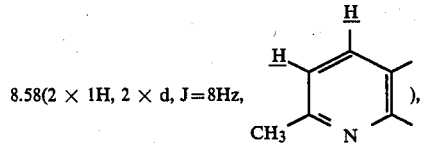), 8.97(1H, s, 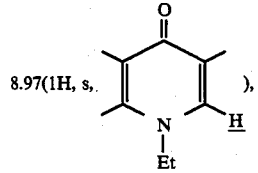), 10.45(1H, d, J=9 Hz, NH).

| Elemental analysis: C$_{17}$H$_{17}$N$_4$NaO$_8$S.H$_2$O | | | |
|---|---|---|---|
| | C (%) | H (%) | N (%) |
| Calcd. | 42.68 | 4.00 | 11.71 |

-continued

Elemental analysis: $C_{17}H_{17}N_4NaO_8S.H_2O$

|  | C (%) | H (%) | N (%) |
| --- | --- | --- | --- |
| Found | 42.62 | 4.28 | 11.57 |

EXAMPLE 54C

To a solution of 409 mg of cis-3-(2-chloroacetyloxy-2-phenylacetamido)-2-oxoazetidine-4-carboxylic acid methyl ester in 2 ml of N,N-dimethylacetamide is added 549 mg of a pyridine-sulfuric anhydride complex, and the mixture is stirred at 70° C. for one hour. To the mixture is added 50 ml of ether, followed by stirring and then discarding the ether layer. This process is conducted twice more. To the remaining insolubles is added 15 ml of 1M-aqueous solution of sodium hydrogen carbonate to make a solution. The solution is stirred at room temperature for one hour, and the reaction solution is allowed to pass through a column of 40 ml of Amberlite IR-120 ($SO_3Na$-form) resin. The desired fractions are twice purified by column chromatography on Amberlite XAD-II, and followed by further purification by column chromatography on Sephadex LH-20. Thus purified product is lyophilized to give sodium cis-3-(2-hydroxy-2-phenylacetamido)-4-methoxycarbonyl-2-oxoazetidine-1-sulfonate as a mixture of diastereoisomers.

IR $\nu_{max}^{KBr}$cm$^{-1}$: 3400, 1770, 1680, 1520, 1445, 1380, 1260, 1100, 1060.

NMR($d_6$-DMSO, ppm): 3.44, 3.56(3H, 2×s, COO$CH_3$), 4.43 4.44(1H, 2×d, J=6 Hz, $C_4$—H), 4.98, 5.01(1H, 2×s, PhCH), 5.31(1H, d.d, J=6, 9 Hz, $C_3$—H), 7.32(5H, s, Ph-), 8.00, 8.33(1H, 2×d, NH).

Elemental analysis: $C_{13}H_{13}N_2NaO_8S.\frac{1}{2}H_2O$

|  | C (%) | H (%) | N (%) |
| --- | --- | --- | --- |
| Calcd. | 40.11 | 3.62 | 7.02 |
| Found | 39.93 | 3.94 | 7.19 |

EXAMPLE 55C

To a solution of 109 mg of cis-3-(D-2-sulfo-2-phenylacetamido)-2-oxoazetidine-4-carboxylic acid methyl ester. sodium salt in 1.5 ml of N,N-dimethylformamide is added under ice-cooling 1.2 ml of a sulfuric anhydride-N,N-dimethylformamide complex (1.2M) with stirring, and the mixture is left standing at 5° C. for 24 hours. To the reaction mixture is added 0.5 ml of pyridine, and the mixture is stirred for 5 minutes, followed by addition of 30 ml of ether. The ether layer is discarded, and 30 ml of ether is again added thereto, followed by discarding the ether layer. The remaining insolubles are dissolved in 2 ml of 1M-aqueous solution of sodium hydrogen carbonate, and the solition is allowed to pass through a column of Amberlite IR-120 ($SO_3Na$-form) resin, and then purified by column chromatography on Amberlite XAD-II and Sephadex LH-20, followed by lyophilization to give cis-3-[D-2-sulfo-2-phenylacetamido]-4-methoxycarbonyl-1-sulfo-2-oxoazetidine.disodium salt as a mixture of diastereoisomers.

IR $\nu_{max}^{KBr}$cm$^{-1}$: 3450, 1770, 1680, 1535, 1440, 1290, 1250, 1100, 1055.

NMR($d_6$-DMSO, ppm): 3.42, 3.66(3H, 2×s, COO$CH_3$), 4.39, 4.42(1H, 2×d, J=6 Hz, $C_4$—H), 4.50, 4.54(1H, 2×s, ph-CH), 5.2-5.5(1H, m, $C_3$—H), 7.1-7.6(5H, m, Ph-), 8.87, 8.96(1H, 2×d, J=9 Hz, NH).

Elemental analysis: $C_{13}H_{12}N_2Na_2O_{10}S_2.4\frac{1}{2}H_2O$

|  | C (%) | H (%) | N (%) |
| --- | --- | --- | --- |
| Calcd. | 28.52 | 3.87 | 5.12 |
| Found | 28.64 | 3.61 | 5.00 |

EXAMPLE 56C

In the same manner as Example 53C, there was obtained sodium cis-3-(2-benzyloxycarbonyl-2-phenylacetamido)-4-methoxycarbonyl-2-oxoazetidine-1-sulfonate as a mixture of diastereoisomers.

IR $\nu_{max}^{KBr}$cm$^{-1}$: 3400, 1780, 1750, 1535, 1450, 1260, 1060.

NMR($d_6$-DMSO, ppm): 3.02, 3.42(3H, 2×s, COO$CH_3$), 4.36, 4.45(1H, 2×d, J=6 Hz, $C_4$—H), 4.86, 4.89(1H, 2×s, Ph-CH), 5.12, 5.15(2H, 2×s, Ph$CH_2$), 5.1-5.4(1H, m, $C_3$—H), 7.34(10H, s, 2×Ph-), 9.11(1H, d, J=9 Hz, NH).

Elemental analysis: $C_{21}H_{19}N_2NaO_9S.H_2O$

|  | C (%) | H (%) | N (%) |
| --- | --- | --- | --- |
| Calcd. | 48.84 | 4.10 | 5.42 |
| Found | 48.60 | 4.25 | 5.63 |

To 6 ml of 80% ethanol are added 106 mg of sodium cis-3-(2-benzyloxycarbonyl-2-phenylacetamido)-4-methoxycarbonyl-2-oxoazetidine-1-sulfonate, 106 mg of 5% palladium-on-carbon and 16.8 mg of sodium hydrogen carbonate, and the mixture is vigorously stirred under hydrogen atmosphere for 3.5 hours at ambient temperature under atmosphere pressure. The reaction mixture is subjected to filtration, and the filtrate is concentrated under reduced pressure. The concentrate is purified by column chromatography on Amberlite XAD-II, followed by lyophilization to give cis-3-(2-carboxy-2-phenylacetamido)-4-methoxycarbonyl-1-sulfo-2-oxoazetidine.disodium salt as a mixture of diastereomers.

IR $\nu_{max}^{KBr}$cm$^{-1}$: 3420, 1770, 1670, 1620, 1530, 1380, 1290, 1250, 1060.

NMR($d_6$-DMSO, ppm): 3.45, 3.46(3H, 2×s, COO$CH_3$), 4.40, 4.48(1H, 2×d, J=6 Hz, $C_4$—H), 5.1-5.4(1H, m, $C_3$—H), 5.59, 5.62(1H, 2×s, Ph-CH), 7.23(5H, s, Ph-), 8.83(1H, d, J=9 Hz, NH).

Elemental analysis: $C_{14}H_{12}N_2Na_2O_9S.3\frac{1}{2}H_2O$

|  | C (%) | H (%) | N (%) |
| --- | --- | --- | --- |
| Calcd. | 34.08 | 3.88 | 5.68 |
| Found | 34.40 | 4.13 | 5.97 |

EXAMPLE 58C

To a solution of 360 mg of cis-3-cyanomethylcarboxamido-2-oxoazetidine-4-carboxylic acid methyl ester in 3 ml of N,N-dimethylformamide is added 480 mg of a pyridinesulfuric anhydride complex, and the mixture is stirred, followed by standing at room temperature for 6 days. To the reaction mixture is added 20 ml of ether, followed by stirring and the ether layer is discarded. To the remainder is added again 10 ml of ether, followed by stirring and the ether layer is discarded. The remaining oily product is dissolved in 10 ml of water. To the aqueous solution is added 10 ml of Dowex 50W (Na-form) resin, and the mixture is stirred at room temperature for 30 minutes. The resin is removed by filtration, and the filtrate is washed four times with 10 ml each portion of water. The filtrate and washings are combined, and lyophilized. Thus lyophilized product is dissolved in a small volume of water, and purified by column chromatography on Amberlite XAD-II, then on Sephadex LH-20, followed by lyophilization to give sodium cis-3-cyanomethylcarboxamido-4-methoxycarbonyl-2-oxoazetidine-1-sulfonate.

IR $\nu_{max}^{KBr}$cm$^{-1}$: 2250, 1780, 1740, 1675, 1570, 1048.

NMR(d$_6$-DMSO, ppm): 3.64(2H, s, CH$_2$), 3.67(3H, s, CH$_3$), 4.48(1H, d, J=6 Hz, C$_4$—H), 5.27(1H, d.d, J=6, 9 Hz, C$_3$—H), 9.12(1H, d, J=9 Hz, NH).

EXAMPLE 59C

To a solution of 341 mg of cis-3-[2-(2-chloroacetamido-4-thiazolyl)-2-methoxyiminoacetamido]-2-oxoazetidine-4-carboxylic acid p-nitrobenzyl ester in 3 ml of N,N-dimethylformamide is added 258 mg of a pyridine-sulfuric anhydride complex, and the mixture is stirred at room temperature for 63 hours. To the mixture is further added 103 mg of a pyridine-sulfuric anhydride complex, followed by stirring for additional 38 hours. To the reaction mixture is added 45 ml of ether, and the ether layer is removed by decantation. This process is conducted twice. The remaining syrupy substance is suspended in 45 ml of water. To the suspension is added 20 ml of Dowex 50W (Na-form) resin, and the mixture is stirred at room temperature for 1.5 hours. The resin is removed by filtration, and the filtrate is concentrated under reduced pressure. The concentrate is purified by column chromatography on Amberlite XAD-II, followed by lyophilization to give colorless powder. The powder is dissolved in 16 ml of water followed by addition of 68 mg of sodium monomethyl dithiocarbamate under ice-cooling with stirring. The mixture is stirred for further one hour at room temperature, followed by supplemental addition of 68 mg of sodium monomethyl dithiocarbamate. The mixture is stirred for further one hour, followed by washing with ethyl acetate. The aqueous layer is purified by column chromatography on Amberlite XAD-II, followed by lyophilization to give sodium cis-3-[2-(2-amino-4-thiazolyl)-2-methoxyiminoacetamido]-4-(4-nitrobenzyloxycarbonyl)-2-oxoazetidine-1-sulfonate (syn-isomer).

IR $\nu_{max}^{KBr}$cm$^{-1}$: 1770, 1750, 1670, 1610, 1280, 1050.
NMR(d$_6$-DMSO, ppm): 3.81(3H, s, NOCH$_3$), 4.60(1H, d, 6 Hz, C$_4$—H), 5.26(2H, ABq, J=14 Hz, OCH$_2$Ar), 5.44(1H, d.d, J=6, 9 Hz, C$_3$—H),

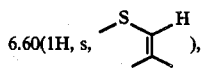

7.13(2H, br.s, NH$_2$), 7.73(2H, d, J=9 Hz, ArH), 8.17(2H, d, J=9 Hz, ArH), 9.48(1H, d, J=9 Hz, C$_3$—NH).

| Elemental analysis: C$_{17}$H$_{15}$N$_6$NaO$_{10}$S$_2$.2H$_2$O | | | |
|---|---|---|---|
| | C (%) | H (%) | N (%) |
| Calcd. | 34.82 | 3.27 | 14.33 |
| Found | 34.74 | 3.26 | 14.28 |

EXAMPLE 60C

In a mixture of 10 ml of tetrahydrofuran and 10 ml of water is dissolved 155 mg of sodium cis-3-[2-(2-amino-4-thiazolyl)-2-methoxyiminoacetamido]-4-(4-nitrobenzyloxycarbonyl)-2-oxoazetidine-1-sulfonate (syn-isomer). To the solution is added 145 mg of 10% palladium-on-carbon, and the mixture is subjected to catalytic reduction at ambient temperature under normal pressure with stirring. Three hours later, 10 ml of an aqueous solution of 25 mg of sodium hydrogen carbonate is added to the reaction mixture. The catalyst is removed by filtration, and the filtrate is washed with ethyl acetate, and concentrated under reduced pressure. The concentrate is purified by column chromatography on Amberlite XAD-II, followed by lyophilization to give cis-3-[2-(2-amino-4-thiazolyl)-2-methoxyiminoacetamido]-4-carboxy-1-sulfo-2-oxoazetidine.-disodium salt (syn-isomer).

IR $\nu_{max}^{KBr}$cm$^{-1}$: 1760, 1660, 1605, 1270, 1050.

NMR(d$_6$-DMSO, ppm): 3.82(3H, s, NOCH$_3$), 4.17(1H, d, J=6 Hz, C$_4$—H), 5.12(1H, d.d, J=6, 9 Hz, C$_3$—H),

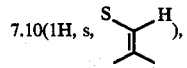

7.13(2H, br.s, NH$_2$), 8.62(1H, d, C$_3$—NH).

| Elemental analysis: C$_{10}$H$_9$N$_5$Na$_2$O$_8$S$_2$.3½H$_2$O | | | |
|---|---|---|---|
| | C (%) | H (%) | N (%) |
| Calcd. | 24.00 | 3.22 | 14.00 |
| Found | 24.00 | 3.14 | 13.86 |

EXAMPLE 61C

In 7 ml of N,N-dimethylformamide is dissolved 462 mg of methyl cis-3-[2-(2-chloroacetamido-4-thiazolyl)-2-methoxycarbonylmethyloxyiminoacetamido]-2-oxoazetidine-4-carboxylate (syn-isomer), and under cooling at −78° C., sulfuric anhydride-N,N-dimethylformamide complex solution (3 mmols) is added. The mixture is stirred at 4° C. for 18 hours, after which pyridine (3 mmols) is added and the mixture is further stirred for an hour. On addition of 100 ml of ether, insolubles are crystallized. The mother fluid is discarded and the crystals are washed twice with 30 ml portions of ether. The crystals are dissolved in 10 ml of water and after addition of 23 ml of Dowex 50W (Na-form) resin, the mixture is stirred at room temperature for 2 hours. The resin is filtered off and 300 ml of water is added to the filtrate. The resulting suspension as such is chromatographed on an Amberlite XAD-II column and after washing the column with 350 ml of water, elution is carried out with 15% ethanol. The eluate (200 ml) is concentrated under reduced pressure and lyophilized to give 420 mg of colorless powder. This powder product is rechromatographed on an Amberlite XAD-II column. The column is washed with 1 l of water and elution is carried out with 100 ml of 15% ethanol. The eluate is concentrated under reduced pressure and lyophilized to give a colorless powder of sodium cis-3-[2-(2-chloroacetamido-4-thiazolyl)-2-methoxycarbonylmethyloxyiminoacetamido]-4-methoxycarbonyl-2-oxoazetidine-1-sulfonate (syn-isomer).

IR $\nu_{max}^{KBr}$cm$^{-1}$: 1790–1730, 1680, 1550, 1055.

NMR(d$_6$-DMSO, ppm): 3.6(3H, s, COOCH$_3$), 3.7(3H, s, COOCH$_3$), 4.4(2H, s, ClCH$_2$), 4.5(1H, d, J=6 Hz, C$_4$—H), 4.68(2H, s, NOCH$_2$), 5.45(1H, d.d, J=6, 9 Hz, C$_3$—H),

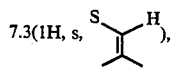 7.3(1H, s,  ), 9.37(1H, d, J=9 Hz, C$_3$—NH).

| Elemental analysis: C$_{15}$H$_{15}$ClN$_5$NaO$_{11}$S$_2$.2½H$_2$O | | | |
|---|---|---|---|
| | C (%) | H (%) | N (%) |
| Calcd. | 29.58 | 3.31 | 11.50 |
| Found | 29.49 | 3.30 | 11.56 |

EXAMPLE 62C

In the same manner as Example 11C, there was obtained sodium cis-3-[2-(2-amino-4-thiazolyl)-2-methoxycarbonylmethyloxyiminoacetamido]-4-methoxycarbonyl-2-oxoazetidine-1-sulfonate (syn-isomer).

IR $\nu_{max}^{KBr}$cm$^{-1}$: 3300, 1790–1730, 1670, 1610, 1530, 1055.

NMR(d$_6$-DMSO, ppm): 3.60(3H, s, COOCH$_3$), 3.69(3H, s, COOCH$_3$), 4.49(1H, d, J=6 Hz, C$_4$—H), 4.64(2H, s, NOCH$_2$), 5.41(1H, d.d, J=6, 9 Hz, C$_3$—H),

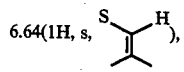 6.64(1H, s,  ), 7.18(2H, br.s, NH$_2$), 9.29(1H, d, J=9 Hz, C$_3$—NH).

| Elemental analysis: C$_{13}$H$_{14}$N$_5$NaO$_{10}$S$_2$.2H$_2$O | | | |
|---|---|---|---|
| | C (%) | H (%) | N (%) |
| Calcd. | 29.83 | 3.47 | 13.38 |
| Found | 30.14 | 3.52 | 13.48 |

EXAMPLE 63C

In 20 ml of dry N,N-dimethylformamide is dissolved 1.35 g of cis-3-[2-(2-chloroacetamido-4-thiazolyl)-2-(p-nitrobenzyloxycarbonylmethyloxyimino)acetamido]-4-methoxycarbonyl-2-oxoacetidine (syn-isomer), and under cooling at −78° C., 4.11 ml of sulfuric anhydride-N,N-dimethylformamide complex solution (1.69M) is added. The mixture is stirred at 4° C. for 72 hours, after which 0.57 ml of pyridine is added and the mixture is stirred for an additional hour. After addition of 500 ml of ether, the mixture is allowed to stand in a refrigerator overnight. The upper ether layer is discarded and the residue is washed twice with 50 ml portions of ether. On addition of 50 ml of water, the syrupy insoluble fraction is partially dissolved to give a gummy product. To this product is added 50 ml of Dowex 50W (Na-form) resin and the mixture is stirred at room temperature for 2 hours. The mother suspension after removal of the resin (ca. 200 ml) is chromatographed on an Amberlite XAD-II column and after washing the column with 1 l of water, elution is carried out with 200 ml of 30% ethanol. The eluate is concentrated under reduced pressure and lyophilized to give sodium cis-3-[2-(2-chloroacetamido-4-thiazolyl)-2-(p-nitrobenzyloxycarbonylmethyloxyimino)acetamido]-4-methoxycarbonyl-2-oxoazetidine-1-sulfonate (syn-isomer).

IR $\nu_{max}^{KBr}$cm$^{-1}$: 3250, 1790–1730, 1670, 1520, 1050.

NMR(d$_6$-DMSO, ppm): 3.61(3H, s, COOCH$_3$), 4.36(2H, s, ClCH$_2$), 4.53(1H, d, J=6 Hz, C$_4$—H), 4.82(2H, s, NOCH$_2$), 5.37(2H, s, CO$_2$CH$_2$), 5.48(1H, d.d, J=6, 9 Hz, C$_3$—H),

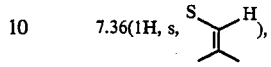 7.36(1H, s,  ), 9.49(1H, d, J=9 Hz, C$_3$—NH), 12.95(1H, s, br. s.ClCH$_2$CONH).

| Elemental analysis: C$_{21}$H$_{18}$ClN$_6$NaO$_{13}$S$_2$.3H$_2$O | | | |
|---|---|---|---|
| | C (%) | H (%) | N (%) |
| Calcd. | 35.22 | 3.38 | 11.74 |
| Found | 34.86 | 3.22 | 11.48 |

EXAMPLE 64C

In the same manner as Example 11C, there was obtained sodium cis-3-[2-(2-amino-4-thiazolyl)-2-(p-nitrobenzyloxycarbonylmethyloxyimino)acetamido]-4-methoxycarbonyl-2-oxoazetidine-1-sulfonate (syn-isomer).

IR $\nu_{max}^{KBr}$cm$^{-1}$: 3450, 3330, 1790–1730, 1680, 1610, 1050.

NMR(d$_6$-DMSO, ppm): 3.6(3H, s, COOCH$_3$), 4.5(1H, d, J=6 Hz, C$_4$—H), 4.77(2H, s, NOCH$_2$), 5.35(2H, s, COOCH$_2$), 5.43(1H, d.d, J=6, 9 Hz, C$_3$—H),

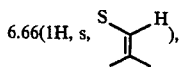 6.66(1H, s,  ), 7.2(2H, br.s, NH$_2$), 9.39(1H, d, J=9 Hz, C$_3$—NH).

| Elemental analysis: C$_{19}$H$_{17}$N$_6$NaO$_{12}$S$_2$.2H$_2$O | | | |
|---|---|---|---|
| | C (%) | H (%) | N (%) |
| Calcd. | 35.40 | 3.28 | 13.04 |
| Found | 35.45 | 3.22 | 12.83 |

EXAMPLE 65C

In a mixture of 25 ml of water and 25 ml of tetrahydrofuran is dissolved 500 mg of sodium cis-3-[2-(2-amino-4-thiazolyl)-2-(p-nitrobenzyloxycarbonylmethyloxyimino)acetamido]-4-methoxycarbonyl-2-oxoazetidine-1-sulfonate (syn-isomer), followed by addition of 500 mg of 10% palladium-on-carbon. The mixture is stirred in a hydrogen atmosphere for one hour. After addition of 25 ml of an aqueous solution of sodium hydrogen carbonate (66 mg), the catalyst is removed by filtration. The filtrate is washed with 30 ml of ethyl acetate and concentrated to 10 ml under reduced pressure. The concentrate is chromatographed on an Amberlite XAD-II column and elution is carried out with water. The first 130 ml fraction is discarded and the immediately succeeding 40 ml fraction is lyophilized to give cis-3-[2-(2-amino-4-thiazolyl)-2-carboxylmethyloxyiminoacetamido]-4-methoxycarbonyl-2-oxoazetidine-1-sulfonic acid disodium salt (syn-isomer).

IR $\nu_{max}^{KBr}$cm$^{-1}$: 3350, 1780, 1750, 1670, 1600, 1055.

NMR(d$_6$-DMSO, ppm): 3.58(3H, s, COOCH$_3$), 4.27(2H, s, NOCH$_2$), 4.5(1H, d, J=6 Hz, C$_4$—H), 5.37(1H, d.d, J=6, 9 Hz, C$_3$—H),

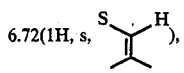
6.72(1H, s, 7.11(2H, br.s, NH$_2$), 11.3(1H, d, J=9 Hz, C$_3$—NH).

| Elemental analysis: C$_{12}$H$_{11}$N$_5$Na$_2$O$_{10}$S$_2$.2½H$_2$O | | | |
|---|---|---|---|
| | C (%) | H (%) | N (%) |
| Calcd. | 26.67 | 2.98 | 12.96 |
| Found | 26.63 | 3.02 | 12.93 |

EXAMPLE 66C

In a mixture of 20 ml of water and 20 ml of tetrahydrofuran is dissolved 950 mg of sodium cis-3-benzyloxycarboxamido-4-methoxycarbonyl-2-oxoazetidine-1-sulfonate as obtained in Example 49, followed by addition of 950 mg of 10% palladium-on-carbon. The mixture is stirred in a hydrogen atmosphere at room temperature for an hour, after which the catalyst is filtered off and washed with 40 ml of water-tetrahydrofuran (1:1). The filtrate and washings are combined, and under ice-cooling and stirring, 504 mg of sodium hydrogen carbonate and 1.55 g of 2-(2-chloroacetamido-4-thiazolyl)-(Z)-2-[1-methyl-1-(p-nitrobenzyloxycarbonyl)ethyloxyimino]acetyl chloride.HCl are added. The mixture is stirred under ice-cooling for 40 minutes and, then, concentrated under reduced pressure. The residue is chromatographed on an Amberlite XAD-II column and lyophilized to give sodium cis-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer) as a colorless powder.

IR $\nu_{max}^{KBr}$cm$^{-1}$: 1775, 1740, 1680, 1550, 1525, 1280, 1055.

NMR(d$_6$-DMSO, ppm): 1.50(6H, s, 2×CH$_3$), 3.62(3H, s, COOCH$_3$), 4.33(2H, s, ClCH$_2$), 4.51(1H, d, J=6 Hz, C$_4$13 H), 5.31(2H, s, COOCH$_2$), 5.52(1H, d.d, J=6, 9 Hz, C$_3$—H),

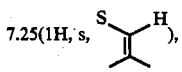
7.25(1H, s, 7.62, 8.07(2×2H, 2×d, aromatic protons).

| Elemental analysis: C$_{23}$H$_{22}$ClN$_6$NaO$_{13}$S$_2$.3H$_2$O | | | |
|---|---|---|---|
| | C (%) | H (%) | N (%) |
| Calcd. | 36.01 | 3.68 | 10.96 |
| Found | 36.09 | 3.36 | 11.06 |

EXAMPLE 67C

In 30 ml of water is dissolved 1.158 g of sodium cis-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer), and under ice-cooling and stirring, 241 mg of sodium monomethyldithiocarbamate is added. The mixture is stirred at room temperature for one hour, after which a further 241 mg of sodium monomethyldithiocarbamate is added. The mixture is further stirred for one hour. The reaction mixture is then washed with ether and concentrated under reduced pressure. The residue is chromatographed on an Amberlite XAD-II column and lyophilized to give sodium cis-3-{2-(2-amino-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer) as a colorless powder.

IR $\nu_{max}^{KBr}$cm$^{-1}$: 1775, 1740, 1680, 1615, 1520, 1280, 1055.

NMR(d$_6$-DMSO, ppm): 1.48(6H, s, 2×CH$_3$), 3.63(3H, s, COOCH$_3$), 4.50(1H, d, J=6 Hz, C$_4$—H), 5.33(2H, s, COOCH$_2$), 5.47(1H, d.d, J=6, 9 Hz, C$_3$—H),

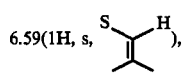
6.59(1H, s, 7.24(2H, br.s, NH$_2$), 7.65, 8.14(2×2H, 2×d, aromatic protons), 9.18(1H, d, J=9 Hz, C$_3$—NH).

| Elemental analysis: C$_{21}$H$_{21}$N$_6$NaO$_{12}$S$_2$.2½H$_2$O | | | |
|---|---|---|---|
| | C (%) | H (%) | N (%) |
| Calcd. | 37.01 | 3.84 | 12.33 |
| Found | 36.99 | 3.87 | 12.34 |

EXAMPLE 68C

In a mixture of 25 ml of water and 25 ml of tetrahydrofuran is dissolved 500 mg of sodium cis-3-{2-(2-amino-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer), followed by addition of 500 mg of 10% palladium-on-carbon. The mixture is stirred in a hydrogen atmosphere at room temperature for one hour. After addition of 25 ml of an aqueous solution of sodium hydrogen carbonate (62 mg), the catalyst is filtered off and the filtrate is washed with ethyl acetate and concentrated under reduced pressure. The residue is chromatographed on an Amberlite XAD-II column and lyophilized to give cis-3-[2-(2-amino-4-thiazolyl)-2-(1-methyl-1-carboxyethyloxyimino)acetamido]-4-methoxycarbonyl-2-oxoazetidine-1-sulfonic acid disodium salt (syn-isomer).

IR $\nu_{max}^{KBr}$cm$^{-1}$: 1775, 1740, 1660, 1630, 1580, 1280, 1055.

NMR(d$_6$-DMSO, ppm): 1.36(3H, s, CH$_3$), 1.45(3H, s, CH$_3$), 3.61(s, COOCH$_3$), 4.53(1H, d, J=6 Hz, C$_4$—H),

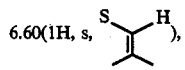
6.60(1H, s, 7.13(2H, br.s, NH$_2$).

| Elemental analysis: C$_{14}$H$_{15}$N$_5$Na$_2$O$_{10}$S$_2$.4H$_2$O | | | |
|---|---|---|---|
| | C (%) | H (%) | N (%) |
| Calcd. | 28.24 | 3.89 | 11.76 |
| Found | 28.26 | 3.68 | 11.62 |

EXAMPLE 69C

In 4 ml of cold water is dissolved 85 mg of cis-3-[2-(2-amino-4-thiazolyl)-2-(1-methyl-1-carboxyethyloxyimino)acetamido]-4-methoxycarbonyl-2-oxoazetidine-1-sulfonic acid disodium salt (syn-isomer), and the solution is chromatographed on a column of Dowex 50W (H-form) resin (10 ml), elution being carried out with water. The UV absorbing fractions are pooled and concentrated under reduced pressure and the residue is chromatographed on a Sephadex LH-20 column and lyophilized to give cis-2-[2-(2-amino-4-thiazolyl)-2-(1-methyl-1-carboxyethyloxyimino)acetamido]-4-methoxycarbonyl-2-oxoazetidine-1-sulfonic acid (syn-isomer) as a colorless powder.

IR $\nu_{max}^{KBr}$cm$^{-1}$: 1775, 1730, 1670, 1630, 1280, 1050.

NMR(d$_6$-DMSO, ppm): 1.50(6H, s, 2×CH$_3$), 3.63(3H, s, COOCH$_3$), 4.53(1H, d, J=6 Hz, C$_4$—H), 5.45(1H, d.d, J=6, 9 Hz, C$_3$—H), 6.87(1H, s, 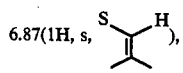), 9.29(1H, d, J=9 Hz, C$_3$—NH).

| Elemental analysis: C$_{14}$H$_{17}$N$_5$O$_{10}$S$_2$.2.3H$_2$O | | | |
|---|---|---|---|
| | C (%) | H (%) | N (%) |
| Calcd. | 32.28 | 4.18 | 13.45 |
| Found | 32.38 | 4.11 | 13.20 |

EXAMPLE 70C

In 3 ml of N,N-dimethylformamide is dissolved 550 mg of cis-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine (syn-isomer), and under cooling at −78° C., 1.6 ml of sulfuric anhydride-N,N-dimethylformamide complex solution (1.69M) is added. The mixture is stirred at 3°–5° C. for 24 hours, after which 0.22 ml of pyridine is added. On addition of 75 ml of ether, a syrupy product separates out. The ether layer is discarded and the ether-insoluble syrup is washed twice with 50 ml portions of ether and suspended in 25 ml of water. After addition of 20 ml of Dowex 50W(Na-form) resin, the mixture is stirred at room temperature for 1.5 hours. The resin is filtered off and the filtrate is concentrated under reduced pressure. The residue is chromatographed on an Amberlite XAD-II column and lyophilized to give a colorless powder of sodium cis-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer). In IR and NMR spectra, this product is in agreement with the compound obtained in Example 66.

| Elemental analysis: C$_{23}$H$_{22}$ClN$_6$NaO$_{13}$S$_2$.H$_2$O | | | |
|---|---|---|---|
| | C (%) | H (%) | N (%) |
| Calcd. | 37.79 | 3.31 | 11.50 |
| Found | 37.50 | 3.42 | 11.69 |

The amino- and carboxy-protecting groups on this product compound can be eliminated by the procedures described in Example 67 and 68, respectively.

EXAMPLE 71C

In the same manner as Example 10C, there was obtained sodium cis-3-[2-(2-chloroacetamido-4-thiazolyl)-2-allyloxyiminoacetamido]-4-methoxycarbonyl-2-oxoazetidine-1-sulfonate (syn-isomer).

IR $\nu_{max}^{KBr}$cm$^{-1}$: 3250, 1780, 1750, 1680, 1055.

NMR(d$_6$-DMSO, ppm): 3.60(3H, s, COOCH$_3$), 4.32(2H, s, ClCH$_2$), 4.49(1H, d, J=6 Hz, C$_4$—H), 7.27(1H, s, 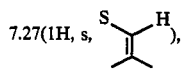), 9.49(1H, d, J=9 Hz, C$_3$—NH).

| Elemental analysis: C$_{15}$H$_{15}$ClN$_5$NaO$_9$S$_2$.1½H$_2$O | | | |
|---|---|---|---|
| | C (%) | H (%) | N (%) |
| Calcd. | 32.23 | 3.25 | 12.53 |
| Found | 32.42 | 3.30 | 12.59 |

EXAMPLE 72C

In the same manner as Example 11C, there was obtained sodium cis-3-[2-(2-amino-4-thiazolyl)-2-allyloxyiminoacetamido]-4-methoxycarbonyl-2-oxoazetidine-1-sulfonate (syn-isomer).

IR $\nu_{max}^{KBr}$cm$^{-1}$: 3325, 1790–1740, 1670, 1050.

NMR(d$_6$-DMSO, ppm): 3.60(3H, s, COOCH$_3$), 4.4–4.7(3H, m, CH$_2$CH=CH$_2$ & C$_4$—H), 5.0–5.5(3H, m, CH$_2$CH=CH$_2$ & C$_3$—H), 5.7–6.2(1H, m, CH$_2$CH=CH$_2$), 6.56(1H, s, 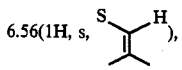), 7.12(2H, br.s, NH$_2$), 9.39(1H, d, J=9 Hz, C$_3$—NH).

| Elemental analysis: C$_{13}$H$_{14}$N$_5$NaO$_8$S$_2$.1½H$_2$O | | | |
|---|---|---|---|
| | C (%) | H (%) . | N (%) |
| Calcd. | 32.36 | 3.55 | 14.52 |
| Found | 32.47 | 3.75 | 14.46 |

EXAMPLE 73C

In 2 ml of water is dissolved 50 mg of sodium trans-3-[2-(2-chloroacetamido-4-thiazolyl)-2-methoxyiminoacetamido]-4-methoxycarbonyl-2-oxoazetidine-1-sulfonate (syn-isomer) as obtained in Example 24C, followed by addition of 15 mg of sodium monomethyldithiocarbamate under ice-water cooling and stirring. The mixture is stirred at room temperature for 30 minutes and after further addition of 15 mg of sodium monomethyldithiocarbamate, the mixture is stirred for 30 minutes. The reaction mixture is filtered and the filtrate is washed with ether. The aqueous layer is chromatographed on an Amberlite XAD-II column and lyophilized to give sodium trans-3-[2-(2-amino-4-thiazolyl)-2-methoxyiminoacetamido]-4-methoxycarbonyl-2-oxoazetidine-1-sulfonate (syn-isomer).

IR $\nu_{max}^{KBr}$cm$^{-1}$: 3400, 1780.

NMR(d$_6$-DMSO, ppm): 3.70(3H, s, COOCH$_3$), 3.85(3H, s, NOCH$_3$), 4.10(1H, s, d, J=2 Hz, C$_4$—H), 4.77 (1H, d.d, J=2 Hz, C$_3$—H), 6.70(1H, s, 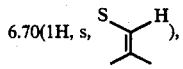), 7.20(2H, br.s, NH₂), 9.47(1H, d, J=9 Hz, C₃—NH).

EXAMPLE 74C

In the same manner as Example 10C, there was obtained sodium cis-3-[2-(2-chloroacetamido-4-thiazolyl)-2-methoxyiminoacetamido]-4-chloromethyl-2-oxoazetidine-1-sulfonate (syn-isomer).

IR $\nu_{max}^{KBr}$cm$^{-1}$: 1770, 1670, 1550, 1270, 1055.

NMR(d₆-DMSO, ppm): 3.89(3H, s, NOCH₃), 4.34(2H, s, ClCH₂), 5.28(1H, d.d, J=6, 9 Hz, C₃—H), 7.38(1H, s, 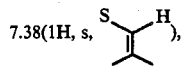), 9.37(1H, d, J=9 Hz, C₃—NH), 12.90(1H, br.s, ClCH₂CONH).

EXAMPLE 75C

In the same manner as Example 11C, there was obtained sodium cis-3-[2-(2-amino-4-thiazolyl)-2-methoxyiminoacetamido]-4-chloromethyl-2-oxoazetidine-1-sulfonate (syn-isomer).

IR $\nu_{max}^{KBr}$cm$^{-1}$: 1770, 1660, 1610, 1530, 1270, 1050.

| Elemental analysis: C₁₀H₁₁ClN₅NaO₆S₂.2H₂O | | | |
|---|---|---|---|
| | C (%) | H (%) | N (%) |
| Calcd. | 26.35 | 3.32 | 15.36 |
| Found | 26.31 | 3.18 | 15.33 |

EXAMPLE 76C

In the same manner as Example 10C, there was obtained sodium cis-3-[2-(2-chloroacetamido-4-thiazolyl)-2-methoxyiminoacetamido]-4-methylsulfonyloxymethyl-2-oxoazetidine-1-sulfonate (syn-isomer).

IR $\nu_{max}^{KBr}$cm$^{-1}$: 1770, 1670, 1560, 1350, 1275, 1175, 1050.

NMR(d₆-DMSO, ppm): 3.10(3H, s, SO₂CH₃), 3.90(3H, s, NOCH₃), 4.35(2H, s, ClCH₂), 5.33(1H, d.d, J=5, 9 Hz, C₃—H), 7.41(1H, s, 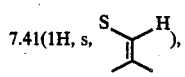), 9.42 (1H, d, J=9 Hz, C₃—NH), 12.91(1H, br.s, ClCH₂CONH).

| Elemental analysis: C₁₃H₁₅ClN₅NaO₁₀S₃.2H₂O | | | |
|---|---|---|---|
| | C (%) | H (%) | N (%) |
| Calcd. | 26.28 | 3.24 | 11.83 |
| Found | 26.54 | 3.26 | 11.72 |

EXAMPLE 77C

In the same manner as Example 11C, there was obtained sodium cis-3-[2-(2-amino-4-thiazolyl)-2-methoxyiminoacetamido]-4-methylsulfonyloxymethyl-2-oxoazetidine-1-sulfonate (syn-isomer).

IR $\nu_{max}^{KBr}$cm$^{-1}$: 1770, 1670, 1620, 1535, 1350, 1280, 1175, 1055.

NMR(d₆-DMSO, ppm): 3.10(3H, s, SO₂CH₃), 3.86(3H, s, NOCH₃), 5.28(1H, d.d, J=5, 9 Hz, C₃—H), 6.74(1H, s, 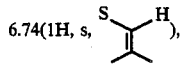), 9.30(1H, d, J=9 Hz, C₃—NH).

| Elemental analysis: C₁₁H₁₄N₅NaO₉S₃.2H₂O | | | |
|---|---|---|---|
| | C (%) | H (%) | N (%) |
| Calcd. | 25.63 | 3.52 | 13.59 |
| Found | 25.64 | 3.41 | 13.56 |

EXAMPLE 78C

In the same manner as Example 10C, there was obtained sodium cis-3-[2-(2-chloroacetamido-4-thiazolyl)-2-methoxyiminoacetamido]-4-azidomethyl-2-oxoazetidine-1-sulfonate (syn-isomer).

IR $\nu_{max}^{KBr}$cm$^{-1}$: 2110, 1765, 1650, 1550, 1260, 1045.

NMR(d₆-DMSO, ppm): 3.65–3.80(2H, m, CH₂N₃), 3.92(3H, s, NOCH₃), 4.25(2H, s, ClCH₂), 5.24(1H, d.d, J=5, 9 Hz, C₃—H), 7.44(1H, s, 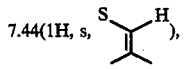), 9.33(1H, d, J=9 Hz, C₃—NH).

| Elemental analysis: C₁₂H₁₂ClN₈NaO₇S₂.2H₂O | | | |
|---|---|---|---|
| | C (%) | H (%) | N (%) |
| Calcd. | 26.75 | 2.99 | 20.79 |
| Found | 26.59 | 2.90 | 20.80 |

EXAMPLE 79C

In the same manner as Example 11C, there was obtained sodium cis-3-[2-(2-amino-4-thiazolyl)-2-methoxyiminoacetamido]-4-azidomethyl-2-oxoazetidine-1-sulfoante (syn-isomer).

IR $\nu_{max}^{KBr}$cm$^{-1}$: 2110, 1765, 1660, 1530, 1270, 1050.

NMR(d₆-DMSO, ppm): 3.60–3.85(2H, m, CH₂N₃), 3.87(3H, s, NOCH₃), 5.20(1H, d.d, J=5, 9 Hz, C₃—H), 6.75(1H, s, 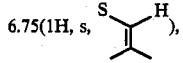), 7.16(2H, br.s, NH₂), 9.22(1H, d, J=9 Hz, C₃—NH).

| Elemental analysis: C₁₀H₁₁N₈NaO₆S₂.2H₂O | | | |
|---|---|---|---|
| | C (%) | H (%) | N (%) |
| Calcd. | 25.98 | 3.27 | 24.23 |
| Found | 26.11 | 3.41 | 24.34 |

EXAMPLE 80C

In the same manner as Example 3C, there was obtained sodium cis-3-[2-(2-chloroacetamido-4-thiazolyl)-

2-methoxyiminoacetamido]-4-benzoyloxymethyl-2-oxoazetidine-1-sulfonate (syn-isomer).

IR $\nu_{max}^{KBr}$ cm$^{-1}$: 3250, 1770, 1720–1660, 1545, 1050.

NMR(d$_6$-DMSO, ppm): 3.69(3H, s, NOCH$_3$), 4.35(2H, s, ClCH$_2$), 5.32(1H, d.d, J=6, 9 Hz, C$_3$—H), 7.35(1H, s, 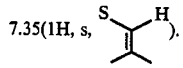).

| Elemental analysis: C$_{19}$H$_{17}$ClN$_5$NaO$_8$S$_2$.3H$_2$O | | | |
|---|---|---|---|
| | C (%) | H (%) | N (%) |
| Calcd. | 36.81 | 3.74 | 11.50 |
| Found | 36.92 | 3.63 | 11.38 |

EXAMPLE 81C

In the same manner as Example 4C, there was obtained sodium cis-3-[2-(2-amino-4-thiazolyl)-2-methoxyiminoacetamido]-4-benzoyloxymethyl-2-oxoazetidine-1-sulfonate (syn-isomer).

IR $\nu_{max}^{KBr}$ cm$^{-1}$: 3300, 1770, 1710, 1665, 1050.

NMR(d$_6$-DMSO, ppm): 3.67(3H, s, NOCH$_3$), 5.28(1H, d.d, J=6, 9 Hz, C$_3$—H), 6.62(1H, s, 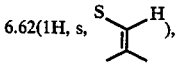), 7.12 (2H, br.s, NH$_2$), 9.38(1H, d, J=9 Hz, C$_3$—NH).

| Elemental analysis: C$_{17}$H$_{16}$N$_5$NaO$_8$S$_2$.1½H$_2$O | | | |
|---|---|---|---|
| | C (%) | H (%) | N (%) |
| Calcd. | 38.34 | 3.60 | 13.15 |
| Found | 38.23 | 3.53 | 13.15 |

EXAMPLE 82C

In the same manner as Example 1C, there was obtained sodium cis-3-[2-(2-chloroacetamido-4-thiazolyl)-2-methoxyiminoacetamido]-4-acetyl-2-oxoazetidine-1-sulfonate (syn-isomer).

IR $\nu_{max}^{KBr}$ cm$^{-1}$: 3420, 1760, 1650, 1540, 1265.

NMR(d$_6$-DMSO, ppm): 2.30(3H, s, COCH$_3$), 3.85(3H, s, NOCH$_3$), 4.34(2H, s, ClCH$_2$), 4.40(1H, d, J=5 Hz, C$_4$—H), 5.18(1H, d.d, J=5, 10 Hz, C$_3$—H), 7.40(1H, s, 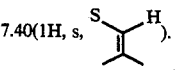).

EXAMPLE 83C

In the same manner as Example 11C, there was obtained sodium cis-3-[2-(2-amino-4-thiazolyl)-2-methoxyiminoacetamido]-4-acetyl-2-oxoazetidine-1-sulfonate (syn-isomer).

IR $\nu_{max}^{KBr}$ cm$^{-1}$: 3400, 1760, 1660, 1535, 1260, 1050.

NMR(d$_6$-DMSO, ppm): 2.30(3H, s, COCH$_3$), 3.81(3H, s, NOCH$_3$), 4.40(1H, d, J=5 Hz, C$_4$—H), 5.26 (1H, t, C$_3$—H), 6.64(1H, s, 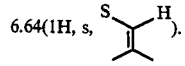).

EXAMPLE 84C

In 2 ml of N,N-dimethylformamide is dissolved 172 mg of cis-3-[2-(2-chloroacetamido-4-thiazolyl)-2-methoxyiminoacetamido]-4-hydroxymethyl-2-oxoazetidine (syn-isomer), followed by addition of 318 mg of sulfuric anhydride-pyridine complex. The mixture is stirred at room temperature for 24 hours, after which 159 mg of sulfuric anhydride-pyridine complex is added and the mixture is further stirred for 106 hours. On addition of ether to the reaction mixture, a syrupy product separates out. The ether layer is discarded and the insolubles are washed with ether. The same procedure is repeated once again, and after the ether layer is discarded the insolubles are dissolved in 20 ml of water. After addition of 40 ml of Dowex 50W (Na-form) resin, the mixture is stirred at room temperature for 2 hours and the resin is filtered off. The filtrate is concentrated under reduced pressure and the residue is chromatographed on an Amberlite XAD-II column and lyophilized to give disodium cis-3-[2-(2-chloroacetamido-4-thiazolyl)-2-methoxyiminoacetamido]-4-sulfonatooxymethyl-2-oxoazetidine-1-sulfonate (syn-isomer).

IR $\nu_{max}^{KBr}$ cm$^{-1}$: 1765, 1665, 1545, 1275, 1240, 1055, 1030.

NMR(d$_6$-DMSO, ppm): 3.90(3H, s, NOCH$_3$), 4.35(2H, s, ClCH$_2$), 5.34(1H, d.d, J=4.5, 9 Hz, C$_3$—H), 7.66(1H, s, 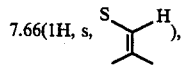), 9.38(1H, d, J=9 Hz, C$_3$—NH).

| Elemental analysis: C$_{12}$H$_{12}$ClN$_5$Na$_2$O$_{11}$S.4H$_2$O | | | |
|---|---|---|---|
| | C (%) | H (%) | N (%) |
| Calcd. | 22.11 | 3.09 | 10.74 |
| Found | 22.25 | 2.92 | 10.47 |

EXAMPLE 85C

In the same manner as Example 1C, there was obtained sodium cis-3-[2-(2-chloroacetamido-4-thiazolyl)-2-methoxyiminoacetamido]-4-chloroacetoxymethyl-2-oxoazetidine-1-sulfonate (syn-isomer).

IR $\nu_{max}^{KBr}$ cm$^{-1}$: 3400, 1760, 1670, 1050.

NMR(d$_6$-DMSO, ppm): 3.80(3H, s, NOCH$_3$), 5.23(1H, d.d, J=5, 9 Hz, C$_3$—H), 7.43(1H, s, 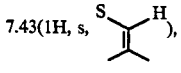), 9.34 (1H, d, J=9 Hz, C$_3$—NH).

| Elemental analysis: C$_{14}$H$_{14}$Cl$_2$N$_5$NaO$_9$S$_2$.2H$_2$O | | | |
|---|---|---|---|
| | C (%) | H (%) | N (%) |
| Calcd. | 28.48 | 2.73 | 11.86 |
| Found | 28.49 | 2.77 | 11.84 |

EXAMPLE 86C

In 2 ml of water is dissolved 70 mg of sodium cis-3-[2-(2-chloroacetamido-4-thiazolyl)-2-methoxyiminoacetamido]-4-chloroacetoxymethyl-2-oxoazetidine-1-sulfonate (syn-isomer), and under ice-cooling and stirring, 39 mg sodium monomethyldithiocarbamate is added. The mixture is stirred at room temperature for one hour. After addition of 10 mg of sodium monomethyldithiocarbamate, the mixture is stirred for 30 minutes. The reaction mixture is then filtered and the filtrate is washed with ether. The aqueous layer is chromatographed on an Amberlite XAD-II column and lyophilized to give sodium cis-3-[2-(2-amino-4-thiazolyl)-2-methoxyiminoacetamido]-4-hydroxymethyl-2-oxoazetidine-1-sulfonate (syn-isomer).

IR $\nu_{max}^{KBr}$cm$^{-1}$: 3400, 1760, 1660, 1050.

NMR(d$_6$-DMSO, ppm): 5.15(1H, d.d, J=5, 9 Hz, C$_3$—H), 6.90(1H, s, 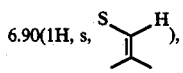

7.60(2H, br.s, NH$_2$), 9.07 (1H, d, J=9 Hz, C$_3$—NH).

| Elemental analysis: C$_{10}$H$_{12}$N$_5$NaO$_7$S$_2$.2H$_2$O | | | |
|---|---|---|---|
| | C (%) | H (%) | N (%) |
| Calcd. | 27.33 | 3.21 | 15.94 |
| Found | 27.16 | 3.44 | 15.70 |

EXAMPLE 87C

In the same manner as Example 31C, there was obtained sodium cis-3-[2-(2-chloroacetamido-4-thiazolyl)-2-methoxyiminoacetamido]-4-(2methylsulfonylethoxycarbonylaminomethyl)-2-oxoazetidine-1-sulfonate (syn-isomer).

IR $\nu_{max}^{KBr}$cm$^{-1}$: 1770, 1690, 1550, 1275, 1050.

NMR (d$_6$-DMSO, ppm): 3.97(3H, s, SO$_2$CH$_3$), 3.44(2H, t, J=6 Hz, CH$_2$SO$_2$), 3.93(3H, s, NOCH$_3$), 4.34(2H, t, J=6 Hz, COOCH$_2$), 4.37(2H, s, ClCH$_2$), 5.21(1H, d.d, J=6, 9 Hz, C$_3$—H), 7.51(1H, s, 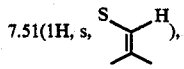

9.48(1H, d, J=9 Hz, C$_3$—NH).

| Elemental analysis: C$_{16}$H$_{20}$ClN$_6$NaO$_{11}$S$_3$.3H$_2$O | | | |
|---|---|---|---|
| | C (%) | H (%) | N (%) |
| Calcd.: | 28.22 | 3.85 | 12.34 |
| Found: | 28.34 | 3.63 | 12.10 |

EXAMPLE 88C

In the same manner as Example 10C, there was obtained sodium cis-3-[2-(2-chloroacetamido-4-thiazolyl)-2-methoxyiminoacetamido]-4-trifluoroacetylaminomethyl-2-oxoazetidine-1-sulfonate (syn-isomer).

IR $\nu_{max}^{KBr}$cm$^{-1}$: 1770, 1710, 1670, 1550, 1270, 1050.

NMR (d$_6$-DMSO, ppm): 3.91(3H, s, NOCH$_3$), 4.36(2H, s, ClCH$_2$), 5.28(1H, d.d, J=6, 9 Hz, C$_3$—H), 7.49(1H, s, 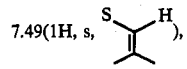

9.46 (1H, d, J=9 Hz, C$_3$—NH).

| Elemental analysis: C$_{14}$H$_{13}$ClF$_3$N$_6$NaO$_8$S$_2$.3H$_2$O | | | |
|---|---|---|---|
| | C (%) | H (%) | N (%) |
| Calcd.: | 26.82 | 3.05 | 13.41 |
| Found: | 26.63 | 2.85 | 13.22 |

EXAMPLE 89C

In the same manner, as Example 11C, there was obtained sodium cis-3-[2-(2-amino-4-thiazolyl)-2-methoxyiminoacetamido]-4-trifluoroacetylaminomethyl-2-oxoazetidine-1-sulfonate (syn-isomer).

IR $\nu_{max}^{KBr}$cm$^{-1}$: 1770, 1720, 1670, 1530, 1050.

NMR (d$_6$-DMSO, ppm): 3.85(3H, s, NOCH$_3$), 5.17(1H, d.d, J=6, 9 Hz, C$_3$—H), 6.80(1H, s, 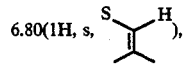

7.12(2H, br.s, NH$_2$), 9.35(1H, d, J=9 Hz, C$_3$—NH).

| Elemental analysis: C$_{12}$H$_{12}$F$_3$N$_6$NaO$_7$S$_2$.3H$_2$O | | | |
|---|---|---|---|
| | C (%) | H (%) | N (%) |
| Calcd.: | 26.19 | 3.30 | 15.27 |
| Found: | 26.30 | 3.07 | 15.05 |

EXAMPLE 90C

In 3.5 ml of N,N-dimethylformamide is dissolved 416 mg of cis-3-[2-(2-chloroacetamido-4-thiazolyl)-2-methoxyiminoacetamido]-4-(p-nitrobenzyloxycarbonylaminomethyl)-2-oxoazetidine (syn-isomer), followed by addition of 239 mg of sulfuric anhydride-pyridine complex. The mixture is stirred at room temperature for 48 hours. After addition of 119 mg of sulfuric anhydride-pyridine complex, the mixture is further stirred for 72 hours. On addition of 55 ml of ether to the reaction mixture, a syrupy product separates out. The upper ether layer is discarded and the insolubles are washed with ether. The same procedure is repeated once again, after which the ether layer is discarded. The syrupy insolubles are suspended in 50 ml of water and after addition of 25 ml of Dowex 50W (Na-form) resin, the mixture is stirred at room temperature for 2 hours. The resin is removed by filtration and the filtrate is concentrated under reduced pressure. The residue is chromatographed on an Amberlite XAD-II column and lyophilized to give 404 mg of colorless powder. The powder is dissolved in 15 ml of water, and under ice-cooling and stirring 87 mg of sodium monomethyldithiocarbamate is added. The mixture is stirred at room temperature for one hour, after which 5 ml of water, 5 ml of tetrahydrofuran and 87 mg of sodium monomethyldithiocarbamate are added. The mixture is stirred for additional one hour. The reaction mixture is washed with ethyl acetate, chromatographed on an Amberlite XAD-II column and lyophilized to give sodium cis-3-[2-(2-amino-4-thiazolyl)-2-methoxyiminoacetamido]-4-

(p-nitrobenzyloxycarbonylaminomethyl)-2-oxoazetidine-1-sulfonate (syn-isomer).

IR $\nu_{max}^{KBr}$cm$^{-1}$: 1765, 1710, 1660, 1615, 1260, 1050.
NMR (d$_6$-DMSO, ppm): 3.87(3H, s, NOCH$_3$), 5.20(2H, s, COOCH$_2$), 6.83(1H, s, 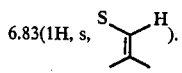 ).

| Elemental analysis: C$_{18}$H$_{18}$N$_7$NaO$_{10}$S$_2$.2½H$_2$O | | | |
|---|---|---|---|
| | C (%) | H (%) | N (%) |
| Calcd.: | 34.62 | 3.72 | 15.70 |
| Found: | 34.53 | 3.52 | 15.70 |

EXAMPLE 91C

In a mixture of 15 ml of water and 15 ml of tetrahydrofuran is dissolved 203 mg of sodium cis-3-[2-(2-amino-4-thiazolyl)-2-methoxyiminoacetamido]-4-(p-nitrobenzyloxycarbonylaminomethyl)-2-oxoazetidine-1-sulfonate (syn-isomer), followed by addition of 190 mg of 10% palladium-on-carbon. The mixture is stirred in a hydrogen atmosphere at room temperature for 3 hours. The catalyst is filtered off and the filtrate is washed with ethyl acetate and concentrated under reduced pressure. The residue is chromatographed on an Amberlite XAD-II column and lyophilized to give a colorless powder. The powder is rechromatographed on a Sephadex LH-20 column and lyophilized to give cis-3-[2-(2-amino-4-thiazolyl)-2-methoxyiminoacetamido]-4-aminomethyl-2-oxoazetidine-1-sulfonic acid (syn-isomer).

IR $\nu_{max}^{KBr}$cm$^{-1}$: 1770, 1660, 1620, 1530, 1275, 1050.
NMR (d$_6$-DMSO, ppm): 3.88(3H, s, NOCH$_3$), 6.84(1H, s, 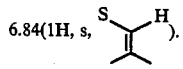 ).

| Elemental analysis: C$_{10}$H$_{14}$N$_6$O$_6$S$_2$.2H$_2$O | | | |
|---|---|---|---|
| | C (%) | H (%) | N (%) |
| Calcd.: | 28.98 | 4.38 | 20.28 |
| Found: | 29.29 | 4.31 | 20.19 |

EXAMPLE 92C

In the same manner as Example 27C, there were obtained beta and alpha forms of sodium cis-3-[D-2-(4-ethyl-2,3-dioxo-1-piperazinecarboxamido)-2-phenylacetamido]-4-methoxycarbonyl-2-oxoazetidine-1-sulfonate.
Beta form
IR $\nu_{max}^{KBr}$cm$^{-1}$: 1770, 1710, 1675, 1510, 1280, 1055.
NMR (d$_6$-DMSO, ppm): 1.10(3H, t, J=7 Hz, N—CH$_2$CH$_3$), 3.10 (3H, s, COOCH$_3$), 4.37(1H, d, J=6 Hz, C$_4$—H), 5.31(1H, d.d, J=6, 9 Hz, C$_3$—H), 5.55(1H, d, J=7 Hz, PhCH), 7.38 (5H, s, Ph-), 9.28(1H, d, J=9 Hz, C$_3$—NH), 9.82(1H, d, J=7Hz, PhCHNH).

| Elemental analysis: C$_{20}$H$_{28}$N$_5$NaO$_{13}$S.3H$_2$O | | | |
|---|---|---|---|
| | C (%) | H (%) | N (%) |
| Calcd.: | 39.94 | 4.69 | 11.74 |
| Found: | 40.08 | 4.53 | 11.53 |

Alpha form
IR $\nu_{max}^{KBr}$cm$^{-1}$: 1780, 1710, 1675, 1510, 1270, 1055.
NMR (d$_6$-DMSO, ppm): 1.10(3H, t, J=6 Hz, N—CH$_2$CH$_3$), 3.59 (3H, s, COOCH$_3$), 4.47(1H, d, J=6 Hz, C$_4$—H), 5.15(1H, d.d, J=6, 9 Hz, C$_3$—H), 5.48(1H, d, J=7 Hz, PhCH), 7.40 (5H, br.s, Ph-), 9.38(1H, d, J=9 Hz, C$_3$—NH), 9.74(1H, d, J=7Hz, PhCHNH).

| Elemental analysis: C$_{20}$H$_{28}$N$_5$NaO$_{13}$S.3H$_2$O | | | |
|---|---|---|---|
| | C (%) | H (%) | N (%) |
| Calcd.: | 39.94 | 4.69 | 11.74 |
| Found: | 40.21 | 4.42 | 11.61 |

EXAMPLE 93C

In the same manner as Example 27C, there were obtained beta and alpha forms of sodium cis-3-[D-2-(4-ethyl-2,3-dioxo-1-piperazinecarboxamido)-2-phenylacetamido]-4-acetoxymethyl-2-oxoazetidine-1-sulfonate.
Beta form
IR $\nu_{max}^{KBr}$cm$^{-1}$: 1770, 1705, 1665, 1500, 1240, 1045.
NMR (d$_6$-DMSO, ppm): 1.10(3H, t, J=8 Hz, CH$_2$CH$_3$), 1.58 (3H, s, COCH$_3$), 5.14(1H, d.d, J=5,9 Hz, C$_3$—H), 5.50 (1H, d, J=7 Hz, PhCH), 9.28(1H, d, J=9 Hz, C$_3$—NH).
Alpha form
IR $\nu_{max}^{KBr}$cm$^{-1}$: 1770, 1710, 1670, 1505, 1240, 1050.
NMR (d$_6$-DMSO, ppm): 1.11(3H, t, J=7 Hz, CH$_2$CH$_3$), 1.86 (3H, s, COCH$_3$), 4.98(1H, d.d, J=5,9 Hz, C$_3$—H), 5.40 (1H, d, J=7 Hz, PhCH), 9.22(1H, d, J=9 Hz, C$_3$—NH).

EXAMPLE 94C

In the same manner as Example 27C, there were obtained beta and alpha forms of sodium cis-3-{D-2-[3-(furan-2-aldoimino)-2-oxo-1-imidazolidinecarboxamido]-2-phenylacetamido}-4-methoxycarbonyl-2-oxoazetidine-1-sulfonate.
Beta form
IR $\nu_{max}^{KBr}$cm$^{-1}$: 1770, 1725, 1665, 1415, 1275, 1240.
NMR (d$_6$-DMSO, ppm): 3.10(3H, s, COOCH$_3$), 3.76(4H, s, NCH$_2$CH$_2$N), 4.35(1H, d, J=6 Hz, C$_4$—H), 5.32(1H, d.d, J=6,9 Hz, C$_3$—H), 5.55(1H, d, J=6 Hz, PhCH), 9.05(1H, d, J=6 Hz, PhCHNH), 9.25(1H, d, J=9 Hz, C$_3$—NH).
Alpha form
IR $\nu_{max}^{KBr}$cm$^{-1}$: 1770, 1725, 1415, 1275, 1240.
NMR (d$_6$-DMSO, ppm): 3.61(3H, s, COOCH$_3$), 3.78(4H, s, NCH$_2$CH$_2$N), 4.46(1H, d, J=6 Hz, C$_4$—H), 5.12(1H, d.d, J=6,9 Hz, C$_3$—H), 5.47(1H, d, J=7 Hz, PhCH), 8.97(1H, d, J=7 Hz, PhCHNH), 9.32(1H, d, J=9 Hz, C$_3$—NH).

EXAMPLE 95C

In the same manner as Example 27C, there were obtained beta and alpha forms of sodium cis-3-{D-2-[3-(thiophene-2-aldimino)-2-oxo-1-imidazolidinecarboxamido]-2-phenylacetamido}-4-methoxycarbonyl-2-oxoazetidine-1-sulfonate.

Beta form

IR $\nu_{max}^{KBr}$cm$^{-1}$: 1770, 1735, 1660, 1530, 1405, 1270, 1235.

NMR (d$_6$-DMSO, ppm): 3.11(3H, s, COOCH$_3$), 3.80(4H, s, NCH$_2$CH$_2$N), 4.33(1H, d, J=6 Hz, C$_4$—H), 5.30(1H, d,d, J=6,9 Hz, C$_3$—H), 5.55(1H, d, J=7 Hz, PhC$\underline{H}$), 8.11(1H, s, N=CH), 9.07(1H, d, J=7 Hz, PhCH$\underline{NH}$), 9.22(1H, d, J=9 Hz, C$_3$—NH).

Alpha form

IR $\nu_{max}^{KBr}$cm$^{-1}$: 1765, 1740, 1680, 1535, 1405, 1270, 1240.

NMR (d$_6$-DMSO, ppm): 3.62(3H, s, COOCH$_3$), 3.80(4H, s, NCH$_2$CH$_2$N), 4.45(1H, d, J=6 Hz, C$_4$—H), 5.11(1H, d,d, J=6,9 Hz, C$_3$—H), 5.47(1H, d, J=7 Hz, PhC$\underline{H}$), 8.10(1H, s, N=CH).

EXAMPLE 96C

In 10 ml of methylene chloride is dissolved the 3-amino compound, which has been prepared from 0.8 g of methyl cis-3-benzyloxycarboxamido-2-oxoazetidine-4-carboxylate in the same manner as Reference Example 3C, and under ice-cooling and stirring 0.4 ml of triethylamine is added, after which a solution of 0.6 g of 2-(2-methyl-4-thiazolyl)-2-methoxyiminoacetyl chloride in methylene chloride is added dropwise. The mixture is stirred under ice-cooling for 20 minutes and at room temperature for 1.5 hours. To the reaction mixture is added water, and the methylene chloride layer is separated. This layer is dried over anhydrous magnesium sulfate and the solvent is distilled off. The residue is cooled to −10° C. and 1.75 ml of sulfuric anhydride-N,N-dimethylformamide complex solution (1.58M) is added. The mixture is allowed to stand at 5° C. in a stoppered flask for 3 days. To this reaction mixture is added 0.29 ml of pyridine, and the mixture is poured into 100 ml of ether, followed by stirring. The supernatant is discarded and the residue is dissolved in 2 ml of water. After addition of 30 ml of Dowex 50W (Naform) resin, the mixture is stirred at room temperature for 30 minutes. The resin is then filtered off and the filtrate is concentrated to 20 ml. The concentrate is chromatographed on an Amberlite XAD-II column and lyophilized to give sodium cis-3-[2-(2-methyl-4-thiazolyl)-2-methoxyiminoacetamido]-4-methoxycarbonyl-2-oxoazetidine-1-sulfonate (syn-isomer).

IR $\nu_{max}^{KBr}$cm$^{-1}$: 3425, 1770, 1750, 1275, 1050.

NMR (D$_2$O, ppm):

2.72(3H, s, 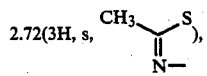), 3.81(3H, s, COOCH$_3$), 4.05(3H, s, NOCH$_3$), 5.04(1H, d, J=6 Hz, C$_4$—H), 5.75 (1H, d, J=6 Hz, C$_3$—H), 7.68(1H, s, 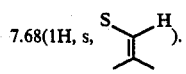).

Elemental analysis: C$_{12}$H$_{13}$N$_4$NaO$_8$S$_2$.2H$_2$O

|  | C (%) | H (%) | N (%) |
|---|---|---|---|
| Calcd.: | 31.03 | 3.69 | 12.06 |
| Found: | 31.10 | 3.48 | 11.94 |

EXAMPLE 97C

To 499 mg of methyl cis-3-[2-(2-chloroacetamido-4-thiazolyl)-2-diethylphosphonacetamido]-2-oxoazetidine-4-carboxylate is added 1.9 ml of sulfuric anhydride-N,N-dimethylformamide complex solution (1.58M) at 10° C., and the mixture is allowed to stand at 5° C. in a stoppered flask for 3 days. To this reaction mixture is added 0.32 ml of pyridine, and the mixture is poured into 100 ml of ether, followed by stirring. The supernatant is discarded and the residue is dissolved in 20 ml of water. After addition of 15 ml of Dowex 50W (Na-form) resin, the mixture is stirred at room temperature for 30 minutes. The resin is filtered off and the filtrate is concentrated to 20 ml. The concentrate is chromatographed on an Amberlite XAD-II column and lyophilized to give sodium cis-3-[2-(2-chloroacetamido-4-thiazolyl)-2-diethylphosphonoacetamido]-4-methoxycarbonyl-2-oxoazetidine-1-sulfonate.

IR $\nu_{max}^{KBr}$cm$^{-1}$: 3450, 1770, 1750, 1670, 1540, 1260, 1230, 1050.

Elemental analysis: C$_{16}$H$_{21}$ClN$_4$NaO$_{11}$PS$_2$.2H$_2$O

|  | C (%) | H (%) | N (%) |
|---|---|---|---|
| Calcd.: | 30.26 | 3.34 | 8.82 |
| Found: | 30.19 | 3.64 | 8.72 |

EXAMPLE 98C

In the same manner as Example 11C, there was obtained sodium cis-3-[2-(2-amino-4-thiazolyl)-2-diethylphosphonoacetamido]-4-methoxycarbonyl-2-oxoazetidine-1-sulfonate.

IR $\nu_{max}^{KBr}$cm$^{-1}$: 3400, 1775, 1750, 1670, 1510, 1270, 1230, 1045.

Elemental analysis: C$_{14}$H$_{20}$N$_4$NaO$_{10}$PS$_2$.2H$_2$O

|  | C (%) | H (%) | N (%) |
|---|---|---|---|
| Calcd.: | 30.11 | 4.33 | 10.03 |
| Found: | 30.39 | 4.14 | 10.20 |

EXAMPLE 99C

In the same manner as Example 97C, there was obtained sodium cis-3-(2-triethylsilylethylcarboxamido)-4-methoxycarbonyl-2-oxoazetidine-1-sulfonate.

IR $\nu_{max}^{KBr}$cm$^{-1}$: 3450, 1775, 1745, 1660, 1540, 1260, 1250, 1055.

NMR (d$_6$-DMSO, ppm): 3.61(3H, s, COOCH$_3$), 4.41(1H, d, J=6 Hz, C$_4$—H), 5.24(1H, d,d, J=6,9 Hz, C$_3$—H), 8.59 (1H, d, J=9 Hz, C$_3$—NH).

Elemental analysis: C$_{14}$H$_{25}$N$_2$NaO$_7$SSi.H$_2$O

|  | C (%) | H (%) | N (%) |
|---|---|---|---|
| Calcd.: | 38.69 | 6.26 | 6.45 |
| Found: | 38.71 | 6.18 | 6.36 |

EXAMPLE 100C

In the same manner as Example 97C, there was obtained sodium cis-3-[2-(2-amino-4-thiazolyl)-2-methoxyiminoacetamido]-4-(2-phenylethyl)-2-oxoazetidine-1-sulfonate (syn-isomer).

IR $\nu_{max}^{KBr}$ cm$^{-1}$: 3450, 1750, 1660, 1540, 1260, 1045.

NMR (d$_6$-DMSO+D$_2$O, ppm): 3.82(1H, s, NOCH$_3$), 4.38(2H, s, ClCH$_2$), 5.32(1H, d, J=6H, C$_3$—H), 7.34(5H, s, Ph-), 7.42(1H, s, 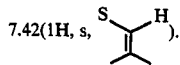 ).

| Elemental analysis: C$_{19}$H$_{19}$ClN$_5$NaO$_7$S$_2$.3½H$_2$O | | | |
|---|---|---|---|
| | C (%) | H (%) | N (%) |
| Calcd.: | 37.10 | 4.26 | 11.39 |
| Found: | 37.00 | 3.97 | 11.64 |

EXAMPLE 101C

In the same manner as Example 11C there was obtained sodium cis-3-[2-(2-amino-4-thiazolyl)-2-methoxyiminoacetamido]-4-(2-phenylethyl)-2-oxoazetidine-1-sulfonate (syn-isomer).

IR $\nu_{max}^{KBr}$ cm$^{-1}$: 3425, 1750, 1660, 1610, 1520, 1240, 1050.

NMR (d$_6$-DMSO, ppm): 3.64(3H, s, NOCH$_3$), 5.15(1H, d.d, J=6,9 Hz, C$_3$—H), 6.66(1H, s, 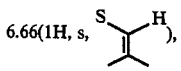 ), 7.10(2H, br.s. NH$_2$), 9.34(1H, d, J=9 Hz, C$_3$—NH).

| Elemental analysis: C$_{17}$H$_{18}$N$_5$NaO$_6$S$_2$.2½H$_2$O | | | |
|---|---|---|---|
| | C (%) | H (%) | N (%) |
| Calcd.: | 39.22 | 4.45 | 13.46 |
| Found: | 39.55 | 4.21 | 13.47 |

EXAMPLE 102C

In the same manner as Example 97C there was obtained sodium cis-3-[2-(2-hydroxy-4-thiazolyl)-2-methoxyiminoacetamido]-4-methoxycarbonyl-2-oxoazetidine-1-sulfonate (syn-isomer).

IR $\nu_{max}^{KBr}$ cm$^{-1}$: 3450, 1770, 1750, 1660, 1530, 1440, 1250, 1050.

NMR (d$_6$-DMSO, ppm): 3.61(3H, s, COOCH$_3$), 3.87(3H, s, NOCH$_3$), 4.50(1H, d, C$_4$—H), 5.38(1H, C$_3$—H), 6.33(1H, s, 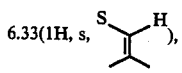 ), 9.60(1H, C$_3$—NH).

| Elemental analysis: C$_{11}$H$_{11}$N$_4$NaO$_9$S$_2$.2H$_2$O | | | |
|---|---|---|---|
| | C (%) | H (%) | N (%) |
| Calcd.: | 28.32 | 3.24 | 12.01 |
| Found: | 28.55 | 3.25 | 12.40 |

EXAMPLE 103C

In the same manner as Example 10C there were obtained the following compounds:

syn- and anti-isomers of sodium cis-3-[2-(2-chloroacetamido-4-thiazolyl)-2-methoxyiminoacetamido]-4-ethoxycarbonyl-2-oxoazetidine-1-sulfonate.

Syn-isomer

IR $\nu_{max}^{KBr}$ cm$^{-1}$: 3350, 1770, 1670, 1610, 1050.

NMR (d$_6$-DMSO, ppm): 1.19(3H, t, J=7 Hz, CH$_2$CH$_3$), 3.86(3H, s, NOCH$_3$), 4.07(2H, q, J=7 Hz, CH$_2$CH$_3$), 4.36(2H, s, ClCH$_2$), 4.46(1H, d, J=5 Hz, C$_4$—H), 5.40(1H, d.d, J=5,9 Hz, C$_3$—H), 7.28(1H, s, 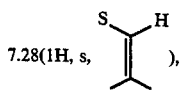 ), 9.44(1H, d, J=9 Hz, C$_3$—NH).

| Elemental analysis: C$_{14}$H$_{15}$ClN$_5$NaO$_9$S$_2$.2H$_2$O | | | |
|---|---|---|---|
| | C (%) | H (%) | N (%) |
| Calcd.: | 30.24 | 3.44 | 12.59 |
| Found: | 30.40 | 3.49 | 12.42 |

Anti-isomer

IR $\nu_{max}^{KBr}$ cm$^{-1}$: 3300, 1760, 1660, 1050.

NMR (d$_6$-DMSO, ppm): 1.20(3H, t, J=7 Hz, CH$_2$CH$_3$), 3.96 (3H, s, NOCH$_3$), 4.16(2H, q, J=7 Hz, CH$_2$CH$_3$), 4.33 (2H, s, ClCH$_2$), 4.47(1H, d, J=5 Hz, C$_4$—H), 5.42(1H, d.d, J=5,9 Hz, C$_3$—H), 8.00(1H, s, 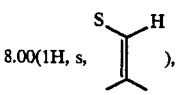 ), 9.12(1H, d, J=9 Hz, C$_3$—NH).

| Elemental analysis: C$_{14}$H$_{15}$ClN$_5$NaO$_9$S$_2$.3H$_2$O | | | |
|---|---|---|---|
| | C (%) | H (%) | N (%) |
| Calcd.: | 29.29 | 3.68 | 12.20 |
| Found: | 29.06 | 3.48 | 11.87 |

EXAMPLE 104C

In the same manner as Example 11C, there were obtained the following compounds:

syn- and anti-isomers of sodium cis-3-[2-(amino-4-thiazolyl)-2-methoxyiminoacetamido]-4-ethoxycarbonyl-2-oxoazetidine-1-sulfonate.

Syn-isomer

IR $\nu_{max}^{KBr}$ cm$^{-1}$: 3450, 3250, 1780, 1730, 1670.

NMR (d$_6$-DMSO, ppm): 1.18(3H, t, J=7 Hz, CH$_2$CH$_3$), 3.80 (3H, s, NOCH$_3$), 4.04(2H, q, J=7 Hz, CH$_2$CH$_3$), 4.43 (1H, d, J=5 Hz, C$_4$—H), 5.36(1H, d.d, J=5,9 Hz, C$_3$—H), 6.57(1H, s, 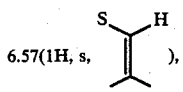), 7.12(2H, br.s, NH$_2$), 9.32(1H, d, J=9 Hz, C$_3$—NH).

| Elemental analysis: C$_{12}$H$_{14}$N$_5$NaO$_8$S$_2$.2½H$_2$O | | | |
|---|---|---|---|
| | C (%) | H (%) | N (%) |
| Calcd.: | 29.50 | 3.92 | 14.33 |
| Found: | 29.39 | 3.71 | 14.09 |

Anti-isomer

IR $\nu_{max}^{KBr}$cm$^{-1}$: 3300, 1770, 1720, 1660.

NMR (d$_6$-DMSO, ppm): 1.18(3H, t, J=7 Hz, CH$_2$CH$_3$), 3.90 (3H, s, NOCH$_3$), 4.15(2H, q, J=7 Hz, CH$_2$CH$_3$), 4.43 (1H, d, J=5 Hz, C$_4$—H), 5.36(1H, d.d, J=5,9 Hz, C$_3$—H), 7.06(2H, br.s, NH$_2$), 7.36(1H, s, 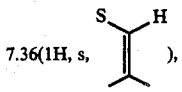), 9.02(1H, d, J=9 Hz, C$_3$—NH).

| Elemental analysis: C$_{12}$H$_{14}$N$_5$NaO$_8$S$_2$.2½H$_2$O | | | |
|---|---|---|---|
| | C (%) | H (%) | N (%) |
| Calcd.: | 29.50 | 3.92 | 14.33 |
| Found: | 29.84 | 3.88 | 14.17 |

EXAMPLE 105C

In the same manner as Example 1C, there was obtained sodium cis-3-[2-(2-chloroacetamido-4-thiazolyl)-2-methoxyiminoacetamido]-4-phenylcarbamoyl-2-oxoazetidine-1-sulfonate (syn-isomer).

IR $\nu_{max}^{KBr}$cm$^{-1}$: 3450, 3250, 1770, 1680, 1050.

NMR (d$_6$-DMSO, ppm): 3.67(3H, s, NOCH$_3$), 4.30(2H, s, ClCH$_2$), 4.60(1H, d, J=5 Hz, C$_4$—H), 5.4(1H, d.d, J=5,9 Hz, C$_3$—H).

EXAMPLE 106C

In the same maanner as Example 11C, there was obtained sodium cis-3-[2-(2-amino-4-thiazolyl)-2-methoxyiminoacetamido]-4-phenylcarbamoyl-2-oxoazetidine-1-sulfonate (syn-isomer).

IR $\nu_{max}^{KBr}$cm$^{-1}$: 3300, 1770, 1680, 1050.

NMR (d$_6$-DMSO, ppm): 3.66(3H, s, NOCH$_3$), 4.55(1H, d, J=5 Hz, C$_4$—H), 5.36(1H, d.d, J=5,9 Hz, C$_3$—H), 6.64(1H, s, 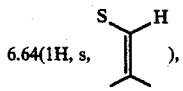), 6.9–7.7(5H, m, Ph-), 9.23(1H, d, J=9 Hz, C$_3$—NH), 9.95(1H, br.s, CONHPh).

EXAMPLE 107C

In the same manner as Example 10C, there was obtained sodium cis-3-[2-(2-chloroacetamido-4-thiazolyl)-2-methoxyiminoacetamido]-4-ethoxycarbonylmethyloxycarbonyl-2-oxoazetidine-1-sulfonate (syn-isomer).

IR $\nu_{max}^{KBr}$cm$^{-1}$: 1780, 1765, 1740, 1670, 1550, 1280, 1055.

NMR (d$_6$-DMSO, ppm): 1.19(3H, t, J=7 Hz, CH$_2$CH$_3$), 3.85(3H, s, NOCH$_3$), 4.11(2H, q, J=7 Hz, CH$_2$CH$_3$), 4.36(2H, s, ClCH$_2$), 4.63(1H, d, J=6 Hz, C$_4$—H), 4.64(2H, q, J=15 Hz, OCH$_2$CO), 5.52(1H, d.d, J=6,9 Hz, C$_3$—H), 7.31(1H, s, 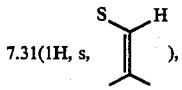), 9.23(1H, d, J=9 Hz, C$_3$—NH).

| Elemental analysis: C$_{16}$H$_{17}$ClN$_5$NaO$_{11}$S$_2$.2H$_2$O | | | |
|---|---|---|---|
| | C (%) | H (%) | N (%) |
| Calcd.: | 31.30 | 3.45 | 11.41 |
| Found: | 31.18 | 3.22 | 11.44 |

EXAMPLE 108C

In the same manner as Example 11C, there was obtained sodium cis-3-[2-(2-amino-4-thiazolyl)-2-methoxyiminoacetamido]-4-ethoxycarbonylmethyloxycarbonyl-2-oxoazetidine-1-sulfonate (syn-isomer).

IR $\nu_{max}^{KBr}$cm$^{-1}$: 1770, 1750, 1670, 1535, 1285, 1055.

NMR (d$_6$-DMSO, ppm): 1.20(3H, t, J=7 Hz, CH$_2$CH$_3$), 3.80 (3H, s, NOCH$_3$), 4.12(2H, q, J=7 Hz, CH$_2$CH$_3$), 4.60 (1H, d, J=6 Hz, C$_4$—H), 4.64(2H, q, J=15 Hz, OCH$_2$CO), 5.48(1H, d.d, J=6,9 Hz, C$_3$—H), 6.59(1H, s, 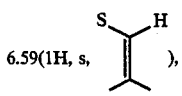), 7.12(2H, br.s, NH$_2$).

| Elemental analysis: C$_{14}$H$_{16}$N$_5$NaO$_{10}$S$_2$.2H$_2$O | | | |
|---|---|---|---|
| | C (%) | H (%) | N (%) |
| Calcd.: | 31.29 | 3.75 | 13.03 |
| Found: | 31.38 | 3.65 | 12.95 |

EXAMPLE 109C

In 3 ml of dry N,N-dimethylformamide is dissolved 630 mg of trans-3-[2-(2-chloroacetamido-4-thiazolyl)-2-methoxyiminoacetamido]-4-acetoxymethyl-2-oxoazetidine (syn-isomer). The solution is cooled to −78° C., followed by addition of 2.68 ml of sulfuric anhydride-N,N-dimethylformamide complex solution (1.69M). The mixture is allowed to stand at 4° C. for 12 hours, and under cooling at 0° C., 358 mg of pyridine and, then, 40 ml of ether are added. The supernatant is discarded and the precipitate is washed three times with 30 ml portions of ether. After removal of the ether, 10 ml of water and 20 ml of Dowex 50W (Na-form) resin are added and the mixture is stirred for 2 hours. The resin is filtered off and the filtrate is concentrated and chromatographed on an Amberlite XAD-II column to give sodium trans-3-[2-(2-chloroacetamido-4-thiazolyl)-2- methoxyiminoacetamido]-4-acetoxymethyl-2-oxoazetidine-1-sulfonate (syn-isomer).

IR $\nu_{max}^{KBr}$cm$^{-1}$: 3450, 1765, 1730, 1640, 1540, 1250, 1040.

NMR (d$_6$-DMSO, ppm): 2.04(3H, s, COCH$_3$), 3.90(3H, s, NOCH$_3$), 4.35(2H, s, ClCH$_2$), 4.77(1H, d.d, J=3,8 Hz, C$_3$—H),

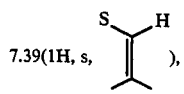 7.39(1H, s, 9.45(1H, d, J=8 Hz, C$_3$—NH).

| Elemental analysis: C$_{14}$H$_{15}$ClN$_5$NaO$_9$S$_2$.H$_2$O | | | |
|---|---|---|---|
| | C (%) | H (%) | N (%) |
| Calcd.: | 31.26 | 3.19 | 13.02 |
| Found: | 31.60 | 3.41 | 12.91 |

EXAMPLE 110C

In the same manner as Example 11C, there was obtained sodium trans-3-[2-(2-amino-4-thiazolyl)-2-methoxyiminoacetamido]-4-acetoxymethyl-2-oxoazetidine-1-sulfonate (syn-isomer).

IR $\nu_{max}^{KBr}$cm$^{-1}$: 3420, 1765, 1730, 1660, 1530, 1245, 1050.

NMR (d$_6$-DMSO, ppm): 2.01(3H, s, COCH$_3$), 3.83(3H, s, NOCH$_3$), 4.76(1H, d.d, J=3,8 Hz, C$_3$—H),

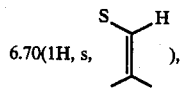 6.70(1H, s, 7.16(1H, br.s, NH$_2$), 9.30(1H, d, J=8 Hz, C$_3$—NH).

| Elemental analysis: C$_{12}$H$_{14}$N$_5$NaO$_8$S$_2$.1½H$_2$O | | | |
|---|---|---|---|
| | C (%) | H (%) | N (%) |
| Calcd.: | 30.64 | 3.64 | 14.89 |
| Found: | 30.66 | 3.65 | 14.94 |

EXAMPLE 111C

In the same procedure as Example 109C, there was obtained sodium trans-3-[2-(2-chloroacetamido-4-thiazolyl)-2-methoxyiminoacetamido]-4-methyl-2-oxoazetidine-1-sulfonate (syn-isomer).

IR $\nu_{max}^{KBr}$cm$^{-1}$: 3420, 1760, 1660, 1560, 1270, 1050, 1030.

NMR (d$_6$-DMSO, ppm): 1.44(3H, d, J=6 Hz, C$_4$—CH$_3$), 3.90 (3H, s, NOCH$_3$), 4.33(2H, s, ClCH$_2$), 4.41(1H, d.d, J=3,8 Hz, C$_3$—H),

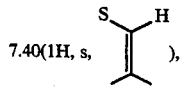 7.40(1H, s, 9.38(1H, d, J=8 Hz, C$_3$—NH).

| Elemental analysis: C$_{12}$H$_{13}$ClN$_5$NaS$_2$O$_7$.2H$_2$O | | | |
|---|---|---|---|
| | C (%) | H (%) | N (%) |
| Calcd.: | 28.94 | 3.44 | 14.07 |
| Found: | 29.11 | 3.48 | 14.06 |

EXAMPLE 112C

In 3 ml of water is dissolved 300 mg of lyophilized sodium cis-3-[2-(2-amino-4-thiazolyl)-2-methoxyiminoacetamido]-4-methoxycarbonyl-2-oxoazetidine-1-sulfonate (syn-isomer) as obtained in Example 2, and the mixture is stirred for a while, whereupon a white turbidity develops to give rise to crystals. The mixture is allowed to stand under cooling overnight, and after addition of 10 ml of ethanol, the mixture is further cooled for 3 hours. The resultant crystalline precipitate is recovered by filtration and dried to give 241 mg of the monohydrate of the above-mentioned compound as colorless crystals, m.p. 235°–245° C. (decomp.).

IR $\nu_{max}^{KBr}$cm$^{-1}$: 1785, 1750, 1690.

| Elemental analysis: C$_{11}$H$_{12}$N$_5$NaO$_8$S$_2$.H$_2$O | | | |
|---|---|---|---|
| | C (%) | H (%) | N (%) |
| Calcd.: | 29.53 | 3.15 | 15.66 |
| Found: | 29.48 | 3.13 | 15.54 |

EXAMPLE 113C

In 3 ml of 1N HCl is dissolved 86 mg of sodium cis-3-[2-(2-aminothiazol-4-yl)-2-methoxyiminoacetamido]-4-methoxycarbonyl-2-azetidinone-1-sulfonate (syn-isomer), and the solution is stirred under ice-cooling. Then, 500 mg of zinc dust is added all at once. The mixture is stirred for 5 minutes, after which the reaction mixture is filtered. The filtrate is chromatographed on an Amberlite XAD-II column and developed with water. The fractions containing the desired product are pooled and lyophilized to give cis-3-[DL-2-(2-aminothiazol-4-yl)-2-ammonioacetamido]-4-methoxycarbonyl-2-azetidinone-1-sulfonate.

IR $\nu_{max}^{KBr}$cm$^{-1}$: 3400, 1775, 1750, 1690.

NMR (d$_6$-DMSO, ppm): 3.44 & 3.66(3H, s each, COOCH$_3$), 4.44 & 4.47(1H, d each, J=5 Hz, C$_4$—H), 4.67 & 4.77(1H, s each, —CHCO), 5.40 & 5.26(1H, dd each, J=5 & 9 Hz, C$_3$—H),

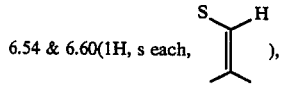 6.54 & 6.60(1H, s each, 7.10 & 7.15(2H, br.s each, NH$_2$), 8.7–9.4 (1H, br., CONH).

EXAMPLE 114C

The procedure of Example 113C is repeated up to the zinc dust reduction and the filtration step to give a filtrate. To this filtrate is added 500 mg of sodium cyanate, and the mixture is stirred at 45° C. for 30 minutes. The reaction mixture is cooled with ice, adjusted to pH 1 with 1N HCl and, then, to pH 7 with 1N sodium hydrogen carbonate. The mixture is chromatographed on Amberlite XAD-II and Sephadex LH-20 columns in this order, using water as the developer solvent. The fractions containing the desired compound are pooled and lyophilized to give sodium cis-3-[DL-2-(2-aminothiazol-4-yl)-2-carbamoylaminoacetamido]-4-methoxycarbonyl-2-azetidinone-1-sulfonate.

IR $\nu_{max}^{KBr}$cm$^{-1}$: 3350, 1770, 1670, 1620.

NMR (d$_6$-DMSO, ppm): 3.48 & 3.62 (3H, s each, COOCH$_3$), 4.36 & 4.40(1H, d each, J=5 Hz, C$_4$—H), 5.0–5.5 (2H, m, —CHCON & C$_3$—H), 5.66(2H, br.s, CONH$_2$),

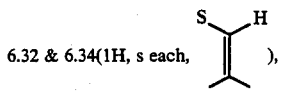
6.32 & 6.34(1H, s each, 6.86(2H, br.s, NH$_2$).

EXAMPLE 115C

A mixture of 60 mg of cis-3-[DL-2-(2-aminothiazol-4-yl)-2-ammonioacetamido]-4-methoxycarbonyl-2-azetidinone-1-sulfonate, 45 mg of diisopropylethylamine, 1 ml of dichloromethane and 3 ml of acetone is stirred under ice-cooling, and 77 μl of 1-chloroformyl-2,3-dioxo-4-ethyl-1,4-piperazine and, then, 1 ml of water are added. After the mixture is vigorously stirred for 30 minutes, the organic solvent is distilled off under reduced pressure. The residue is chromatographed on columns of Amberlite IR-120 (Na-form), Amberlite XAD-II and Sephadex LH-20 in this order, using water as the eluent. The fractions containing the desired product are pooled and lyophilized to give sodium cis-3-[DL-2-(2-aminothiazol-4-yl)-2-(2,3-dioxo-4-ethyl-1,4-piperazin-1-yl)carbonylaminoacetamido]-4-methoxycarbonyl-2-azetidinone-1-sulfonate.

IR $\nu_{max}^{KBr}$cm$^{-1}$: 3400, 1780, 1720, 1680, 1620.

NMR (d$_6$-DMSO, ppm): 1.10(3H, t, J=7 Hz, CH$_3$CH$_2$—), 3.45 & 3.62(3H, s each, COOCH$_3$), 3.2–4.2(4H, m, —CH$_2$CH$_2$—), 4.37 & 4.43(1H, d each, J=5 hz, 4—H), 5.0–5.5(1H, m, 3—H), 5.38(1H, d, J=8 Hz, —CHCON),

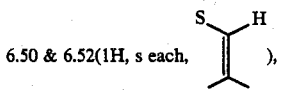
6.50 & 6.52(1H, s each, 8.72 & 8.92(1H, d each, J=8 Hz, —CONH—C$_3$), 9.52 & 9.56 (1H, d each, J=8 Hz, NCONH).

EXAMPLE 116C

In 2 ml of acetonitrile is suspended 40 mg of cis-3-[DL-2-(2-aminothiazol-4-yl)-2-ammonioacetamido]-4-methoxycarbonyl-2-azetidinone-1-sulfonate, and after the suspension is stirred under ice-cooling, 150 μl of aceticformic anhydride is added. The mixture is stirred for 5 minutes, after which a solution of 20 mg of sodium hydrogen carbonate in 2 ml of water is added. The mixture is stirred for 30 minutes and concentrated to one-third of its original volume. To the residue is added 1 ml of sodium hydrogen carbonate solution (1M), and the resulting mixture is chromatographed on columns of Amberlite XAD-II and Sephadex LH-20 in this order, using water as the eluent. The fractions containing the desired product are pooled and lyophilized to give sodium cis-3-[DL-2-(2-aminothiazol-4-yl)-2-formamidoacetamido]-4-methoxycarbonyl-2-azetidinone-1-sulfonate.

IR $\nu_{max}^{KBr}$cm$^{-1}$: 3400, 1780, 1670, 1620.

NMR (D$_2$O, ppm): 3.63 & 3.74(3H, s each, COOCH$_3$), 4.89 & 4.93(1H, d each, J=6 Hz, C$_4$—H), 5.38 & 5.56(1H, d each, J=6 Hz, C$_3$—H), 5.44(1H, s, —CH=),

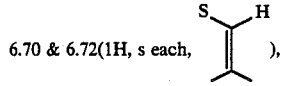
6.70 & 6.72(1H, s each, 8.17 & 8.19(1H, s each, NCHO).

EXAMPLE 117C

In a mixture of 1 ml of acetonitrile and 0.5 ml of dimethylacetamide is suspended 40 mg of cis-3-[DL-2-(2-aminothiazol-4-yl)-2-ammonioacetamido]-4-methoxycarbonyl-2-azetidinone-1-sulfonate, and under stirring at −20° C., 50 μl of methanesulfonyl chloride and 100 μl of diisopropylethylamine are added. The mixture is stirred at that temperature for 10 minutes and, then, at 0° C. for 20 minutes. The reaction mixture is cooled to −50° C., followed by addition of ether and shaking (30 ml×3). The resultant syrupy insolubles are separated and 5 ml of water is added thereto. The solution is chromatographed on columns of Amberlite IR-120 (Na-form) and Amberlite XAD-II in this order, using water as the eluent. The fractions containing the desired product are pooled and lyophilized to give sodium cis-3-[DL-2-(2-aminothiazol-4-yl)-2-methanesulfonylaminoacetamido]-4-methoxycarbonyl-2-azetidinone-1-sulfonate.

IR $\nu_{max}^{KBr}$cm$^{-1}$: 3400, 1780, 1690, 1630.

NMR (D$_2$O, ppm): 3.03 & 3.06 (3H, s each, CH$_3$SO$_2$), 3.76 & 3.65(3H, s each, COOCH$_3$), 4.91 & 4.94(1H, d each, J=6 Hz, C$_4$—H), 5.12(1H, br.s, CHCON), 5.41 & 5.56(1H, d each, J=6 Hz, C$_3$—H),

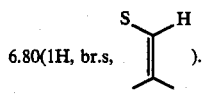
6.80(1H, br.s,                ).

EXAMPLE 118C

In 3 ml of acetonitrile is suspended 80 mg of cis-3-[DL-2-(2-aminothiazol-4-yl)-2-ammonioacetamido]-4-methoxycarbonyl-2-azetidinone-1-sulfonate, and under ice-cooling and stirring, 38 μl of benzoyl chloride and then 1 ml of 1N sodium hydrogen carbonate are added. The mixture is stirred for 30 minutes, followed by addition of 10 ml of water and 15 ml of ethyl acetate. After shaking, the aqueous layer is taken and chromatographed on an Amberlite XAD-II column, using water as the eluent. The fractions containing the desired product are pooled and lyophilized to give sodium cis-3-[DL-2-(2-aminothiazol-4-yl)-2-benzoylaminoacetamido]-4-methoxycarbonyl-2-azetidinone-1-sulfonate.

IR $\nu_{max}^{KBr}$cm$^{-1}$: 3300, 1770, 1750(sh), 1640.

NMR (D$_2$O, ppm): 3.60 & 3.73(3H, s each, COOCH$_3$), 4.89 & 4.93(1H, d each, J=6 Hz, C$_4$—H), 5.43 & 5.58(1H, d each, J=6 Hz, C$_3$—H), 5.58(1H, s, CHCON),

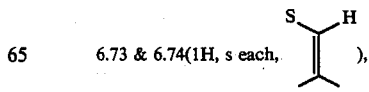
6.73 & 6.74(1H, s each, 7.4–8.0(5H, m, aromatic protons).

EXAMPLE 119C

In 1 ml of dimethylacetamide is suspended 80 mg of cis-3-[DL-2-(2-aminothiazol-4-yl)-2-ammonioacetamido]-4-methoxycarbonyl-2-azetidinone-1-sulfonate, and under ice-cooling and stirring, 50 mg of p-toluenesulfonyl chloride and then 120 μl of diisopropylethylamine are added. The mixture is stirred for 30 minutes. The reaction mixture is further stirred at room temperature for 2 hours, followed by addition of ether and shaking (30 ml×3). The resultant syrupy insolubles are chromatographed on columns of Amberlite IR-120 (Na-form), Amberlite XAD-II and Sephadex LH-20 in this order, using water as the eluent. The fractions containing the desired product are pooled and lyophilized to give sodium cis-3-[DL-2-(2-aminothiazol-4-yl)-2-p-toluenesulfonylaminoacetamido]-4-methoxycarbonyl-2-azetidinone-1-sulfonate.

IR $\nu_{max}^{KBr}$cm$^{-1}$: 3400, 1770, 1690, 1620.

NMR (D$_2$O, ppm): 2.40(3H, s, CH$_3$), 3.56 & 3.72(3H, s, each, COOCH$_3$), 4.82 & 4.88(1H, d each, J=6 Hz, C$_4$—H), 4.92(1H, s, NCHCON), 5.30 & 5.35(1H, d each, J=6 Hz, C$_3$—H),

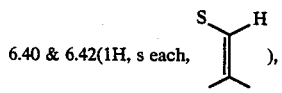

6.40 & 6.42(1H, s each, 7.36 & 7.62(4H, d each, J=8 Hz, aromatic protons).

EXAMPLE 120C

In 1 ml of dimethylacetamide is suspended 80 mg of cis-3-[DL-2-(2-aminothiazol-4-yl)-2-ammonioacetamido]-4-methoxycarbonyl-2-azetidinone-1-sulfonate, and under ice-cooling and stirring, 20 μl of 2-methoxyacetyl chloride is added. The mixture is stirred at room temperature for 2 hours, and then cooled with ice and 300 mg of 1N sodium hydrogen carbonate is added. The mixture is further stirred for 20 minutes, followed by addition of ethyl ether and shaking (30 ml×3). The resultant syrupy insolubles are chromatographed on columns of Amberlite XAD-II and Sephadex LH-20 in this order, using water as the eluent. The fractions containing the desired product are pooled and lyophilized to give sodium cis-3-[DL-2-(2-aminothiazol-4-yl)-2-(2-methoxyacetamido)acetamido]-4-methoxycarbonyl-2-azetidinone-1-sulfonate.

IR $\nu_{max}^{KBr}$cm$^{-1}$: 3400, 1770, 1670, 1630.

NMR (D$_2$O, ppm): 3.46(3H, s, CH$_3$O), 3.66 & 3.76(3H, s each, COOCH$_3$), 4.10(2H, s, OCH$_2$C), 4.91 & 4.94 (1H, d each, J=6 Hz, C$_4$—H), 5.41 & 5.55(1H, d each, J=6 Hz, C$_3$—H), 5.49(1H, s, —CHCO),

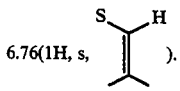

6.76(1H, s,

EXAMPLE 121C

In 2 ml of acetonitrile is suspended 80 mg of cis-3-[DL-2-(2-aminothiazol-4-yl)-2-ammonioacetamido]-4-methoxycarbonyl-2-azetidinone-1-sulfonate, and the suspension is cooled with ice and stirred. To this suspension are added 200 μl of acetic anhydride, 60 mg of sodium acetate and 2 ml of water, and the mixture is stirred for 10 minutes. The mixture is further stirred at room temperature for one hour, after which 3.6 ml of sodium hydrogen carbonate solution (1M) is added. The resultant mixture is chromatographed on columns of Amberlite XAD-II and, then, Sephadex LH-20, using water as the eluent. The fractions containing the desired product are pooled and lyophilized to give sodium cis-3-[DL-2-(2-aminothiazol-4-yl)-2-acetamidoacetamido]-4-methoxycarbonyl-2-azetidinone-1-sulfonate.

IR $\nu_{max}^{KBr}$cm$^{-1}$: 3400, 1770, 1660, 1520.

NMR (D$_2$O, ppm): 1.93 & 2.08 (3H, s each, COCH$_3$), 3.63 & 3.74(3H, s each, COOCH$_3$), 4.89 & 4.92(1H, d each, J=6 Hz, C$_4$—H), 5.34(1H, s, —CHCON), 5.40 & 5.56(1H, d each, J=6 Hz, C$_3$—H),

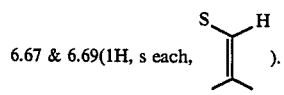

6.67 & 6.69(1H, s each,

EXAMPLE 122C

In 20 ml of dry N,N-dimethylformamide is suspended 402 mg of cis-3-[2-(2-chloroacetamido-4-thiazolyl)-2-methoxyiminoacetamido]-4-methylcarbamoyl-2-oxoazetidine (syn-isomer), followed by addition of 320 mg of sulfuric anhydride-pyridine complex. The mixture is stirred for 24 hours, and after addition of 40 ml of dry N,N-dimethylformamide and 320 mg of sulfuric anhydride-pyridine complex, the mixture is stirred for 72 hours. The reaction mixture is poured into 500 ml of ether and the insolubles are collected by filtration, washed with ether and suspended in 500 ml of water. After addition of 30 ml of Dowex 50W (Na-form) resin, the suspension is stirred for 3 hours. The resin is filtered off and the filtrate is lyophilized to give a colorless powder. This powder is dissolved in water, and the aqueous solution is chromatographed on an Amberlite XAD-II column and lyophilized to give sodium cis-3-[2-(2-chloroacetamido-4-thiazolyl)-2-methoxyiminoacetamido]-4-methylcarbamoyl-2-oxoazetidine-1-sulfonate (syn-isomer).

IR $\nu_{max}^{KBr}$cm$^{-1}$: 3250, 1770, 1650, 1050.

NMR (d$_6$-DMSO, ppm): 2.68(3H, d, J=5 Hz, NHCH$_3$), 3.85(3H, s, NOCH$_3$), 5.35(1H, d.d, J=5, 9 Hz, C$_3$—H),

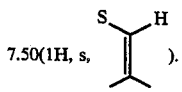

7.50(1H, s,

EXAMPLE 123C

In the same manner as Example 11C, there was obtained sodium cis-3-[2-(2-amino-4-thiazolyl)-2-methoxyiminoacetamido]-4-methylcarbamoyl-2-oxoazetidine-1-sulfonate (syn-isomer).

IR $\nu_{max}^{KBr}$cm$^{-1}$: 3350, 1770, 1670, 1050.

NMR (d$_6$-DMSO, ppm): 2.60(3H, d, J=5 Hz, NHCH$_3$), 3.80(3H, s, NOCH$_3$), 4.35(1H, d, J=5 Hz, C$_4$—H), 5.28(1H, d.d, J=5, 9 Hz, C$_3$—H),

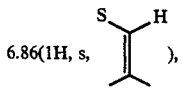

6.86(1H, s, 7.13(2H, br.s, NH$_2$), 7.65(1H, d, J=5 Hz, NHCH$_3$), 9.01(1H, d, J=9 Hz, C$_3$—NH).

EXAMPLE 124C

In the same manner as Example 70C, there was obtained sodium trans-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine-1-sulfonate.

IR $\nu_{max}^{KBr}$cm$^{-1}$: 3400–3200, 2980, 1780, 1740, 1680, 1050.

| Elemental analysis: C$_{23}$H$_{22}$ClN$_6$NaO$_{13}$S$_2$.2H$_2$O | | | |
|---|---|---|---|
| | C (%) | H (%) | N (%) |
| Calcd.: | 36.88 | 3.50 | 11.22 |
| Found: | 37.02 | 3.41 | 11.54 |

EXAMPLE 125C

In the same manner as Example 67C, there was obtained sodium trans-3-{2-(2-amino-4-thiazolyl)-2-[1-methyl-1-(p-nitrobenzyloxycarbonyl)ethyloxyimino]acetamido}-4-methoxycarbonyl-2-oxoazetidine-1-sulfonate (syn-isomer).

IR $\nu_{max}^{KBr}$cm$^{-1}$: 3325, 1780, 1740, 1670, 1600, 1520, 1050.

NMR (d$_6$-DMSO, ppm): 1.5(6H, s, 2×CH$_3$), 3.69(3H, s, COOCH$_3$), 4.15(1H, d, J=3 Hz, C$_4$—H), 4.82(1H, d.d, J=3, 9 Hz, C$_3$—H), 5.33(2H, s, COOCH$_2$),

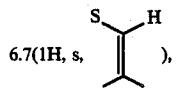

6.7(1H, s, ), 7.25(2H, br.s, NH$_2$), 7.65, 8.15(2×2H, 2×d, aromatic protons), 9.37(1H, d, J=9 Hz, C$_3$—NH).

| Elemental analysis: C$_{21}$H$_{21}$N$_6$NaO$_{12}$S$_2$.2½H$_2$O | | | |
|---|---|---|---|
| | C (%) | H (%) | N (%) |
| Calcd.: | 37.01 | 3.84 | 12.33 |
| Found: | 36.90 | 3.78 | 12.30 |

EXAMPLE 126C

In the same manner as Example 68C, there was obtained trans-3-[2-(2-amino-4-thiazolyl)-2-(1-carboxy-1-methylethoxyimino)acetamido]-4-methoxycarbonyl-2-oxoazetidine-1-sulfonic acid disodium salt (syn-isomer).

IR $\nu_{max}^{KBr}$cm$^{-1}$: 3375, 1780, 1745, 1580, 1050.

NMR (d$_6$-DMSO, ppm): 1.40, 1.43(2×3H, 2×s, 2×CH$_3$), 3.7 (3H, s, COOCH$_3$), 4.17(1H, d, J=3 Hz, C$_4$—H), 4.85(1H, d.d, J=3, 9 Hz, C$_3$—H),

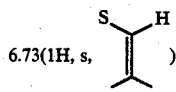

6.73(1H, s, ), 7.12(2H, s, NH$_2$), 11.7(1H, d, J=9 Hz, C$_3$—NH).

| Elemental analysis: C$_{14}$H$_{15}$N$_5$Na$_2$O$_{10}$S$_2$.5H$_2$O | | | |
|---|---|---|---|
| | C (%) | H (%) | N (%) |
| Calcd.: | 27.41 | 4.11 | 11.42 |
| Found: | 27.10 | 3.90 | 11.46 |

EXAMPLE 127C

In the same manner as Example 61C, there was obtained sodium cis-3-[2-(2-chloroacetamido-4-thiazolyl)-2-(1-methoxycarbonyl-1-methylethoxyimino)acetamido]-4-methoxycarbonyl-2-oxoazetidine-1-sulfonate (syn-isomer).

IR $\nu_{max}^{KBr}$cm$^{-1}$: 3250, 2950, 1780, 1740, 1680.

NMR (d$_6$-DMSO, ppm): 1.46(6H, s, NOCMe$_2$), 3.63, 3.66 (2×3H, 2×s, 2×COOCH$_3$), 4.33(2H, s, ClCH$_2$), 4.5(1H, d, J=6 Hz, C$_4$—H), 5.49(1H, d.d, J=6, 9 Hz, C$_3$—H),

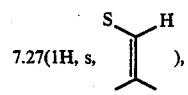

7.27(1H, s, ), 9.22(1H, d, J=9 Hz, C$_3$—NH), 12.93(1H, br.s, ClCH$_2$CONH).

| Elemental analysis: C$_{17}$H$_{19}$ClN$_5$NaO$_{11}$S$_2$.1½H$_2$O | | | |
|---|---|---|---|
| | C (%) | H (%) | N (%) |
| Calcd.: | 32.99 | 3.58 | 11.32 |
| Found: | 33.26 | 3.64 | 11.14 |

EXAMPLE 128C

In the same manner as Example 62C, there was obtained sodium cis-3-[2-(2-amino-4-thiazolyl)-2-(1-methoxycarbonyl-1-methylethoxyimino)acetamido]-4-methoxycarbonyl-2-oxoazetidine-1-sulfonate (syn-isomer).

IR $\nu_{max}^{KBr}$cm$^{-1}$: 3400, 1780, 1735, 1670.

NMR (d$_6$-DMSO, ppm): 1.43(6H, s, NOCMe$_2$), 3.62, 3.64 (2×3H, 2×s, 2×COOCH$_3$), 4.48(1H, d, J=6 Hz, C$_4$—H), 5.43(1H, d.d, J=6, 9 Hz, C$_3$—H),

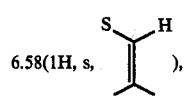

6.58(1H, s, ), 7.2 (2H, s, NH$_2$), 9.05(1H, d, J=9 Hz, C$_3$—NH).

| Elemental analysis: C$_{15}$H$_{18}$N$_5$NaO$_{10}$S$_2$.2H$_2$O | | | |
|---|---|---|---|
| | C (%) | H (%) | N (%) |
| Calcd.: | 32.67 | 4.02 | 12.70 |
| Found: | 32.63 | 3.96 | 12.43 |

EXAMPLE 129C

In the same manner as Example 61C, there was obtained sodium cis-3-{2-(2-chloroacetamido-4-thiazolyl)-2-[1-methyl-1-(2-trimethylsilylethoxycarbonyl)ethoxyimino]acetamido}-4-methoxycarbonyl-2-oxoazetidine-1-sulfonate (syn-isomer).

IR $\nu_{max}^{KBr}$cm$^{-1}$: 3400, 1775, 1740.

NMR (d$_6$-DMSO, ppm): 0.92(2H, CH$_2$Si), 1.45(6H, s, NOCMe$_2$), 3.64(3H, s, COOCH$_3$), 4.16(2H, COOCH$_2$), 4.35(2H, s, ClCH$_2$), 4.50(1H, d, J=6 Hz, C$_4$—H), 5.50(1H, d.d, J=6, 9 Hz, C$_3$—NH),

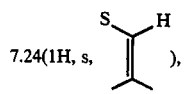
7.24(1H, s,   ), 9.11(1H, d, J=9 Hz, C₃—NH), 12.89(1H, br.s, ClCH₂CONH).

EXAMPLE 130C

In the same manner as Example 62C, there was obtained sodium cis-3-{2-(2-amino-4-thiazolyl)-2-[1-methyl-1-(2-trimethylsilylethoxycarbonyl)ethoxyimino]acetamido}-4-methoxycarbonyl-2-oxoazetidine-1-sulfonate (syn-isomer).

IR $\nu_{max}^{KBr}$cm$^{-1}$: 3410, 1780, 1740, 1675.

NMR (d₆-DMSO, ppm): 0.95(2H, CH₂Si), 1.48(6H, s, NOCMe₂), 3.66(3H, s, COOCH₃), 4.18(2H, COOCH₂), 4.50(1H, d, J=6 Hz, C₄—H), 5.47(1H, d.d, J=6, 9 Hz, C₃—H),

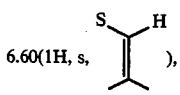
6.60(1H, s,   ), 7.19(2H, br.s, NH₂), 8.98(1H, d, J=9 Hz, C₃NH).

EXAMPLE 131C

In 2 ml of dry N,N-dimethylformamide is dissolved 630 mg of cis-3-{2-(2-chloroacetamido-4-thiazolyl)-2-[1-methyl-1-(p-nitrobenzyloxycarbonyl)ethyloxyimino]acetamido}-4-carbamoyl-2-oxoazetidine (syn-isomer) as obtained in Reference Example 166C. Then, at −78° C., 1.69 ml of sulfuric anhydride-N,N-dimethylformamide complex solution (1.56M) is added. The mixture is allowed to stand at 4° C. in a refrigerator overnight. To this reaction mixture are added 208 mg of pyridine under ice-cooling and then 30 ml of ether, and the resultant spyrupy precipitate is washed with ether by the decantation method (20 ml×3). The precipitate is dissolved in 15 ml of water, and after addition of 15 ml of Dowex 50W (Na-form) resin, the mixture is stirred at room temperature for 2 hours. The resin is filtered off and the filtrate is concentrated under reduced pressure. The residue is chromatographed on an Amberlite XAD-II column and serial elution is carried out with water and 10-20% ethanol to give the disulfo compound (Example 134C), followed by further elution with 40% ethanol. The fraction of 40% ethanol including desired compound is lyophilized to give sodium cis-3-{2-(2-chloroacetamido-4-thiazolyl)-2-[1-methyl-1-(p-nitrobenzyloxycarbonyl)ethyloxyimino]-acetamido}-4-carbamoyl-2-oxoazetidine-1-sulfonate (syn-isomer).

IR $\nu_{max}^{KBr}$cm$^{-1}$: 3420, 1770, 1730, 1690, 1520, 1350, 1280, 1055.

NMR (d₆-DMSO, ppm): 1.50(6H, s, 2×CH₃), 4.34(2H, s, ClCH₂), 4.38(1H, d, J=6 Hz, C₄—H), 5.31(2H, s, COOCH₂), 5.34(1H, d.d., J=6, 9 Hz, C₃—H),

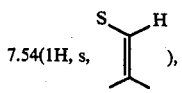
7.54(1H, s,   ), 7.62, 8.07(2×2H, 2×d, aromatic protons).

EXAMPLE 132C

In 20 ml of water is dissolved 280 mg of sodium cis-3-{2-(2-chloroacetamido-4-thiazolyl)-2-[1-methyl-1-(p-nitrobenzyloxycarbonyl)ethyloxyimino]acetamido}-4-carbamoyl-2-oxoazetidine-1-sulfonate (syn-isomer) as obtained in Example 131C, and under ice-cooling and stirring, 104 mg of sodium monomethyldithiocarbamate is added. The mixture is stirred at room temperature for 1.5 hours. The reaction mixture is twice washed with ether, and then purified by column chromatography on Amberlite XAD-II (40 g), eluting with water and then 20% ethanol. The fractions including the desired product are combined and lyophilized to give sodium cis-3-{2-(2-amino-4-thiazolyl)-2-[1-methyl-1-(p-nitrobenzyloxycarbonyl)ethyloxyimino]acetamido}-4-carbamoyl-2-oxoazetidine-1-sulfonate (syn-isomer).

IR $\nu_{max}^{KBr}$cm$^{-1}$: 3410, 1770, 1730, 1685, 1525, 1350, 1280, 1055.

NMR (d₆-DMSO, ppm): 1.48(6H, s, 2×CH₃), 4.37(1H, d, J=6 Hz, C₄—H), 5.33(2H, s, COOCH₂),

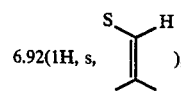
6.92(1H, s,   ), 7.21(2H, br.s, NH₂), 7.40(2H, br.s, NH₂), 7.68, 8.16(2H each, d, J=9 Hz, aromatic protons), 8.82 (1H, d, J=9 Hz, C₃—NH).

EXAMPLE 133C

In 10 ml of water is dissolved 200 mg of sodium cis-3-{2-(2-amino-4-thiazolyl)-2-[1-methyl-1-(p-nitrobenzyloxycarbonyl)ethyloxyimino]acetamido}-4-carbamoyl-2-oxoazetidine-1-sulfonate (syn-isomer) as obtained in Example 132C, followed by addition of 200 mg of 10% palladium-on-carbon. The mixture is stirred in a hydrogen atmosphere at room temperature for one hour. The catalyst is filtered off, and under icecooling 27 mg of sodium hydrogen carbonate is added. The mixture is stirred for 5 minutes and washed with ethyl acetate. To the aqueous layer is added 30 ml of Dowex 50W (H-form) resin, and the mixture is stirred for 1.5 hours. The resin is filtered off and the filtrate is concentrated under reduced pressure to about a half volume thereof. The residue is chromatographed on an Amberlite XAD-II (40 g) column, eluting with water and then 15% ethanol. The fractions including the desired product are combined and lyophilized to give cis-3-[2-(2-amino-4-thiazolyl)-2-(1-methyl-1-carboxyethyloxyimino)acetamido]-4-carbamoyl-2-oxoazetidine-1-sulfonic acid (syn-isomer).

IR $\nu_{max}^{KBr}$cm$^{-1}$: 3250, 1770, 1690, 1625, 1280, 1230, 1045.

NMR (d₆-DMSO, ppm): 1.51(6H, s, 2×CH₃), 4.36(1H, d, J=6 Hz, C₄—H), 5.33(1H, d.d, J=6, 9 Hz, C₃—H),

7.18(1H, s,   ), 9.18(1H, d, J=9 Hz, C₃—NH).

| Elemental analysis: $C_{13}H_{16}N_6O_9S_2 \cdot 1\frac{1}{2}H_2O$ | | | |
|---|---|---|---|
| | C (%) | H (%) | N (%) |
| Calcd.: | 31.77 | 3.90 | 17.10 |
| Found: | 31.69 | 3.90 | 17.00 |

EXAMPLE 134C

The 10–20% ethanol eluate fractions as obtained by Amberlite XAD-II column chromatography in Example 131C are lyophilized to give 174 mg of cis-3-{2-(2-chloroacetamido-4-thiazolyl)-2-[1-methyl-1-(p-nitrobenzyloxycarbonyl)ethyloxyimino]acetamido}-4-sulfoaminocarbonyl-2-oxoazetidine-1-sulfonic acid disodium salt (syn-isomer) as a colorless powder. The amino-protecting group and then the carboxylprotecting group are removed from this product in the same manner as Examples 132C and 133C, respectively, to give cis-3-[2-(2-amino-4-thiazolyl)-2-(1-methyl-1-carboxyethyloxyimino)acetamido]-4-sulfoaminocarbonyl-2-oxoazetidine-1-sulfonic acid trisodium salt (syn-isomer).

IR $\nu_{max}^{KBr}$cm$^{-1}$: 3400, 1770, 1630.

NMR (d$_6$DMSO+D$_2$O, ppm): 1.34(3H, s, CH$_3$), 1.50(3H, s, CH$_3$), 4.49(1H, d, J=6 Hz, C$_4$—H), 5.45(1H, d, J=6 Hz, C$_3$—H),

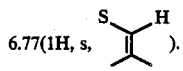

6.77(1H, s,          ).

EXAMPLE 135C cis-4-Acetoxymethyl-3-benzyloxycarboxamido-2-oxoazetidine as obtained in Reference Example 7C is reacted in the same manner as Reference Example 91C to give cis-3-[2-(2-chloroacetamido-4-thiazolyl)-2-[1-methyl-1-(p-nitrobenzyloxycarbonyl)ethyloxyimino]acetamido]-4-acetoxymethyl-2-oxoazetidine (syn-isomer) as colorless crystals melting at 120°–123° C.

IR $\nu_{max}^{Nujol}$cm$^{-1}$: 3250, 1740, 1670.

The above product is sulfonated in the same manner as Example 70C. Then, the procedure of Example 67C was followed to remove the amino-protecting group to give sodium cis-3-{2-(2-amino-4-thiazolyl)-2-[1-methyl-1-(p-nitrobenzyloxycarbonyl)ethyloxyimino]acetamido}-4-acetoxymethyl-2-oxoazetidine-1-sulfonate (syn-isomer).

IR $\nu_{max}^{KBr}$cm$^{-1}$: 3400, 1770, 1740, 1670.

NMR (d$_6$-DMSO, ppm): 1.47(6H, s, 2×CH$_3$), 1.95(3H, s, COCH$_3$),

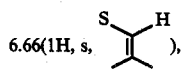

6.66(1H, s,          ), 7.13(2H, br.s, NH$_2$).

| Elemental analysis: $C_{22}H_{23}N_6O_{12}S_2Na \cdot 2H_2O$ | | | |
|---|---|---|---|
| | C (%) | H (%) | N (%) |
| Calcd.: | 38.48 | 3.96 | 12.24 |
| Found: | 38.46 | 4.09 | 12.18 |

EXAMPLE 136C

In the same manner as Example 68C, there was obtained cis-3-[2-(2-amino-4-thiazolyl)-2-(1-methyl-1-carboxyethyloxyimino)acetamido]-4-acetoxymethyl-2-oxoazetidine-1-sulfonic acid disodium salt (syn-isomer).

IR $\nu_{max}^{KBr}$cm$^{-1}$: 3350, 1760, 1650.

NMR (d$_6$-DMSO, ppm): 1.36(3H, s, CH$_3$), 1.43(3H, s, CH$_3$), 1.93(3H, s, COCH$_3$), 5.25(1H, d.d, J=5, 9 Hz, C$_3$—H),

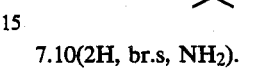

6.70(1H, s,          ), 7.10(2H, br.s, NH$_2$).

EXAMPLE 137C

The procedure of Reference Example 3C is followed to remove the 3-amino-protecting group from cis-3-benzyloxycarboxamido-4-carbamoyloxymethyl-2-oxoazetidine as obtained in Reference Example 167C to give the corresponding 3-amino compound as colorless crystals.

IR $\nu_{max}^{Nujol}$cm$^{-1}$: 3430, 1740, 1695.

The above product is acylated in the same manner as Reference Example 4C to give cis-3-[2-(2-chloroacetamido-4-thiazolyl)-2-methoxyiminoacetamido]-4-carbamoyloxymethyl-2-oxoazetidine (syn-isomer) as colorless crystals.

IR $\nu_{max}^{Nujol}$cm$^{-1}$: 3250, 1750, 1680, 1660.

The above product is sulfonated in the same manner as Example 1C to give sodium cis-3-[2-(2-chloroacetamido-4-thiazolyl)-2-methoxyiminoacetamido]-4-carbamoyloxymethyl-2-oxoazetidine-1-sulfonate (syn-isomer).

IR $\nu_{max}^{KBr}$cm$^{-1}$: 1770, 1700, 1690, 1650.

NMR (d$_6$-DMSO, ppm): 3.87(3H, s, NOCH$_3$), 4.33(2H, s, ClCH$_2$), 5.27(1H, d.d, J=5, 9 Hz, C$_3$—H), 6.38(2H, br.s, NH$_2$),

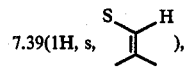

7.39(1H, s,          ), 9.16(1H, d, J=9 Hz, C$_3$—H).

| Elemental analysis: $C_{13}H_{14}ClN_6O_9S_2Na \cdot 2.5H_2O$ | | | |
|---|---|---|---|
| | C (%) | H (%) | N (%) |
| Calcd.: | 27.59 | 3.38 | 14.85 |
| Found: | 27.86 | 3.32 | 14.73 |

EXAMPLE 138C

In the same manner as Example 2C, there was obtained sodium cis-3-[2-(2-amino-4-thiazolyl)-2-methoxyiminoacetamido]-4-carbamoyloxymethyl-2-oxoazetidine-1-sulfonate (syn-isomer).

IR $\nu_{max}^{KBr}$cm$^{-1}$: 3400, 1780, 1690, 1645.

NMR (d$_6$-DMSO, ppm): 3.83(3H, s, NOCH$_3$), 5.24(1H, d.d, J=5, 9 Hz, C$_3$—H), 6.36(2H, br.s, NH$_2$),

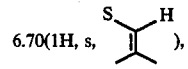

6.70(1H, s,          ), 7.10(2H, br.s, NH$_2$), 9.10(1H, d, J=9 Hz, C$_3$—NH).

| Elemental analysis: C₁₁H₁₃N₆O₈S₂Na.3H₂O | | | |
|---|---|---|---|
| | C (%) | H (%) | N (%) |
| Calcd.: | 26.50 | 3.84 | 16.86 |
| Found: | 26.51 | 3.49 | 16.42 |

EXAMPLE 139C

In 3 ml of dry N,N-dimethylformamide is dissolved 1.08 g of cis-3-benzyloxycarboxamido-4-iodomethyl-2-oxoazetidine as obtained in Reference Example 12C and at $-78°$ C., 5.8 ml (1.56M conc.) of a sulfuric anhydride-N,N-dimethylformamide complex solution is added. The mixture is stirred at 3°–5° C. for 17 hours, after which 0.73 ml of pyridine is added, followed by addition of 95 ml of ether. The solid precipitate is collected by filtration, washed with ether and suspended in 50 ml of water. After addition of 30 ml of Dowex 50W (Na-form) resin, the suspension is stirred at room temperature for 2 hours. The resin is filtered off and the filtrate is concentrated under reduced pressure. The residue is purified by chromatography using an Amberlite XAD-2 column, elution being carried out with 10–20% ethanol. This eluate is concentrated and lyophilized to give sodium cis-3-benzyloxycarboxamido-4-iodomethyl-2-oxoazetidine-1-sulfonate as a colorless powder.

IR $\nu_{max}^{KBr}$cm$^{-1}$: 1770, 1690.

NMR (d₆-DMSO, ppm): 3.2–3.7(2H, m, CH₂I), 4.0–4.3(1H, m, C₄—H), 4.94(1H, d.d, J=5, 10 Hz, C₃—H), 5.08(2H, s, COOCH₂), 8.13(1H, d.J=10 Hz, C₃—NH).

| Elemental analysis: C₁₂H₁₂IN₂NaO₆S.H₂O | | | |
|---|---|---|---|
| | C (%) | H (%) | N (%) |
| Calcd.: | 30.01 | 2.94 | 5.83 |
| Found: | 30.08 | 2.73 | 6.06 |

EXAMPLE 140C

In 30 ml of pyridine is suspended 320 mg of sodium cis-3-benzyloxycarboxamido-4-iodomethyl-2-oxoazetidine-1-sulfonate and the suspension is heated under reflux for 9 hours. The pyridine is distilled off under reduced pressure and 50 ml of ether is added to the residue, whereupon a syrup substance separates out. The ether layer is discarded and the insolubles are washed twice with ether. Following addition of 50 ml of water, the insolubles are filtered off and the filtrate is concentrated under reduced pressure. The residue is purified by chromatography using an Amberlite XAD-2 column, elution being carried out with 20% ethanol. This eluate is concentrated and lyophilized to give cis-3-benzyloxycarboxamido-4-pyridiniomethyl-2-oxoazetidine-1-sulfonate as a colorless powder.

IR $\nu_{max}^{KBr}$cm$^{-1}$: 1770, 1710.

NMR (d₆-DMSO, ppm): 4.5–4.7(1H, m, C₄—H), 4.87(2H, d, J=6 Hz, C₄—CH₂), 5.06(2H, s, COOCH₂), 5.08(1H, d.d, J=6, 10 Hz, C₃—H), 7.37(5H, s, C₆H₅), 7.96–8.26, 8.4–8.7, 8.9–9.2(m, C₃—NH, pyridine ring protons).

| Elemental analysis: C₁₇H₁₇N₃O₆S | | | |
|---|---|---|---|
| | C (%) | H (%) | N (%) |
| Calcd.: | 49.87 | 4.67 | 10.26 |

| Elemental analysis: C₁₇H₁₇N₃O₆S | | | |
|---|---|---|---|
| | C (%) | H (%) | N (%) |
| Found: | 49.66 | 4.50 | 10.20 |

EXAMPLE 141C

In 12 ml of dry N,N-dimethylformamide is suspended 1.537 g of cis-3-benzyloxycarboxamido-4-carbamoyl-2-oxoazetidine as obtained in Reference Example 165C and under cooling at $-78°$ C. a sulfuric anhydride-N,N-dimethylformamide complex solution (10.51 mmol) is added. The mixture is allowed to stand in a refrigerator for 3 hours and under ice-cooling 0.85 ml of pyridine and then 40 ml of ether are added. The insolubles are washed three times with 50 ml portions of ether and the ether is distilled off under reduced pressure. To the residue are added 10 ml of water and 40 ml of Dowex 50W (Na-form) resin, and the mixture is stirred at room temperature for 2 hours. The resin is filtered off and the filtrate is purified by chromatography using an Amberlite XAD-2 column (eluate: water) and lyophilized to give sodium cis-3-benzyloxycarboxamido-4-carbamoyl-2-oxoazetidine-1-sulfonate.

IR $\nu_{max}^{KBr}$cm$^{-1}$: 3410, 3250, 1780, 1680.

NMR (d₆-DMSO, ppm): 4.26(1H, d, J=6 Hz, C₄—H), 4.98(1H, d.d, J=6, 9 Hz, C₃—H), 5.02(2H, s, C₆H₅CH₂), 7.32 (5H, s, C₆H₅), 7.67(1H, d, J=9 Hz, C₃—NH).

trans-3-Benzyloxycarboxamido-4-carbamoyl-2-oxoazetine as obtained in Reference Example 168C was reacted in the same manner as above to give sodium trans-3-benzyloxycarboxamido-4-carbamoyl-2-oxoazetidine-1-sulfonate. This product was a hydroscopic powder and, therefore, was used immediately in the next reaction.

EXAMPLE 142C

Sodium cis-3-benzyloxycarboxamido-4-carbamoyl-2-oxoazetidine-1-sulfonate is reacted in the same manner as Example 66C to give sodium cis-3-{2-(2-chloroacetamido-4-thiazolyl)-2-[1-methyl-1-(p-nitrobenzyloxycarbonyl)ethyloxyimino]acetamido}-4-carbamoyl-2-oxoazetidine-1-sulfonate (syn-isomer). The elution of the product through Amberlite XAD-II column was conducted using 40% ethanol. The IR and NMR spectra of this product are identical with those of the product obtained in Example 131C.

EXAMPLE 143C

Sodium trans-3-benzyloxycarboxamido-4-carbamoyl-2-oxoazetidine-1-sulfonate is first reduced and acylated as in Example 66C. Then, as in Example 67C, the chloroacetyl group is removed to give sodium trans-3-{2-(2-amino-4-thiazolyl)-2-[1-methyl-1-(p-nitrobenzyloxycarbonyl)ethyloxyimino]acetamido}-4-carbamoyl-2-oxoazetidine-1-sulfonate (syn-isomer).

IR $\nu_{max}^{KBr}$cm$^{-1}$: 3400, 1765, 1730, 1690, 1670.

NMR (d₆-DMSO, ppm): 1.50(6H, s, 2×CH₃), 5.32(2H, s, CO₂CH₂), 6.85(1H, s, 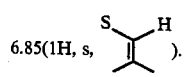 ).

EXAMPLE 144C

In the same manner as Example 133C, there was obtained trans-3-[2-(2-amino-4-thiazolyl)-2-(1-methyl-1-carboxyethyloxyimino)acetamido]-4-carbamoyl-2-oxoazetidine-1-sulfonic acid (syn-isomer).

IR $\nu_{max}^{KBr}$cm$^{-1}$: 3280, 1760, 1660.

NMR (d$_6$-DMSO+D$_2$O, ppm): 1.61(6H, s, 2×CH$_3$), 4.17(1H, d, J=3 Hz, C$_4$—H), 4.84(1H, d, J=3 Hz, C$_3$—H), 7.11(1H, s, 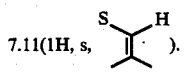 ).

EXAMPLE 145C cis-4-Acetamidomethyl-3-benzyloxycarboxamido-2-oxoazetidine as obtained in Reference Example 50C was reacted in the same manner as Reference Example 91C to give cis-3-{2-(2-chloroacetamido-4-thiazolyl)-2-[1-methyl-1-(p-nitrobenzyloxycarbonyl)ethyloxyimino]acetamido}-4-acetamidomethyl-2-oxoazetidine (syn-isomer).

IR $\nu_{max}^{KBr}$cm$^{-1}$: 3300, 1780–1730, 1650.

NMR (d$_6$-DMSO, ppm): 1.49(3H, s, CH$_3$), 1.51(3H, s, CH$_3$), 1.81(3H, s, COCH$_3$), 4.35(2H, s, ClCH$_2$), 5.20(1H, d.d, J=6, 9 Hz, C$_3$—H), 5.32(2H, s, CO$_2$CH$_2$)

7.39(1H, s, 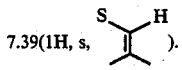 ).

The above product was sulfonated in the same manner as Example 70C to give sodium cis-3-{2-(2-chloroacetamido-4-thiazolyl)-2-[1-methyl-1-(p-nitrobenzyloxycarbonyl)ethyloxyimino]acetamido}-4-acetamidomethyl-2-oxo-azetidine-1-sulfonate (syn-isomer).

IR $\nu_{max}^{KBr}$cm$^{-1}$: 3350, 1780–1730, 1690–1630.

NMR (d$_6$-DMSO, ppm): 1.52(6H, s, 2×CH$_3$), 1.81(3H, s, COCH$_3$), 4.35(2H, s, ClCH$_2$), 5.2(1H, d.d, J=6, 9 Hz, C$_3$—H), 5.31(2H, s, CO$_2$CH$_2$), 7.37(1H, s, 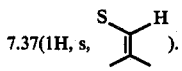 ).

| Elemental analysis: C$_{24}$H$_{25}$ClN$_7$NaO$_{12}$S$_2$.2H$_2$O: | | | |
|---|---|---|---|
| | C (%) | H (%) | N (%) |
| Calcd.: | 37.82 | 3.84 | 12.87 |
| Found: | 38.04 | 3.71 | 12.87 |

EXAMPLE 146C

In the same manner as Example 67C, there was obtained sodium cis-3-{2-(2-amino-4-thiazolyl)-2-[1-methyl-1-(p-nitrobenzyloxycarbonyl)ethyloxyimino]acetamido}-4-acetamidomethyl-2-oxoazetidine-1-sulfonate (syn-isomer).

IR $\nu_{max}^{KBr}$cm$^{-1}$: 3350, 1780–1730, 1680–1600.

NMR (d$_6$-DMSO, ppm): 1.5(6H, s, 2×CH$_3$), 1.74(3H, s, COCH$_3$), 5.13(1H, d, J=6, 9 Hz, C$_3$—H), 5.31(2H, s, CO$_2$CH$_2$), 6.67(1H, s, 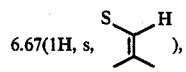 ), 9.29(1H, d, J=9 Hz, C$_3$—NH).

| Elemental analysis: C$_{22}$H$_{24}$N$_7$O$_{11}$S$_2$.3H$_2$O | | | |
|---|---|---|---|
| | C (%) | H (%) | N (%) |
| Calcd.: | 37.55 | 4.29 | 13.94 |
| Found: | 37.56 | 4.12 | 14.03 |

EXAMPLE 147C

In the same manner as Example 133C, there was obtained cis-3-[2-(2-amino-4-thiazolyl)-2-(1-methyl-1-carboxyethyloxyimino)acetamido]-4-acetamidomethyl-2-oxoazetidine-1-sulfonic acid (syn-isomer).

IR $\nu_{max}^{KBr}$cm$^{-1}$: 3325, 1770, 1720, 1670, 1635.

NMR (d$_6$-DMSO, ppm): 1.49(3H, s, CH$_3$), 1.51(3H, s, CH$_3$), 1.8(3H, s, COCH$_3$), 5.17(1H, d.d, J=6, 9 Hz, C$_3$—H), 7.0(1H, s, 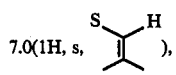 ), 9.35(1H, d, J=9 Hz, C$_3$—NH).

| Elemental analysis: C$_{15}$H$_{20}$N$_6$O$_9$S$_2$.2½H$_2$O | | | |
|---|---|---|---|
| | C (%) | H (%) | N (%) |
| Calcd.: | 33.51 | 4.69 | 15.64 |
| Found: | 33.70 | 4.75 | 15.33 |

EXAMPLE 148C

In a mixture of 15 ml of tetrahydrofuran and 15 ml of water is dissolved 216 mg of cis-3-amino-4-isopropyl-2-oxoazetidine, and under ice-cooling and stirring, 438 mg of sodium hydrogen carbonate and 1.0 g of 2-(2-chloroacetamido-4-thiazolyl)-2-(Z)-[1-methyl-1-(p-nitrobenzyloxycarbonyl)ethyloxyimino]acetyl chloride hydrochloride are added. The mixture is stirred at room temperature for 2 hours and the reaction mixture is concentrated under reduced pressure. The residue is shaken with 30 ml of water and 50 ml of ethyl acetate. The ethyl acetate layer is taken, washing with aqueous sodium hydrogen carbonate and water in this order and dried over anhydrous sodium sulfate. The solvent is then distilled off under reduced pressure. The residue is dissolved in 2 ml of N,N-dimethylformamide and sulfonated as in Example 70C to give sodium cis-3-{2-(2-chloroacetamido-4-thiazolyl)-2-[1-methyl-1-(p-nitrobenzyloxycarbonyl)ethyloxyimino]-acetamido}-4-isopropyl-2-oxoazetidine-1-sulfonate (syn-isomer).

IR $\nu_{max}^{KBr}$cm$^{-1}$: 3400–3250, 1770–1730, 1680, 1050.

NMR (d$_6$-DMSO, ppm): 0.92(3H, d, J=6 Hz, CH$_3$), 1.04(3H, d, J=6 Hz.CH$_3$), 1.49(3H, s, CH$_3$), 1.52(3H, s, CH$_3$), 3.73 (1H, d.d, J=6, 7 Hz, C$_4$—H), 4.33(2H, s, ClCH$_2$), 5.15(1H, d.d, J=6, 9 Hz, C$_3$—H), 7.32(1H, s, 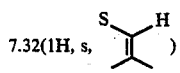 )

| Elemental analysis: $C_{24}H_{26}ClN_6NaO_{11}S_2 \cdot 2H_2O$ | | | |
|---|---|---|---|
| | C (%) | H (%) | N (%) |
| Calcd.: | 39.32 | 4.12 | 11.46 |
| Found: | 39.57 | 3.82 | 11.54 |

EXAMPLE 149C

In the same manner as Example 67C, there was obtained sodium cis-3-{2-(2-amino-4-thiazolyl)-2-[1-methyl-1-(p-nitrobenzyloxycarbonyl)ethyloxyimino]acetamido}-4-isopropyl-2-oxoazetidine-1-sulfonate (syn-isomer).

IR $\nu_{max}^{KBr}$cm$^{-1}$: 3300, 1770–1730, 1670.

NMR (d$_6$-DMSO, ppm): 0.89(3H, d, CH$_3$), 1.03(3H, d, CH$_3$), 1.49(3H, s, CH$_3$), 1.52(3H, s, CH$_3$), 5.31(2H, s, CO$_2$CH$_2$), 6.64(1H, s, 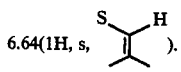 ).

| Elemental analysis: $C_{22}H_{25}N_6NaO_{10}S_2 \cdot 2H_2O$ | | | |
|---|---|---|---|
| | C (%) | H (%) | N (%) |
| Calcd.: | 40.24 | 4.45 | 12.80 |
| Found: | 40.10 | 4.22 | 12.69 |

EXAMPLE 150C

In the same manner as Example 133C, there was obtained cis-3-[2-(2-amino-4-thiazolyl)-2-(1-methyl-1-carboxyethyloxyimino)acetamido]-4-isopropyl-2-oxoazetidine-1-sulfonic acid (syn-isomer).

NMR (d$_6$-DMSO, ppm): 3.71(1H, d.d, J=6, 9 Hz, C$_4$—H), 5.13 (1H, d.d, J=6, 9 Hz, C$_3$—H), 6.90(1H, s, 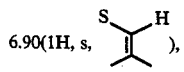 ), 9.27 (1H, d, J=9 Hz, C$_3$—NH).

| Elemental analysis: $C_{15}H_{21}N_5O_8S_2 \cdot 3H_2O$ | | | |
|---|---|---|---|
| | C (%) | H (%) | N (%) |
| Calcd.: | 34.81 | 5.26 | 13.53 |
| Found: | 34.51 | 4.96 | 13.25 |

EXAMPLE 151C

In the same manner as Example 148C, there was obtained sodium cis-3-{2-(2-chloroacetamido-4-thiazolyl)-2-[1-methyl-1-(p-nitrobenzyloxycarbonyl)ethyloxyimino]acetamido}-4-methylcarbamoyl-2-oxoazetidine-1-sulfonate (syn-isomer).

IR $\nu_{max}^{KBr}$cm$^{-1}$: 3350, 1780, 1670.

NMR (d$_6$-DMSO, ppm): 1.52(6H, s, 2×CH$_3$), 2.63(3H, d, J=5 Hz, NHCH$_3$), 4.33(2H, s, ClCH$_2$), 4.43(1H, d, J=5 Hz, C$_4$—H), 5.33(2H, s, CO$_2$CH$_2$), 7.53(1H, s, 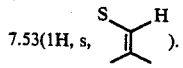 ).

| Elemental analysis: $C_{23}H_{23}ClN_7NaO_{11}S_2 \cdot 2H_2O$ | | | |
|---|---|---|---|
| | C (%) | H (%) | N (%) |
| Calcd.: | 36.92 | 3.64 | 13.10 |
| Found: | 36.80 | 3.53 | 13.15 |

EXAMPLE 152C

In the same manner as Example 67C, there was obtained sodium cis-3-{2-(2-amino-4-thiazolyl)-2-[1-methyl-1-(p-nitrobenzyloxycarbonyl)ethyloxyimino]acetamido}-4-methylcarbamoyl-2-oxoazetidine-1-sulfonate (syn-isomer).

IR $\nu_{max}^{KBr}$cm$^{-1}$: 3330, 1770, 1760.

NMR (d$_6$-DMSO, ppm): 1.49(6H, s, 2×CH$_3$), 2.60(3H, d, J=4 Hz, NHCH$_3$), 4.38(1H, d, J=5 Hz, C$_4$—H), 6.86(1H, s, 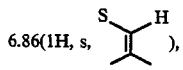 ), 7.21(2H, Br.s, NH$_2$).

| Elemental analysis: $C_{21}H_{22}N_7NaO_{11}S_2 \cdot 2H_2O$ | | | |
|---|---|---|---|
| | C (%) | H (%) | N (%) |
| Calcd.: | 37.55 | 3.90 | 14.59 |
| Found: | 37.54 | 3.80 | 14.63 |

EXAMPLE 153C

In the same manner as Example 133C, there was obtained cis-3-[2-(2-amino-4-thiazolyl)-2-(1-methyl-1-carboxyethyloxyimino)acetamido]-4-methylcarbamoyl-2-oxoazetidine-1-sulfonic acid (syn-isomer).

IR $\nu_{max}^{KBr}$cm$^{-1}$: 1800, 1650.

NMR (d$_6$-DMSO, ppm): 1.50(6H, s, 2×CH$_3$), 2.62(3H, d, J=4 Hz, NHCH$_3$), 4.40(1H, d, J=5 Hz, C$_4$—H), 5.33(1H, d.d, J=5, 9 Hz, C$_3$—H), 7.16(1H, s, 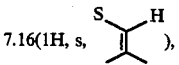 ), 7.83(1H, q, J=4 Hz, NHCH$_3$).

| Elemental analysis: $C_{14}H_{18}N_6O_9S_2 \cdot 2\frac{1}{2}H_2O$ | | | |
|---|---|---|---|
| | C (%) | H (%) | N (%) |
| Calcd.: | 32.11 | 4.42 | 16.05 |
| Found: | 32.39 | 4.30 | 15.87 |

EXAMPLE 154C

In 2 ml of N,N-dimethylformamide is dissolved 240 mg of cis-3-[2-(2-chloroacetamido-4-thiazolyl)-2-methoxyiminoacetamido]-4-(E)-styryl-1-(tert-butyldimethylsilyl)-2-oxoazetidine (syn-isomer), and at −10° C., 0.83 ml (1.58M conc.) of a sulfuric anhydride-N,N-dimethylformamide complex solution is added. The reaction mixture is allowed to stand under sealing at 5° C. for 2 days. To this solution is added 0.136 ml of pyridine, followed by addition of 100 ml of ether. The ether layer is discarded and the insolubles are dissolved in a mixture of 20 ml of water and 10 ml of ethanol and to the solution is added 10 ml of Dowex 50W (Na-form)

resin, followed by stirring for 20 minutes. The resin is filtered off and the filtrate is concentrated to about 20 ml, then purified by chromatography using an Amberlite XAD-2 column (eluent: 10% EtOH) and lyophilized to give sodium cis-3-[2-(2-chloroacetamido-4-thiazolyl)-2-methoxyiminoacetamido]-4-(E)-styryl-2-oxoazetidine-1-sulfonate (syn-isomer).

IR $\nu_{max}^{KBr}$cm$^{-1}$: 3450, 1760, 1660.

NMR (d$_6$-DMSO, ppm): 3.64(3H, s, OCH$_3$), 4.27(2H, s, ClCH$_2$), 4.65(1H, d.d, J=6, 7 Hz, C$_4$—H), 5.30(1H, d.d, J=6, 9 Hz, C$_3$—H), 7.11(1H, s, 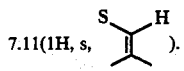 ).

| Elemental analysis: C$_{19}$H$_{17}$ClN$_5$NaO$_7$S$_2$.3¼H$_2$O | | | |
|---|---|---|---|
| | C (%) | H (%) | N (%) |
| Calcd.: | 37.22 | 3.95 | 11.43 |
| Found: | 37.09 | 3.82 | 11.44 |

EXAMPLE 155C

In the same manner as Example 11C, there was obtained sodium cis-3-[2-(2-amino-4-thiazolyl)-2-methoxyiminoacetamido]-4-(E)-styryl-2-oxoazetidine-1-sulfonate (syn-isomer).

IR $\nu_{max}^{KBr}$cm$^{-1}$: 3400, 1755, 1660.

NMR (d$_6$-DMSO, ppm): 3.62(3H, s, OCH$_3$), 4.62(1H, d.d, J=6, 7 Hz, C$_4$—H), 5.25(1H, d.d, J=6, 9 Hz, C$_3$—H), 6.43(1H, s, 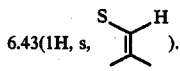 ).

| Elemental analysis: C$_{17}$H$_{16}$N$_5$NaO$_6$S$_2$.2¼H$_2$O | | | |
|---|---|---|---|
| | C (%) | H (%) | N (%) |
| Calcd. | 39.38 | 4.08 | 13.51 |
| Found | 39.29 | 4.03 | 13.54 |

EXAMPLE 156C

In 10 ml of methanol is suspended 145 mg of a cis- and trans-mixture (1:4) of 3-azido-4-methoxycarbonylmethyl-2-oxoazetidine, followed by addition of 100 mg of 10% palladium-on-carbon. The suspension is stirred in a hydrogen atomsphere at room temperature for 30 minutes. The catalyst is then filtered off and the filtrate is concentrated under reduced pressure. The residue is dissolved in 20 ml of tetrahydrofuran, and after addition of 0.35 ml of triethylamine, 332 mg of 2-(2-chloroacetamido-4-thiazolyl)-2-methoxyiminoacetyl chloride hydrochloride is added under ice-cooling and stirring. The mixture is stirred under ice-cooling for 15 minutes and then at room temperature for 1.5 hours. The tetrahydrofuran is distilled off under reduced pressure and the residue is shaken with ethyl acetate and water. The ethyl acetate layer is taken, washed with water and dried over anhydrous sodium sulfate. It is then concentrated to dryness under reduced pressure to give a cis- and trans-mixture (1:4) of 3-[2-(2-chloroacetamido-4-thiazolyl)-2-methoxyiminoacetamido]-4-methoxycarbonylmethyl-2-oxoazetidine (syn-isomer) as a powder.

IR $\nu_{max}^{KBr}$cm$^{-1}$: 3350, 1750, 1730, 1670.

The above product was sulfonated in the same manner as Example 109C to give a cis- and trans-mixture (1:4) of sodium 3-[2-(2-chloroacetamido-4-thiazolyl)-2-methoxyiminoacetamido]-4-methoxycarbonylmethyl-2-oxoazetidine-1-sulfonate (syn-isomer).

IR $\nu_{max}^{KBr}$cm$^{-1}$: 3455, 1760, 1730, 1660.

NMR (d$_6$-DMSO+D$_2$O, ppm); 4.88(d, J=2 Hz, trans-C$_3$—H), 5.35(d, J=5 Hz, cis-C$_3$—H).

The above product was treated in the same manner as Example 11C to remove the amino protecting group. By this procedure was obtained a cis- and trans-mixture (1:4) of sodium 3-[2-(2-amino-4-thiazolyl)-2-methoxyiminoacetamido]-4-methoxycarbonylmethyl-2-oxoazetidine-1-sulfonate (syn-isomer).

IR $\nu_{max}^{KBr}$cm$^{-1}$: 3400, 1762, 1730, 1665.

NMR (d$_6$-DMSO+D$_2$O, ppm): 4.84(d, J=2 Hz, trans-C$_3$—H), 5.32(d, J=5 Hz, cis-C$_3$—H), 6.88(1H, s, 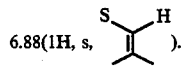 ).

| Elemental analysis: C$_{12}$H$_{14}$N$_5$NaO$_8$S$_2$.2H$_2$O | | | |
|---|---|---|---|
| | C (%) | H (%) | N (%) |
| Calcd. | 30.06 | 3.78 | 14.61 |
| Found | 30.13 | 3.71 | 14.43 |

EXAMPLE 157C

The procedure of Example 141C was followed to sulfonate trans-3-azido-4-methoxycarbonylmethyl-2-oxoazetidine as obtained in Reference Example 177C to give sodium trans-3-azido-4-methoxycarbonylmethyl-2-oxoazetidine-1-sulfonate.

IR $\nu_{max}^{KBr}$cm$^{-1}$: 3425, 2125, 1762, 1730.

EXAMPLE 158C

In 5 ml of N,N-dimethylformamide is dissolved 266 mg of sodium trans-3-azido-4-methoxycarbonylmethyl-2-oxoazetidine-1-sulfonate, followed by addition of 150 mg of 10% palladium-on-carbon. The mixture is stirred in a hydrogen atmosphere at room temperature for 45 minutes. The catalyst is then separated by filtration and washed with 5 ml of N,N-dimethylformamide. The filtrate and washings are combined, followed by the addition of 284 mg of 2-(2-chloroacetamido-4-thiazolyl)-2-[1-methyl-1-(tertbutoxycarbonyl)ethyloxyimino]acetic acid, 110 mg of N-hydroxybenzotriazole monohydrate and 150 mg of dicyclohexylcarbodiimide. The mixture is stirred at room temperature for 4 hours and then allowed to stand at 5° C. overnight. After addition of 20 ml of water, the insolubles are separated by filtration and washed with 5 ml of water. The filtrate and washings are combined and sodium monomethyldithiocarbamate is added. This mixture is reacted in the same manner as Example 11C to give sodium trans-3-{2-(2-amino-4-thiazolyl)-2-[1-methyl-1-(tert-butoxycarbonyl)ethyloxyimino]acetamido}-4-methoxycarbonylmethyl-2-oxo-azetidine-1-sulfonate (syn-isomer).

IR $\nu_{max}^{KBr}$cm$^{-1}$: 3425, 1760, 1725, 1660.

Under ice-cooling and stirring, 84 mg of the above product is added to 2 ml of trifluoroacetic acid and the mixture is stirred for 3 hours. The reaction mixture is concentrated to dryness under reduced pressure. The residue is dissolved in 5 ml of water and purified by chromatography on Amberlite XAD-II (eluent: water and then 10% ethanol) and then Sephadex LH-20 columns (eluent: water). The lyophilizate obtained is dissolved in 5 ml of water and stirred with 2 g of Dowex 50W (H-form) resin for 10 minutes. The resin is filtered off and the filtrate is lyophilized to give trans-3-[2-(2-amino-4-thiazolyl)-2-(1-methyl-1-carboxyethyloxyimino)acetamido]-4-methoxycarbonylmethyl-2-oxo-azetidine-1-sulfonic acid (syn-isomer).

Ir R $\nu_{max}^{KBr}$cm$^{-1}$: 3375, 1760, 1725.

NMR (D$_2$O, ppm): 1.72(6H, s, 2×CH$_3$), 3.24(2H, m, C$_4$—CH$_2$), 3.86(3H, s, CO$_2$CH$_3$), 4.60(1H, m, C$_4$—H), 5.08(1H, d, J=2 Hz, C$_3$—H),

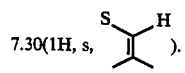
7.30(1H, s, ).

EXAMPLE 159C

The procedure of Example 141C was followed to sulfonate cis-3-benzyloxycarboxamido-4-methoxyaminocarbonyl-2-oxo-azetidine as obtained in Reference Example 178C to give sodium cis-3-benzyloxycarboxamido-4-methoxyaminocarbonyl-2-oxoazetidine-1-sulfonate.

IR $\nu_{max}^{KBr}$cm$^{-1}$: 3270, 1760, 1680.

| Elemental analysis: C$_{13}$H$_{14}$N$_3$NaO$_8$S.1½H$_2$O | | | |
|---|---|---|---|
| | C (%) | H (%) | N (%) |
| Calcd. | 36.97 | 4.06 | 9.95 |
| Found | 36.99 | 4.06 | 9.97 |

EXAMPLE 160C

In the same manner as Example 143C, there was obtained sodium cis-3-{2-(2-amino-4-thiazolyl)-2-[1-methyl-1-(p-nitrobenzyloxycarbonyl)ethyloxyimino]acetamido}-4-methoxyaminocarbonyl-2-oxoazetidine-1-sulfonate (syn-isomer).

IR $\nu_{max}^{KBr}$cm$^{-1}$: 3400, 1775, 1730, 1680.

NMR(d$_6$-DMSO, ppm): 1.51(6H, s, 2×CH$_3$), 3.57(3H, s, OCH$_3$), 4.33(1H, d, J=6 Hz, C$_4$—H), 5.36 (2H, s, CO$_2$CH$_2$),

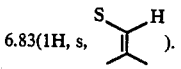
6.83(1H, s, ).

| Elemental analysis: C$_{21}$H$_{22}$N$_7$NaO$_{12}$S$_2$.2H$_2$O | | | |
|---|---|---|---|
| | C (%) | H (%) | N (%) |
| Calcd. | 36.68 | 3.81 | 14.26 |
| Found | 36.68 | 4.11 | 14.28 |

EXAMPLE 161C

In the same manner as Example 133C, there was obtained cis-3-[2-(2-amino-4-thiazolyl)-2-(1-methyl-1-carboxyethyloxyimino)acetamido]-4-methoxyaminocarbonyl-2-oxoazetidine-1-sulfonic acid (syn-isomer).

IR $\nu_{max}^{KBr}$cm$^{-1}$: 3280, 1770, 1730, 1670.

NMR(d$_6$-DMSO, ppm): 1.52(6H, s, 2×CH$_3$), 3.60(3H, s, OCH$_3$), 4.34(1H, d, J=6 Hz, C$_4$—H), 5.38(1H, d.d, J=6, 9 Hz, C$_3$—H),

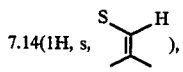
7.14(1H, s, ), 9.02(1H, d, J=9 Hz, C$_3$—NH).

| Elemental analysis: C$_{14}$H$_{17}$N$_6$O$_{10}$S$_2$.2½H$_2$O | | | |
|---|---|---|---|
| | C (%) | H (%) | N (%) |
| Calcd. | 31.23 | 4.12 | 15.61 |
| Found | 31.06 | 3.96 | 15.40 |

EXAMPLE 162C

The procedure of Example 70C was followed to sulfonate cis-3-{2-(2-chloroacetamido-4-thiazolyl)-2-[1-methyl-1-(p-nitrobenzyloxycarbonyl)ethyloxyimino]acetamido}-4-cyanomethyl-2-oxoazetidine (syn-isomer) as obtained in Reference Example 181C. In the same manner as Example 67C the amino-protecting group was removed from the product obtained above to give sodium cis-3-{2-(2-amino-4-thiazolyl)-2-[1-methyl-1-(p-nitrobenzyloxycarbonyl)ethyloxyimino]acetamido}-4-cyanomethyl-2-oxoazetidine-1-sulfonate (syn-isomer).

IR $\nu_{max}^{KBr}$cm$^{-1}$: 3420, 2250, 1765, 1670, 1620, 1520, 1345, 1280, 1050.

EXAMPLE 163C

In the same manner as Example 133C, there was obtained cis-3-[2-(2-amino-4-thiazolyl)-2-(1-methyl-1-carboxyethyloxyimino)acetamido]-4-cyanomethyl-2-oxoazetidine-1-sulfonic acid (syn-isomer).

IR $\nu_{max}^{KBr}$cm$^{-1}$: 3290, 2250, 1775, 1635.

NMR(d$_6$-DMSO, ppm): 1.56(6H, s, 2×CH$_3$), 5.29(1H, d.d, J=6, 9 Hz, C$_3$—H),

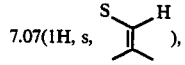
7.07(1H, s, ), 9.42 (1H, d, J=9 Hz, C$_3$—NH).

| Elemental analysis: C$_{14}$H$_{14}$N$_6$O$_8$S$_2$.2½H$_2$O | | | |
|---|---|---|---|
| | C (%) | H (%) | N (%) |
| Calcd. | 33.27 | 4.18 | 16.63 |
| Found | 33.57 | 4.01 | 16.28 |

EXAMPLE 164C

In 20 ml of methylene chloride is dissolved 708 mg of 1-methyl-1H-tetrazol-5-ylthioacetic acid as obtained in Reference Example 183C. Under ice-cooling, 806 mg of thionyl chloride is added and the mixture is heated under reflux for an hour. The reaction mixture is then concentrated under reduced pressure and the residue is dissolved in 10 ml of methylene chloride.

In a mixture of 50 ml of tetrahydrofuran, 50 ml of methylene chloride and 0.5 ml of pyridine is dissolved 1 g of cis-3-(p-nitrobenzyloxycarboxamido)-4-hydroxymethyl-2-oxoazetidine as obtained in Reference Example 182C. Then, at room temperature the solution containing acid chloride as prepared above is added dropwise. The mixture is stirred at room temperature for 4 hours and extracted with ethyl acetate-tetrahydrofuran (3:1). The extract is washed with 3N hydrochloric acid, saturated aqueous sodium hydrogen carbonate and aqueous sodium chloride in this order, dried over anhydrous magnesium sulfate and concentrated under reduced pressure. The residue is purified by silica gel column chromatography [silica gel: 140 g; eluent: ethyl acetate and then ethyl acetate-methanol (8:1 and then 4:1)] to give 1.52 of cis-3-(p-nitrobenzyloxycarboxamido)-4-(1-methyl-1H-tetrazol-5-yl)thioacetoxymethyl-2-oxoazetidine. This product is sulfonated in the same manner as Example 141C to give sodium cis-3-(p-nitrobenzyloxycarboxamido)-4-(1-methyl-1H-tetrazol-5-yl)thioacetoxymethyl-2-oxoazetidine-1-sulfonate.

IR $\nu_{max}^{KBr}$cm$^{-1}$: 3400, 3320, 1760, 1730, 1685.

NMR(d$_6$-DMSO, ppm): 3.98(3H, s, N—CH$_3$), 4.90(1H, d.d, J=6, 9 Hz, C$_3$—H).

| Elemental analysis: C$_{16}$H$_{16}$N$_7$NaO$_{10}$S$_2$.H$_2$O | | | |
|---|---|---|---|
| | C (%) | H (%) | N (%) |
| Calcd. | 33.63 | 3.17 | 17.16 |
| Found | 33.42 | 3.05 | 17.17 |

EXAMPLE 165C

In a mixture of 20 ml of tetrahydrofuran and 20 ml of water is dissolved 1.02 g of sodium cis-3-(p-nitrobenzyloxycarboxamido)-4-(1-methyl-1H-tetrazol-5-yl)thioacetoxymethyl-2-oxoazetidine-1-sulfonate, followed by addition of 1 g of 10% palladium-on-carbon. The mixture is stirred in a hydrogen atmosphere for 5 hours. The catalyst is filtered off, and the filtrate is made neutral with aqueous sodium hydrogen carbonate and washed twice with ethyl acetate. To the aqueous layer is added 30 ml of tetrahydrofuran, and under ice-cooling, 356 mg of sodium hydrogen carbonate and then 1.16 g of 2-(2-chloroacetamido-4-thiazolyl)-2-(1-methyl-1-benzhydryloxycarbonylethyloxyimino)acetyl chloride hydrochloride are added. The mixture is stirred under ice-cooling for one hour, and after addition of 476 mg of sodium monomethyldithiocarbamate, the mixture is stirred at room temperature for one hour. The reaction mixture is washed twice with ether and concentrated. The residue is purified by chromatography using an Amerlite XAD-II column (eluent: water, 20% ethanol and then 30% ethanol) and then, lyophilized to give sodium cis-3-[2-(2-amino-4-thiazolyl)-2-(1-methyl-1-benzhydryloxycarbonylethyloxyimino)acetamido]-4-(1-methyl-1H-tetrazol-5-yl)thioacetoxymethyl-2-oxoazetidine-1-sulfonate (syn-isomer).

IR $\nu_{max}^{KBr}$cm$^{-1}$: 3420, 1760, 1740, 1670.

In 2.5 ml of anisole is suspended 545 mg of the above product, and under cooling at −12° C., 12 ml of trifluoroacetic acid is added. The mixture is stirred at −10° to −12° C. for 30 minutes, followed by addition of 40 ml of ether and 20 ml of hexane. The resultant solid precipitate is washed three times with 60 ml portions of ether and then dissolved in 40 ml of water. After addition of sodium hydrogen carbonate, the mixture is filtered. The filtrate is concentrated and purified by chromatography using an Amberlite XAD-II column (eluent: water) and lyophilized to give cis-3-[2-(2-amino-4-thiazolyl)-2-(1-methyl-1-carboxyethyloxyimino)acetamido-4-(1-methyl-1H-tetrazol-5-yl)thioacetoxymethyl-2-oxoazetidine-1-sulfonic acid disodium salt (syn-isomer).

IR $\nu_{max}^{KBr}$cm$^{-1}$: 3400, 1760, 1680.

NMR(d$_6$-DMSO, ppm): 1.38(3H, s, CH$_3$), 1.43(3H, s, CH$_3$), 3.97(3H, s, N—CH$_3$), 5.27(1H, d.d, J=6, 9 Hz, C$_3$—H), 6.77(1H, s, 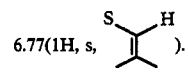 ).

EXAMPLE 166C

In a mixture of 30 ml of tetrahydrofuran and 15 ml of water is dissolved 2.56 g of cis-3-benzyloxycarboxamido-2-oxoazetidine-4-carboxylic acid as obtained in Reference Example 68C, followed by the addition of 895 mg of sodium hydrogen carbonate, 2.23 g of 1-ethyl-3-(3-dimethylaminopropyl)carbodiimide hydrochloride and 3.62 g of alanine benzyl ester p-toluenesulfonate. The mixture is stirred at room temperature for 12 hours. The reaction mixture is extracted with ethyl acetate-tetrahydrofuran (2:1) and the extract is washed with water, 3N hydrochloric acid (twice), saturated aqueous sodium hydrogen carbonate, and aqueous sodium chloride in this order, and dried over anhydrous magnesium sulfate. The solvent is then distilled off and the residue is subjected to silica gel column chromatography [silica gel: 450 g; eluent: chloroform-ethylacetate (1:1) and then chloroform-ethyl acetate-methanol (20:20:1 and then 10:10:1) to obtain diastereoisomers (beta and alpha forms; cf. Reference Example 39C) of cis-3-benzyloxycarboxamido-4-[1-(L.)-benzyloxycarbonylethyl]aminocarbonyl-2-oxoazetidine.

These products are sulfonated in the same manner as Example 141C to give beta and alpha forms of sodium cis-3-benzyloxycarboxamido-4-[1-(L.)-benzyloxycarbonylethyl]aminocarbonyl-2-oxoazetidine-1-sulfonate.

Beta form

IR $\nu_{max}^{KBr}$cm$^{-1}$: 3300, 1770, 1735, 1690, 1660.

| Elemental analysis: C$_{22}$H$_{22}$N$_3$NaO$_9$S.1½H$_2$O | | | |
|---|---|---|---|
| | C (%) | H (%) | N (%) |
| Calcd. | 47.65 | 4.54 | 7.58 |
| Found | 47.55 | 4.53 | 7.44 |

Alpha form

IR $\nu_{max}^{KBr}$cm$^{-1}$: 3300, 1770, 1695, 1660.

| Elemental analysis: C$_{22}$H$_{22}$N$_3$NaO$_9$S.1½H$_2$O | | | |
|---|---|---|---|
| | C (%) | H (%) | N (%) |
| Calcd. | 47.65 | 4.54 | 7.58 |
| Found | 47.51 | 4.45 | 7.47 |

EXAMPLE 167C

In the same manner as Example 66C, beta and alpha forms of sodium cis-3-benzyloxycarboxamido-4-[1-(L.)-benzyloxycarbonylethyl]aminocarbonyl-2-oxoazetidine-1-sulfonate is reduced to give beta and alpha forms of sodium cis-3-amino-4-[1-(L.)-carboxyethyl]aminocarbonyl-2-oxoazetidine-1-sulfonate. These products are acylated as in Example 66C and then the chloroacetyl group is removed as in Example 67C to give beta and alpha forms of sodium cis-3-{2-(2-amino-4-thiazolyl)-2-[1-methyl-1-(p-nitrobenzyloxycarbonyl)ethyloxyimino]acetamido}-4-[1-(L)-carboxyethylaminocarbonyl-2-oxoazetidine-1-sulfonate (syn-isomer).

Beta form

IR $\nu_{max}^{KBr}$cm$^{-1}$: 3400, 1775, 1730, 1665.

Alpha form

IR $\nu_{max}^{KBr}$cm$^{-1}$: 3400, 1780, 1730, 1670.

EXAMPLE 168C

In the same manner as Example 133C, there were obtained beta and alpha forms of cis-3-[2-(2-amino-4-thiazolyl)-2-(1-methyl-1-carboxyethyloxyimino)acetamido]-4-[1-(L)-carboxyethyl]aminocarbonyl-2-oxoazetidine-1-sulfonic acid (syn-isomer).

Beat form

IR $\nu_{max}^{KBr}$cm$^{-1}$: 3300, 1770, 1720, 1665.

NMR(d$_6$-DMSO, ppm): 1.27(3H, d, J=7 Hz, CH$_3$), 1.51(6H, s, 2×CH$_3$), 4.48(1H, d, J=6 Hz, C$_4$—H), 5.45 (1H, d.d, J=6, 10 Hz, C$_3$—H), 7.14(1H, s, 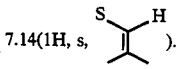 ).

Alpha form

IR $\nu_{max}^{KBr}$cm$^{-1}$: 3300, 1775, 1720, 1670.

NMR(d$_6$-DMSO, ppm): 1.25(3H, d, J=7 Hz, CH$_3$) 1.51(6H, s, 2×CH$_3$), 4.48(1H, d, J=6 Hz, C$_4$—H), 5.34 (1H, d.d, J=6, 9 Hz, C$_3$—H), 7.23(1H, s, 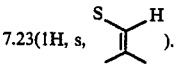 ).

EXAMPLES 169C–173C cis-3-[DL-2-(2-Aminothiazol-4-yl)-2-ammonioacetamido]-4-methoxycarbonyl-2-azetidine-1-sulfonate was reacted with the acylating agents indicated below in the table to give the corresponding sodium cis-3-[DL-2-acylamido-2-(2-aminothiazol-4-yl)acetamido]-4-methoxycarbonyl-2-azetidinone-1-sulfonate compounds which are also shown in the same table.

| Example No. | Acylating agent | Reaction conditions | Product R= | IR Spectrum $\nu_{max}$ cm$^{-1}$ | NMR Spectrum δ ppm |
|---|---|---|---|---|---|
| 169C | C$_2$H$_5$COCl | The same as in Example 118, except that acetone was used instead of acetonitrile. | R=C$_2$H$_5$— | (KBr): 3400, 1775, 1760, 1740, 1620, 1515, 1380, 1340, 1280, 1250, 1050 | (D$_2$O): 1.13 & 1.15(3H,each t,J=7Hz, CH$_3$CH$_2$CO), 2.37 & 2.41(2H,each q, J=7Hz, CH$_3$CH$_2$CO), 3.65 & 3.77(3H, each s,COOCH$_3$), 4.91 & 4.95 (1H,each d, J=6Hz,C$_4$—H), 5.40(1H,s, —CHCO), 5.49 & 5.59(1H,each d, J=6Hz, C$_3$—H), 6.73(1H,s,thiazole 5-H). |
| 170C | CH$_3$OCOCl | The same as in Example 118, except that acetone was used instead of acetonitrile. | R=CH$_3$O— | (KBr): 3400, 1780, 1730, 1630, 1520, 1450, 1350, 1280, 1250, 1060. | (D$_2$O): 3.66 & 3.75(3H,each s,COOCH$_3$), 3.72(3H,s, NHCOOCH$_3$), 4.90 & 4.93(1H, each d,J=6Hz,C$_4$—H), 5.22 (1H,s, —CHCON), 5.41 & 5.54 (1H,each d,J=6Hz,C$_3$—H), 6.72(1H,s,thiazole 5-H). |
| 171C | COCl<br>CH$_3$—C—CH$_3$<br>COCl | The same as in Example 118, except that acetone was used instead of acetonitrile. The amount of NaHCO$_3$ doubled. | R=NaOCOC—<br>CH$_3$<br>CH$_3$ | (KBr): 3400, 1770, 1660, 1620, 1510, 1400, 1350, 1280, 1255, 1055 | (D$_2$O): 1.41(6H,s, —C(CH$_3$)$_2$—), 3.63 & 3.74(3H,each s, COOCH$_3$), 4.88 & 4.92 (1H,d, J=6Hz,C$_4$—H), 5.38 & 5.53 (1H,d,J=6Hz,C$_3$—H), 5.40(1H, s, —CHCON), 6.72(1H,s, thiazole 5-H). |
| 172C | (diketone structure) | The same as in Example 120 | R=NaOCO—CH$_2$CH$_2$— | (KBr): 3400, 1770, 1660, 1570, 1520, 1405, 1280,1055, 815. | (D$_2$O): 2.54(4H,t,J=5Hz,—CH$_2$CH$_2$—), 3.64 & 3.76(3H,each s,COOCH$_3$), 4.81 & 4.94(1H,each d,J=6Hz, C$_4$—H), 5.16 & 5.40(1H,each d, J=6Hz,C$_3$—H), 6.69(1H,s, thiazole 5-H). |

-continued

| Example No. | Acylating agent | Reaction conditions | Product | IR Spectrum $\nu_{max}$cm$^{-1}$ | NMR Spectrum $\delta$ ppm |
|---|---|---|---|---|---|
| 173C | (structure) | The same as in Example 120 | R=NaOCO–CH=C(H)– (structure shown) | (KBr): 3400, 3410, 1765, 1580, 1520, 1440, 1340, 1280, 1250, 1055. | (D$_2$O): 3.63 & 3.75(3H,each s, COOCH$_3$), 4.90 & 4.93(1H,each d, J=6Hz,C$_4$—H), 5.38 & 5.54(1H, each d,J=6Hz,C$_3$—H), 5.40(1H,s, —CHCON), 6.00(1H,d,J=12Hz, –CH=CH– ,J=12Hz), 6.70 & 6.72(1H,each s, thiazole 5-H). |

EXAMPLE 174C

In the same manner as Example 145C, there was obtained sodium cis-3-[2-(2-chloroacetamido-4-thiazolyl)-2-(1-methyl-1-benzhydryloxycarbonylethyloxyimino)acetamido]-4-carbamoyloxymethyl-2-oxoazetidine-1-sulfonate (syn-isomer).

IR $\nu_{max}^{KBr}$cm$^{-1}$: 3400, 1750, 1720.

EXAMPLE 175C

In the same manner as Example 67C, there was obtained sodium cis-3-[2-(2-amino-4-thiazolyl)-2-(1-methyl-1-benzhydryloxycarbonylethyloxyimino)acetamido]-4-carbamoyloxymethyl-2-oxoazetidine-1-sulfonate (syn-isomer).

IR $\nu_{max}^{KBr}$cm$^{-1}$: 1760, 1720, 1670.

EXAMPLE 176C

To 1 ml of anisole is added 250 mg of sodium cis-3-[2-(2-amino-4-thiazolyl)-2-(1-methyl-1-benzhydryloxycarbonylethyloxyimino)acetamido]-4-carbamoyloxymethyl-2-oxoaetidine-1-sulfonate (syn-isomer) and under stirring at −20° C., 5 ml of trifluoroacetic acid is added dropwise. The mixture is stirred at −15° C. for 30 minutes, after which 10 ml of ether and 10 ml of petroleum ether are added. The resultant powder is recovered by centrifugation and dissolved in water. To the solution is Dowex 50W (H-form) resin, followed by stirring. The resin is filtered off and the filtrate is concentrated and purified by chromatography using an Amberlite XAD-2 (eluent: water, 100 ml; 10% ethanol, 100 ml; 30% ethanol, 100 ml and then 40% ethanol, 50 ml) and the fractions of 30% ethanol and 40% ethanol are lyophilized to give cis-3-[2-(2-amino-4-thiazolyl)-2-(1-methyl-1-carboxyethyloxyimino)acetamido]-4-carbamoyloxymethyl-2-oxoazetidine-1-sulfonic acid (syn-isomer).

IR $\nu_{max}^{KBr}$cm$^{-1}$: 1760, 1710, 1630.

NMR(d$_6$-DMSO, ppm): 1.51(6H, s, 2×CH$_3$), 7.01(1H, s, 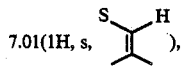 ), 9.23(1H, d, J=9 Hz, C$_3$—NH).

In the same manner as above Examples, there would be obtained the following compounds:

Disodium salt of cis-3-[2-(2-amino-4-thiazolyl)-2-carboxymethyloxyiminoacetamido]-4-acetoxymethyl-2-oxoazetidine-1-sulfonic acid (syn-isomer).

Disodium salt of cis-3-[2-(2-amino-4-thiazolyl)-2-(1-methyl-1-carboxyethyloxyimino)acetamido]-4-acetamidomethyl-2-oxoazetidine-1-sulfonic acid (syn-isomer).

Disodium salt of cis-3-[2-(2-amino-4-thiazolyl)-2-carboxymethyloxyiminoacetamido]-4-acetamidomethyl-2-oxoazetidine-1-sulfonic acid (syn-isomer)

Disodium salt of cis-3-[2-(2-amino-4-thiazolyl)-2-(1-methyl-1-carboxyethyloxyimino)acetamido]-4-isopropyl-2-oxoazetidine-1-sulfonic acid (syn-isomer).

Disodium salt of cis-3-[2-(2-amino-4-thiazolyl)-2-(1-methyl-1-carboxyethyloxyimino)acetamido]-4-methoxycarbonylmethyl-2-oxoazetidine-1-sulfonic acid (syn-isomer).

Disodium salt of cis-3-[2-(2-amino-4-thiazolyl)-2-(1-methyl-1-carboxyethyloxyimino)acetamido]-4-methylcarbamoyl-2-oxoazetidine-1-sulfonic acid (syn-isomer).

EXAMPLE 177C

To a solution of di-(p-toluoyl)-L-tartaric acid (40.8 g) in acetonitrile (500 ml) is added a solution of (±)-cis-3-amino-2-oxoazetidine-4-carboxylic acid methyl ester (14.55 g) as obtained in Reference Example 3C in acetonitrile 250 ml. The mixture is shaken well and left on standing. The resulting crystals are collected by filtration and dried to give 32.2 g of crystals. Recrystallization from 500 ml of acetonitrile gives 19.3 g of crystals. Further recrystallization from 300 ml of acetonitrile gives 11.7 g of crystals, which are then dissolved in a mixture of water (110 ml) and tetrahydrofuran (220 ml). To this stirred, ice-cooled solution is added sodium hydrogen carbonate (5.6 g), followed by a dropwise addition of carbobenzoxychloride (4 ml) over 15 minutes. The mixture is stirred for 45 minutes at 0°–5° C. and then for 15 minutes at room temperature. Ethyl acetate (880 ml) and water (660 ml) are added to the reaction mixture and the whole mixture is shaken well. The upper layer is separated and the lower layer is extracted with ethyl acetate (440 ml). The ethyl acetate solutions are combined, washed with an aqueous sodium hydrogen carbonate solution (250 ml, twice) and an aqueous saturated sodium chloride solution successively, and then dried over anhydrous sodium sulfate. After filtration, the filtrate is concentrated under a reduced pressure. Benzene is added to the residue and the solution is concentrated again under a reduced pressure. Ether (110 ml) is added to the residue and the resulting precipitate is collected by filtration to give 3.5 g of crystals. A suspension of the crystals in ethyl acetate (25 ml) is heated, and after an addition of a small amount of charcoal the mixture is filtered. Hexane (20 ml) is added to the hot filtrate and the resultant solution is left on standing at room temperature. The resulting crystals are collected and washed with a mixture of hexane and ethyl acetate (1:1) to give 1.95 g of (−)-cis-3-benzyloxycarboxamido-2-oxoazetidine-4-carboxylic acid methyl ester as colourless crystals, m.p. 112°–124° C.

$[\alpha]_D^{23.5}$ = 87.5° (C=1.025, chloroform).

IR $\nu_{max}^{Nujol}$cm$^{-1}$; 3320, 3230, 1790, 1735, 1700.

Anal. Calcd. for C$_{13}$H$_{14}$N$_2$O$_5$: C 56.11, H, 5.07, N 10.07; Found: C 56.10, H 4.88, N9.89.

To a solution of (−)-cis-3-benzyloxycarboxamido-2-oxoazetidine-4-carboxylic acid methyl ester (1.245 g) in tetrahydrofuran (20 ml) is added 2.1 ml of an aqueous ammonium hydroxide solution (25–28%), and the mixture is stirred for 16 hours at room temperature. Tetrahydrofuran is evaporated under a reduced pressure and water (60 ml) is added to the residue. The resulting precipitate is collected by filtration, washed with water and ether successively, and then dried to give 839 mg of (−)-cis-3-benzyloxycarboxamido-4-carbamoyl-2-oxoazetidine as colorless crystals, m.p. 235°–237° C. (decomp.).

$[\alpha]_D^{25}$ = −8.7° (C=0.9, DMSO).

IR $\nu_{max}^{KBr}$cm$^{-1}$: 3380, 3280, 1765, 1730, 1665, 1345, 1270, 1175, 1070, 755, 695.

(−)-cis-3-benzyloxcarboxamido-4-carbamoyl-2-oxoazetidine obtained above is sulfonated and the product is purified in the same manner as Example 141C to give sodium (+)-cis-3-benzyloxycarboxamido-4-carbamoyl-2-oxoazetidine-1-sulfonate.

$[\alpha]_D^{24}$ = +13.5° (C=0.26, water).

After removal of the amino-protecting group of this compound, the amino group is acylated in the same manner as Example 142C, followed by removal of protecting groups of the acyl moiety in the same manner as Example 132C and 133C to give (+)-cis-3-[2-(2-amino-4-thiazolyl)-2-(1-carboxy-1-methyl-ethyloxyimino)acetamido]-4-carbamoyl-2-oxoazetidine-1-sulfonic acid (syn-isomer).

$[\alpha]_D^{24} = +38.2°$ (C=0.92, water).

When di-(p-toluoyl)-D-tartaric acid is used in place of di-(p-toluoyl)-L-tartaric acid in the first reaction mentioned above, the optical enantiomers of the compounds mentioned above would be obtained in a series of the reaction steps, and the final product would be (−)-cis-3-[2-(2-amino-4-thiazolyl)-2-(1-carboxy-1-methylethyloxyimino)acetamido]-4-carbamoyl-2-oxoazetidine-1-sulfonic acid (syn-isomer).

$[\alpha]_D^{24} = -38.2°$ (C=0.9, water).

REFERENCE EXAMPLE 1C

Under ice-cooling and stirring, 6.7 ml of propylene oxide and then 3.24 g of carbobenzoxy chloride are added to a solution of 2.94 g of cis-3-amino-1-(2,4-dimethoxybenzyl)-2-oxoazetidine-4-carboxylic acid methyl ester in 12 ml of methylene chloride. The reaction mixture is stirred for 30 minutes at room temperature. The solvent is distilled off in vacuo, ether is then added to the residue and the precipitated crystals are collected by filtration to give cis-3-benzyloxycarboxamido-1-(2,4-dimethoxybenzyl)-2-oxoazetidine-4-carboxylic acid methyl ester, m.p. 115°–116° C.

| Elemental analysis: $C_{22}H_{24}N_2O_7$ | | | |
|---|---|---|---|
| | C (%) | H (%) | N (%) |
| Calc. | 61.67 | 5.65 | 6.54 |
| Found | 61.64 | 5.67 | 6.49 |

REFERENCE EXAMPLE 2C

A solution of 2.7 g of cis-3-benzyloxycarboxamido-1-(2,4-dimethoxybenzyl)-2-oxoazetidine-4-carboxylic acid methyl ester in 150 ml of acetonitrile is heated to 90°–95° C. in a stream of nitrogen under stirring, and 55 ml of an aqueous solution containing 2.73 g of potassium persulfate and 1.65 g of dipotassium phosphate is added dropwise thereto. At the end of the dropwise addition, the mixture is stirred at that temperature for 3 hours. Upon cooling, dipotassium phosphate is added to adjust the pH to 6–7, and the acetonitrile and water are then distilled off in vacuo. The residue is dissolved in chloroform and the solution is washed successively with water and an aqueous sodium chloride. The chloroform solution is dried over anhydrous sodium sulfate and the solvent is then distilled off in vacuo. The residue is subjected to column chromatography on silica gel. Elution with ethyl acetate gives cis-3-benzyloxycarboxamido-2-oxoazetidine-4-carboxylic acid methyl ester, m.p. 127°–128° C.

| Elemental analysis: $C_{13}H_{14}N_2O_5$ | | | |
|---|---|---|---|
| | C (%) | H (%) | N (%) |
| Calc. | 56.11 | 5.07 | 10.07 |
| Found | 56.03 | 5.01 | 9.99 |

REFERENCE EXAMPLE 3C

To a suspension of 0.8 g of cis-3-benzyloxycarboxamido-2-oxoazetidine-4-carboxylic acid methyl ester in 20 ml of ethanol is added 0.8 g of 5% palladium on charcoal, and the catalytic reduction is carried out at atmospheric pressure under stirring. After the hydrogen uptake has ceased, the catalyst is removed by filtration. The filtrate is concentrated in vacuo and the residual oil is allowed to stand under cooling. The precipitated crystals are collected by filtration to give 0.38 g (92%) of cis-3-amino-2-oxoazetidine-4-carboxylic acid methyl ester, m.p. 59°–61° C.

| Elemental analysis: $C_5H_8N_2O_3$ | | | |
|---|---|---|---|
| | C (%) | H (%) | N (%) |
| Calc. | 41.66 | 5.59 | 19.44 |
| Found | 41.54 | 5.59 | 19.67 |

REFERENCE EXAMPLE 4C

Under ice-cooling and stirring, 6 ml of an aqueous solution containing 288 mg of cis-3-amino-2-oxoazetidine-4-carboxylic acid methyl ester and 561 mg of sodium hydrogen carbonate is added to a suspension of 1.18 g of 2-(2-chloroacetamido-4-thiazolyl)-2-methoxyiminoacetyl chloride (syn isomer) in 10 ml of tetrahydrofuran. After the mixture is stirred for 2 hours at room temperature, the solvent is distilled off in vacuo to leave a residue, which solidifies. Water is added to the solid, followed by filtration, and the collected crystals are washed successively with water and ethanol to give cis-3-[2-(2-chloroacetamido-4-thiazolyl)-2-methoxyiminoacetamido]-2-oxoazetidine-4-carboxylic acid methyl ester (syn isomer), m.p. 270°–275° C. (dec.).

| Elemental analysis: $C_{13}H_{14}ClN_5O_6S$ | | | |
|---|---|---|---|
| | C (%) | H (%) | N (%) |
| Calc. | 38.66 | 3.49 | 17.35 |
| Found | 38.50 | 3.78 | 17.25 |

REFERENCE EXAMPLE 5C

Under ice-cooling and stirring, 250 ml of an aqueous solution containing 2.65 g of sodium borohydride is added to a solution of 12 g of cis-3-benzyloxycarboxamido-1-(2,4-dimethoxybenzyl)-2-oxoazetidine-4-carboxylic acid methyl ester in 500 ml of tetrahydrofuran. The reaction mixture is stirred for 5 hours at room temperature. The tetrahydrofuran is distilled off in vacuo, water is then added to the residue and the precipitated crystals are collected by filtration and dried to give 9.8 g (87%) of cis-3-benzyloxycarboxamido-1-(2,4-dimethoxybenzyl)-4-hydroxymethyl-2-oxoazetidine, m.p. 129°–131° C.

| Elemental analysis: $C_{21}H_{24}N_2O_6$ | | | |
|---|---|---|---|
| | C (%) | H (%) | N (%) |
| Calc. | 62.99 | 6.04 | 7.00 |
| Found | 62.78 | 5.91 | 7.05 |

REFERENCE EXAMPLE 6C

Under stirring at 0° C., 3.8 ml of pyridine is added and 2.04 ml of acetyl chloride is then added dropwise to a solution of 5.1 g of cis-3-benzyloxycarboxamido-1-(2,4-dimethoxybenzyl)-4-hydroxymethyl-2-oxoazetidine in 50 ml of methylene chloride. After the reaction mixture is stirred for 30 minutes, the solvent is distilled off in vacuo. The residue is subjected to column chromatography on silica gel eluting with ethyl acetate to give 5.45 g of (96%) of cis-4-acetoxymethyl-3-benzyloxycarboxamido-1-(2,4-dimethoxybenzyl)-2-oxoazetidine, m.p. 110°–111° C.

| Elemental analysis: $C_{23}H_{26}N_2O_7$ | | | |
|---|---|---|---|
|  | C (%) | H (%) | N (%) |
| Calc. | 62.43 | 5.92 | 6.33 |
| Found | 62.26 | 5.68 | 6.07 |

REFERENCE EXAMPLE 7C

A solution of 4.862 g of cis-4-acetoxymethyl-3-benzyloxycarboxamido-1-(2,4-dimethoxybenzyl)-2-oxoazetidine in 275 ml of acetonitrile is heated to 80°–83° C. in a stream of nitrogen under stirring. To the solution, 110 ml of an aqueous solution containing 4.752 g of potassium persulfate and 2.871 g of dipotassium phosphate is added dropwise. At the end of the dropwise addition, the mixture is stirred at 90° C. for 2.5 hours. Upon cooling, dipotassium phosphate is added to adjust the pH to 6–7 and the acetonitrile and water are distilled off in vacuo. Chloroform is added to the residue and the insoluble matters are collected by filtration, washed with water and chloroform in this order, and dried to give cis-4-acetoxymethyl-3-benzyloxycarboxamido-2-oxoazetidine, m.p. 137°–138° C.

| Elemental analysis: $C_{14}H_{16}N_2O_5$ | | | |
|---|---|---|---|
|  | C (%) | H (%) | N (%) |
| Calc. | 57.53 | 5.52 | 9.59 |
| Found | 57.38 | 5.43 | 9.58 |

REFERENCE EXAMPLE 8C

To a suspension of 1.46 g of cis-4-acetoxymethyl-3-benzyloxycarboxamido-2-oxoazetidine in 50 ml of ethanol is added 1.5 g of 5% palladium on charcoal and the mixture is subjected to catalytic reduction at atmospheric pressure under stirring. The reaction goes to completion in 30 minutes. The catalyst is removed by filtration and the filtrate is concentrated in vacuo to give 750 mg (95%) of cis-4-acetoxymethyl-3-amino-2-oxoazetidine as colorless oil.

IR $\nu_{max}^{neat}$cm$^{-1}$: 3300, 1770–1710.

NMR(CDCl$_3$, ppm): 1.83(br.s, —NH$_2$), 2.1(s, —CH$_3$), 3.6–4.1(m, —CH$_2$—), 4.1–4.8(m, C$_3$—H and C$_4$—H), 6.0–6.3(br.s, NH).

REFERENCE EXAMPLE 9C

Under ice-cooling and stirring, 12 ml of an aqueous solution containing 632 mg of cis-4-acetoxymethyl-3-amino-2-oxoazetidine and 1.122 g of sodium hydrogen carbonate is added to a suspension of 2.36 g of 2-(2-chloroacetamido-4-thiazolyl)-2-methoxyiminoacetyl chloride (syn-isomer) in 20 ml of tetrahydrofuran. The mixture is stirred for 2 hours at room temperature and the solvent is then distilled off in vacuo to leave the residue, which solidifies. Water is added to the solidified residue, followed by filtration. The collected crystals are washed successively with an aqueous sodium hydrogen carbonate solution, water and ether and dried to give cis-4-acetoxymethyl-3-[2-(2-chloroacetamido-4-thiazolyl)-2-methoxyiminoacetamido]-2-oxoazetidine (syn-isomer), m.p. 180°–190° C. (dec.).

| Elemental analysis: $C_{14}H_{16}ClN_5O_6S$ | | | |
|---|---|---|---|
|  | C (%) | H (%) | N (%) |
| Calc. | 40.24 | 3.86 | 16.76 |
| Found | 39.89 | 3.67 | 16.60 |

REFERENCE EXAMPLE 10C

Under ice-cooling and stirring, 1.94 g of methanesulfonyl chloride is added to a solution of 4.5 g of cis-3-benzyloxycarboxamido-1-(2,4-dimethoxybenzyl)-4-hydroxymethyl-2-oxoazetidine in 30 ml of pyridine. The mixture is stirred for 30 minutes at room temperature, and 100 ml of ethyl acetate and 50 ml of water are added to the reaction mixture, which is then acidified with dilute hydrochloric acid. The precipitated crystals are collected by filtration and the filtrate is separated into the aqueous and organic layers. The organic layer is concentrated in vacuo, water is added to the residue, and the resulting crystals are collected by filtration and combined with the crystals obtained above. The combined crystals are washed successively with an aqueous sodium hydrogen carbonate solution, water and ether and dried to give 5.0 g (93%) of cis-3-benzyloxycarboxamido-1-(2,4-dimethoxybenzyl)-4-methanesulfonyloxymethyl-2-oxoazetidine, m.p. 140°–141° C.

| Elemental analysis: $C_{22}H_{26}N_2O_8S$ | | | |
|---|---|---|---|
|  | C (%) | H (%) | N (%) |
| Calc. | 55.22 | 5.48 | 5.85 |
| Found | 55.16 | 5.40 | 5.61 |

REFERENCE EXAMPLE 11C

A solution of 3.83 g of cis-3-benzyloxycarboxamido-1-(2,4-dimethoxybenzyl)-4-methanesulfonyloxymethyl-2-oxoazetidine in 200 ml of acetonitrile is heated to 80°–83° C. in a stream of nitrogen under stirring. To the solution is added dropwise 80 ml of an aqueous solution containing 3.46 g of potassium persulfate and 2.09 g of dipotassium phosphate. At the end of the dropwise addition, the mixture is stirred at 85°–90° C. for 3 hours. The solvent is then distilled off in vacuo, 200 ml of water is added to the residue and the resulting crystals are collected by filtration, then washed with water and ether in this odrer and dried to give cis-3-benzyloxycarboxamido-4-methanesulfonyloxymethyl-2-oxoazetidine, m.p. 132°–133° C.

IR $\nu_{max}^{KBr}$cm$^{-1}$: 3325, 1770, 1690.

REFERENCE EXAMPLE 12C

To 55 ml of methyl ethyl ketone are added 1.4 g of cis-3-benzyloxycarboxamido-4-methanesulfonyloxymethyl-2-oxoazetidine and 4.2 g of sodium iodide and the mixture is stirred for 2 hours at 90° C. and then for 12 hours at 60° C. The solvent is then distilled off in vacuo. The residue is thoroughly shaken with 100 ml of water and 50 ml of chloroform, and the insoluble matters are collected by filtration, washed with water and chloroform in this order and dried to give cis-3-benzyloxycarboxamido-4-iodomethyl-2-oxoazetidine, m.p. 160°–162° C.

| Elemental analysis: $C_{12}H_{13}IN_2O_3$ | | | |
|---|---|---|---|
| | C (%) | H (%) | N (%) |
| Calc. | 40.02 | 3.64 | 7.78 |
| Found | 40.26 | 3.64 | 7.93 |

REFERENCE EXAMPLE 13C

To a solution of 103.5 mg of sodium dissolved in 9 ml of methanol is added 522 mg of 1-methyl-5-tetrazolylmercaptane and the mixture is stirred for 15 minutes at room temperature. The methanol is distilled off in vacuo and 12 ml of N,N-dimethylformamide is added to the residue to dissolve it. To the resulting solution 900 mg of cis-3-benzyloxycarboxamido-4-iodomethyl-2-oxoazetidine is added and the mixture is stirred for 19 hours at room temperature. To the reaction mixture 100 ml of water is added and the precipitated crystals are collected by filtration and washed with water and ether in this order. The crystals are then dissolved in ethyl acetate and passed through a small column of silica gel. The effluent is collected and the solvent is distilled off in vacuo to give 780 mg (90%) of cis-3-benzyloxycarboxamido-4-(1-methyl-5-tetrazolylthiomethyl)-2-oxoazetidine as colorless crystals, m.p. 151°–152° C.

| Elemental analysis: $C_{14}H_{16}N_6O_3S$ | | | |
|---|---|---|---|
| | C (%) | H (%) | N (%) |
| Calc. | 48.26 | 4.63 | 24.13 |
| Found | 48.38 | 4.65 | 23.89 |

REFERENCE EXAMPLE 14C

Under ice-cooling and stirring, 6 ml of an aqueous solution containing 288 mg of cis-3-amino-2-oxoazetidine-4-carboxylic acid methyl ester and 561 mg of sodium hydrogen carbonate is added to a suspension of 1.18 g of 2-(2-chloroacetamido-4-thiazolyl)-2-methoxyiminoacetyl chloride (anti isomer) in 10 ml of tetrahydrofuran. The mixture is stirred for 2 hours at room temperature and the solvent is then distilled off in vacuo to leave a residue, which solidifies. Water is added to the solidified residue, followed by filtration. The filtrate is neutralized with an aqueous sodium hydrogen carbonate solution and then extracted with chloroform. The chloroform layer is dried over anhydrous sodium sulfate and the solvent is distilled off in vacuo to give cis-3-[2-(2-chloroacetamido-4-thiazolyl)-2-methoxyiminoacetamido]-2-oxoazetidine-4-carboxylic acid methyl ester (anti-isomer). m.p. 119°–129° C.

| Elemental analysis: $C_{13}H_{14}ClN_5O_6S$ | | | |
|---|---|---|---|
| | C (%) | H (%) | N (%) |
| Calc. | 38.66 | 3.49 | 17.34 |
| Found | 38.56 | 3.60 | 17.05 |

REFERENCE EXAMPLE 15C

Under ice-cooling and stirring, 2.10 ml of triethylamine is added to a solution of 2.94 g of cis-3-amino-1-(2,4-dimethoxybenzyl)-2-oxoazetidine-4-carboxylic acid methyl ester in 40 ml of methylene chloride, and a solution of 2.31 g of phenylacetyl chloride in 15 ml of methylene chloride is then added dropwise over 1 hour. The stirring is continued for another one hour under ice-cooling, and the reaction mixture is then washed successively with dilute hydrochloric acid, 5% aqueous sodium hydrogen carbonate and an aqueous sodium chloride solution, and dried over magnesium sulfate, and the solvent is distilled off in vacuo. Ether is added to the residue and the precipitated crystals are collected by filtration to give cis-1-(2,4-dimethoxybenzyl)-3-phenylacetamido-2-oxoazetidine-4-carboxylic acid methyl ester, m.p. 124°–126° C.

| Elemental analysis: $C_{22}H_{24}N_2O_6$ | | | |
|---|---|---|---|
| | C (%) | H (%) | N (%) |
| Calc. | 64.07 | 5.86 | 6.79 |
| Found | 63.98 | 5.98 | 6.70 |

REFERENCE EXAMPLE 16C

A mixture of 412 mg of cis-1-(2,4-dimethoxybenzyl)-3-phenylacetamido-2-oxoazetidine-4-carboxylic acid methyl ester, 810 mg of potassium persulfate and 261 mg of dipotassium phosphate in 20 ml of acetonitrile and 20 ml of water is heated under reflux for one hour. The reaction mixture is concentrated in vacuo and the residue is dissolved in ethyl acetate, and washed successively with an aqueous 5% sodium hydrogen carbonate solution and an aqueous sodium chloride solution, and dried over magnesium sulfate, and the solvent is then distilled off in vacuo. Ethyl acetate is added to the residue and the precipitated crystals are collected by filtration to give cis-3-phenylacetamido-2-oxoazetidine-4-carboxylic acid methyl ester, m.p. 176°–180° C.

IR $\nu_{max}^{KBr}$cm$^{-1}$: 1790, 1740, 1655.

NMR($d_6$-DMSO, ppm): 3.47(s, CH$_2$CO & OCH$_3$), 4.20(d, J=6 Hz, C$_4$—H), 5.35(d, d, J=6, 8 Hz, C$_3$—H), 7.32(s, C$_6$H$_5$), 8.44(s, NH), 8.62(d, J=8 Hz, CONH).

REFERENCE EXAMPLE 17C

Under ice-cooling and stirring, 12 ml of an aqueous solution containing 570 mg of sodium borohydride is added to a solution of 2.06 g of cis-1-(2,4-dimethoxybenzyl)-3-phenylacetamido-2-oxoazetidine-4-carboxylic acid methyl ester in 24 ml of tetrahydrofuran. The reaction mixture is stirred for 30 minutes under ice-cooling and then for 1.5 hours at room temperature. The tetrahydrofuran is distilled off in vacuo and an aqueous sodium chloride solution and ethyl acetate are added to the residue. The resulting ethyl acetate layer is separated and washed successively with an aqueous sodium hydrogen carbonate and an aqueous sodium chloride. It is then dried over magnesium sulfate and the solvent is distilled off in vacuo. Ether is added to the residue and the precipitated crystals are collected by filtration to give 1.75 g (91%) of cis-1-(2,4-dimethoxybenzyl)-4-hydroxymethyl-3-phenylacetamido-2-oxoazetidine, m.p. 152°–154° C.

| Elemental analysis: $C_{21}H_{24}N_2O_5$ | | | |
|---|---|---|---|
| | C (%) | H (%) | N (%) |
| Calc. | 65.61 | 6.29 | 7.29 |
| Found | 65.37 | 6.47 | 7.55 |

REFERENCE EXAMPLE 18C

Under stirring at 0° C., 1.73 g of cis-1-(2,4-dimethoxybenzyl)-4-hydroxymethyl-3-phenylacetamido-2-oxoazetidine is added to a solution of 1.12 g of p- toluenesulfonyl chloride in 6 ml of pyridine. The reaction mixture is stirred for 2 hours and then allowed to stand overnight in a refrigerator. To the reaction mixture is added 0.68 ml of lactic acid and the mixture is stirred for one hour. The reaction mixture is diluted with 45 ml of ethyl acetate and 15 ml of tetrahydrofuran, and then washed with dilute hydrochloric acid, and aqueous sodium chloride solution, an aqueous sodium hydrogen carbonate solution and an aqueous sodium chloride solution in this order. The organic solution is dried over magnesium sulfate and the solvent is distilled off in vacuo. To the residue is added a mixed solvent of ether and ethyl acetate (5:1) and the resulting crystals are collected by filtration to give 2.21 g (91%) of cis-1-(2,4-dimethoxybenzyl)-3-phenylacetamido-4-(p-toluenesulfonyloxymethyl)-2-oxoazetidine, m.p. 109°–110° C.

| Elemental analysis: $C_{28}H_{30}N_2O_7S$ | | | |
|---|---|---|---|
| | C (%) | H (%) | N (%) |
| Calc. | 62.43 | 5.63 | 5.20 |
| Found | 62.18 | 5.72 | 5.07 |

REFERENCE EXAMPLE 19C

To 70 ml of acetone was added 2.27 g of cis-1-(2,4-dimethoxybenzyl)-3-phenylacetamido-4-(p-toluenesulfonyloxymethyl)-2-oxoazetidine and 4.95 g of sodium iodide, and the mixture is heated under reflux for 6 hours with stirring, and then concentrated in vacuo. To the residue are added methylene chloride and water to dissolve it, and the methylene chloride layer is separated and washed successively with an aqueous sodium thiosulfate solution and an aqueous sodium chloride solution. The methylene chloride layer is then dried over magnesium sulfate and the solvent is distilled off in vacuo. Ethyl acetate is added to the residue and the precipitated crystals are collected by filtration to give cis-1-(2,4-dimethoxybenzyl)-4-iodomethyl-3-phenylacetamido-2-oxoazetidine, m.p. 181°–182° C.

| Elemental analysis: $C_{21}H_{23}IN_2O_4$ | | | |
|---|---|---|---|
| | C (%) | H (%) | N (%) |
| Calc. | 51.03 | 4.69 | 5.67 |
| Found | 51.14 | 4.64 | 5.81 |

REFERENCE EXAMPLE 20C

To 6 ml of N,N-dimethylformamide are added 740 mg of cis-1-(2,4-dimethoxybenzyl)-4-iodomethyl-3-phenylacetamido-2-oxoazetidine and 146 mg of sodium azide and the mixture is stirred for 4 days at room temperature. The solvent is distilled off in vacuo, and ethyl acetate and water are added to the residue. The ethyl acetate layer is separated, washed with an aqueous sodium chloride solution, and dried over magnesium sulfate. The solvent is distilled off in vacuo. To the residue, ether is added and the precipitated crystals are collected by filtration to give cis-4-azidomethyl-1-(2,4-dimethoxybenzyl)-3-phenylacetamido-2-oxoazetidine, m.p. 110°–111° C.

IR $\nu_{max}^{KBr}$ cm$^{-1}$: 3270, 2210, 1755, 1650.

NMR(CDCl$_3$, ppm): 3.32(m, —CH$_2$N$_3$), 3.63(s, CH$_2$CO), 3.83(s, OCH$_3 \times 2$), 4.36(d, d, J=14 Hz, CH$_2$Ar), 5.28(q, J=5 Hz, C$_3$—H), 6.40–6.80(m, ArH & CONH), 7.16(m, ArH), 7.15(s, C$_6$H$_5$).

REFERENCE EXAMPLE 21C

To a solution of 449 mg of cis-4-azidomethyl-1-(2,4-dimethoxybenzyl)-3-phenylacetamido-2-oxoazetidine in 80 ml of ethanol is added 200 mg of 10% palladium on charcoal, and the mixture is subjected to hydrogenation for 1.5 hours at room temperature and atmospheric pressure. The reaction mixture is filtered to remove the catalyst and the filtrate is concentrated to dryness in vacuo. The residue is taken up in 30 ml of methylene chloride. Under stirring at 0° C., 0.20 ml of triethylamine is added to the resulting methylene chloride solution, and a solution of 0.10 ml of acetyl chloride in methylene chloride is added dropwise over 10 minutes thereto. The reaction mixture is stirred for 40 minutes and then washed with dilute hydrochloric acid, water, an aqueous sodium hydrogen carbonate solution and an aqueous sodium chloride solution in this order, and dried over magnesium sulfate, and the solvent is distilled off in vacuo. Ethyl acetate is added to the residue and the resulting crystals are collected by filtration to give cis-4-acetamidomethyl-1-(2,4-dimethoxybenzyl)-3-phenylacetamido-2-oxoazetidine, m.p. 205°–207° C.

IR $\nu_{max}^{KBr}$ cm$^{-1}$: 3270, 1750, 1640.

REFERENCE EXAMPLE 22C

A mixture of 298 mg of cis-4-acetamidomethyl-1-(2,4-dimethoxybenzyl)-3-phenylacetamido-2-oxoazetidine, 576 mg of potassium persulfate and 183 mg of dipotassium phosphate in 15 ml of water and 15 ml of acetonitrile is heated under reflux for 1.5 hours. The reaction mixture is concentrated in vacuo. The residue is taken up in ethyl acetate and the solution is washed successively with an aqueous sodium hydrogen carbonate solution and an aqueous sodium chloride solution. The ethyl acetate solution is dried over magnesium sulfate and the solvent is then distilled off in vacuo. Ethyl acetate is added to the residue and the precipitated crystals are collected by filtration to give cis-4-acetamidomethyl-3-phenylacetamido-2-oxoazetidine, m.p. 200°–202° C.

IR $\nu_{max}^{KBr}$ cm$^{-1}$: 3250, 1750, 1640, 1520.

NMR(d$_6$-DMSO, ppm): 1.77(s, COCH$_3$), 3.11(m, CH$_2$N), 3.69(d, t, J=5,6 Hz, C$_4$—H), 5.00(d, d, J=5,8 Hz), 7.26(s, C$_6$H$_5$), 7.59(m, NH),

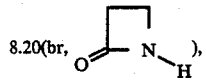
8.20(br, ), 8.75(d, CONH, J=8 Hz,).

REFERENCE EXAMPLE 23C

To 200 ml of benzene are added 8.5 g of cis-1-(2,4-dimethoxybenzyl)-3-phthalimido-2-oxoazetidine-4-carboxylic acid methyl ester and 3.1 g of 1,8-diazabicyclo[5,4,0]-7-undecene, and the mixture is heated under reflux for 72 hours. To the reaction mixture, after cooling, is added 100 ml of ethyl acetate, followed by washing with 100 ml and 50 ml of 1N-HCl, and 100 ml of water in this order. To the resulting mixture is added 100 ml of chloroform and dried over anhydrous sodium sulfate. The solvent was evaporated under reduced pressure. To the residue is added 50 ml of ethyl acetate. The resulting insolubles are collected by filtration, and washed with 30 ml of ethyl acetate to yield 6.4 g of crude product, which is recrystallized from 220 ml of ethyl acetate to yield trans-1-(2,4-dimethoxybenzyl)-3-phthalimido-2-oxoazetidine-4-carboxylic acid methyl ester, m.p. 186°-188° C.

| Elemental analysis: $C_{22}H_{20}N_2O_7$ | | | |
|---|---|---|---|
| | C (%) | H (%) | N (%) |
| Calc. | 62.26 | 4.75 | 6.60 |
| Found | 62.13 | 4.64 | 6.43 |

REFERENCE EXAMPLE 24C

To 83 ml of methylene chloride are added 8.3 g of 2,4-dimethoxybenzylamine and 6.0 g of anhydrous magnesium sulfate, and to the mixture is added dropwise under ice-water cooling a solution of 6.5 g of glyoxylic acid n-butyl ester in 65 ml of methylene chloride with stirring, followed by stirring for further two hours. The reaction mixture is subjected to filtration. To the filtrate is added 5 g of triethylamine, followed by addition of a solution of 11 g of phthalimido-acetyl chloride in 110 ml of methylene chloride. The mixture is stirred overnight, then washed with dilute hydrochloric acid, an aqueous solution of sodium chloride, an aqueous solution of sodium bicarbonate and an aqueous solution of sodium chloride in this order, and dried over anhydrous sodium sulfate. The mixture is subjected to filtration, and the filtrate is concentrated. To the residue is added ether, and the insolubles are removed by filtration. The filtrate is concentrated under reduced pressure to yield 20.1 g (86%) of cis-1-(2,4-dimethoxybenzyl-3-phthalimido-2-oxoazetidine-4-carboxylic acid n-butyl ester as orange-colored oily product. A portion of the product is purified on a silica-gel chromatography to give a colorless foamy product. For the reactions shown hereinafter, however, the above product is employed in the crude state.

IR $\nu_{max}^{Nujol}$ cm$^{-1}$: 1770, 1720. NMR(CDCl$_3$, ppm): 4.26(1H, d, J=5 Hz, C$_4$—H), 5.63(1H, d, J=5 Hz, C$_3$—H).

REFERENCE EXAMPLE 25C

To a solution of 19 g of cis-1-(2,4-dimethoxybenzyl)-3-phthalimido-2-oxoazetidine-4-carboxylic acid n-butyl ester in 190 ml of methylene chloride is added 3.7 g of methyl hydrazine. The mixture is stirred overnight at room temperature. The reaction mixture is subjected to filtration, and the filtrate is concentrated under reduced pressure. To the residue is added ethyl acetate, and the insolubles are removed by filtration. The filtrate is subjected to extraction twice, with 100 ml each of 1N-HCl. The extracts are neutralized with sodium hydrogen carbonate, and extracted with ethyl acetate. The extract is washed with an aqueous solution of sodium chloride, dried over anhydrous sodium sulfate, followed by evaporation of the solvent under reduced pressure to yield 12 g (87.5%) of cis-3-amino-1-(2,4-dimethoxybenzyl)-2-oxoazetidine-4-carboxylic acid n-butyl ester as oily product.

IR $\nu_{max}^{neat}$ cm$^{-1}$: 3400, 1750.

NMR(CDCl$_3$, ppm): 3.83, 3.93(2×3H, 2×s, 2×OCH$_3$).

Similarly prepared was:
Trans-3-amino-1-(2,4-dimethoxybenzyl)-2-oxoazetidine-4-carboxylic acid methyl ester as oily product.

IR $\nu_{max}^{neat}$ cm$^{-1}$: 3400, 3330, 1760.

NMR(CDCl$_3$, ppm): 3.70(1H, d, J=2 Hz, C$_3$—H), 3.79, 3.80, 3.81(3×3H, 3×s, 3×CH$_3$), 4.21(1H, d, J=2 Hz, C$_4$—H), 4.45(2H, q, J=14 Hz, CH$_2$).

REFERENCE EXAMPLE 26C

To a solution of 10 g of cis-3-amino-1-(2,4-dimethoxybenzyl)-2-oxoazetidine-4-carboxylic acid n-butyl ester in 40 ml of methylene chloride are added under ice-cooling and stirring 1.8 g of propylene oxide and then 5.5 g of carbobenzoxy chloride. The mixture is warmed to room temperature and stirred for one hour. The solvent is evaporated under reduced pressure. To the residue is added isopropylether, and the resulting crystals are collected by filtration to yield 11.7 g (83.5%) of cis-3-benzyloxycarboxamido-1-(2,4-dimethoxybenzyl)-2-oxoazetidine-4-carboxylic acid n-butyl ester as colorless crystals, m.p. 97°-98° C.

| Elemental analysis: $C_{25}H_{30}N_2O_7$ | | | |
|---|---|---|---|
| | C (%) | H (%) | N (%) |
| Calc. | 63.81 | 6.42 | 5.95 |
| Found | 63.51 | 6.26 | 6.09 |

Similarly prepared was:
Trans-3-benzyloxycarboxamido-1-(2,4-dimethoxybenzyl)-2-oxoazetidine-4-carboxylic acid methyl ester.

As this product did not crystallize by treating similarly as the above, it was purified on a column chromatography (silica-gel, eluent: hexane-ethyl acetate, 1:1) to yield a colorless oily product. The yield is 89%.

IR $\nu_{max}^{neat}$ cm$^{-1}$: 3340, 1770, 1740-1720.

NMR(CDCl$_3$, ppm): 3.93(1H, d, J=3 Hz, C$_4$—H), 5.07(2H, s, CH$_2$Ph).

REFERENCE EXAMPLE 27C

To a mixture of 60 ml each of acetonitrile and water are added 2.35 g of cis-3-benzyloxycarboxamido-1-(2,4-dimethoxybenzyl)-2-oxoazetidine-4-carboxylic acid n-butyl ester, 4.05 g of potassium persulfate and 1.74 g of dipotassium hydrogen phosphate, and the resulting mixture is heated under reflux for one hour under the atmosphere of argon. Acetonitrile is evaporated under reduced pressure. To the residue are added ethyl acetate and water, and the mixture is shaken. The ethyl acetate layer is separated, then washed with an aqueous solution of sodium bicarbonate and an aqueous solution of sodium chloride in this order, and dried over anhydrous sodium sulfate. The solvent is evaporated under reduced pressure, and the residue is subjected to column chromatography on silica gel, eluting with a mixture of ethyl acetate-hexane (1:1) to yield crystals of cis-3-benzyloxycarboxamido-2-oxoazetidine-4-carboxylic acid n-butyl ester, m.p. 112°-113° C.

| Elemental analysis: $C_{16}H_{20}N_2O_5$ | | | |
|---|---|---|---|
| | C (%) | H (%) | N (%) |
| Calc. | 59.98 | 6.29 | 8.74 |
| Found | 60.25 | 6.33 | 8.53 |

Similarly synthesized was:
Trans-3-benzyloxycarboxamido-2-oxoazetidine-4-carboxylic acid methyl ester, m.p. 139°-140° C.

REFERENCE EXAMPLE 28C

To a suspension of 640 mg of cis-3-benzyloxycarboxamido-2-oxoazetidine-4-carboxylic acid n-butyl ester in 23 ml of ethanol is added 640 mg of 10% palladium on carbon, and the mixture is subjected to catalytic reduction with stirring under normal pressure. After the hydrogen uptake has ceased, the reaction mixture is subjected to filtration to remove the catalyst. The filtrate is concentrated under reduced pressure, and the residue is crystallized to yield 330 mg (87.1%) of cis-3-amino-2-oxoazetidine-4-carboxylic acid n-butyl ester. A portion of the product is recrystallized from a mixture of ethyl acetate and hexane to yield orange-colored scale-like crystals, m.p. 87°–89° C.

| Elemental analysis: $C_8H_{14}N_2O_3$ | | | |
|---|---|---|---|
| | C (%) | H (%) | N (%) |
| Calc. | 51.60 | 7.57 | 15.04 |
| Found | 51.35 | 7.58 | 14.80 |

Similarly synthesized was:
Trans-3-amino-2-oxoazetidine-4-carboxylic acid methyl ester, m.p. 135°–136° C.

REFERENCE EXAMPLE 29C

To a solution of 13.6 g of 2-hydroxyiminoacetoacetic acid methyl ester in 70 ml of acetone is added under ice cooling 20.8 g of potassium carbonate. To the mixture is added dropwise 17.0 g of n-propyl iodide in the course of 30 minutes. At the end of the dropwise addition, the mixture is stirred at room temperature for 2 hours. Acetone is evaporated under reduced pressure. To the residue is added 250 ml of water, and the mixture is subjected to extraction with methylene chloride. The extract is washed with water twice, dried over anhydrous sodium sulfate, followed by evaporation of the solvent under reduced pressure to yield 2-(n-propoxyimino)acetoacetic acid methyl ester as a pale yellow oily product.

IR $\nu_{max}^{neat}$ cm$^{-1}$: 2975, 1750, 1695, 1600.
NMR(CDCl$_3$, ppm): 0.95(3H, t, J=7 Hz, CH$_2$CH$_2$CH$_3$), 1.75(2H, sextet, J=7 Hz, CH$_2$CH$_2$CH$_3$), 2.38(3H, s, CH$_3$CO), 3.86(3H, s, COOCH$_3$).

Similarly synthesized were:
2-(n-Butoxyimino)acetoacetic acid methyl ester pale yellow oily product, yield 80%.

IR $\nu_{max}^{neat}$ cm$^{-1}$: 2975, 1755, 1700, 1600.
NMR(CDCl$_3$, ppm): 0.94(3H, t, J=6 Hz, CH$_2$CH$_2$CH$_2$CH$_3$), 1.2–2.0(4H, m, CH$_2$CH$_2$CH$_2$CH$_3$), 2.36(3H, s, CH$_3$CO), 3.85(3H, s, COOCH$_3$), 4.29(2H, t, J=6 Hz, CH$_2$CH$_2$CH$_2$CH$_3$).

2-Benzyloxyiminoacetoacetic acid methyl ester pale yellow oily product, yield 98%.

IR $\nu_{max}^{neat}$ cm$^{-1}$: 1750, 1690.
NMR(CDCl$_3$, ppm): 2.36(3H, s, CH$_3$CO), 3.83(3H, s, COOCH$_3$), 5.28(2H, s, CH$_2$), 7.27(5H, s, —Ph).

REFERENCE EXAMPLE 30C

To a solution of 7.4 g of 2-(n-propoxyimino)acetoacetic acid methyl ester in 7.4 ml of acetic acid is added 5.5 g of sulfuryl chloride, and the mixture is stirred for 10 minutes at 40° C., then for 6 hours at room temperature. The reaction solution is poured into 100 ml of ice-water, and subjected to extraction twice with chloroform. The extract is washed with an aqueous solution of sodium chloride, and aqueous solution of sodium bicarbonate and water in this order, and dried over anhydrous sodium sulfate. The solvent is evaporated under reduced pressure to yield 8.2 g (94%) of 4-chloro-2-(n-propoxyimino)acetoacetic acid methyl ester as a pale yellow oily product.

IR $\nu_{max}^{neat}$ cm$^{-1}$: 2980, 1750, 1720, 1595.
NMR(CDCl$_3$, ppm): 0.97(3H, t, J=7 Hz, CH$_2$CH$_2$CH$_3$), 1.77(2H, sextet, J=7 Hz, CH$_2$CH$_2$CH$_3$), 3.89(3H, s, COOCH$_3$), 4.30(2H, t, J=7 Hz, CH$_2$CH$_2$CH$_3$), 4.56(2H, s, ClCH$_2$).

Similarly synthesized were:
4-Chloro-2-(n-butoxyimino)acetoacetic acid methyl ester pale yellow oily product, yield 92%.

IR $\nu_{max}^{neat}$ cm$^{-1}$: 2975, 1750, 1720, 1595.
NMR(CDCl$_3$, ppm): 0.97(3H, t, J=6 Hz, CH$_2$CH$_2$CH$_2$CH$_3$), 1.2–2.0(4H, m, CH$_2$CH$_2$CH$_2$CH$_3$), 3.88(3H, s, COOCH$_3$), 4.33(2H, t, J=6 Hz, CH$_2$CH$_2$CH$_2$CH$_3$), 4.56(2H, s, ClCH$_2$).

4-Chloro-2-benzyloxyiminoacetoacetic acid methyl ester pale yellow oily product, yield 97%.

IR $\nu_{max}^{neat}$ cm$^{-1}$: 1755, 1720.
NMR(CDCl$_3$, ppm): 3.87(3H, s, COOCH$_3$), 4.50(2H, s, ClCH$_2$), 5.29(2H, s, CH$_2$—Ph), 7.28(5H, s, —Ph).

REFERENCE EXAMPLE 31C

To a mixture solution of 20 ml of water and 25 ml of ethanol are added 7.0 g of 4-chloro-2-(n-propoxyimino)acetoacetic acid methyl ester, 2.4 g of thiourea and 4.3 g of sodium acetate(trihydrate). The mixture is stirred for one hour at 40° C. The reaction mixture is, under cooling, adjusted to pH 6.5 with a saturated aqueous solution of potassium carbonate, followed by stirring for 30 minutes. The resulting crystals are collected by filtration, washed with water and isopropyl ether in this order, and dried to yield 2-(2-amino-4-thiazolyl)-(Z)-2-(n-propoxyimino)acetic acid methyl ester as crystals, m.p. 115°–116° C.

| Elemental analysis: $C_9H_{13}N_3O_3S$ | | | |
|---|---|---|---|
| | C (%) | H (%) | N (%) |
| Calc. | 44.43 | 5.39 | 17.27 |
| Found | 44.20 | 5.38 | 17.11 |

Similarly synthesized were:
2-(2-Amino-4-thiazolyl)-(Z)-2-(n-butoxyimino)acetic acid methyl ester, m.p. 118° C.
2-(2-Amino-4-thiazolyl)-(Z)-2-benzyloxyiminoacetic acid methyl ester, m.p. 148°–149° C.

REFERENCE EXAMPLE 32C

To a solution of 5.0 g of 2-(2-amino-4-thiazolyl)-(Z)-2-(n-propoxyimino)acetic acid methyl ester in 35 ml of N,N-dimethylacetamido is added dropwise under ice-cooling and stirring 3.25 g of chloroacetyl chloride in the course of 10 minutes. The mixture is stirred for one hour at room temperature, then poured into 200 ml of ice-water, whereupon an oily product separates out, which is left standing to crystallize. The crystals are collected by filtration, washed with water and dried to yield 6.35 g (96.7%) of 2-(2-chloroacetamido-4-thiazolyl)-(Z)-2-(n-propoxyimino)-acetic acid methyl ester, m.p. 100° C.

| Elemental analysis: $C_{11}H_{14}ClN_3O_4S$ | | | |
|---|---|---|---|
| | C (%) | H (%) | N (%) |
| Calc. | 41.31 | 4.41 | 13.14 |
| Found | 41.35 | 4.34 | 13.14 |

Similarly synthesized were:

2-(2-Chloroacetamido-4-thiazolyl)-(Z)-2-(n-butoxyimino)acetic acid methyl ester, m.p. 86°–87° C. Yield 85%.

2-(2-Chloroacetamido-4-thiazolyl)-(Z)-2-benzyloxyimino)acetic acid methyl ester, m.p. 110°–115° C. Yield 96%.

REFERENCE EXAMPLE 33C

To a solution of 3.2 g of 2-(2-chloroacetamido-4-thiazolyl)-(Z)-2-(n-propoxyimino)acetic acid methyl ester in 50 ml of ethanol is added under ice-cooling and stirring a solution of 2.23 g of potassium hydroxide (85%) in 20 ml of water, and the mixture is stirred for 5 hours at room temperature, followed by concentration under reduced pressure. The concentrate is dissolved in 30 ml of water, and washed twice with 30 ml each portion of ethyl acetate, followed by addition of activated charcoal. The charcoal is removed by filtration and the filtrate is then adjusted to pH 2 with 1N-HCl, and the resulting crystals are collected by filtration, washed with water, hexane and ether in this order to yield 2-(2-chloroacetamido-4-thiazolyl)-(Z)-2-(n-propoxyimino)acetic acid, m.p. 170°–171° C. (decomp.).

| | Elemental analysis: $C_{10}H_{12}ClN_3O_4S$ | | |
|---|---|---|---|
| | C (%) | H (%) | N (%) |
| Calc. | 39.28 | 3.96 | 13.74 |
| Found | 39.34 | 3.84 | 13.41 |

Similarly synthesized were:
2-(2-Chloroacetamido-4-thiazolyl)-(Z)-2-(n-butoxyimino)acetic acid, m.p. 167°–168° C. (decomp.).
2-(2-Chloroacetamido-4-thiazolyl)-(Z)-2-benzyloxyimino acetic acid, m.p. 160°–161° C. (decomp.).

REFERENCE EXAMPLE 34C

To a suspension of 583 mg of 2-(2-chloroacetamido-4-thiazolyl)-(Z)-2-ethoxyimino-acetic acid in 5 ml of methylene chloride is added under ice-cooling 243 mg of triethylamine. To the mixture is added 416.5 mg of phosphorus pentachloride, which is stirred for 30 minutes at room temperature. Methylene chloride is evaporated under reduced pressure. The residue is washed three times with hexane, and suspended in 7 ml of tetrahydrofuran. To the suspension is added dropwise a solution of 216 mg of cis-3-amino-2-oxoazetidine-4-carboxylic acid methyl ester and 308 mg of sodium hydrogen carbonate in 4.2 ml of water. The mixture is stirred for 2 hours at room temperature, followed by evaporation of the solvent. To the residue is added 20 ml of water, followed by addition of sodium hydrogen carbonate to make weakly alkaline. Then the insolubles are collected by filtration, washed with an aqueous solution of sodium bicarbonate, water, hexane and ether in this order, and dried to yield cis-3-[2-(2-chloroacetamido-4-thiazolyl)-2-ethoxyiminoacetamido]-2-oxoazetidine-4-carboxylic acid methyl ester (syn-isomer), m.p. 270°–280° C. (decomp.).

| | Elemental analysis: $C_{14}H_{16}ClN_5O_6S$ | | |
|---|---|---|---|
| | C (%) | H (%) | N (%) |
| Calc. | 40.24 | 3.86 | 16.76 |
| Found | 39.98 | 3.80 | 16.91 |

Similarly synthesized were:

Cis-3-[2-(2-chloroacetamido-4-thiazolyl)-2-(n-propoxyimino)acetamido]-2-oxoazetidine-4-carboxylic acid methyl ester (syn-isomer), m.p. 260°–270° C. (decomp.).

Cis-3-[2-(2-chloroacetamido-4-thiazolyl)-2-isopropoxyiminoacetamido]-2-oxoazetidine-4-carboxylic acid methyl ester (syn-isomer), m.p. 215°–225° C. (decomp.).

Cis-3-[2-(2-chloroacetamido-4-thiazolyl)-2-(n-propoxyimino)acetamido]-2-oxoazetidine-4-carboxylic acid methyl ester (syn-isomer), m.p. 275°–280° C. (decomp.).

Cis-3-[2-(2-chloroacetamido-4-thiazolyl)-2-benzyloxyiminoacetamido]-2-oxoazetidine-4-carboxylic acid methyl ester (syn-isomer), m.p. 275°–285° C. (decomp.).

Cis-3-[2-(5-chloro-2-chloroacetamido-4-thiazolyl)-2-methoxyiminoacetamido]-2-oxoazetidine-4-carboxylic acid methyl ester (syn-isomer), m.p. 215°–220° C. (decomp.).

Cis-3-[2-(2-chloroacetamido-4-thiazolyl)-2-methoxyiminoacetamido]-2-oxoazetidine-4-carboxylic n-butyl ester (syn-isomer), m.p. 235°–239° C. (decomp.).

Trans-3-[2-(2-chloroacetamido-4-thiazolyl)-2-methoxyiminoacetamido]-2-oxoazetidine-4-carboxylic acid methyl ester (syn-isomer), m.p. 137°–139° C.

| | Elemental analysis: $C_{13}H_{14}ClN_5O_6S \cdot CH_3OH$ | | |
|---|---|---|---|
| | C (%) | H (%) | N (%) |
| Calc. | 38.57 | 4.16 | 16.07 |
| Found | 38.93 | 4.15 | 16.04 |

REFERENCE EXAMPLE 35C

To a solution of 9.3 g of 2-amino-4-thiazolyl acetic acid ethyl ester in 50 ml of N,N-dimethylacetamide is added under ice-cooling 7.91 g of chloroacetyl chloride with stirring. The mixture is stirred for one hour at room temperature, to which is added 300 ml of water. Then the resulting crystals are collected by filtration. The crystals are washed with water and ether in this order, followed by drying over phosphorus pentachloride to yield 12.1 g (92%) of 2-chloroacetamido-4-thiazolyl-acetic acid ethyl ester, m.p. 145°–146° C.

| | Elemental analysis: $C_9H_{11}ClN_2O_3S$ | | |
|---|---|---|---|
| | C (%) | H (%) | N (%) |
| Calc. | 41.14 | 4.22 | 10.66 |
| Found | 41.16 | 4.14 | 10.86 |

REFERENCE EXAMPLE 36C

To a solution of 2.5 g of potassium hydroxide in a mixture of 10 ml of water and 100 ml of ethanol is added 3.0 g of 2-chloroacetamido-4-thiazolyl acetic acid ethyl ester, and the mixture is stirred for one hour at room temperature. The solvent is evaporated under reduced pressure. To the residue is added 10 ml of water. The resulting aqueous solution is washed with ethyl acetate, and then adjusted to pH 2 with 10% hydrochloric acid, whereupon crystals separate out. The crystals are collected by filtration, washed with water, and dried to yield 2.2 g (84%) of 2-chloroacetamido-4-thiazolyl acetic acid, m.p. 193°–195° C.

| Elemental analysis: C₇H₇ClN₂O₃S | | | |
|---|---|---|---|
| | C (%) | H (%) | N (%) |
| Calc. | 35.83 | 3.01 | 11.94 |
| Found | 36.00 | 3.15 | 12.24 |

REFERENCE EXAMPLE 37C

To a suspension of 1.41 g of 2-chloroacetamido-4-thiazolyl acetic acid in 30 ml of methylene chloride is added under ice-cooling and stirring 1.5 g of phosphorus pentachloride. The mixture is then stirred at room temperature for 40 minutes, followed by filtration to afford 1.7 g (98%) of the corresponding acid chloride hydrochloride, as colorless crystals, m.p. 123°–125° C. (decomp.).

IR $\nu_{max}^{KBr}$ cm$^{-1}$: 1780, 1712.

Subsequently, to a solution of cis-3-amino-2-oxoazetidine-4-carboxylic acid methyl ester in a mixture of 4 ml of water and 4 ml of tetrahydrofuran are added under ice-cooling and stirring 840 mg of sodium hydrogen carbonate and then 864 mg of the above mentioned acid chloride hydrochloride. The mixture is stirred at room temperature for two hours, and then concentrated to dryness under reduced pressure. To the residue is added 5 ml of water, and the insolubles are collected by filtration, and washed with an aqueous solution of sodium bicarbonate, water, hexane and ether in this order, and dried to afford cis-3-[2-(2-chloroacetamido-4-thiazolyl)acetamido]-2-oxoazetidine-4-carboxylic acid methyl ester, m.p. 120°–122° C.

| Elemental analysis: C₁₂H₁₃ClN₄O₅S.½H₂O | | | |
|---|---|---|---|
| | C (%) | H (%) | N (%) |
| Calc. | 38.97 | 3.82 | 15.15 |
| Found | 39.01 | 4.23 | 15.40 |

REFERENCE EXAMPLE 38C

To a solution of 1 g of 1-(n-butyl)-2,3-dioxopiperazine in 10 ml of dry methylene chloride is added 0.766 g of trimethyl chlorosilane. To the mixture is added under nitrogen streams 0.712 g of triethylamine at room temperature, followed by stirring for one hour. The reaction mixture is cooled to −30° C., followed by dropwise addition of 0.39 ml of trichloromethyl chloroformate. The temperature of this mixture is gradually raised, and the mixture is stirred at room temperature for 30 minutes, followed by concentration to dryness under reduced pressure.

On the other hand, to a suspension of 0.924 g of D-(2-thienyl)glycine in 20 ml of dry methylene chloride is added 1.28 g of trimethyl chlorosilane, followed by addition of 1.19 g of triethylamine at room temperature and stirring for one hour. The reaction mixture is cooled to 0° C., to which is added the solid matter obtained by the above concentration. The mixture is stirred at room temperature for 2 hours, and dissolved in ethyl acetate. The solution is washed with water and an aqueous solution of sodium chloride in this order, dried over anhydrous magnesium sulfate, and concentrated under reduced pressure to afford D-2-[4-(n-butyl)-2,3-dioxo-1-piperazinecarboxamido]-2-(2-thienyl)acetic acid as a solid compound, quantitatively.

IR $\nu_{max}^{KBr}$ cm$^{-1}$: 1715, 1510, 1180.

NMR(CDCl₃, ppm): 5.72 (1H, d, J=6 Hz, CHCOOH), 9.70 (1H, d, NH).

Similarly synthesized were:

D-2-[4-(n-Octyl)-2,3-dioxo-1-piperazinecarboxamido]-2-(2-thienyl)acetic acid.

IR $\nu_{max}^{Nujol}$ cm$^{-1}$: 3250, 1720.

NMR(CDCl₃, ppm): 5.72(1H, d, J=6 Hz, CHCOOH), 9.75(1H, d, J=6 Hz, NH).

D-2-[4-(n-Butyl)-2,3-dioxo-1-piperazinecarboxamido]-2-phenylacetic acid.

IR $\nu_{max}^{KBr}$ cm$^{-1}$: 1715.

NMR(CDCl₃, ppm): 5.40(1H, d, J=7 Hz, CHCOOH), 7.22(5H, s, —Ph), 9.73(1H, d, NH).

REFERENCE EXAMPLE 39C

To a solution of 362 mg of D-2-[4-(n-butyl)-2,3-dioxo-1-piperazinecarboxamido]-2-phenylacetic acid and 150 mg of cis-3-amino-2-oxoazetidine-4-carboxylic acid methyl ester in 3 ml of dry N,N-dimethylformamide is added under ice-cooling 236 mg of dicyclohexylcarbodiimide. The mixture is stirred under nitrogen streams at room temperature for 5 hours, followed by addition of tetrahydrofuran, and the insoluble matter is removed by filtration. The filtrate is concentrated under reduced pressure, and the residue is purified on a column-chromatography (silica-gel 200 g, eluent: ethyl acetate-chloroform 1:1, and then ethyl acetate-chloroform-methanol, 15:15:1), whereby the objective cis-3-{D-2-[4-(n-butyl)-2,3-dioxo-1-piperazinecarboxamido]-2-phenylacetamido}-2-oxoazetidine-4-carboxylic acid methyl ester is obtained as a mixture of diastereoisomers, and the preceding eluated compound in the above column-chromatography is tentatively called as beta-form and the succeeding eluated compound is tentatively called as alpha-form.

Beta form

IR $\nu_{max}^{KBr}$ cm$^{-1}$: 3280, 1780, 1715, 1680.

NMR(CDCl₃, ppm): 3.12(3H, s, COOCH₃), 7.24(5H, br.s, —Ph).

Alpha form

IR $\nu_{max}^{KBr}$ cm$^{-1}$: 3295, 1780, 1720, 1680.

NMR(CDCl₃, ppm): 3.44(3H, br.s, COOCH₃), 7.27(5H, br. s, —Ph).

Similarly synthesized were:

Cis-3-{D-2-[4-(n-butyl)-2,3-dioxo-1-piperazinecarboxamido]-2-(2-thienyl)acetamido}-2-oxoazetidine-4-carboxylic acid methyl ester.

Beta form

IR $\nu_{max}^{KBr}$ cm$^{-1}$: 3300, 1775, 1710, 1675.

NMR(CDCl₃, ppm): 3.30(3H, s, COOCH₃).

Alpha form

IR $\nu_{max}^{KBr}$ cm$^{-1}$: 3300, 1780, 1720, 1680.

Cis-3-{D-2-[4-(n-octyl)-2,3-dioxo-1-piperazinecarboxamido]-2-(2-thienyl)acetamido}-2-octazetidine-4-carboxylic acid methyl ester.

Beta form

NMR(CDCl₃, ppm): 3.31(3H, s, COOCH₃), 4.42(1H, d, J=5 Hz, C₄—H).

Alpha form

NMR(CDCl₃, ppm): 3.45(3H, s, COOCH₃), 4.40(1H, d, J=5 Hz, C₄—H).

Trans-3-{D-2-[4-(n-octyl)-2,3-dioxo-1-piperazinecarboxamido]-2-(2-thienyl)acetamido}-2-oxoazetidine-4-carboxylic acid methyl ester.

Beta form

IR $\nu_{max}^{KBr}$ cm$^{-1}$: 3280, 2920, 1780, 1710, 1670.

NMR(CDCl₃, ppm): 3.68(3H, s, COOCH₃), 4.15(1H, d, J=2 Hz, C₄—H).

Alpha form
IR and NMR data are the same as those of beta-form.

REFERENCE EXAMPLE 40C

To a solution of 1.18 g of cis-3-amino-1-(2,4-dimethoxybenzyl)-2-oxoazetidine-4-carboxylic acid methyl ester in 5 ml of methylene chloride is added under ice-cooling 2.7 ml of propylene oxide with stirring, followed by dropwise addition of a solution of 0.83 ml of 2,2,2-trichloroethylchloroformate in 1 ml of methylene chloride over 10 minutes. The mixture is stirred for 30 minutes at room temperature. The solvent is evaporated under reduced pressure, whereupon the residue crystallizes. The crystals are washed with ether and dried to afford 1.67 g (89%) of cis-1-(2,4-dimethoxybenzyl)-3-(2,2,2-trichloroethoxycarboxamido)-2-oxoazetidine-4-carboxylic acid methyl ester, m.p. 135°–136° C.

| Elemental analysis: $C_{17}H_{19}Cl_3N_7O$ | | | |
|---|---|---|---|
| | C (%) | H (%) | N (%) |
| Calc. | 43.51 | 4.34 | 6.34 |
| Found | 43.64 | 4.42 | 6.16 |

REFERENCE EXAMPLE 41C

To a solution of 939 mg of cis-1-(2,4-dimethoxybenzyl)-3-(2,2,2-trichloroethoxycarboxamido)-2-oxoazetidine-4-carboxylic acid methyl ester in 10 ml of tetrahydrofuran is added under ice-cooling a solution of 228 mg of sodium borohydride in 10 ml of water with stirring. The mixture is stirred for 10 minutes under ice-cooling and then 4.5 hours at room temperature. The excess sodium borohydride is decomposed with acetic acid under ice-cooling, and the solvent is evaporated under reduced pressure. To the residue is added a saturated aqueous solution of sodium chloride, followed by extraction with ethyl acetate. The extract is washed with a 5% aqueous solution of sodium bicarbonate, a saturated aqueous solution of sodium chloride, dilute hydrochloric acid and a saturated aqueous solution of sodium chloride, successively, and dried over anhydrous magnesium sulfate. The solvent is evaporated under reduced pressure and the residue is purified on column chromatography (silica-gel 30 g, eluent: ethyl acetate-chloroform, 2:1). The eluting solvent is evaporated, and ether is added to the residue. The resulting crystals are collected by filtration to yield cis-1-(2,4-dimethoxybenzyl)-4-hydroxymethyl-3-(2,2,2-trichloroethoxycarboxamido)-2-oxoazetidine, m.p. 112°–114° C.

| Elemental analysis: $C_{16}H_{19}Cl_3N_2O_6$ | | | |
|---|---|---|---|
| | C (%) | H (%) | N (%) |
| Calc. | 43.51 | 4.34 | 6.34 |
| Found | 43.64 | 4.42 | 6.16 |

REFERENCE EXAMPLE 42C

To a solution of 340 mg of cis-1-(2,4-dimethoxybenzyl)-4-hydroxymethyl-3-(2,2,2-trichloroethoxycarboxamido)-2-oxoazetidine in 3 ml of pyridine is added under ice-cooling 132 mg of methanesulfonyl chloride with stirring. The mixture is stirred at room temperature for 50 minutes, followed by addition of water and ethyl acetate, and adjusted to pH 2 with dilute hydrochloric acid. The ethyl acetate layer is separated and washed with a saturated aqueous solution of sodium chloride, an aqueous solution of sodium bicarbonate and a saturated aqueous solution of sodium chloride, successively, and dried over anhydrous magnesium sulfate. The solvent is evaporated under reduced pressure, whereupon the residue crystallizes. To the crystals is added ether, and the crystals are collected by filtration to afford 375 mg (94%) of cis-1-(2,4-dimethoxybenzyl)-4-methanesulfonyloxymethyl-3-(2,2,2-trichloroethoxycarboxamido)-2-oxoazetidine as colorless crystals, m.p. 139°–140° C.

| Elemental analysis: $C_{17}H_{21}Cl_3N_2O_8S$ | | | |
|---|---|---|---|
| | C (%) | H (%) | N (%) |
| Calc. | 39.28 | 4.07 | 5.39 |
| Found | 39.21 | 4.16 | 5.48 |

REFERENCE EXAMPLE 43C

To a solution of 8.32 g of cis-1-(2,4-dimethoxybenzyl)-4-methanesulfonyloxymethyl-3-(2,2,2-trichloroethoxycarboxamido)-2-oxoazetidine in 450 ml of acetonitrile is added dropwise under stirring a solution of 7.79 g of potassium persulfate and 4.70 g of dipotassium hydrogen phosphate in 180 ml of water over 20 minutes under nitrogen streams at 85°–90° C. The mixture is stirred at the same temperature for further 2.5 hours, and after cooling, adjusted to pH 6–7 with dipotassium hydrogen phosphate, followed by concentration under reduced pressure. The residue is extracted with ethyl acetate, and the extract is washed with a saturated aqueous solution of sodium chloride, followed by drying over magnesium sulfate. The solvent is evaporated under reduced pressure, and the residue is purified on a column-chromatography (silica-gel 270 g, eluent: ethyl acetate-hexane, 2:1 and ethyl acetate) to afford cis-4-methanesulfonyloxymethyl-3-(2,2,2-trichloroethoxycarboxamido)-2-oxoazetidine as colorless crystals, m.p. 85°–86° C.

| Elemental analysis: $C_8H_{11}Cl_3N_2O_6S$ | | | |
|---|---|---|---|
| | C (%) | H (%) | N (%) |
| Calc. | 26.00 | 3.00 | 7.58 |
| Found | 26.15 | 3.04 | 7.62 |

REFERENCE EXAMPLE 44C

To 130 ml portion of methylethylketone are added 3.7 g of cis-4-methanesulfonyloxymethyl-3-(2,2,2-trichloroethoxycarboxamido)-2-oxoazetidine and 8.85 g of sodium iodide, and the mixture is heated under reflux in the stream of nitrogen for 3 hours. The solvent is evaporated under reduced pressure. To the residue, are added water and ethyl acetate, and the mixture is shaken. The ethyl acetate layer is separated and washed with an aqueous solution of sodium sulfite and an aqueous solution of sodium chloride in this order, followed by drying over anhydrous sodium sulfate. On evaporation of the solvent under reduced pressure, the residue crystallizes. To the crystals is added ether, and the crystals are collected by filtration to afford 3.56 g (88.6%) of cis-3-(2,2,2-trichloroethoxycarboxamido)-4-iodomethyl-2-oxoazetidine as colorless crystals, m.p. 152°–154° C.

| Elemental analysis: $C_7H_8Cl_3IN_2O_3$ | | | |
|---|---|---|---|
| | C (%) | H (%) | N (%) |
| Calc. | 20.95 | 2.01 | 6.98 |
| Found | 21.19 | 2.06 | 7.21 |

REFERENCE EXAMPLE 45C

To a solution of 3.21 g of cis-3-(2,2,2-trichloroethoxycarboxamido)-4-iodomethyl-2-oxoazetidine in 40 ml of N,N-dimethylformamide is added 0.78 g of sodium azide, and the mixture is stirred at room temperature for 43 hours, followed by supplementing 260 mg of sodium azide. The mixture is stirred at 35° C. for further 12 hours. N,N-Dimethylformamide is evaporated under reduced pressure. To the residue, are added water and ethyl acetate, and the mixture is shaken. The ethyl acetate layer is separated and washed with a saturated aqueous solution of sodium chloride, followed by drying over anhydrous magnesium sulfate. The solvent is evaporated under reduced pressure, and the residue is purified on a column-chromatography (silica-gel 150 g, eluent: ethyl acetate-hexane, 1:1) to afford cis-4-azidomethyl-3-(2,2,2-trichloroethoxycarboxamido)-2-oxoazetidine as colorless crystals, m.p. 93°–95° C.

REFERENCE EXAMPLE 46C

To a solution of 1.12 g of cis-4-azidomethyl-3-(2,2,2-trichloroethoxycarboxamido)-2-oxoazetidine in 35 ml of ethanol is added 560 mg of 5% palladium-on-carbon, and the mixture is stirred under hydrogen streams at ambient temperature and pressure for 2 hours. The catalyst is removed by filtration, and the filtrate is concentrated under reduced pressure. The residue is dissolved in a mixture of 10 ml of methylene chloride and 10 ml of N,N-dimethylacetamide. To the solution are added under ice-cooling and stirring 2.45 ml of propylene oxide and 0.50 ml of acetyl chloride successively. The mixture is stirred at room temperature for 2 hours, followed by evaporation of the solvents under reduced pressure. To the residue is added 50 ml of a saturated aqueous solution of sodium chloride, and the mixture is subjected to extraction with a mixture of ethyl acetate and tetrahydrofuran (4:1). The extract is washed with dilute hydrochloric acid, a saturated aqueous solution of sodium chloride, an aqueous solution of sodium bicarbonate and a saturated aqueous solution of sodium chloride successively, followed by drying over anhydrous magnesium sulfate. The solvent is evaporated under reduced pressure. To the residue is added 40 ml of hexane, and the mixture is left standing overnight under cooling. The resulting crystals are collected by filtration, and washed with ether to afford cis-4-acetamidomethyl-3-(2,2,2-trichloroethoxycarboxamido)-2-oxoazetidine, m.p. 178°–180° C.

| Elemental analysis: $C_9H_{12}Cl_3N_3O_4$ | | | |
|---|---|---|---|
| | C (%) | H (%) | N (%) |
| Calc. | 32.50 | 3.64 | 12.63 |
| Found | 32.83 | 3.60 | 12.79 |

REFERENCE EXAMPLE 47C

To a solution of 372 mg of cis-4-acetamidomethyl-3-(2,2,2-trichloroethoxycarboxamido)-2-oxoazetidine in 30 ml of tetrahydrofuran is added 3.0 g of activated zinc. To the mixture is added 6 ml of an aqueous solution of phosphoric acid-potassium dihydrogen phosphate (1 mol concentration), followed by stirring at room temperature for 8 hours. To the reaction mixture is added 30 ml of tetrahydrofuran, followed by removal of zinc by filtration. The filtrate is concentrated under reduced pressure. To the residue are added 15 ml of water and 20 ml of ethyl acetate, and the mixture is shaken. The aqueous layer is separated and concentrated under reduced pressure until its volume is reduced to 11 ml. To the concentrate is added 11 ml of tetrahydrofuran, and to the mixture are added under ice-cooling 282 mg of sodium hydrogen carbonate and 559 mg of 2-(2-chloroacetamido-4-thiazolyl)-(Z)-2-methoxyiminoacetyl chloride successively, while stirring. The mixture is stirred under ice-cooling for 1 hour, followed by addition of 2 g of sodium hydrogen carbonate and a saturated aqueous solution of sodium chloride, and extracted with a mixture of ethyl acetate and tetrahydrofuran. The extract is washed with a saturated aqueous solution of sodium chloride, and dried over anhydrous magnesium sulfate. Upon evaporation of the solvents under reduced pressure, the residue crystallizes. To the crystals is added a mixture of ethyl acetate and ether, and the crystals are collected by filtration to afford cis-4-acetamidomethyl)-3-[2-(2-chloroacetamido-4-thiazolyl)-2-methoxyiminoacetamido]-2-oxoazetidine (syn-isomer) as colorless crystals showing no specific melting point, while being decomposed gradually with coloration at a temperature range of 140°–165° C.

IR $\nu_{max}^{KBr}$ cm$^{-1}$: 3380, 3250, 1760, 1660.

NMR(d$_6$-DMSO, ppm): 1.73(3H, s, COCH$_3$), 3.6–4.0(1H, m, C$_4$—H), 3.90(3H, s, OCH$_3$), 4.33(2H, s, ClCH$_2$), 5.16(1H, q, J=5, 9 Hz, C$_3$—H), 7.46(1H, s 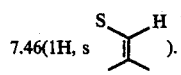 ).

REFERENCE EXAMPLE 48C

In 20 ml of tetrahydrofuran are dissolved 1.0 g of cis-3-benzyloxycarboxamido-1-(2,4-dimethoxybenzyl)-4-hydroxymethyl-2-oxoazetidine, 787 mg of triphenylphosphine and 441 mg of phthalimide. To the solution is added 0.471 ml of azodicarboxylic acid diethyl ester, and the mixture is stirred at room temperature for 1 hour. On evaporation of the solvents under reduced pressure, the residue solidifies. To the solid residue is added 30 ml of ethyl acetate, and insolubles are collected by filtration, followed by washing with ethyl acetate, whereby 882 mg of cis-3-benzyloxycarboxamido-1-(2,4-dimethoxybenzyl)-4-phthalimidomethyl-2-oxoazetidine as colorless crystals. The mother liquor and washings are combined, and purified on a silica-gel column-chromatography to afford further 280 mg of colorless crystals. The total yield is 1.16 g (87.8%), m.p. 182°–184° C.

| Elemental analysis: $C_{29}H_{27}N_3O_7$ | | | |
|---|---|---|---|
| | C (%) | H (%) | N (%) |
| Calc. | 65.11 | 5.20 | 7.85 |
| Found | 65.05 | 5.17 | 7.80 |

REFERENCE EXAMPLE 49C

To a suspension of 1.059 g of cis-3-benzyloxycarboxamido-1-(2,4-dimethoxybenzyl)-4-phthalimidomethyl-2-oxoazetidine in 80 ml of ethanol is added 0.39 ml of hydrazine hydrate, followed by heating under reflux for 3.5 hours. The reaction mixture is cooled, and the resulting crystals are removed by filtration. The filtrate is concentrated under reduced pressure, to which is added 30 ml of methylene chloride, followed by removing insolubles by filtration. The filtrate is washed with water and dried over anhydrous magnesium sulfate. The solvent is evaporated under reduced pressure, and the residue is dissolved in a mixture of 10 ml of methylene chloride and 5 ml of N,N-dimetylacetamide. To the solution are added under ice-cooling 1.4 ml of propylene oxide and 0.28 ml of acetylchloride, successively. The mixture is stirred at room temperature for 1 hour. To the mixture are added 10 ml of methylene chloride and 50 ml of an aqueous solution of sodium bicarbonate. The mixture is shaken, and the methylene chloride layer is separated, washed with water, dilute hydrochloric acid and a saturated aqueous solution of sodium chloride, successively, and then dryed over anhydrous magnesium sulfate. The solvent is evaporated under reduced pressure, and the residue is purified on a column-chromatography (silica-gel 100 g, eluent: chloroform-acetonitrile, 4:1 and 3:2). The eluting solvent is evaporated under reduced pressure, and to the residue is added a mixture of ethyl acetate and ether (1:3), and the resulting crystals are collected by filtration to afford cis-4-acetamidomethyl-3-benzyloxycarboxamido-1-(2,4-dimethoxybenzyl)-2-oxoazetidine, m.p. 195°–196° C.

| | Elemental analysis: $C_{23}H_{27}N_3O_6$ | | |
|---|---|---|---|
| | C (%) | H (%) | N (%) |
| Calc. | 62.57 | 6.16 | 9.52 |
| Found | 62.20 | 6.08 | 9.41 |

Similarly synthesized was:
Cis-3-benzyloxycarboxamido-4-benzamidomethyl-1-(2,4-dimethoxybenzyl)-2-oxoazetidine, m.p. 112°–115° C.

REFERENCE EXAMPLE 50C

To a suspension of 1.104 g of cis-4-acetamidomethyl-3-benzyloxycarboxamido-1-(2,4-dimethoxybenzyl)-2-oxoazetidine in 65 ml of acetonitrile is added dropwise a solution of 1.081 g of potassium persulfate and 653 mg of dipotassium hydrogen phosphate in 25 ml of water over 15 minutes under nitrogen streams while heating under reflux. The reaction mixture, after heating under reflux for 1.5 hours, is neutralized with an aqueous solution of sodium bicarbonate, followed by concentration under reduced pressure. The residue is subjected to extraction with a mixed solution of ethyl acetate and tetrahydrofuran (1:1), and the extract is washed with an aqueous solution of sodium bicarbonate and a saturated aqueous solution of sodium chloride, successively, and dried over magnesium sulfate. And the solvent is evaporated, and to the residue is added ethyl acetate, and the resulting crystals are collected by filtration to afford cis-4-acetamidomethyl-3-benzyloxycarboxamido-2-oxoazetidine, m.p. 226°–228° C.

Similarly synthesized was:
Cis-3-benzyloxycarboxamido-4-benzamidomethyl-2-oxoazetidine, m.p. 209°–211° C.

REFERENCE EXAMPLE 51C

To a suspension of 364 mg of cis-4-acetamidomethyl-3-benzyloxycarboxamido-2-oxoazetidine in a mixture of 80 ml of ethanol and 20 ml of methanol is added 364 mg of 5% palladium-on-carbon. The mixture is subjected to catalytic reduction while stirring at ambient temperature and user normal pressure. The catalyst is removed by filtration, and the filtrate is concentrated under reduced pressure. The residue is dissolved in a mixture of 12 ml of tetrahydrofuran and 12 ml of water. To the mixture solution is added under ice-cooling 315 mg of sodium hydrogen carbonate while stirring, followed by addition of 624 mg of 2-(2-chloroacetamido-4-thiazolyl)-(Z)-2-methoxyiminoacetyl chloride hydrochloride. The mixture is stirred under ice-cooling for 1 hour, followed by addition of an aqueous solution of sodium bicarbonate, a saturated aqueous solution of sodium chloride and a mixture of ethyl acetate and tetrahydrofuran (2:1), which is shaken, and then the organic layer is separated. The aqueous layer is subjected to extraction four times with a mixture of ethyl acetate and tetrahydrofuran (2:1). The organic layers are combined, and washed with a saturated aqueous solution of sodium chloride, followed by drying over magnesium sulfate. The solvent is evaporated under reduced pressure to cause the residue crystallize, followed by addition of a mixture of ethyl acetate and ether (1:2). The crystals are collected by filtration to give cis-4-acetamidomethyl-3-[2-(2-chloroacetamido-4-thiazolyl)-2-methoxyiminoacetamido]-2-oxoazetidine (syn-isomer) as colorless crystals showing no clear melting point but decomposing gradually while coloring within the range from 140° C. to 165° C. The IR and NMR spectra of this product are completely identical with those of the product obtained in Reference Example 47C.

Similarly synthesized was:
Cis-4-benzamidomethyl-3-[2-(2-chloroacetamido-4-thiazolyl)-2-methoxyiminoacetamido]-2-oxoazetidine syn-isomer). This product does not show specific melting point but decomposes gradually while coloring within the range from 130° C. to 150° C.

IR $\nu_{max}^{KBr}$ cm$^{-1}$: 3420, 3260, 1755, 1660.

| | Elemental analysis: $C_{19}H_{19}ClN_6O_5S$ | | |
|---|---|---|---|
| | C (%) | H (%) | N (%) |
| Calc. | 47.65 | 4.00 | 17.55 |
| Found | 47.48 | 3.86 | 17.26 |

REFERENCE EXAMPLE 52C

To a solution of 557 mg of cis-3-benzyloxycarboxamido-2-oxoazetidine-4-carboxylic acid methyl ester in 2.6 ml of tetrahydrofuran is added under ice-cooling 1.3 ml of an aqueous solution of 189 mg of sodium borohydride while stirring. The mixture is stirred under ice-cooling for 80 minutes, and the excess sodium borohydride is decomposed with acetic acid. Tetrahydrofuran is evaporated under reduced pressure. To the residue is added a saturated aqueous solution of sodium chloride, followed by extraction with ethyl acetate. The extract is washed with a saturated aqueous solution of sodium chloride, dried over anhydrous magnesium sulfate, and the solvent is evaporated under reduced pressure. The residue is purified on a column-chromatography (silica-gel 30 g, eluent: ethyl acetate-acetonitrile 4:1) to afford cis-3-benzyloxycarboxamido-4-hydroxymethyl-2-oxoazetidine as colorless crystals, m.p. 103°–104° C.

| Elemental analysis: $C_{12}H_{14}N_2O_4$ | | | |
|---|---|---|---|
| | C (%) | H (%) | N (%) |
| Calc. | 57.59 | 5.64 | 11.19 |
| Found | 57.32 | 5.41 | 11.12 |

REFERENCE EXAMPLE 53C

To a solution of 250 mg of cis-3-benzyloxycarboxamido-4-hydroxymethyl-2-oxoazetidine in 5 ml of ethanol is added 250 mg of 5% palladium-on-carbon, and the mixture is subjected to catalytic reduction at ambient temperature under normal pressure while stirring. The catalyst is removed by filtration, and the filtrate is concentrated under reduced pressure, followed by being left standing under cooling thereby to cause the residue crystallize. The crystals are covered by filtration to afford 108 mg (93%) of cis-3-amino-4-hydroxymethyl-2-oxoazetidine, m.p. 105°–107° C.

| Elemental analysis: $C_4H_8N_2O_2$ | | | |
|---|---|---|---|
| | C (%) | H (%) | N (%) |
| Calc. | 41.37 | 6.94 | 24.12 |
| Found | 41.40 | 6.84 | 23.85 |

REFERENCE EXAMPLE 54C

To a solution of 58 mg of cis-3-amino-4-hydroxymethyl-2-oxoazetidine in a mixture of 5 ml of methylene chloride and 1 ml of N,N-dimethylacetamide is added under ice-cooling and stirring 0.4 ml of triethylamine, followed by addition of 498 mg of 2-(2-chloroacetamido-4-thiazolyl)-(Z)-2-methoxyiminoacetyl chloride hydrochloride. The mixture is stirred under ice-cooling for 1 hour, to which is added 20 ml of water, followed by adjusting to pH 7–8 with sodium hydrogen carbonate. The reaction mixture is concentrated under reduced pressure, and the residue is subjected to extraction with a mixture of ethyl acetate and tetrahydrofuran (2:1). The extract is washed with a saturated aqueous solution of sodium chloride and dried over anhydrous magnesium sulfate. The solvent is evaporated under reduced pressure, whereupon the residue crystallizes, to which is added a mixture of ethyl acetate and ether (1:2), followed by collecting the crystals by filtration to afford cis-3-[2-(2-chloroacetamido-4-thiazolyl)-(Z)-2-methoxyiminoacetamido-4-[2-(2-chloroacetamido-4-thiazolyl)-(Z)-2-methoxyiminoacetoxymethyl]-2-oxoazetidine as yellow crystals, m.p. 157°–159° C.

| Elemental analysis: $C_{20}H_{20}Cl_2N_8O_8S_2$ | | | |
|---|---|---|---|
| | C (%) | H (%) | N (%) |
| Calc. | 37.80 | 3.17 | 17.63 |
| Found | 37.85 | 3.27 | 17.22 |

REFERENCE EXAMPLE 55C

To a solution of cis-1-(2,4-dimethoxybenzyl)-3-(2,2,2-trichloroethoxycarboxamido)-2-oxoazetidine-4-carboxylic acid methyl ester in 20 ml of acetonitrile is added dropwise over 10 minutes with heating under reflux a solution of 1.08 g of potassium persulfate and 716 mg of crystalline disodium hydrogen phosphate in 20 ml of water. The reflux is continued under heating for further 30 minutes. After cooling the reaction mixture acetonitrile is evaporated under reduced pressure. The residue is extracted with ethyl acetate, washed with a 5% aqueous solution of sodium bicarbonate and a saturated aqueous solution of sodium chloride in this order, and dried over anhydrous magnesium sulfate. The solvent is evaporated under reduced pressure, and the residue is purified on a column-chromatography (silica-gel 20 g, eluent:chloroform-ethyl acetate, 1:2) to afford cis-3-(2,2,2-trichloroethoxycarboxamido)-2-oxoazetidine-4-carboxylic acid methyl ester as colorless crystals, m.p. 140°–141° C.

| Elemental analysis: $C_8H_9Cl_3N_2O_5$ | | | |
|---|---|---|---|
| | C (%) | H (%) | N (%) |
| Calc. | 30.07 | 2.84 | 8.77 |
| Found | 30.30 | 2.82 | 8.87 |

To a solution of 1.41 g of cis-3-(2,2,2-trichloroethoxycarboxamido)-2-oxoazetidine-4-carboxylic acid methyl ester in 40 ml of tetrahydrofuran is added under ice-cooling and stirring a solution of 417 mg of sodium borohydride in 20 ml of water. The mixture is stirred for 30 minutes under ice-cooling and for 1 hour at room temperature, followed by evaporating tetrahydrofuran under reduced pressure. The residue is dissolved in ethyl acetate, and washed twice with an aqueous solution of sodium chloride, followed by drying over anhydrous magnesium sulfate. On concentration under reduced pressure, the residue crystallizes, to which is added ether, followed by collecting the crystals by filtration to afford cis-4-hydroxymethyl-3-(2,2,2-trichloroethoxycarboxamido)-2-oxoazetidine, m.p. 162°–164° C.

IR $\nu_{max}^{KBr}$cm$^{-1}$: 3450, 3300, 1720, 1700.

REFERENCE EXAMPLE 57C

To a solution of 468 mg of 2-thienylacetic acid in 7 ml of dry methylene chloride is added 424 mg of thionyl chloride, and the mixture is heated under reflux for 2 hours. The reaction mixture is concentrated under reduced pressure, and the residue is dissolved in 5 ml of dry methylene chloride.

On the other hand, to a solution of cis-4-hydroxymethyl-3-(2,2,2-trichloroethoxycarboxamido)-2-oxoazetidine in 30 ml of dry methylene chloride is added 416 mg of triethylamine. To this mixture, while stirring under ice-cooling, is added dropwise the methylene chloride solution of 2-thienylacetyl chloride prepared above. The resulting mixture is stirred under ice-cooling for 20 minutes and at room temperature overnight. To the reaction mixture is added ethyl acetate, and the mixture is washed with 3N-HCl, an aqueous solution of sodium hydrogen carbonate and an aqueous solution of sodium chloride, successively, dried over anhydrous magnesium sulfate, and then concentrated under reduced pressure. Finally, the residue is purified by column-chromatography (silica-gel 60 g, eluent:hexane-ethyl acetate, 1:1 and 2:3) to give cis-4-(2-thienylacetoxymethyl)-3-(2,2,2-trichloroethoxycarboxamido)-2-oxoazetidine.

NMR(CDCl$_3$, ppm):

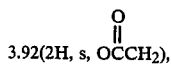
3.92(2H, s, OCCH$_2$), 4.71(2H, s, CCl$_3$CH$_2$), 5.14(1H, d.d, J=5,9 Hz, C$_3$—H),

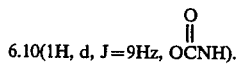
6.10(1H, d, J=9Hz, OCNH).

REFERENCE EXAMPLE 58C

To a solution of 600 mg of cis-4-(2-thienylacetoxymethyl)-3-(2,2,2-trichloroethoxycarboxamido)-2-oxoazetidine in a mixture of 25 ml of tetrahydrofuran and 5 ml of 1N-aqueous solution of ammonium acetate is added 2.16 g of activated zinc, and the mixture is stirred at room temperature for 5 hours. The mixture is subjected to filtration through celite. To the filtrate is added methylene chloride, followed by drying over anhydrous magnesium sulfate. The filtrate is concentrated under reduced pressure, and the residue is dissolved in a mixture of 2 ml of tetrahydrofuran and 2 ml of water, followed by addition of 850 mg of sodium hydrogen carbonate under ice-cooling. To the mixture is added 720 mg of 2-(2-chloroacetamido-4-thiazolyl)-(Z)-2-methoxyiminoacetyl chloride hydrochloride, followed by vigorous stirring under ice-cooling for 15 minutes. The reaction mixture is stirred at room temperature for a further 1 hour, followed by evaporation of the solvent under reduced pressure. To the residue is added water, and the resulting crystals are collected by filtration and washed with water, an aqueous solution of sodium bicarbonate, ether and hexane in this order to afford cis-3-[2-(2-chloroacetamido-4-thiazolyl)-2-methoxyiminoacetamido]-4-(2-thienylacetoxymethyl)-2-oxoazetidine (syn-isomer), m.p. 201°–204° C.(decomp.).

IR $\nu_{max}^{KBr}$cm$^{-1}$: 3280, 1760, 1660.
NMR(d$_6$-DMSO, ppm): 3.86(3H, s, OCH$_3$),

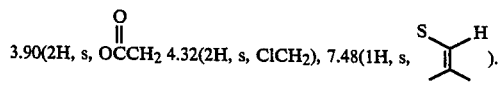
3.90(2H, s, OCCH$_2$ 4.32(2H, s, ClCH$_2$), 7.48(1H, s, ).

REFERENCE EXAMPLE 59C

To a solution of 314 mg of 1-methyl-1H-tetrazol-5-yl mercaptane in 2 ml of dry N,N-dimethylformamide is added under ice-cooling 65 mg of sodium hydride. The mixture is stirred under ice-cooling for 10 minutes, and at room temperature for 10 minutes, to which is added a solution of 724 mg of cis-3-(2,2,2-trichloroethoxycarboxamido)-4-iodomethyl-2-oxoazetidine in 3 ml of N,N-dimethylformamide, followed by stirring at room temperature for 2 days. The reaction mixture is dissolved in ethyl acetate, washed with water five times and further with an aqueous solution of sodium chloride, followed by drying over anhydrous magnesium sulfate, and then concentrated under reduced pressure, and the residue in purified by column-chromatography (silica-gel 60 g, eluent: hexane-ethyl acetate, 1:2 and then 1:4) to give 610 mg (86.8%) of cis-4-(1-methyl-1H-tetrazol-5-yl-thiomethyl)-3-(2,2,2-trichloroethoxycarboxamido)-2-oxoazetidine as crystals, m.p. 67°–69° C.

IR $\nu_{max}^{KBr}$cm$^{-1}$: 3300, 1740.

REFERENCE EXAMPLE 60C

To 10 ml of tetrahydrofuran is added 1.49 ml of a solution of methylmercaptane in 4N-tetrahydrofuran, followed by dropwise addition under ice-cooling 1.37 ml of a solution of n-butyl lithium in 1.6N-hexane. The mixture is stirred under nitrogen streams for 10 minutes under ice-cooling and then cooled to −45° C., to which is added dropwise a solution of 800 mg of cis-3-(2,2,2-trichloroethoxycarboxamido)-4-iodomethyl-2-oxoazetidine in 5 ml of tetrahydrofuran. The temperature of the reaction mixture is gradually raised to a temperature within the range of −20° C.~ −30° C., where the reaction mixture is stirred for 4 hours. The reaction mixture is dissolved in ethyl acetate, and after addition of a saturated aqueous solution of ammonium chloride, the mixture is stirred. The organic layer is separated, washed with an aqueous solution of sodium chloride, dried over anhydrous magnesium sulfate, and then concentrated under reduced pressure. The residue is purified by column-chromatography (silica-gel 100 g, eluent:hexane-ethyl acetate, 2:1 and 1:1) to give cis-4-methylthiomethyl-3-(2,2,2-trichloroethoxycarboxamido)-2-oxoazetidine as crystals, m.p. 114°–115° C.

IR $\nu_{max}^{KBr}$cm$^{-1}$: 3350, 1780, 1715.

REFERENCE EXAMPLE 61C

To a solution of 674 mg of cis-4-(1-methyl-1H-tetrazol-5-ylthiomethyl)-3-(2,2,2-trichloroethoxycarboxamido)-2-oxoazetidine in 10 ml of tetrahydrofuran is added 2 ml of 1N-aqueous solution of ammonium acetate. To the mixture is added 1 g of activated zinc, followed by stirring at room temperature for 3 hours. The reaction mixture is subjected to filtration. To the filtrate is added methylene chloride, and the mixture is dried over anhydrous magnesium sulfate, and concentrated under reduced pressure. The residue is dissolved in a mixture of 3 ml of tetrahydrofuran and 3 ml of water, followed by addition of 1.02 g of sodium hydrogen carbonate under ice-cooling. To the mixture is then added 863 mg of 2-(2-chloroacetamido-4-thiazolyl)-(Z)-2-methoxyiminoacetyl chloride hydrochloride, followed by stirring under ice-cooling for 15 minutes and further at room temperature for 1 hour. The solvent is evaporated under reduced pressure. To the residue is added water, and the resulting crystals are collected by filtration, and washed with water, an aqueous solution of sodium bicarbonate, ether and hexane, successively to afford cis-3-[2-(2-chloroacetamido-4-thiazolyl)-2-methoxyiminoacetamido]-4-(1-methyl-1H-tetrazol-5-ylthiomethyl)-2-oxoazetidine (syn-isomer) as crystals, m.p. 195°–198° C.(decomp.).

IR $\nu_{max}^{KBr}$cm$^{-1}$: 3270, 1760, 1660.

Similarly synthesized was:
Cis-3-[2-(2-chloroacetamido-4-thiazolyl)-2-methoxyiminoacetamido]-4-methylthiomethyl-2-oxoazetidine (syn-isomer), m.p. 172°–176° C.(decomp.).

REFERENCE EXAMPLE 62C

To a suspension of 1.0 g of cis-3-benzyloxycarboxamido-1-(2,4-dimethoxybenzyl)-4-methanesulfonyloxymethyl-2-oxoazetidine in 50 ml of methylethylketone is added 1.88 g of sodium iodide. The mixture is stirred under heating at 90° C. for 6 hours, and the solvent is evaporated under reduced pressure. To the residue are added 150 ml of ethyl acetate and 100 ml of water, and the mixture is shaken. The ethyl acetate layer is separated and washed with water, followed by drying over anhydrous sodium sulfate. The solvent is evaporated under reduced pressure, and the resulting solid residue is recrystallized from 50 ml of a mixture of hexane and ethyl acetate (1:1) to afford 850 mg (80%) of cis-3-benzyloxycarboxamido-1-(2,4-dimethoxybenzyl)-4-iodomethyl-2-oxoazetidine and colorless needles, m.p. 165°–166° C.

| Elemental analysis: $C_{21}H_{23}IN_2O_5$ | | | |
|---|---|---|---|
| | C (%) | H (%) | N (%) |
| Calc. | 49.43 | 4.54 | 5.49 |
| Found | 49.55 | 4.56 | 5.67 |

REFERENCE EXAMPLE 63C

To a solution of 3.29 g of cis-3-benzyloxycarboxamido-1-(2,4-dimethoxybenzyl)-4-iodomethyl-2-oxoazetidine in 10 ml of hexamethylphosphoric triamide is added 1.62 g of sodium cyano borohydride. The mixture is stirred under nitrogen streams at 90°–100° C. for 5 hours. The reaction mixture is added to 250 ml of ether, washed with 20 ml each portion of water six times and with an aqueous solution of sodium chloride once, then dried over anhydrous magnesium sulfate, followed by concentration under reduced pressure. To the resulting solid residue are added ether and hexane, followed by filtration to afford 2.15 g (86.7%) of cis-3-benzyloxycarboxamido-1-(2,4-dimethoxybenzyl)-4-methyl-2-oxoazetidine, m.p. 130°–132° C.

| Elemental analysis: $C_{21}H_{24}N_2O_5$ | | | |
|---|---|---|---|
| | C (%) | H (%) | N (%) |
| Calc. | 65.61 | 6.29 | 7.29 |
| Found | 65.23 | 6.49 | 7.53 |

5.10 g of 2,4-dimethoxybenzylamine hydrochloride is added to an aqueous solution of potassium carbonate, and the resulting oily portion is subjected to extraction with 120 ml of benzene. The extract is washed with water and dried over anhydrous sodium sulfate, followed by addition 3.50 g of p-chlorobenzaldehyde. The mixture is subjected to reflux under heating for 1 hour with a moisture-separating device. On evaporation of the solvent, the residue crystallizes, and the crystals are dissolved in 68 ml of methylene chloride. To the resulting solution, while stirring at −5° C. ~ −10° C., is added a solution of 3.8 ml of triethylamine in 20 ml of methylene chloride, followed by dropwise addition of a solution of 6.15 g of phthalimidoacetyl chloride in 25 ml of methylene chloride. To the mixture, 20 minutes later, are added a solution of 1.9 ml of triethylamine in 10 ml of methylene chloride and a solution of 3.1 g of phthalimide acetyl chloride in 13 ml of methylene chloride, successively. The resulting mixture is stirred for 7 hours under ice-cooling, left standing overnight under cooling, and washed with water, an aqueous solution of sodium bicarbonate, a 5% hydrochloric acid and water, successively, then dried over anhydrous sodium sulfate, followed by evaporation of the solvent under reduced pressure. The residue is purified on a column-chromatography (silica-gel 60 g, eluent:chloroform-methanol, 20:1) to afford 9.4 g (84%) of cis-4-(4-chlorophenyl)-1-(2,4-dimethoxybenzyl)-3-phthalimido-2-oxoazetidine as colorless crystals. Recrystallization from acetone-hexane gives colorless prisms, m.p. 178°–180° C.

| Elemental analysis: $C_{26}H_{21}ClN_2O_5$ | | | |
|---|---|---|---|
| | C (%) | H (%) | N (%) |
| Calc. | 65.46 | 4.44 | 5.87 |
| Found | 65.42 | 4.42 | 5.90 |

REFERENCE EXAMPLE 65C

To a solution of 4 g of cis-4-(4-chlorophenyl)-1-(2,4-dimethoxybenzyl)-3-phthalimido-2-oxoazetidine in 50 ml of methylene chloride is added 0.89 ml of methyl hydrazine. The mixture is stirred at 35°–40° C. for 17 hours, then subjected to filtration, and the filtrate is concentrated under reduced pressure. To the residue is added ethyl acetate, and the resulting insolubles are removed by filtration. The filtrate (about 100 ml) is subjected to extraction with a mixture of 30 ml of water and 10 ml of 10% hydrochloric acid. The extract is neutralized with an aqueous solution of sodium bicarbonate, subjected to extraction with methylene chloride twice, and with a saturated aqueous solution of sodium chloride. The washed extract is dried over anhydrous sodium sulfate, and the solvent is evaporated under reduced pressure. The residue (2.6 g) is dissolved in 30 ml of methylene chloride, followed by addition of 5.5 ml of propylene oxide while stirring under ice-cooling and dropwise addition of 2.3 g of carbobenzoxychloride. The mixture is stirred at room temperature for 2 hours, and the solvent is evaporated under reduced pressure. To the residue is added hexane, and the resulting crystals are collected by filtration. The crystals are washed with isopropylether to afford 3.31 g (81%) of cis-3-benzyloxycarboxamido-4-(4-chlorophenyl)-1-(2,4-dimethoxybenzyl)-2-oxoazetidine.

IR $\nu_{max}^{KBr}$cm$^{-1}$: 3325, 1759, 1688.

NMR(CDCl$_3$, ppm): 3.59, 3.77(2×3H, 2×s, 2×OCH$_3$), 4.70(1H, d, J=5 Hz, C$_4$—H), 5.20(1H, d.d, J=5,9 Hz, C$_3$—H), 5.82(1H, d, J=9 Hz, NH).

REFERENCE EXAMPLE 66C

To a solution of 2.15 g of cis-3-benzyloxycarboxamido-1-(2,4-dimethoxybenzyl)-4-methyl-2-oxoazetidine in 150 ml of acetonitrile is added dropwise a solution of 2.42 g of potassium persulfate and 1.46 g of dipotassium hydrogen phosphate in 75 ml of water at 90°–100° C. The mixture is heated under reflux at the same temperature for 1.5 hours, and acetonitrile is evaporated under reduced pressure. To the residue are added ethyl acetate and water, followed by shaking. The ethyl acetate layer is separated, washed with an aqueous solution of sodium chloride, and then dried over anhydrous magnesium sulfate. The solvent is evaporated under reduced pressure, and the residue is purified by column-chromatography (silica-gel 200 g, eluent:hexane-ethyl acetate, 1:2) to afford cis-3-benzyloxycarboxamido-4-methyl-2-oxoazetidine as crystals, m.p. 168°–169° C.

| Elemental analysis: $C_{12}H_{14}N_2O_3$ | | | |
|---|---|---|---|
| | C (%) | H (%) | N (%) |
| Calc. | 61.53 | 6.02 | 11.96 |
| Found | 61.36 | 6.05 | 11.65 |

Similarly synthesized was:
Cis-3-benzyloxycarboxamido-4-(4-chlorophenyl)-2-oxoazetidine.

IR $\nu_{max}^{KBr}$cm$^{-1}$: 3310, 3225, 1772, 1722, 1684.
NMR(d$_6$-DMSO, ppm): 4.85(2H, s, CH$_2$), 7.74(1H, d, J=9Hz, OCNH), (where OCNH shows the O double bonded above the C)

8.55(1H, br.s, N$_1$—H), 6.90–7.50(9H, aromatic protons).

REFERENCE EXAMPLE 67C

To a suspension of 210 mg of cis-3-benzyloxycarboxamido-4-methyl-2-oxoazetidine in 10 ml of ethanol is added 210 mg of 5% palladium-carbon, followed by stirring under hydrogen streams for one hour. The mixture is subjected to filtration, and the filtrate is concentrated. The residue crystallizes (m.p. 111°–112° C.). To the crystals are added 1 ml of water and 1 ml of tetrahydrofuran, followed by addition, under ice-cooling, 382 mg of sodium hydrogen carbonate. To the mixture is added, while vigorously stirring, 453 mg of 2-(2-chloroacetamido-4-thiazolyl)-(Z)-2-methoxyiminoacetyl chloride. The resulting mixture is stirred under ice-cooling for 15 minutes, and at room temperature for one hour, followed by concentration under reduced pressure. To the residue is added water, and the resulting insolubles are collected by filtration, and washed with water, aqueous solution of sodium bicarbonate, ether and hexane in this order to afford 276 mg (84%) of cis-3-[2-(2-chloroacetamido-4-thiazolyl)-2-methoxyiminoacetamido]-4-methyl-2-oxoazetidine (syn-isomer) as crystals, m.p. 212°–215° C.(decomp.).

IR $\nu_{max}^{KBr}$cm$^{-1}$: 3260, 1745, 1670.

NMR(d$_6$-DMSO, ppm): 1.16(3H, d, J=6 Hz, C$_4$—CH$_3$), 3.90(3H, s, OCH$_3$), 4.36(2H, s, ClCH$_2$), 5.15(1H, d.d, J=5,9 Hz, C$_3$—H),

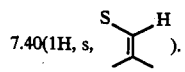

7.40(1H, s, ).

Similarly synthesized was:
Cis-3-[2-(2-chloroacetamido-4-thiazolyl)-2-methoxyiminoacetamido]-4-(4-chlorophenyl)-2-oxoazetidine (syn-isomer).

IR $\nu_{max}^{KBr}$cm$^{-1}$: 3250, 1740, 1652.

NMR(d$_6$-DMSO, ppm): 3.66(3H, s, OCH$_3$), 4.30(2H, s, ClCH$_2$), 4.96(1H, d, J=5 Hz, C$_4$—H), 5.39(1H, d.d, J=5,9 Hz),

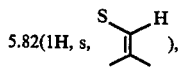

5.82(1H, s, ), 9.24(1H, d, J=9 Hz, C$_3$—NH).

REFERENCE EXAMPLE 68C

To a solution of 1.4 g of cis-3-benzyloxycarboxamido-2-oxoazetidine-4-carboxylic acid methyl ester in 14 ml of methanol is added dropwise under ice-cooling a solution of 0.9 g of potassium carbonate in 9 ml of water. The mixture is stirred at room temperature for one hour, and methanol is evaporated. The remaining aqueous solution is washed with ethyl acetate, followed by neutralizing with dilute hydrochloric acid. Thus neutralized solution is subjected to extraction with ethyl acetate, and the extract is washed with an aqueous solution of sodium chloride, then dried over anhydrous sodium sulfate. The solvent is evaporated under reduced pressure, then the residue crystallizes. To the crystals is added ethyl acetate, followed by filtration to afford 1.1 g (84.6%) of cis-3-benzyloxycarboxamido-2-oxoazetidine-4-carboxylic acid, which is recrystallized from acetonitrile to yield crystals, m.p. 156°–157° C.

| Elemental analysis: C$_{12}$H$_{12}$N$_2$O$_5$ | | | |
|---|---|---|---|
| | C (%) | H (%) | N (%) |
| Calc. | 54.54 | 4.57 | 10.60 |
| Found | 54.55 | 4.45 | 10.77 |

REFERENCE EXAMPLE 69C

To a solution of 1.32 g of cis-3-benzyloxycarboxamido-2-oxoazetidine-4-carboxylic acid in dry tetrahydrofuran is added 4 g of dicyclohexylcarbodiimide. Ten minutes later, 0.5 ml of 40% aqueous solution of dimethylamine is added to the mixture, followed by stirring at room temperature for 2 hours. Insolubles are removed by filtration, and the filtrate is concentrated under reduced pressure. To the residue are added ethyl acetate and an aqueous solution of sodium bicarbonate, followed by shaking. The ethyl acetate layer is separated, washed with an aqueous solution of sodium chloride, dried over anhydrous sodium sulfate, and the solvent is evaporated under reduced pressure. The residue is purified by column-chromatography (silica-gel) to yield cis-3-benzyloxycarboxamido-4-(N,N-dimethylcarbamoyl)-2-oxoazetidine as crystals.

IR $\nu_{max}^{Nujol}$cm$^{-1}$: 3280, 1785, 1770, 1730, 1690, 1640.

NMR(d$_6$-DMSO, ppm): 2.77, 2.80(2×3H, 2×s, 2×CH$_3$), 4.53(1H, d, J=5 Hz, C$_4$—H), 5.36(1H, d.d, J=5,9 Hz, C$_3$—H).

REFERENCE EXAMPLE 70C

To a solution of 291 mg of cis-3-benzyloxycarboxamido-4-(N,N-dimethylcarbamoyl)-2-oxoazetidine in 10 ml of methanol is added 291 mg of 5% palladium-on-carbon, followed by catalytic reduction at ambient temperature under normal pressure. The reaction mixture is subjected to filtration after two hours, and the filtrate is concentrated to afford 141 mg (90%) of cis-3-amino-4-(N,N-dimethylcarbamoyl)-2-oxoazetidine as colorless crystals. This product is allowed to react, in the same manner as Reference Example 34, with 2-(2-chloroacetamido-4-thiazolyl)-(Z)-2-methoxyiminoacetyl chloride to afford cis-3-[2-(2-chloroacetamido-4-thiazolyl)-2-methoxyiminoacetamido]-4-(N,N-dimethylcarbamoyl)-2-oxoazetidine as crystals, m.p. 160°–165° C.

IR $\nu_{max}^{Nujol}$cm$^{-1}$: 3200, 1760, 1640.

REFERENCE EXAMPLE 71C

To a mixture of 288 mg of cis-3-amino-2-oxoazetidine-4-carboxylic acid methyl ester, 10 ml of tetrahydrofuran and 5 ml of 1N-sodium hydrogen carbonate, which is previously stirred under ice-cooling, is added dropwise a solution of 0.32 ml of 2-thienyl acetyl chloride in 10 ml of tetrahydrofuran. To the mixture, after being stirred for 10 minutes, are added 100 ml of ethyl acetate and 20 ml of a saturated aqueous solution of sodium chloride, followed by stirring, and the organic layer is separated. The aqueous layer is subjected to extraction with 30 ml of ethyl acetate, and the extract is combined with the organic layer. The whole organic layer is washed with a saturated aqueous solution of sodium chloride (20 ml×3), dried and concentrated under reduced pressure. To the residue is added 4 ml of a mixed solution (ethyl acetate:hexane=1:2), and the resulting crystals are collected by filtration and dried to afford 430 mg (80%) of cis-3-(2-thienylacetamido)-2-oxoazetidine-4-carboxylic acid methyl ester, m.p. 133°-136° C.

| Elemental analysis: $C_{11}H_{12}N_2O_4S$ | | | |
|---|---|---|---|
| | C (%) | H (%) | N (%) |
| Calc. | 49.43 | 4.15 | 10.48 |
| Found | 49.00 | 4.37 | 10.20 |

REFERENCE EXAMPLE 72C

To a mixture of 288 mg of cis-3-amino-2-oxoazetidine-4-carboxylic acid methyl ester, 4 ml of propylene oxide and 3 ml of N,N-dimethylacetamide, which is stirred previously under ice-cooling, is added dropwise 400 mg of 1H-tetrazol-1-yl acetyl chloride, followed by stirring for 30 minutes. To the mixture is added 50 ml of ethyl ether, followed by stirring under cooling at −30° C., and then the upper layer is removed by decantation. The lower layer is subjected to the same procedure as above twice, followed by addition of 10 ml of acetone. The resultant solution is developed and purified by column-chromatography on silica-gel (40 g, 3×10 cm) using a mixture of acetone:methylene chloride (1:1) as eluent, followed by drying to give 403 mg (84%) of cis-3-(1H-tetrazol-1-ylacetamido)-2-oxoazetidine-4-carboxylic acid methyl ester.

| Elemental analysis: $C_8H_{10}N_6O_4.\tfrac{1}{3}CH_3COCH_3$ | | | |
|---|---|---|---|
| | C (%) | H (%) | N (%) |
| Calc. | 41.00 | 4.82 | 28.69 |
| Found | 41.16 | 5.08 | 28.65 |

REFERENCE EXAMPLE 73C

To a mixture of 696.7 mg of nalidixic acid and 10 ml of methylene chloride previously stirred at room temperature, is added 2 ml of thionyl chloride, followed by stirring for one hour. The reaction mixture is concentrated to dryness under reduced pressure, and the residue is dissolved in 5 ml of N,N-dimethylacetamide. On the other hand, a mixture of 288 mg of cis-3-amino-2-oxoazetidine-4-carboxylic acid methyl ester, 6 ml of propylene oxide and 3 ml of N,N-dimethylacetamide is stirred under ice-cooling beforehand, to which is added 5 ml of the N,N-dimethylacetamide solution obtained as above, followed by stirring at room temperature for two hours. Insolubles are removed by filtration by means of suction, and the filtrate is shaken together with a mixture of 100 ml of ethyl acetate and 200 ml of water. The organic layer is separated, washed with a saturated aqueous solution of sodium chloride (50 ml×3), dried, and concentrated to dryness under reduced pressure. The residue is purified by column chromatography on silica-gel to give cis-3-(1-ethyl-1,4-dihydro-7-methyl-4-oxo-1,8-naphthyridin-3-yl-carbonylamino)-2-oxoazetidine-4-carboxylic acid methyl ester, m.p. 223°-224° C.

IR $\nu_{max}^{KBr}$cm$^{-1}$: 3400, 1780, 1765, 1745.

REFERENCE EXAMPLE 74C

To a solution of 288 mg of cis-3-amino-2-oxoazetidine-4-carboxylic acid methyl ester in 2 ml of N,N-dimethylacetamide, which is stirred under ice-cooling beforehand, is added 534 mg of mandelic-carbonic anhydride, followed by stirring at room temperature for 30 minutes. The mixture is stirred beforehand under ice-cooling, to which is added dropwise 1.05 ml of chloroacetyl chloride, followed by stirring at room temperature for 3 hours. The reaction mixture is shaken with 100 ml of ethyl acetate and 20 ml of 1N-HCl, then the organic layer is separated. The organic layer is washed with a saturated aqueous solution of sodium chloride (30 ml×3), 20 ml of 1N-NaHCO$_3$ aqueous solution and a saturated aqueous solution of sodium chloride (30 ml×3), successively, dried, and the solvent is evaporated under reduced pressure. The residue is purified by column-chromatography on silica-gel to afford cis-3-(2-chloroacetyloxy-2-phenylacetamido)-2-oxoazetidine-4-carboxylic acid methyl ester.

IR $\nu_{max}^{KBr}$cm$^{-1}$: 3300, 1760, 1695, 1530, 1220, 1160, 740, 700.

REFERENCE EXAMPLE 75C

To a mixture of 288 mg of cis-3-amino-2-oxoazetidine-4-carboxylic acid methyl ester, 1 ml of tetrahydrofuran, 2 ml of water and 15 ml of 1N-NaHCO$_3$ aqueous solution, which is stirred beforehand under ice-cooling, is added dropwise 469 mg of D-α-sulfophenyl acetyl chloride, followed by stirring under ice-cooling for 10 minutes and then at room temperature for one hour. The reaction mixture is concentrated under reduced pressure, and the residue is dissolved in 5 ml of water. The aqueous solution is subjected to a column-chromatography on Amberlite XAD-II, then a column-chromatography on Sephadex LH-20 for purification, followed by lyophilization to give cis-3-(D-2-sulfo-2-phenylacetamido)-2-oxoazetidine-4-carboxylic acid methyl ester sodium salt.

| Elemental analysis: $C_{13}H_{13}N_2NaO_7S.3/2H_2O$ | | | |
|---|---|---|---|
| | C (%) | H (%) | N (%) |
| Calc. | 39.90 | 4.12 | 7.16 |
| Found | 39.78 | 4.48 | 7.29 |

REFERENCE EXAMPLE 76C 2.7 g of phenyl malonic acid monobenzyl ester and 5 ml of thionyl chloride are stirred at room temperature for 16 hours, followed by concentration under reduced pressure. To the residue is added methylene chloride to make the whole volume to be 10 ml. On the other hand, a mixture of 288 mg of cis-3-amino-2-oxoazetidine-4-carboxylic acid methyl ester, 0.42 ml of triethylamine and 10 ml of methylene chloride is stirred under ice-cooling, to which is added dropwise 3 ml of the methylene chloride mixture obtained as above, followed by stirring for 3 hours. The solvent is evaporated under reduced pressure. To the residue are added 200 ml of ethyl acetate and 30 ml of water, followed by shaking, and the organic layer is separated. The organic layer is washed with a saturated aqueous solution of sodium chloride (30 ml ×3), 20 ml of 1N-HCl, and with a saturated aqueous solution of sodium chloride (20 ml×2), then dried, followed by evaporation of the solvent under reduced pressure. The residue is purified by column-chromatography on silica-gel with ethyl acetate:methylene chloride (1:1) as eluent to give cis-3-(2-benzyloxycarbonyl-2-phenylacetamido)-2-oxoazetidine-4-carboxylic acid methyl ester.

IR $\nu_{max}^{KBr}$cm$^{-1}$: 3300, 1780, 1740, 1690, 1530, 1270, 1210, 1160.

REFERENCE EXAMPLE 77C

3-Amino compound prepared from 400 mg of cis-3-benzyloxycarboxamido-2-oxoazetidine-4-carboxylic acid methyl ester in a similar manner as Reference Example 3C is dissolved in 15 ml of tetrahydrofuran. To the solution is added 120 mg of cyanoacetic acid, followed by stirring under ice-cooling. To the mixture is added 290 mg of dicyclohexylcarbodiimide, followed by stirring at room temperature for two hours. The reaction mixture is subjected to filtration, and the filtrate is concentrated. To the residue is added 30 ml of ethyl acetate, again followed by filtration, and the filtrate is concentrated. The concentrate is purified by column-chromatography (silica-gel, 20 g, eluent: ethyl acetate) to give cis-3-(2-cyanoacetamido)-2-oxoazetidine-4-carboxylic acid methyl ester.

IR $\nu_{max}^{KBr}$cm$^{-1}$: 3300, 2250, 1758, 1680

NMR(d$_6$-DMSO, ppm): 3.60(2H, s, CH$_2$), 3.67(3H, s, CH$_3$), 4.39(1H, d, J=6 Hz, C$_4$—H), 5.28(1H, d.d, J=6, 9 Hz, C$_3$—H).

REFERENCE EXAMPLE 78C

To a suspension of 808 mg of cis-3-[2-(2-chloroacetamido-4-thiazolyl)-2-methoxyiminoacetamido]-2-oxoazetidine-4-carboxylic acid methyl ester (syn-isomer) in 40 ml of methanol is added dropwise under ice-cooling a solution of 552 mg of potassium carbonate in 12 ml of water. The mixture is stirred at room temperature for one hour. To the reaction mixture is added 6 ml of 1N-HCl, followed by evaporation of methanol. The remaining aqueous mixture is washed with ethyl acetate and adjusted to pH 2 with dilute hydrochloric acid, followed by extraction with a mixture of ethyl acetate and tetrahydrofuran (1:2). The extract is washed with a saturated aqueous solution of sodium chloride, and dried over anhydrous magnesium sulfate. The solvent is evaporated under reduced pressure, and the residue is suspended in a mixture of 40 ml of methylene chloride and 10 ml of tetrahydrofuran. To the suspension, while stirring at room temperature, is added 1.0 ml of pyridine, followed by dropwise addition of a solution of 864 mg of p-nitrobenzylchloroformate in 4 ml of methylene chloride over 30 minutes. The mixture is stirred at room temperature for 30 minutes, and washed with water, dilute hydrochloric acid, water, an aqueous solution of sodium bicarbonate and an aqueous solution of sodium chloride, successively, and then dried over anhydrous magnesium sulfate, followed by evaporation of the solvent under reduced pressure. The residue is purified by column-chromatography (silica-gel 100 g, eluent: ethyl acetate) to give cis-3-[2-(2-chloroacetamido-4-thiazolyl)-2-methoxyiminoacetamido]-2-oxoazetidine-4-carboxylic acid p-nitrobenzyl ester (syn-isomer) as crystals, m.p. 231°–236° C.(decomp.).

IR $\nu_{max}^{KBr}$cm$^{-1}$: 3250, 1760, 1750, 1670, 1550, 1510.

NMR(d$_6$-DMSO, ppm): 3.83(3H, s, NOCH$_3$), 4.33(2H, s, ClCH$_2$), 4.58(1H, d, J=6 Hz, C$_4$—H), 5.25(2H, s, OCH$_2$Ar), 5.48(1H, d.d, J=6, 9Hz, C$_3$—H), 7.31(1H, s, 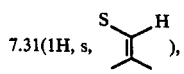 ), 7.66(2H, d, J=9 Hz, ArH), 8.17(2H, d, J=9 Hz, ArH), 8.77(1H, br.s, N$_1$—H), 9.56(1H, d, J=9 Hz, C$_3$—NH), 12.87(1H, br.s, ClCH$_2$CO$\underline{NH}$).

REFERENCE EXAMPLE 79C

In a mixture of 510 ml of dioxane and 42.6 ml of acetic acid is dissolved 53.2 g of ethyl 2-chloroacetamido-4-thiazolylacetate, followed by addition of 28.3 g of selenium dioxide, and the mixture is stirred under heating at 110°–115° C. for 4 hours. After cooling, the resultant black precipitate is discarded and thus obtained solution is concentrated under reduced pressure. The residue is dissolved in 3 l of ethyl acetate and washed twice with aqueous sodium hydrogen carbonate, and, then, twice with water. The solution is dried over anhydrous sodium sulfate and concentrated to 1 l. The concentrate is heated under reflux to dissolve the precipitate and after addition of 800 ml of hexane, the solution is cooled to give yellow needles to ethyl 2-chloroacetamido-4-thiazolylglyoxylate, which, on recrystallization from ethyl acetate-hexane, melts at 178°–180° C.

IR $\nu_{max}^{KBr}$cm$^{-1}$: 3220, 3000, 1740, 1680, 1550.

NMR(d$_6$-DMSO, ppm): 1.31(3H, t, CH$_2$C$\underline{H_3}$), 4.35(2H, q, C$\underline{H_2}$CH$_3$), 4.40(2H, s, ClCH$_2$), 8.49(1H, s, 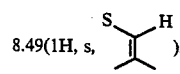 ).

| Elemental analysis: C$_9$H$_9$ClN$_2$O$_4$S | | | |
|---|---|---|---|
| | C (%) | H (%) | N (%) |
| Calc. | 39.07 | 3.28 | 10.12 |
| Found | 39.16 | 3.21 | 10.13 |

REFERENCE EXAMPLE 80C

In 646 ml of ethanol is suspended 35 g of ethyl 2-chloroacetamido-4-thiazolylglyoxylate, and 250 ml of 1N aqueous sodium hydroxide solution is added dropwise under ice-cooling and stirring. The mixture is stirred at room temperature for one hour, after which it is concentrated to 200 ml under reduced pressure. After addition of 200 ml of water, the concentrate is washed with 400 ml of ethyl acetate. After decolorization with activated carbon, the concentrate is adjusted to pH 1.5 with 10% hydrochloric acid, whereupon light-yellow crystals separate out. The crystals are recovered by filtration, washed with water and hexane in this order, and dried to give 2-chloroacetamido-4-thiazolylglyoxylic acid. Recrystallization from ethyl acetate-hexane gives light-yellow prisms, m.p. 205°–210° C.(decomp.).

IR $\nu_{max}^{KBr}$cm$^{-1}$: 3450, 3200, 1730–1690, 1680, 1560.

NMR(d$_6$-DMSO, ppm): 4.29(2H, s, ClCH$_2$), 8.30(1H, s, 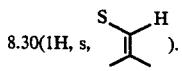 ).

| Elemental analysis: C$_7$H$_5$ClN$_2$O$_4$S | | | |
|---|---|---|---|
| | C (%) | H (%) | N (%) |
| Calc. | 33.81 | 2.03 | 11.27 |
| Found | 33.94 | 2.04 | 11.23 |

REFERENCE EXAMPLE 81C

To 50 ml of dry N,N-dimethylformamide are added 10 g of N-hydroxyphthalimide and 9.38 g of methyl bromoacetate, followed by addition of 8.5 g of potassium carbonate. The mixture is stirred at room temperature for 2 days and, then, poured into 400 ml of water. The resulting crystalline precipitate is recovered by filtration, washed with water, hexane and ether in this order to give colorless needles of N-methoxycarbonylmethyloxyphthalimide, m.p. 137°–142° C.

IR $\nu_{max}^{KBr}$cm$^{-1}$: 1790, 1760, 1730.

NMR(d$_6$-DMSO, ppm): 3.71(3H, s, COOCH$_3$), 4.8(2H, s, NOCH$_2$), 7.77(4H, s, aromatic protons).

In the same manner as above, there was synthesized the following compound:

N-(p-Nitrobenzyloxycarbonylmethyloxy)phthalimide, m.p. 158°–160° C.

IR $\nu_{max}^{KBr}$cm$^{-1}$: 1785, 1760, 1730.

NMR(d$_6$-DMSO, ppm): 4.94(2H, s, NOCH$_2$), 5.32(2H, s, COOCH$_2$).

| Elemental analysis: C$_{17}$H$_{12}$N$_2$O$_7$ | | | |
|---|---|---|---|
| | C (%) | H (%) | N (%) |
| Calc. | 57.31 | 3.40 | 7.86 |
| Found | 57.22 | 3.32 | 7.93 |

REFERENCE EXAMPLE 82C

In 60 ml of methylene chloride is dissolved 3.5 g of N-methoxycarbonylmethyloxyphthalimide and under ice-cooling and stirring 745 mg of hydrazine hydrate is added. The mixture is stirred at room temperature for 2 hours, after which 149 mg of hydrazine hydrate is further added. The mixture is stirred for 2 hours and the resultant crystalline precipitate is filtered off. The filtrate is washed with 15 ml of dilute aqueous ammonia and, then, with 15 ml of water. The solution is dried over anhydrous sodium sulfate and the solvent is distilled off. To the residue is added 10 ml of ether and the insolubles are filtered off. Concentration of the filtrate gives a light-yellow oil of O-methoxycarbonylmethylhydroxylamine.

IR $\nu_{max}^{neat}$cm$^{-1}$: 3320, 2950, 1740.

NMR(CDCl$_3$+d$_6$-DMSO, ppm): 3.73(3H, s, CH$_3$), 4.2(2H, s, CH$_2$), 6.07(2H, br.s, NH$_2$).

In the same manner as above, there is synthesized the following compound:

O-(p-Nitrobenzyloxycarbonylmethyl)hydroxylamine.

IR $\nu_{max}^{neat}$cm$^{-1}$: 3325, 1760, 1720, 1600.

NMR(CDCl$_3$, ppm): 4.33(2H, s, NOCH$_2$).

REFERENCE EXAMPLE 83C

In a mixture of 20 ml of water and 12 ml of tetrahydrofuran is dissolved 1.0 g of 2-chloroacetamido-4-thiazolylglyoxylic acid as obtained in Example 80C, and under ice-cooling 465 mg of O-methoxycarbonylmethylhydroxylamine is added. The mixture is adjusted to pH 5 by addition of 1N aqueous sodium hydroxide and stirred at room temperature for 20 hours. The mixture is adjusted to pH 7 with aqueous sodium hydrogen carbonate and washed twice with 15 ml portions of ethyl acetate. The aqueous layer is separated and adjusted to pH 2 with 2N-HCl and the resultant crystalline precipitate is recovered by filtration and washed with water, hexane, and ether in this order. The procedure gives colorless crystals of 2-(2-chloroacetamido-4-thiazolyl)-(Z)-2-methoxycarbonylmethyloxyiminoacetic acid, m.p. 177°–179° C.(decomp.).

IR $\nu_{max}^{KBr}$cm$^{-1}$: 3200, 1750, 1725, 1690.

NMR(d$_6$-DMSO, ppm): 3.69(3H, s, COOCH$_3$), 4.39(2H, s, ClCH$_2$), 4.71(2H, s, NOCH$_2$), 7.41(1H, s, 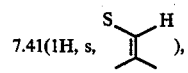 ), 12.7(1H, br.s, NH).

In the same manner as above, there was synthesized the following compound:

2-(2-Chloroacetamido-4-thiazolyl)-(Z)-2-(p-nitrobenzyloxycarbonylmethyloxyimino)acetic acid, m.p. 168°–170° C.(decomp.).

IR $\nu_{max}^{KBr}$cm$^{-1}$: 3200, 1760, 1710–1680, 1520.

NMR(d$_6$-DMSO, ppm): 4.34(2H, s, ClCH$_2$), 4.84(2H, s, NOCH$_2$), 5.33(2H, s, COOCH$_2$), 7.48(1H, s, 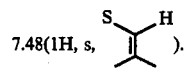 ).

| Elemental analysis: C$_{16}$H$_{13}$ClN$_4$O$_8$S | | | |
|---|---|---|---|
| | C (%) | H (%) | N (%) |
| Calc. | 42.06 | 2.87 | 12.27 |
| Found | 41.95 | 2.86 | 12.30 |

REFERENCE EXAMPLE 84C

In 20 ml of methylene chloride is suspended 810 mg of 2-(2-chloroacetamido-4-thiazolyl)-(Z)-2-methoxycarbonylmethyloxyiminoacetic acid and under ice-cooling and stirring 602 mg of phosphorus pentachloride is added. The mixture is stirred under ice-cooling for one hour and at room temperature for 30 minutes, after which 30 ml of hexane is added under ice-cooling. The resultant crystals are recovered by filtration and washed with hexane to give 910 mg of 2-(2-chloroacetamido-4-thiazolyl)-(Z)-2-methoxycarbonylmethyloxyiminoacetyl chloride hydrochloride, m.p. 77°–80° C.

IR $\nu_{max}^{KBr}$cm$^{-1}$: 3000, 1775, 1740, 1695.

| Elemental analysis: C$_{10}$H$_9$Cl$_2$N$_3$O$_5$S.HCl | | | |
|---|---|---|---|
| | C (%) | H (%) | N (%) |
| Calc. | 30.74 | 2.58 | 10.76 |
| Found | 30.69 | 2.46 | 10.89 |

In the same manner as above, there was synthesized the following compound:

2-(2-Chloroacetamido-4-thiazolyl)-(Z)-2-(p-nitrobenzyloxycarbonylmethyloxyimino)acetyl chloride hydrochloride, m.p. 158°–161° C.

IR $\nu_{max}^{KBr}$cm$^{-1}$: 2940, 1780, 1740, 1680.

| Elemental analysis: C$_{16}$H$_{12}$Cl$_2$N$_4$O$_7$S.HCl | | | |
|---|---|---|---|
| | C (%) | H (%) | N (%) |
| Calc. | 37.55 | 2.56 | 10.59 |
| Found | 37.61 | 2.65 | 10.87 |

REFERENCE EXAMPLE 85C

In a mixture of 5 ml of tetrahydrofuran and 5 ml of water is dissolved 280 mg of cis-3-amino-2-oxoazetidine-4-carboxylate, and 773 mg of sodium hydrogen carbonate is added. Then under ice-cooling and stirring, 910 mg of 2-(2-chloroacetamido-4-thiazolyl-(Z)-2-methoxycarbonylmethyloxyiminoacetyl chloride hydrochloride is added. The mixture is stirred at room temperature for 2 hours. To the reaction mixture is added water and the resultant crystals are recovered by filtration and washed with water, hexane and ether in this order to give methyl cis-3-[2-(2-chloroacetamido-4-thiazolyl)-2-methoxycarbonylmethyloxyiminoacetamido]-2-oxoazetidine-4-carboxylate (syn-isomer), m.p. 260°–265° C.(decomp.).

Ir $\nu_{max}^{KBr}$ cm$^{-1}$: 3290, 2950, 1780–1730, 1685, 1660.

| Elemental analysis: $C_{15}H_{16}ClN_5O_8S$ | | | |
|---|---|---|---|
| | C (%) | H (%) | N (%) |
| Calc. | 39.01 | 3.49 | 15.17 |
| Found | 39.00 | 3.58 | 15.06 |

In the same manner as above, there was synthesized the following compound:

cis-3-[2-(2-Chloroacetamido-4-thiazolyl)-2-(p-nitrobenzyloxycarbonylmethyloxyimino)acetamido]-4-methoxycarbonyl-2-oxoazetidine (syn-isomer), m.p. 270°–275° C.(decomp.).

Ir $\nu_{max}^{KBr}$ cm$^{-1}$: 3250, 1760, 1740, 1700, 1675.

| Elemental analysis: $C_{21}H_{19}ClN_6O_{10}S$ | | | |
|---|---|---|---|
| | C (%) | H (%) | N (%) |
| Calc. | 43.27 | 3.29 | 14.42 |
| Found | 42.85 | 3.38 | 14.27 |

REFERENCE EXAMPLE 86C

In 250 ml of dry ether is dissolved 15.3 g of p-nitrobenzyl alcohol, followed by addition of 8.90 ml of pyridine under ice-cooling and stirring. Then, 25.3 g of α-bromoisobutylbromide is added dropwise over 50 minutes. The mixture is stirred at room temperature for 5 hours and the resultant crystalline precipitate is separated by filtration and washed with ether. The filtrate and washings are combined and 150 ml of ethyl acetate is added. The mixture is washed with dilute hydrochloric acid, water, aqueous sodium hydrogen carbonate and aqueous sodium chloride in this order, and dried over anhydrous magnesium sulfate. The solvent is then distilled off under reduced pressure and the residue is chromatographed on a silica gel column [silica gel: 600 g; eluent: chloroform-hexane (1:1)] to give 29.6 g p of p-nitrobenzyl α-bromoisobutyrate as a yellow oil. This product solidifies on standing under cooling.

IR $\nu_{max}^{liq}$ cm$^{-1}$: 1735, 1520, 1345, 1150.

NMR(CDCl$_3$, ppm): 1.96(6H, s, 2×CH$_3$), 5.27(2H, s, COOCH$_2$), 7.49, 8.13(2×2H, 2×d, aromatic protons).

REFERENCE EXAMPLE 87C

In 75 ml of dry N,N-dimethylformamide are dissolved 14.7 g of N-hydroxyphthalimide and 27.2 g of p-nitrobenzyl α-bromoisobutyrate, followed by addition of 12.4 g of potassium carbonate. The mixture is stirred at room temperature for one hour. The stirring becomes difficult due to precipitation of an orange-colored solid and, therefore, 75 ml of dry N,N-dimethylformamide is added. After 24 hours of stirring at room temperature, the reaction mixture is concentrated under reduced pressure to about half its original volume and the concentrate is put in 700 ml of water with ice-cooling and stirring. The mixture is further stirred for 30 minutes and the resultant crystalline precipitate is recovered by filtration and washed with water. The crystals are dissolved in 500 ml of methylene chloride, washed with water and dried over anhydrous magnesium sulfate. The solvent is then distilled off under reduced pressure. The solid residue is washed with ether-petroleum ether (1:1) and a small amount of ether in this order to give 27.0 g of N-[1-methyl-1-(p-nitrobenzyloxycarbonyl)ethyloxy]phthalimide as colorless crystals, m.p. 145°–146° C.

IR $\nu_{max}^{KBr}$ cm$^{-1}$: 1790, 1740, 1725, 1520, 1345.

NMR(d$_6$-DMSO, ppm): 1.61(6H, s, 2×CH$_3$), 5.28(2H, s, NOCH$_2$), 7.59, 8.10(2 × 2H, 2 × d, 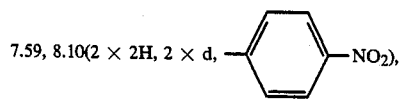 —NO$_2$), 7.75(4H, s, 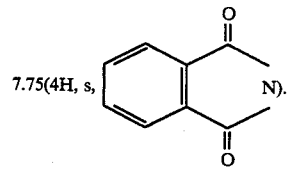 N).

| Elemental analysis: $C_{19}H_{16}N_2O_7$ | | | |
|---|---|---|---|
| | C (%) | H (%) | N (%) |
| Calc. | 59.38 | 4.20 | 7.29 |
| Found | 59.14 | 4.27 | 7.26 |

REFERENCE EXAMPLE 88C

In 80 ml of methylene chloride is dissolved 7.68 g of N-[1-methyl-1-(p-nitrobenzyloxycarbonyl)ethyloxy]phthalimide and under ice-cooling and stirring 0.97 ml of hydrazine hydrate is added. The mixture is stirred at room temperature for 2 hours, after which 0.97 ml of hydrazine hydrate is further added. The mixture is stirred for 3 hours and the resultant crystalline precipitate is separated by filtration and washed with methylene chloride. The filtrate and washings are combined and further washed with diluted aqueous ammonia and water in this order, and dried over anhydrous magnesium sulfate. The solvent is then distilled off under reduced pressure and the residue is chromatographed on a silica gel column [silica gel: 300 g; eluent: ethyl acetate-hexane (1:1)] to give 4.58 g of O-[1-methyl-1-(p-nitrobenzyloxycarbonyl)ethyl]hydroxylamine as a yellow oil. This product solidifies on cooling.

IR $\nu_{max}^{KBr}$ cm$^{-1}$: 3310, 3250, 2980, 2930, 1740, 1535, 1350.

NMR(CDCl$_3$, ppm): 1.46(6H, s, 2×CH$_3$), 5.26(2H, s, COOCH$_2$), 5.33(2H, br.s, NH$_2$), 7.48, 8.17(2×2H, 2×d, aromatic protons).

REFERENCE EXAMPLE 89C

In a mixture of 30 ml of water and 18 ml of tetrahydrofuran is dissolved 1.49 g of 2-chloroacetamido-4-thiazolylglyoxylic acid and under ice-cooling and stirring 1.83 g of O-[1-methyl-1-(p-nitrobenzyloxycarbonyl)ethyl]hydroxylamine is added. The mixture is adjusted to pH 5.0 with 1N aqueous sodium hydroxide and stirred at room temperature for 12 hours. The reaction mixture is then adjusted to pH 7.0 with aqueous sodium hydrogen carbonate and the tetrahydrofuran is distilled off under reduced pressure. The remaining aqueous solution is washed with ether, adjusted to pH 2 with dilute hydrochloric acid, and extracted with ethyl acetate. The extract is washed with aqueous sodium chloride and dried over anhydrous magnesium sulfate. The solvent is then distilled off under reduced pressure, and the residue is dissolved in ether and poured into twice its volume of petroleum ether. The resulting powdery precipitate is recovered by filtration to give 2-(2-chloroacetamido-4-thiazolyl)-(Z)-2-[1-methyl-1-(p-nitrobenzyloxycarbonyl)ethyloxyimino]acetic acid.

IR $\nu_{max}^{KBr}$cm$^{-1}$: 1740, 1695, 1540, 1520, 1345.

NMR(CDCl$_3$, ppm): 1.61(6H, s, 2×CH$_3$), 4.29(2H, s, ClCH$_2$), 5.23(2H, s, NOCH$_2$), 7.26(1H, s, 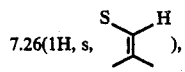 ), 7.43, 8.05(2×2H, 2×d, aromatic protons).

REFERENCE EXAMPLE 90C

In 15 ml of methylene chloride is dissolved 1.445 g of 2-(2-chloroacetamido-4-thiazolyl)-(Z)-2-[1-methyl-1-(p-nitrobenzyloxycarbonyl)ethyloxyimino]acetic acid and under ice-cooling and stirring 686 mg of phosphorus pentachloride is added. The mixture is stirred under ice-cooling for 30 minutes, after which 4.5 ml of hexane is added. The resultant crystalline precipitate is collected by filtration and washed with hexane to give 2-(2-chloroacetamido-4-thiazolyl)-(Z)-2-[1-methyl-1-(p-nitrobenzyloxycarbonyl)ethyloxyimino]acetyl chloride hydrochloride, m.p. 79°-82° C.

IR $\nu_{max}^{KBr}$cm$^{-1}$: 2998, 1775, 1735, 1715, 1565, 1520, 1340, 1140.

| Elemental analysis: C$_{18}$H$_{17}$Cl$_3$N$_4$O$_7$S | | | |
|---|---|---|---|
| | C (%) | H (%) | N (%) |
| Calc. | 40.05 | 3.17 | 10.38 |
| Found | 39.80 | 3.31 | 10.30 |

REFERENCE EXAMPLE 91C

In 20 ml of ethanol is suspended 417 mg of methyl cis-3-benzyloxycarboxamido-2-oxoazetidine-4-carboxylate as obtained in Reference Example 2C and 200 mg of 5% palladium-on-carbon is added. The mixture is stirred in a hydrogen atmosphere at room temperature for 30 minutes, after which the catalyst is filtered off. The filtrate is concentrated under reduced pressure and the residue is dissolved in a mixture of 15 ml of water and 15 ml of tetrahydrofuran. Then under ice-cooling and stirring, 336 mg of sodium hydrogen carbonate and 972 mg of 2-(2-chloroacetamido-4-thiazolyl)-(Z)-2-[1-methyl-1-(p-nitrobenzyloxycarbonyl)ethyloxyimino]acetyl chloride hydrochloride are added. After stirring for 30 minutes, the reaction mixture is extracted with ethyl acetate-tetrahydrofuran. The extract is washed with aqueous sodium hydrogen carbonate and aqueous sodium chloride in this order and dried over anhydrous magnesium sulfate. The solvent is then distilled off under reduced pressure and the solid residue is washed with etherethyl acetate (5:1) and ether in this order to give colorless crystals of cis-3-{2-(2-chloroacetamido-4-thiazolyl)-2-[1-methyl-1-(p-nitrobenzyloxycarbonyl)ethyloxyimino]acetamido}-4-methoxycarbonyl-2-oxoazetidine (syn-isomer), m.p. 198°-202° C. (decomp.).

IR $\nu_{max}^{KBr}$cm$^{-1}$: 3360, 1770, 1745, 1690, 1525, 1350.

NMR(d$_6$-DMSO, ppm): 1.52(6H, s, 2×CH$_3$), 3.63(3H, s, COOCH$_3$), 4.34(2H, s, ClCH$_2$), 4.47(1H, d, J=6 Hz, C$_4$—H), 5.29(2H, s, COOCH$_2$), 5.48(1H, d.d, J=6, 9 Hz, C$_3$—H), 7.23(1H, s, 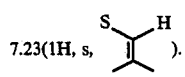 ).

REFERENCE EXAMPLE 92C

In 50 ml of methylene chloride is dissolved 19 g of methyl 2-hydroxyiminoacetoacetate and under ice-cooling and stirring 19.6 g of sulfuryl chloride is added dropwise. The mixture is stirred at room temperature for 3 days, after which the methylene chloride is distilled off under reduced pressure. The residue is dissolved in 200 ml of ether and washed seven times with 100 ml portions of water. The ether layer is dried over anhydrous sodium sulfate and concentrated under reduced pressure to give 20.2 g of methyl 4-chloro-2-hydroxyiminoacetoacetate as a light-yellow oil.

NMR(CDCl$_3$, ppm): 2.65(1H, br.s, N—OH), 3.90(3H, s, COOCH$_3$), 4.57(2H, s, ClCH$_2$).

This product is dissolved in 200 ml of a mixture of water and tetrahydrofuran (1:1) and under ice cooling 16.96 g of thiourea and 49.27 g of sodium acetate. 3H$_2$O are added. The mixture is stirred at room temperature overnight. The reaction mixture is then adjusted to pH 7.0 with sodium hydrogen carbonate and saturated with sodium chloride, whereupon the organic layer separates out. The aqueous layer is extracted with tetrahydrofuran and this tetrahydrofuran extract and the above organic layer are combined, washed twice with saturated aqueous sodium chloride, and dried over anhydrous sodium sulfate. The solvent is then distilled off and the oily residue is crystallized from 100 ml of ether. After standing overnight, the crystals are collected by filtration and washed well with water. The resultant crystals are dissolved in a 5:1 mixture of ethyl acetate and methanol and concentrated until a crystalline precipitate begins to form. The concentrate is allowed to stand overnight and the resultant crystalline precipitate is collected by filtration and dried to give light-yellow granules of methyl 2-(2-amino-4-thiazolyl)-(Z)-2-hydroxyiminoacetate, m.p. 191°-192° C. (decomp.).

IR $\nu_{max}^{KBr}$cm$^{-1}$: 3430, 3300, 3220, 3130, 1730, 1620.

NMR(d$_6$-DMSO, ppm): 3.80(3H, s, COOCH$_3$), 6.87(1H, s, 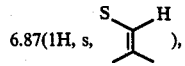 ), 7.17(2H, br.s, NH$_2$), 11.67(1H, s, N—OH).

| Elemental analysis: $C_6H_7N_3O_3S$ | | | |
|---|---|---|---|
| | C (%) | H (%) | N (%) |
| Calc. | 35.81 | 3.51 | 20.89 |
| Found | 36.05 | 3.52 | 20.96 |

REFERENCE EXAMPLE 93C

In 10 ml of N,N-dimethylformamide is dissolved 4.62 g of methyl 2-(2-amino-4-thiazolyl)-(Z)-2-hydroxyiminoacetate, followed by addition of 3 ml of triethylamine. Then, under stirring at −30° C., 6.42 g of trityl chloride is added over one hour. The mixture is further stirred at that temperature for one hour and, then at 15° C. for an additional 2 hours. To this reaction mixture is added 200 ml of water, followed by extraction with 200 ml of ethyl acetate. The ethyl acetate extract is washed twice with 200 ml portions of water and dried over anhydrous sodium sulfate. The solvent is then distilled off. The residue is purified by column chromatography [silica gel: 100 g; eluent: hexane-ethyl acetate (1:1)] and the resultant crystals are recrystallized from ethyl acetate to give methyl 2-(2-tritylamino-4-thiazolyl)-(Z)-2-hydroxyiminoacetate as colorless granules, m.p. 204°–205° C.

IR $\nu_{max}^{KBr}$cm$^{-1}$: 3375, 1740.

NMR(d$_6$-DMSO, ppm): 3.45(3H, s, COOCH$_3$), 6.70(1H, s, 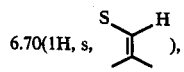 ), 7.18(15H, s, 3×Ph), 8.47(1H, br.s, NH), 11.27(1H, s, N—OH).

| Elemental analysis: $C_{25}H_{21}N_3O_3S$ | | | |
|---|---|---|---|
| | C (%) | H (%) | N (%) |
| Calc. | 67.70 | 4.77 | 9.48 |
| Found | 67.55 | 4.67 | 9.14 |

REFERENCE EXAMPLE 94C

To 70.5 ml of N,N-dimethylformamide are added 7.05 g of methyl 2-(2-tritylamino-4-thiazolyl)-(Z)-2-hydroxyiminoacetate and 3.3 g of potassium carbonate. Then, under ice-cooling and stirring 2.12 g of allyl bromide is added dropwise over a period of 5 minutes. The mixture is further stirred under ice-cooling for 4 hours. To this reaction mixture are added 1.65 g of potassium carbonate and 1.06 g of allyl bromide, and the mixture is stirred for an additional 4 hours. The reaction mixture is diluted with 150 ml of water and extracted three times with 100 ml portions of ether. The ether extract is washed twice with 100 ml portios of aqueous sodium chloride and dried over anhydrous sodium sulfate. The solvent is then distilled off and the residue is purified by column chromatography [silica gel: 300 g; eluent: hexane-ethyl acetate (1:1)] and crystallized from ether-hexane to give 7.0 g of methyl 2-(2-tritylamino-4-thiazolyl)-(Z)-2-allyloxyiminoacetate, m.p. 115°–116° C.

IR $\nu_{max}^{KBr}$cm$^{-1}$: 3360, 1740.

NMR(CDCl$_3$, ppm): 3.88(3H, s, COOCH$_3$), 6.53(1H, s, 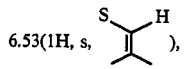 ), 6.93(1H, br.s, NH), 7.30(15H, s, 3×Ph).

| Elemental analysis: $C_{28}H_{25}N_3O_3S$ | | | |
|---|---|---|---|
| | C (%) | H (%) | N (%) |
| Calc. | 69.54 | 5.21 | 8.69 |
| Found | 69.57 | 5.18 | 8.51 |

REFERENCE EXAMPLE 95C

In 32 ml of tetrahydrofuran is dissolved 6.45 g of methyl 2-(2-tritylamino-4-thiazolyl)-(Z)-2-allyloxyiminoacetate, followed by addition of 32 ml of 50% formic acid. The mixture is stirred at 60° C. for 40 minutes. The reaction mixture is concentrated under reduced pressure and the solid residue is dissolved in ethyl acetate, washed with aqueous sodium hydrogen carbonate and aqueous sodium chloride in this order, and dried over anhydrous sodium sulfate. The solvent is then distilled off under reduced pressure and the residue is purified by column chromatography [silica gel: 150 g; eluent: hexane-ethyl acetate (1:1)]. The solvent is distilled off and the solid residue is washed with hexane and a small amount of ether in this order, and then dried to give methyl 2-(2-amino-4-thiazolyl)-(Z)-2-allyloxyiminoacetate, m.p. 133°–134° C.

IR $\nu_{max}^{KBr}$cm$^{-1}$: 3430, 3230, 1720, 1610, 1540.

NMR(CDCl$_3$, ppm): 3.90(3H, s, COOCH$_3$), 5.98(2H, br.s, NH$_2$), 6.67(1H, s, 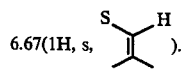 ).

REFERENCE EXAMPLE 96C

In the same manner as Reference Example 32C, there was synthesized methyl 2-(2-chloroacetamido-4-thiazolyl)-(Z)-2-allyloxyiminoacetate, m.p. 114°–115° C.

IR $\nu_{max}^{KBr}$cm$^{-1}$: 3150, 3060, 2950, 1740, 1710, 1680, 1565.

NMR(CDCl$_3$, ppm): 3.93(3H, s, COOCH$_3$), 4.28(2H, s, ClCH$_2$), 7.25(1H, s, 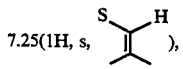 ), 10.12(1H, br.s, CONH).

REFERENCE EXAMPLE 97C

In the same manner as Reference Example 33C, there was synthesized 2-(2-chloroacetamido-4-thiazolyl)-(Z)-2-allyloxyiminoacetic acid, m.p. 162° C. (decomp.).

IR $\nu_{max}^{KBr}$cm$^{-1}$: 3180, 2950, 1715–1680.

NMR(d$_6$-DMSO, ppm): 4.33(2H, s, ClCH$_2$), 7.42(1H, s, 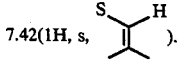 ).

| Elemental analysis: $C_{10}H_{10}ClN_3O_4S$ | | | |
|---|---|---|---|
| | C (%) | H (%) | N (%) |
| Calc. | 39.54 | 3.32 | 13.84 |
| Found | 39.41 | 3.55 | 13.71 |

REFERENCE EXAMPLE 98C

In 13 ml of methylene chloride is suspended 610 mg of 2-(2-chloroacetamido-4-thiazolyl)-(Z)-2-allyloxyiminoacetic acid and under ice-cooling and stirring 502.4 mg of phosphorus pentachloride is added. The mixture is stirred at room temperature for 30 minutes, after which 100 ml of hexane is added to the reaction mixture. The resulting crystals are recovered by filtration and washed with hexane to give 2-(2-chloroacetamido-4-thiazolyl)-(Z)-2-allyloxyiminoacetyl chloride hydrochloride, m.p. 67°–70° C.

| Elemental analysis: $C_{10}H_9Cl_2N_3O_3S\cdot HCl$ | | | |
|---|---|---|---|
| | C (%) | H (%) | N (%) |
| Calc. | 33.49 | 2.81 | 11.72 |
| Found | 33.87 | 2.76 | 11.79 |

REFERENCE EXAMPLE 99C

In a mixture of 2 ml of tetrahydrofuran and 2 ml of water is dissolved 185.5 mg of methyl cis-3-amino-2-oxoazetidine-4-carboxylate and under ice-cooling and stirring 469.6 mg of sodium hydrogen carbonate and successively, 600 mg of 2-(2-chloroacetamido-4-thiazolyl)-(Z)-allyloxyiminoacetyl chloride hydrochloride is added. The mixture is stirred at room temperature for 2 hours and concentrated under reduced pressure. To the residue is added 20 ml of water and the insolubles are collected by filtration, washed with aqueous sodium hydrogen carbonate, water, hexane and ether in this order, and dried to give methyl cis-3-[2-(2-chloroacetamido-4-thiazolyl)-2-allyloxyiminoacetamido]-2-oxoazetidine-4-carboxylate (syn isomer) as light-yellow granules, m.p. 270°–280° C. (decomp.).

IR $\nu_{max}^{KBr}$ cm$^{-1}$: 3260, 1770, 1745, 1720, 1680.

NMR(d$_6$-DMSO, ppm): 3.60(3H, s, COOCH$_3$), 4.33(2H, s, ClCH$_2$), 4.45(1H, d, J=6 Hz, C$_4$—H),

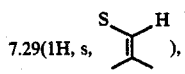
7.29(1H, s,     ), 9.49(1H, d, J=9 Hz, C$_3$—NH).

| Elemental analysis: $C_{15}H_{16}ClN_5O_6S$ | | | |
|---|---|---|---|
| | C (%) | H (%) | N (%) |
| Calc. | 41.91 | 3.75 | 16.29 |
| Found | 41.83 | 3.85 | 16.37 |

REFERENCE EXAMPLE 100C

In 7.8 ml of N,N-dimethylformamide is dissolved 657 mg of cis-3-benzyloxycarboxamido-4-methylsulfonyloxymethyl-2-oxoazetidine as obtained in Reference Example 11C and the solution is poured into a solution of 861 mg lithium chloride in 7.8 ml N,N-dimethylformamide. The mixture is stirred in an argon atmosphere at 73° C. for 3 hours. The reaction mixture is cooled, poured into 60 ml of aqueous sodium chloride and extracted with ethyl acetate. The extract is washed with aqueous sodium chloride and dried over anhydrous magnesium sulfate. The solvent is then distilled off under reduced pressure and the residue is purified by column chromatography [silica gel: 50 g; eluent: hexane-ethyl acetate (1:2)]. The resultant crystals are washed with ether to give cis-3-benzyloxycarboxamido-4-chloromethyl-2-oxoazetidine, m.p. 147°–149° C.

| Elemental analysis: $C_{12}H_{13}ClN_2O_3$ | | | |
|---|---|---|---|
| | C (%) | H (%) | N (%) |
| Calc. | 53.64 | 4.88 | 10.43 |
| Found | 53.49 | 4.81 | 10.35 |

REFERENCE EXAMPLE 101C

In 20 ml of methanol is suspended 376 mg of cis-3-benzyloxycarboxamido-4-chloromethyl-2-oxoazetidine, followed by addition of 376 mg of 5% palladium-on-carbon. The mixture is stirred in a hydrogen atmosphere at room temperature for 20 minutes. The catalyst is filtered off and the filtrate is concentrated. The solid residue is dissolved in 28 ml of a 1:1 mixture of tetrahydrofuran and water, and under ice-cooling and stirring 470 mg of sodium hydrogen carbonate is added, after which 698 mg of 2-(2-chloroacetamido-4-thiazolyl)-2-methoxyiminoacetyl chloride hydrochloride (syn-isomer) is added. Under ice-cooling the mixture is stirred for 30 minutes, and extracted with ethyl acetate. The aqueous layer is extracted again with a mixture of ethyl acetate and tetrahydrofuran. The extract are combined, washed with aqueous sodium hydrogencarbonate and aqueous sodium chloride in this order, dried over anhydrous magnesium sulfate, and concentrated under reduced pressure. The solid residue is washed with ethyl acetate-ether (1:3) to give cis-3-[2-(2-chloroacetamido-4-thiazolyl)-2-methoxyiminoacetamido]-4-chloromethyl-2-oxoazetidine (syn-isomer) as colorless crystals, m.p. 212°–217° C. (decomp.).

IR $\nu_{max}^{KBr}$ cm$^{-1}$: 3420, 3260, 1755, 1660, 1560.

NMR(d$_6$-DMSO, ppm): 3.90(3H, s, NOCH$_3$), 4.34(2H, s, ClCH$_2$), 5.28(1H, d.d, J=5, 9 Hz, C$_3$—H),

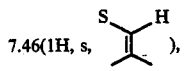
7.46(1H, s,     ), 8.72(1H, br.s, N$_1$—H), 9.33(1H, d, J=9 Hz, C$_3$—NH), 12.57(1H, br.s, ClCH$_2$CONH).

REFERENCE EXAMPLE 102C cis-3-Benzyloxycarboxamido-4-methylsulfonyloxymethyl-2-oxoazetidine as obtained in Reference Example 11C was reacted in the same manner as Reference Example 88C to synthesize cis-3-[2-(2-chloroacetamido-4-thiazolyl)-2-methoxyiminoacetamido]-4-methylsulfonyloxymethyl-2-oxoazetidine (syn-isomer), m.p. 186°–189° C. (decomp.).

| Elemental analysis: $C_{13}H_{16}ClN_5O_7S_2$ | | | |
|---|---|---|---|
| | C (%) | H (%) | N (%) |
| Calc. | 34.40 | 3.55 | 15.43 |
| Found | 34.27 | 3.63 | 15.28 |

REFERENCE EXAMPLE 103C

In 100 ml of ethanol is suspended 3.28 g of cis-3-benzyloxycarboxamido-4-methylsulfonyloxymethyl-2-oxoazetidine as obtained in Reference Example 11C, followed by addition of 3.28 g of 5% palladium-on-carbon. The mixture is stirred in a hydrogen atmosphere at room temperature for 50 minutes. The catalyst is then filtered off and the filtrate is concentrated under reduced pressure. The residue is dissolved in a mixture of 100 ml of methylene chloride and 15 ml of N,N-dimethylacetamido, and under ice-cooling and stirring 6.99 ml of propylene oxide and, then, a solution of 2.79 g of 2-methylsulfonylethyl chloroformate is 25 ml of methylene chloride are added. The mixture is stirred at room temperature for 2 hours and the methylene chloride is distilled off. To the residue are added water and a 1:1 mixture of ethyl acetate and tetrahydrofuran, and the mixture is shaken. The organic layer is separated and the aqueous layer is concentrated to dryness under reduced pressure. The residue is dissolved in tetrahydrofuran, dried over anhydrous magnesium sulfate and combined with the above-mentioned organic layer. The combined mixture is dried again over anhydrous magnesium sulfate and concentrated under reduced pressure. The residue is purified by column chromatography [silica gel: 150 g; eluent: ethyl acetate and then ethyl acetate-ethanol (9:1)] and the resultant crystals are washed with ethyl acetate-ether (1:1) to give cis-3-(2-methylsulfonylethoxycarboxamido)-4-methylsulfonyloxymethyl-2-oxoazetidine as colorless crystals, m.p. 141°–142° C.

| Elemental analysis: $C_9H_{16}N_2O_8S_2$ | | | |
|---|---|---|---|
| | C (%) | H (%) | N (%) |
| Calc. | 31.39 | 4.68 | 8.14 |
| Found | 31.34 | 4.76 | 8.34 |

REFERENCE EXAMPLE 104C

In 75 ml of methyl ethyl ketone are suspended 1.894 g of cis-3-(2-methylsulfonylethoxycarboxamido)-4-methylsulfonyloxymethyl-2-oxoazetidine and 4.864 g of sodium iodide, and the suspension is heated under reflux in a nitrogen atmosphere for 3 hours. The reaction mixture is concentrated under reduced pressure, and water, ethyl acetate and aqueous sodium thiosulfate are added to the residue. The resultant crystalline precipitate is recovered by filtration and washed with water, ethyl acetate and ether in this order to give 382 mg of cis-3-(2-methylsulfonylethoxycarboxamido)-4-iodomethyl-2-oxoazetidine as colorless crystals. The filtrate and washings are combined and the organic layer is separated. The aqueous layer is saturated with sodium chloride and extracted with tetrahydrofuran-ethyl acetate (4:1). The extract and the organic layer are combined and dried over anhydrous magnesium sulfate. The solvent is then distilled off under reduced pressure and the crystalline residue is washed with ethyl acetate to give 1.367 g of the above-mentioned 4-iodomethyl-compound, m.p. 186°–190° C. (decomp.).

| Elemental analysis: $C_8H_{13}IN_2O_5S$ | | | |
|---|---|---|---|
| | C (%) | H (%) | N (%) |
| Calc. | 25.54 | 3.48 | 7.45 |
| Found | 25.64 | 3.53 | 7.34 |

REFERENCE EXAMPLE 105C

To 20 ml of N,N-dimethylformamide are added 1.504 g of cis-3-(2-methylsulfonylethoxycarboxamido)-4-iodomethyl-2-oxoazetidine and 390 mg of sodium azide and the mixture is stirred at room temperature for 66 hours and, then, at 40° C. for 24 hours. The reaction mixture is concentrated under reduced pressure and the residue is purified by column chromatography [silica gel: 100 g, eluent: ethyl acetate and then ethyl acetate-ethanol (9:1)]. The solvent is then distilled off and the residue is crystallized from ethyl acetate and filtered to give colorless crystals of cis-3-(2-methylsulfonylethoxycarboxamido)-4-azidomethyl-2-oxoazetidine, m.p. 158°–160° C.

IR $\nu_{max}^{KBr}$cm$^{-1}$: 3200, 2110, 1780, 1700, 1550.

REFERENCE EXAMPLE 106C

To a mixture of 60 ml of ethanol and 6 ml of N,N-dimethylformamide is added 757 mg of cis-3-(2-methylsulfonylethoxycarboxamido)-4-azidomethyl-2-oxoazetidine and under ice-cooling and stirring 11.4 ml of 0.5N ethanolic sodium hydroxide is added. After 40 minutes, 5.7 ml of 1N HCl is added and the mixture is concentrated under reduced pressure. To the residue are added 15 ml of water and 15 ml of tetrahydrofuran and, then, under ice-cooling and stirring 874 mg of sodium hydrogen carbonate is added. After addition of 1.297 g of 2-(2-chloroacetamido-4-thiazolyl)-2-methoxyiminoacetyl chloride hydrochloride (syn-isomer), the mixture is stirred for 40 minutes. The reaction mixture is diluted with water and extracted with ethyl acetate. The extract is washed with water and aqueous sodium chloride and dried over anhydrous magnesium sulfate. The solvent is then distilled off under reduced pressure and the crystalline residue is washed with ethyl acetate and ether in this order to give colorless crystals of cis-3-[2-(2-chloroacetamido-4-thiazolyl)-2-methoxyiminoacetamido]-4-azidomethyl-2-oxoazetidine (syn-isomer), m.p. 223°–230° C. (decomp.).

IR $\nu_{max}^{KBr}$cm$^{-1}$: 3420, 3250, 2110, 1760, 1660, 1550.
NMR(d$_6$-DMSO, ppm): 3.4–3.6(2H, m, CH$_2$N$_3$), 3.90(3H, s, NOCH$_3$), 4.34(2H, s, ClCH$_2$), 5.22(1H, d.d, J=5, 9 Hz, C$_3$—H),

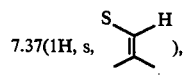

7.37(1H, s, 8.49(1H, br.s, N$_1$—H), 9.20(1H, d, J=9 Hz, C$_3$—NH).

REFERENCE EXAMPLE 107C

In 50 ml of methylene chloride is dissolved 5.0 g of cis-3-benzyloxycarboxamido-1-(2,4-dimethoxybenzyl)-4-hydroxymethyl-2-oxoazetidine as obtained in Reference Example 5C, followed by addition of 3.75 ml of pyridine under stirring at 0° C. After dropwise addition of 3.94 g of benzoyl chloride, the mixture is stirred at room temperature for 1.5 hours. To the reaction mixture is added 100 ml of ice-water, and the organic layer, which separates, is washed with aqueous sodium hydrogen carbonate and dried over anhydrous sodium sulfate. The solvent is then distilled off and the residue is purified by column chromatography [silica gel: 325 g; eluent: hexane-ethyl acetate (1:2)]. The solvent is distilled off and, after addition of hexane, the crystalline residue is recovered by filtration to give colorless crystals of cis-3-benzyloxycarboxamido-4-benzoyloxymethyl-1-(2,4-dimethoxybenzyl)-2-oxoazetidine, m.p. 133°–134° C.

Elemental analysis: $C_{28}H_{28}N_2O_7$

|  | C (%) | H (%) | N (%) |
| --- | --- | --- | --- |
| Calc. | 66.65 | 5.59 | 5.55 |
| Found | 66.48 | 5.49 | 5.36 |

REFERENCE EXAMPLE 108C

In the same manner as Reference Example 7C, there was synthesized cis-3-benzyloxycarboxamido-4-benzoyloxymethyl-2-oxoazetidine, m.p. 188°–189° C.

IR $\nu_{max}^{KBr}$cm$^{-1}$: 3300, 1770, 1725, 1690.

Elemental analysis: $C_{19}H_{18}N_2O_5$

|  | C (%) | H (%) | N (%) |
| --- | --- | --- | --- |
| Calc. | 64.40 | 5.12 | 7.91 |
| Found | 64.42 | 4.96 | 7.86 |

REFERENCE EXAMPLE 109C

In 20 ml of ethanol is suspended 550 mg of cis-3-benzyloxycarboxamido-4-benzoyloxymethyl-2-oxoazetidine and following addition of 550 mg of 5% palladium-on-carbon. The suspension is stirred in a hydrogen atmosphere for 2.5 hours. The catalyst is filtered off and the filtrate is concentrated under reduced pressure to give colorless crystals of cis-3-amino-4-benzoyloxymethyl-2-oxoazetidine, m.p. 150°–151° C.

IR $\nu_{max}^{KBr}$cm$^{-1}$: 3200, 1735, 1710.

Elemental analysis: $C_{11}H_{12}N_2O_3$

|  | C (%) | H (%) | N (%) |
| --- | --- | --- | --- |
| Calc. | 59.99 | 5.49 | 12.72 |
| Found | 60.06 | 5.66 | 12.84 |

REFERENCE EXAMPLE 110C

In the same manner as Reference Example 9C, there was synthesized cis-3-[2-(2-chloroacetamido-4-thiazolyl)-2-methoxyiminoacetamido]-4-benzoyloxymethyl-2-oxoazetidine (syn-isomer), m.p. 210°–220° C. (decomp.).

IR $\nu_{max}^{KBr}$cm$^{-1}$: 3250, 1760, 1715, 1660.

Elemental analysis: $C_{19}H_{18}ClN_5O_6S$

|  | C (%) | H (%) | N (%) |
| --- | --- | --- | --- |
| Calc. | 47.55 | 3.78 | 14.59 |
| Found | 47.06 | 3.63 | 14.53 |

REFERENCE EXAMPLE 111C

To 250 ml of benzene are added 35 g of α-methylcinnamaldehyde and 29.5 g of p-anisidine and the mixture is heated under refluxed for one hour, with water being azeotropically removed. The solvent is distilled off under reduced pressure and the residue is dissolved in 1 l of methylene chloride. Under ice-cooling and stirring 29 g of triethylamine is added and, then, a solution of 53.5 g of phthalimidoacetyl chloride in 250 ml of methylene chloride is added dropwise over 45 minutes. The mixture is stirred at room temperature for 24 hours, after which it is washed with water, dried over anhydrous magnesium sulfate and concentrated. The solid residue is recrystallized from ethyl acetate-hexane to give cis-3-phthalimido-4-(α-methylstyryl)-1-(4-methoxyphenyl)-2-oxoazetidine, m.p. 105°–107° C.

IR $\nu_{max}^{KBr}$cm$^{-1}$: 1760, 1725, 1515, 1385, 1250.

NMR(CDCl$_3$, ppm): 1.70(3H, br.s, =C—CH$_3$), 3.74(3H, s, NOCH$_3$), 4.77(1H, d, J=6 Hz, C$_4$—H), 5.52(1H, d, J=6 Hz, C$_3$—H), 6.50(1H, br.s, =CH—Ph).

REFERENCE EXAMPLE 112C

In 200 ml of dimethoxyethane is dissolved 28 g of cis-3-phthalimido-4-(α-methylstyryl)-1-(4-methoxyphenyl)-2-oxoazetidine, followed by addition of 10.2 g of methylhydrazine. The mixture is stirred at room temperature for 12 hours. The resultant crystalline precipitate is filtered off and the filtrate is concentrated. The residue is dissolved in 200 ml of methylene chloride, followed by a serial addition of 14.8 g of propylene oxide and 10.62 g of carbobenzoxy chloride. The mixture is stirred for one hour and concentrated under reduced pressure. The residue is purified by column chromatography [silica gel: 300 g, eluent: hexane-ethyl acetate (1:1 and then 1:2)] to give cis-3-benzyloxycarboxamido-4-(α-methylstyryl)-1-(4-methoxyphenyl)-2-oxoazetidine.

IR $\nu_{max}^{KBr}$cm$^{-1}$: 1750, 1720, 1680.

NMR(CDCl$_3$, ppm): 1.85(3H, br.s, =C—CH$_3$), 3.75(3H, s, OCH$_3$), 5.08(2H, s, PhCH$_2$), 5.50(1H, d.d, J=6, 9 Hz, C$_3$—H), 6.43(1H, br.s, =CH—Ph), 7.84(1H, d, J=9 Hz, C$_3$—NH).

REFERENCE EXAMPLE 113C

In 750 ml of methylene chloride is dissolved 75 g of cis-3-benzyloxycarboxamido-4-(α-methylstyryl)-1-(4-methoxyphenyl)-2-oxoazetidine and an excess of ozone is passed through the solution at −78° C. Nitrogen gas is then passed therethrough to purge the excess ozone, followed by addition of 11.6 g of dimethyl sulfide. Thereafter, the mixture is stirred for 30 minutes at room temperature and then concentrated under reduced pressure. The residue is purified by column chromatography [silica gel: 400 g; eluent: hexane-ethyl acetate (1:2 and then 1:4)] to give cis-3-benzyloxycarboxamido-4-acetyl-1-(4-methoxyphenyl)-2-oxoazetidine, m.p. 188°–191° C.

IR $\nu_{max}^{KBr}$cm$^{-1}$: 1760, 1720, 1700, 1655.

NMR(d$_6$-DMSO, ppm): 2.20(3H, s, COCH$_3$), 3.74(3H, s, OCH$_3$), 5.15(2H, s, PhCH$_2$), 5.20(1H, d, J=6 Hz, C$_4$—H), 5.64(1H, d.d, J=6, 9 Hz, C$_3$—H), 9.48 (1H, d, J=9 Hz, C$_3$—NH).

REFERENCE EXAMPLE 114C

In a mixture of 50 ml of acetonitrile and 25 ml of water is dissolved 1 g of cis-3-benzyloxycarboxamido-4-acetyl-1-(4-methoxyphenyl)-2-oxoazetidine. Under cooling at −15° C., 3 g of ammonium cerium (IV) nitrate is added and the mixture is stirred for 10 minutes. After addition of a saturated aqueous solution of sodium sulfite to terminate the reaction, the pH is adjusted to 5–6 with sodium hydrogen carbonate. Then, the acetonitrile is distilled off under reduced pressure and the residue is made acidic with 3N-hydrochloric acid and extracted with chloroform. The aqueous layer is extracted twice with chloroform-ethanol (4:1). The extracts are combined, dried over anhydrous magnesium sulfate and concentrated under reduced pressure. The residue is subjected to column chromatography [silica gel: 80 g; eluent: hexane-ethyl acetate (1:2), ethyl acetate and then ethyl acetate-methanol (9:1)] to give cis-3-benzyloxycarboxamido-4-acetyl-2-oxoazetidine.

IR $\nu_{max}^{KBr}$cm$^{-1}$: 3240, 1770, 1705, 1635, 1540, 1450, 1380, 1305, 1180.

NMR(CDCl$_3$, ppm): 2.20(3H, s, COCH$_3$), 4.58(1H, d, J=6 Hz, C$_4$—H), 5.20(2H, s, PhC$\underline{H}_2$), 8.18(1H, d, J=9 Hz, C$_3$—NH).

REFERENCE EXAMPLE 115C

In the same manner as Reference Example 67C, there was synthesized cis-3-[2-(2-chloroacetamido-4-thiazolyl)-2-methoxyiminoacetamido]-4-acetyl-2-oxoazetidine (syn-isomer).

IR $\nu_{max}^{KBr}$cm$^{-1}$: 3350, 1760, 1650, 1545.

NMR(d$_6$-DMSO, ppm): 2.12(3H, s, COCH$_3$), 3.73(3H, br.s, NOCH$_3$), 4.35(2H, s, ClCH$_2$), 7.90(1H, s, 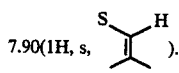 ).

REFERENCE EXAMPLE 116C

In a mixture of 2 ml of tetrahydrofuran and 2 ml of water is dissolved 75 mg of cis-3-amino-4-hydroxymethyl-2-oxoazetidine as obtained in Reference Example 53C and, under ice-cooling and stirring 168 mg of sodium hydrogen carbonate and then 332 mg of 2-(2-chloroacetamido-4-thiazolyl)-(Z)-2-methoxyiminoacetyl chloride hydrochloride are added. The mixture is stirred under ice-cooling for one hour and the reaction mixture is made neutral with aqueous sodium hydrogen carbonate and extracted with ethyl acetate-tetrahydrofuran (2:1). The extract is washed with saturated aqueous sodium chloride and dried over anhydrous magnesium sulfate. The solvent is then distilled off under reduced pressure and, after addition of ethyl acetate-ether (1:2), the crystalline residue is recovered by filtration to give cis-3-[2-(2-chloroacetamido-4-thiazolyl)-2-methoxyiminoacetamido]-4-hydroxymethyl-2-oxoazetidine (syn-isomer) as colorless crystals, m.p. 238°–241° C. (decomp.).

IR $\nu_{max}^{KBr}$cm$^{-1}$: 3400(br), 1750, 1660, 1045.

NMR(d$_6$-DMSO, ppm): 207(1H, s, OH), 3.89(3H, s, NOCH$_3$), 4.34(2H, s, ClCH$_2$), 5.20(1H, d.d, J=5, 9 Hz), C$_3$—H, 7.50(1H, s, 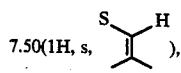 ), 9.15(1H, d, J=9 Hz, C$_3$—NH).

REFERENCE EXAMPLE 117C

In a mixture of 17 ml of methylene chloride and 6 ml of N,N-dimethylformamide is dissolved 172 mg of cis-3-[2-(2-chloroacetamido-4-thiazolyl)-2-methoxyiminoacetamido]-4-hydroxymethyl-2-oxoazetidine (syn-isomer), followed by addition of 0.2 ml of pyridine. While the mixture is cooled with ice-sodium chloride mixture and stirred, 0.12 ml of chloroacetyl chloride is added dropwise. The mixture is stirred under cooling for 30 minutes and the solvent is distilled off. To the residue are added aqueous sodium chloride and ethyl acetate, and the mixture is shaken well. The organic layer is separated and washed with aqueous sodium chloride and dried over anhydrous sodium sulfate. The solvent is then distilled off and the residue is crystallized from ether. Recrystallization from chloroform-methanol gives colorless crystals of cis-3-[2-(2-chloroacetamido-4-thiazolyl)-2-methoxyiminoacetamido]-4-chloroacetoxymethyl-2-oxoazetidine (syn-isomer), m.p. 225°–227° C. (decomp.).

| Elemental analysis: C$_{14}$H$_{15}$Cl$_2$N$_5$O$_6$S | | | |
|---|---|---|---|
| | C (%) | H (%) | N (%) |
| Calc. | 37.17 | 3.34 | 15.48 |
| Found | 36.79 | 3.37 | 15.44 |

REFERENCE EXAMPLE 118C

In 320 ml of ethanol is suspended 4.45 g of cis-3-benzyloxycarboxamido-1-(2,4-dimethoxybenzyl)-4-phthalimidomethyl-2-oxoazetidine as obtained in Reference Example 48C, followed by addition of 2.03 ml of hydrazine hydrate. The mixture is heated under reflux for 2 hours and cooled. The reaction mixture is filtered and the filtrate is concentrated under reduced pressure. To the residue is added 200 ml of methylene chloride and the insolubles are filtered off. The filtrate is washed with water, dried over anhydrous magnesium sulfate and concentrated under reduced pressure. The residue is dissolved in a mixture of 84 ml of methylene chloride and 11 ml of N,N-dimethylacetamide and under ice-cooling and stirring 5.88 ml of propylene oxide and, then, a solution of 2.35 g of $\beta$-methylsulfonylethyl chloroformate in 20 ml of methylene chloride are added dropwise. The mixture is stirred at room temperature for one hour, washed with water, aqueous sodium bicarbonate, water, dilute hydrochloric acid and saturated aqueous sodium chloride in this order, and dried over anhydrous magnesium sulfate. The solvent is then distilled off under reduced pressure and the crystalline residue is washed with ethyl acetate to give 2.94 g of cis-3-benzyloxycarboxamido-1-(2,4-dimethoxybenzyl)-4-(2-methylsulfonylethoxycarbonylaminomethyl)-2-oxoazetidine, m.p. 172°–174° C.

IR $\nu_{max}^{KBr}$cm$^{-1}$: 3400, 1755, 1690, 1610, 1535, 1125.

NMR(d$_6$-DMSO, ppm): 2.97(3H, s, SO$_2$CH$_3$), 3.38(2H, t, J=6 Hz, CH$_2$SO$_2$), 3.75, 3.77(2×CH$_3$, 2×s, 2×OCH$_3$), 4.24(2H, q, J=15 Hz, N$_1$—CH$_2$), 4.28 (2H, t, J=6 Hz, COOCH$_2$), 4.82(1H, d.d, J=5, 9 Hz, C$_3$—H), 5.05(2H, s, PhC$\underline{H}_2$), 7.37(5H, s, Ph—), 8.05(1H, d, J=9 Hz, C$_3$—NH).

REFERENCE EXAMPLE 119C

In the same manner as Reference Example 50C, there was synthesized cis-3-benzyloxycarboxamido-4-(2-methylsulfonylethoxycarbonylaminomethyl)-2-oxoazetidine, m.p. 149°–150° C.

| Elemental analysis: C$_{16}$H$_{21}$N$_3$O$_7$S | | | |
|---|---|---|---|
| | C (%) | H (%) | N (%) |
| Calc. | 48.11 | 5.30 | 10.52 |
| Found | 47.99 | 5.22 | 10.37 |

REFERENCE EXAMPLE 120C

In the same manner as Reference Example 51C, there was synthesized cis-3-[2-(2-chloroacetamido-4-thiazolyl)-2-methoxyiminoacetamido]-4-(2-methylsulfonylethoxycarbonylaminomethyl)-2-oxoazetidine (syn-isomer). This product discolors gradually at 150°–170° C. and decomposes at 195°–199° C.

IR $\nu_{max}^{KBr}$cm$^{-1}$: 3250, 1760, 1690, 1650, 1550.

| Elemental analysis: $C_{16}H_{21}ClN_6O_8S_2$ | | | |
|---|---|---|---|
| | C (%) | H (%) | N (%) |
| Calc. | 36.61 | 4.03 | 16.01 |
| Found | 36.48 | 4.08 | 15.92 |

REFERENCE EXAMPLE 121C

In 3 ml of N,N-dimethylformamide are dissolved 1.197 g of cis-3-benzyloxycarboxamido-4-(2-methylsulfonylethoxycarbonylaminomethyl)-2-oxoazetidine as obtained in Reference Example 119C and 475 mg of dimethyl-tert-butylsilyl chloride, and under cooling at 0° C., 0.46 ml of triethylamine is added dropwise. The mixture is stirred under ice-cooling for 30 minutes, after which water and ethyl acetate are added. The ethyl acetate layer is taken, washed with dilute hydrochloric acid and aqueous sodium chloride in this order, and dried over anhydrous magnesium sulfate. The solvent is then distilled off under reduced pressure and the residue is subjected to column chromatography [silica gel: 100 g; eluent: hexane-ethyl acetate (1:2 and then 1:3)] to give cis-3-benzyloxycarboxamido-4-(2-methylsulfonylethoxycarbonylaminomethyl)-1-dimethyl-tert-butylsilyl-2-oxoazetidine as a frothy product.

IR $\nu_{max}^{KBr}$cm$^{-1}$: 3330, 1750, 1720, 1695.

NMR(CDCl$_3$, ppm): 0.26(3H, s, SiCH$_3$), 0.28(3H, s, SiCH$_3$), 0.96(9H, s, tert-Bu), 2.93(3H, s, SO$_2$CH$_3$), 3.28(2H, t, J=6 Hz, CH$_2$SO$_2$), 4.50(2H, t, J=6 Hz, COOCH$_2$), 5.03(1H, d.d, J=5, 9 Hz, C$_3$—H), 5.15(2H, s, PhCH$_2$), 6.18(1H, d, J=9 Hz, C$_3$—NH), 7.38(5H, s, Ph).

REFERENCE EXAMPLE 122C

In 20 ml of ethanol is dissolved 514 mg of cis-3-benzyloxycarboxamido-4-(2-methylsulfonylethoxycarbonylaminomethyl)-1-dimethyl-tert-butylsilyl-2-oxoazetidine, and under ice-cooling and stirring 4.4 ml of ethanolic sodium hydroxide (0.5N) is added. The mixture is stirred under ice-cooling for 15 minutes and to the reaction mixture is added 2.2 ml of 1N hydrochloric acid. The solvent is distilled off under reduced pressure and the residue is extracted with methylene chloride-tetrahydrofuran. The extract is washed with aqueous sodium chloride and dried over anhydrous magnesium sulfate. The solvent is then distilled off under reduced pressure and under ice-cooling 4 ml of dry trifluoroacetic acid and 2 ml of trifluoroacetic acid are added. The mixture is stirred for 30 minutes and concentrated under reduced pressure. The residue is purified by column chromatography [silica gel: 40 g; eluent: hexane-ethyl acetate (1:1 and then 1:2)] to give cis-3-benzyloxycarboxamido-4-trifluoroacetylaminomethyl-2-oxoazetidine, m.p. 197°–201° C.

IR $\nu_{max}^{KBr}$cm$^{-1}$: 3280, 1760, 1705, 1690.

| Elemental analysis: $C_{14}H_{14}F_3N_3O_4$ | | | |
|---|---|---|---|
| | C (%) | H (%) | N (%) |
| Calc. | 48.70 | 4.09 | 12.17 |
| Found | 48.31 | 4.00 | 12.01 |

By the above reaction, there are also obtained yellow crystals (m.p. 130°–135° C.) of cis-3-benzyloxycarboxamido-4-trifluoroacetylaminomethyl-1-dimethyl-tert-butylsilyl-2-oxoazetidine as a by product.

IR $\nu_{max}^{KBr}$cm$^{-1}$: 3300, 1765, 1700, 1685.

REFERENCE EXAMPLE 123C

In the same manner as Reference Example 67C, there was synthesized cis-3-[2-(2-chloroacetamido-4-thiazolyl)-2-methoxyiminoacetamido]-4-trifluoroacetylaminomethyl-2-oxoazetidine (syn-isomer), m.p. 220°–225° C.(decomp.).

IR $\nu_{max}^{KBr}$cm$^{-1}$: 3270, 1760, 1705, 1660.

NMR(d$_6$-DMSO, ppm): 3.89(3H, s, NOCH$_3$), 4.31(2H, s, ClCH$_2$), 5.22(1H, d.d, J=5, 9 Hz, C$_3$—H), 7.43(1H, s, 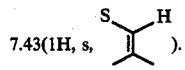 ).

REFERENCE EXAMPLE 124C

In a mixture of 25 ml of ethanol and 5 ml of N,N-dimethylformamide is suspended 525 mg of cis-3-[2-(2-chloroacetamido-4-thiazolyl)-2-methoxyiminoacetamido]-4-(2-methylsulfonylethoxycarbonylaminomethyl)-2-oxoazetidine (syn-isomer) as obtained in Reference Example 119C, followed by addition of 5 ml of ethanolic sodium hydroxide (0.5N). The mixture is stirred at room temperature for 20 minutes, after which 2.5 ml of 1N HCl is added. The ethanol is distilled off under reduced pressure and the residue is dissolved in a mixture of 8 ml of water and 10 ml of tetrahydrofuran. Under ice-cooling and stirring, 185 mg of sodium hydrogen carbonate is added, followed by dropwise addition of a solution of 432 mg of p-nitrobenzyl chloroformate in 10 ml of tetrahydrofuran over 50 minutes. The mixture is stirred under ice-cooling for 20 minutes and to this reaction mixture are added 10 ml of water and 20 ml of ethyl acetate. The mixture is shaken well, whereupon the organic layer separates out. The aqueous layer is extracted with ethyl acetate and this ethyl acetate extract and the above organic layer are combined, washed with aqueous sodium chloride and dried over anhydrous magnesium sulfate. The solvent is then distilled off under reduced pressure and the residue is crystallized from ethyl acetate and recovered by filtration to give cis-3-[2-(2-chloroacetamido-4-thiazolyl)-2-methoxyiminoacetamido]-4-(p-nitrobenzyloxycarbonylaminomethyl)-2-oxoazetidine (syn-isomer), m.p. 235°–245° C. (decomp.).

IR $\nu_{max}^{KBr}$cm$^{-1}$: 3380, 3230, 1760, 1690, 1660, 1550, 1520.

REFERENCE EXAMPLE 125C

In the same manner as Reference Example 39C, there were synthesized the following compounds:
Methyl cis-3-[D-2-(4-ethyl-2,3-dioxo-1-piperazinecarboxamido)-2-phenylacetamido]-2-oxoazetidine-4-carboxylate.
Beta form IR $\nu_{max}^{KBr}$cm$^{-1}$: 1770, 1740, 1710, 1675.

NMR(d$_6$-DMSO, ppm): 1.11(3H, t, J=7 Hz, N—CH$_2$CH$_3$), 3.08 (3H, s, COOCH$_3$), 4.30(1H, d, J=6 Hz, C$_4$—H), 5.38(1H, d.d, J=6, 9 Hz, C$_3$—H), 5.52(1H, d, J=7 Hz, PhCH—), 8.68(1H, s, N$_1$—H), 9.26(1H, d, J=9 Hz, C$_3$—NH), 9.86(1H, d, J=7Hz, PhCHNH).

Alpha form

IR $\nu_{max}^{KBr}$cm$^{-1}$: 1770, 1740, 1710, 1670.

NMR(d$_6$-DMSO, ppm): 1.10(3H, t, J=7 Hz, N—CH$_2$CH$_3$), 3.55 (3H, s, COOCH$_3$), 4.40(1H, d, J=6 Hz, C$_4$—H), 5.20(1H, d.d, J=6, 9 Hz, C$_3$—H), 5.47(1H, d, J=7 Hz, PhCH), 8,70(1H, s, N$_1$—H), 9.25(1H, d, J=9 Hz, C$_3$—NH), 9.80(1H, d, J=7Hz, PhCHNH).

cis-3-[D-2-(4-Ethyl-2,3-dioxo-1-piperazinecarboxamido)-2-phenylacetamido]-4-methyl-2-oxoazetidine.
Beta form
  IR $\nu_{max}^{KBr}$cm$^{-1}$: 1750, 1710, 1670.
  NMR(CDCl$_3$, ppm): 1.15(3H, d, J=4 Hz, C$_4$—CH$_3$).
Alpha form
  IR $\nu_{max}^{KBr}$cm$^{-1}$: 1760, 1715, 1690.
  NMR(CDCl$_3$, ppm): 1.39(3H, d, J=4 Hz, C$_4$—CH$_3$).
cis-3-[D-2-(4-Ethyl-2,3-dioxo-1-piperazinecarboxamido)-2-phenylacetamido]-4-acetoxymethyl-2-oxoazetidine.
Beta form
  IR $\nu_{max}^{KBr}$cm$^{-1}$: 1770, 1710, 1670.
  NMR(CDCl$_3$, ppm): 1.85(3H, s, OCOCH$_3$).
Alpha form
  IR $\nu_{max}^{KBr}$cm$^{-1}$: 1770, 1720, 1670.
  NMR(CDCl$_3$, ppm): 1.90(3H, s, OCOCHL$_3$).

REFERENCE EXAMPLE 126C

In the same manner as Reference Example 39C, 300 mg of D-2-[3-(furan-2-aldimino)-2-oxo-1-imidazolidinecarboxamido]-2-phenylacetic acid were reacted with 110 mg of methyl cis-3-amino-2-oxoazetidine-4-carboxylate to synthesize methyl cis-3-{D-2-[3-(furan-2-aldimino)-2-oxo-1-imidazolidinecarboxamido]-2-phenylacetamido}-2-oxoazetidine-4-carboxylate.
Beta form
  IR $\nu_{max}^{KBr}$cm$^{-1}$: 1760, 1720, 1660.
Alpha form
  IR $\nu_{max}^{KBr}$cm$^{-1}$: 1770, 1720, 1660.

In the same manner as above, there was synthesized the following compound:
Methyl cis-3-{D-2-[3-(thiophene-2-aldimino-2-oxo-1-imidazolidinecarboxamido]-2-phenylacetamido}-2-oxoazetidine-4-carboxylate.
Beta form
  IR $\nu_{max}^{KBr}$cm$^{-1}$: 1765, 1725, 1660.
Alpha form
  IR $\nu_{max}^{KBr}$cm$^{-1}$: 1770, 1720, 1660.

REFERENCE EXAMPLE 127C

The 3-amino compound (prepared from 0.8 g of methyl cis-3-benzyloxycarboxamido-2-oxoazetidine-4-carboxylate in the same manner as Reference Example 3C) is dissolved in 10 ml of tetrahydrofuran and under ice-cooling and stirring 1.2 ml of triethylamine is added, followed by dropwise addition of a solution of 1.2 g of 2-(2-chloroacetamido-4-thiazolyl)-2-diethylphosphonoacetyl chloride in 10 ml of tetrahydrofuran. The mixture is stirred at room temperature for 2.5 hours and the tetrahydrofuran is distilled off. To the residue, ethyl acetate and water are added and the mixture is shaken well. The organic layer is taken, washed with saturated aqueous sodium chloride and dried over anhydrous sodium sulfate. The solvent is then distilled off and the residue is purified by silica-gel column-chromatography [eluent: chloroform-methanol (95:5)] to give methyl cis-3-[2-(2-chloroacetamido-4-thiazolyl)-2-diethylphosphonoacetamido]-2-oxoazetidine-4-carboxylate.

IR $\nu_{max}^{KBr}$cm$^{-1}$: 3250, 1770, 1750, 1685, 1540, 1230, 1050, 1025.

REFERENCE EXAMPLE 128C

The 3-amino compound (prepared from 0.8 g of methyl cis-3-benzyloxycarboxamido-2-oxoazetidine-4-carboxylate in the same manner as Reference Example 3C) is dissolved in 20 ml of tetrahydrofuran, followed by a serial addition of 0.42 ml of triethylamine and 0.56 g of 3-triethylsilylpropionyl chloride under ice-cooling and stirring. The mixture is stirred at room temperature for 3 hours and the tetrahydrofuran is distilled off. To the residue are added water and ethyl acetate. After phase separation, the organic layer is washed with water and saturated aqueous sodium chloride, dried over anhydrous sodium sulfate and concentrated under reduced pressure. The residue is crystallized from chloroform-ether and recovered by filtration to give methyl cis-3-(2-triethylsilylethylcarboxamido)-2-oxoazetidine-4-carboxylate, m.p. 143°-145° C.

IR $\nu_{max}^{KBr}$cm$^{-1}$: 3260, 1790, 1750, 1640, 1540.

| Elemental analysis: $C_{14}H_{26}N_2O_4Si$ | | | |
|---|---|---|---|
| | C (%) | H (%) | N (%) |
| Calc. | 53.47 | 8.33 | 8.91 |
| Found | 53.54 | 8.40 | 8.73 |

REFERENCE EXAMPLE 129C

In 100 ml of methylene chloride is dissolved 5.01 g of 2,4-dimethoxybenzylamine, followed by addition of 4.2 g of trans-cinnamaldehyde and 30 g of anhydrous magnesium sulfate. The mixture is stirred at room temperature for 3.5 hours and filtered. To the filtrate, under ice-cooling and stirring, is added 8.4 ml of triethylamine, followed by dropwise addition of a solution of 7.0 g of phthalimidoacetyl chloride in 50 ml of methylene chloride over 30 minutes. The mixture is stirred at room temperature for 2.5 hours, washed with water, dried over anhydrous sodium sulfate and concentrated under reduced pressure. To the concentrate is added 50 ml of chloroform and the precipitate is filtered off. The filtrate is concentrated and the residue is passed through a silica gel column (30 g). The eluate is concentrated and the solid residue is recrystallized from ethyl acetate to give cis-3-phthalimido-4-(E)-styryl-1-(2,4-dimethoxybenzyl)-2-oxoazetidine, m.p. 173°-177° C.

IR $\nu_{max}^{KBr}$cm$^{-1}$: 1750, 1720, 1390.

| Elemental analysis: $C_{28}H_{24}N_2O_5$ | | | |
|---|---|---|---|
| | C (%) | H (%) | N (%) |
| Calc. | 71.78 | 5.16 | 5.98 |

| Elemental analysis: C28H24N2O5 | | | |
|---|---|---|---|
| | C (%) | H (%) | N (%) |
| Found | 72.14 | 5.01 | 5.85 |

REFERENCE EXAMPLE 130C

In 150 ml of tetrahydrofuran is dissolved 5 g of cis-3-phthalimido-4-(E)-styryl-1-(2,4-dimethoxybenzyl)-2-oxoazetidine, followed by addition of 2.5 g of 10% palladium-on-carbon. The mixture is stirred in a hydrogen atmosphere for 30 minutes. The catalyst is filtered off and the filtrate is concentrated under reduced pressure. The residue is crystallized from ether and recovered by filtration to give 4.8 g of cis-3-phthalimido-4-(2-phenylethyl)-1-(2,4-dimethoxybenzyl)-2-oxoazetidine, m.p. 148°–150° C.

IR $\nu_{max}^{KBr}$cm$^{-1}$: 1750, 1720, 1390.

| Elemental analysis: C28H26N2O5 | | | |
|---|---|---|---|
| | C (%) | H (%) | N (%) |
| Calc. | 71.47 | 5.57 | 5.96 |
| Found | 71.55 | 5.45 | 5.75 |

REFERENCE EXAMPLE 131C

In 35 ml of dimethoxyethane is suspended 4.1 g of cis-3-phthalimido-4-(2-phenylethyl)-1-(2,4-dimethoxybenzyl)-2-oxoazetidine, followed by addition of 1.4 ml of methylhydrazine. The mixture is allowed to stand at room temperature for 3 days. The resulting precipitate is filtered off and the filtrate is concentrated. The residue is dissolved in ethyl acetate and extracted three times with dilute hydrochloric acid. The extract is adjusted to pH 7–8 with sodium hydrogen carbonate and extracted three times with chloroform. This extract is washed with saturated aqueous sodium chloride, dried over anhydrous sodium sulfate and concentrated under reduced pressure. The residue is dissolved in 50 ml of methylene chloride, followed by addition of 20 ml of propylene oxide and dropwise addition of 3 ml of carbobenzoxy chloride. The mixture is stirred at room temperature for 2 hours and concentrated under reduced pressure. The residue is subjected to silica-gel column-chromatography, elution being carried out with chloroform-ethyl acetate (1:1). The solvent is then distilled off and the residue is crystallized from ether and recovered by filtration to give cis-3-benzyloxycarboxamido-4-(2-phenylethyl)-1-(2,4-dimethoxybenzyl)-2-oxoazetidine, m.p. 150°–152° C.

IR $\nu_{max}^{KBr}$cm$^{-1}$: 3300, 1760, 1680, 1535, 1265.

| Elemental analysis: C28H30N2O5 | | | |
|---|---|---|---|
| | C (%) | H (%) | N (%) |
| Calc. | 70.86 | 6.37 | 5.90 |
| Found | 70.68 | 6.44 | 6.09 |

REFERENCE EXAMPLE 132C

In the same manner as Reference Example 2C, there was synthesized cis-3-benzyloxycarboxamido-4-(2-phenylethyl)-2-oxoazetidine, m.p. 173°–175° C.

IR $\nu_{max}^{KBr}$cm$^{-1}$: 3300, 1770, 1685, 1540, 1260.

| Elemental analysis: C19H20N2O3 | | | |
|---|---|---|---|
| | C (%) | H (%) | N (%) |
| Calc. | 70.35 | 6.22 | 8.64 |
| Found | 70.13 | 6.05 | 8.48 |

REFERENCE EXAMPLE 133C

In the same manner as Reference Example 67C, there was synthesized cis-3-[2-(2-chloroacetamido-4-thiazolyl)-2-methoxyiminoacetamido]-4-(2-phenylethyl)-2-oxoazetidine (syn isomer).

IR $\nu_{max}^{KBr}$cm$^{-1}$: 3260, 1740, 1700, 1650, 1540.

REFERENCE EXAMPLE 134C

In 40 ml of chloroform is dissolved 9.6 g of methyl 2-methoxyiminoacetoacetate, and a solution of 9.1 g of bromine in 10 ml of chloroform is added dropwise under stirring at 40° C. The mixture is stirred for 20 minutes and poured into an ice-water. The organic layer is taken, washed with saturated aqueous sodium hydrogen carbonate and water in this order and dried over anhydrous sodium sulfate. The solvent is then distilled off under reduced pressure to give 13.12 g of methyl 4-bromo-2-methoxyimino acetoacetate as an oil. To 40 ml of ethanol are added 10.74 g of this oil and 4.4 g of methyl thiocarbamate, and the mixture is heated under reflux for 1.5 hours. The ethanol is then distilled off and the residue is dissolved in chloroform, washed with water and dried over anhydrous sodium sulfate. The solvent is then distilled off under reduced pressure to give crystals of methyl 2-(2-hydroxy-4-thiazolyl)-(Z)-2-methoxyiminoacetate, m.p. 97°–98° C.

IR $\nu_{max}^{KBr}$cm$^{-1}$: 1720, 1670, 1440, 1260, 1150, 1040.
NMR(CDCl3, ppm): 3.93, 4.03(2×3H, 2×s, COOCH3, NOCH3), 6.35(1H, s, 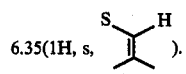 ).

REFERENCE EXAMPLE 135C

In 3 ml of ethanol is dissolved 1.0 g of methyl 2-(2-hydroxy-4-thiazolyl)-(Z)-2-methoxyimionacetate, and under ice-cooling 5 ml of an aqueous solution of potassium hydroxide (1.3 g) is added dropwise. The mixture is allowed to stand for 4 hours, adjusted to pH 2–3 with 1N hydrochloric acid, and extracted three times with n-butanol. The extracts are combined, dried over anhydrous sodium sulfate and concentrated under reduced pressure. The procedure gives a light-brown powder of 2-(2-hydroxy-4-thiazolyl)-(Z)-2-methoxyiminoacetic acid, m.p. 143°–144° C. (decomp.).

IR $\nu_{max}^{KBr}$cm$^{-1}$: 1740, 1690, 1620, 1450, 1170, 1040.
NMR(d6-DMSO, ppm): 4.02(3H, s, NOCH3), 6.79(1H, s, 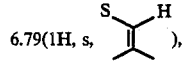 ), 11.76(1H, s, COOH).

REFERENCE EXAMPLE 136C

In the same manner as Reference Example 34C, there was synthesized cis-3-[2-(2-hydroxy-4-thiazolyl)-2- methoxyiminoacetamido]-4-methoxycarbonyl-2-oxoazetidine (syn-isomer), m.p. 202°–204° C. (decomp.).

IR $\nu_{max}^{KBr}$cm$^{-1}$: 3260, 1775, 1735, 1685, 1660, 1520, 1440, 1220, 1040.

NMR(d$_6$-DMSO, ppm): 3.50(3H, s, COOCH$_3$), 3.86(3H, s, NOCH$_3$), 4.33(1H, d, J=5 Hz, C$_4$—H), 5.25(1H, d.d, J=5,8 Hz),

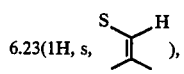
6.23(1H, s, 8.53(1H, br.s, N$_1$—H), 9.33(1H, d, J=8 Hz, C$_3$—NH).

REFERENCE EXAMPLE 137C

In 150 ml of methanol is dissolved 2.14 g of methyl cis-3-benzyloxycarboxamido-1-(2,4-dimethoxybenzyl)-2-oxoazetidine-4-carboxylate as obtained in Reference Example 1C, and under ice-cooling and stirring 25 ml of an aqueous solution of potassium carbonate (0.83 g) is added. The mixture is stirred at room temperature for 6.5 hours and the methanol is distilled off under reduced pressure. To the residue, water is added and the mixture is washed with ethyl acetate-ether and acidified with 1N hydrochloric acid. The resulting precipitate is collected by filtration, washed with water and dried to give 1.95 g of cis-3-benzyloxycarboxamido-1-(2,4-dimethoxybenzyl)-2-oxoazetidine-4-carboxylic acid, m.p. 189°–191° C.

IR $\nu_{max}^{Nujol}$cm$^{-1}$: 3300, 1760, 1705, 1690.

REFERENCE EXAMPLE 138C

In 80 ml of dry tetrahydrofuran is dissolved 4.1 g of cis-3-benzyloxycarboxamido-1-(2,4-dimethoxybenzyl)-2-oxoazetidine-4-carboxylic acid, followed by addition of 4 ml of oxalyl chloride. The mixture is heated under reflux for 30 minutes and the solvent is distilled off. The residue is washed with hexane and dissolved in 80 ml of methylene chloride. Under ice-water cooling 4 ml of ethanol is added and the mixture is stirred for 20 minutes. The solvent is then distilled off. The residue is crystallized from ether and filtered to give colorless crystals of ethyl cis-3-benzyloxycarboxamido-1-(2,4-dimethoxybenzyl)-2-oxoazetidine-4-carboxylate, which, on recrystallization from ethanol, melts at 117°–118° C.

IR $\nu_{max}^{KBr}$cm$^{-1}$: 3250, 1770, 1735, 1680.

| Elemental analysis: C$_{23}$H$_{26}$N$_2$O$_7$ | | | |
|---|---|---|---|
| | C(%) | H(%) | N(%) |
| Calc. | 62.43 | 5.92 | 6.33 |
| Found | 62.43 | 5.91 | 6.05 |

REFERENCE EXAMPLE 139C

In the same manner as Reference Example 2C, there was synthesized ethyl cis-3-benzyloxycarboxamido-2-oxoazetidine-4-carboxylate, m.p. 134°–135° C.

IR $\nu_{max}^{Nujol}$cm$^{-1}$: 3300, 1800, 1740, 1720.

| Elemental anlaysis: C$_{14}$H$_{16}$N$_2$O$_5$ | | | |
|---|---|---|---|
| | C(%) | H(%) | N(%) |
| Calc. | 57.52 | 5.51 | 9.58 |
| Found | 57.58 | 5.44 | 9.60 |

REFERENCE EXAMPLE 140C

In the same manner as Reference Example 3C, there was synthesized ethyl cis-3-amino-2-oxoazetidine-4-carboxylate, m.p. 105°–106° C. (decomp.).

IR $\nu_{max}^{Nujol}$cm$^{-1}$: 3400, 3200, 1745, 1720, 1700.

| Elemental analysis: C$_6$H$_{10}$N$_2$O$_3$ | | | |
|---|---|---|---|
| | C(%) | H(%) | N(%) |
| Calc. | 45.56 | 6.37 | 17.71 |
| Found | 45.66 | 6.20 | 17.70 |

REFERENCE EXAMPLE 141C

In the same manner as Reference Example 4C, there were synthesized the following compounds:

Ethyl cis-3-[2-(2-chloroacetamido-4-thiazolyl)-2-methoxyiminoacetamido]-2-oxoazetidine-4-carboxylate.

Syn-isomer, m.p. 280°–283° C. (decomp.).
IR $\nu_{max}^{Nujol}$cm$^{-1}$: 3230, 1750, 1730, 1670.
NMR(d$_6$-DMSO, ppm): 1.20(3H, t, J=7 Hz, CH$_2$CH$_3$), 5.73 (1H, d.d, J=5,9 Hz, C$_3$—H),

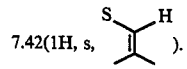
7.42(1H, s,

Anti-isomer, m.p. 108°–110° C.
IR $\nu_{max}^{Nujol}$cm$^{-1}$: 3250, 1760, 1720, 1650.
NMR(d$_6$-DMSO, ppm): 1.20(3H, t, J=7 Hz, CH$_2$CH$_3$), 5.50(1H, d.d, J=5,9 Hz, C$_3$—H),

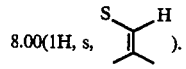
8.00(1H, s,

REFERENCE EXAMPLE 142C

In 60 ml of dry tetrahydrofuran is dissolved 2 g of cis-3-benzyloxycarboxamido-1-(2,4-dimethoxybenzyl)-2-oxoazetidine-4-carboxylic acid as obtained in Reference Example 137C followed by addition of 2 ml of oxalyl chloride. The mixture is heated under reflux for 30 minutes. The solvent is then distilled off, and the residue is washed with hexane and dissolved in 40 ml of dry tetrahydrofuran. After addition of aniline (1 ml) under ice-water cooling, the mixture is stirred for 30 minutes. The resultant crystalline precipitate is recovered by filtration and washed with ether and methanol in this order to give cis-3-benzyloxycarboxamido-1-(2,4-dimethoxybenzyl)-4-phenylcarbamoyl-2-oxoazetidine, which, on recrystallization from chloroform-methanol, melts at 255°–257° C.

IR $\nu_{max}^{Nujol}$cm$^{-1}$: 3250, 1760, 1690, 1670.

| Elemental analysis: C$_{27}$H$_{27}$N$_3$O$_6$ | | | |
|---|---|---|---|
| | C(%) | H(%) | N(%) |
| Calc. | 66.24 | 5.55 | 8.58 |
| Found | 65.80 | 5.34 | 8.43 |

REFERENCE EXAMPLE 143C

In the same manner as Reference Example 2C, there was synthesized cis-3-benzyloxycarboxamido-4-phenylcarbamoyl-2-oxoazetidine, m.p. 235°–238° C. (decomp.).

IR $\nu_{max}^{KBr}$cm$^{-1}$: 3270, 1760, 1690, 1670.

NMR(d$_6$-DMSO, ppm): 4.4(1H, d, J=5 Hz, C$_4$—H), 5.0(2H, s, PhCH$_2$), 5.15(1H, d.d, J=5,9 Hz, C$_3$—H).

REFERENCE EXAMPLE 144C

In the same manner as Reference Example 3C, there was synthesized cis-3-amino-4-phenylcarbamoyl-2-oxoazetidine, m.p. 152°–154° C. (decomp.).

IR $\nu_{max}^{Nujol}$cm$^{-1}$: 3300, 1740, 1690.

REFERENCE EXAMPLE 145C

In the same manner as Reference Example 4C, there was synthesized cis-3-[2-(2-chloroacetamido-4-thiazolyl)-2-methoxyiminoacetamido]-4-phenylcarbamoyl-2-oxoazetidine (syn-isomer).

NMR(d$_6$-DMSO, ppm): 3.53(3H, s, NOCH$_3$), 4.3(2H, s, ClCH$_2$), 4.48(1H, d, J=5 Hz, C$_4$—H), 5.57(1H, d.d, J=5,9 Hz, C$_3$—H).

REFERENCE EXAMPLE 146C

In 160 ml of methanol is dissolved 2.502 g of methyl cis-3-benzyloxycarboxamido-2-oxoazetidine-4-carboxylate as obtained in Reference Example 2C, and under ice-cooling and stirring 50 ml of an aqueous solution of potassium carbonate (1.242 g) is added. The mixture is stirred at room temperature for 70 minutes, followed by addition of 9 ml of 1N hydrochloric acid under ice-cooling and stirring. The methanol is then distilled off under reduced pressure and the residual aqueous solution is washed with ethyl acetate and concentrated further under reduced pressure. The residue is chromatographed on an Amberlite XAD-II column and lyophilized to give a colorless powder of potassium cis-3-benzyloxycarboxamido-2-oxoazetidine-4-carboxylate.

IR $\nu_{max}^{KBr}$cm$^{-1}$: 1770, 1755, 1705, 1675, 1590, 1410, 1320.

NMR(d$_6$-DMSO, ppm): 3.82(1H, d, J=5 Hz, C$_4$—H), 4.78(1H, d.d, J=5,9 Hz, C$_3$—H), 5.01(2H, s, CH$_2$), 7.29 (5H, s, Ph-), 7.31(1H, d, J=9 Hz, C$_3$—NH), 8.26 (1H, br.s, N$_1$—H).

REFERENCE EXAMPLE 147C

In 5 ml of N,N-dimethylformamide is dissolved 717 mg of potassium cis-3-benzyloxycarboxamido-2-oxoazetidine-4-carboxylate, and under ice-cooling and stirring 0.25 ml of ethyl bromoacetate is added. The mixture is stirred at room temperature for one hour, followed by addition of 50 ml of water, and extracted with ethyl acetate. The extract is washed with aqueous sodium chloride and dried over anhydrous magnesium sulfate. The solvent is distilled off under reduced pressure and after addition of ether the solid residue is collected by filtration to give colorless crystals of cis-3-benzyloxycarboxamido-4-ethoxycarbonylmethyloxycarbonyl-2-oxoazetidine, m.p. 109°–111° C.

IR $\nu_{max}^{KBr}$cm$^{-1}$: 3350, 3260, 1775, 1765, 1750, 1710, 1675.

| Elemental analysis: $C_{16}H_{18}N_2O_7$ | | | |
|---|---|---|---|
| | C(%) | H(%) | N(%) |
| Calc. | 54.86 | 5.18 | 8.00 |
| Found | 54.90 | 5.24 | 7.79 |

REFERENCE EXAMPLE 148C

In the same manner as Reference Example 67C, there was synthesized cis-3-[2-(2-chloroacetamido-4-thiazolyl)-2-methoxyiminoacetamido]-4-ethoxycarbonylmethyloxycarbonyl-2-oxoazetidine (syn-isomer), m.p. 226°–231° C. (decomp.).

IR $\nu_{max}^{KBr}$cm$^{-1}$: 3270, 1765, 1750, 1690, 1670.

| Elemental analysis: $C_{16}H_{18}ClN_5O_8S$ | | | |
|---|---|---|---|
| | C(%) | H(%) | N(%) |
| Calc. | 40.38 | 3.81 | 14.72 |
| Found | 40.08 | 3.97 | 14.51 |

REFERENCE EXAMPLE 149C

Ether is added to methyl trans-3-benzyloxycarboxamido-1-(2,4-dimethoxybenzyl)-2-oxoazetidine-4-carboxylate as obtained in Reference Example 26C and the mixture is allowed to cool. On standing, crystals separate gradually out. The crystals are collected by filtration and washed with ether to give colorless crystals, m.p. 65°–68° C.

| Elemental analysis: $C_{22}H_{24}N_2O_7$ | | | |
|---|---|---|---|
| | C(%) | H(%) | N(%) |
| Calc. | 61.67 | 5.65 | 6.54 |
| Found | 61.84 | 5.48 | 6.36 |

The above product is reduced with sodium borohydride in the same manner as Reference Example 5C and then purified by silica-gel column-chromatography [eluent:hexane-ethyl acetate (1:4)] to give a colorless oil of trans-3-benzyloxycarboxamido-1-(2,4-dimethoxybenzyl)-4-hydroxymethyl-2-oxoazetidine.

IR $\nu_{max}^{Neat}$cm$^{-1}$: 3400, 3325, 1740 (br.), 1030

REFERENCE EXAMPLE 150C

In 50 ml of methylene chloride is dissolved 5.8 g of trans-3-benzyloxycarboxamido-1-(2,4-dimethoxybenzyl)-4-hydroxymethyl-2-oxoazetidine, and under ice-cooling and stirring 2.29 g of pyridine and then 1.54 ml of acetyl chloride are added. The mixture is stirred at room temperature for one hour and the solvent is distilled off under reduced pressure. The residue is dissolved in ethyl acetate, washed with 3N hydrochloric acid, aqueous sodium hydrogen carbonate and aqueous sodium chloride in this order, dried over anhydrous magnesium sulfate and concentrated under reduced pressure. The residue is dissolved in 300 ml of acetonitrile, and under reflux with heating an aqueous solution containing 5.87 g of potassium persulfate and 3.78 g of dipotassium hydrogen phosphate is added dropwise. After completion of dropwise addition, the mixture is further heated under reflux for one hour. The acetonitrile is distilled off under reduced pressure and the residual aqueous solution is extracted with ethyl acetate. The extract is washed with saturated aqueous sodium hydrogen carbonate and aqueous sodium chloride in this order, dried over anhydrous magnesium sulfate, and concentrated under reduced pressure. The residue is purified by column chromatography [silica gel: 140 g, eluent:hexane-ethyl acetate (1:2)] to give trans-3-benzyloxycarboxamido-4-acetoxymethyl-2-oxoazetidine, m.p. 119°–121° C.

IR $\nu_{max}^{KBr}$cm$^{-1}$: 3245, 1750, 1725, 1705, 1550, 1270, 1250, 1035.

REFERENCE EXAMPLE 151C

In the same manner as Reference Example 67C, there was synthesized trans-3-[2-(2-chloroacetamido-4-thiazolyl)-2-methoxyiminoacetamido]-4-acetoxymethyl-2-oxoazetidine (syn isomer), m.p. 177°–190° C. (decomp.).

IR $\nu_{max}^{KBr}$cm$^{-1}$: 3180, 1760, 1735, 1710, 1640, 1565, 1040.

REFERENCE EXAMPLE 152C

In 50 ml of pyridine is dissolved 18.3 g of trans-3-benzyloxycarboxamido-1-(2,4-dimethoxybenzyl)-4-hydroxymethyl-2-oxoazetidine, and under ice-cooling 5.76 g of methanesulfonyl chloride is added. The mixture is stirred at room temperature for one hour. The reaction mixture is added to ethyl acetate and the mixture is washed with 6N hydrochloric acid, aqueous sodium hydrogen carbonate and aqueous sodium chloride in this order, dried over anhydrous magnesium sulfate and concentrated under reduced pressure. The residue is dissolved in 400 ml of methyl ethyl ketone, followed by addition of 34.25 g of sodium iodide. The mixture is heated under reflux for 2.5 hours and concentrated under reduced pressure. The residue is dissolved in ethyl acetate and the solution is washed with saturated aqueous sodium bisulfite and aqueous sodium chloride in this order, dried over anhydrous magnesium sulfate and concentrated under reduced pressure. The procedure gives an oil of trans-3-benzyloxycarboxamido-4-iodomethyl-1-(2,4-dimethoxybenzyl)-2-oxoazetidine.

IR $\nu_{max}^{neat}$cm$^{-1}$: 3300, 1760, 1710, 1605, 1510, 1285, 1260, 1210.

NMR(CDCl$_3$, ppm): 3.78(6H, s, 2×OCH$_3$), 5.00(2H, s, Ph—CH$_2$), 7.28(5H, s, Ph-).

REFERENCE EXAMPLE 153C

In the same manner as Reference Example 63C, there was synthesized trans-3-benzyloxycarboxamido-1-(2,4-dimethoxybenzyl)-4-methyl-2-oxoazetidine. This compound does not crystallize. Therefore, it is purified by column chromatography, [silica gel: 350 g; eluent:hexane-ethyl acetate (2:1 then 1:2)].

IR $\nu_{max}^{neat}$cm$^{-1}$: 3280, 2950, 1750, 1710, 1605, 1505, 1260, 1210.

NMR(CDCl$_3$, ppm): 1.20(3H, d, J=6 Hz, C$_4$—CH$_3$), 3.75(6H, s, 2×OCH$_3$), 5.02(2H, s, Ph—CH$_2$), 5.55(1H, d.d, J=6,8 Hz, C$_3$—H), 7.21(5H, s, Ph-).

REFERENCE EXAMPLE 154C

In the same manner as Reference Example 66C, there was synthesized trans-3-benzyloxycarboxamido-4-methyl-2-oxoazetidine, m.p. 109°–111° C.

IR $\nu_{max}^{KBr}$cm$^{-1}$: 3320, 3220, 1780, 1690, 1535, 1450, 1265, 1045, 730.

REFERENCE EXAMPLE 155C

In the same manner as Reference Example 67C, there was synthesized trans-3-[2-(2-chloroacetamido-4-thiazolyl)-2-methoxyiminoacetamido]-4-methyl-2-oxoazetidine (syn-isomer), m.p. 240°–248° C. (decomp.).

IR $\nu_{max}^{KBr}$cm$^{-1}$: 3330, 1740, 1680, 1665, 1575, 1540, 1355, 1045.

REFERENCE EXAMPLE 156C

In 1.4 ml of dry tetrahydrofuran is dissolved 140 mg of cis-3-benzyloxycarboxamido-4-methoxycarbonyl-2-oxoazetidine, followed by addition of 0.1 ml of 40% methylamine solution and one drop of acetic acid. The mixture is allowed to stand in the cold (5° C.) for four hours and the resultant crystalline precipitate is recovered by filtration and washed with ether to give cis-3-benzyloxycarboxamido-4-methylcarbamoyl-2-oxoazetidine, which, on recrystallization from ethyl acetate-methanol, melts at 207°–208° C.

IR $\nu_{max}^{Nujol}$cm$^{-1}$: 3270, 1770, 1700, 1660.

NMR(d$_6$-DMSO, ppm): 2.56(3H, d, J=5 Hz, NHCH$_3$), 4.13(1H, d, J=5 Hz, C$_4$—H), 7.33(5H, s, Ph-), 8.33(1H, d, J=5 Hz, NHCH$_3$).

| Elemental analysis: C$_{13}$H$_{15}$N$_3$O$_4$ | | |
|---|---|---|
| | C(%) | H(%) | N(%) |
| Calc. | 56.30 | 5.45 | 15.15 |
| Found | 56.17 | 5.31 | 15.23 |

REFERENCE EXAMPLE 157C

In a mixture of 50 ml of tetrahydrofuran and 50 ml of methanol is dissolved 831 mg of cis-3-benzyloxycarboxamido-4-methylcarbamoyl-2-oxoazetidine, followed by addition of 830 mg of 5% palladium-on-carbon. The mixture is stirred in a hydrogen atmosphere for one hour. The catalyst is then filtered off and the filtrate is concentrated under reduced pressure to give 410 mg of cis-3-amino-4-methylcarbamoyl-2-oxoazetidine as a colorless powder.

IR $\nu_{max}^{Nujol}$cm$^{-1}$: 3300, 1750, 1650.

NMR(d$_6$-DMSO, ppm): 2.70(3H, d, J=5 Hz, NHCH$_3$), 3.96, 4.23(2×1H, 2×d, J=5 Hz, C$_3$—H, C$_4$—H).

This product (320 mg) is dissolved in a mixture of 6 ml of water and 6 ml of tetrahydrofuran, followed by addition of 500 mg of sodium hydrogen carbonate. Under ice-cooling and stirring, 960 mg of 2-(2-chloroacetamido-4-thiazolyl)-2-(Z)-methoxyiminoacetyl chloride hydrochloride is added and the mixture is stirred for one hour. The tetrahydrofuran is distilled off and the residual mixture is filtered. The resultant powder is washed with aqueous sodium hydrogen carbonate, water, ethanol and ether in this order to give cis-3-[2-(2-chloroacetamido-4-thiazolyl)-2-methoxyiminoacetamido]-4-methylcarbamoyl-2-oxoazetidine (syn-isomer).

IR $\nu_{max}^{Nujol}$cm$^{-1}$: 3220, 1750, 1700, 1660.

NMR(d$_6$-DMSO, ppm): 2.50(3H, d, J=5 Hz, NHCH$_3$), 3.76(3H, s, NOCH$_3$), 5.3(1H, d.d, J=5,9 Hz, C$_3$—H), 7.28(1H, s, 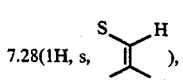 ), 7.8(1H, d, J=5 Hz, NHCH$_3$), 8.3 (1H, br.s, N$_1$—H).

REFERENCE EXAMPLE 158C

The procedure of Reference Example 91C is repeated except that methyl trans-3-benzyloxycarboxamido-2-oxoazetidine-4-carboxylate is used in lieu of the corresponding ciscompound, whereby trans-3-{2-(2-chloroacetamido-4-thiazolyl)-2-[1-methyl-1-(p- nitrobenzyloxycarbonyl)ethyloxyimino]acetamido}-4-methoxycarbonyl-2-oxoazetidine (syn-isomer) is obtained as crystals, m.p. 110°-120° C. (decomp.).

IR $\nu_{max}^{KBr}$ cm$^{-1}$: 3280, 2980, 1790-1740, 1680, 1525.

| Elemental analysis: $C_{23}H_{23}ClN_6O_{10}S$ | | | |
|---|---|---|---|
| | C(%) | H(%) | N(%) |
| Calc. | 45.21 | 3.79 | 13.76 |
| Found | 45.60 | 4.14 | 13.14 |

REFERENCE EXAMPLE 159C

In the same manner as Reference Example 81C, there were synthesized the following compounds:

N-(1-Methoxycarbonyl-1-methylethoxy)phthalimide m.p. 106°-107° C.

IR $\nu_{max}^{KBr}$ cm$^{-1}$: 2990, 2960, 1790, 1740.

| Elemental analysis: $C_{13}H_{13}NO_5$ | | | |
|---|---|---|---|
| | C(%) | H(%) | N(%) |
| Calc. | 59.31 | 4.98 | 5.32 |
| Found | 59.60 | 4.98 | 5.22 |

N-[1-Methyl-1-(2-trimethylsilylethoxycarbonyl)ethoxy]phthalimide.

IR $\nu_{max}^{neat}$ cm$^{-1}$: 2940, 1790, 1735.

NMR(CDCl$_3$, ppm): 0.10(9H, s, SiMe$_3$), 0.92(2H, t, J=9 Hz, CH$_2$Si), 1.62(6H, s, NOCMe$_2$), 4.31(2H, t, J=9 Hz, COOCH$_2$), 7.73(4H, s, aromatic protons).

REFERENCE EXAMPLE 160C

In the same manner as Reference Example 82C, there were synthesized the following compounds:

O-(1-Methoxycarbonyl-1-methylethyl)hydroxylamine.

IR $\nu_{max}^{neat}$ cm$^{-1}$: 3325, 2980, 2950, 1735.

NMR(CDCl$_3$, ppm): 1.43(6H, s, CMe$_2$), 3.75(3H, s, COOCH$_3$), 5.33(2H, br.s, NH$_2$).

O-[1-Methyl-1-(2-trimethylsilylethoxycarbonyl)ethyl]-hydroxylamine.

IR $\nu_{max}^{neat}$ cm$^{-1}$: 3320, 2950, 1730.

NMR(CDCl$_3$, ppm): 0.10(9H, s, SiMe$_3$), 1.12(2H, t, CH$_2$Si), 1.45(6H, s, NOCMe$_2$), 4.25(2H, t, J=9 Hz, COOCH$_2$), 5.12-5.43(2H, br., NH$_2$).

REFERENCE EXAMPLE 161C

In the same manner as Reference Example 83C, there were synthesized the following compounds:

2-(2-Chloroacetamido-4-thiazolyl)-2-(1-methoxycarbonyl-1-methylethoxyimino)acetic acid.

IR $\nu_{max}^{KBr}$ cm$^{-1}$: 3200, 2980, 1750-1680.

NMR(CDCl$_3$, ppm): 1.58(6H, s, CMe$_2$), 3.72(3H, s, COOCH$_3$), 4.3(2H, s, ClCH$_2$), 7.33(1H, s, thiazol-5-H).

2-(2-Chloroacetamido-4-thiaozlyl)-2-[1-methyl-1-(2-trimethylsilylethoxycarbonyl)ethoxyimino]acetic acid.

IR $\nu_{max}^{KBr}$ cm$^{-1}$: 3420, 3200, 2960, 1740, 1730

REFERENCE EXAMPLE 162C

In the same manner as Reference Example 84C, there was synthesized 2-(2-chloroacetamido-4-thiazolyl)-2-(1-methoxycarbonyl-1-methylethoxyimino)acetyl chloride hydrochloride, m.p. 105°-115° C.

IR $\nu_{max}^{KBr}$ cm$^{-1}$: 2980, 1790, 1745, 1700.

| Elemental analysis: $C_{12}H_{13}Cl_2N_3O_5S \cdot HCl$ | | | |
|---|---|---|---|
| | C(%) | H(%) | N(%) |
| Calc. | 34.42 | 3.37 | 10.03 |
| Found | 34.94 | 3.46 | 10.21 |

REFERENCE EXAMPLE 163C

In the same manner as Reference Example 85C, there was synthesized cis-3-[2-(2-chloroacetamido-4-thiazolyl)-2-(1-methoxycarbonyl-1-methylethoxyimino)acetamido]-4-methoxycarbonyl-2-oxoazetidine (syn-isomer), m.p. 212°-214° C. (decomp.).

IR $\nu_{max}^{KBr}$ cm$^{-1}$: 3300, 3080, 2975, 1780-1750, 1720, 1660.

| Elemental analysis: $C_{17}H_{20}ClN_5O_8S$ | | | |
|---|---|---|---|
| | C(%) | H(%) | N(%) |
| Calc. | 41.68 | 4.12 | 14.30 |
| Found | 41.47 | 4.14 | 14.06 |

REFERENCE EXAMPLE 164C

In 25 ml of methylene chloride is dissolved 820 mg of 2-(2-chloroacetamido-4-thiazolyl)-2-[1-methyl-1-(2-trimethylsilylethoxycarbonyl)]ethoxyiminoacetic acid, and under ice-cooling 221 mg of triethylamine and then 380 mg of phosphorus pentachloride are added. The mixture is stirred under ice-cooling for 15 minutes and then at room temperature for 2 hours. The reaction mixture is concentrated under reduced pressure and the residue is dissolved in 5 ml of tetrahydrofuran to prepare a solution containing the acid chloride. On the other hand, 219 mg of cis-3-amino-4-methoxycarbonyl-2-oxoazetidine is dissolved in a mixture of 5 ml of tetrahydrofuran and 10 ml of water, followed by addition of 638 mg of sodium hydrogen carbonate under ice-cooling. To this solution is added dropwise the above acid chloride solution under stirring. The mixture is stirred under ice-cooling for 15 minutes and then at room temperature for one hour and extracted with ethyl acetate. The extract is dried over anhydrous magnesium sulfate and the solvent is distilled off to give cis-3-{2-(2-chloroacetamido-4-thiazolyl)-2-[1-methyl-1-(2-trimethylsilylethoxycarbonyl)ethoxyimino]acetamido}-4-methoxycarbonyl-2-oxoazetidine (syn-isomer).

IR $\nu_{max}^{KBr}$ cm$^{-1}$: 3280, 2950, 1760, 1730, 1685.

NMR(CDCl$_3$+d$_6$-DMSO, ppm): 1.18(2H, CH$_2$Si), 1.81(6H, NOCMe$_2$), 4.40(2H, COOCH$_2$), 4.44(2H, s, ClCH$_2$), 4.67(1H, d, J=6 Hz, C$_4$—H), 5.88(1H, d.d, J=6, 9 Hz, C$_3$H), 7.57(1H, s, 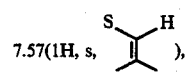 ), 8.03 (1H, br.s, N$_1$—H), 8.29(1H, d, J=9 Hz, C$_3$—NH).

REFERENCE EXAMPLE 165C

In 20 ml of tetrahydrofuran is dissolved 1.5 g of methyl cis-3-benzyloxycarboxamido-2-oxoazetidine-4-carboxylate as obtained in Reference Example 2C, followed by addition of 10 ml of 1M aqueous ammonium chloirde. Under stirring at room temperature, 0.5 ml of aqueous ammonia (25–28%) is added and the mixture is stirred for 3 hours, after which 2 ml of aqueous ammonia is further added. The mixture is stirred for 16 hours. The tetrahydrofuran is distilled off under reduced pressure and the resultant crystalline precipitate is collected by filtration, washed with water and ether in this order, and dried to give cis-3-benzyloxycarboxamido-4-carbamoyl-2-oxoazetidine, m.p. 236°–237° C. (decomp.).

IR $\nu_{max}^{KBr}$ cm$^{-1}$: 3400, 3300, 3200, 1760, 1670.

NMR(d$_6$-DMSO, ppm): 4.14(1H, d, J=6 Hz, C$_4$—H), 5.05(2H, s, PhCH$_2$), 5.08(1H, d.d, J=6, 10 Hz, C$_3$—H), 7.36 (5H, s, aromatic protons).

| Elemental analysis: C$_{12}$H$_{13}$N$_3$O$_4$ | | | |
|---|---|---|---|
| | C(%) | H(%) | N(%) |
| Calc. | 54.75 | 4.98 | 15.96 |
| Found | 54.93 | 4.90 | 15.65 |

In the same manner as above, there is obtained the corresponding trans-compound.

REFERENCE EXAMPLE 166C

In 15 ml of ethanol is suspended 304 mg of cis-3-benzyloxycarboxamido-4-carbamoyl-2-oxoazetidine, followed by addition of 304 mg of 5% palladium-on-carbon. The mixture is stirred in a hydrogen atmosphere at room temperature for 1.5 hours. The catalyst is then filtered off and the filtrate is concentrated under reduced pressure. The residue is dissolved in a mixture of 6 ml of tetrahydfofuran and 6 ml of water, and under ice-cooling 534 mg of sodium hydrogen carbonate is added. To this solution is added 686 mg of 2-(2-chloroacetamido-4-thiazolyl)-(Z)-2-[1-methyl-1-(p-nitrobenzyloxycarbonyl)ethyloxyimino]acetyl chloride hydrochloride as obtained in Reference Example 90. The mixture is stirred under ice-cooling for 15 minutes and at room temperature for one hour. Then, 200 ml of ethyl acetate is added and extraction is carried out. The organic layer is washed twice with 0.1N aqueous sodium hydroxide and once with aqueous sodium chloride in this order, dried over anhydrous magnesium sulfate and concentrated under reduced pressure to give cis-3-{2-(2-chloroacetamido-4-thiazolyl)-2-[1-methyl-1-(p-nitrobenzyloxycarbonyl)ethyloxyimino]acetamido}-4-carbamoyl-2-oxoazetidine (syn-isomer) as a frothy product, m.p. 144°–147° C.

IR $\nu_{max}^{KBr}$ cm$^{-1}$: 3380, 1760, 1750, 1680.

NMR(d$_6$-DMSO, ppm): 1.52(6H, s, 2×CH$_3$), 4.27(1H, d, J=6 Hz, C$_4$—H), 4.34(2H, s, ClCH$_2$), 5.32(2H, s, COOCH$_2$), 5.46(1H, d.d, J=6, 9 Hz, C$_3$—H), 7.41(1H, s, 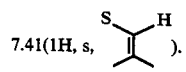 ).

In the same manner as above, there is obtained the corresponding trans-compound.

REFERENCE EXAMPLE 167C

In 80 ml of methylene chloride is dissolved 4 g of cis-3-benzyloxycarboxamido-1-(2,4-dimethoxybenzyl)-4-hydroxymethyl-2-oxoazetidine as obtained in Reference Example 5C and under ice-water cooling, 0.9 ml of chlorosulfonyl isocyanate is added, after which the mixture is stirred for 30 minutes. The same amount of chlorosulfonyl isocyanate as above is further added and the mixture is stirred for an additional 10 minutes. The reaction mixture is added to 60 ml of an aqueous solution of sodium sulfite (2.8 g) dropwise under ice-water cooling and stirring. The mixture is stirred at room temperature for one hour, whereupon crystals separates out. The crystals are dissolved by addition of methylene chloride and, then, the methylene chloride layer is taken, washed with aqueous sodium chloride and dried over anhydrous sodium sulfate. The solvent is then distilled off and ether is added to the residue. The resultant crystals are collected by filtration to give 3.3 g of cis-3-benzyloxycarboxamido-1-(2,4-dimethoxybenzyl)-4-carbamoyloxymethyl-2-oxoazetidine.

IR $\nu_{max}^{Nujol}$ cm$^{-1}$: 3400, 3300, 3200, 1760, 1690.

The above product is added to a mixture of 75 ml of acetonitrile and 37.5 ml of water, followed by addition of 6.5 g of potassium persulfate and 3.9 g of dipotassium hydrogen phosphate. The mixture is stirred in a stream of argon under heating at 95° C. for one hour. After cooling, ethyl acetate is added and the organic layer is taken, washed with aqueous sodium chloride and dried over anhydrous sodium sulfate. The solvent is then distilled off and ether is added to the residue. The insolubles are collected by filtration and purified by silica gel column chromatography [silica gel: 90 g; eluent: chloroform-methanol-ethyl acetate (85:10:5)] to give cis-3-benzyloxycarboxamido-4-carbamoyloxymethyl-2-oxoazetidine as colorless crystals, melting at 205°–207° C.

IR $\nu_{max}^{Nujol}$ cm$^{-1}$: 3430, 3300, 1760, 1700.

NMR(d$_6$-DMSO, ppm): 6.33(2H, br.s, NH$_2$), 7.30(5H, s, C$_6$H$_5$), 7.8(1H, d, J=9 Hz, C$_3$—NH), 8.16(1H, br. s, N$_1$—H).

| Elemental analysis: C$_{13}$H$_{15}$N$_3$O$_5$ | | | |
|---|---|---|---|
| | C(%) | H(%) | N(%) |
| Calcd. | 53.23 | 5.15 | 14.32 |
| Found | 53.33 | 4.90 | 14.09 |

REFERENCE EXAMPLE 168C

In a mixture of 30 ml of tetrahydrofuran and 30 ml of water is dissolved 3 g of methyl trans-3-benzyloxycarboxamido-2-oxoazetidine-4-carboxylate as obtained in Reference Example 27C and under ice-cooling, 6 ml (1M) of an aqueous solution of ammonium chloride and then 4 ml of 25–28% aqueous ammonia are added. The mixture is stirred at room temperature for 3 hours. The tetrahydrofuran is then distilled off under reduced pressure, and sodium chloride is added to the residual aqueous solution, followed by extraction twice with chloroform-ethanol (3:1). The extracts are combined, dried over anhydrous magnesium sulfate and concentrated under reduced pressure. The residue is purified by silica gel column chromatography [silica gel: 180 g; eluent: ethyl acetate and then ethyl acetate-methanol (8:1)] to give trans-3-benzyloxycarboxamido-4-carbamoyl-2-oxoazetidine, melting at 179°–184° C.

IR $\nu_{max}^{KBr}$ cm$^{-1}$: 3280, 1760, 1695, 1660.

NMR(d$_6$-DMSO, ppm): 3.90(1H, d, J=3 Hz, C$_4$-H), 4.42(1H, d.d, J=3, 9 Hz, C$_3$-H), 8.04(1H, d, J=9 Hz, C$_3$—NH).

REFERENCE EXAMPLE 169C

In 300 ml of methylene chloride is dissolved 31.0 g of freshly distilled methacrolein, followed by addition 36.9 g of 2,4-dimethoxybenzylamine. To this solution are added 100 g of anhydrous sodium sulfate and 440 mg of p-toluenesulfonic acid monohydrate, and the mixture is stirred at room temperature for 3 hours. The reaction mixture is filtered and the filtrate is concentrated under reduced pressure. The residue is dissolved in 300 ml of methylene chloride and under ice-cooling and stirring, a solution of 24.5 g of triethylamine in 100 ml of methylene chloride is added dropwise. Then a solution of 49.4 g of phthalimidoacetyl chloride in 300 ml of methylene chloride is added dropwise over a period of about one hour. The mixture is stirred at room temperature overnight. This reaction mixture is filtered and the insolubles are washed with methylene chloride. The filtrate and washings are combined and concentrated to 0.5 l under reduced pressure. The concentrate is washed with 200 ml of 1N hydrochloric acid, 200 ml of water, 300 ml of 2% aqueous sodium hydrogen carbonate (twice), and 200 ml of water, in this order and dried over anhydrous sodium sulfate. The solvent is then distilled off under reduced pressure and the residue is chromatographed on a silica gel column [silica gel: 400 g; eluent: hexane-ethyl acetate (1:1)] to give 55.8 g of cis-3-phthalimido-4-isopropenyl-1-(2,4-dimethoxybenzyl)-2-oxoazetidine as a crude product. This product is dissolved in 500 ml of methanol, followed by addition of 25 g of 5% palladium-on-carbon. The solution is stirred in a hydrogen atmosphere for 7 hours, whereby 870 cc of hydrogen is absorbed. The catalyst is filtered off and the filtrate is concentrated under reduced pressure. The residue is dissolved in ethyl acetate, washed three times with 100 ml portions of 1N hydrochloric acid and once with aqueous sodium chloride in this order and dried over anhydrous sodium sulfate. The solvent is then distilled off under reduced pressure to give 47 g of a residue. This residue is dissolved in 700 ml of ethanol, followed by addition of 47 g of 5% palladium-on-carbon. The mixture is stirred in a hydrogen atmosphere for 24 hours, whereby 1900 cc of hydrogen is absorbed. The reaction mixture is filtered and the filtrate is concentrated. The residue is purified by column chromatography [silica gel: 400 g; eluent: hexane-ethyl acetate (1:1)], and the solvent is distilled off, followed by addition of ethanol. The resultant crystalline precipitate is collected by filtration to give 8.6 g of cis-3-phthalimido-4-isopropyl-1-(2,4-dimethoxybenzyl)-2-oxoazetidine. The mother liquor is concentrated and the residue is dissolved in 450 ml of ethanol. Catalytic reduction is carried out again using 15 g of 5% palladium-on-carbon, whereby 700 cc of hydrogen is absorbed. The catalyst is filtered off and the filtrate is concentrated to give a crystalline precipitate. It is collected by filtration and a washed with ethanol to give an additional crop (5.3 g) of the above-mentioned 4-isopropyl derivative. Recrystallization from ethanol yields colorless crystals melting at 151°–152° C.

Mass spectrum m/e 408 (M+).
IR $\nu_{max}^{Nujol}$ cm$^{-1}$: 1760, 1715.

| | Elemental analysis: $C_{23}H_{24}N_2O_5$ | | |
|---|---|---|---|
| | C(%) | H(%) | N(%) |
| Calcd. | 67.63 | 5.92 | 6.86 |
| Found | 67.53 | 5.89 | 6.79 |

REFERENCE EXAMPLE 170C

In 170 ml of dimethoxyethane is dissolved 8.5 g of cis-3-phthalimido-4-isopropyl-1-(2,4-dimethoxybenzyl)-2-oxoazetidine and under ice-cooling and stirring, 2.1 ml of methylhydrazine is added dropwise. The mixture is stirred at room temperature for 4 hours and then at 35°–40° C. for 2 hours. The reaction mixture is filtered and the filtrate is concentrated under reduced pressure. The crystals previously collected by filtration are added to the residue, followed by addition of 120 ml of dichloroethane and the mixture is stirred at 60°–70° C. for 3 hours. After cooling, this reaction mixture is filtered and the filtrate is concentrated under reduced pressure. The residue is dissolved in ethyl acetate and extracted with 50 ml and 20 ml portions of 1N hydrochloric acid in this order, and the extract is washed with ether. On addition of 8.4 g of sodium hydrogen carbonate, an oil separates out. This oil is extracted with chloroform, washed with aqueous sodium chloride and dried over anhydrous sodium sulfate. The solvent is then distilled off under reduced pressure and the residue is dissolved in 10 ml of methylene chloride, followed by addition of 30 ml of propylene oxide. Then, unde ice-cooling and stirring, a solution of 3.55 g of carbobenzoxy chloride in 10 ml of methylene chloride is added dropwise, whereupon crystals separates out. After addition of 70 ml of propylene oxide and 30 ml of methylene chloride, the mixture is stirred at room temperature, whereupon the above-mentioned crystals dissolve gradually to ultimately give a clear solution in 4 hours. The solvent is then distilled off and the residue is purified by column chromatography [silica gel: 250 g; eluent: hexane-ethyl acetate (1:1)] and crystallized from ether to give 4.7 g of cis-3-benzyloxycarboxamido-4-isopropyl-1-(2,4-dimethoxybenzyl)-2-oxoazetidine, melting at 123°–125° C.

IR $\nu_{max}^{Nujol}$ cm$^{-1}$: 3300, 1760, 1690

| | Elemental analysis: $C_{23}H_{28}N_2O_5$ | | |
|---|---|---|---|
| | C(%) | H(%) | N(%) |
| Calcd. | 66.97 | 6.84 | 6.79 |
| Found | 66.96 | 6.83 | 6.81 |

REFERENCE EXAMPLE 171C

To a mixture of 50 ml of acetonitrile and 25 ml of water are added 2.06 g of cis-3-benzyloxycarboxamido-4-isopropyl-1-(2,4-dimethoxybenzyl)-2-oxoazetidine, 1.89 g of potassium persulfate and 1.13 g of dipotassium hydrogen phosphate, and the mixture is refluxed under stirring at 95° C. for 2 hours. After cooling, the acetonitrile is distilled off under reduced pressure and after addition of 50 ml of water, the residual aqueous solution is extracted with 200 ml of ethyl acetate. The extract is washed twice with 100 ml of portions of 2% aqueous sodium hydrogen carbonate and once with aqueous sodium chloride in this order and dried over anhydrous sodium sulfate. The solvent is then distilled off under reduced pressure and the residue is warmed a little with 50 ml of benzene and, then, allowed to cool. The insolubles are collected by filtration and washed with benzene and a small amount of ether in this order to give 1.1 g of cis-3-benzyloxycarboxamido-4-isopropyl-2-oxoazetidine, melting at 184°–185° C.

IR $\nu_{max}^{Nujol}$ cm$^{-1}$: 3340, 1760, 1690.

| | Elemental analysis: $C_{14}H_{18}N_2O_3$ | | |
|---|---|---|---|
| | C(%) | H(%) | N(%) |
| Calcd. | 64.10 | 6.92 | 10.68 |
| Found | 63.85 | 6.75 | 10.47 |

REFERENCE EXAMPLE 172C

In 30 ml of ethanol is suspended 1.0 g of cis-3-benzyloxycarboxamido-4-isopropyl-2-oxoazetidine and after addition of 1.0 g of 5% palladium-on-carbon, the suspension is stirred in a hydrogen atmosphere for 30 minutes. The catalyst is then filtered off and the filtrate is concentrated under reduced pressure to give 430 mg of cis-3-amino-4-isopropyl-2-oxoazetidine as crystals, melting at 91°–93° C.

IR $\nu_{max}^{KBr}$ cm$^{-1}$: 3350–3150, 1735.

NMR(CDCl$_3$, ppm): 0.95(6H, d, J=6 Hz, 2×CH$_3$), 1.59(2H, br.s, NH$_2$), 3.2(1H, d.d, J=5, 9 Hz, C$_4$—H), 4.17(1H, d, J=5 Hz, C$_3$—H).

| Elemental analysis: C$_6$H$_{12}$N$_2$O | | | |
|---|---|---|---|
| | C(%) | H(%) | N(%) |
| Calcd. | 56.22 | 9.44 | 21.86 |
| Found | 56.35 | 9.45 | 21.38 |

REFERENCE EXAMPLE 173C

In 100 ml of methylene chloride is dissolved 3.7 g of p-anisidine and after addition of 4.2 g of trans-cinnamaldehyde and 30 g of anhydrous magnesium sulfate, the mixture is stirred at room temperature for 2 hours. The reaction mixture is filtered and washed with 60 ml of dichloromethane. The filtrate and washings are combined and under ice-cooling and stirring, 8.4 ml of triethylamine is added, followed by dropwise addition of a solution of 7 g of phthalimidoacetyl chloride in 50 ml of methylene chloride. The mixture is stirred at room temperature for 1.5 hours and the reaction mixture is washed with water and aqueous sodium chloride in this order. The methylene chloride is then distilled off under reduced pressure, after which 50 ml of chloroform is added to the residue. The insolubles are filtered off and the filtrate is concentrated under reduced pressure. The residue is crystallized from 25 ml of ethyl acetate and filtered to give cis-3-phthalimido-4-(E)-styryl-1-(p-methoxyphenyl)-2-oxoazetidine, melting at 202°–203° C.

IR $\nu_{max}^{KBr}$ cm$^{-1}$: 1740, 1720.

NMR (CDCl$_3$, ppm): 3.74(3H, s, OCH$_3$), 5.00(1H, d.d, J=5, 7 Hz, C$_4$—H), 5.65(1H, d, J=5 Hz, C$_3$—H), 6.24(1H, d.d, J=7,16Hz, 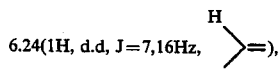), 6.78(1H, d, J=16Hz, 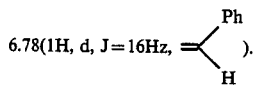).

| Elemental analysis: C$_{16}$H$_{20}$N$_2$O$_4$ | | | |
|---|---|---|---|
| | C(%) | H(%) | N(%) |
| Calcd. | 73.57 | 4.75 | 6.60 |
| Found | 73.56 | 4.58 | 6.87 |

REFERENCE EXAMPLE 174C

In 25 ml of tetrahydrofuran is dissolved 1 g of cis-3-phthalimido-4-(E)-styryl-1-(p-methoxyphenyl)-2-oxoazetidine and under stirring at −5° C. to −10° C., solution of ammonium cerium (IV) nitrate (3 g) in 10 ml of water is added dropwise over a period of 5 minutes. Then, the mixture is stirred at −5° C. to 0° C. for 20 minutes. The tetrahydrofuran is distilled off under reduced pressure and the residue is shaken with ethyl acetate and water. The ethyl acetate layer is taken, washed with aqueous sodium sulfite and aqueous sodium chloride in this order and dried over anhydrous sodium sulfate. The solvent is then distilled off and the residue is purified by silica gel column chromatography [eluent: chloroform-ethyl acetate (7:3)] and crystallized from ethyl acetate-ether to give cis-3-phthalimido-4-(E)-styryl-2-oxoazetidine, melting at 168°–170° C.

IR $\nu_{max}^{KBr}$ cm$^{-1}$: 3250, 1750, 1720.

NMR(CDCl$_3$, ppm): 4.68(1H, d.d., J=5, 8 Hz, C$_4$—H), 5.57 (1H, d, J=5 Hz, C$_3$—H), 6.66(1H, s, N$_1$—H).

| Elemental analysis: C$_{19}$H$_{14}$N$_2$O$_3$ | | | |
|---|---|---|---|
| | C(%) | H(%) | N(%) |
| Calcd. | 71.69 | 4.43 | 8.80 |
| Found | 71.61 | 4.37 | 8.55 |

REFERENCE EXAMPLE 175C

In 6 ml of N,N-dimethylformamide is dissolved 546 mg of cis-3-phthalimido-4-(E)-styryl-2-oxoazetidine and under ice-cooling and stirring, 0.36 ml of triethylamine and 323 mg of tert-butyldimethylsilyl chloride are added. The mixture is stirred for 30 minutes and further stirred at room temperature for 4 hours and, then, the reaction mixture is shaken with ethyl acetate and water. The ethyl acetate layer is taken, washed twice with water and once with saturated aqueous sodium chloride in this order and dried over anhydrous sodium sulfate. It is concentrated under reduced pressure and the residue is purified by silica gel column chromatography (eluent: chloroform) and crystallized from ether to give cis-3-phthalimido-4-(E)-styryl-1-(tertbutyldimethylsilyl)-2-oxoazetidine, melting at 167°–168° C.

IR $\nu_{max}^{KBr}$ cm$^{-1}$: 1750, 1715.

NMR(CDCl$_3$, ppm): 4.58(1H, m, C$_4$—H), 5.62(1H, d, J=6 Hz, C$_3$—H).

| Elemental analysis: C$_{25}$H$_{28}$N$_2$O$_3$Si | | | |
|---|---|---|---|
| | C(%) | H(%) | N(%) |
| Calcd. | 69.41 | 6.52 | 6.48 |
| Found | 69.22 | 6.46 | 6.48 |

REFERENCE EXAMPLE 176C

In 5 ml of dimethoxyethane is suspended 440 mg of cis-3-phthalimido-4-(E)-styryl-1-(tert-butyldimethylsilyl)-2-oxoazetidine and after addition of 0.26 ml of methylhydrazine, the mixture is stirred at room temperature for 30 minutes. The solvent is then distilled off under reduced pressure and the residue is dissolved by addition of 5 ml of methylene chloride and allowed to stand overnight. The precipitate is filtered off and the filtrate is concentrated under reduced pressure. The residue is purified by silica gel column chromatography [eluent: chloroform-ethyl acetate (6:4)] to give an oil of cis-3-amino-4-(E)-styryl-1-(tert-butyldimethylsilyl)-2-oxoazetidine. This oil is dissolved in 10 ml of tetrahydrofuran and under ice-cooling and stirring, 0.2 ml of triethylamine is added, followed by addition of 0.212 g of 2-(2-chloroacetamido-4-thiazolyl)-2-methoxyiminoacetyl chloride hydrochloride. The mixture is stirred under ice-cooling for 10 minutes and then at room temperature for 30 minutes, after which the reaction mixture is shaken with ethyl acetate and water. The ethyl acetate layer is taken, washed with saturated aqueous sodium chloride and dried over anhydrous sodium sulfate. The solvent is then distilled off under reduced pressure and the residue is purified by silica gel column chromatography [eluent: chloroform-ethyl acetate (7:3)] and crystallized from ether to give cis-[2-(2-chloroacetamido-4-thiazolyl)-2-methoxyiminoacetamido]-4-(E)-styryl-1-(tert-butyldimethylsilyl)-2-oxoazetidine (syn-isomer), melting at 228°–231° C. (decomp.).

IR $\nu_{max}^{KBr}$cm$^{-1}$: 1725, 1670.

NMR(CDCl$_3$, ppm): 3.15(3H, s, OCH$_3$), 4.20(2H, s, ClCH$_2$), 4.63(1H, m, C$_4$—H), 5.50(1H, d.d, J=6, 6 Hz, C$_3$—H), 7.20(1H, s, 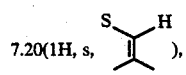), 8.50(1H, d, J=6 Hz, C$_3$—NH).

| | Elemental analysis: C$_{25}$H$_{32}$ClN$_5$O$_4$SSi | | |
|---|---|---|---|
| | C(%) | H(%) | N(%) |
| Calcd. | 53.41 | 5.74 | 12.46 |
| Found | 53.09 | 5.71 | 12.47 |

REFERENCE EXAMPLE 177C

In a nitrogen stream under stirring, 50 ml of dry tetrahydrofuran is cooled to −78° C. and, then, 20 ml of a solution of 15% n-butyllithium in n-hexane is added thereto. After dropwise addition of 3.66 ml of diisopropylamine, the mixture is stirred at −78° C. for 15 minutes. A solution of 3.1 g of 2,2-dimethyl-1-aza-3-oxabicyclo[4.2.0]octan-8-one in 15 ml of dry tetrahydrofuran is added dropwise and the mixture is stirred at −78° C. for one hour. Then, a solution of 4.34 g of p-toluenesulfonyl azide in 15 ml of dry tetrahydrofuran is added dropwise and the mixture is stirred at −50° C. to −60° C. for 1.5 hours. To this mixture 5.1 ml of trimethylsilyl chloride is added dropwise and the reaction mixture is heated under reflux for 5 hours. After cooling, the insolubles are filtered off and the filtrate is concentrated under reduced pressure. The residue is shaken with water and ethyl acetate and the ethyl acetate layer is separated, washed with water, dried over anhydrous sodium sulfate and concentrated under reduced pressure. The solvent is then distilled off and the residue is purified by silica gel column chromatography to give 2,2-dimethyl-7-azido-1-aza-3-oxabicyclo[4.2.0]octan-8-one as a 1:4 mixture of cis- and trans-isomers.

IR $\nu_{max}^{KBr}$cm$^{-1}$: 2100, 1750.

NMR(CDCl$_3$, ppm): 4.20(d, J=1.5 Hz, trans-C$_3$—H), 4.68(d, J=5 Hz, cis-C$_3$—H).

Crystallization of the above mixture from diisopropyl ether selectively yields the trans-compound as crystals, melting at 78°–80° C.

REFERENCE EXAMPLE 178C

In 30 ml of acetone is dissolved 330 mg of trans-2,2-dimethyl-7-azido-1-aza-3-oxabicyclo[4.2.0]octan-8-one and under ice-cooling and stirring, 3.3 ml (8N solution) of Jones reagent is added. The mixture is stirred for 2.5 hours, after which 5 ml of isopropyl alcohol is added and the mixture is further stirred for 10 minutes. The insolubles are filtered off with the aid of Celite and the filtrate is concentrated under reduced pressure. The residue is shaken with tetrahydrofuran and a small amount of saturated aqueous sodium chloride. The tetrahydrofuran layer is taken and extracted three times with tetrahydrofuran. The tetrahydrofuran layers are combined, dried over anhydrous sodium sulfate and, after additiion of a solution of diazomethane in ether, the mixture is allowed to stand. The solvent is then distilled off and the residue is shaken with water and ethyl acetate. The ethyl acetate layer is taken, washed with aqueous sodium hydrogen carbonate and water in this order and dried over anhydrous sodium sulfate. It is concentrated under reduced pressure and the residue is purified by silica gel column chromatography to give trans-3-azido-4-methoxycarbonylmethyl-2-oxoazetidine.

NMR(CDCl$_3$, ppm): 2.76(2H, d, J=6 Hz, C$_4$—CH$_2$), 3.70(3H, s, CO$_2$CH$_3$), 3.82(1H, m, C$_4$—H), 4.36(1H, C$_3$—H), 6.75(1H, s, N$_1$—H).

Proceeding in the same manner but starting with a 1:4 cis-trans mixture, there was obtained the 2-oxoazetidine compound in the form of a 1:4 cis-trans mixture.

NMR(CDCl$_3$, ppm): 4.83(cis-C$_3$—H).

REFERENCE EXAMPLE 179C

In a mixture of 20 ml of tetrahydrofuran and 10 ml of water is dissolved 800 mg of cis-3-benzyloxycarboxamido-2-oxoazetidine-4-carboxylic acid as obtained in Reference Example 68C. Under ice-cooling, 280 mg of sodium hydrogen carbonate is added and, after addition of 303 mg of o-methylhydroxylamine hydrochloride and 638 mg of 1-ethyl-3-(3-dimethylaminopropyl)-carbodiimide hydrochloride, the mixture is stirred at room temperature. After 3 hours, sodium chloride is added and the reaction mixture is extracted with ethyl acetate-ethanol (10:1). The extract is washed with 3N hydrochloric acid, saturated aqueous sodium hydrogen carbonate and aqueous sodium chloride in this order and dried over anhydrous sodium sulfate. The solvent is then distilled off under reduced pressure to give cis-3-benzyloxycarboxamido-4-methoxyaminocarbonyl-2-oxoazetidine, melting at 212°–216° C. (decomp.).

IR $\nu_{max}^{KBr}$cm$^{-1}$: 3290, 1760, 1680.

REFERENCE EXAMPLE 180C

To 8 ml of dry dimethyl sulfoxide are added 5.1 g of cis-3-benzyloxycarboxamido-1-(2,4-dimethoxybenzyl)-4-iodomethyl-2-oxoazetidine as obtained in Reference Example 62C, 2.6 g of potassium cyanide and 50 mg of 18-Crown-6. The mixture is stirred at room temperature for 2 days and then at 50° C. for 3 hours, after which it is poured into 250 ml of ethyl acetate. This reaction mixture is washed three times with water and once with aqueous sodium chloride in this order, dried over magnesium sulfate and concentrated. The residue is purified by silica gel column chromatography [silica gel: 400 g; eluent: ethyl acetate-hexane (1:2 and then 2:1)] to give cis-3-benzyloxycarboxamido-4-cyanomethyl-1-(2,4-dimethoxybenzyl)-2-oxoazetidine.

IR $\nu_{max}^{KBr}$cm$^{-1}$: 3290, 2920, 2240, 1770, 1690.

NMR(CDCl$_3$, ppm): 2.48(2H, d, J=6 Hz, CH$_2$CN), 3.78(3H, s, OCH$_3$), 3.80(3H, s, OCH$_3$), 4.82(1H, d.d, J=5, 8 Hz, C$_3$—H).

REFERENCE EXAMPLE 181C

In a mixture of 210 ml of acetonitrile and 70 ml of water is dissolved 1.7 g of cis-3-benzyloxycarboxamido-4-cyanomethyl-1-(2,4-dimethoxybenzyl)-2-oxoazetidine, and after addition of 1.68 g of potassium persulfate and 1.085 g of dipotassium hydrogen phosphate, the mixture is refluxed at 85°–90° C. for 2.5 hours. The acetonitrile is then distilled off under reduced pressure and the residue is extracted with ethyl acetate. The extract is washed with saturated aqueous sodium hydrogen carbonate and aqueous sodium chloride in this order, dried over anhydrous magnesium sulfate, and concentrated under reduced pressure. The residue is purified by silica gel column chromatography [silica gel: 140 g; eluent: ethyl acetate-hexane (1:2 and then 3:1)] to give cis-3-benzyloxycarboxamido-4-cyanomethyl-2-oxoazetidine, melting at 113°–115° C.

IR $\nu_{max}^{KBr}$ cm$^{-1}$: 3300, 2250, 1760, 1685.

REFERENCE EXAMPLE 182C

In the same manner as Reference Example 166C, there was synthesized cis-3-{2-(2-chloroacetamido-4-thiazolyl)-2-[1-methyl-1-(p-nitrobenzyloxycarbonyl)ethyloxyimino]-acetamido}-4-cyanomethyl-2-oxoazetidine (syn-isomer).

IR $\nu_{max}^{KBr}$ cm$^{-1}$: 3360, 2980, 2250, 1740, 1680, 1600, 1520, 1345, 1140.

REFERENCE EXAMPLE 183C

In a mixture of 100 ml of tetrahydrofuran and 100 ml of water is dissolved 4 g of methyl cis-3-benzyloxycarboxamido-2-oxoazetidine-4-carboxylate as obtained in Reference Example 2C and under ice-cooling, 1.359 g of sodium borohydride is added. The mixture is stirred under ice-cooling for one hour and then at room temperature for 2 hours. The tetrahydrofuran is then distilled off under reduced pressure. The residue is extracted three times with chloroform and the extract is dried over anhydrous magnesium sulfate and concentrated under reduced pressure. The residue is dissolved in 30 ml of ethanol and after addition of 1 g of 5% palladium-on-carbon, the mixture is stirred in a hydrogen atmosphere for 4 hours. The catalyst is then filtered off and the filtrate is concentrated. The residue is dissolved in a mixture of 20 ml of water and 20 ml of tetrahydrofuran and, under ice-cooling, 3.62 g of sodium hydrogen carbonate is added. After addition of 3.41 g of p-nitrobenzyloxycarbonyl chloride, the mixture is stirred at room temperature for 2 hours. This reaction mixture is extracted three times with chloroform and the extract is dried over anhydrous magnesium sulfate. The solvent is then distilled off under reduced pressure and the residue is purified by silica gel column chromatography [silica gel: 160 g; eluent: ethyl acetate and then ethyl acetate-methanol (4:1)] to give cis-3-(p-nitrobenzyloxycarboxamido-4-hydroxymethyl-2-oxoazetidine, melting at 166°–167° C.

IR $\nu_{max}^{KBr}$ cm$^{-1}$: 3280, 1770, 1700.

| Elemental analysis: $C_{12}H_{13}N_3O_6$ | | | |
|---|---|---|---|
| | C(%) | H(%) | N(%) |
| Calcd. | 48.82 | 4.44 | 14.23 |
| Found | 48.58 | 4.53 | 13.87 |

REFERENCE EXAMPLE 184C

In 40 ml of dry tetrahydrofuran is suspended 2.28 g of sodium hydride and under ice-cooling, a solution of 3 g of 1-methyl-1H-tetrazol-5-ylthiol in 40 ml of tetrahydrofuran is added. Then, a solution of 3.59 g of bromoacetic acid in 80 ml of dry ethanol is added and the mixture is stirred under ice-cooling for 30 minutes and then at room temperature for one hour. It is concentrated under reduced pressure and the residue is shaken with 100 ml of water and 100 ml of ether. The aqueous layer is taken, acidified with 3N hydrochloric acid and extracted twice with chloroform-ethanol (3:1). The extract is dried over anhydrous magnesium sulfate and, then, the solvent is distilled off to give 1-methyl-1H-tetrazol-5-ylthioacetic aicd.

IR $\nu_{max}^{KBr}$ cm$^{-1}$: 2990, 1700.

NMR(CDCl$_3$+d$_6$-DMSO, ppm): 3.82(3H, s, CH$_3$), 3.98(2H, s, CH$_2$), 4.10(1H, s, CO$_2$H).

What is claimed is:

1. A compound of the formula $$\begin{array}{c} X \quad R'' \\ R^1 \diagdown \diagup \\ \square \\ O \diagup \quad \diagdown N \\ \qquad \diagdown SO_3H \end{array}$$

wherein R$^1$ represents
 (1) amino,
 (2) an acylated amino group wherein the acyl moiety is
  (i) a group of the formula:

R$^5$—CO— wherein R$^5$ is an alkyl other than C$_{1-5}$alkyl-CH$_2$- or a heterocyclic* group;
  (ii) a group of the formula:

R$^6$—NH—CH—CO—
  $\qquad\qquad\quad |$
  $\qquad\qquad\quad$R$^7$ wherein R$^6$ is hydrogen, glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophanyl, an amino-protective group or a group R$^8$—(CH$_2$)$_{n1}$—CO— where R$^8$ is a heterocyclic* group and n$_1$ is an integer of 0 to 2, and R$^7$ is an alkyl, phenyl*, heterocyclic*-carbonylamino or a heterocyclic* group;
  (iii) a group of the formula:

R$^9$—R$^{10}$—CO— wherein R$^9$ is a group

R$^{11}$—C—
  $\qquad\;\|$
  $\qquad\;$N
  $\qquad\;\;\diagdown$
  $\qquad\;\;\;$O—R$^{12}$ where R$^{11}$ is alkyl*, heterocyclic* group or phenyl* and R$^{12}$ is hydrogen, an alkyl, alkenyl or a group -R$^{13}$-R$^{14}$ where R$^{13}$ is an alkylene or alkenylene and R$^{14}$ is phenyl*, carboxyl or an alkyl ester thereof or mono- or di-alkylamino, and R$^{10}$ is a direct bond or a group

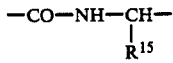

where R$^{15}$ is an alkyl, phenyl* or thiazolyl*;
(iv) a group of the formula:

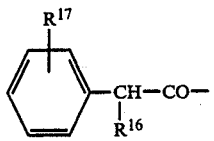

wherein R$^{16}$ is hydroxyl, hydroxysulfonyloxy, carboxy, ureido*, sulfamoyl*, sulfo, phenoxycarbonyl* or formyloxy and R$^{17}$ is hydrogen, an alkyl, an alkoxy, halogen, nitro or hydroxy; or
(v) a group of the formula:

wherein R$^{18}$ is cyano, phenyl*, phenoxy*, an alkyl*, alkenyl* or a heterocyclic* group and R$^{19}$ is a direct bond or —S—;
and, in symbols R$^5$ through R$^{19}$ (a) the heterocyclic group is 2- or 3-pyrrolyl; 2- or 3-furyl; 2- or 3-thienyl; 2- or 3-pyrrolidinyl; 2-, 3- or 4-pyridyl; N-oxido-2-, 3- or 4-pyridyl; 2-, 3- or 4-piperidinyl; 2-, 3- or 4-pyranyl; 2-, 3- or 4-thiopyranyl; pyrazinyl; 2-, 4- or 5-thiazolyl; 2-, 4- or 5-oxazolyl; 3-, 4- or 5-isothiazolyl; 3-, 4- or 5-isoxazolyl; 2-, 4- or 5-imidazolyl; 3-, 4- or 5-pyrazolyl; 3- or 4-pyridazinyl; N-oxido-3- or 4-pyridazinyl; 2-, 4- or 5-pyrimidinyl; N-oxido-2-, 4- or 5-pyrimidinyl; piperazinyl; 4- or 5-(1,2,3-thiadiazolyl); 3- or 5-(1,2,4-thiadiazolyl); 1,3,4-thiadiazolyl; 1,2,5-thiadiazolyl; 4- or 5-(1,2,3-oxadiazolyl); 3- or 5-(1,2,4-oxadiazolyl); 1,3,4-oxadiazolyl; 1,2,5-oxadiazolyl; 1,2,3- or 1,2,4-triazolyl; 1H- or 2H-tetrazolyl; pyrido[2,3-d]pyrimidyl; benzopyranyl; 1,8-, 1,5-, 1,6-, 1,7-, 2,7- or 2,6-naphthyridyl; quinolyl or thieno[2,3-b]pyridyl, (b) the amino-protective group in R$^6$ is phthaloyl, p-nitrobenzoyl, p-tert-butylbenzoyl, p-tert-butylbenzenesulfonyl, benzenesulfonyl, toluenesulfonyl, formyl, acetyl, propionyl, monochloroacetyl, dichloroacetyl, trichloroacetyl, methanesulfonyl, ethanesulfonyl, trifluoroacetyl, maleyl, succinyl, methoxycarbonyl, ethoxycarbonyl, t-butoxycarbonyl, isopropoxycarbonyl, 2-cyanoethoxycarbonyl, β,β,β-trichloroethoxycarbonyl, β-trimethysilylethoxycarbonyl, β-methylsulfonylethoxycarbonyl, benzyloxycarbonyl, p-nitrobenzyloxycarbonyl, p-methoxybenzyloxycarbonyl, di-phenylmethyloxycarbonyl, methoxymethyloxycarbonyl, acetylmethyloxycarbonyl, isobornyloxycarbonyl, phenyloxycarbonyl, trityl, 2-nitrophenylthio, benzylidene, 4-nitrobenzylidene, trialkylsilyl, benzyl or p-nitrobenzyl, (c) the heterocyclic, phenyl, thiazolyl, phenoxycarbonyl and phenoxy with a superscript asterisk "*" may be substituted with one to three substituents selected from the group consisting of alkyl, alkoxy, alkenyl, aryl, aralkyl, mercapto, alkylthio, arylthio, aralkylthio, alkylsulfonyl, arylsulfonyl, aralkylsulfonyl, hydroxyl, oxo, thioxo, halogen, nitro, amino, cyano, carbamoyl, carboxy, acyl, acyloxy, acylamino, hydroxyalkyl, carboxyalkyl, haloalkyl and mono- or dialkylaminoalkyl, wherein the acyl group and the acyl moiety of acyloxy and acylamino are C$_{1-6}$ alkylcarbonyl; benzoyl which may be substituted with hydroxyl or methoxy; C$_{7-9}$ aralkylcarbonyl which may be substituted with hydroxyl or methoxy; 2-thienylcarbonyl; 2-furylcarbonyl; 2-, 4- or 5-thiazolylacetyl; 2- or 3-thienylacetyl; 2- or 3-furylacetyl or 2-amino-4- or 5-thiazolylacetyl, (d) the alkyl with a superscript asterisk "*" may be substitituted with one to three members selected from halogen, hydroxyl, cyano and trifluoromethyl, (e) the ureido with a superscript asterisk "*" may be substituted with sulfo in the form of a salt with sodium or potassium, carbamoyl, sulfamoyl, amidino or alkyl, (f) the sulfamoyl with a superscript asterisk "*" may be substituted with an alkyl or amidino, (g) the alkenyl with a superscript asterisk "*" may be substituted with one to three members selected from carboxyl and cyano, wherein the amino group, the carboxyl group and the hydroxyl group may be protected, or (3) amino protected with phthalyl, p-nitrobenzoyl, p-tert-butylbenzoyl, p-tert-butylbenzenesulfonyl, benzenesulfonyl, toluenesulfonyl, formyl, monochloroacetyl, dichloroacetyl, trichloroacetyl, methanesulfonyl, ethanesulfonyl, trifuluoroacetyl, maleyl, succinyl, methoxycarbonyl, ethoxycarbonyl, t-butoxycarbonyl, isopropoxycarbonyl, 2-cyanoethoxycarbonyl, β,β,β-trichloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, di-phenylmethyloxycarbonyl, methoxymethyloxycarbonyl, acetylmethyloxycarbonyl, isobornyloxycarbonyl, phenyloxycarbonyl, trityl, 2-nitrophenylthio, benzylidene, 4-nitrobenzylidene, trialkylsilyl, benzyl or p-nitrobenzyl, X represents hydrogen or methoxy, and R" is a group of the formula

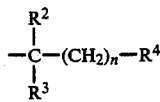

wherein n is an integer of 0 to 3; R$^2$ and R$^3$, which may be the same or different, stand for hydrogen, alkyl, cycloalkyl*, aralkyl*, aryl*, heterocyclic* group, alkoxycarbonyl or acyl, R$^4$ is cycloalkyl*, aryl*, a heterocyclic* group, alkoxy, aryl*-oxy, aralkyl*-oxy, acyloxy, carbamoyloxy, hydroxysulfonyloxy, nitro, carboxyl, alkoxycarbonyl, alkoxycarbonylalkyloxy, aminocarbonyl, alkylthiocarbonyl, acyl, alkylthio, aminoalkylthio, acylaminoalkylthio, heterocyclic*-thio or quarternary ammonium*;
wherein (a') the heterocyclic group is as defined above in R¹, (b') the acyl group and the acyl moiety of acyloxy and acylaminoalkylthio group is an alkylcarbonyl, haloalkylcarbonyl, arylcarbonyl or a group of the formula: wherein X is

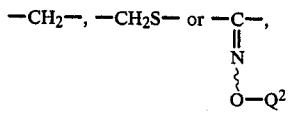

and Q¹ is a 2- or 3-thienyl, 2- or 3-furyl or 2-, 4- or 5-thiazolyl which may be substituted with amino or an alkyl, and Q² is an alkyl group, (c') the quaternary ammonium is pyridinium or quinolinium group, said group forming an inner salt with the sulfo group at the 1-position of the 2-oxoazetidine nucleus, and (d') the cycloakyl, heterocyclic, aryl, aralkyl and quaternary ammonium group with a superscript asterisk "*" may be substituted with alkyl, alkoxy, alkenyl, aryl, aralkyl, mercapto, alkylthio, arylthio, aralkylthio, alkylsulfonyl, arylsulfonyl, aralkylsulfonyl, hydroxyl, oxo, thioxo, halogen, nitro, amino, cyano, carbamoyl, carboxyl, acyl, acyloxy, acylamino, hydroxyalkyl, carboxyalkyl, or mono- or dialkylaminoalkyl wherein the acyl group and the acyl moiety of the acyloxy and acylamino is as defined above in (b'), further among the above groups, the amino, carboxyl and hydroxyl group may be protected, and within the above groups R¹ and R", alkyl is $C_{1-6}$ alkyl; alkenyl is $C_{2-6}$ alkenyl; alkoxy is $C_{1-6}$ alkoxy; aryl is phenyl, α-naphthyl, β-naphthyl, biphenyl or anthryl; aralkyl is benzyl, phenethyl, phenylpropyl or naphthylmethyl; alkylene is $C_{1-3}$ alkylene and alkenylene is $C_{2-4}$ alkenylene, or a pharmaceutically acceptable salt thereof, or an alkoxymethyl, α-alkoxyethyl, alkylthiomethyl, pivaloyloxymethyl, α-acetoxybutyl, ethoxycarbonyloxymethyl or α-ethoxycarbonyloxyethyl ester in the carboxyl group or groups contained in the group R¹ and/or R" thereof.

2. A compound of the formula

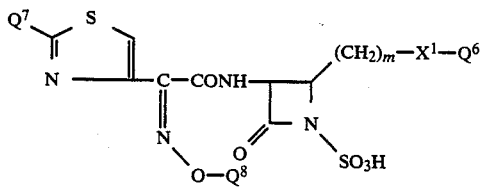

wherein $Q^7$ is amino or a protected amino group; $Q^8$ is a $C_{1-6}$ alkyl, a $C_{2-6}$ alkenyl, a group —CH₂COOQ⁹ or a group

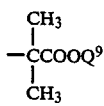

wherein COOQ⁹ is carboxyl or a $C_{1-6}$ alkyl ester thereof; m is an integer of 1 to 4; X¹ is —NH—, —S—, —O— or a direct bond; and Q⁶ is (1) carbamoyl, (2) $C_{1-6}$ alkylcarbonyl which may be substituted with a halogen, (3) $C_{1-6}$ alkyl, (4) benzoyl, (5) 5- or 6-membered nitrogen-containing heterocyclic group which may be substituted with a $C_{1-6}$ alkyl group, or (6) 5- or 6-membered nitrogen-containing heterocyclic-thioacetyl wherein the heterocyclic may be substituted with a $C_{1-6}$ alkyl, with the proviso that when X¹ is a direct bond, Q₆ is other than $C_{1-6}$ alkyl, the 5- or 6-membered nitrogen-containing heterocyclic group being pyrrolyl, thiazolyl, thiadiazolyl, diazolyl, oxazolyl, oxadiazolyl, triazolyl or tetrazolyl.

3. Cis-3-[2-(2-Amino-4-thiazolyl)-2-(1-methyl-1-carboxyethyloxyimino)acetamido]-4-acetamidomethyl-2-oxoazetidine-1-sulfonic acid (syn-isomer).

4. A compound as claimed in claim 1, wherein R" is a group of the formula:

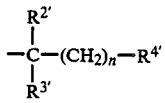

wherein n is an integer of 0 to 3, $R^{2'}$ and $R^{3'}$ which may be the same or different, stand for hydrogen or $C_{1-6}$ alkyl, and $R^{4'}$ is aryl*, $C_{1-6}$ alkoxy, aralkyl*-oxy, acyloxy, carbamoyloxy, sulfooxy, carboxyl, $C_{1-6}$ alkoxycarbonyl, $C_{1-6}$ alkoxycarbonyl-$C_{1-6}$-alkyloxy, $C_{1-6}$ alkylthio, heterocyclic*-thio or quaternary ammonium* group; and the groups with a superscript asterisk "*" are as defined in claim 1 and the acyl moiety of the acyloxy is as defined in claim 1.

5. A compound as claimed in claim 4, wherein both $R^{2'}$ nd $R^{3'}$ are hydrogen, n is zero, and $R^{4'}$ is $C_{1-4}$ alkoxy; $C_{1-4}$ alkylcarbonyloxy; pyrrolyl, thiazolyl, thiadiazolyl, diazolyl, oxazolyl, oxadiazolyl, triazolyl or tetrazolyl which may be substituted with a $C_{1-4}$ alkyl group.

6. A compound as claimed in claim 4, wherein the aralkyl*-oxy group is benzyloxy which may be substituted with nitro.

7. A compound as claimed in claim 1, wherein the heterocycle*-thio group is tetrazolylthio group which may be substituted with a $C_{1-6}$ alkyl group.

8. A compound as claimed in claim 4, wherein the quaternary ammonium* group is pyridinium.

9. Cis-3-[2-(2-Chloroacetamido-4-thiazolyl)-2-methoxyiminoacetamido]-4-acetyl-2-oxoazetidine-1-sulfonic acid or a pharmaceutically acceptable salt thereof.

10. Cis-3-[2-(2-Amino-4-thiazolyl)-2-methoxyiminoacetamido]-4-acetyl-2-oxoazetidine-1-sulfonic acid or a pharmaceutically acceptable salt thereof.

11. Cis-3-[2-(2-Chloroacetamido-4-thiazolyl)-2-methoxyiminoacetamido]-4-(2-methylsulfonylethoxycarbonylaminomethyl)-2-oxoazetidine-1-sulfonic acid or a pharmaceutically acceptable salt thereof.

12. Cis-3-[2-(2-Chloroacetamido-4-thiazolyl)-2-methoxyiminoacetamido]-4-trifluoroacetylaminomethyl-2-oxoazetidine-1-sulfonic acid or a pharmaceutically acceptable salt thereof.

13. Cis-3-[2-(2-Amino-4-thiazolyl)-2-methoxyiminoacetamido]-4-trifluoroacetylaminomethyl-2-oxoazetidine-1-sulfonic acid or a pharmaceutically acceptable salt thereof.

14. Cis-3-{2-(2-Chloroacetamido-4-thiazolyl)-2-[1-methyl-1-(p-nitrobenzyloxycarbonyl)ethyloxyimino]acetamido}-4-acetamidomethyl-2-oxoazetidine- 1-sulfonic acid or a pharmaceutically acceptable salt thereof.

15. Cis-3-{2-(2-Amino-4-thiazolyl)-2-[1-methyl-1-(p-nitrobenzyloxycarbonyl)ethyloxyimino]acetamido}-4-acetamidomethyl-2-oxoazetidine-1-sulfonic acid or a pharmaceutically acceptable salt thereof.

16. Cis-3-[2-(2-Amino-4-thiazolyl)-2-[1-methyl-1-carboxyethyloxyimino)acetamido]-4-acetamidomethyl-2-oxoazetidine-1-sulfonic acid or a pharmaceutically acceptable salt thereof.

17. Trans-3-Azido-4-methoxycarbonylmethyl-2-oxoazetidine-1-sulfonic acid or a pharmaceutically acceptable salt thereof.

18. An antibacterial composition which comprises as an active ingredient an antibacterially effective amount of a compound or a pharmaceutically acceptable salt or ester thereof as defined by claim 1 and a pharmaceutically acceptable carrier or carriers therefor.

19. Cis-4-Acetamidomethyl-3-phenylacetamido-2-oxoazetidine-1-sulfonic acid or a pharmaceutically acceptable salt thereof.

20. Cis-4-Acetamidomethyl-3-[2-(2-chloroacetamido-4-thiazolyl)-2-methoxyiminoacetamido]-2-oxoazetidine-1-sulfonic acid or a pharmaceutically acceptable salt thereof.

21. Cis-4-Acetamidomethyl-3-[2-(2-amino-4-thiazolyl)-2-methoxyiminoacetamido]-2-oxoazetidine-1-sulfonic acid or a pharmaceutically acceptable salt thereof.

22. Cis-4-Benzamidomethyl-3-[2-(2-chloroacetamido-4-thiazolyl)-2-methoxyiminoacetamido]-2-oxoazetidine-1-sulfonic acid or a pharmaceutically acceptable salt thereof.

23. Cis-3-[2-(2-Amino-4-thiazolyl)-2-methoxyiminoacetamido]-4-benzamidomethyl-2-oxoazetidine-1-sulfonic acid or a pharmaceutically acceptable salt thereof.

* * * * *